US012466849B2

(12) United States Patent
Shomar Monges et al.

(10) Patent No.: US 12,466,849 B2
(45) Date of Patent: Nov. 11, 2025

(54) ANTI-VIRAL AND ANTI-TUMORAL COMPOUNDS

(71) Applicant: YEDA RESEARCH AND DEVELOPMENT CO. LTD, Rehovot (IL)

(72) Inventors: Helena Shomar Monges, Tel Aviv (IL); Rotem Sorek, Rehovot (IL); Lianet Noda Garcia, Tel Aviv (IL); Arthur Machlenkin, Gedera (IL); David Sperandio, Palo Alto, CA (US)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 894 days.

(21) Appl. No.: 17/583,378

(22) Filed: Jan. 25, 2022

(65) Prior Publication Data

US 2023/0072222 A1 Mar. 9, 2023

Related U.S. Application Data

(63) Continuation-in-part of application No. PCT/IB2021/057599, filed on Aug. 18, 2021.

(60) Provisional application No. 63/085,218, filed on Sep. 30, 2020.

(51) Int. Cl.

| | |
|---|---|
| *C07H 19/20* | (2006.01) |
| *A61P 31/14* | (2006.01) |
| *C07H 19/10* | (2006.01) |

(52) U.S. Cl.

CPC .............. *C07H 19/20* (2013.01); *A61P 31/14* (2018.01); *C07H 19/10* (2013.01)

(58) Field of Classification Search

None

See application file for complete search history.

(56) References Cited

U.S. PATENT DOCUMENTS

| | | | |
|---|---|---|---|
| 3,791,932 | A | 2/1974 | Schuurs et al. |
| 3,839,153 | A | 10/1974 | Schuurs et al. |
| 3,850,578 | A | 11/1974 | McConnell |
| 3,850,752 | A | 11/1974 | Schuurs et al. |
| 3,853,987 | A | 12/1974 | Dreyer |
| 3,867,517 | A | 2/1975 | Ling |
| 3,879,262 | A | 4/1975 | Schuurs et al. |
| 3,901,654 | A | 8/1975 | Gross |
| 3,935,074 | A | 1/1976 | Rubinstein et al. |
| 3,984,533 | A | 10/1976 | Uzgiris |
| 3,996,345 | A | 12/1976 | Ullman et al. |
| 4,034,074 | A | 7/1977 | Miles |
| 4,098,876 | A | 7/1978 | Piasio et al. |
| 4,551,433 | A | 11/1985 | Deboer |
| 4,666,828 | A | 5/1987 | Gusella |
| 4,683,202 | A | 7/1987 | Mullis |
| 4,689,406 | A | 8/1987 | Banks et al. |
| 4,738,921 | A | 4/1988 | Belagaje et al. |
| 4,801,531 | A | 1/1989 | Frossard |
| 4,879,219 | A | 11/1989 | Wands et al. |
| 5,011,771 | A | 4/1991 | Bellet |
| 5,028,530 | A | 7/1991 | Lai et al. |
| 5,192,659 | A | 3/1993 | Simons |
| 5,272,057 | A | 12/1993 | Smulson et al. |
| 5,281,521 | A | 1/1994 | Trojanowski et al. |
| 5,464,764 | A | 11/1995 | Capecchi et al. |
| 5,487,992 | A | 1/1996 | Capecchi et al. |
| 6,242,194 | B1 | 6/2001 | Kullen et al. |
| 8,324,179 | B2 | 12/2012 | Chen et al. |
| 8,877,733 | B2 | 11/2014 | Cho et al. |
| 2019/0315785 | A1 | 10/2019 | Boojamra et al. |

FOREIGN PATENT DOCUMENTS

| | | | |
|---|---|---|---|
| CN | 108640959 | A | 10/2018 |
| CN | 108640959 | B | 1/2021 |
| EP | 0121775 | A1 | 10/1984 |
| EP | 0036776 | B1 | 5/1988 |
| EP | 0267851 | B1 | 1/1994 |
| WO | WO 2011/035231 | A1 | 3/2011 |
| WO | WO 2012/087596 | A1 | 6/2012 |
| WO | WO 2014/093924 | A1 | 6/2014 |
| WO | WO 2018/220616 | A2 | 12/2018 |
| WO | WO 2019/040418 | A1 | 2/2019 |
| WO | WO 2019/053696 | A1 | 3/2019 |

(Continued)

OTHER PUBLICATIONS

Beadle et al. "Synthesis and antiviral evaluation of octadecyloxyethyl benzyl 9-[(2-Phosphonomethoxy) ethyl] guanine (ODE-Bn-PMEG), a potent inhibitor of transient HPV DNA amplification" Journal of medicinal chemistry. Dec. 8, 2016;59(23):10470-8.

Bernheim et al. "Prokaryotic viperins produce diverse antiviral molecules" Nature. Jan. 2021;589(7840):120-4.

Broderick et al. "Radical S-adenosylmethionine enzymes" Chemical reviews. Apr. 23, 2014;114(8):4229-317.

Brosius et al. "Spacing of the-10 and-35 regions in the tac promoter. Effect on its in vivo activity" Journal of biological chemistry. Mar. 25, 1985;260(6):3539-41.

Chemaly et al. "In vitro comparison of currently available and investigational antiviral agents against pathogenic human double-stranded DNA viruses: A systematic literature review" Antiviral research. Mar. 1, 2019;163:50-8.

(Continued)

Primary Examiner — Patrick T Lewis

(74) Attorney, Agent, or Firm — Mark S. Cohen; PEARL COHEN ZEDEK LATZER BARATZ LLP

(57) ABSTRACT

Disclosed herein are 3,4-didehydro- and 3'-deoxy-3,4-didehydro-compounds and pharmaceutical compositions thereof. Methods of use of these pharmaceutical compositions include those for treating diseases including virus-induced diseases, cancer, autoimmune diseases, immune disorders, and bacterial-associated diseases or infections, or combinations thereof. Examples of viral-induced diseases include viral infections by RNA or DNA viruses, for example SAR-CoV-2, EBV, BKV, JCV and HCMV.

20 Claims, 76 Drawing Sheets
(6 of 76 Drawing Sheet(s) Filed in Color)

Specification includes a Sequence Listing.

(56) References Cited

FOREIGN PATENT DOCUMENTS

WO WO 2020/202142 A2 10/2020
WO WO 2022/038539 A2 2/2022

OTHER PUBLICATIONS

Cho et al. "Synthesis and antiviral activity of a series of 1'-substituted 4-aza-7, 9-dideazaadenosine C-nucleosides" Bioorganic & medicinal chemistry letters. Apr. 15, 2012;22(8):2705-7.
Database UniProt [online] Nov. 13, 2019 "SubName: Full= molybdenum cofactor biosynthesis enzyme {ECO:0000313 ¦ EMBL:AA007825.2};", XP055719251, retrieved from EBI accession No. Uniprot:A0A3Q0KZ59, Database accession No. A0A3Q0KZ59.
Database UniProt [online] Jun. 15, 2010 "SubName: Full=Radical SAM domain protein {ECO:0000313 ¦ EMBL:EMBL:ADE54200.1};", XP055719253, retrieved from EBI accession No. Uniprot: D5EID4, Database accession No. D5EID4.
Database UniProt [online] Jan. 20, 2016 "SubName: Full=FeS reductase {ECO:0000313 ¦ EMBL:KPQ31663.1};", XP055719254, retrieved from EBI accession No. Uniprot:A0A0P7Z657, Database accession No. A0A0P7Z657.
Database UniProt [online] Jul. 18, 2018 "SubName: Full=Radical SAM protein {ECO:0000313 ¦ EMBL:PSW18885.1};", XP055719255, retrieved from EBI accession No. Uniprot: A0A2T3NRM3, Database accession No. A0A2T3NRM3.
Database UniProt [online] Apr. 13, 2016 "SubName: Full= Molybdenum Cofactor Biosynthesis Protein mOAa1 {ECO:0000313 ¦ EMBL:AMH94978.1};", XP055719256, retrieved from EBI accession No. Uniprot: A0A110A2W7, Database accession No. A0A110A2W7.
Database UniProt [online] Oct. 7, 2020 "SubName: Full=Radical S-adenosyl methionine domain-containing protein 2 {ECO:0000313 ¦ EMBL:SHL73076.1};", XP055719257, retrieved from EBI accession No. Uniprot:A0A1M7DOR2, Database accession No. A0A1M7DOR2.
Database UniProt [online] Oct. 25, 2017 "rECnAME: Full=Radical_SAMdomain-containing Protein {ECO:0000259 ¦ PFAM:PF04055};", XP055719258, retrieved from EBI accession No. Uniprot:A0A244CMP0, Database accession No. A0A244CMP0.
Database UniProt [Online] Apr. 12, 2017 (Apr. 12, 2017), retrieved from EBI accession No. Uniprot: A0A1H0NKS3 Database accession No. A0A1H0NKS3 the whole document.
Davies et al. "Plasmid-determined resistance to antimicrobial agents" Annual Reviews in Microbiology. Oct. 1978;32(1):469-508.
De Boer et al. "The tac promoter: a functional hybrid derived from the trp and lac promoters" Proceedings of the National Academy of Sciences. Jan. 1, 1983;80(1):21-5.
De Clercq et al. "Antiviral prodrugs—the development of successful prodrug strategies for antiviral chemotherapy" British journal of pharmacology. Jan. 2006;147(1):1-1.
Doron et al. "Systematic discovery of antiphage defense systems in the microbial pangenome" Science. Mar. 2, 2018;359(6379).
Dousson CB. "Current and future use of nucleo (s) tide prodrugs in the treatment of hepatitis C virus infection" Antiviral Chemistry and Chemotherapy. Feb. 2018;26:2040206618756430.
Drosu et al. "Tenofovir prodrugs potently inhibit Epstein-Barr virus lytic DNA replication by targeting the viral DNA polymerase" Proceedings of the National Academy of Sciences. Jun. 2, 2020;117(22):12368-74.
Fenwick et al. "Structural studies of viperin, an antiviral radical SAM enzyme" Proceedings of the National Academy of Sciences. Jun. 27, 2017;114(26):6806-11.
Fenwick "Structural basis of the substrate selectivity of viperin" Biochemistry. Jan. 9, 2020;59(5):652-62.
Fortier et al. "Phage production and maintenance of stocks, including expected stock lifetimes" In Bacteriophages 2009 (pp. 203-219). Humana Press.
GenBank: MN908947.3, Version 3, Mar. 18, 2020.
GenBank: AAH98387.1, Version 1, Sep. 23, 2014.
GenBank: NP_001332824.1, Version 1, Jan. 2, 2022.
Ghosh et al. "Viperin: An ancient radical SAM enzyme finds its place in modern cellular metabolism and innate immunity" Journal of Biological Chemistry. Aug. 14, 2020;295(33):11513-28.
Gilboa et al. "Transfer and expression of cloned genes using retroviral vectors" BioTechniques. 1986;4(6):504-12.
Gill et al. "Conserved retinoblastoma protein-binding motif in human cytomegalovirus UL97 kinase minimally impacts viral replication but affects susceptibility to maribavir" Virology Journal. Dec. 2009;6(1):1-5.
Gizzi et al. "A naturally occurring antiviral ribonucleotide encoded by the human genome" Nature. Jun. 2018;558(7711):610-4.
Goeddel et al. "Synthesis of human fibroblast interferon by *E. coli*" Nucleic Acids Research. Sep. 25, 1980;8(18):4057-74.
Goldfarb et al. "BREX is a novel phage resistance system widespread in microbial genomes" The EMBO journal. Jan. 14, 2015;34(2):169-83.
Hartline et al. "A standardized approach to the evaluation of antivirals against DNA viruses: Orthopox-, adeno-, and herpesviruses" Antiviral research. Nov. 1, 2018;159:104-12.
Honarmand et al. "Mechanism of diol dehydration by a promiscuous radical-SAM enzyme homologue of the antiviral enzyme viperin (RSAD2)" ChemBioChem. Jun. 2, 2020;21(11): 1605-12.
Jordheim et al. "Advances in the development of nucleoside and nucleotide analogues for cancer and viral diseases" Nature reviews Drug discovery. Jun. 2013;12(6):447-64.
Keith et al. "A standardized approach to the evaluation of antivirals against DNA viruses: Polyomaviruses and lymphotropic herpesviruses" Antiviral research. Nov. 1, 2018:159:122-9.
Makarova et al. "Defense islands in bacterial and archaeal genomes and prediction of novel defense systems" Journal of bacteriology. Nov. 1, 2011;193(21):6039-56.
NCBI Accession No. NP_542388.2 Version 2, Mar. 15, 2015.
NCBI Accession No. AF442151.1 Version 1, Mar. 11, 2011.
NCBI Accession No. NP_620236.1 Version 1, Jul. 3, 2021.
NCBI Accession No. NP_067359.2 Version 2, Jun. 22, 2021.
NCBI Accession No. NP_001020727.1 Version 1, Aug. 8, 2021.
Ofir et al. "Disarm is a widespread bacterial defence system with broad anti-phage activities" Nature microbiology. Jan. 2018;3(1):90-8.
Prichard et al. "Activity and mechanism of action of N-methanocarbathymidine against herpesvirus and orthopoxvirus infections" Antimicrobial agents and chemotherapy. Apr. 2006;50(4):1336-41.
Prichard et al. Benzimidazole analogs inhibit human herpesvirus 6 Antimicrobial agents and chemotherapy. May 2011;55(5):2442-5.
Raibaud et al. "Positive control of transcription initiation in bacteria" Annual review of genetics. Dec. 1984;18(1):173-230.
Ray et al. "Tenofovir alafenamide: a novel prodrug of tenofovir for the treatment of human immunodeficiency virus" Antiviral research. Jan. 1, 2016;125:63-70.
Santamaria-Araujo et al. "The tetrahydropyranopterin structure of the sulfur-free and metal-free molybdenum cofactor precursor" Journal of Biological Chemistry. Apr. 16, 2004;279(16):15994-9.
Seley-Radtke et al. "The evolution of nucleoside analogue antivirals: A review for chemists and non-chemists. Part 1: Early structural modifications to the nucleoside scaffold" Antiviral research. Jun. 1, 2018;154:66-86.
Seo et al. "Viperin: a multifunctional, interferon-inducible protein that regulates virus replication" Cell host & microbe. Dec. 15, 2011;10(6):534-9.
Shimatake et al. "Purified A regulatory protein c II positively activates promoters for lysogenic development" Nature. Jul. 1981;292(5819):128-32.
Shomar Monges H. "*Producing high-value chemicals in Escherichia coli through synthetic biology and metabolic Engineering*" (Doctoral dissertation, Delft University of Technology), published Mar. 28, 2019.
Studier et al. "Use of bacteriophage T7 RNA polymerase to direct selective high-level expression of cloned genes" Journal of molecular biology. May 5, 1986;189(1):113-30.

(56) References Cited

OTHER PUBLICATIONS

Swarts et al. “DNA-guided DNA interference by a prokaryotic Argonaute” Nature. Mar. 2014;507(7491):258-61.
Tabor et al. “A bacteriophage T7 Rna polymerase/promoter system for controlled exclusive expression of specific genes” Proc. Natl. Acad. Sci. USA. 1985;82:1074-8.
Thiem et al. “Preparative-enzymatic formation of cytidine 5'-monophosphosialate by integrated cytidine 5'-triphosphate regeneration” Liebigs Annalen der Chemie. Nov. 12, 1990;1990(11):1101-5.
Thomson et al. “Nucleoside analogues as antibacterial agents” Frontiers in microbiology. May 22, 2019;10:952.
Yelverton et al. “Bacterial synthesis of a novel human leukocyte interferon” Nucleic acids research. Feb. 11, 1981;9(3):731-41.
Zabala et al. “Optimization of the Tet-on system to regulate interleukin 12 expression in the liver for the treatment of hepatic tumors” Cancer research. Apr. 15, 2004;64(8):2799-804.
Zhang et al. “Design and synthesis of dipeptidyl glutaminyl fluoromethyl ketones as potent severe acute respiratory syndrome coronovirus (SARS-CoV) inhibitors” Journal of medicinal chemistry. Feb. 9, 2006;49(3):1198-201.
Zheng et al. “Assembly of iron-sulfur clusters: identification of an iscSUA-hscBA-fdx gene cluster from Azotobacter vinelandii” Journal of Biological Chemistry. May 22, 1998;273(21):13264-72.
Balzarini et al. “Conversion of 2', 3'-dideoxyadenosine (ddA) and 2', 3'-didehydro-2', 3'-dideoxyadenosine (d4A) to their corresponding aryloxyphosphoramidate derivatives markedl potentiates their activity against human immunodeficiency virus and hepatitis B virus” FEBS letters. Jun. 30, 1997;410(2-3):324-8.
Gao et al. “Efficacies of B-L-D4A against hepatitis B virus in 2.2. 15 cells” World Journal of Gastroenterology: WJG. Feb. 2, 2008;14(8):1263.
International Search Report for PCT Application No. PCT/IB21/57599 dated Feb. 14, 2022.
International Search Report for PCT Application No. PCT/IL2022/050395 dated Jul. 8, 2022.
Pubchem 3',4'-Didehydro-3'-deoxyadenosine. SID 274859250. Pubchem Entry (online). National Center for Biotechnology Information. Nov. 21, 2016 [retrieved on Nov. 4, 2021], Retrieved from the Internet: [URL: https://pubchem.ncbi.ntm.nih.gov/substance/274859250].
Pubchem 5-[(2S)-3,4-dihydroxy-5-(hydroxymethyl)-2,3-dihydrofuran-2-yl]-1H-pyrimidine-2,4-dione J C9H10N2O6—PubChem, Pubchem,Dec. 7, 2019 (Dec. 7, 2019), pp. 1-8, XP055935068, Retrieved from the Internet: URL:https://pubchem.ncbi.nlm.nih.gov/compound/144647520#section-[retrieved on Jun. 24, 2022] abstract.
Pubchem 5-[(2S)-3,4-dihydroxy-5-(hydroxymethyl)-2,3-dihydrofuran-2-yl]-IH-pyrimidin-I-ium-2,4-dionel C9H 11N2O6+—PubChem, Pubchem, Dec. 7, 2019 (Dec. 7, 2019), pp. 1-8,XP055935067, Retrieved from the Internet: URL:https://pubchem.ncbi.nlm.nih.gov/compound/144647519[retrieved on Jun. 24, 2022] abstract.
Supplementary European Search Report for European Application No. EP 21857883 dated Aug. 6, 2024.

MoaA pVip6 pVip12 pVip19 pVip27 pVip39 pVip34 pVip47 pVip60 pVip8 pVip62 pVip63

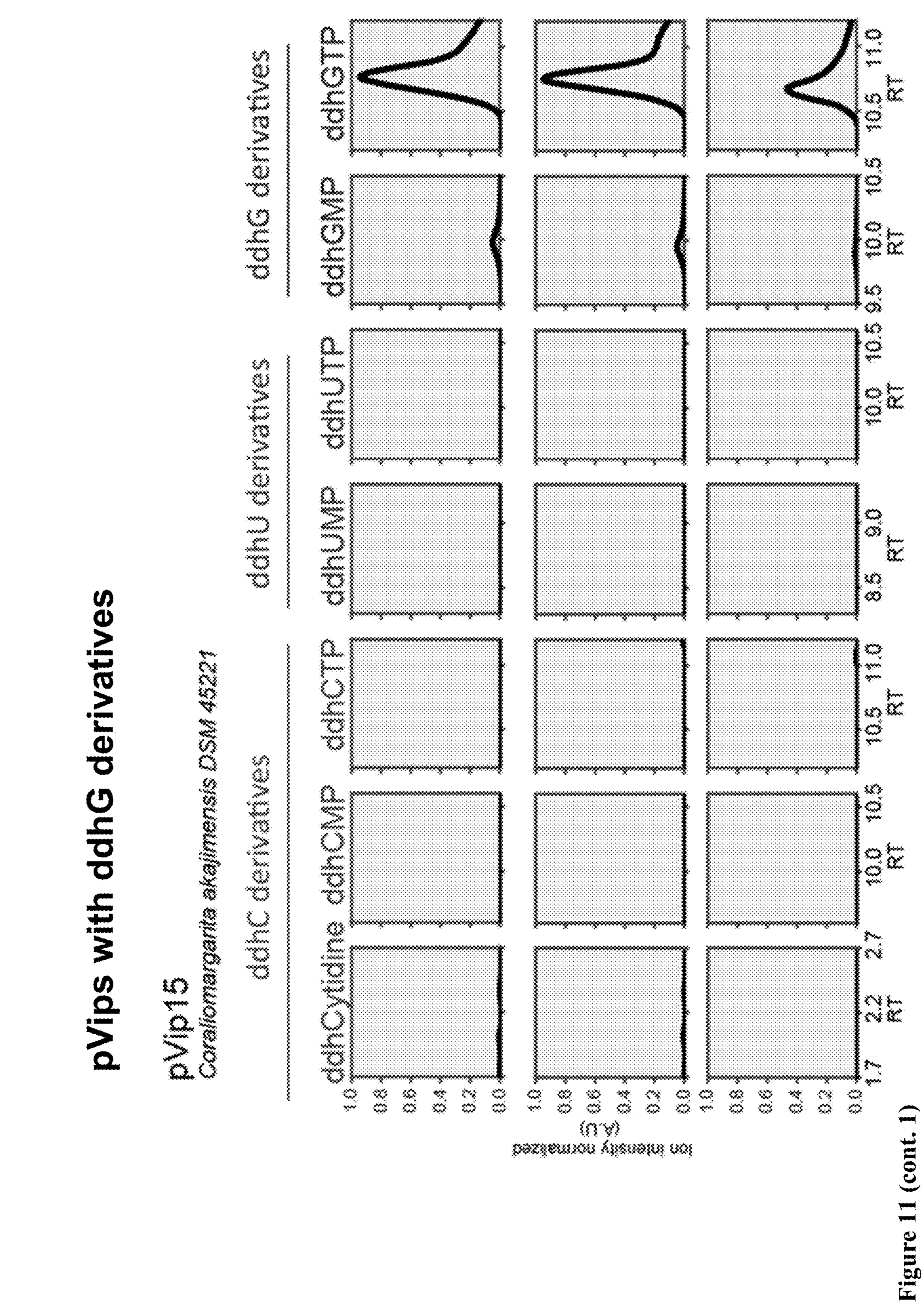
Figure 11 (cont. 1)

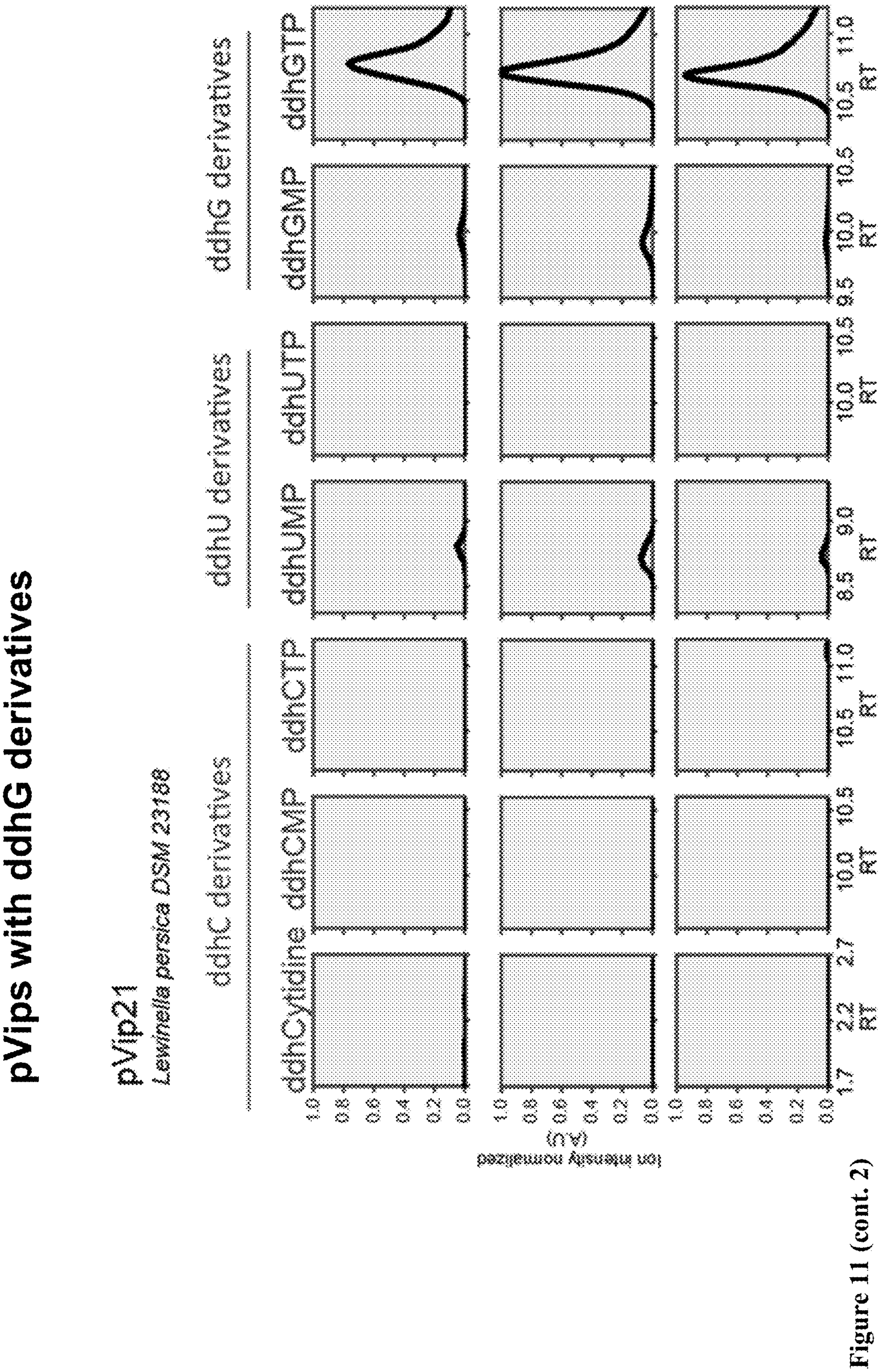
Figure 11 (cont. 2)

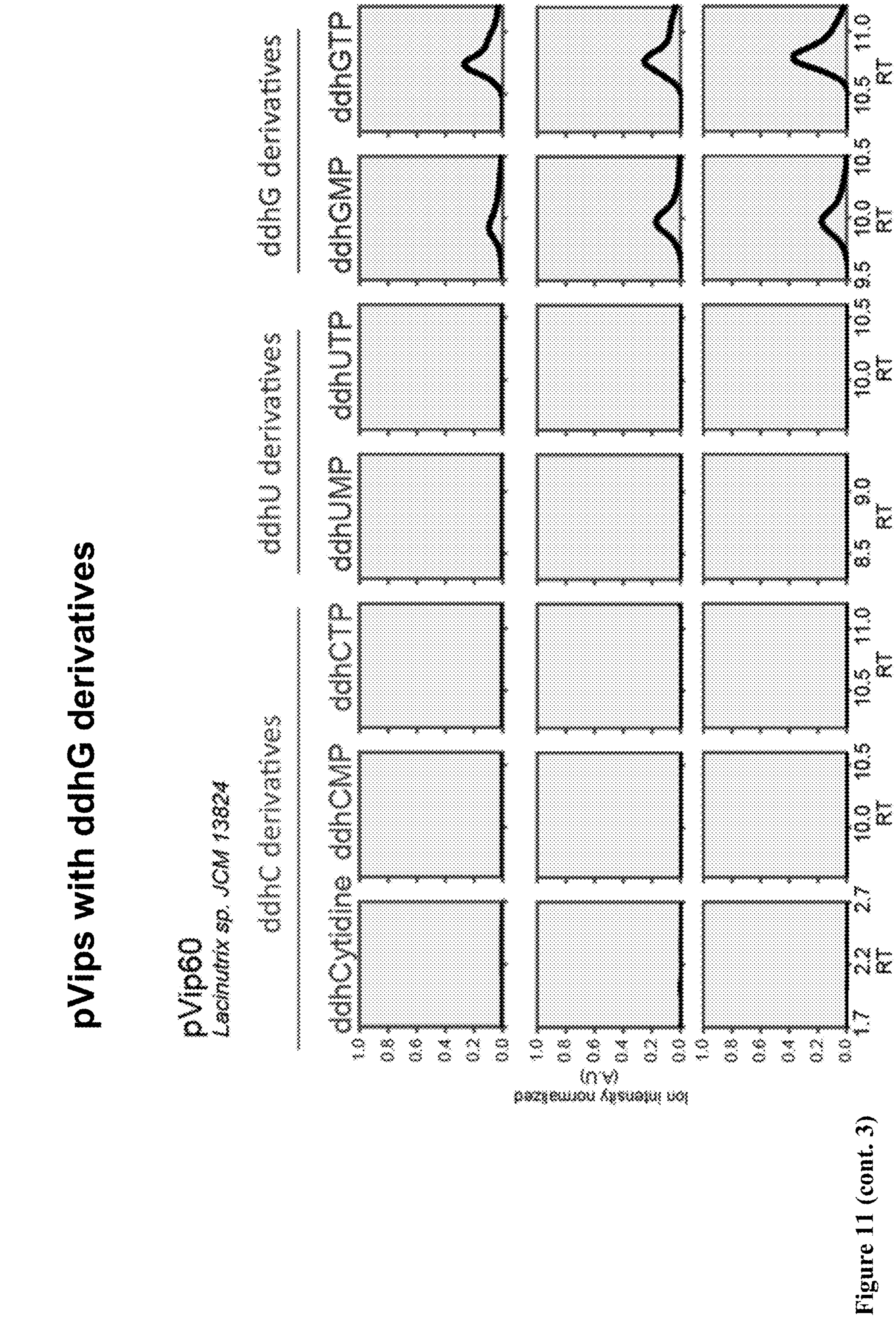
Figure 11 (cont. 3)

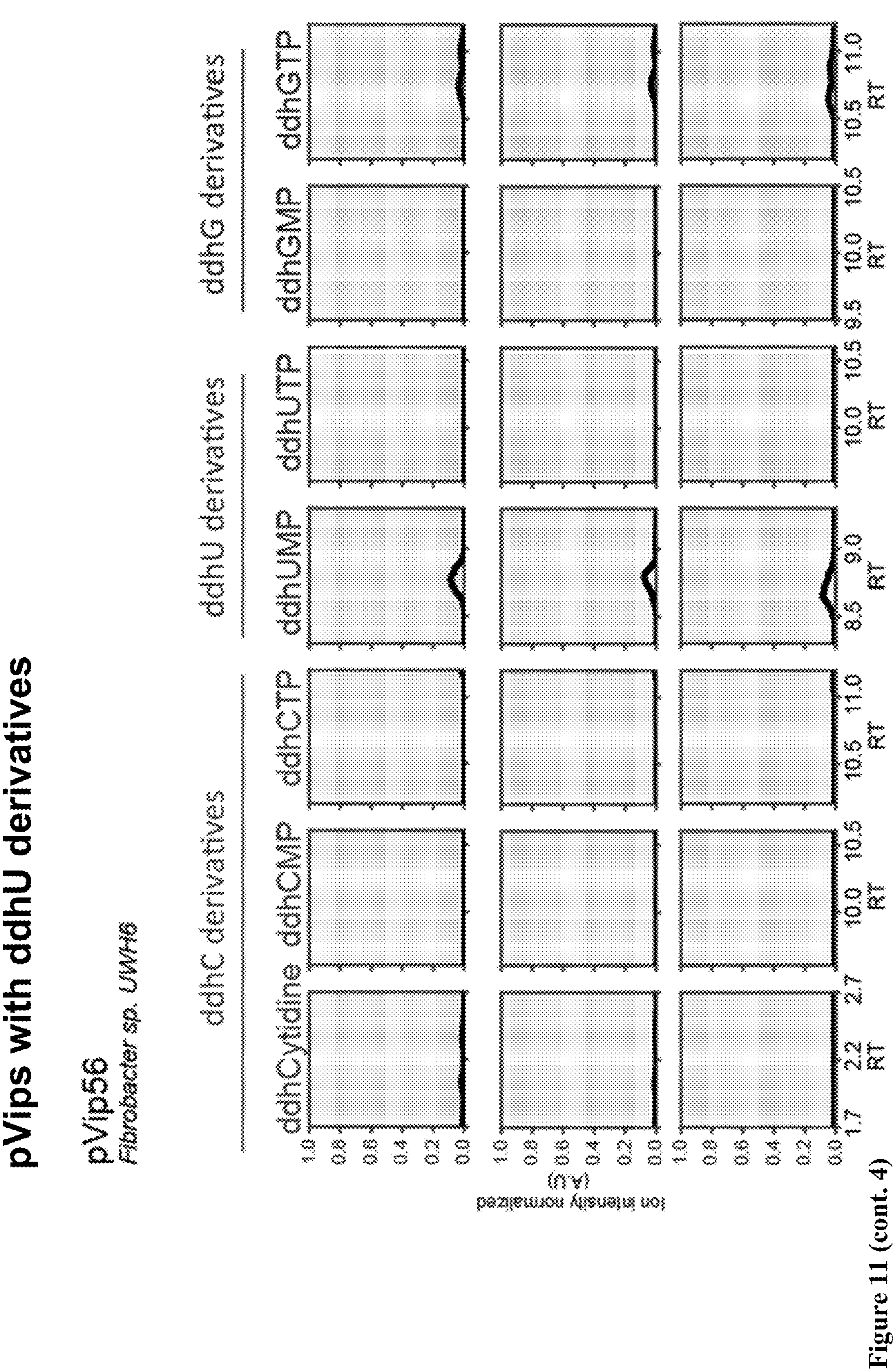
Figure 11 (cont. 4)

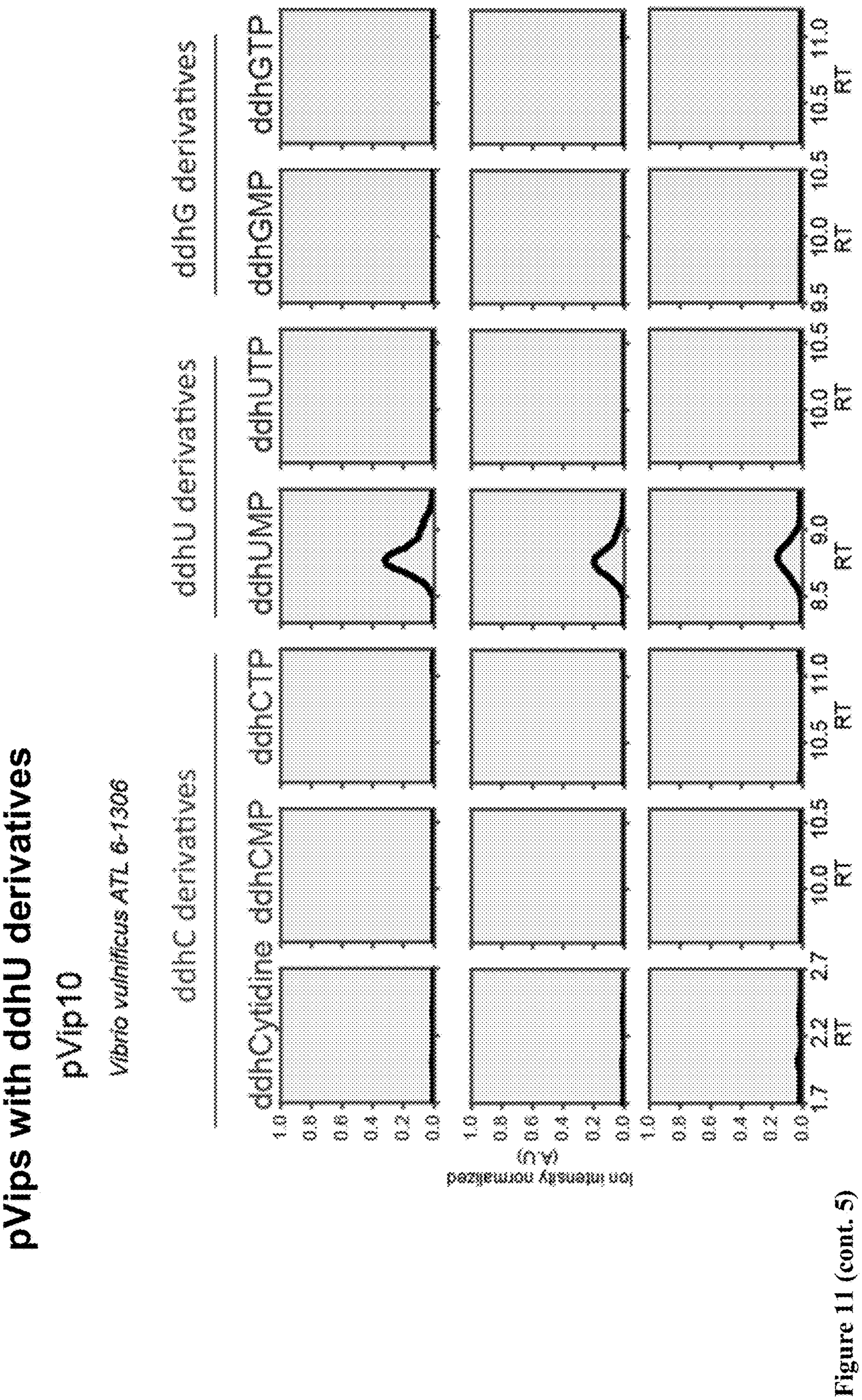
Figure 11 (cont. 5)

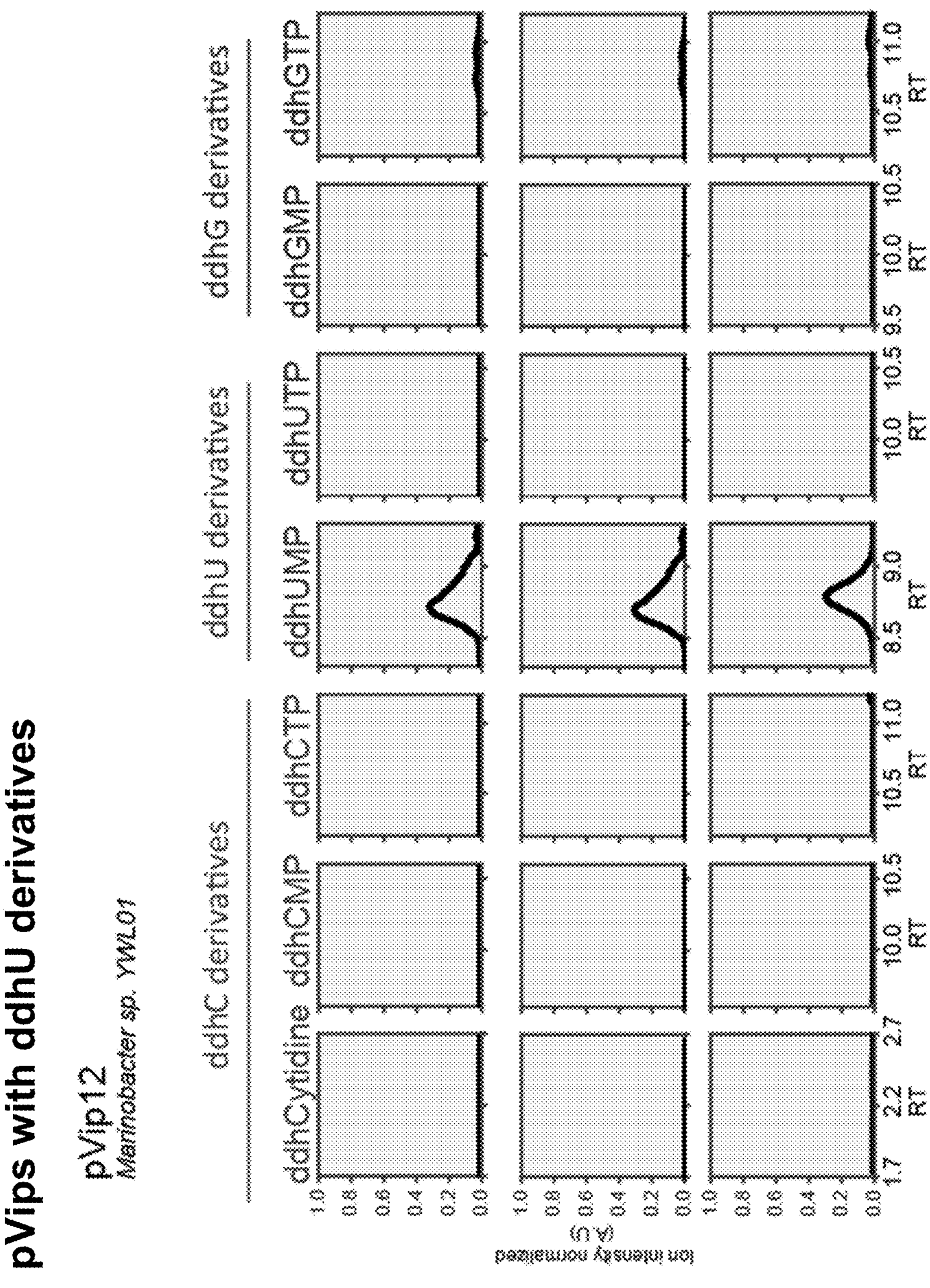
Figure 11 (cont. 6)

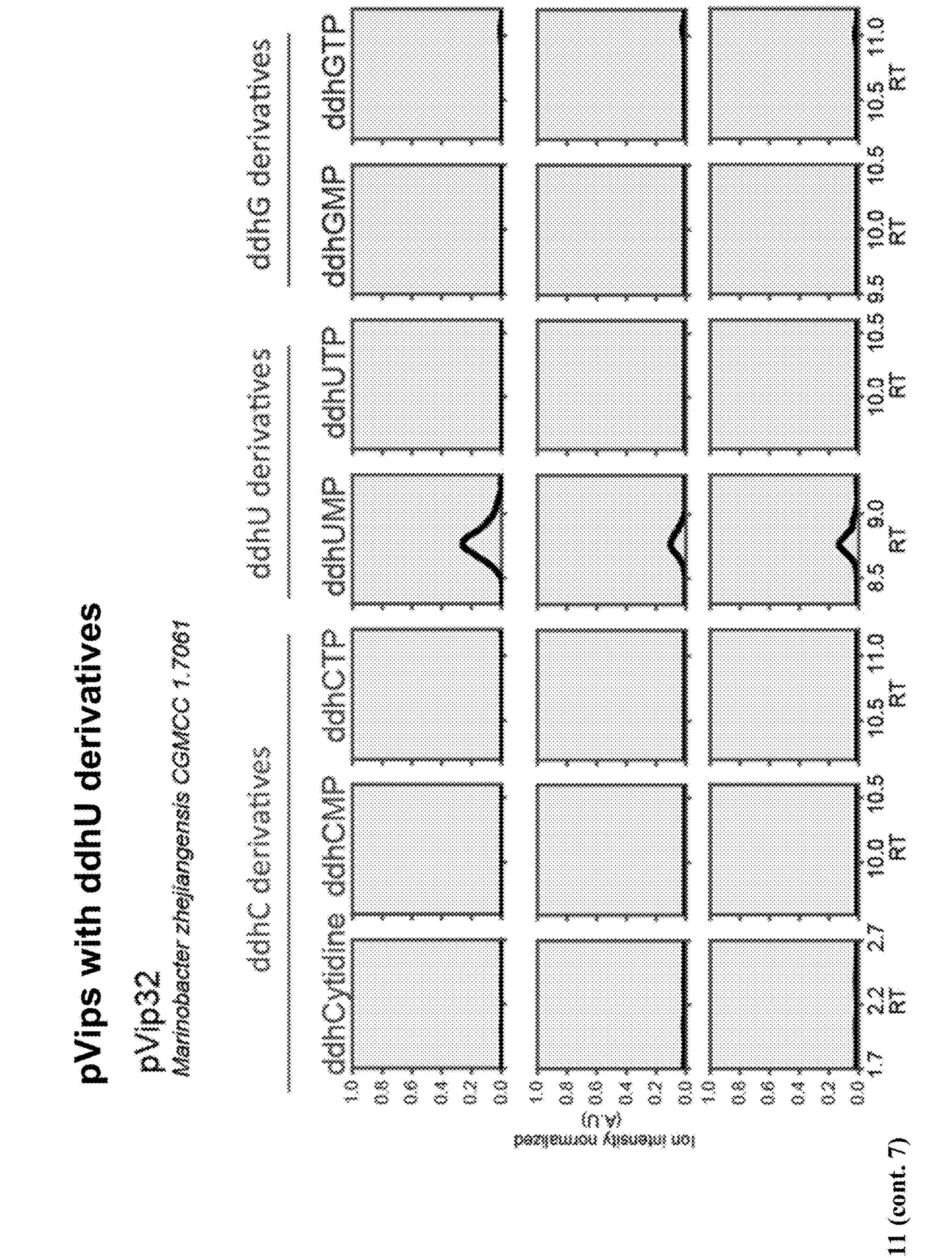
Figure 11 (cont. 7)

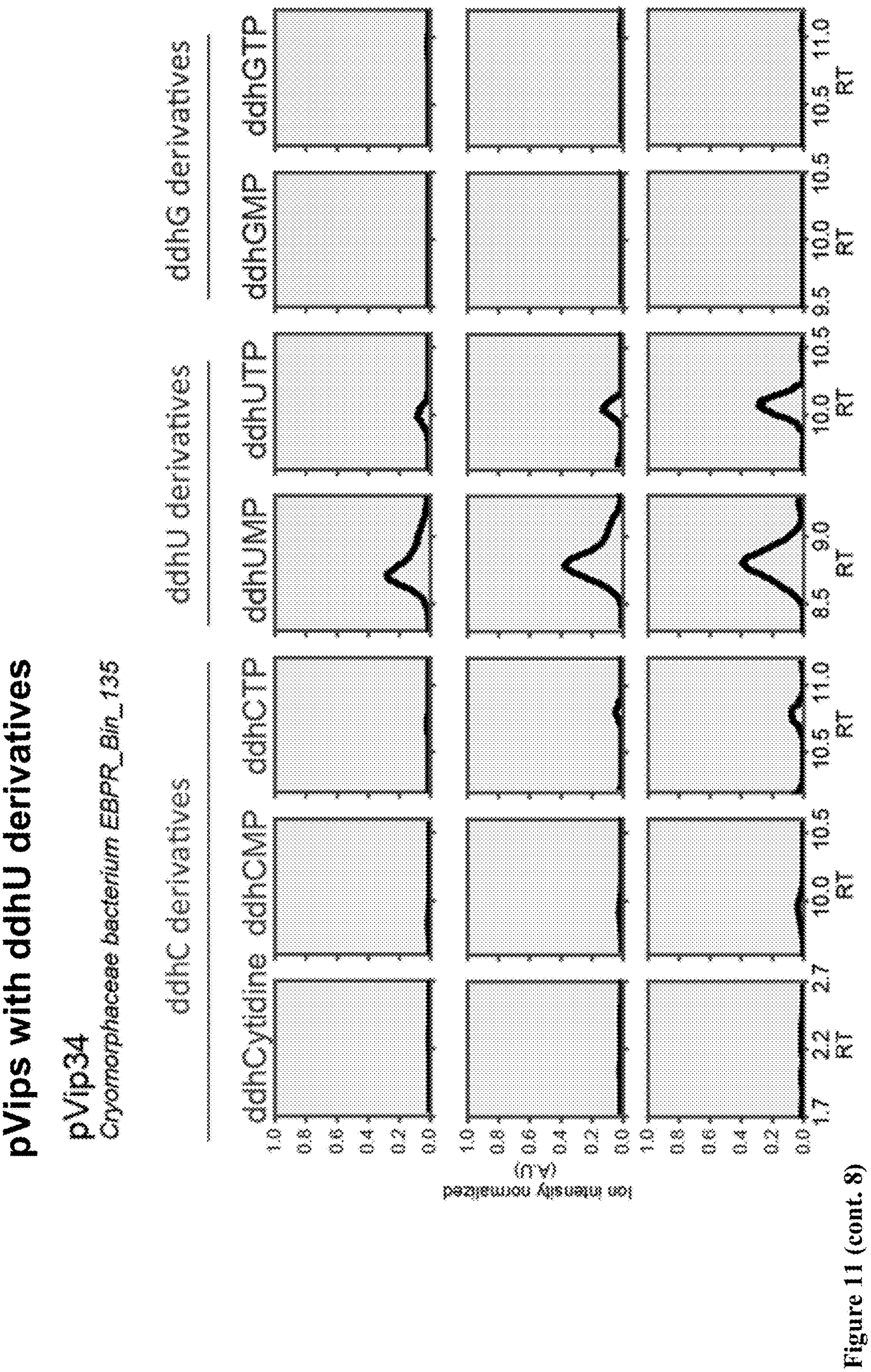
Figure 11 (cont. 8)

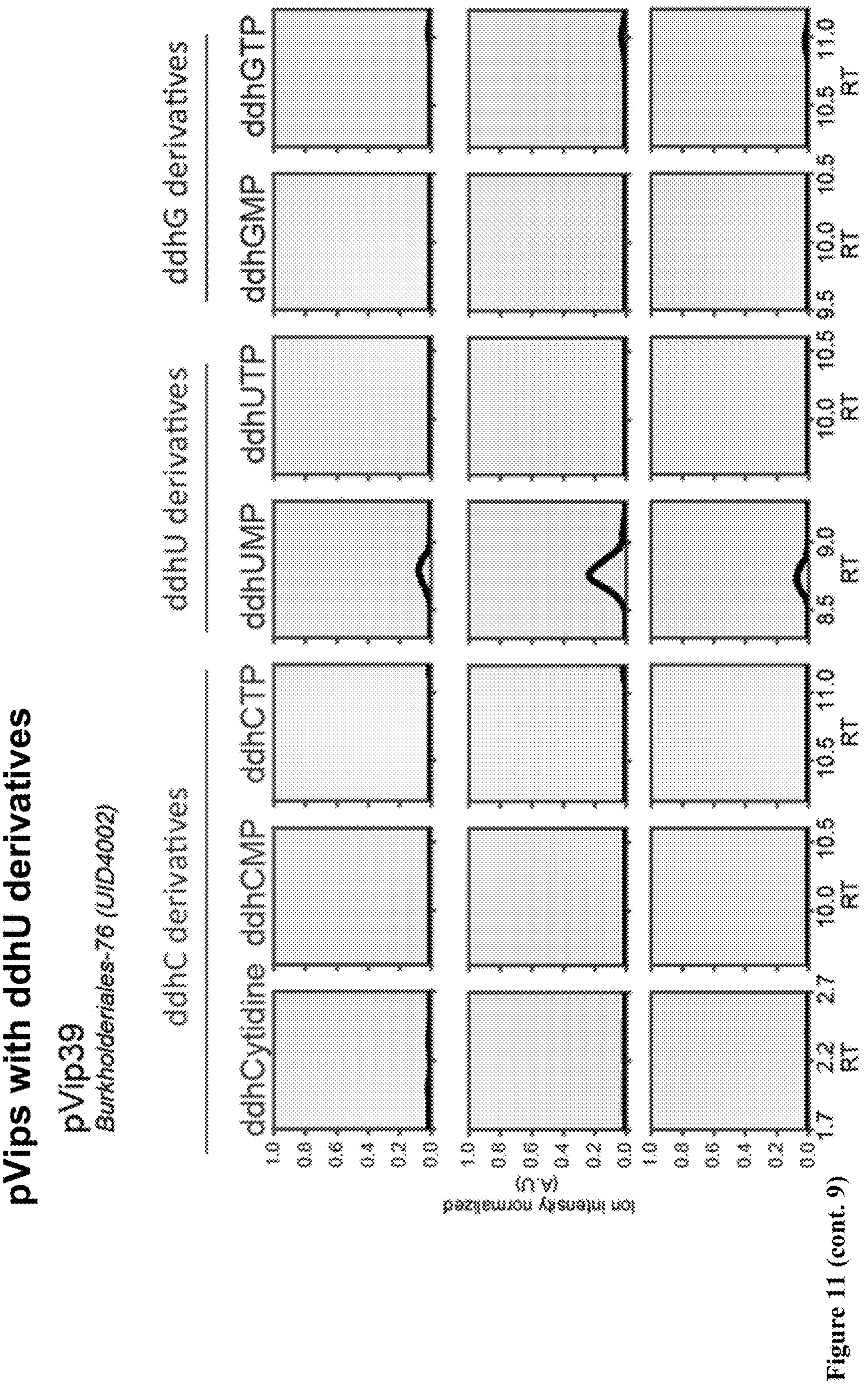
Figure 11 (cont. 9)

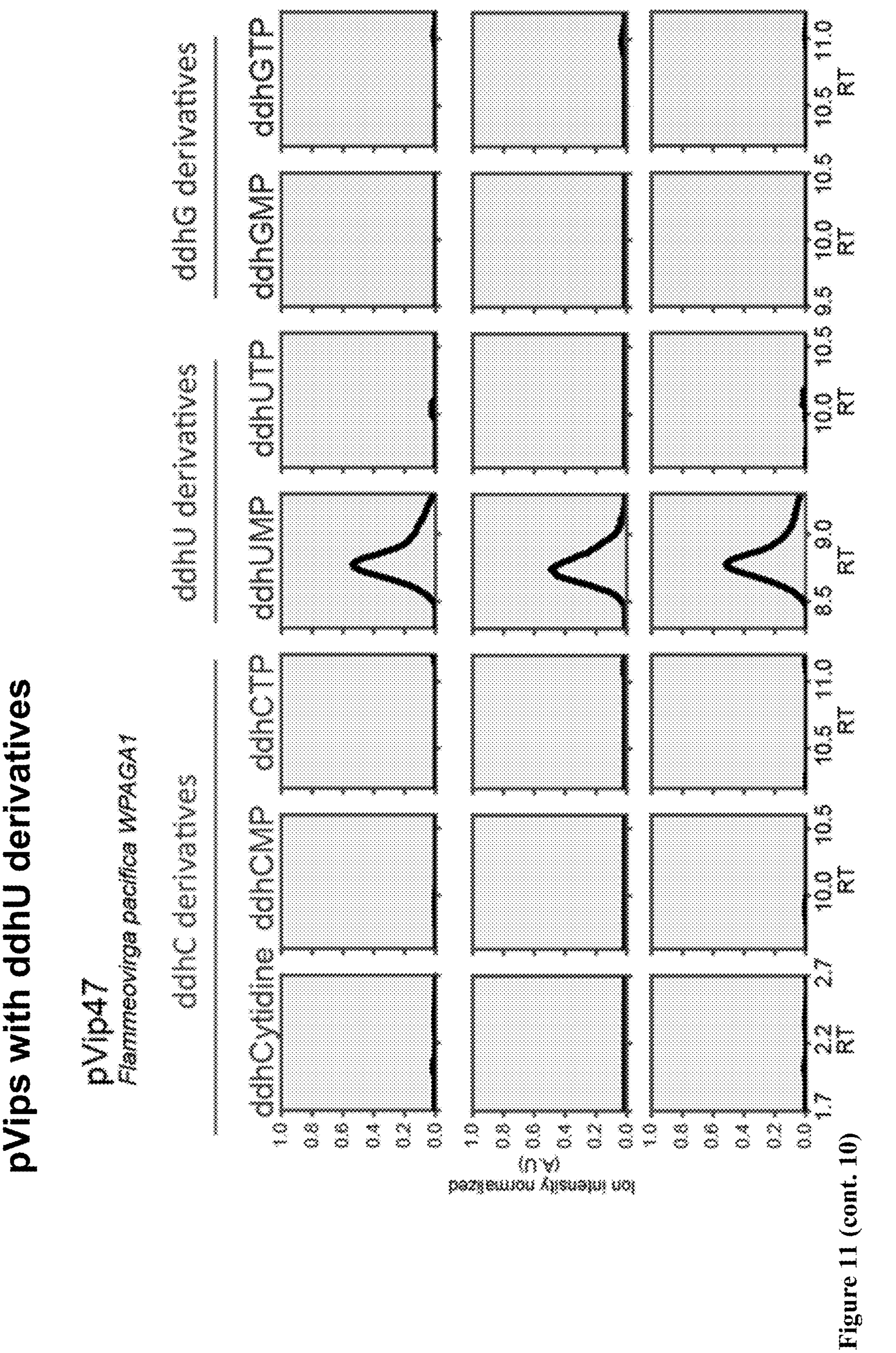
Figure 11 (cont. 10)

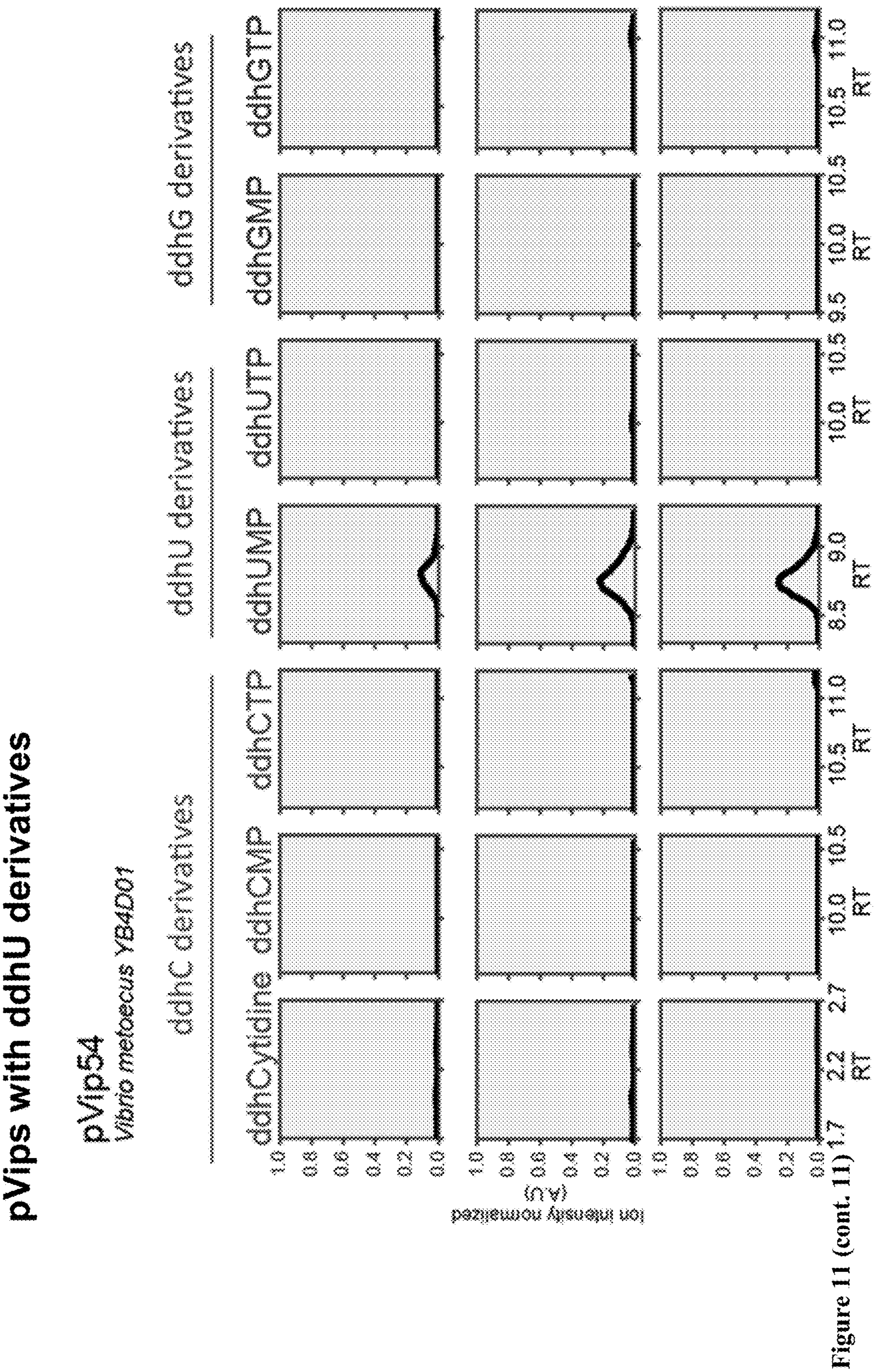
Figure 11 (cont. 11)

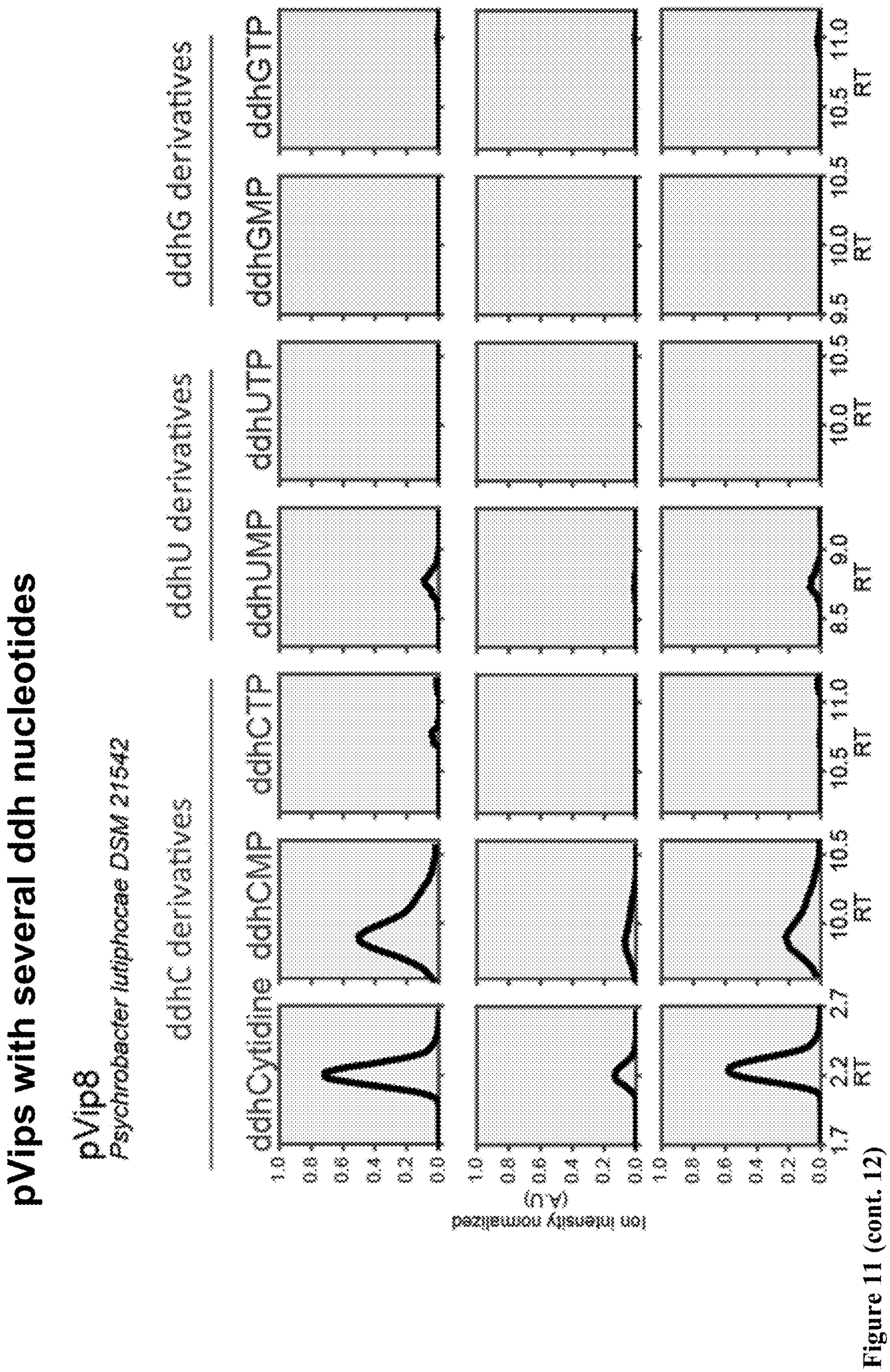
Figure 11 (cont. 12)

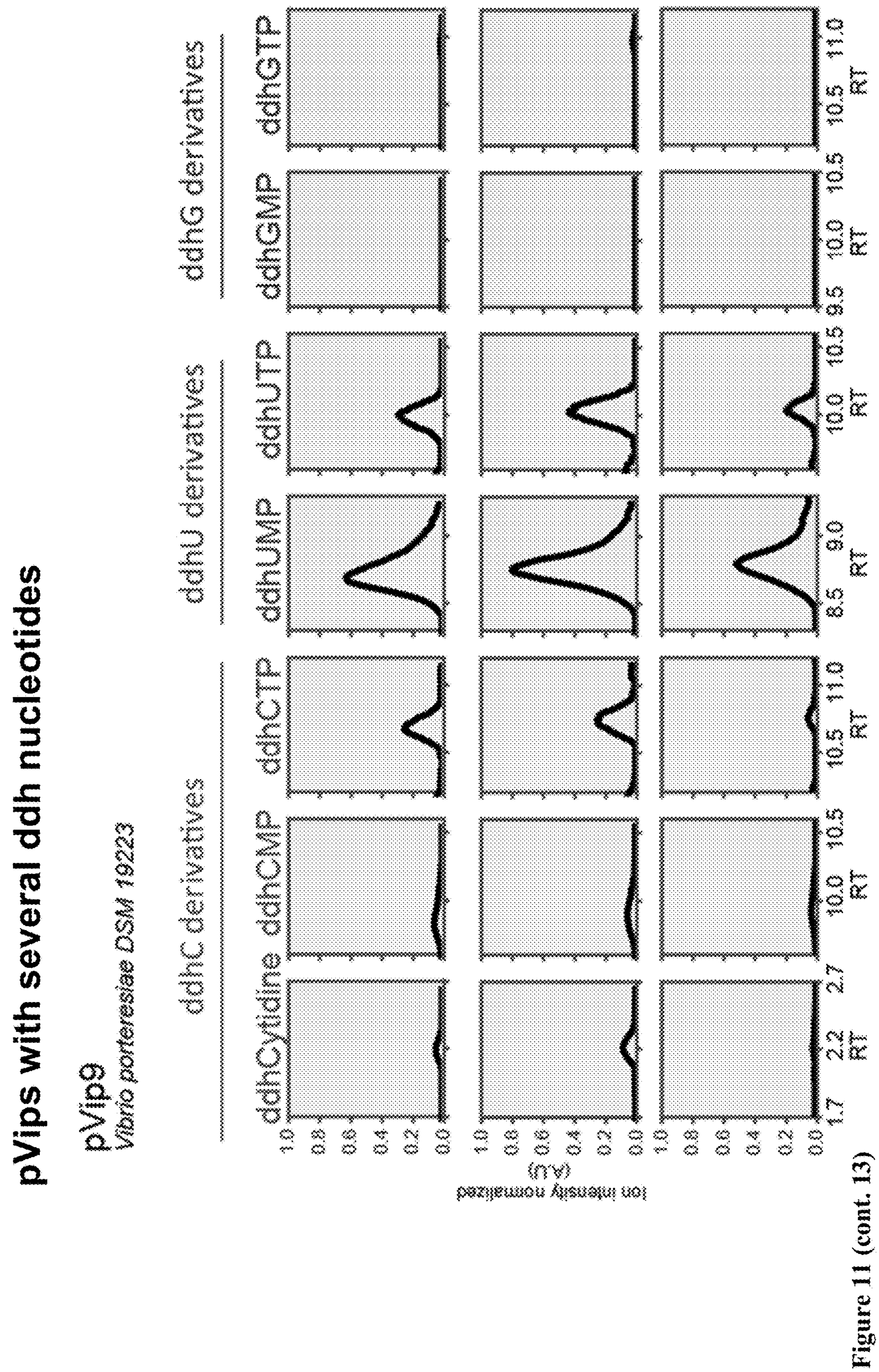
Figure 11 (cont. 13)

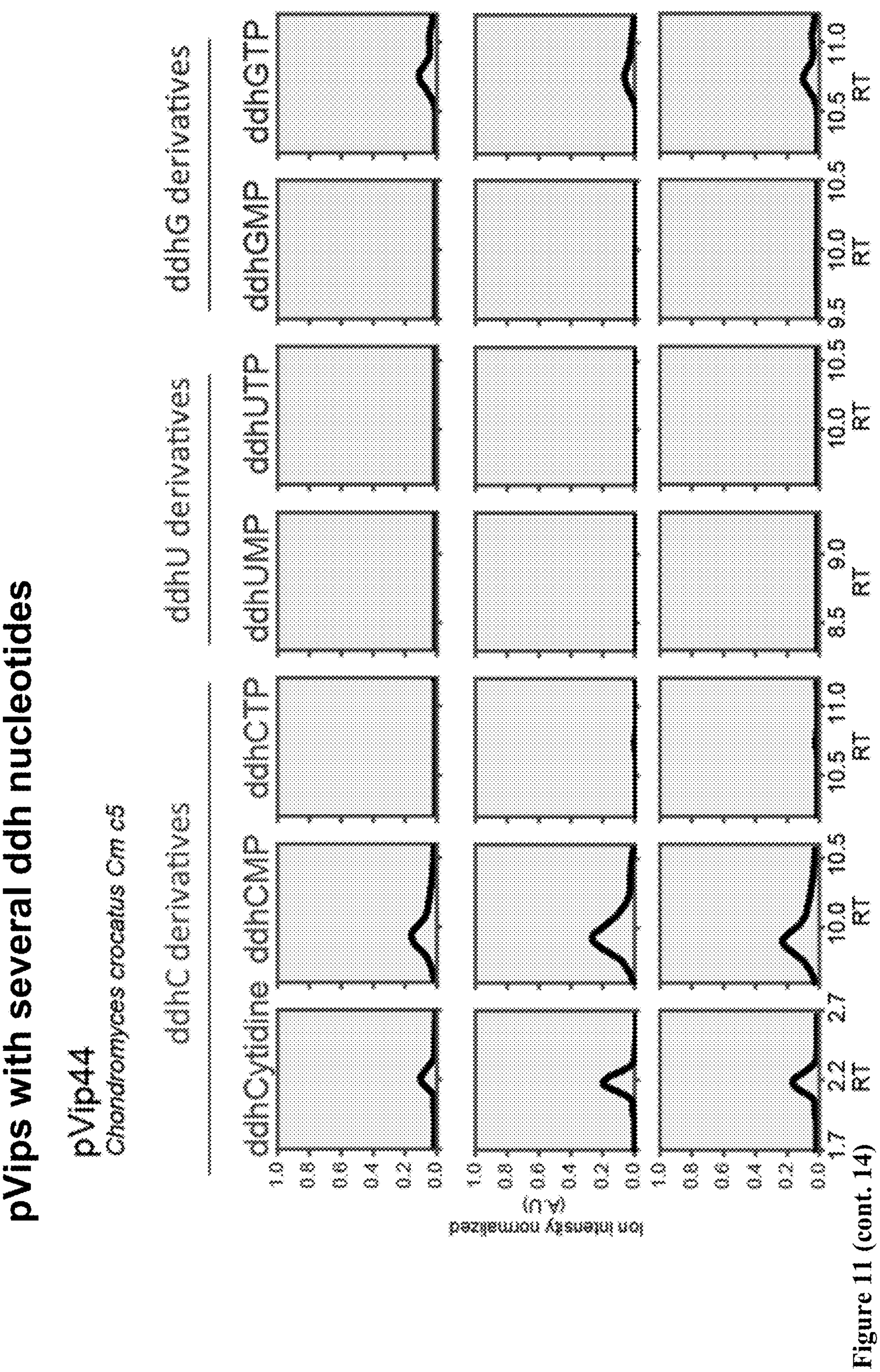
Figure 11 (cont. 14)

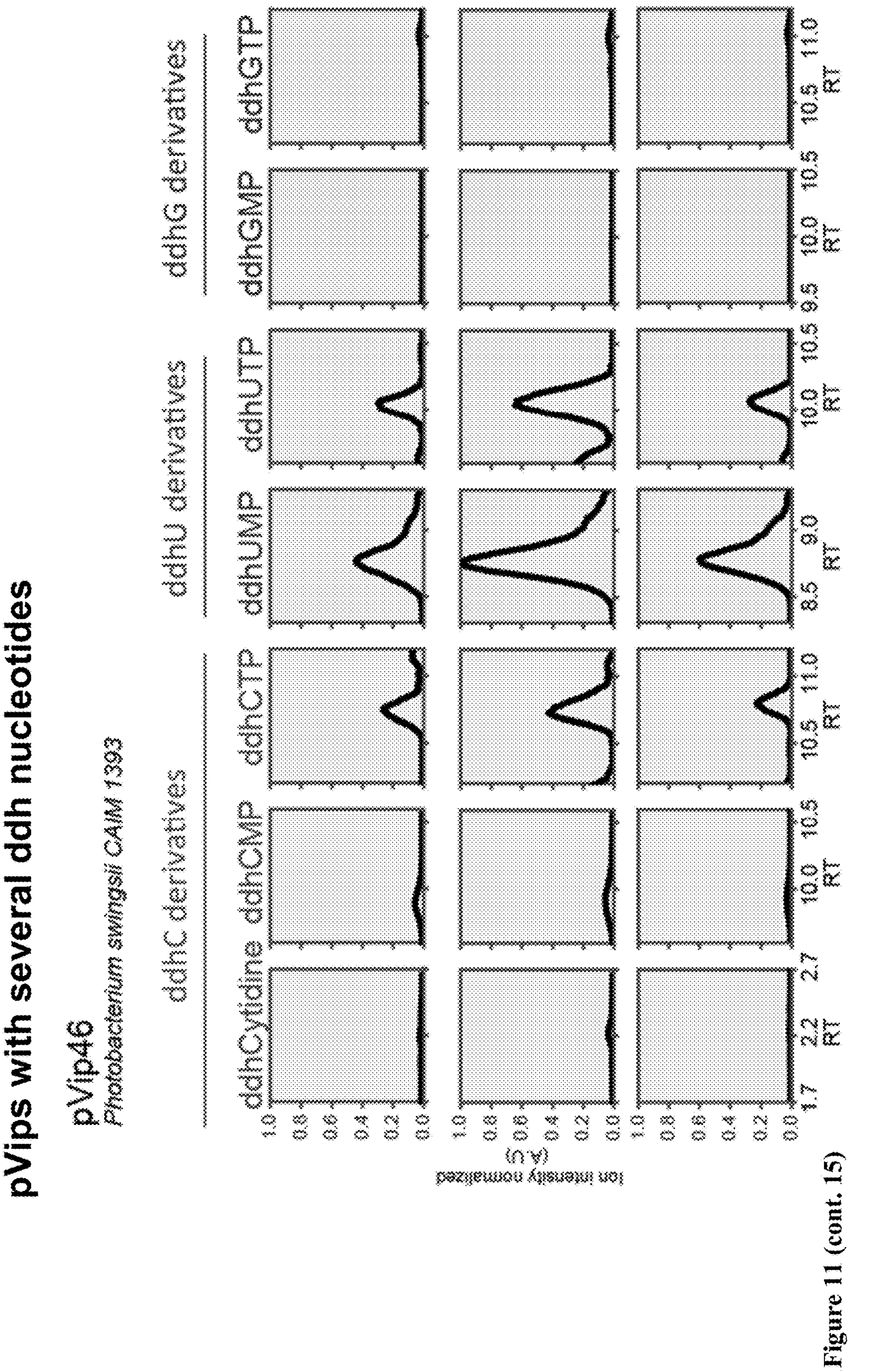
Figure 11 (cont. 15)

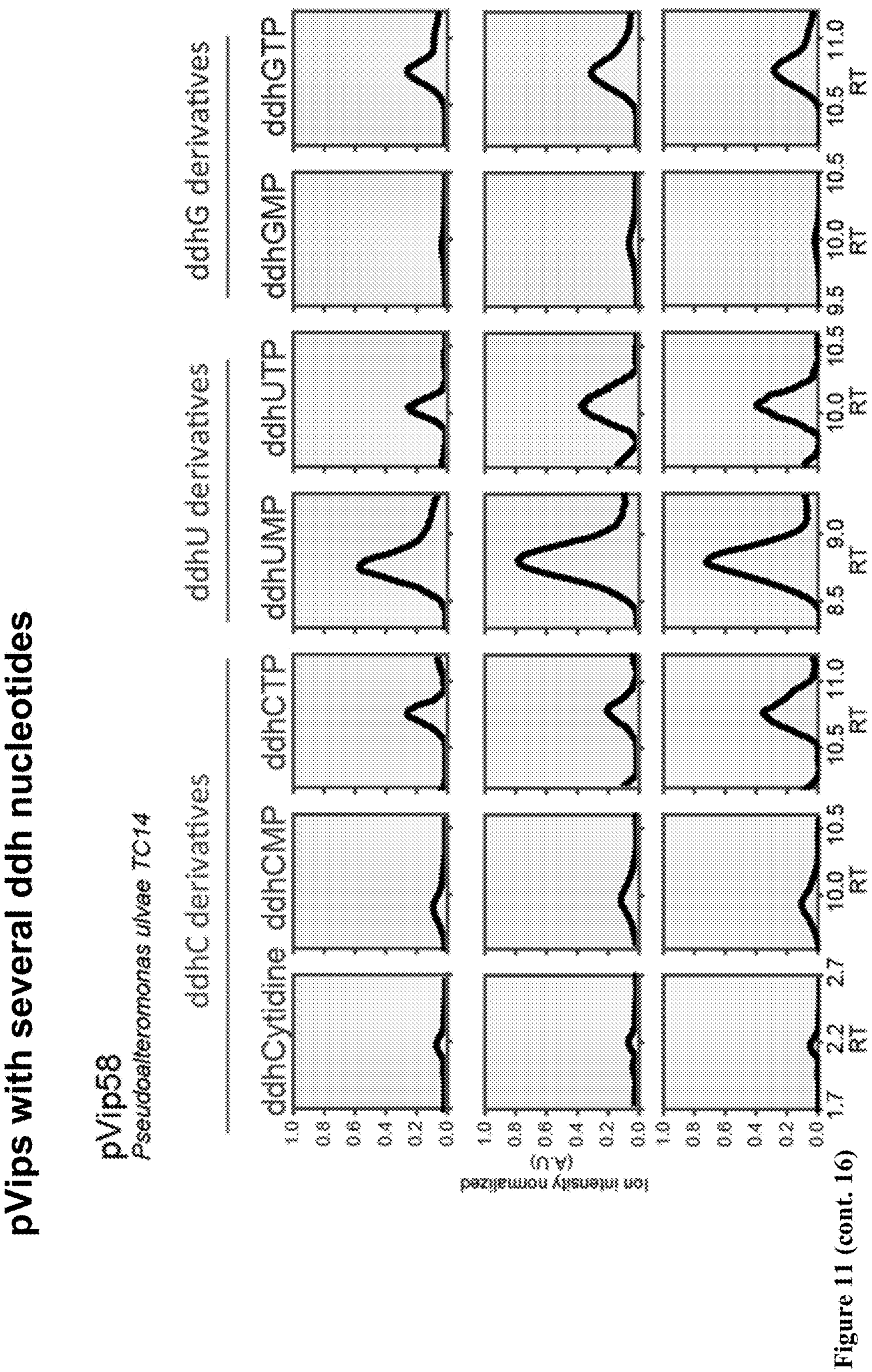
Figure 11 (cont. 16)

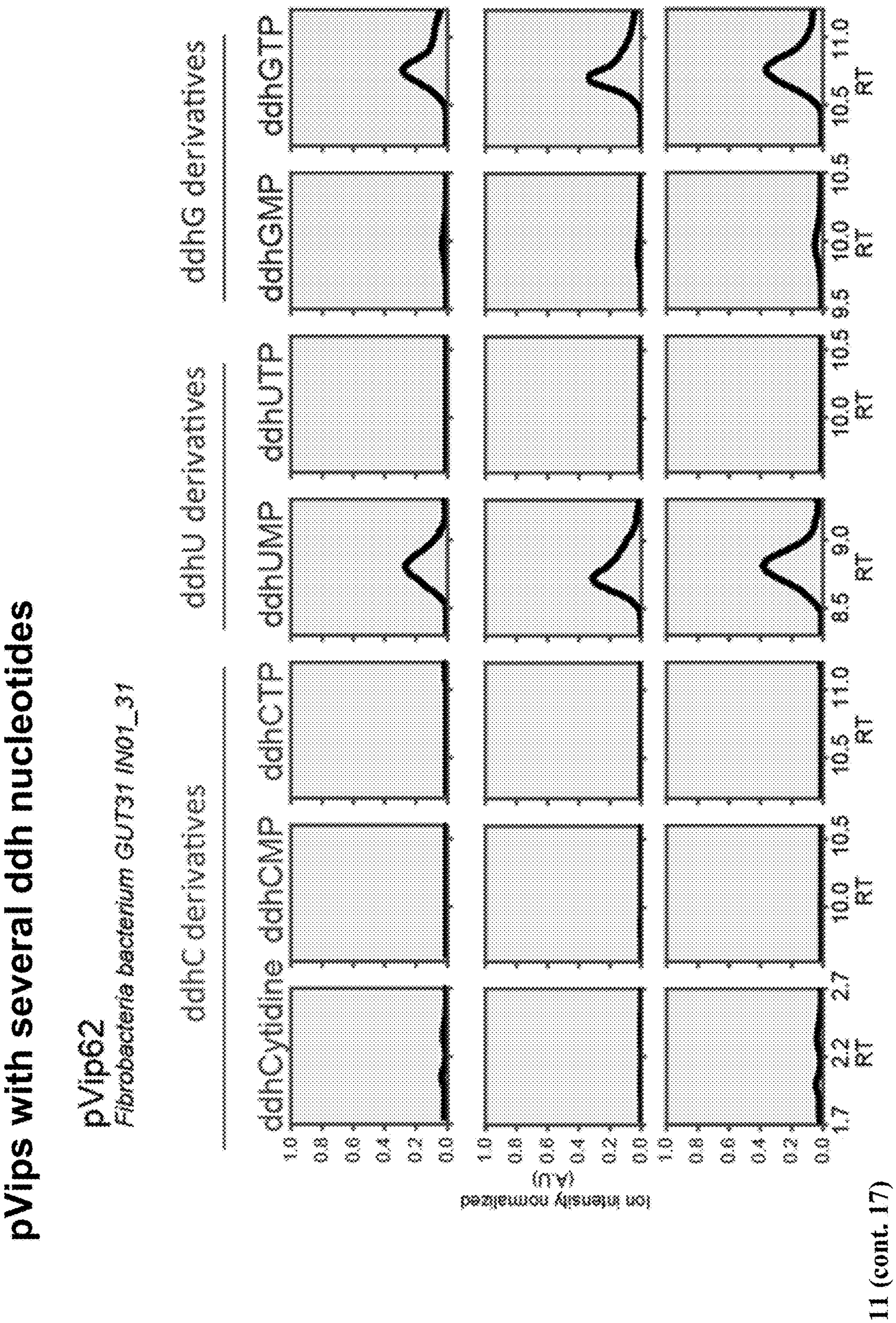
Figure 11 (cont. 17)

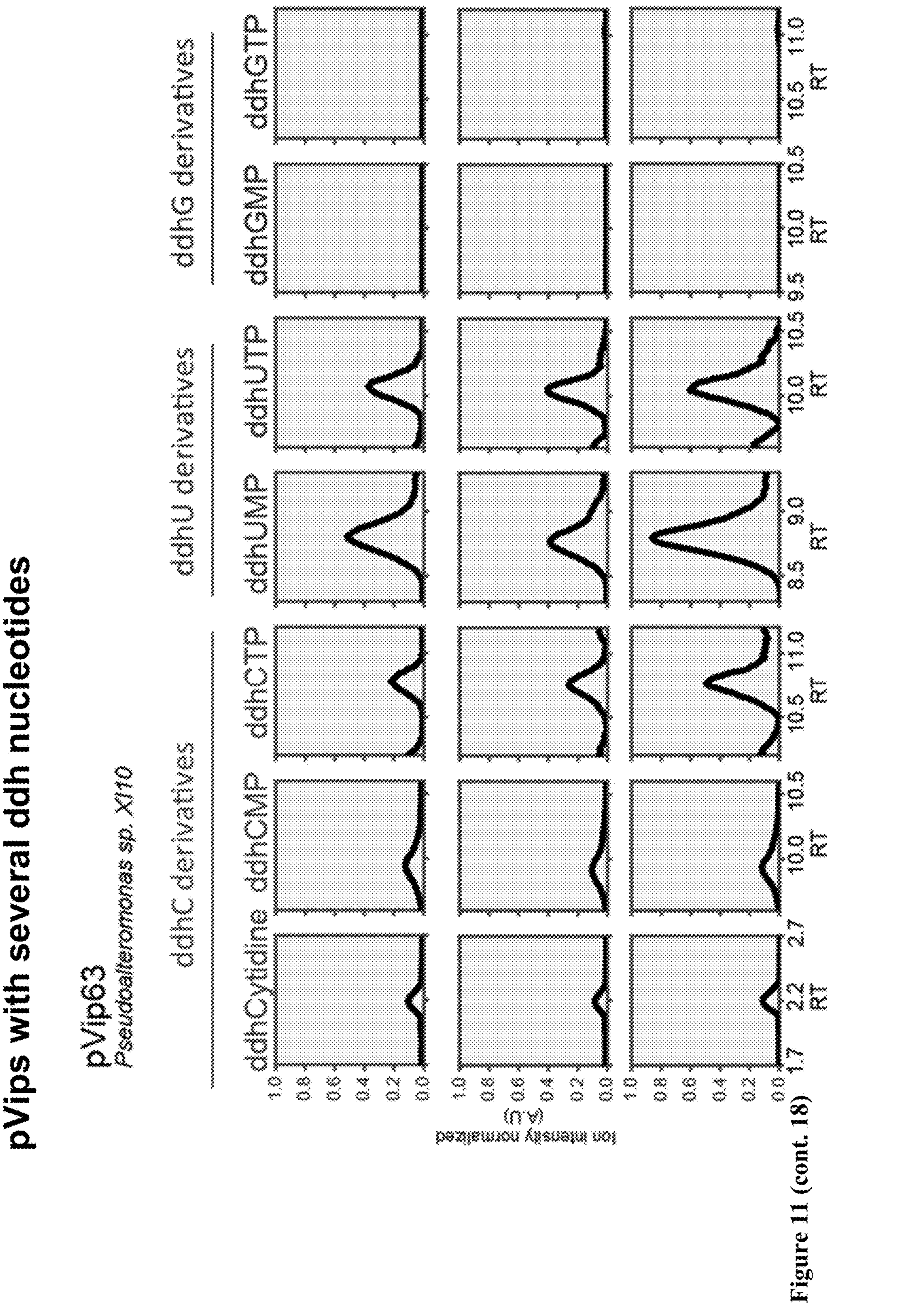
Figure 11 (cont. 18)

pVips with no detected ddh nucleotides
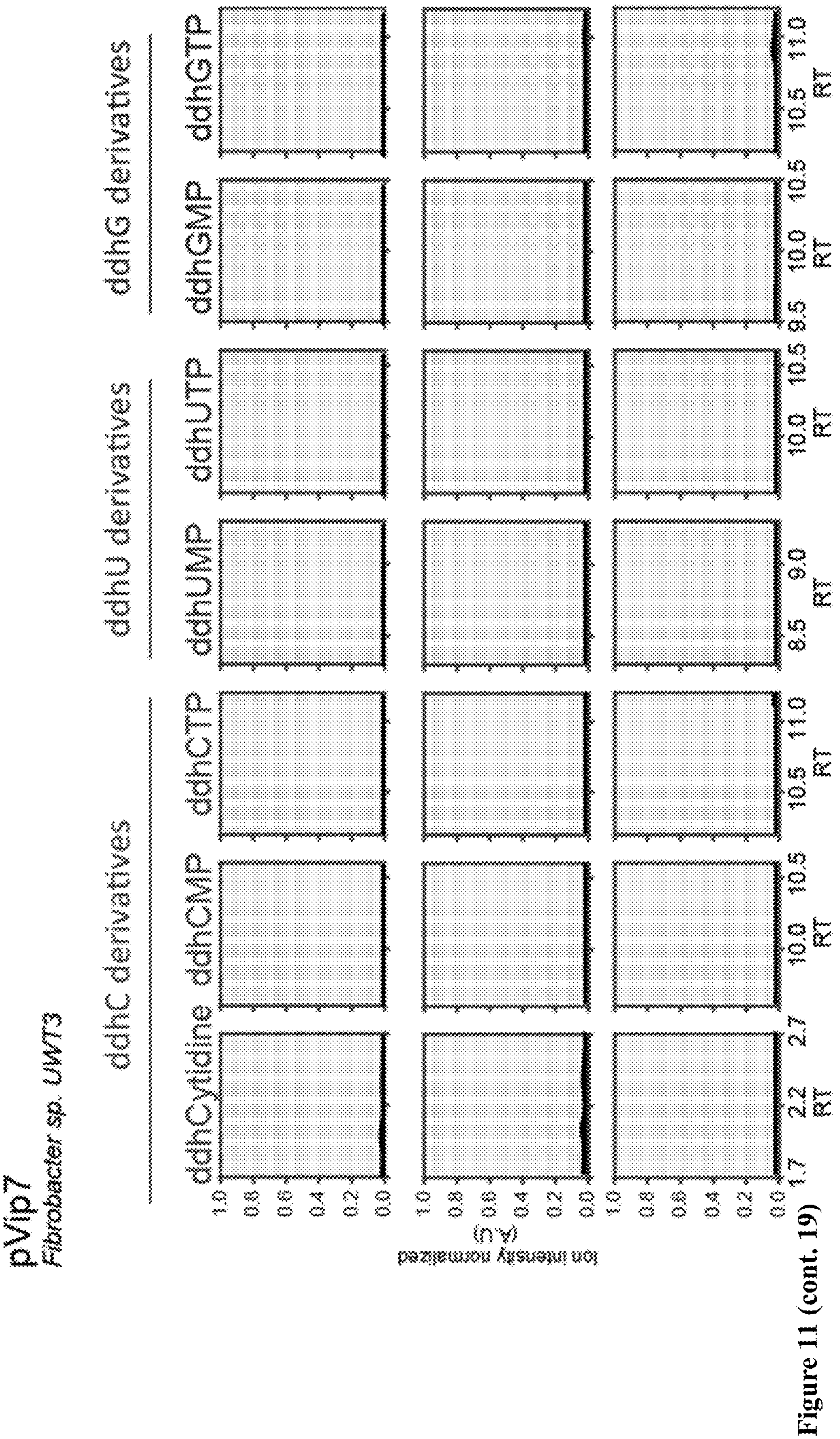
Figure 11 (cont. 19)

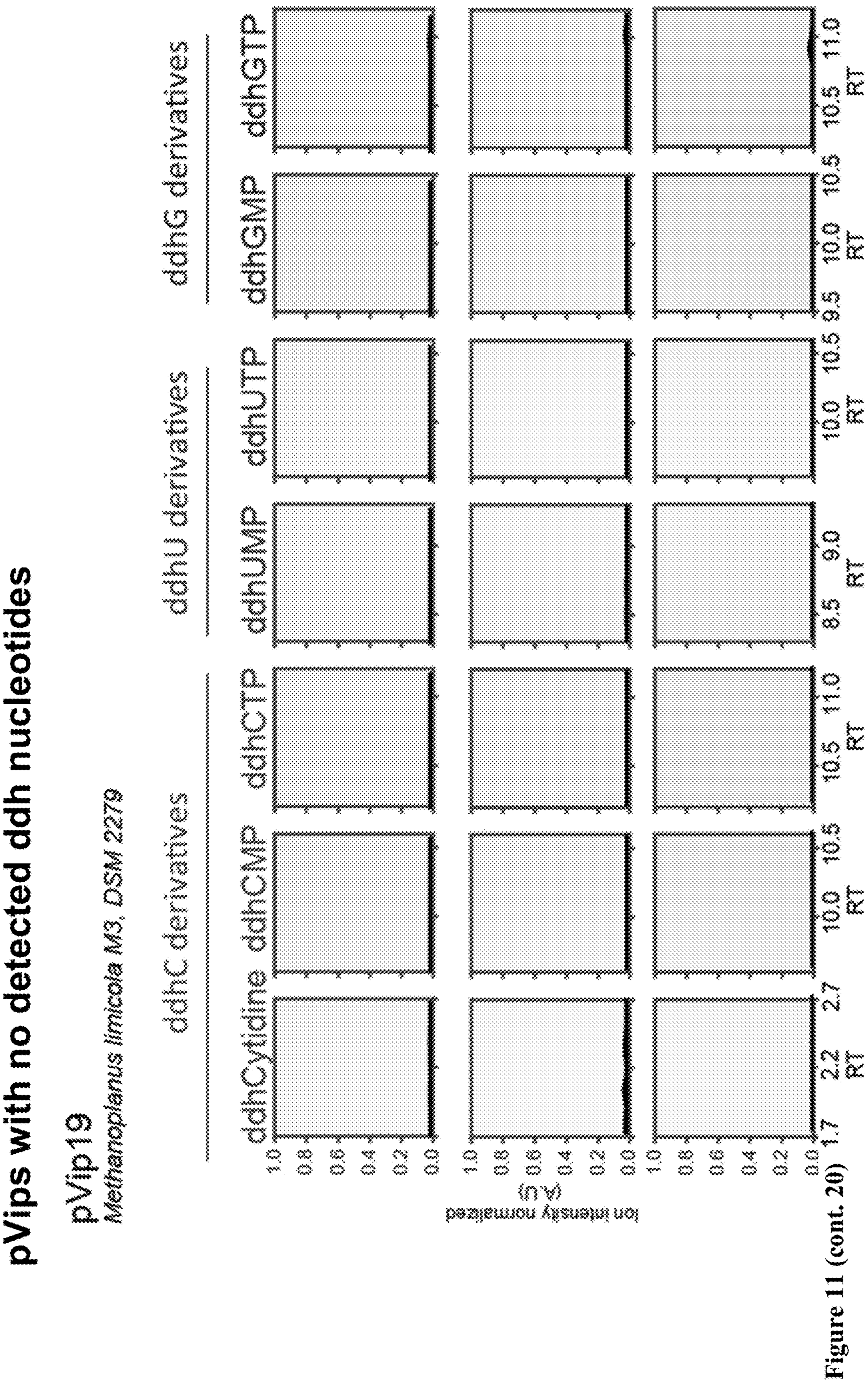
Figure 11 (cont. 20)

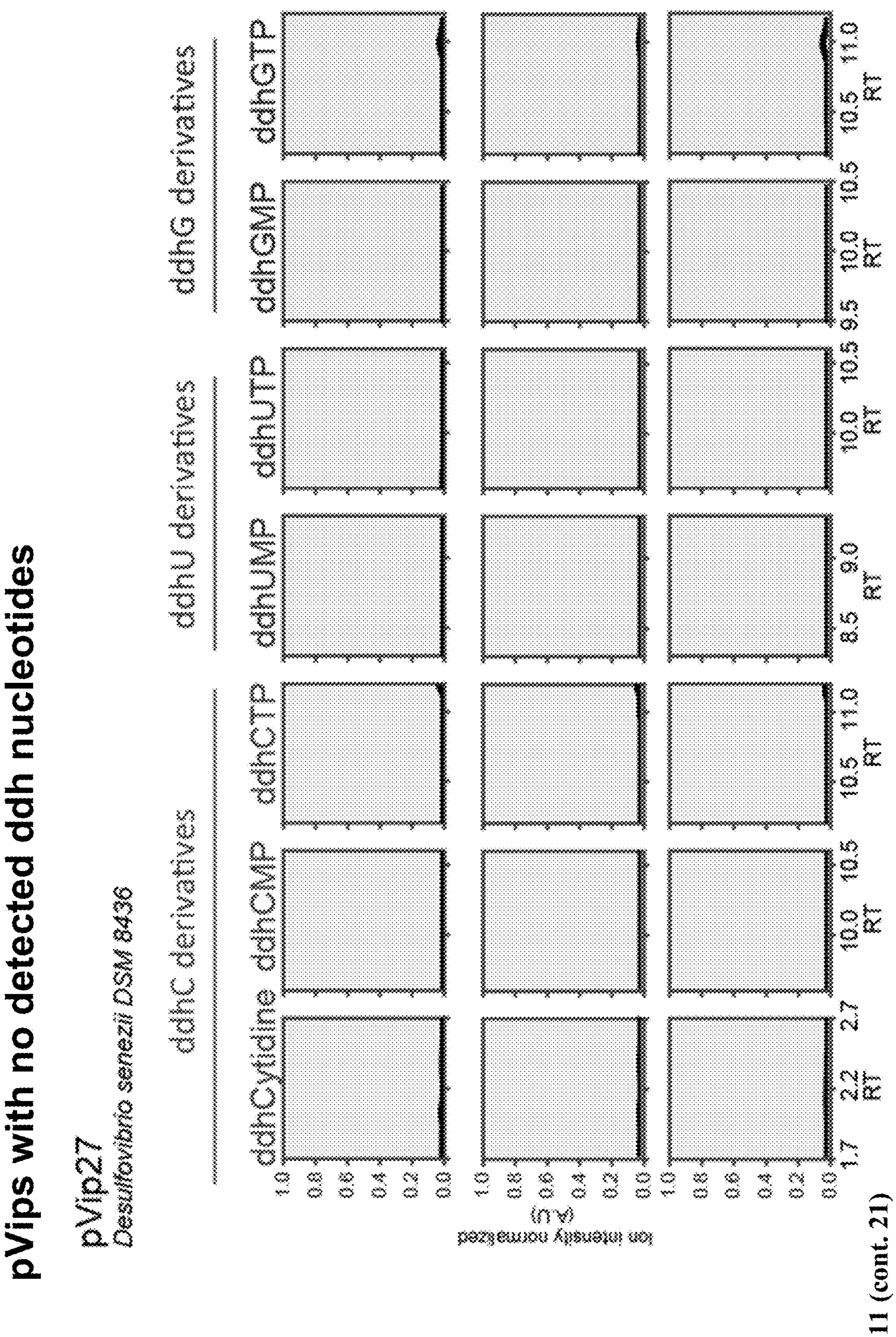
Figure 11 (cont. 21)

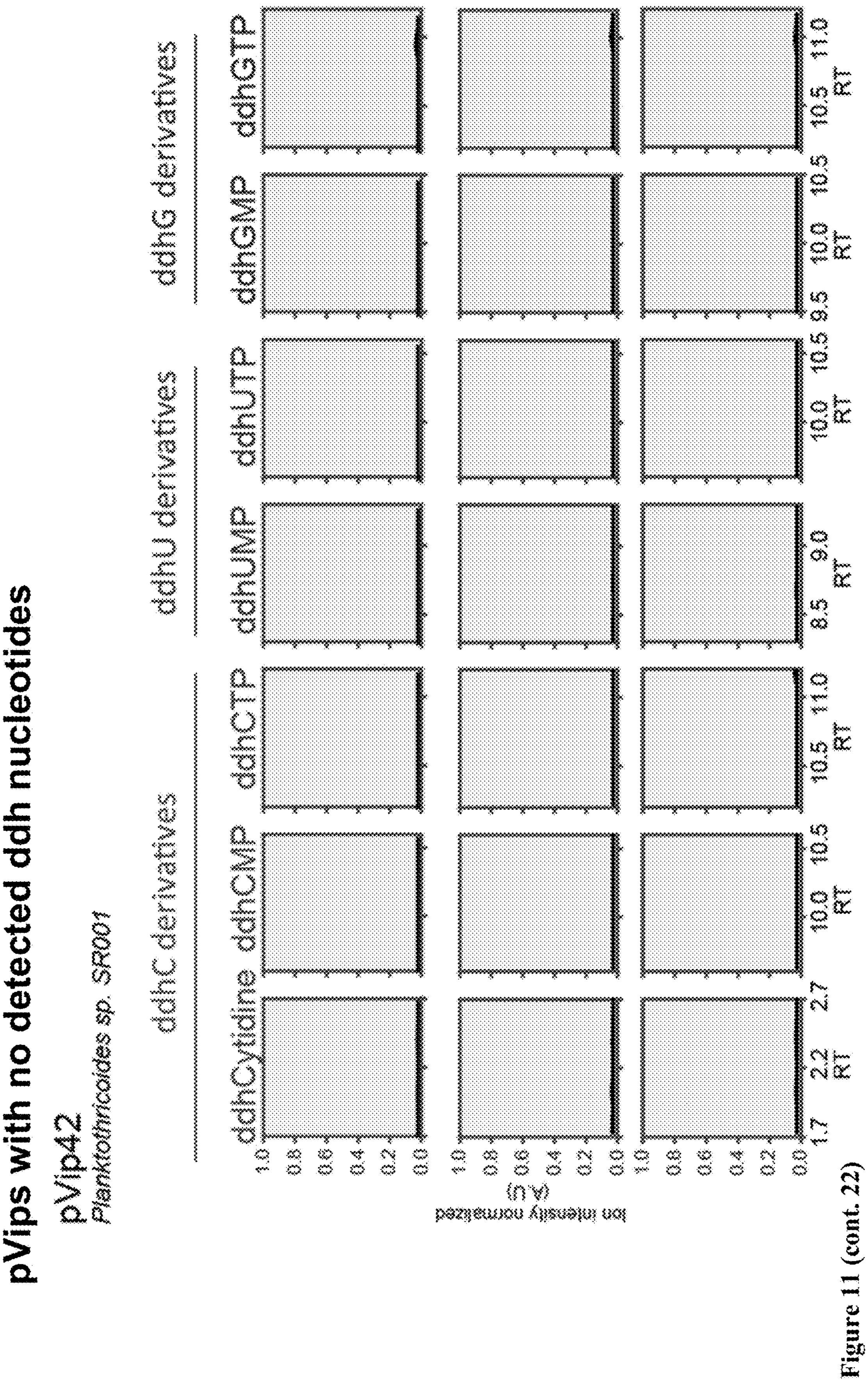
Figure 11 (cont. 22)

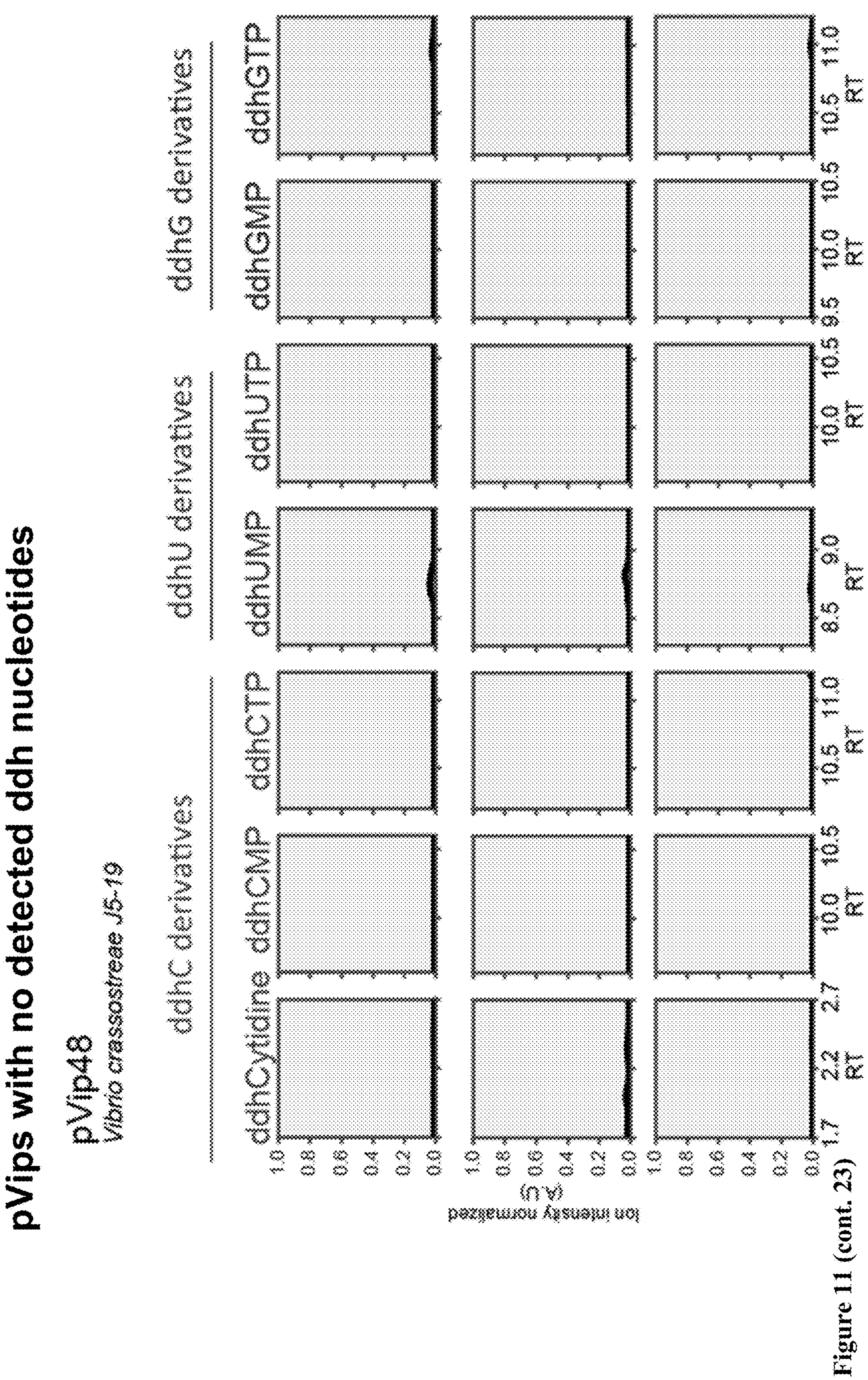
Figure 11 (cont. 23)

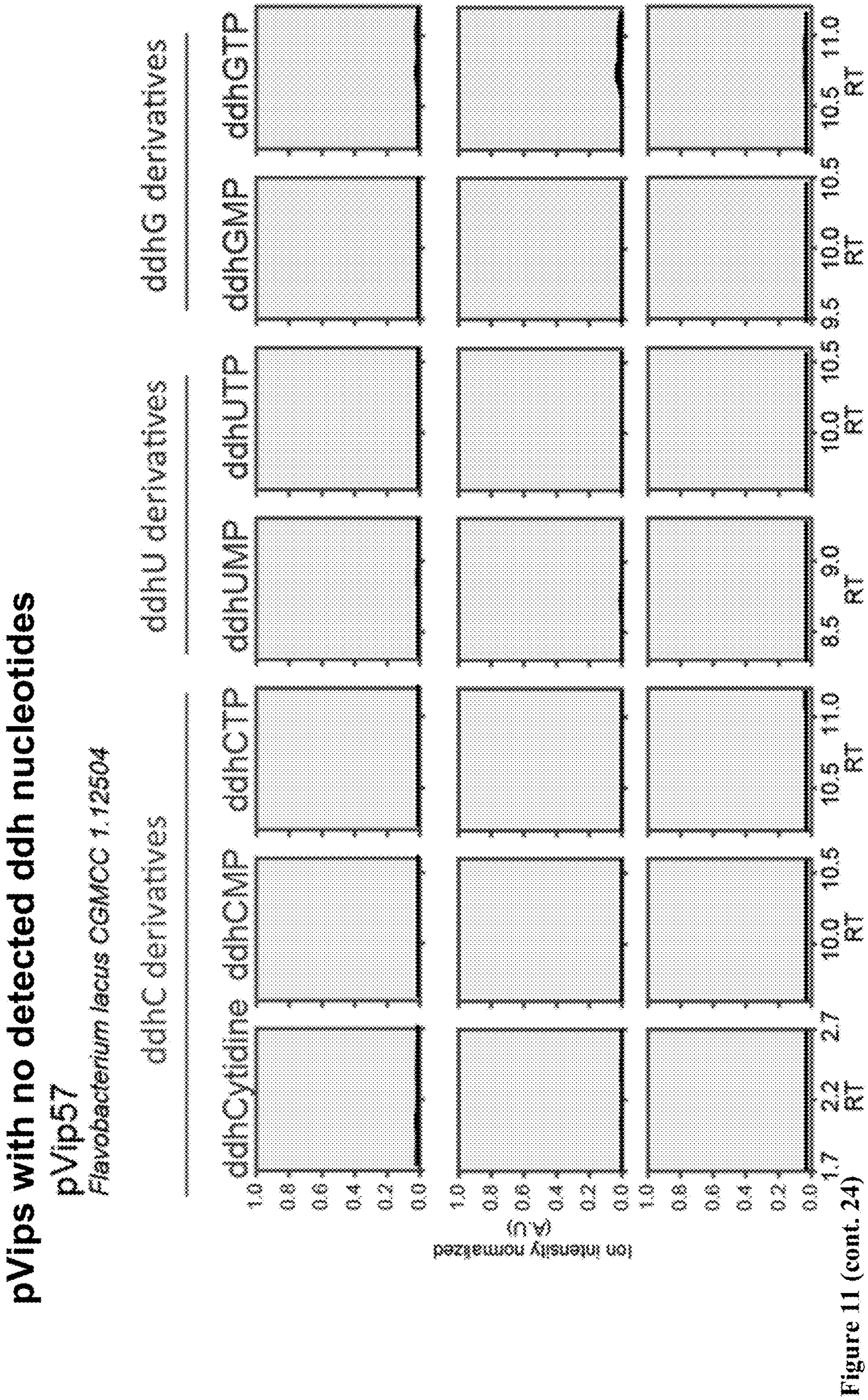
Figure 11 (cont. 24)

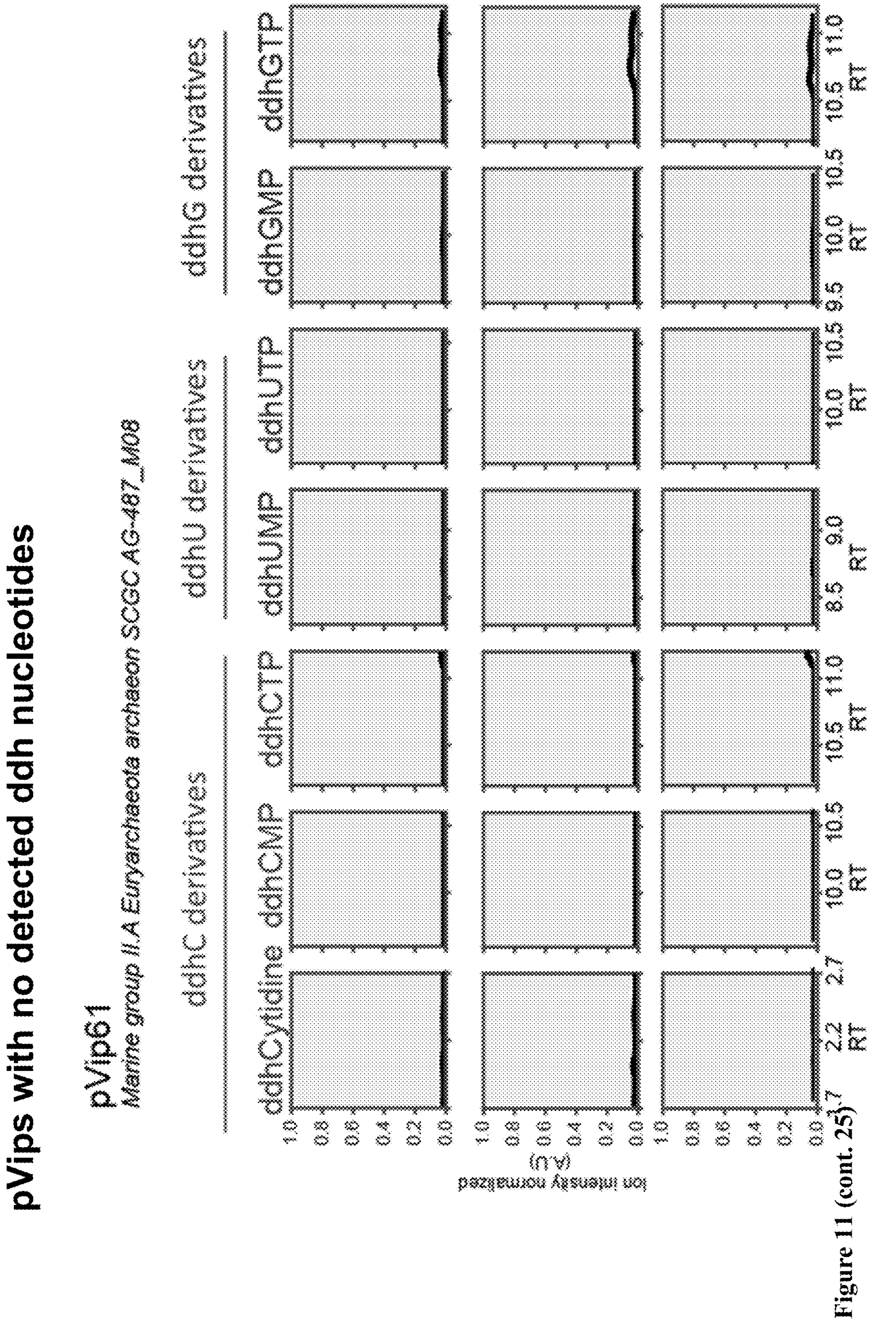
Figure 11 (cont. 25)

A B

Ra = OH,  ,  or

Rg = Heterocyclic Nitrogen based ring, O-aryl or aryl and isomers therof

A B

A B

A B ddhUTP
Formula: $C_9H_{13}N_2O_{14}P_3$
Mass: 465.958 ddhCTP
Formula: $C_9H_{14}N_3O_{13}P_3$
Mass: 464.9739 ddhATP
Formula: $C_{10}H_{14}N_5O_{12}P_3$
Mass: 488.9852 ddhGTP
Formula: $C_{10}H_{14}N_5O_{13}P_3$
Mass: 504.9801

ANTI-VIRAL AND ANTI-TUMORAL COMPOUNDS

CROSS-REFERENCE TO RELATED APPLICATIONS

This application is a Continuation-in-Part of PCT International Application No. PCT/IB2021/057599, International Filing Date Aug. 18, 2021, claiming the benefit of U.S. Patent Application No. 63/085,218, filed Sep. 30, 2020, and IL Patent Application No. 276794, filed Aug. 18, 2020, which are hereby incorporated by reference.

SEQUENCE LISTING

The instant application contains a Sequence Listing which has been submitted electronically in ASCII format and is hereby incorporated by reference in its entirety. Said ASCII copy, created on Nov. 1, 2020, is named P-595088-PC-SQL-01NOV20.txt and is 1,589,425 bytes in size.

FIELD OF INTEREST

Disclosed herein are 3,4-didehydro- and 3'-deoxy-3,4-didehydro-compounds, pharmaceutical compositions thereof, and uses thereof. Uses of the compounds and compositions disclosed include as anti-viral therapeutic agents against RNA and DNA viruses.

BACKGROUND

It has been shown that the enzyme viperin from *Rattus norvegicus* (rVip) produces 3'-deoxy-3,4-didehydro-CTP (ddhCTP) from CTP. ddhCTP acts as a chain terminator for certain viral RNA-dependent RNA polymerases, leading to inhibition of viral replication. In human cells, viperin's activity confers broad antiviral effects. To date, two additional eukaryotic viperins have been characterized, the human and fungal homologues. Similar to the rVip, both human and fungal viperins produce ddhCTP, while the fungal viperin can also produce 3'-deoxy-3,4-didehydro-UTP (ddhUTP) from UTP. Currently, it is known that eukaryotic viperins can only produce a limited set of nucleotide analogues.

Prokaryotic viperins (pVips) are newly discovered viperin homologs that have been demonstrated to take part in defense against phages. A total of 381 different pVips were computationally found and grouped in 7 different phylogenetic clades (International patent application No. PCT/IL2020/050377, filed Mar. 29, 2020). From this set of pVips, 27 homologues were experimentally proven to protect bacteria from phage infection. LC-MS analysis of lysates from *E. coli* cultures overexpressing this set of 27 pVips demonstrated that many of them produce derivatives of one or multiple ddh-ribonucleotides, such as ddhCTP and ddhUTP (like the eukaryotic viperins) but also ddhGTP which was not previously reported as a product of eukaryotic viperins. These results revealed unprecedented insights into the substrate promiscuity of pVips, showing that pVips, in contrast to eukaryotic viperins, can accept multiple substrates.

Nucleotide/nucleoside analogs are crucial components of our medicinal chemistry arsenal, with more than 30 approved molecules in the market and many more currently in development. They are currently employed to treat a wide array of pathologies, including viral and microbial infections, as well as to inhibit the proliferation of cancer cells. Moreover, it is known that minor changes in their chemical structure have profound effects on their activity against specific targets, as well as on potential undesired side-effects.

Thus, substituted compounds (for example as presented herein) may mimic the overall structure of nucleotide/nucleoside analogs and may include: (1) heterocyclic nitrogen based ring or O-aryl or aryl and isomers thereof attached to position 1' of the 5 membered ring (to the ddh or deoxy-ddh ribose sugar analog); and/or (2) different substitutions on the 5 member ribose sugar (position 2', 3', 4' and/or 5'); and/or (3) substitution of the O of the 5-member ring with N or $CH_2$ or CH or $CCH_2$; and/or (4) an open etheric ring instead of the 5 member ring, may comprise unique novel activities. Accordingly, these substituted compounds (substituted ddh or deoxy-ddh compounds) may add unique therapeutic compounds to the medicinal chemistry arsenal.

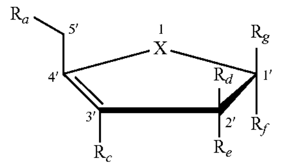

X is O, NH, $CH_2$, CH, $CCH_2$,

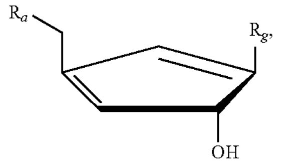

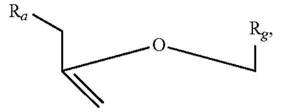

There remains a need for targeted active compounds for treating diseases in a subject including viral and microbial infections, as well as to inhibit the proliferation of cancer cells. Thus, there is a need for creating novel structural modifications of existing compound to generate new therapeutic variants with selective antiviral, antimicrobial, or anti-cancer activities, or a combination of activities thereof. The present disclosure describes novel ddh and deoxy-ddh variant compounds, for therapeutic use as antiviral, anti-tumoral, and/or antibacterial agents. Further, the present disclosure describes the utilization of pVips enzymes as a versatile platform for the synthesis of ddh and deoxy-ddh variants with novel antiviral, anti-tumoral, and/or antibacterial activities.

SUMMARY OF THE DISCLOSURE

In one aspect, provided herein is a compound represented by the structure of

Formula IIB:
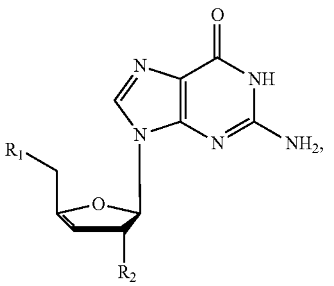
or Formula IVB:
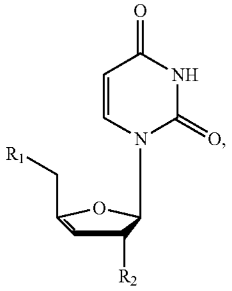
wherein
$R_1$ is
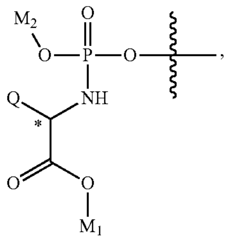, 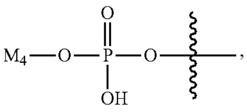, or
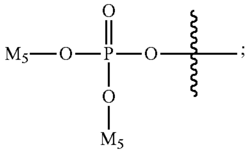;
Q is a side chain of an amino acid;
$M_1$ is an alkyl;
$M_2$ is an aryl, a substituted aryl, a heteroaryl or a substituted heteroaryl;
$M_4$ is $-(C_2\text{-}C_6)$alkyl-O$-(C_{10}\text{-}C_{20})$alkyl;
each $M_5$ is $-(CH_2)_n-S-C(=O)-(C_1\text{-}C_8)$alkyl;
n is 1-4; and
$R_2$ is —OH.
In one aspect, the compound has the structure of
Compound 2
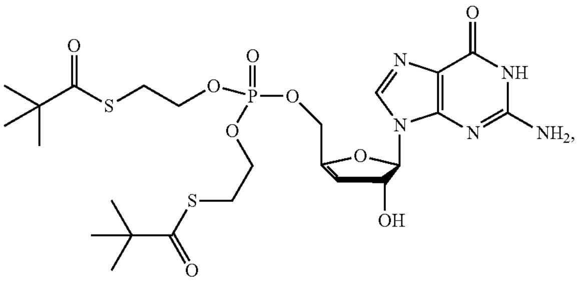,
Compound 4
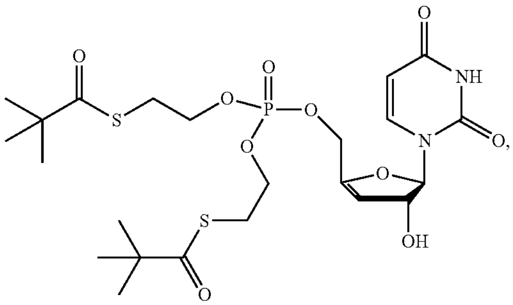,
Compound 103
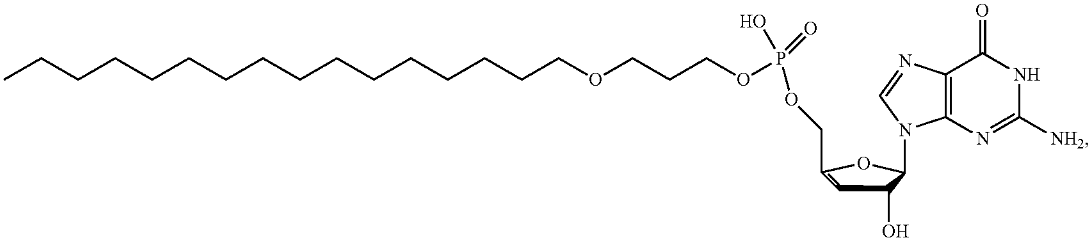, -continued
Compound 104
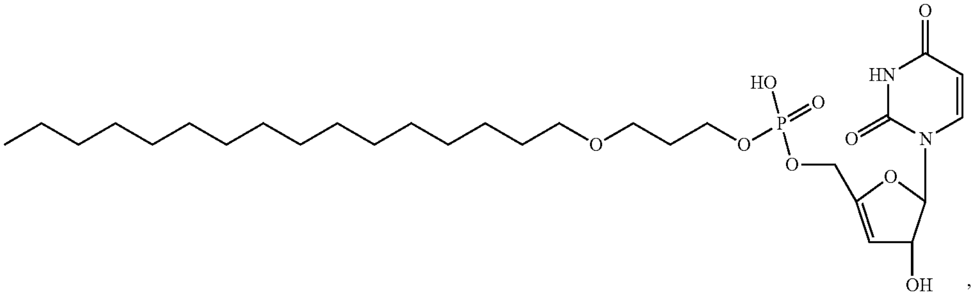
,
Compound 33
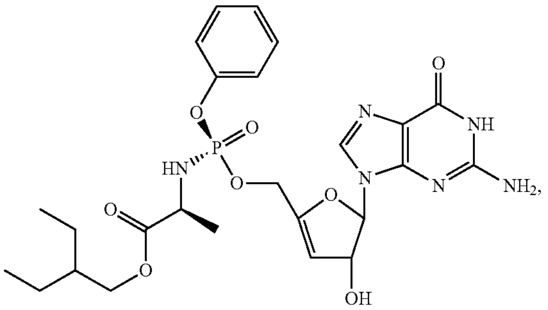
or
Compound 26
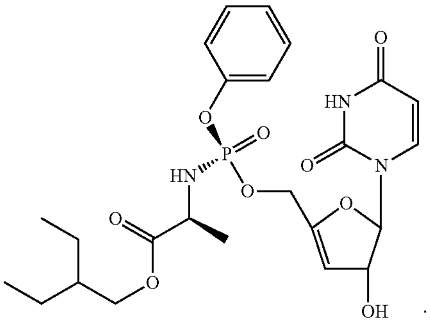
.
In one aspect, the compound has the structure of
Compound 2
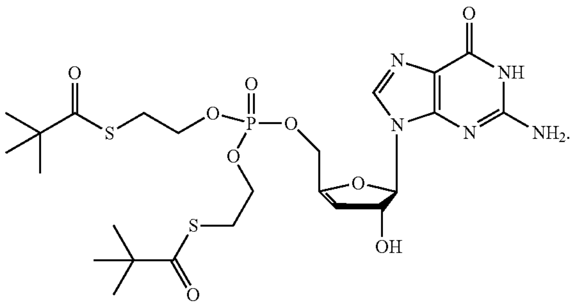
In one aspect, the compound has the structure of
Compound 4
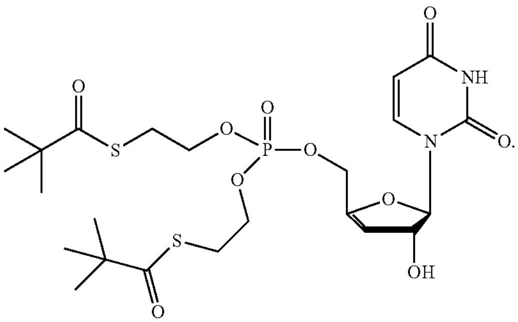
In one aspect, the compound has the structure of
Compound 103
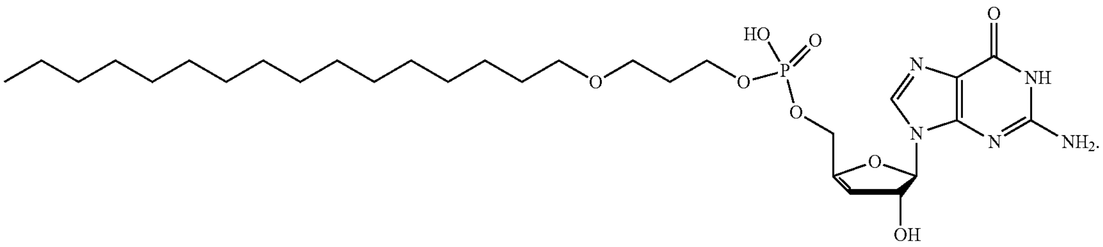

In one aspect, the compound has the structure of

Compound 104

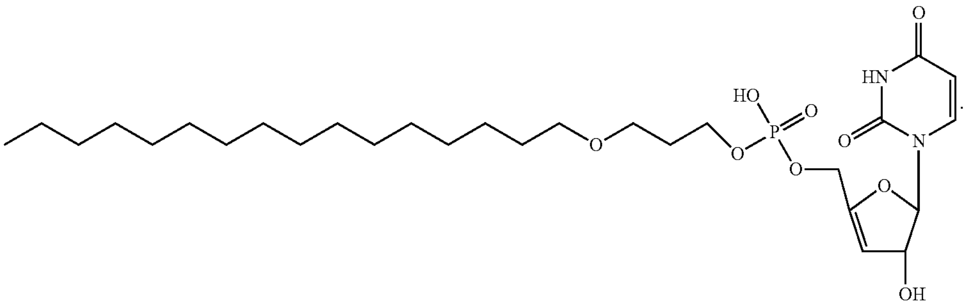

In one aspect, the compound has the structure of

Compound 33

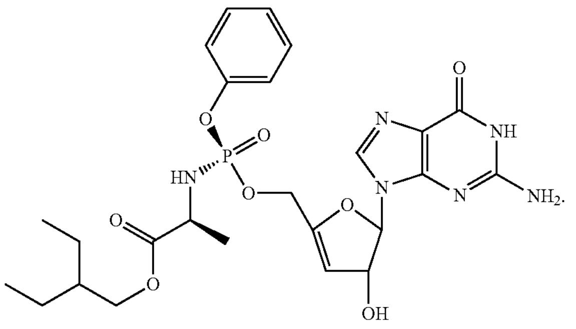

In one aspect, the compound has the structure of

Compound 26

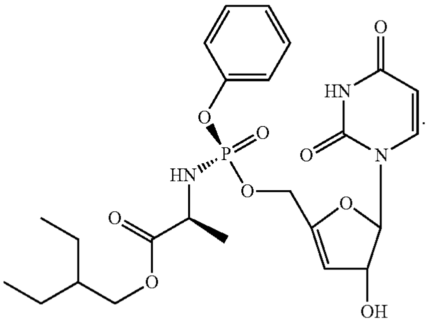

In one aspect, provided herein is a pharmaceutical composition comprising one or more compounds disclosed herein.

In one aspect, provided herein is a pharmaceutical composition comprising at least two compounds disclosed herein. In a related aspect, the composition comprises a pharmaceutically acceptable carrier.

In one aspect, provided herein is a method of treating a disease in a subject in need thereof, comprising administering the pharmaceutical composition disclosed herein. In a related aspect, the disease comprises a virus-induced disease, a cancer, an autoimmune disease, an immune disorder, a bacterial associated disease or infection, or a combination thereof.

In a further related aspect, disease is caused by a virus selected from the group consisting of norovirus, rotavirus, hepatitis virus A, B, C, D, or E, rabies virus, West Nile virus, enterovirus, echovirus, coxsackievirus, herpes simplex virus (HSV), varicella-zoster virus, mosquito-borne viruses, arbovirus, St. Louis encephalitis virus, California encephalitis virus, lymphocytic choriomeningitis virus, human immunodeficiency virus (HIV), poliovirus, zika virus, rubella virus, cytomegalovirus, human papillomavirus (HPV), enterovirus D68, severe acute respiratory syndrome (SARS) coronavirus, Middle East respiratory syndrome coronavirus (MERS-CoV), SARS coronavirus 2 (SARS-CoV-2), Epstein-Barr virus (EBV), influenza virus, influenza virus A2, influenza virus B, influenza virus A(H1N1), respiratory syncytial virus (RSV), polyoma viruses, BK virus, JC virus, Tacaribe virus, Ebola virus, Dengue virus, and any combination thereof. In another further related aspect, the virus-induced disease is COVID-19 caused by SARS-CoV-2.

In another related aspect, t treating a disease terminates polynucleotide chain synthesis in a cell. In a further related aspect, terminating polynucleotide chain synthesis increases termination of DNA chain synthesis, or increases termination of RNA chain synthesis, or a combination thereof. In another further related aspect, terminating polynucleotide chain synthesis confers viral resistance to said cell. In yet another further related aspect, the cell is a eukaryotic cell. In still another further related aspect, the eukaryotic cell is a tumor cell, or is a cell infected by a virus or a foreign DNA.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The subject matter disclosed describing ddh and deoxy-ddh compounds and uses thereof, is particularly pointed out and distinctly claimed in the concluding portion of the specification. The compounds, synthesis of, and use thereof, however, both as to organization and method of operation, together with objects, features, and advantages thereof, may best be understood by reference to the following detailed description when read with the accompanying drawings.

FIG. 3A shows the phylogenetic tree of the pVip genes disclosed herein. Branch colors correspond to major clades. Filled circles represent presence of nucleotide kinases. Purple circles: predicted thymidilate kinases; brown circles: predicted cytidilate kinases; blue circles: predicted adenylate kinases. Stars represent pVip genes that we have experimentally showed to have anti-phage activity. Colors of stars represent different defense phenotypes for different pVips. Red stars: anti T7 and anti P1/lambdactivity; green star: anti T7 activity; light blue star: anti P1 and anti-lambdactivity. FIG. 3B shows the phylogenetic tree of pVip genes including sequences extracted from metagenomes. Branch colors correspond to major clades of FIG. 3A. Black branches are sequences from metagenomes.

FIGS. 5A and 5B show plaque assays of bacteria transformed with pVip9 (FIG. 5A) or pVip10 (FIG. 5B). The left panel shows WT MG1655 colonies. The right panel shows Keio ΔiscR colonies. Bacteria were challenged with phages SECPhi6, SECPhi17, SECPhi18, SECPhi27, SECPhi32, and T7 (dilutions from $10^{-3}$ to $10^{-8}$). A star indicates phages in which pVip anti-viral activity was observed. Shown is an experiment representative of triplicates.

FIG. 6A shows Keio ΔiscR control colonies transfected with MoaA. Three main defense phenotypes were observed for the different pVips: activity against P1 and lambda but not T7 (FIGS. 6B-6H) activity against T7 only (FIGS. 6I-6M), and activity against P1, lambdand T7 (FIGS. 6N-6Z). All experiments were performed at 37° C.

FIG. 7A shows in vivo anti-viral activity of pVip7 in solid plaque assays. The left panel shows colonies in which pVip7 expression was not induced. The right panel shows colonies in which pVip7 expression was induced by 1 mM IPTG. *B. subtilis* colonies were challenged with the following phages: SBSphiC, SPO1, rho14, spbeta, SPR, phi3T (dilution from $10^{-1}$ to $10^{-6}$ of the original stock). A star indicates phages for which pVip7 anti-viral activity was observed. Shown here is an experiment representative of triplicates. FIG. 7B shows in vivo anti-viral activity of pVip7 in a liquid infection assay using phage phi3T (MOI=0.1). (−−) and (−+)=non-infected controls, (+−)=phage-infected bacteria in which pVip7 expression was not induced, (++)=phage-infected bacteria in which pVip7 expression was induced. Shown here is one representative experiment of triplicates.

FIG. 8A shows the experimental design of the assay. A GFP reporter operably linked to a T7 promoter was cloned into a plasmid and transfected to bacterial cells expressing the T7 RNAP. T7 polymerase is activated by a pLac promoter inducible by IPTG. pVips are activated by a pAra promoter inducible by arabinose. A plasmid cloned with MoaA instead of pVips was used as a control. Cells were first provided with arabinose and then IPTG, thus inducing first pVip and then T7 RNAP. The expressed T7 RNAP in turn transcribed GFP. It was reasoned that if T7 RNAP is sensitive to pVip products, the presumed chain terminator will be incorporated generating prematurely terminated transcripts, leading to reduced GFP translation and signal. FIGS. 8B-8G show the experimental results. FIG. 8B shows that activation of the control plasmid, expressing MoaA, did not affect GFP expression. FIGS. 8C-8G show that co-expression of pVip8, pVip9, pVip37, pVip46, and pVip63, respectively, affected GFP expression. Graphs represent GFP divided by optical density (OD) (A.U). Bottom grey curves ("No GFP") indicate no GFP induction (no IPTG), light grey curves ("GFP/no Vip") indicate GFP induction but no pVip induction (IPTG 0.01 mM, no arabinose), dark grey curves ("GFP/Vip induced") indicate GFP and pVip induction (IPTG 0.01 mM, arabinose 0.02%).

FIG. 9A shows extracted ion chromatogram for singly charged masses corresponding to ddhC (m/z 226.08223, retention time (RT) of 2.2 minutes), ddhCMP (m/z 306.04856, RT 9.7), ddhCTP (m/z 465.98122, RT 11.1), ddhUMP (m/z 307.03258, RT 8.7), ddhUTP (m/z 466.96524, RT 9.5), ddhGMP (m/z 266.08838, RT 9.8), and ddhGTP (m/z 505.98737, RT 10.6). X-axis depicts RT in minutes. Y axis, normalized ion intensity (arbitrary units). Normalization was performed on all pVips and MoaA samples, with maximal value set to 1.0. Representative of 3 replicates. FIG. 9B shows production of ddh nucleotide derivatives by pVips. Colored boxes depict detected compounds. Lighter color corresponds to compounds detected in a smaller quantity.

FIG. 13A shows enzymatic modification of non-natural substrate represented by the structure of a 5-member etheric ring (sugar ribose) substituted with hydroxy at 3' position to obtain a double bond at positions 3'-4' by pVips. FIG. 13B shows enzymatic modification of non-natural substrate represented by the structure of a 5-membered nitrogen based ring (sugar ribose analog) substituted with hydroxy at 3' position, to obtain a double bond at positions 3'-4' by pVips. FIG. 13C shows enzymatic modification of non-natural substrate represented by the structure of a 5-membered carbon based (sugar ribose analog) substituted with hydroxy at 3' position to obtain a double bond at positions 3'-4' by pVips. FIG. 13D shows enzymatic modification of non-natural substrate represented by the structure of 5-membered carbon based ring contain a double bond at positions 4'-1, substituted with hydroxy at positions 3' to obtain a double bond at positions 3'-4' and 1-1' by pVips. FIG. 13E shows enzymatic modification of non-natural substrate represented by the structure of 5-membered carbon based ring substituted at position 1 with $=CH_2$, substituted with hydroxy at positions 3' to obtain a double bond at positions 3'-4' by pVips. FIG. 13F shows enzymatic modification of non-natural substrate represented by the structure of an etheric chain which is terminally substituted with hydroxy to obtain a terminal double bond, by pVips.

FIG. 15A presents chromatographs showing the presence of a product with a mass corresponding to ddhUTP (negative mode) in reaction samples where the enzyme (here pVip8) was incubated with UTP as substrate. This product was not observed in control samples: dithionite (reducing agent) or UTP. FIG. 15B presents MS/MS analysis of this product indicating the observed fragments result from ddhUTP. Potential fragments are indicated for each peak.

FIG. 16A presents chromatographs showing the presence of a product with a mass corresponding to ddhCTP (negative mode) in reaction samples where the enzyme (here pVip6) was incubated with CTP as substrate. This product was not observed in control samples: dithionite (reducing agent) or CTP. FIG. 16B presents MS/MS analysis of this product indicating the observed fragments result from ddhCTP. Potential fragments are indicated for each peak.

FIG. 17A presents chromatographs showing the presence of a product with a mass corresponding to ddhATP (negative mode) in reaction samples where the enzyme (here pVip6) was incubated with ATP as substrate. This product was not observed in control samples: dithionite (reducing agent) or ATP. FIG. 17B presents MS/MS analysis of this product indicating the observed fragments result from ddhATP. Potential fragments are indicated for each peak.

FIG. 18A presents chromatographs showing the presence of a product with a mass corresponding to ddhITP (negative mode) in reaction samples where the enzyme (here pVip62) was incubated with ITP as substrate. This product was not observed in control samples: dithionite (reducing agent) or ITP. FIG. 18B presents MS/MS analysis of this product indicating the observed fragments result from ddhITP. Potential fragments are indicated for each peak.

FIG. 19A presents chromatographs showing the presence of a product with a mass corresponding to ddhdUTP (negative mode) in reaction samples where the enzyme (here pVip62) was incubated with dUTP as substrate. This product was not observed in control samples: dithionite (reducing agent) or dUTP. FIG. 19B presents MS/MS analysis of this product indicating the observed fragments result from ddhdUTP. Potential fragments are indicated for each peak.

FIG. 20A presents chromatographs showing the presence of a product with a mass corresponding to ddhGTP (negative mode) in reaction samples where the enzyme (here pVip56) was incubated with GTP as substrate. This product was not observed in control samples: dithionite (reducing agent) or GTP. FIG. 20B presents MS/MS analysis of this product indicating the observed fragments result from ddhGTP. Potential fragments are indicated for each peak.

FIG. 22A. Serial dilutions of 0 mM:0 mM for nsp7-8. FIG. 22B. Serial dilutions of 0.25 mM:0.05 mM for nsp7-8. FIG. 22C. Serial dilutions of 0.5 mM:0.1 mM for nsp7-8. FIG. 22D. Serial dilutions of 1 mM:0.2 mM for nsp7-8. FIG. 22E. Serial dilutions of 2.5 mM:0.5 mM for nsp7-8.

FIG. 23A. Serial dilutions of 5 mM:1 mM for nsp7-8. FIG. 23B. Serial dilutions of 10 mM:2 mM for nsp7-8.

FIG. 26A and FIG. 26C—A representative image of the REM and ddhREM IC50 calculation for the inhibition of the RNA synthesis catalyzed by SARS-Cov2 RdRp. FIG. 26B and FIG. 26D—Quantitative analysis of REM-TP and ddhREM-TP. Product formation was quantified using ImageLab software (BioRad, California, USA). IC50 values were calculated by fitting the product formation using the following equation: Y=A+(D−A)/(1+([In]/C)^B), where Y represents SARS-Cov2 RdRp activity; [In]—concentration of inhibitor at mM; A—inhibition at inhibitor concentration equal zero; D—inhibition at the highest inhibitor concentration; B—slope of the at the mid-range concentration point; C—mid-range concentrate point (IC50).

FIG. 27A. Incorporation of UTP and its analogs, 3'-dUTP and ddhUTP into RNA template. FIG. 27B. Chain termination ability of ddhUTP in primer extension reaction. 3'-dUTP was used as a positive control for chain termination.

FIG. 28A. Incorporation of GTP and its analogs, 3'-dGTP and ddhGTP into RNA template. FIG. 28B. Chain termination ability of ddhGTP in primer extension reaction. 3'-dGTP was used as a positive control for chain termination.

FIG. 29A and FIG. 29C. A representative image of the ddhUTP and ddhGTP IC50 calculation for the inhibition of the RNA synthesis catalyzed by SARS-Cov2 RdRp. FIG. 29B and FIG. 29D. Quantitative analysis of ddhUTP and ddhGTP. Product formation was quantified using ImageLab software (BioRad, California, USA). IC50 values were calculated by fitting the product formation using the following equation: Y=A+(D−A)/(1+([In]/C)^B), where Y represents SARS-Cov2 RdRp activity; [In]—concentration of inhibitor at mM; A—inhibition at inhibitor concentration equal zero; D—inhibition at the highest inhibitor concentration; B—slope of the at the mid-range concentration point; C—mid-range concentrate point (IC50).

FIG. 30A. A representative image of the ddhREM-TP IC50 calculation for the inhibition of the DNA synthesis catalyzed by POLRMT. FIG. 30B. Quantitative analysis of ddhREM-TP. Product formation was quantified using ImageLab software (BioRad, California, USA). IC50 values were calculated by fitting the product formation using the following equation: Y=A+(D−A)/(1+([In]/C)^B), where Y represents POLMRT activity; [In]—concentration of inhibitor at mM; A—inhibition at inhibitor concentration equal zero; D—inhibition at the highest inhibitor concentration; B—slope of the at the mid-range concentration point; C—mid-range concentrate point (IC50).

FIG. 31A. A representative image of the ddhUTP IC50 calculation for the inhibition of the DNA synthesis catalyzed by POLRMT. FIG. 31B. Quantitative analysis of ddhUTP. Product formation was quantified using ImageLab software (BioRad, California, USA). IC50 values were calculated by fitting the product formation using the following equation: Y=A+(D−A)/(1+([In]/C)^B), where Y represents POLRMT activity; [In]—concentration of inhibitor at mM; A—inhibition at inhibitor concentration equal zero; D—inhibition at the highest inhibitor concentration; B—slope of the at the mid-range concentration point; C—mid-range concentrate point (IC50).

FIG. 32A and FIG. 32C. A representative image of the ddhREM-TP and ddhUTP IC50 calculation for the inhibition of the DNA synthesis catalyzed by POLG1. FIG. 32B and FIG. 32D. Quantitative analysis of ddhREM-TP and ddhUTP. Product formation was quantified using ImageLab software (BioRad, California, USA). IC50 values were calculated by fitting the product formation using the following equation: Y=A+(D−A)/(1+([In]/C)^B), where Y represents POLG1 activity; [In]—concentration of inhibitor at mM; A—inhibition at inhibitor concentration equal zero; D—inhibition at the highest inhibitor concentration; B—slope of the at the mid-range concentration point; C—mid-range concentrate point (IC50).

FIG. 33A and FIG. 33B. A representative image of the ddhUTP and ddhUTP for the inhibition of the DNA synthesis catalyzed by PrimPol.

FIG. 34A. MPA (dots) and RMP (squares) inhibition on IMPDH activity with IC50 of 76±10 nM and 2.6±1.8 mM, respectively. FIG. 34B. ddhUMP (dots) and ddhGMP (squares) inhibition on IMPDH activity with IC50>1 mM.

FIG. 35A. Plasma concentration of AB23040 (compound 103; Formula IIB) and its metabolite AB21651 (compound 31; Formula IIB; ddhG) after intravenous (IV) and oral (PO) administration. FIG. 35B. Plasma concentration of Brincidofovir (BCV) and its metabolite Cidofovir (CDV) after intravenous (IV) and oral (PO) administration.

FIG. 36A. Tissue concentration of AB23040 (compound 103; Formula IIB) and BCV after 2 hours from administration. FIG. 36B. Tissue concentration of AB23040 (compound 103; Formula IIB) and BCV after 24 hours from administration. FIG. 36C. Tissue concentration of AB23040 (compound 103; Formula IIB) and BCV after 72 hours from administration.

DETAILED DESCRIPTION

Figure 1:
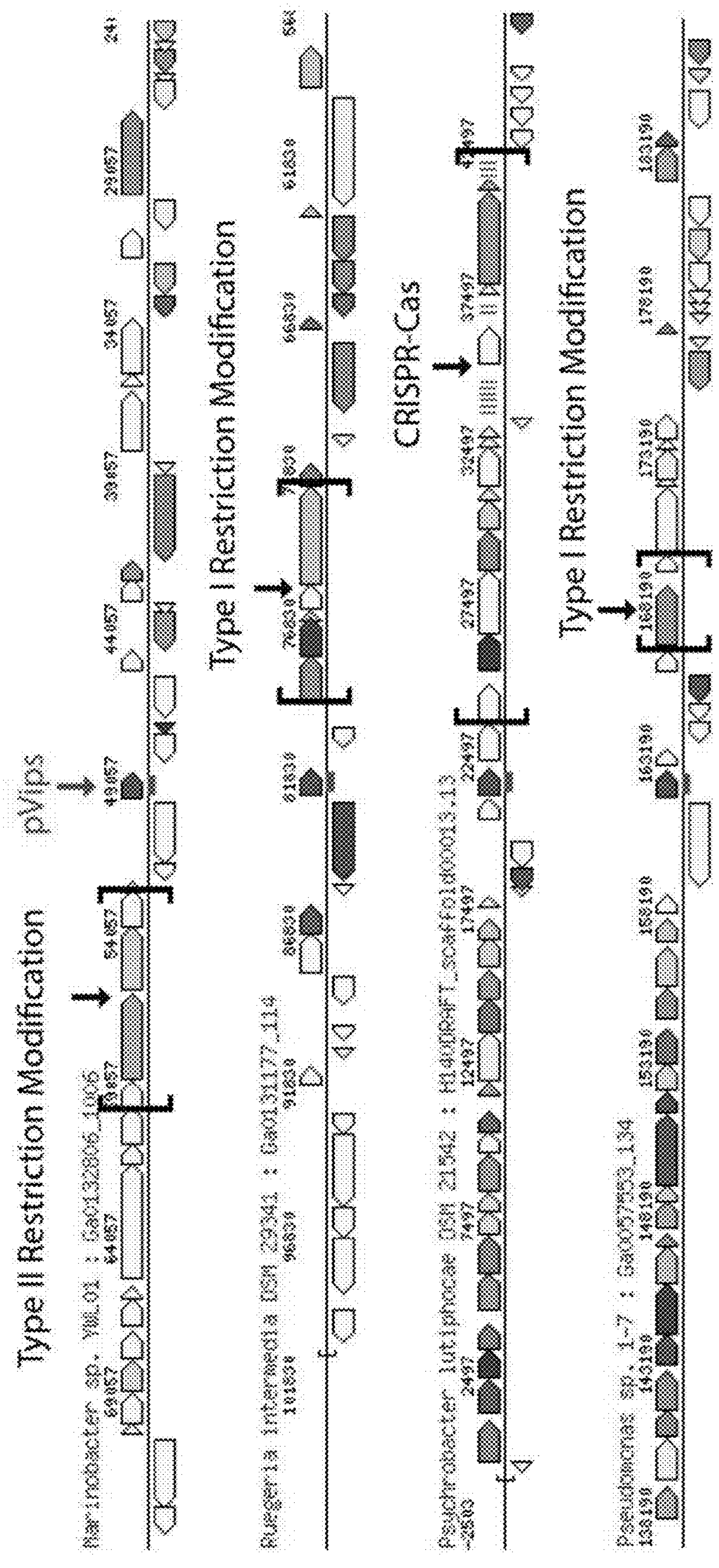
FIG. 1 shows an embodiment of the defensive genomic context of pVip genes. pVip genes are marked as red. Black arrows point to known anti-phage defense systems (bracketed by black brackets).
Figure 1:
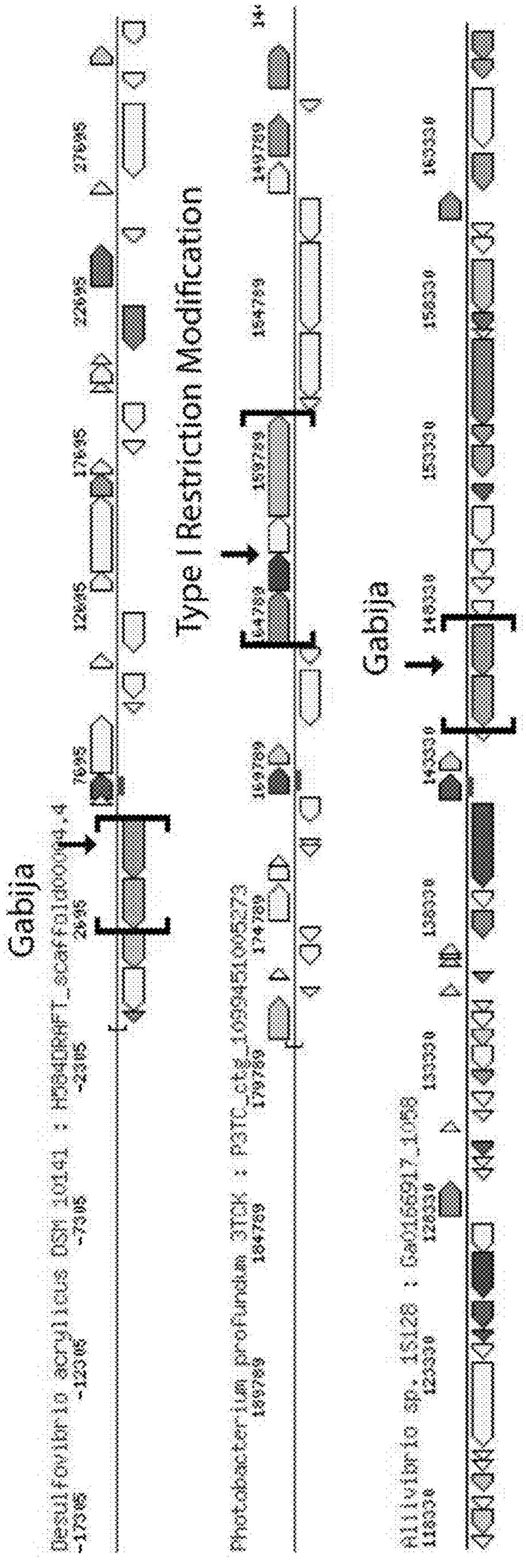

In the following detailed description, numerous specific details and embodiments are set forth in order to provide a thorough understanding of the anti-viral, anti-bacterial, and anti-tumoral chain terminator compounds disclosed herein, including descriptions of the 3,4-didehydro 3'-(ddh) or deoxy-3,4-didehydro (deoxy-ddh) compounds, methods of use thereof for terminating polynucleotide chain synthesis in a cell; methods of use thereof for treating a disease; and methods for producing these compounds including methods using pVip enzymes. In some instances, well-known methods, procedures, and components have not been described in detail so as not to obscure the present disclosure.

The substrate compounds from which the ddh- and deoxy-ddh-compounds may be synthesized chemically or produced enzymatically, may in certain embodiments be considered non-natural substrates of pVip enzymes. One skilled in the art would appreciate that the term "non-natural substrates" may encompass nucleotides/nucleosides derivatives or other substrates that are not the natural (in vivo) substrates of enzymatic reactions catalyzed by Vips or pVips in vivo.

The substrate compounds from which the ddh- and deoxy-ddh-compounds may be synthesized chemically or produced enzymatically, may in certain embodiments be considered analogs. One skilled in the art would appreciate that the term "analog" may encompass a molecule having a structure similar to that of another molecule, but differing from it in respect to a certain component. In some embodiments, the terms "analog", "structural analog", "chemical analog" and "substrate analog" are used herein interchangeably, having all the same qualities and meanings.

In some embodiments, the substrate compounds from which the ddh- and deoxy-ddh-compounds may be synthesized chemically or produced enzymatically, refer to compounds "A" in Table 1, Table 2, and in FIGS. 13A-13F. In certain embodiments, the substrate compounds are defined as non-natural substrate. A skilled artisan would appreciate that the ddh- and deoxy-ddh-compounds described in detail herein, encompass structures comprising compounds "B" in Table 1, Table 2, and FIGS. 13A-13F. In some embodiments, a ddh- and deoxy-ddh-compounds comprises a structure of a nucleotide/nucleoside analogs comprising substituted compounds (for example as presented herein) wherein the ddh- and deoxy-ddh-compound mimics the overall structure of nucleotide/nucleoside analogs and may include: (1) heterocyclic nitrogen based ring or O-aryl or aryl and isomers thereof attached to position 1' of the 5 membered ring (to the ddh or deoxy-ddh ribose sugar analog); and/or (2) different substitutions on the 5 member ring (position 2', 3', 4' and/or 5'); and/or (3) substitution of the O of the 5-member ring with N or $CH_2$ or CH or $CCH_2$; and/or (4) an open etheric ring instead of the 5 member ring, may comprise unique novel activities. Accordingly, these substituted compounds (substituted ddh or deoxy-ddh compounds) may add unique therapeutic compounds to the medicinal chemistry arsenal.

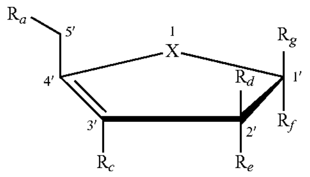

X is O, NH, $CH_2$, CH, $CCH_2$,

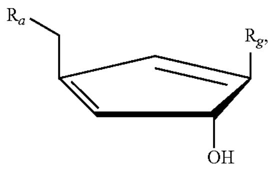

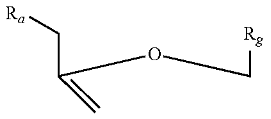

In some embodiments, ddh- and deoxy-ddh-compounds comprise a ddh-compound. In some embodiments, ddh- and deoxy-ddh-compounds comprise a deoxy-ddh-compound. In some embodiments, ddh- and deoxy-ddh-compounds comprise a prodrug of a ddh or deoxy-ddh-compound. In some embodiments, ddh- and deoxy-ddh-compounds comprise compounds wherein the 5-member ring (ribose sugar or analog) is substituted at position 2' with hydroxyl group.

In some embodiments, ddh- and deoxy-ddh-compounds comprise compounds wherein the 5-member ring (ribose sugar or ribose sugar analog) is not substituted at position 2' with hydroxyl group. In some embodiments, the 5-member ring is ribose sugar. In some embodiments, 5-member ring is ribose sugar analog. In some embodiments, the ribose sugar analog is 5-member oxygen or nitrogen or carbon based ring. In some embodiments, the 5-membered ring is 5-member oxygen based ring. In another embodiment, the 5-member ring is dihydrofuran. In some embodiments, the 5-member ring is a 5-member nitrogen based ring. In another embodiments, the 5-member nitrogen based ring is dihydropyrrole. In some embodiments, the 5-member ring is 5-member carbon based ring. In another embodiments, the 5-member carbon based ring is cyclopentene. In some embodiments, ddh- and deoxy-ddh-compounds do not contain a 5-member ring. In another embodiment, in some embodiments, ddh- and deoxy-ddh-compounds comprise an etheric chain.

The term "ddh- and deoxy-ddh-compound", "ddh- and deoxy-ddh-product", ddh- and deoxy-ddh-prodrug" and "a compound" may in some embodiments be used herein interchangeably, having all the same qualities and meanings. The term "deoxy-ddH-", "ddh-d-", and "ddh-deoxy-" may in some embodiments be used herein interchangeably, having all the same qualities and meanings.

In some embodiments, the substrate compounds from which the ddh- and deoxy-ddh-compounds may be synthesized chemically or produced enzymatically, comprise nucleotide/nucleoside analogs. One skilled in the art would appreciate that the term ddh- and deoxy-ddh-compounds may encompass compounds generated by the pVips or synthesized chemically to include 3,4-didehydro 3'-(ddh) or deoxy-3,4-didehydro (deoxy-ddh) compounds that can be used to treat a disease. In some embodiments, ddH- and deoxy-ddH-compounds may be used as DNA or RNA chain terminators. In some embodiment, the nucleotide/nucleoside analogs are generated by the pVips from non-natural substrates.

In some embodiments, while a molecule in the nucleotide form can be a DNA or RNA chain terminator, its corresponding nucleoside form, without any phosphate group, can cross cell membrane and enter into a cell. Once inside the cell, the nucleoside can be phosphorylated by one or more viral or cellular kinases to become a nucleotide. The nucleotide can be in the form of monophosphate, diphosphate or triphosphate. Each step of phosphorylation can be mediated by the same or different viral or cellular kinases. For example, the nucleoside is converted to monophosphate nucleotide by a first kinase, the monophosphate nucleotide is converted to diphosphate nucleotide by another kinase, and the diphosphate nucleotide is converted to triphosphate nucleotide by yet another kinase.

In some embodiments, the present disclosure describes the use of pVips to produce novel ddh- and deoxy-ddh compounds from non-natural substrates. Enzymatic reactions between pVips and the non-natural substrates may in some embodiments, be performed in vitro. In some embodiments, the novel ddh- and deoxy-ddh compounds are chemically synthesized from non-natural substrates using methods known in the art. In some embodiments, the novel ddh- and deoxy-ddh compounds from non-natural substrates are provided in the form of a pro-drug. The substrates can have 0 to 3 phosphate groups, i.e. being non-phosphorylated, or in the form of monophosphate, diphosphate or triphosphate nucleotide. As described in the Examples below, results from the enzymatic reactions led to the discovery of a number of non-natural substrates that can be converted by the pVips into ddh- and deoxy-ddh compounds. These ddh- and deoxy-ddh compounds can then be tested to see whether they possess the function of DNA or RNA chain termination. The products generated from the non-natural substrates can have 0 to 3 phosphate groups, i.e. being non-phosphorylated, or in the form of monophosphate, diphosphate or triphosphate nucleotide. In other embodiments, the products generated from may be in the form of a pro-drug.

In some embodiments, the ddh- and deoxy-ddh compounds can be used to block cellular DNA or RNA replication. In some embodiments, the ddh- and deoxy-ddh compounds can be used to treat a disease in a subject in need thereof. Methods of these ddh- and deoxy-ddh compounds includes treating viral infections including RNAnd DNA virus.

In some embodiments, the ddh- and deoxy-ddh compounds or prodrugs thereof, can be synthesized or enzymatically produced, and administered directly to cells of a subject. Upon entering the cells, these ddh- and deoxy-ddh compounds or prodrugs thereof, can be phosphorylated by one or more viral or cellular kinases to produce active forms of the compound that can inhibit DNA/RNA replication.

In certain embodiments, the ddh- and deoxy-ddh compounds or prodrugs thereof described herein can be used to block cellular DNA/RNA replication or treat a disease in a subject. In some embodiments, the ddh- and deoxy-ddh compounds or prodrugs thereof are administered to cells in a form that can enter the cells (e.g. nucleoside form or prodrug form). Once inside the cells, these the ddh- and deoxy-ddh compounds or prodrugs thereof can be converted (e.g. phosphorylation by one or more viral or cellular kinases).

Compounds

In some embodiments, provided herein is a compound represented by the structure of Formula B(i), Formula B(ii), Formula B(iii):

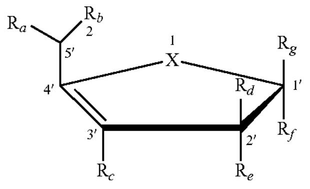

X is O, NH, $CH_2$, CH, $CCH_2$

Formula B(ii)

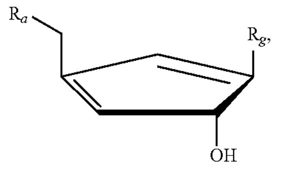

Formula B(iii)

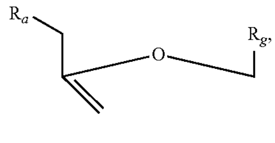

wherein $R_a$ is OH,

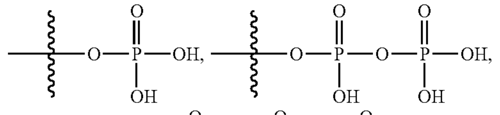

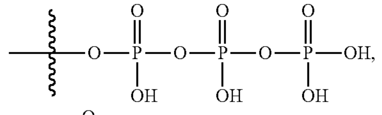

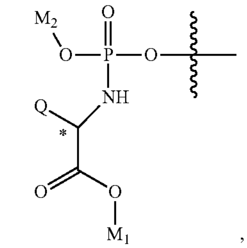

,

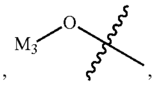

,

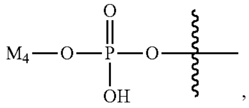

, or

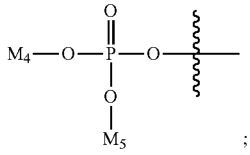

;

—OC(=O)$R^{12}$, —OC(=O)$OR^{12}$, —OC(=O)$NR^{12}R^{13}$, —OC(=O)$SR^{12}$, —OS(O)$R^{12}$, —OS$(O)_2R^{12}$, —OS(O)($OR^{12}$), —OS$(O)_2$($OR^{12}$), —$OSO_2NR^{12}R^{13}$ or the group of Formula (Ic)

Formula Ic

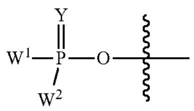

wherein

Y is O, S, NR, $^+$N(O)(R), N(OR), $^+$N(O)(OR), or N—NR;

$W^1$ and $W^2$, when taken together, are —$Y^3(C(R^y)_2)_3Y^3$—;

or one of $W^1$ and $W^2$ together with Rc is —$Y^3$— and the other of $W^1$ or $W^2$ is Formula Id;

or $W^1$ and $W^2$ are each, independently, a group of Formula Id:

Formula Id

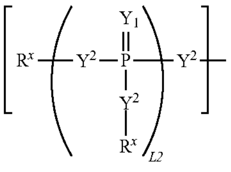

Wherein each $Y^1$ is independently O, S, NR, $^+$N(O)(R), N(OR), $^+$N(O)(OR), or N—$NR_2$;

each $Y^2$ is independently a bond, O, $CR_2$, NR, $^+$N(O)(R), N(OR), $^+$N(O)(OR), N—$NR_2$, S, S—S, S(O), or $S(O)_2$;

each $Y^3$ is independently O, S, or NR;

L2 is 0, 1, or 2;

Each $R^x$ is a group of Formula Ie:

Formula Ie

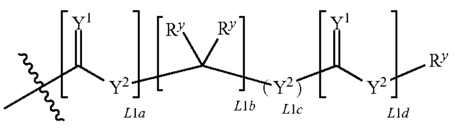

wherein each L1a, L1c, and L1d is independently O or 1;

L1b is 0, 1, 2, 3, 4, 5, 6, 7, 8, 9, 10, 11 or 12;

each $R^y$ is independently H, F, Cl, Br, I, —CN, —$N_3$, —$NO_2$, —OR, —$C(R)_2$—O—$C(R)_3$, —C(═$Y^1$)R, C(═$Y^1$)$R^{14}$, —C(═$Y^1$)OR, —C(═$Y^1$)$N(R)_2$, —$N(R)_2$, —$^+N(R)_3$, —SR, —S(O)R, —$S(O)_2$R, —S(O)$R^{14}$, —$S(O)_2R^{14}$, —S(O)(OR), $S(O)_2$(OR), —OC(═$Y^1$)R, —OC(═$Y^1$)OR, —OC(═$Y^1$)($N(R)_2$), —SC(═$Y^1$)R, —SC(═$Y^1$)OR, —SC(═$Y^1$)($N(R)_2$), —N(R)C(═$Y^1$)R, —N(R)C(═$Y^1$)OR, —N(R)C(═$Y^1$)$N(R)_2$, —$SO_2NR_2$, ($C_1$-$C_{18}$) alkyl, ($C_2$-$C_8$) alkenyl, ($C_2$-$C_8$) alkynyl, ($C_6$-$C_{20}$) aryl, ($C_3$-$C_{20}$) cycloalkyl, ($C_2$-$C_{20}$) heterocyclyl, arylalkyl, or heteroarylalkyl, wherein each ($C_1$-$C_8$) alkyl, ($C_2$-$C_8$) alkenyl, ($C_2$-$C_8$) alkynyl, ($C_6$-$C_{20}$) aryl, ($C_3$-$C_{20}$) cycloalkyl, ($C_2$-$C_{20}$) heterocyclyl, arylalkyl, or heteroarylalkyl is optionally substituted with 1-3 $R^{15}$ groups; or when taken together, two $R^y$ on the same carbon atom from a cycloalkyl ring of 3 to 7 carbon atoms;

each R is independently H, ($C_1$-$C_8$) alkyl, ($C_2$-$C_8$) alkenyl, ($C_2$-$C_8$) alkynyl, ($C_6$-$C_{20}$) aryl, ($C_3$-$C_{20}$) cycloalkyl, ($C_2$-$C_{20}$) heterocyclyl, or arylalkyl;

each $R^{12}$ or $R^{13}$ is independently H, ($C_1$-$C_8$) alkyl, ($C_2$-$C_8$) alkenyl, ($C_2$-$C_8$) alkynyl, ($C_4$-$C_8$) cycloalkylalkyl, ($C_3$-$C_{20}$) cycloalkyl, ($C_2$-$C_{20}$) heterocyclyl, optionally substituted aryl, optionally substituted heteroaryl, —C(═O)($C_1$-$C_8$)alkyl, —$S(O)_n$($C_1$-$C_8$)alkyl or aryl ($C_1$-$C_8$)alkyl; or $R^{12}$ and $R^{13}$ taken together with a nitrogen to which they are both attached form a 3- to 7-membered heterocyclic ring wherein any one carbon atom of said heterocyclic ring can optionally be replaced with —O—, —S—, or —$NR_{16}$—;

each $R^{14}$ is independently a cycloalkyl or heterocycle optionally substituted with 1-3 R or $R^{15}$ groups;

each $R^{15}$ is independently, halogen, CN, —$N_3$, —$N(R)_2$, OR, —SR, —S(O)R, —$S(O)_2$R, —S(O)(OR), —$S(O)_2$(OR), —C(═$Y^1$)R, —C(═$Y^1$)OR, or —C(═$Y^1$)$N(R)_2$;

Q is a side group of an amino acid;

$M_1$ is an alkyl;

$M_2$ is an aryl, a substituted aryl, a heteroaryl or a substituted heteroaryl;

$M_3$ is

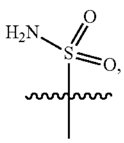, 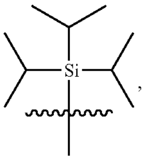, 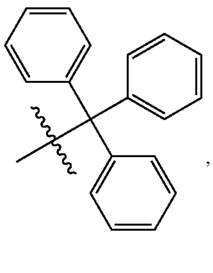, or

-continued

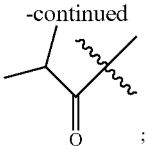;

$M_4$ is —($C_2$-$C_6$)alkyl-O—($C_{10}$-$C_{20}$)alkyl;

each $M_5$ is —$(CH_2)_n$—S—C(═O)—($C_1$-$C_8$)alkyl;

n is 1-4;

wherein each alkyl, alkenyl, alkynyl, aryl or heteroaryl of each of R, $R^{12}$, $R^{13}$, $M_1$ or $M_2$ is, independently, optionally substituted with 1 to 3 halo, hydroxy, CN, —$N_3$, $N(R^{16})$2 or $OR^{16}$; and wherein 1 to 3 of the non-terminal carbon atoms of each said ($C_1$-$C_8$) alkyl may be optionally replaced with —O—, —S—, or —$NR_{16}$—;

each $R^{16}$ is independently H, ($C_1$-$C_8$)alkyl, —($C_2$-$C_8$) alkenyl, ($C_2$-$C_8$)alkynyl, aryl($C_1$-$C_8$)alkyl, ($C_4$-$C_8$)cycloalkylalkyl, —C(═O)$R^{12}$, —C(═O)$OR^{12}$, —C(═O)$NR^{12}R^{13}$, —C(═O)$SR^{12}$, —S(O)$R^{12}$, —S(O)($OR^{12}$), —$S(O)_2$($OR^{12}$), or —$SO_2NR^{12}R^{13}$;

$R_b$ is H or ($C_1$-$C_6$) alkyl;

$R_c$ is H, or ($C_1$-$C_6$) alkyl;

$R_d$ is H, a halo, an alkyl, an alkyne, or —OH;

$R_e$ is H, —OH, —O—COO-alkyl, a halo or an alkoxy;

$R_f$ is H or —CN;

$R_g$ is

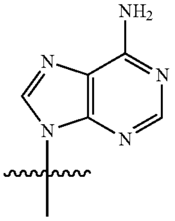, 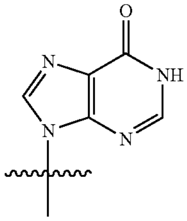,

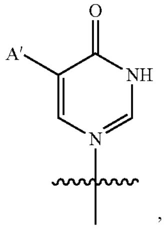, 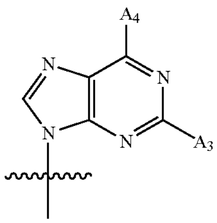,

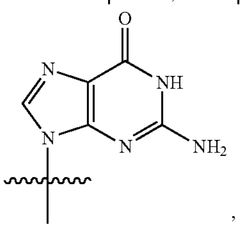, 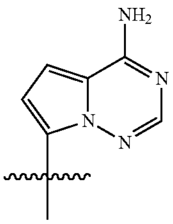,

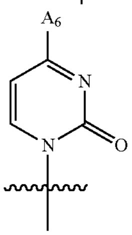, 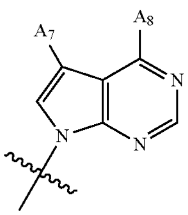, 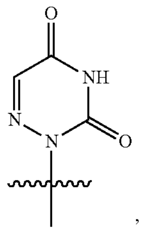,

-continued
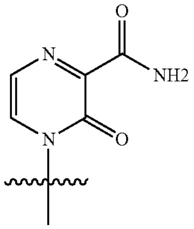 , 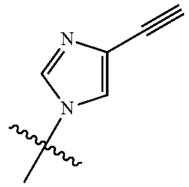 ,
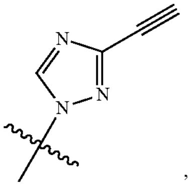 , 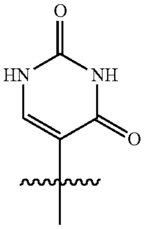 , 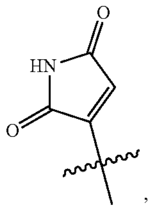 ,
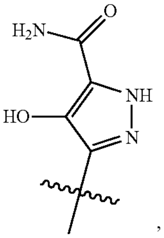 , 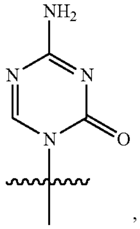 , 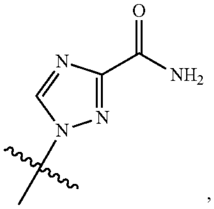 ,
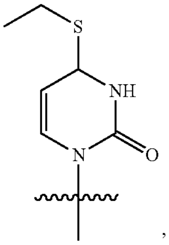 , 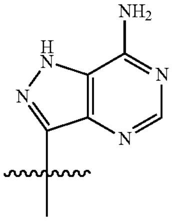 , 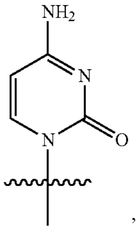 ,
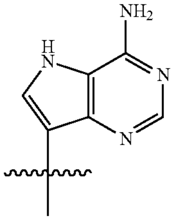 , 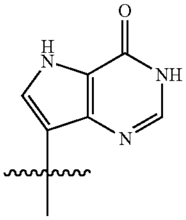 ,
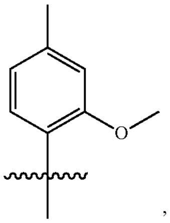 , 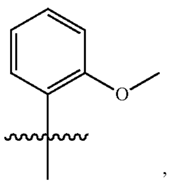 , 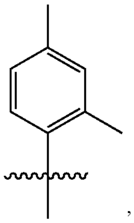 ,
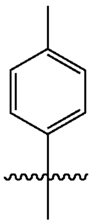 , 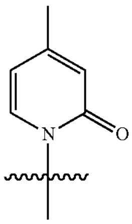 , 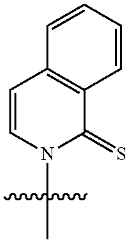 ,
-continued
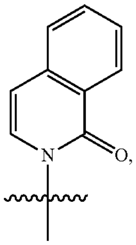 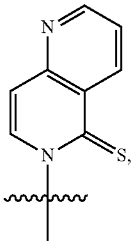 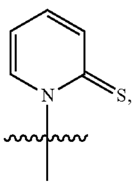
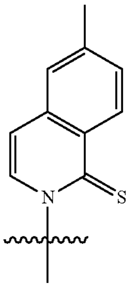 , 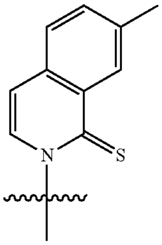 , or 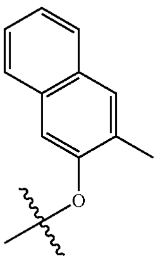 ;
wherein A' is H, a halo, a haloalkyl, an alkyl, a hydroxy, an alkyne or,
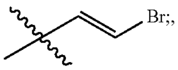 [SMILES: */C=C/Br]
$A_3$ is H, a halo or an amino; $A_4$ is H, an amino, an alkoxy or an alkyl; $A_6$ is H, an amino or an hydroxylamine; $A_7$ is H or an amido; $A_8$ is an amino or an alkyl.
In one embodiment, provided herein is a compound represented by the structure of Formula IB:
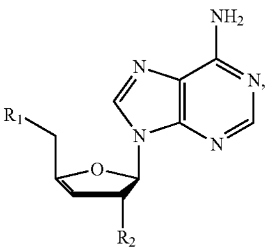
wherein
$R_1$ is OH,
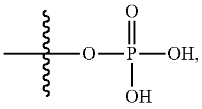 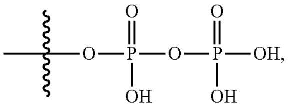
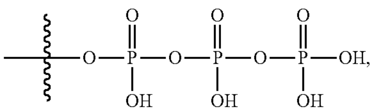

-continued

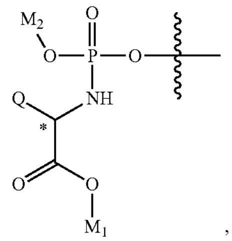
,
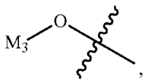
,
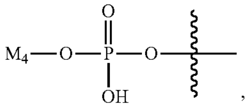
, or
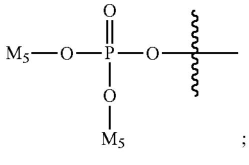
;

Q is a side chain of an amino acid;

$M_1$ is an alkyl;

$M_2$ is an aryl, a substituted aryl, a heteroaryl or a substituted heteroaryl;

$M_3$ is

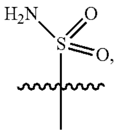
,
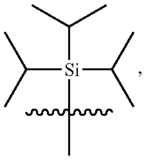
,
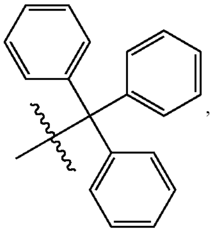
, or
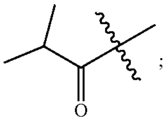
;

$M_4$ is —($C_2$-$C_6$)alkyl-O—($C_{10}$-$C_{20}$)alkyl;

each $M_5$ is —$(CH_2)_n$—S—C(═O)—($C_1$-$C_8$)alkyl;

n is 1-4;

$R_2$ is —OH or —O—COO-alkyl; and

In another embodiment, in the compound of Formula IB, if $R_1$ is OH, then $R_2$ is —O—COO-alkyl.

In another embodiment, a compound of Formula IB, is represented by the structure of Compound 1:

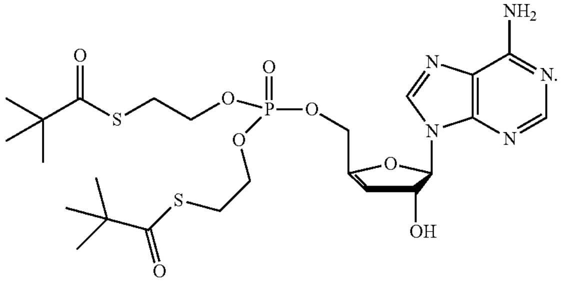 [SMILES: CC(C)(C)C(=O)SCCOP(=O)(OCCSC(=O)C(C)(C)C)OCC1=C[C@H](O)[C@H](n2cnc3c(N)ncnc32)O1]

In one embodiment, provided herein is a compound represented by the structure of Formula IIB:

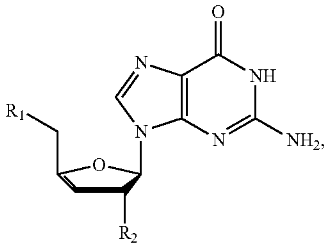

wherein $R_1$ and $R_2$ are as described in Formula IB. In another embodiment, in the compound of Formula IIB, if $R_1$ is OH, then $R_2$ is —O—COO-alkyl.

In another embodiment, a compound of Formula IB, is represented by the structure of Compound 2:

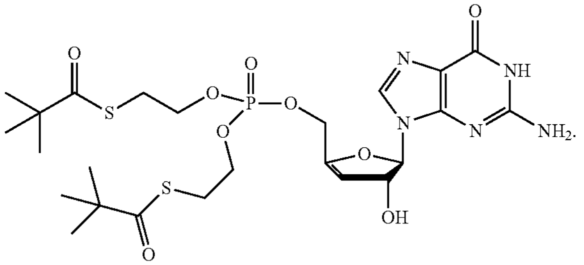 [SMILES: CC(C)(C)C(=O)SCCOP(=O)(OCCSC(=O)C(C)(C)C)OCC1=C[C@H](O)[C@H](n2cnc3c(=O)[nH]c(N)nc32)O1]

In another embodiment, a compound of Formula IIB, is represented by the structure of Compound 33:

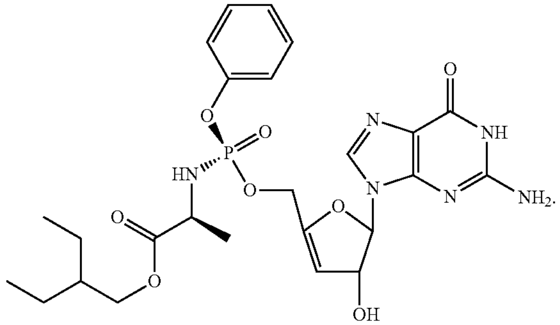 [SMILES: CCC(CC)COC(=O)[C@H](C)N[P@](=O)(OCC1=CC(O)C(n2cnc3c(=O)[nH]c(N)nc32)O1)Oc1ccccc1]

In another embodiment, a compound of Formula IIB, is represented by the structure of Compound 31:

(AB21651)

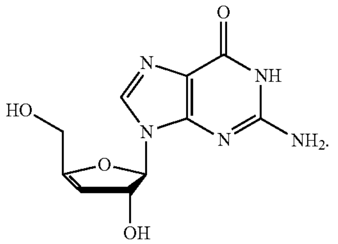

In another embodiment, a compound of Formula IIB, is represented by the structure of Compound 103:

(AB23040)

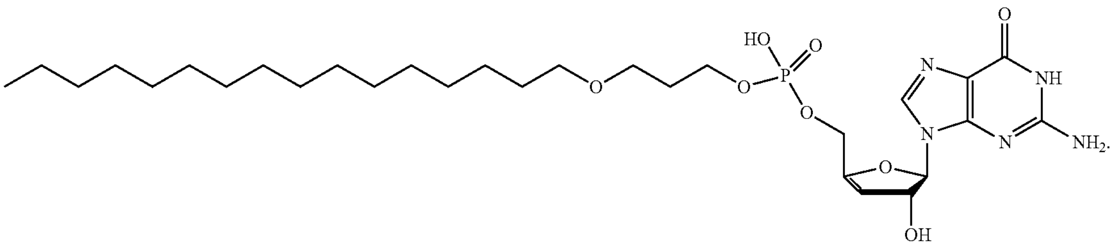

In one embodiment, provided herein is a compound represented by the structure of Formula IIIB:

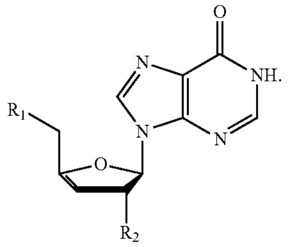

wherein $R_1$ and $R_2$ are as described in Formula IB. In another embodiment, in the compound of Formula IIIB, if $R_1$ is OH, then $R_2$ is —O—COO-alkyl.

In another embodiment, a compound of Formula IIIB, is represented by the structure of Compound 3:

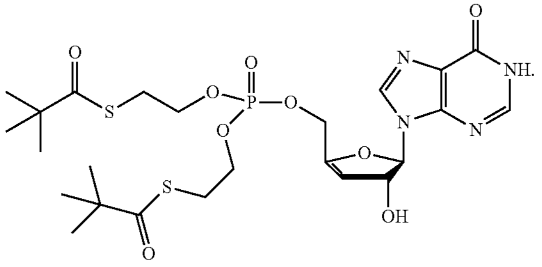 [SMILES: CC(C)(C)C(=O)SCCOP(=O)(OCCSC(=O)C(C)(C)C)OCC1=C[C@H](O)[C@H](n2cnc3c(=O)[nH]cnc32)O1]

In one embodiment, provided herein is a compound, represented by the structure of Formula IVB:

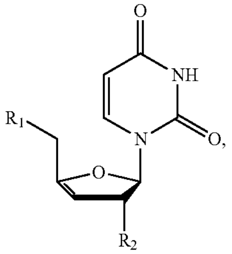

wherein $R_1$ and $R_2$ are as described in Formula IB. In another embodiment, in the compound of Formula IVB, if $R_1$ is OH, then $R_2$ is —O—COO-alkyl.

In another embodiment, a compound of Formula IVB, is represented by the structure of Compound 4:

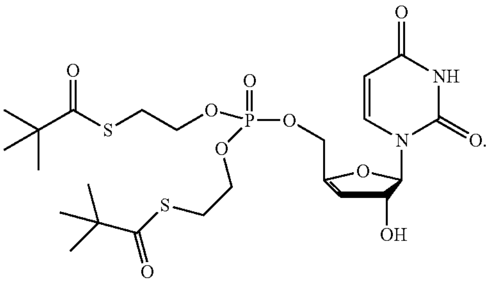 [SMILES: CC(C)(C)C(=O)SCCOP(=O)(OCCSC(=O)C(C)(C)C)OCC1=C[C@H](O)[C@H](n2ccc(=O)[nH]c2=O)O1]

In another embodiment, a compound of Formula IVB, is represented by the structure of Compound 26:

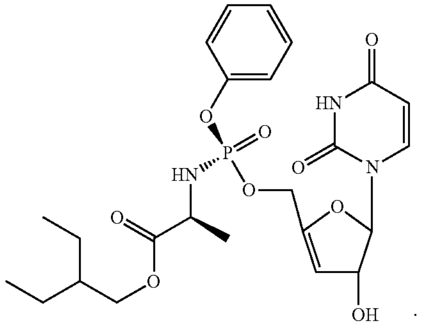 [SMILES: CCC(CC)COC(=O)[C@H](C)N[P@](=O)(OCC1=CC(O)C(n2ccc(=O)[nH]c2=O)O1)Oc1ccccc1]

In another embodiment, a compound of Formula IVB, is represented by the structure of Compound 24:

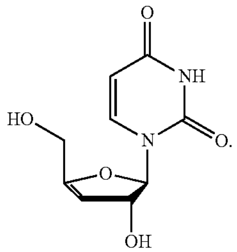 [SMILES: O=c1ccn([C@@H]2OC(CO)=C[C@@H]2O)c(=O)[nH]1]

In another embodiment, a compound of Formula IVB, is represented by the structure of Compound 104:

(AB23039)

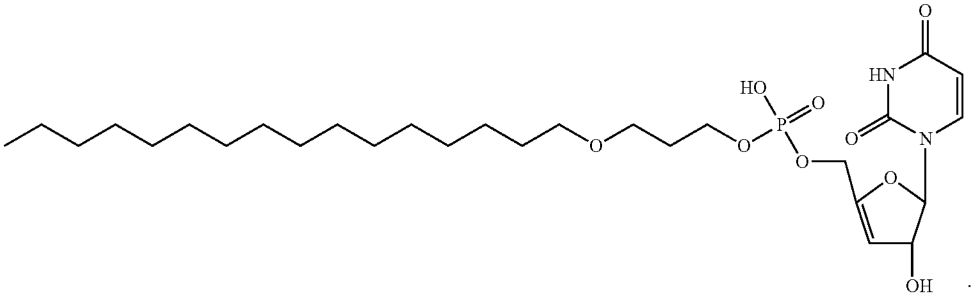

In one embodiment, provided herein is a compound represented by the structure of Formula VB:

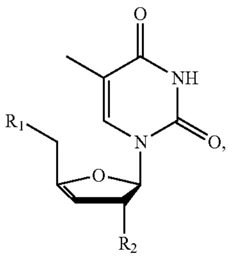

wherein $R_1$ and $R_2$ are as described in Formula IB. In another embodiment, in the compound of Formula VB, if $R_1$ is OH, then $R_2$ is —O—COO-alkyl.

In one embodiment, provided herein is a compound represented by the structure of Formula IB, IIB, IIIB, IVB, or VB, wherein R1 and R2 are as described in Formula IB. In another embodiment, in the compound represented by the structure of Formula IB, IIB, IIIB, IVB, or VB, if $R_1$ is OH, then $R_2$ is —O—COO-alkyl.

In one embodiment, provided herein is a compound represented by the structure of Formula VB1:

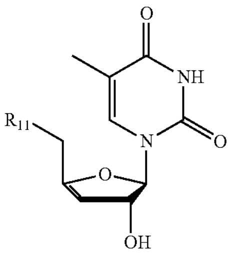

wherein $R_{11}$ is

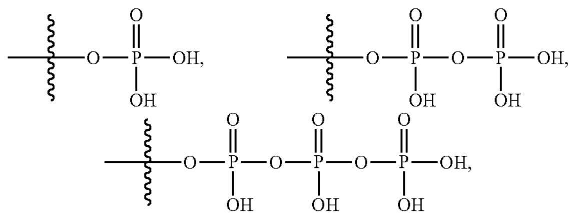

-continued

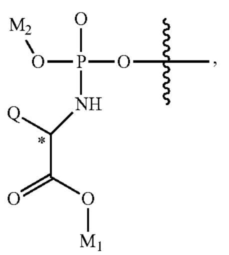

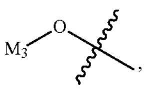

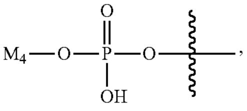

or

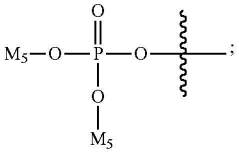

Q is a side chain of an amino acid;

$M_1$ is an alkyl;

$M_2$ is an aryl, a substituted aryl, a heteroaryl or a substituted heteroaryl;

$M_3$ is

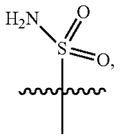

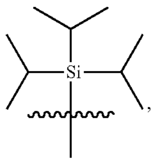

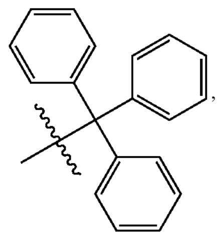

or

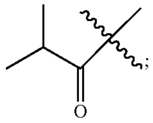

$M_4$ is —$(C_2$-$C_6)$alkyl-O—$(C_{10}$-$C_{20})$alkyl;

each $M_5$ is —$(CH_2)_n$—S—C(═O)—$(C_1$-$C_8)$alkyl; and n is 1-4.

In one embodiment, provided herein is a compound represented by the structure of Formula VIB:

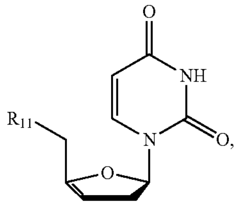

wherein $R_{11}$ is

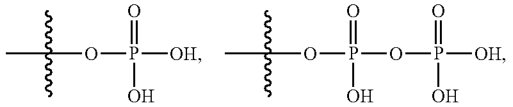

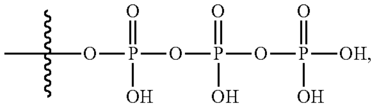

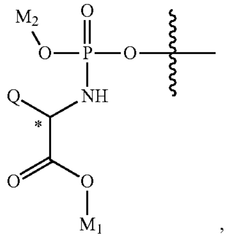

,

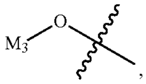

,

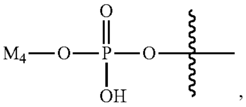

, or

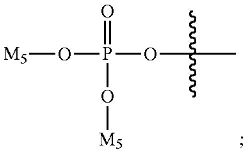

;

Q is a side chain of an amino acid;

$M_1$ is an alkyl;

$M_2$ is an aryl, a substituted aryl, a heteroaryl or a substituted heteroaryl;

$M_3$ is

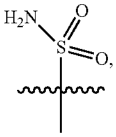

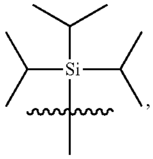

,

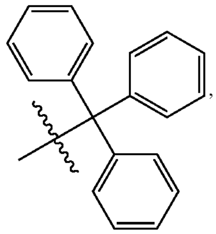

, or

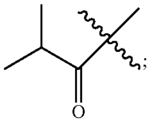

;

$M_4$ is $-(C_2\text{-}C_6)$alkyl-O$-(C_{10}\text{-}C_{20})$alkyl;

each $M_5$ is $-(CH_2)_n-S-C(=O)-(C_1\text{-}C_8)$alkyl; and n is 1-4.

In another embodiment, a compound of Formula VIB, is represented by the structure of Compound 5:

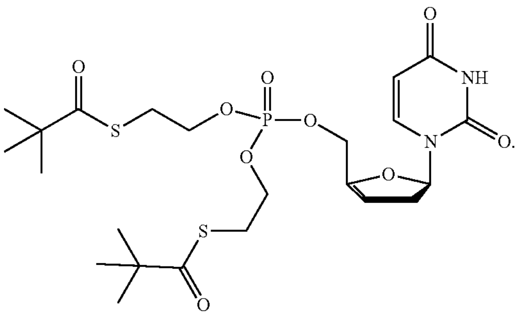

In one embodiment, provided herein is a compound represented by the structure of Formula VIIB:

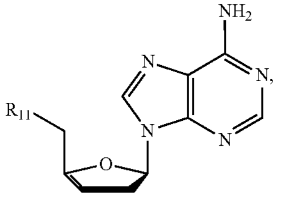

wherein $R_{11}$ is as described in Formula VIB.

In one embodiment, provided herein is a compound represented by the structure of Formula VIIIB:

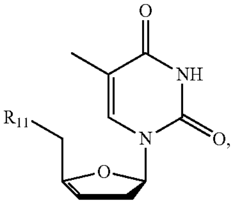

wherein $R_{11}$ is as described in Formula VIB.

In some embodiments, provided herein is a compound represented by the structure of Formula VIB, Formula VIIB, or Formula VIIIB, wherein $R_{11}$ is as described in Formula VIB.

In one embodiment, provided herein is a compound represented by the structure of Formula IXB:

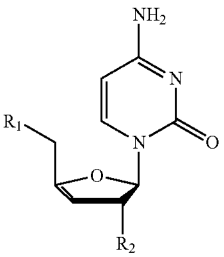

wherein $R_1$ is OH,

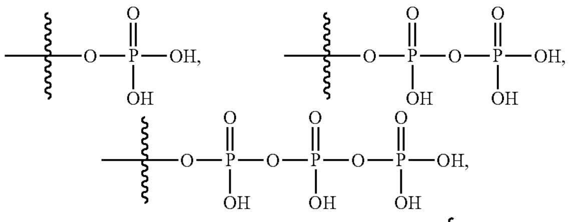

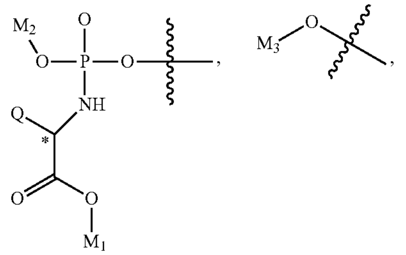

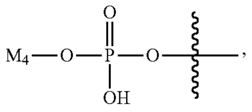

or

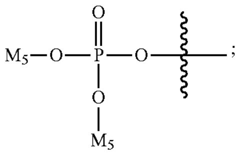

Q is a side chain of an amino acid;

$M_1$ is an alkyl;

$M_2$ is an aryl, a substituted aryl, a heteroaryl or a substituted heteroaryl;

$M_3$ is

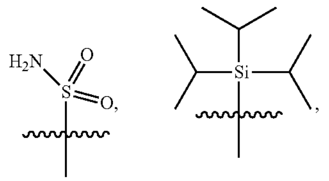

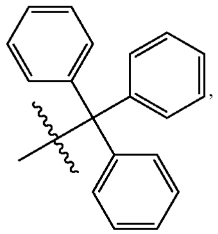

or

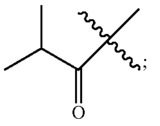

$M_4$ is —($C_2$-$C_6$)alkyl-O—($C_{10}$-$C_{20}$)alkyl;

each $M_5$ is —$(CH_2)_n$—S—C(═O)—($C_1$-$C_8$)alkyl;

n is 1-4; and $R_2$ is —OH or —O—COO-alkyl.

In another embodiment, in the compound of Formula IXB, if $R_1$ is OH or

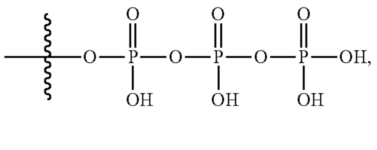 [SMILES: *OP(=O)(O)OP(=O)(O)OP(=O)(O)O]

then $R_2$ is not OH.

In another embodiment, a compound of Formula IXB, is represented by the structure of Compound 6:

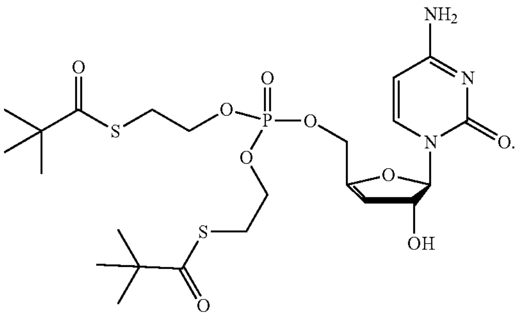 [SMILES: CC(C)(C)C(=O)SCCOP(=O)(OCCSC(=O)C(C)(C)C)OCC1=C[C@H](O)[C@H](n2ccc(N)nc2=O)O1]

In one embodiment, provided herein is a compound represented by the structure of Formula XB:

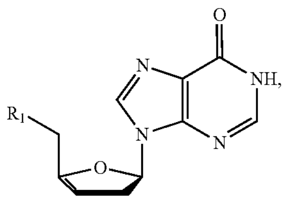

wherein $R_1$ is OH,

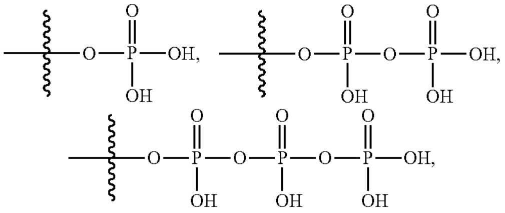

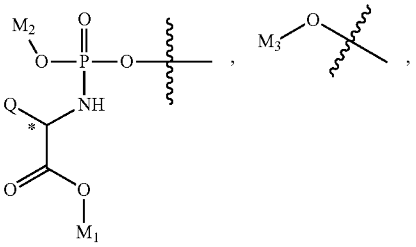

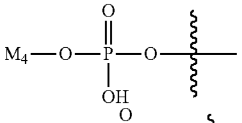

, or

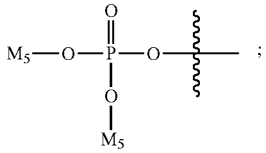

Q is a side chain of an amino acid; $M_1$ is an alkyl;

$M_2$ is an aryl, a substituted aryl, a heteroaryl or a substituted heteroaryl;

$M_3$ is

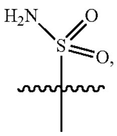, 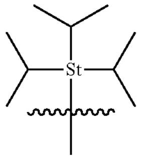,

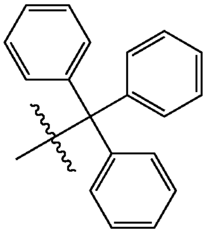, or 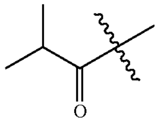;

$M_4$ is —$(C_2$-$C_6)$alkyl-O—$(C_{10}$-$C_{20})$alkyl;

each $M_5$ is —$(CH_2)_n$—S—C(═O)—$(C_1$-$C_8)$alkyl; and n is 1-4.

In one embodiment, provided herein is a compound, represented by the structure of Formula XIB:

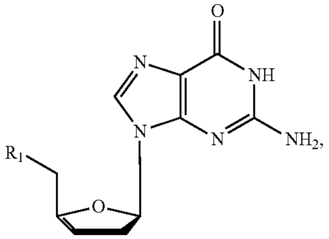

wherein $R_1$ is as described in Formula XB.

In one embodiment, provided herein is a compound, represented by the structure of Formula XIIB:

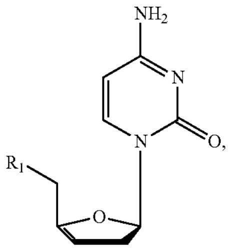

wherein $R_1$ is as described in Formula XB.

In one embodiment, provided herein is a compound, represented by the structure of Formula XB, Formula XIB, or Formula XIIB, wherein $R_1$ is as described in Formula XB.

In one embodiment, provided herein is a compound, represented by the structure of formula XIIIB:

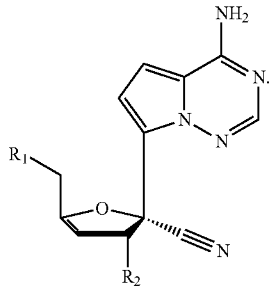

$R_1$ is OH,

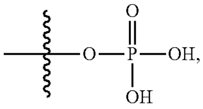 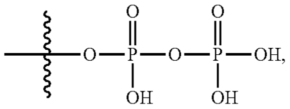

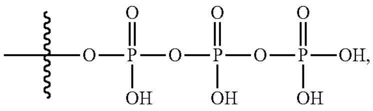

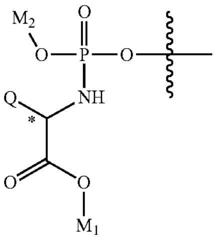, 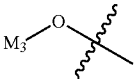,

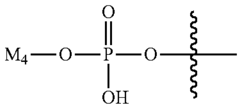, or

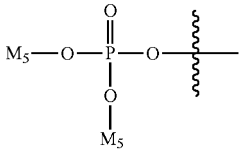;

Q is a side chain of an amino acid;

$M_1$ is an alkyl;

$M_2$ is an aryl, a substituted aryl, a heteroaryl or a substituted heteroaryl;

$M_3$ is

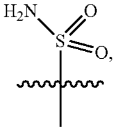, 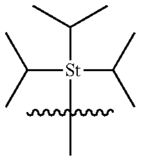,

-continued

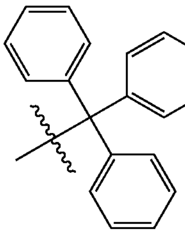
, or
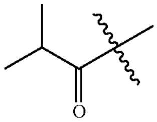
;

$M_4$ is —($C_2$-$C_6$)alkyl-O—($C_{10}$-$C_{20}$)alkyl;

each $M_5$ is —$(CH_2)_n$—S—C(═O)—($C_1$-$C_8$)alkyl;

n is 1-4; and $R_2$ is —OH or —O—COO-alkyl.

In another embodiment a compound of Formula XIIIB, is represented by the structure of Formula XIIIB1:

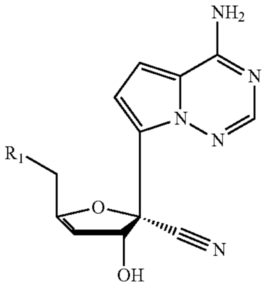

wherein $R_1$ is as defined in the structure of Formula XIIIB.

In another embodiment, a compound of Formula XIIIB1, is represented by the structure of Compound 100:

(AB23050)

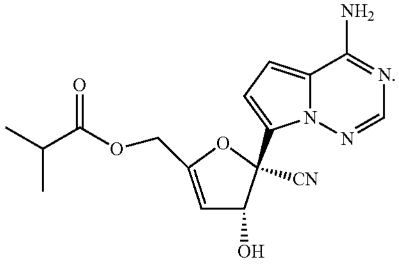

In another embodiment, a compound of Formula XIIIB1, is represented by the structure of Compound 101:

(AB23046)

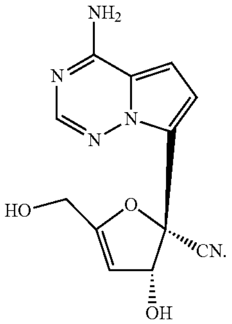

In another embodiment, a compound of Formula XIIIB1, is represented by the structure of Compound 102:

(AB23048)

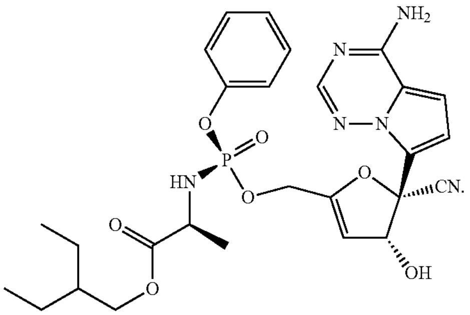

In one embodiment, provided herein is a compound represented by the structure of Formula XIVB

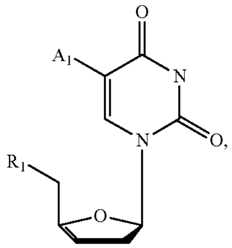

wherein $R_1$ is OH,

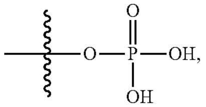
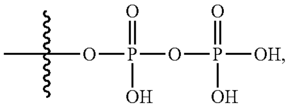
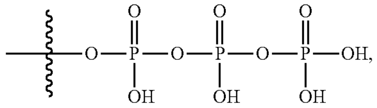
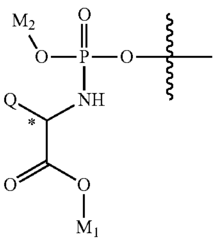
,
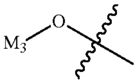
,
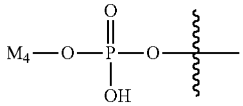
, or
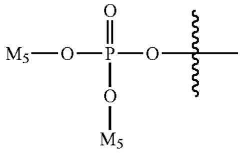
;

Q is a side chain of an amino acid;

$M_1$ is an alkyl;

$M_2$ is an aryl, a substituted aryl, a heteroaryl or a substituted heteroaryl;

$M_3$ is;

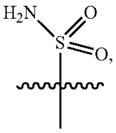,
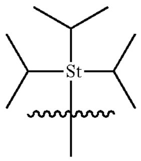,

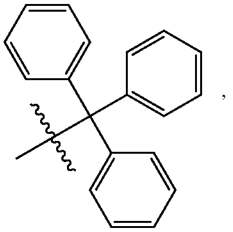, or 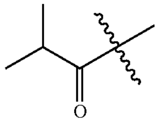;

$M_4$ is —$(C_2\text{-}C_6)$alkyl-O—$(C_{10}\text{-}C_{20})$alkyl;

each $M_5$ is —$(CH_2)_n$—S—C(═O)—$(C_1\text{-}C_8)$alkyl;

n is 1-4; and $A_1$ is a halo a haloalkyl, an alkyl, or

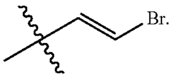.

In another embodiment a compound of Formula XIVB, is represented by the structure of Formula XIVB1:

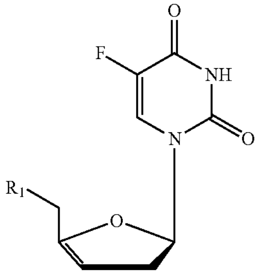

wherein $R_1$ is as defined in the structure of Formula XIVB.

In another embodiment a compound of Formula XIVB, is represented by the structure of Formula XIVB2:

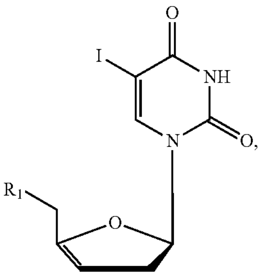, wherein $R_1$ is as defined in the structure of Formula XIVB.

In another embodiment a compound of Formula XIVB, is represented by the structure of Formula XIVB3:

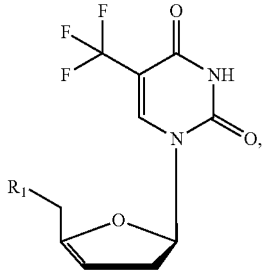, wherein $R_1$ is as defined in the structure of Formula XIVB.

In another embodiment a compound of Formula XIVB, is represented by the structure of Formula XIVB4:

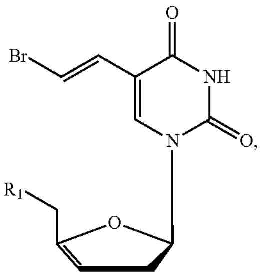, wherein $R_1$ is as defined in the structure of Formula XIVB.

In one embodiment, provided herein is a compound of Formula XIVB, represented by the structure of Formula XIVB5:

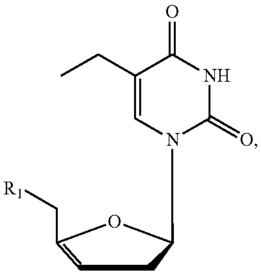, wherein R1 is represented XIVB.

In one embodiment, provided herein is a compound represented by the structure of Formula XVB:

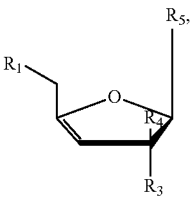, wherein $R_1$ is OH,

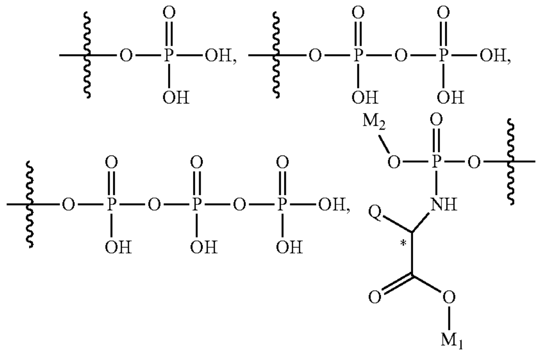

or

;

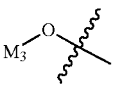

Q is a side chain of an amino acid;

$M_1$ is an alkyl;

$M_2$ is an aryl, a substituted aryl, a heteroaryl or a substituted heteroaryl;

$M_3$ is

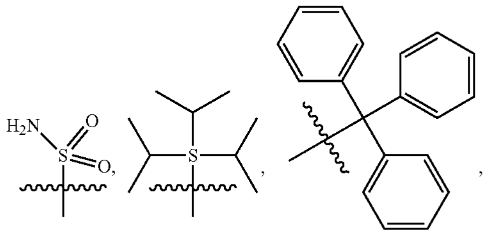

, or

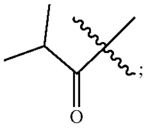

;

$M_4$ is $-(C_2\text{-}C_6)$alkyl-O$-(C_{10}\text{-}C_{20})$alkyl;

each $M_5$ is $-(CH_2)_n-S-C(=O)-(C_1\text{-}C_8)$alkyl; wherein n is 1-4;

$R_3$ is H, a halo or an alkoxy;

$R_4$ is H, a halo or an alkyl;

$R_5$ is

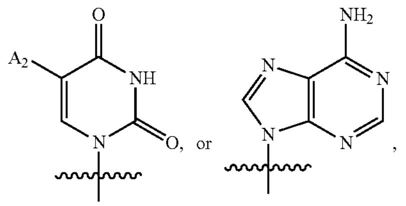

and wherein $A_2$ is selected from the group consisting of H, a halo or an alkyl.

In another embodiment, in the compound of Formula XVB, $R_3$ is not the same as $R_4$.

In another embodiment, a compound of Formula XVB, is represented by the structure of Formula XVB1:

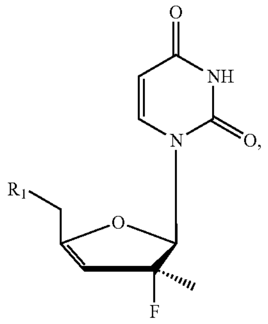

wherein $R_1$ is as defined in the structure of Formula XVB.

In another embodiment, a compound of Formula XVB, is represented by the structure of Formula XVB2:

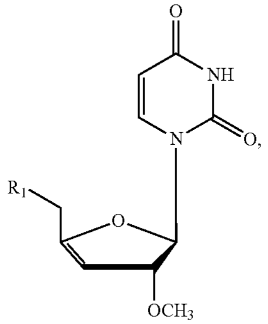

wherein $R_1$ is as defined in the structure of Formula XVB.

In another embodiment, a compound of Formula XVB, is represented by the structure of Formula XVB3:

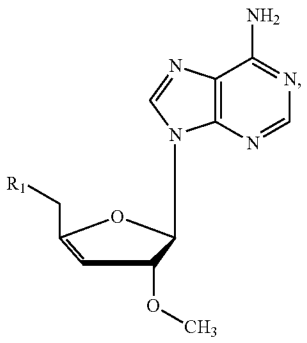

wherein $R_1$ is as defined in the structure of Formula XVB.

In another embodiment, a compound of Formula XVB, is represented by the structure of Formula XVB4:

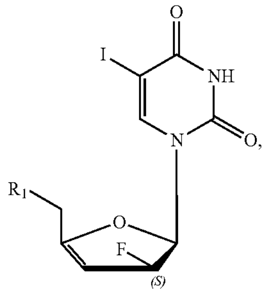

wherein $R_1$ is as defined in the structure of Formula XVB. In another embodiment, a compound of Formula XVB, is represented by the structure of Formula XVB5

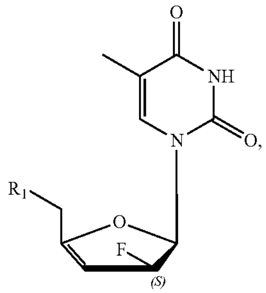

wherein $R_1$ is as defined in the structure of Formula XVB. In another embodiment, a compound of Formula XVB, is represented by the structure of Formula XVB6

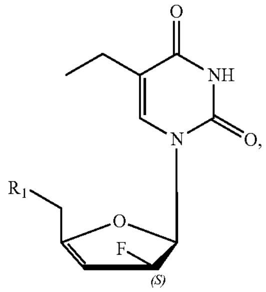

wherein $R_1$ is as defined in the structure of Formula XVB.

In one embodiment, provided herein is a compound represented by the structure of Formula XVIB,

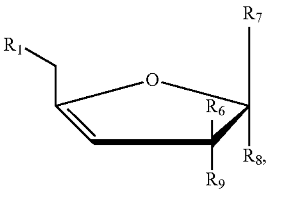

wherein $R_1$ is of OH,

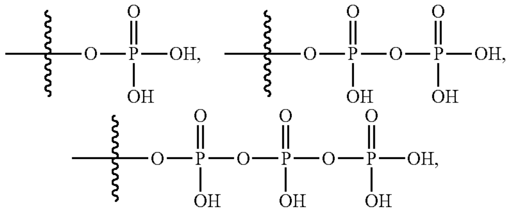

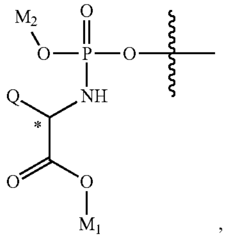

,

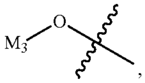

,

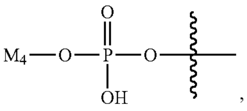

, or

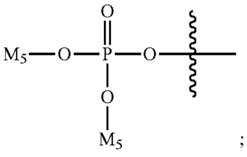

;

Q is a side chain of an amino acid;

$M_1$ is an alkyl;

$M_2$ is selected from the group consisting of an aryl, a substituted aryl, a heteroaryl or a substituted heteroaryl;

$M_3$ is

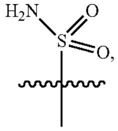

,

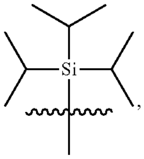

,

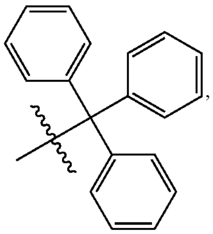

, or

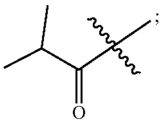

;

$M_4$ is $-(C_2\text{-}C_6)$alkyl-O$-(C_{10}\text{-}C_{20})$alkyl;

each $M_5$ is $-(CH_2)_n-S-C(=O)-(C_1\text{-}C_8)$alkyl;

n is 1-4;

$R_9$ is H, OH, or —O—COO-alkyl;

$R_6$ is H, Me, —CCH or OH;

$R_8$ is H;

$R_7$ is

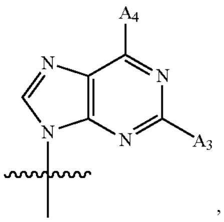

,

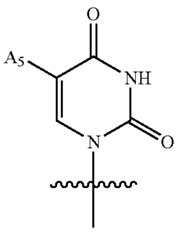

,

-continued

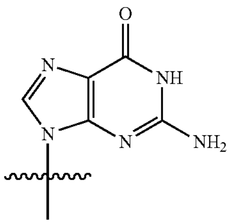
,
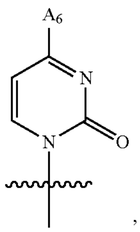
,
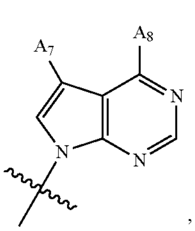
,
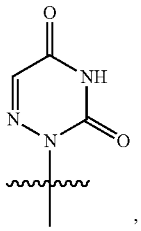
,
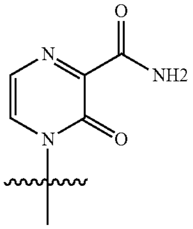
,
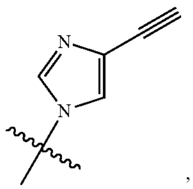
,
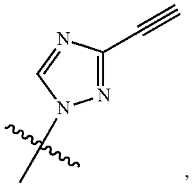
,
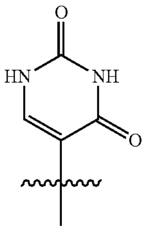
,
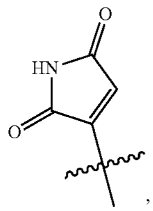
,
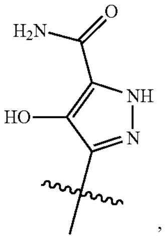
,
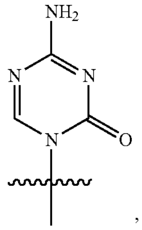
,
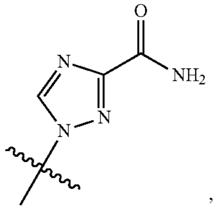
,
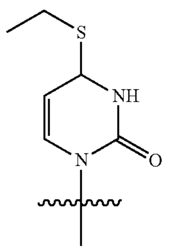
or
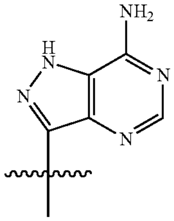
, wherein $A_3$ is H, a halo or an amino; $A_4$ is H, an amino, an alkoxy, or an alkyl; $A_5$ is H, a halo, a hydroxy or an alkyne; $A_6$ is H, an amino or a hydroxylamino; $A_7$ is H or an amido; and $A_8$ is an amino or an alkyl. In another embodiment, in the compound of Formula XVIB if $R_1$ is OH and $R_7$ is

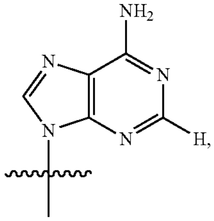
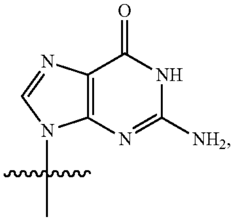
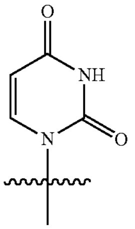
or
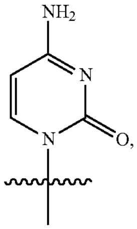

and $R_9$ is OH then $R_6$ is not H. In another embodiment, in the compound of Formula XVIB if $R_1$ is

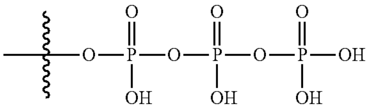 [SMILES: *OP(=O)(O)OP(=O)(O)OP(=O)(O)O]

and $R_7$ is

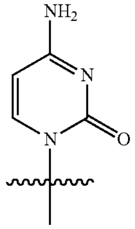 [SMILES: *n1ccc(N)nc1=O]

and $R_9$ is OH, then $R_6$ is not H.

In another embodiment of formula XVIB, the compound is represented by the structure of Formula XVIB1

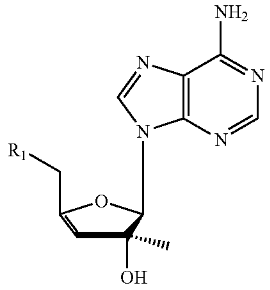

wherein $R_1$ is as defined in the structure of Formula XVIB. In another embodiment a compound of Formula XVIB, is represented by the structure of Formula XVIB2

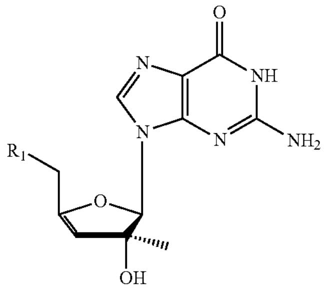

wherein $R_1$ is as defined in the structure of Formula XVIB. In another embodiment a compound of Formula XVIB, is represented by the structure of Formula XVIB3

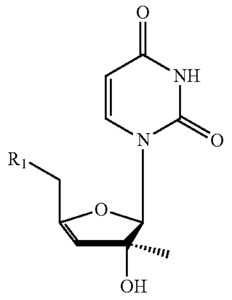

wherein $R_1$ is as defined in the structure of Formula XVIB. In another embodiment a compound of Formula XVIB, is represented by the structure of Formula XVIB4

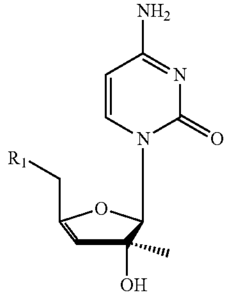

wherein $R_1$ is as defined in the structure of Formula XVIB. In another embodiment a compound of Formula XVIB, is represented by the structure of Formula XVIB5

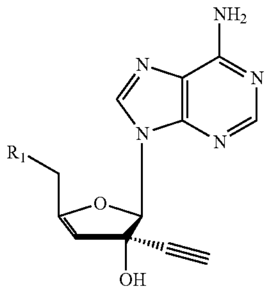

wherein $R_1$ is as defined in the structure of Formula XVIB. In another embodiment a compound of Formula XVIB, is represented by the structure of Formula XVIB6

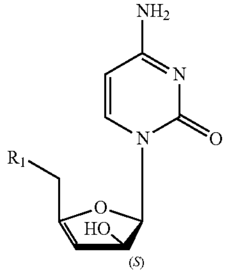

wherein $R_1$ is as defined in the structure of Formula XVIB. In another embodiment a compound of Formula XVIB, is represented by the structure of Formula XVIB7

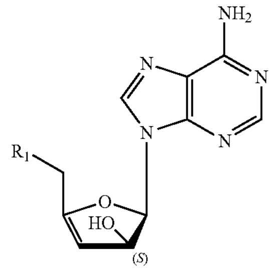

wherein $R_1$ is as defined in the structure of Formula XVIB. In another embodiment a compound of Formula XVIB, is represented by the structure of Formula XVIB8

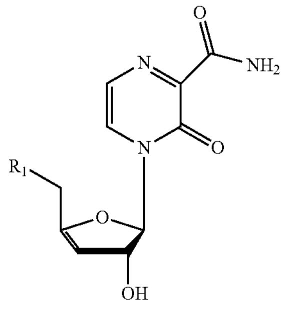

wherein $R_1$ is as defined in the structure of Formula XVIB. In another embodiment a compound of Formula XVIB, is represented by the structure of Formula XVIB9

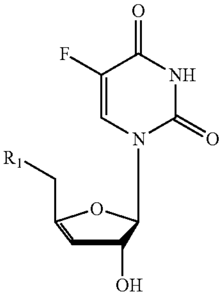

wherein $R_1$ is as defined in the structure of Formula XVIB. In another embodiment a compound of Formula XVIB, is represented by the structure of Formula XVIB10

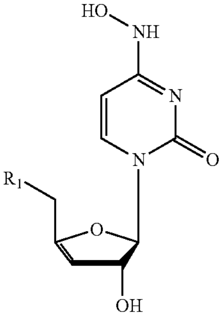

wherein $R_1$ is as defined in the structure of Formula XVIB. In another embodiment a compound of Formula XVIB, is represented by the structure of Formula XVIB11

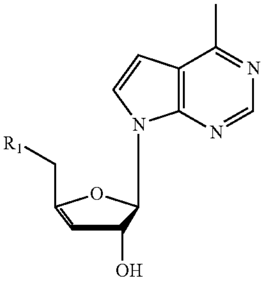

wherein $R_1$ is as defined in the structure of Formula XVIB. In another embodiment a compound of Formula XVIB, is represented by the structure of Formula XVIB12

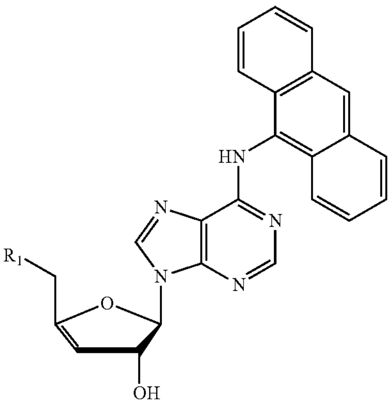

wherein $R_1$ is as defined in the structure of Formula XVIB. In another embodiment a compound of Formula XVIB, is represented by the structure of Formula XVIB13

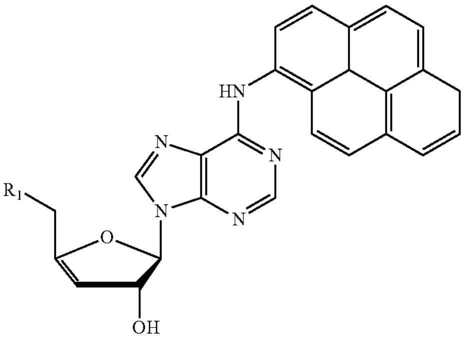

wherein $R_1$ is as defined in the structure of Formula XVIB. In another embodiment a compound of Formula XVIB, is represented by the structure of Formula XVIB14

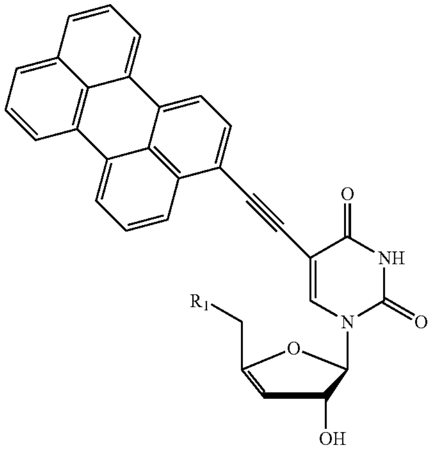

wherein $R_1$ is as defined in the structure of Formula XVIB. In another embodiment a compound of Formula XVIB, is represented by the structure of Formula XVIB15

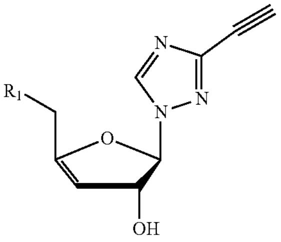

wherein $R_1$ is as defined in the structure of Formula XVIB. In another embodiment a compound of Formula XVIB, is represented by the structure of Formula XVIB16

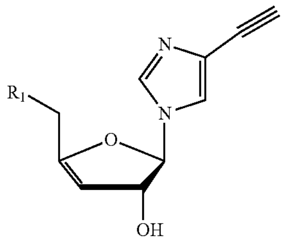

wherein $R_1$ is as defined in the structure of Formula XVIB. In another embodiment a compound of Formula XVIB, is represented by the structure of Formula XVIB17

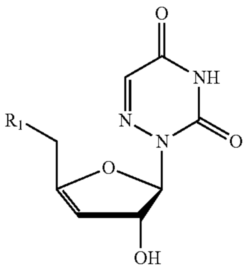

wherein $R_1$ is as defined in the structure of Formula XVIB. In another embodiment a compound of Formula XVIB, is represented by the structure of Formula XVIB18

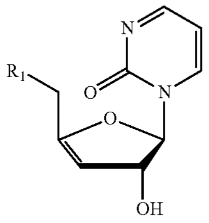

wherein $R_1$ is as defined in the structure of Formula XVIB. In another embodiment a compound of Formula XVIB, is represented by the structure of Formula XVIB19

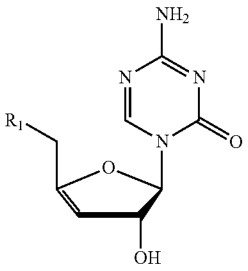

wherein $R_1$ is as defined in the structure of Formula XVIB. In another embodiment a compound of Formula XVIB, is represented by the structure of Formula XVIB20

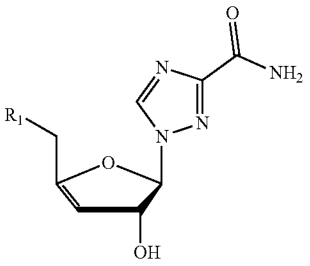

wherein $R_1$ is as defined in the structure of Formula XVIB. In another embodiment a compound of Formula XVIB, is represented by the structure of Formula XVIB21

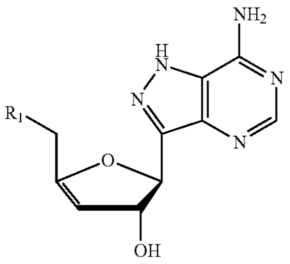

wherein $R_1$ is as defined in the structure of Formula XVIB. In another embodiment a compound of Formula XVIB, is represented by the structure of Formula XVIB22

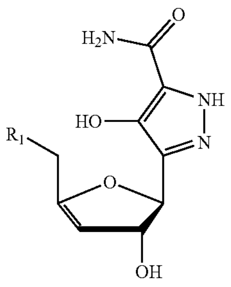

wherein $R_1$ is as defined in the structure of Formula XVIB. In another embodiment a compound of Formula XVIB, is represented by the structure of Formula XVIB23

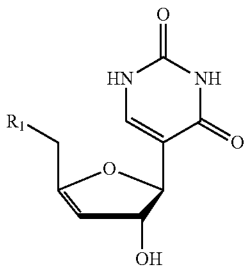

wherein $R_1$ is as defined in the structure of Formula XVIB. In another embodiment a compound of Formula XVIB, is represented by the structure of Formula XVIB24

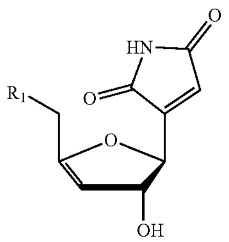

wherein $R_1$ is as defined in the structure of Formula XVIB. In another embodiment a compound of Formula XVIB, is represented by the structure of Formula XVIB25

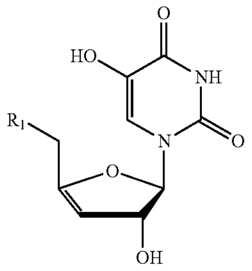

wherein $R_1$ is as defined in the structure of Formula XVIB. In another embodiment a compound of Formula XVIB, is represented by the structure of Formula XVIB26

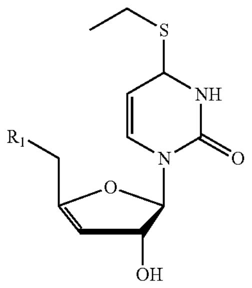

wherein $R_1$ is as defined in the structure of Formula XVIB. In another embodiment a compound of Formula XVIB, is represented by the structure of Formula XVIB27

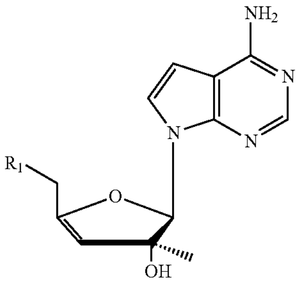

wherein $R_1$ is as defined in the structure of Formula XVIB. In another embodiment a compound of Formula XVIB, is represented by the structure of Formula XVIB28

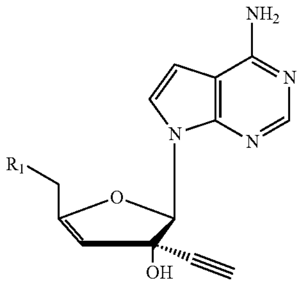

wherein $R_1$ is as defined in the structure of Formula XVIB. In another embodiment a compound of Formula XVIB, is represented by the structure of Formula XVIB29

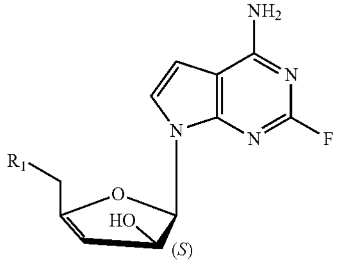

wherein $R_1$ is as defined in the structure of Formula XVIB. In another embodiment a compound of Formula XVIB, is represented by the structure of Formula XVIB30

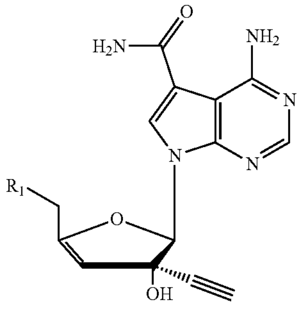

wherein $R_1$ is as defined in the structure of Formula XVIB. In another embodiment a compound of Formula XVB, is represented by the structure of Formula XVB31

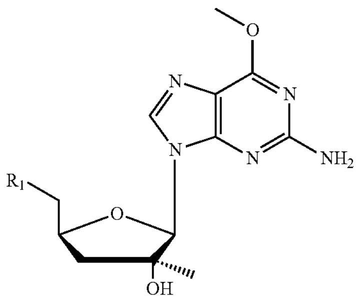

wherein $R_1$ is as defined in the structure of Formula XVIB. In another embodiment a compound of Formula XVIB, is represented by the structure of Formula XVIB32

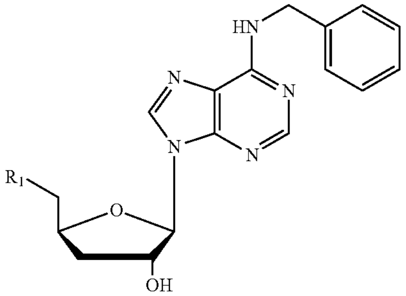

wherein $R_1$ is as defined in the structure of Formula XVIB. In another embodiment a compound of Formula XVIB, is represented by the structure of Formula XVIB33

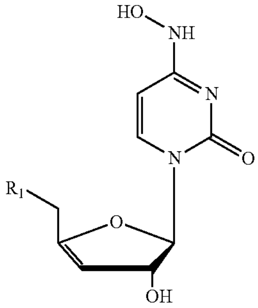

wherein $R_1$ is as defined in the structure of Formula XVIB.

In one embodiment, provided herein is a compound represented by the structure of Formula XVIIB,

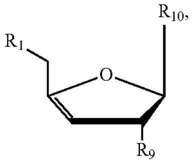

wherein $R_1$ is OH,

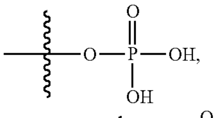

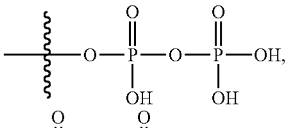

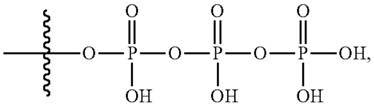

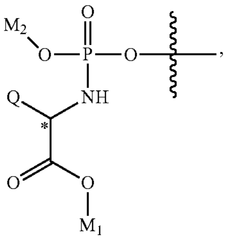

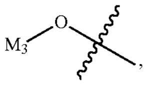

-continued

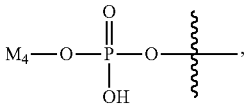 or

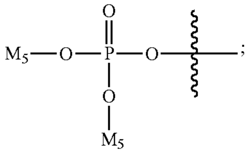

Q is a side chain of an amino acid;

$M_1$ is an alkyl;

$M_2$ is an aryl, a substituted aryl, a heteroaryl or a substituted heteroaryl;

$M_3$ is

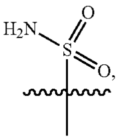

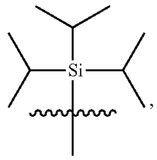

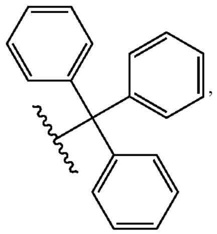 or 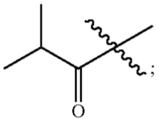

$M_4$ is $-(C_2-C_6)$alkyl-O$-(C_{10}-C_{20})$alkyl;

each $M_5$ is $-(CH_2)_n-S-C(=O)-(C_1-C_8)$alkyl;

n is 1-4;

$R_9$ is H, OH or —O—COO-alkyl; and $R_{10}$ is

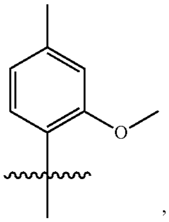 , 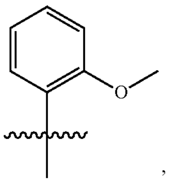 , 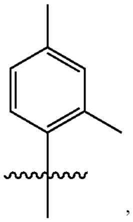 ,

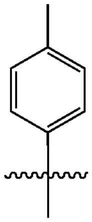 , 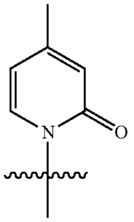 , 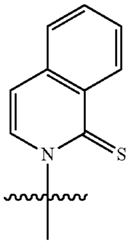 ,

-continued

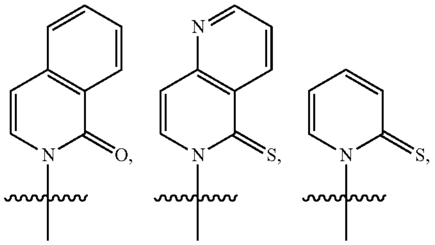

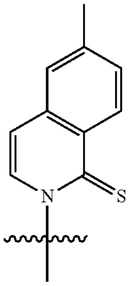
,
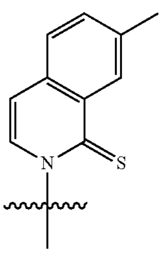
, or
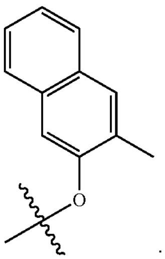
.

In one embodiment, provided herein is a compound, represented by the structure of Formula XVIIIB:

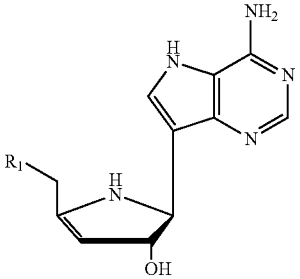

wherein $R_1$ is OH,

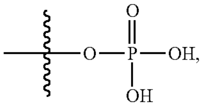

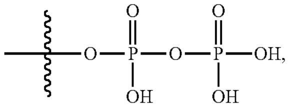

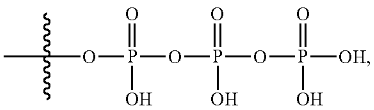

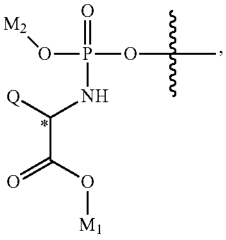
,
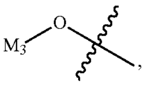
,
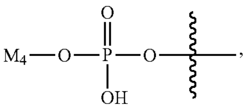
, or

-continued

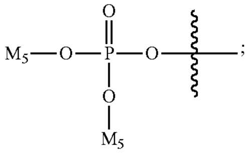
;

Q is a side chain of an amino acid;

$M_1$ is an alkyl;

$M_2$ is an aryl, a substituted aryl, a heteroaryl or a substituted heteroaryl;

$M_3$ is

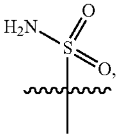

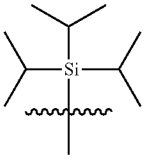
,

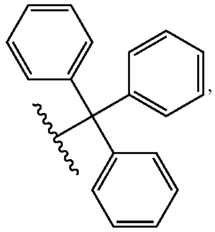
, or
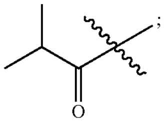
;

$M_4$ is —($C_2$-$C_6$)alkyl-O—($C_{10}$-$C_{20}$)alkyl;

each $M_5$ is —$(CH_2)_n$—S—C(═O)—($C_1$-$C_8$)alkyl; and n is 1-4.

In one embodiment, provided herein is a compound represented by the structure of Formula XXB:

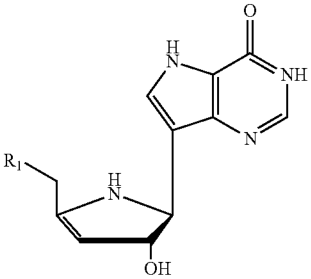

wherein $R_1$ is as described in Formula XVIIIB.

In one embodiment, provided herein is a compound represented by the structure of Formula XVIIIB or Formula XXB, wherein $R_1$ is as described in Formula XVIIIB.

In one embodiment, provided herein is a compound represented by the structure of Formula XIXB:

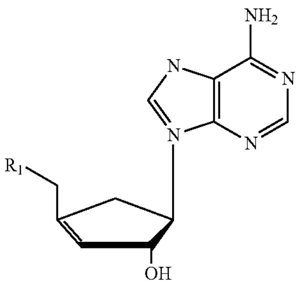

wherein $R_1$ is OH,

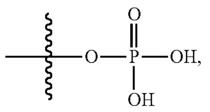

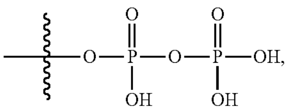

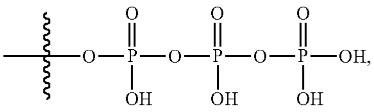

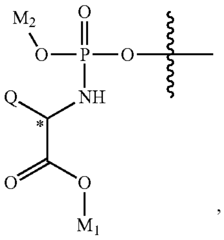

,

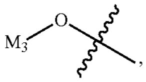

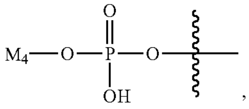

, or

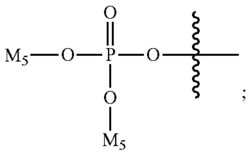

;

Q is a side chain of an amino acid;

$M_1$ is an alkyl;

$M_2$ is an aryl, a substituted aryl, a heteroaryl or a substituted heteroaryl;

$M_3$ is

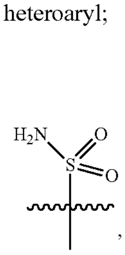

,

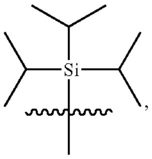

-continued

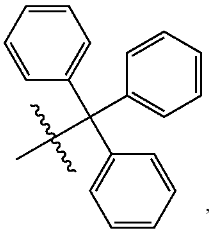

, or

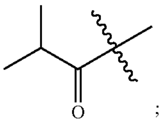

;

$M_4$ is $-(C_2-C_6)$alkyl-O$-(C_{10}-C_{20})$alkyl;

each $M_5$ is $-(CH_2)_n-S-C(=O)-(C_1-C_8)$alkyl; and n is 1-4.

In one embodiment, provided herein is a compound represented by the structure of Formula XXIIB:

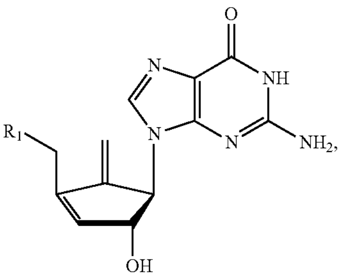

wherein $R_1$ is OH,

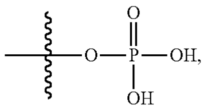

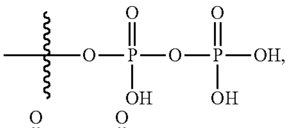

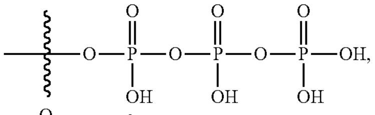

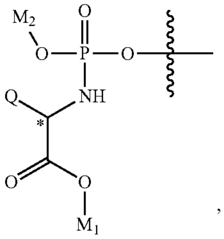

,

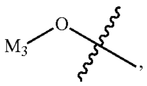

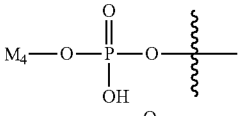

, or

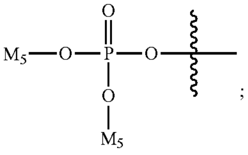

;

Q is a side chain of an amino acid;

$M_1$ is an alkyl;

$M_2$ is an aryl, a substituted aryl, a heteroaryl or a substituted heteroaryl;

$M_3$ is

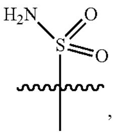, 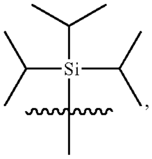,

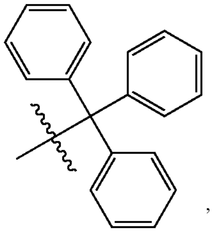, or 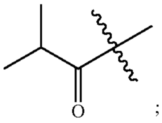;

$M_4$ is —($C_2$-$C_6$)alkyl-O—($C_{10}$-$C_{20}$)alkyl;

each $M_5$ is —$(CH_2)_n$—S—C(=O)—($C_1$-$C_8$)alkyl; and n is 1-4.

In one embodiment, provided herein is a compound represented by the structure of Formula XXIIIB:

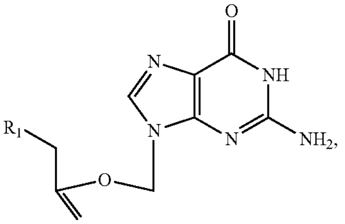

wherein $R_1$ is OH,

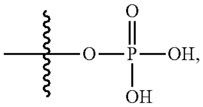 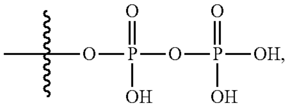 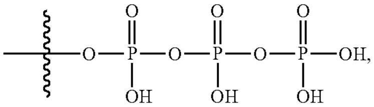 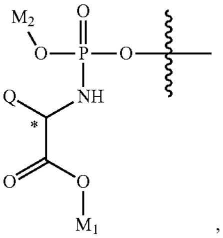, 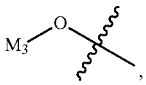, 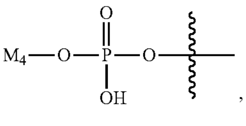, or 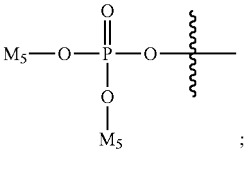;

Q is a side chain of an amino acid;

$M_1$ is an alkyl;

$M_2$ is an aryl, a substituted aryl, a heteroaryl or a substituted heteroaryl;

$M_3$ is

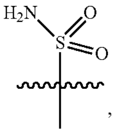, 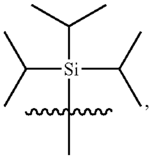,

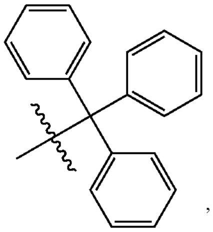, or 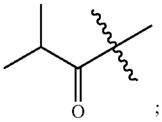;

$M_4$ is —($C_2$-$C_6$)alkyl-O—($C_{10}$-$C_{20}$)alkyl;

each $M_5$ is —$(CH_2)_n$—S—C(=O)—($C_1$-$C_8$)alkyl; and n is 1-4;

In one embodiment, provided herein is a compound represented by the structure of Formula XXIVB:

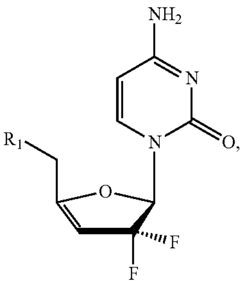

wherein $R_1$ is OH,

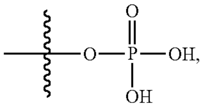 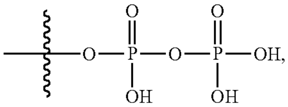 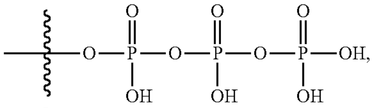 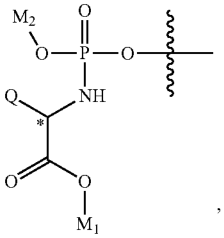, 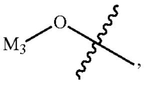, 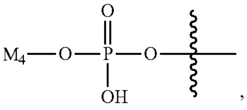, or

-continued

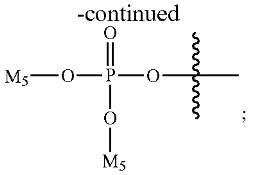
;

Q is a side chain of an amino acid;

$M_1$ is an alkyl;

$M_2$ is an aryl, a substituted aryl, a heteroaryl or a substituted heteroaryl;

$M_3$ is

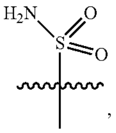
,
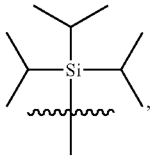
,
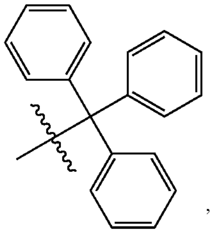
, or
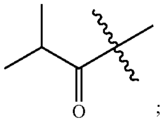
;

$M_4$ is —$(C_2-C_6)$alkyl-O—$(C_{10}-C_{20})$alkyl;

each $M_5$ is —$(CH_2)_n$—S—C(═O)—$(C_1-C_8)$alkyl; and n is 1-4.

In one embodiment, provided herein is a compound represented by the structure of Formula XXVB:

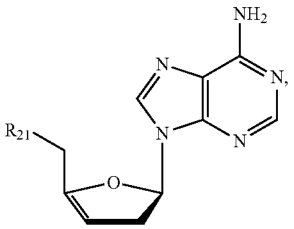

wherein $R_{21}$ is

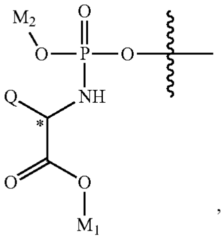
,
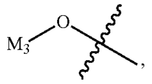
,
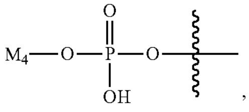
, or

-continued

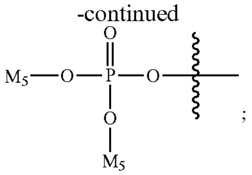
;

Q is a side chain of an amino acid;

$M_1$ is an alkyl;

$M_2$ is an aryl, a substituted aryl, a heteroaryl or a substituted heteroaryl;

$M_3$ is

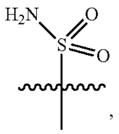
,
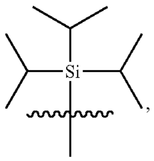
,
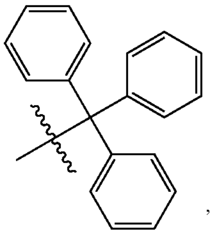
, or
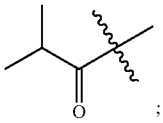
;

$M_4$ is —$(C_2-C_6)$alkyl-O—$(C_{10}-C_{20})$alkyl;

each $M_5$ is —$(CH_2)_n$—S—C(═O)—$(C_1-C_8)$alkyl; and n is 1-4.

In one embodiment, $R_1$ of Formula IB, Formula IIB, Formula IIIB, Formula IVB, Formula VB, Formula IXB, Formula XB, Formula XIB, Formula XIIB, Formula XIIIB, Formula XIIIB1, Formula XIVB, Formula XIVB1, Formula XIVB2, Formula XIV3, Formula XIV4, Formula XIV5, Formula XVB, Formula XVB1, Formula XVB2, Formula XVB3, Formula XVB4, Formula XVB5, Formula XVB6, Formula XVIB, Formula XVIB1, Formula XVIB2, Formula XVIB3, Formula XVIB4, Formula XVIB5, Formula XVIB6, Formula XVIB7, Formula XVIB8, Formula XVIB9, Formula XVIB10, Formula XVIB11, Formula XVIB12, Formula XVIB13, Formula XVIB14, Formula XVIB15, Formula XVIB16, Formula XVIB17, Formula XVIB18, Formula XVIB19, Formula XVIB20, Formula XVIB21, Formula XVIB22, Formula XVIB23, Formula XVIB24, Formula XVIB25, Formula XVIB26, Formula XVIB27, Formula XVIB28, Formula XVIB29, Formula XVIB30, Formula XVIB31, Formula XVIB32, Formula XVIB33, Formula XVIIB, Formula XVIIIB, Formula XXB, Formula XIXB, Formula XXIB, Formula XXIIB, Formula XXXIIIB, or Formula XXIVB is OH,

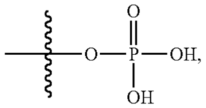 [SMILES: *OP(=O)(O)O]
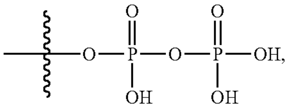
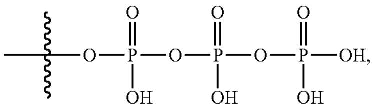

-continued

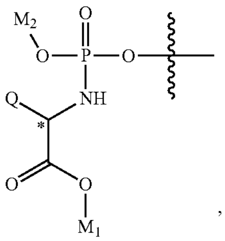

,

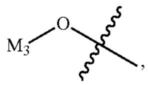

,

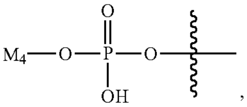

, or

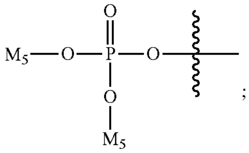

;

In another embodiment, $R_1$ is OH. In another embodiment, $R_1$ is

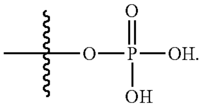

In another embodiment, $R_1$ is

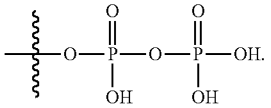 [SMILES: *OP(=O)(O)OP(=O)(O)O]

In another embodiment, $R_1$ is

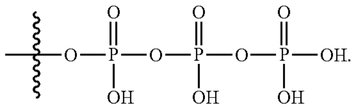 [SMILES: *OP(=O)(O)OP(=O)(O)OP(=O)(O)O]

In another embodiment, $R_1$ is

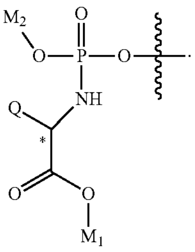

In another embodiment, $R_1$ is

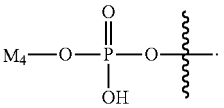

In another embodiment, $R_1$ is

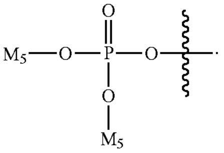

In one embodiment, Q of $R_1$ is a side chain of an amino acid.

In one embodiment, $M_1$ of $R_1$ is an alkyl. In another embodiment, $M_1$ is

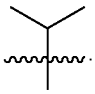

In another embodiment, $M_1$ is

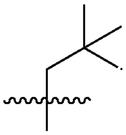

In another embodiment, $M_1$ is

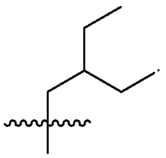

In one embodiment, $M_2$ of $R_1$, is an aryl, a substituted aryl, a heteroaryl or a substituted heteroaryl. In another embodiment, $M_2$ is

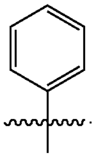

In another embodiment, $M_2$ is

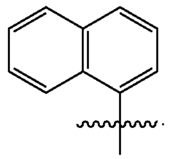

In another embodiment, $M_2$ is an aryl. In another embodiment, $M_2$ is a substituted aryl. In another embodiment, $M_2$ is a heteroaryl. In another embodiment, $M_2$ is an a substituted heteroaryl. In one embodiment, $R_1$ is

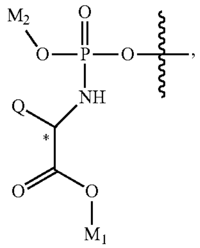

wherein $M_1$ is

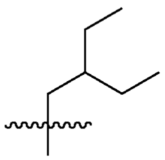

and $M_2$ is

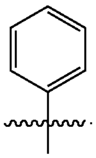

In another embodiment, the chiral carbon of

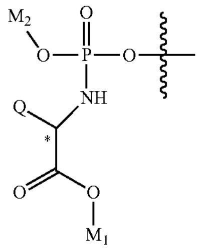

is an S. In another embodiment, the chiral carbon of

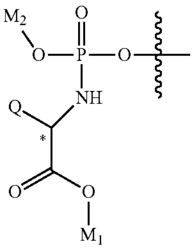

is an R. In another embodiment, the chiral carbon of

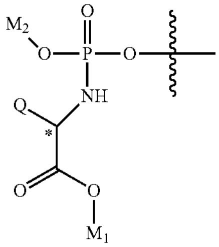

is a racemate.

In one embodiment, $M_3$ of $R_1$ is

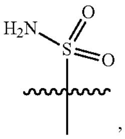,

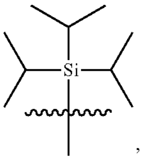,

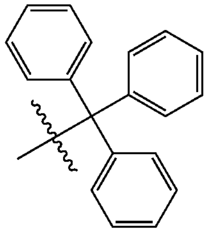

or

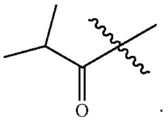.

In another embodiment, $M_3$ is

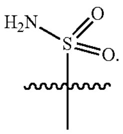

In another embodiment, $M_3$ is

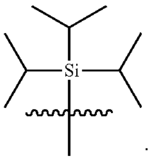 [SMILES: *[Si](C(C)C)(C(C)C)C(C)C].

In another embodiment, $M_3$ is

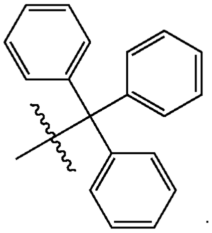 [SMILES: *C(c1ccccc1)(c1ccccc1)c1ccccc1]

.

In another embodiment, $M_3$ is

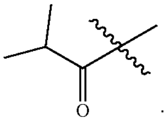 [SMILES: *C(=O)C(C)C]

.

In one embodiment, $M_4$ of $R_1$ is $-(C_2-C_6)alkyl-O-(C_{10}-C_{20})alkyl$. In another embodiment, $M_4$ is $-(CH_2)_3-O-(CH_2)_{15}CH_3$. In one embodiment, each $M_5$ of $R_1$, is $-(CH_2)_n-S-C(=O)-(C_1-C_8)alkyl$. In another embodiment, each $M_5$ is $-(CH_2)_2-S-C(=O)-C(CH_3)_3$. In one embodiment n of $M_5$ is 1-4. In another embodiment, n is 1. In another embodiment, n is 2. In another embodiment, n is 3. In another embodiment, n is 4.

In some embodiments, a compound described herein comprises a prodrug. In some embodiments, embodiment, the ddh or deoxy-ddh products or prodrugs thereof, or active metabolites thereof can be synthesized and administered directly to cells or a subject. Upon entering the cells, these ddh or deoxy-ddh products or prodrugs thereof can be phosphorylated by one or more viral or cellular kinases to produce the active metabolites that inhibit DNA/RNA replication. In one embodiment, the ddh or deoxy-ddh products comprise a prodrug.

One skilled in the art would appreciate that the term "prodrug" may in certain embodiments, encompass any compound that when administered to a biological system could be converted into an active compound or metabolite thereof as a result of spontaneous chemical reaction(s), enzyme catalyzed chemical reaction(s), photolysis, and/or metabolic chemical reaction(s). The active compound or metabolites in the present disclosure are the DNA/RNA chain terminators, which in some embodiments comprise the products produced by the pVip or synthesized using methods known in the art, from non-natural substrates as described herein. pVips, the nucleotide sequence encoding them, and their activities are described in detail elsewhere in this application.

In some embodiments, a prodrug facilitates the crossing of the plasma membrane of a cell by the compound. In some embodiments, the prodrug form of a compound facilitates passive diffusion through the cell membrane by masking negative charge until the compound is within the cell.

In some embodiments, a prodrug comprises a protective chemical group. In some embodiments, a protective chemical group comprises a

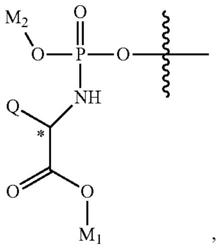

,

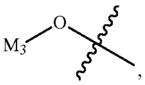

,

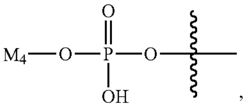

, or

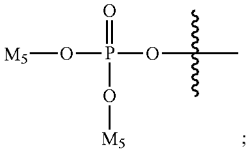

;

Q is a side chain of an amino acid; $M_1$ is an alkyl;

$M_2$ is an aryl, a substituted aryl, a heteroaryl or a substituted heteroaryl;

$M_3$ is

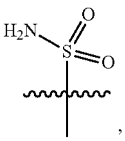

,

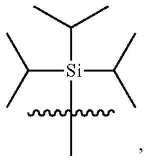

,

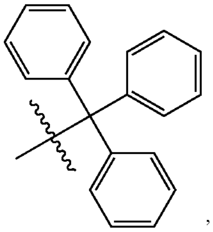

, or

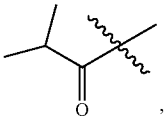

, $M_4$ is $-(C_2-C_6)alkyl-O-(C_{10}-C_{20})alkyl$;

each $M_5$ is $-(CH_2)_n-S-C(=O)-(C_1-C_8)alkyl$;

wherein n is 1-4;

at the $R_1$, $R_{11}$, or $R_{21}$ position in a compound disclosed herein.

In another embodiment, the chiral carbon of

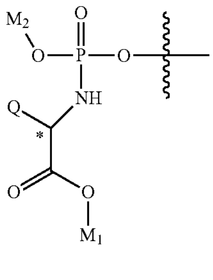

is an S. In another embodiment, the chiral carbon of

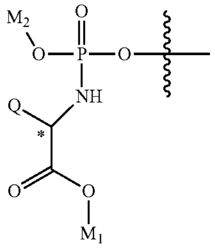

is an R. In another embodiment, the chiral carbon of

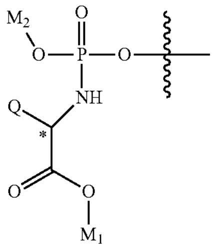

is a racemate.

In some embodiments, the present disclosure includes all forms of prodrugs that are covalently modified analogs or latent forms of the therapeutically active metabolites (the DNA/RNA chain terminators). In one embodiment, the prodrugs comprise the ddh or deoxy-ddh compounds described herein or modified structures thereof. The prodrug form can serve to enhance solubility, absorption and lipophilicity to optimize drug delivery, bioavailability and efficacy of the comprise the ddh or deoxy-ddh compounds. In one embodiment, a prodrug comprises the comprise the ddh or deoxy-ddh compounds with a chemical structure that can be oxidized, reduced, aminated, deaminated, esterified, deesterified, alkylated, dealkylated, acylated, deacylated, phosphorylated, dephosphorylated, photolyzed, hydrolyzed, or other functional group change or conversion to produce the therapeutically active metabolite (the DNA/RNA chain terminators), or produce the active metabolite that can be transported across cell membrane. Enzymes which are capable of enzymatic activation of prodrugs include, but are not limited to, amidases, esterases, microbial enzymes, phospholipases, cholinesterases, and phosphases. Designs and uses of prodrugs are generally known in the art, e.g. Bundgaard, Hans, "Design and Application of Prodrugs" in *Textbook of Drug Design and Development* (1991), P. Krogsgaard-Larsen and H. Bundgaard, Eds. Harwood Academic Publishers.

In one embodiment, $R_1$ is

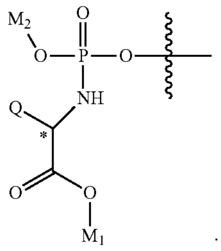

.

In another embodiment, the chiral carbon of

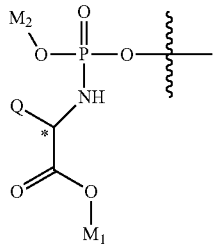

is an S. In another embodiment, the chiral carbon of

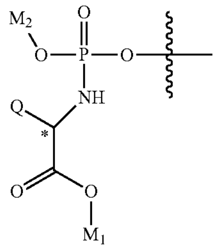

is an R. In another embodiment, the chiral carbon of

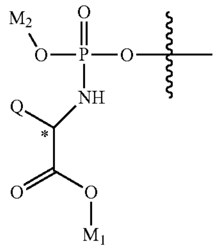

is a racemate. In another embodiment, $R_1$ is

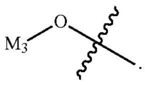

.

In another embodiment, $R_1$ is

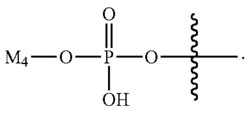

.

In another embodiment, $R_1$ is

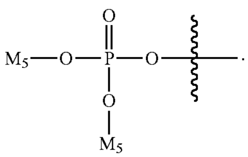

.

In one embodiment, $R_{11}$ is

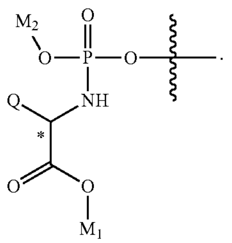

In another embodiment, $R_{11}$ is

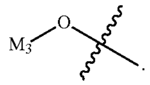

In another embodiment, $R_{11}$ is

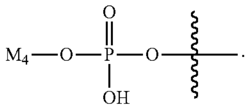

In another embodiment, $R_{11}$ is

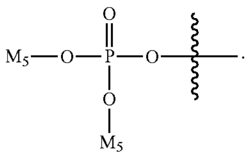

In one embodiment, $R_{21}$ is

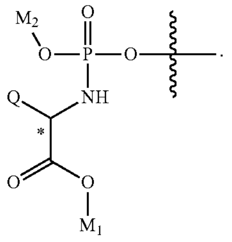

In another embodiment, $R_{21}$ is

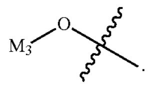

In another embodiment, $R_{21}$ is

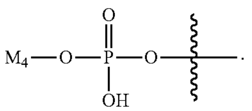

In another embodiment, $R_{21}$ is

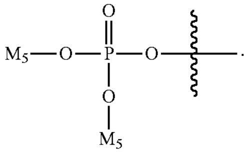

In one embodiment, Q of $R_1$ is a side chain of an amino acid. In one embodiment, $M_1$ of $R_1$, $R_{11}$, $R_{21}$ is an alkyl. In another embodiment, $M_1$ is

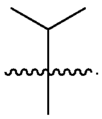 [SMILES: *C(C)C]

In another embodiment, $M_1$ is

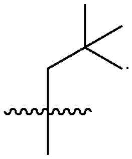 [SMILES: *CC(C)(C)C]

In another embodiment, $M_1$ is

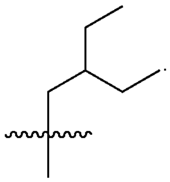 [SMILES: *CC(CC)CC]

In another embodiment, $M_1$ is an alkyl. In one embodiment, $M_2$ of $R_1$, $R_{11}$ or $R_{21}$ is an aryl, a substituted aryl, a heteroaryl or a substituted heteroaryl. In another embodiment, $M_2$ is

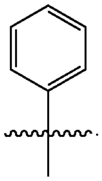 [SMILES: *c1ccccc1]

In another embodiment, $M_2$ is

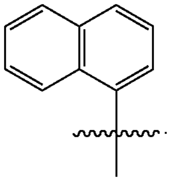 [SMILES: *c1cccc2ccccc12]

In another embodiment, $M_2$ is an aryl. In another embodiment, $M_2$ is a substituted aryl. In another embodiment, $M_2$ is a heteroaryl. In another embodiment, $M_2$ is an a substituted heteroaryl. In one embodiment, $R_1$, $R_{11}$ or $R_{21}$ is

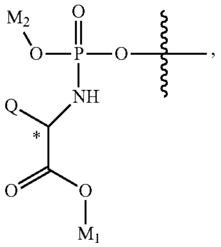

wherein $M_1$ is

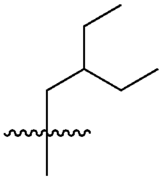 [SMILES: *CC(CC)CC]

and $M_2$ is

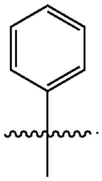

In one embodiment, $R_1$, $R_{11}$ or $R_{21}$ is

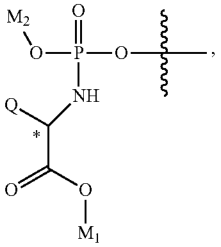

wherein $M_1$ is

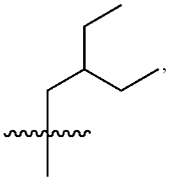 [SMILES: *CC(CC)CC]

$M_2$ is

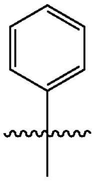 [SMILES: *c1ccccc1]

and Q is methyl. In one embodiment, Q of $R_1$, $R_{11}$ or $R_{21}$ is methyl. In one embodiment, the chiral carbon of

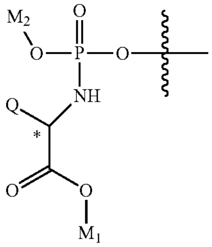

is an S. In another embodiment, the chiral carbon of

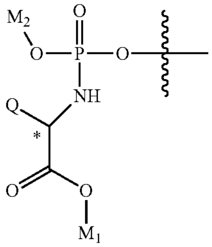

is an R. In another embodiment, the chiral carbon of

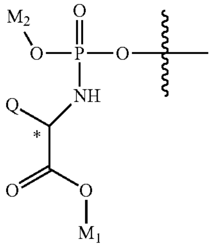

is a racemate.

In one embodiment, $M_3$ of $R_1$, $R_{11}$, or $R_{21}$ is

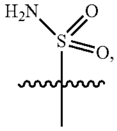,
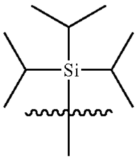,
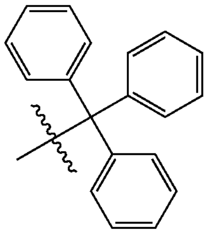 or 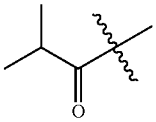

In another embodiment, $M_3$ is

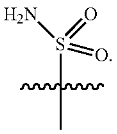 [SMILES: *S(N)(=O)=O].

In another embodiment, $M_3$ is

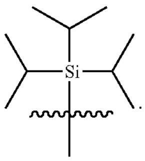 [SMILES: *[Si](C(C)C)(C(C)C)C(C)C].

In another embodiment, $M_3$ is

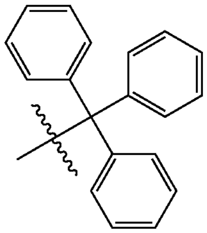.

In another embodiment, $M_3$ is

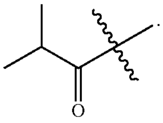 [SMILES: *C(=O)C(C)C].

In one embodiment, $M_4$ of $R_1$, $R_{11}$, or $R_{21}$ is —($C_2$-$C_6$) alkyl-O—($C_{10}$-$C_{20}$)alkyl. In another embodiment, $M_4$ is —$(CH_2)_3$—O—$(CH_2)_{15}CH_3$. In one embodiment, each $M_5$ of $R_1$, $R_{11}$, or $R_{21}$ is —$(CH_2)_n$—S—C(═O)—($C_1$-$C_8$)alkyl. In another embodiment, each $M_5$ is —$(CH_2)_2$—S—C(═O)—$C(CH_3)_3$. In one embodiment n of $M_5$ is 1-4. In another embodiment, n is 1. In another embodiment, n is 2.

In another embodiment, n is 3. In another embodiment, n is 4. In another embodiment, the chiral carbon of

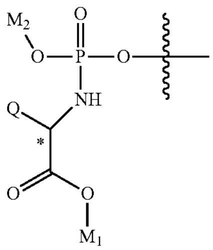

of $R_1$, $R_{11}$ or $R_{21}$ is an S. In another embodiment, the chiral carbon of

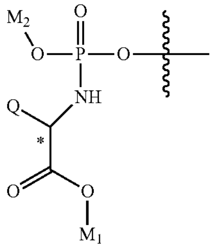

of $R_1$, $R_{11}$ or $R_{21}$ is an R. In another embodiment, the chiral carbon of

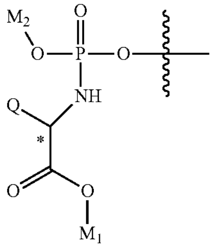

of $R_1$, $R_{11}$ or $R_{21}$ is a racemate.

In one embodiment, $R_2$ of Formula IB, Formula IIB, Formula IIIB, Formula IVB, Formula VB, Formula IXB and Formula XIIIB is OH or —O—COO-alkyl. In another embodiment, $R_2$ is OH. In another embodiment, $R_2$ is —O—COO-alkyl.

In one embodiment, if $R_1$ of Formula IB, Formula IIB, Formula IIIB, Formula IVB, Formula VB is OH, then $R_2$ of is —O—COO-alkyl.

In one embodiment, if $R_1$ of Formula IXB is OH or

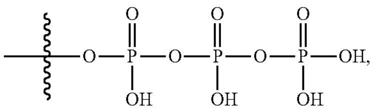 [SMILES: *OP(=O)(O)OP(=O)(O)OP(=O)(O)O], then $R_2$ is not OH.

In one embodiment, $R_{11}$ of Formula VB1, Formula VIB, Formula VIIB or Formula VIIIB is

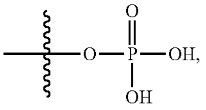
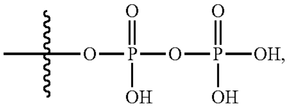
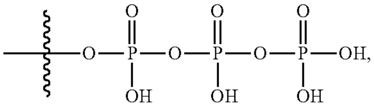
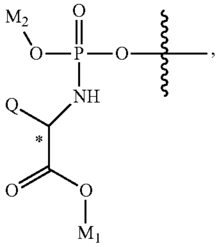
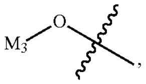
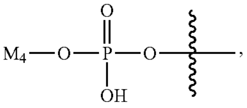
or
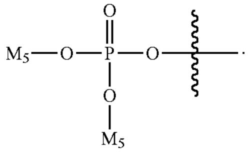

In another embodiment, $R_{11}$ is

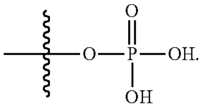 [SMILES: *OP(=O)(O)O]

In another embodiment, $R_{11}$ is

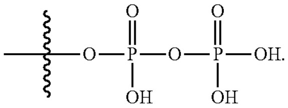 [SMILES: *OP(=O)(O)OP(=O)(O)O]

In another embodiment, $R_{11}$ is

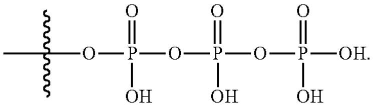 [SMILES: *OP(=O)(O)OP(=O)(O)OP(=O)(O)O]

In another embodiment, $R_{11}$ is

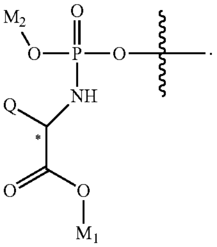

In another embodiment, $R_{11}$ is

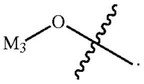

In another embodiment, $R_{11}$ is

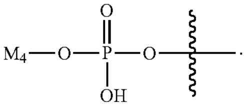

In another embodiment, $R_{11}$ is

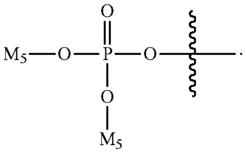

In one embodiment, Q of $R_{11}$ is a side chain of an amino acid. In one embodiment, $M_1$ of $R_{11}$ is an alkyl. In another embodiment, $M_1$ is

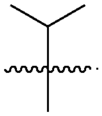 [SMILES: *C(C)C]

In another embodiment, $M_1$ is

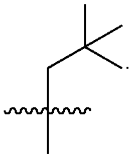 [SMILES: *CC(C)(C)C]

In another embodiment, $M_1$ is

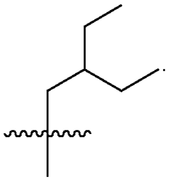 [SMILES: *CC(CC)CC]

In one embodiment, $M_2$ of $R_{11}$ is an aryl, a substituted aryl, a heteroaryl or a substituted heteroaryl. In another embodiment, $M_2$ is

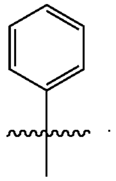 [SMILES: *c1ccccc1]

In another embodiment, $M_2$ is

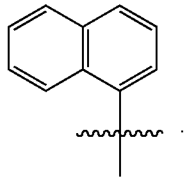 [SMILES: *c1cccc2ccccc12]

In another embodiment, $M_2$ is an aryl. In another embodiment, $M_2$ is a substituted aryl. In another embodiment, $M_2$ is a heteroaryl. In another embodiment, $M_2$ is a substituted heteroaryl. In one embodiment, $M_3$ of $R_{11}$ is

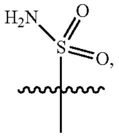

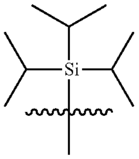

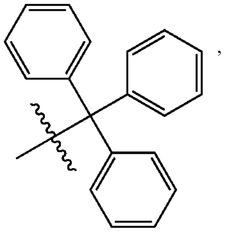

, or

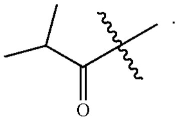

In another embodiment, $M_3$ is

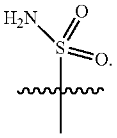 [SMILES: *S(N)(=O)=O]

In another embodiment, $M_3$ is

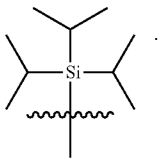 [SMILES: *[Si](C(C)C)(C(C)C)C(C)C]

In another embodiment, $M_3$ is

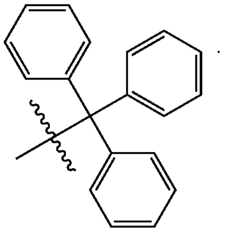 [SMILES: *C(c1ccccc1)(c1ccccc1)c1ccccc1]

In another embodiment, $M_3$ is

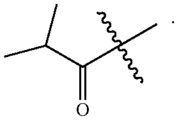 [SMILES: *C(=O)C(C)C]

In one embodiment, $M_4$ of $R_{11}$ is —$(C_2\text{-}C_6)$alkyl-O—$(C_{10}\text{-}C_{20})$alkyl. In another embodiment, $M_4$ is —$(CH_2)_3$—O—$(CH_2)_{15}CH_3$. In one embodiment, each $M_5$ of $R_{21}$ is —$(CH_2)_n$—S—C(═O)—$(C_1\text{-}C_8)$alkyl. In another embodiment, each $M_5$ is —$(CH_2)_2$—S—C(═O)—$C(CH_3)_3$. In one embodiment n of $M_5$ is 1-4. In another embodiment, n is 1. In another embodiment, n is 2. In another embodiment, n is 3. In another embodiment, n is 4.

In one embodiment, $R_{21}$ of Formula XXVB is

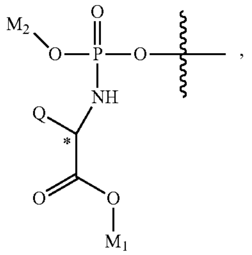

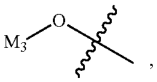

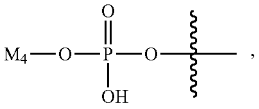

or

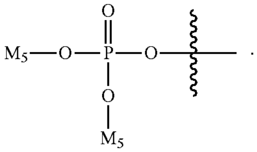

In another embodiment, $R_{21}$ is

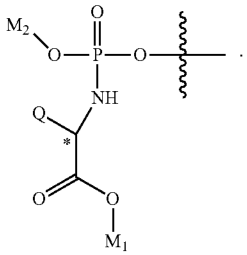

In another embodiment, $R_{21}$ is

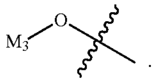

In another embodiment, $R_{21}$ is

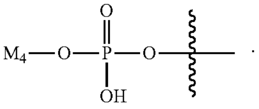

In another embodiment, $R_{21}$ is

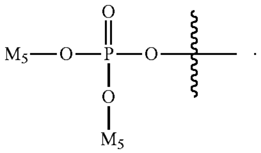

In one embodiment, Q of $R_{21}$ is a side chain of an amino acid. In one embodiment, Mof $R_{21}$ is an alkyl. In another embodiment, $M_1$ is

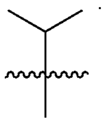

In another embodiment, $M_1$ is

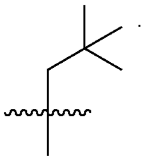 [SMILES: *CC(C)(C)C]

In another embodiment, $M_1$ is

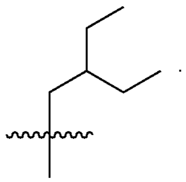 [SMILES: *CC(CC)CC]

In one embodiment, $M_2$ of $R_{21}$ is, or an aryl. In another embodiment, $M_2$ is

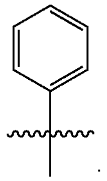 [SMILES: *c1ccccc1]

In another embodiment, $M_2$ is

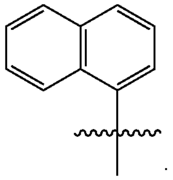 [SMILES: *c1cccc2ccccc12]

In another embodiment, $M_2$ is an aryl. In one embodiment, $M_3$ of $R_{21}$ is

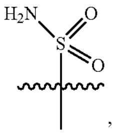

,

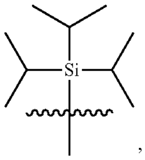

,

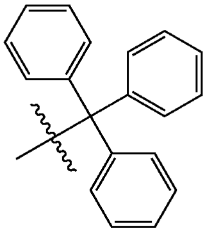

or

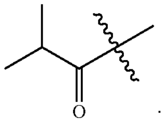

In another embodiment, $M_3$ is

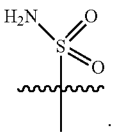

In another embodiment, $M_3$ is

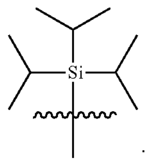 [SMILES: *[Si](C(C)C)(C(C)C)C(C)C]

In another embodiment, $M_3$ is

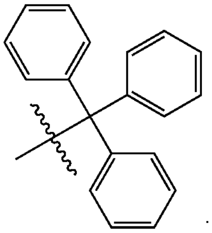 [SMILES: *C(c1ccccc1)(c1ccccc1)c1ccccc1]

In another embodiment, $M_3$ is

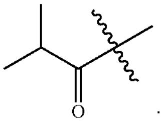 [SMILES: *C(=O)C(C)C]

In one embodiment, $M_4$ of $R_{21}$ is $-(C_2\text{-}C_6)$alkyl-O$-(C_{10}\text{-}C_{20})$alkyl. In another embodiment, $M_4$ is $-(CH_2)_3-O-(CH_2)_{15}CH_3$. In one embodiment, each $M_5$ of $R_{21}$ is $-(CH_2)_n-S-C(=O)-(C_1\text{-}C_8)$alkyl. In another embodiment, each $M_5$ is $-(CH_2)_2-S-C(=O)-C(CH_3)_3$. In one embodiment n of $M_5$ is 1-4. In another embodiment, n is 1. In another embodiment, n is 2. In another embodiment, n is 3. In another embodiment, n is 4.

In another embodiment, the chiral carbon of

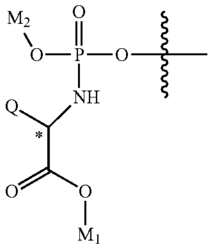

is an S. In another embodiment, the chiral carbon of

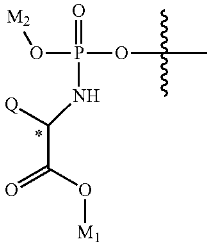

is an R. In another embodiment, the chiral carbon of

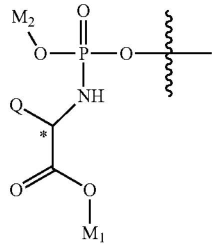

is a racemate.

In one embodiment, $A_1$ of Formula XIVB is a halo, a haloalkyl, an alkyl, or

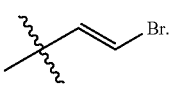 [SMILES: */C=C/Br]

In another embodiment, $A_1$ is a halo. In another embodiment, $A_1$ is a haloalkyl. In another embodiment, $A_1$ is an alkyl. In another embodiment, $A_1$ is

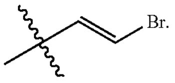 [SMILES: */C=C/Br]

In one embodiment, $R_3$ of Formula XVB is H, a halo or an alkoxy. In another embodiment, $R_3$ is H. In another embodiment, $R_3$ is a halo. In another embodiment, $R_3$ is an alkoxy.

In one embodiment, $R_4$ of Formula XVB is H, a halo, or an alkyl. In another embodiment, $R_4$ is H. In another embodiment, $R_4$ is a halo. In another embodiment, $R_4$ is an alkyl.

In one embodiment, $R_3$ of Formula XVB is not the same as $R_4$.

In one embodiment, $R_9$ of Formula XVIB and Formula XVIIB is H, OH, or —O—COO-alkyl. In another embodiment, $R_9$ is H. In another embodiment, $R_9$ is OH. In another embodiment, $R_9$ is —O—COO-alkyl.

In one embodiment, $R_6$ of Formula XVIB is H, OH, —CCH or Me. In another embodiment, $R_6$ is H. In another embodiment, $R_6$ is OH. In another embodiment, $R_6$ is —CCH. In another embodiment, $R_6$ is Me.

In one embodiment, $R_8$ of Formula XVIB is H or CN. In another embodiment, $R_7$ is H. In another embodiment, $R_8$ is CN.

In one embodiment, $R_7$ of Formula XVIB is

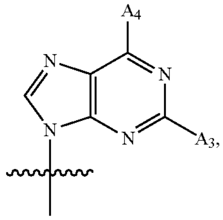
,

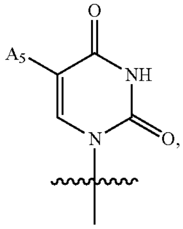
,

-continued
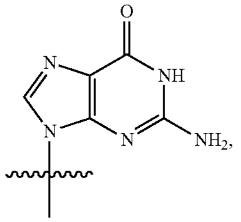
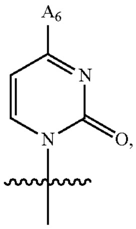
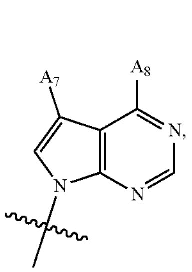
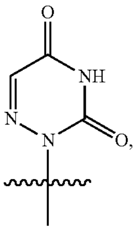
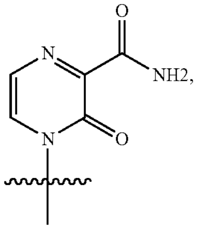
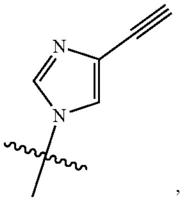
,
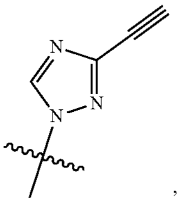
,
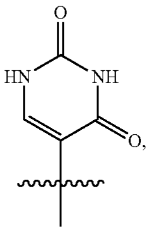
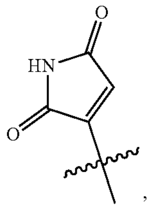
,
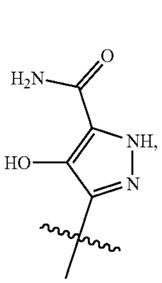
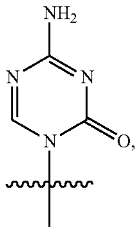
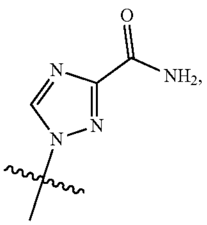
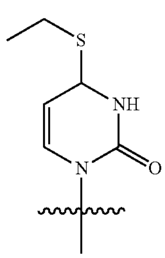
or
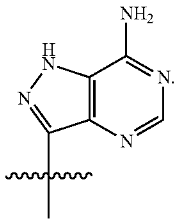
In another embodiment, $R_7$ is
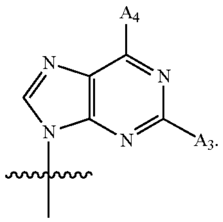
In another embodiment, $R_7$ is
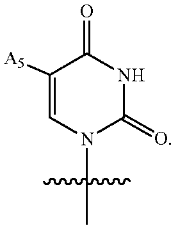
In another embodiment, $R_7$ is
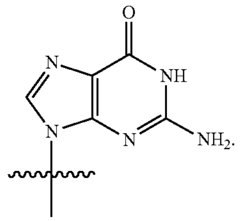
In another embodiment, $R_7$ is
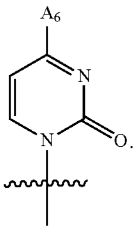
In another embodiment, $R_7$ is
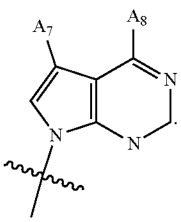

In another embodiment, $R_7$ is
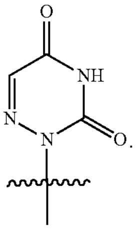 [SMILES: *n1ncc(=O)[nH]c1=O]
In another embodiment, $R_7$ is
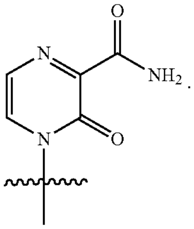 [SMILES: *n1ccnc(C(N)=O)c1=O]
In another embodiment, $R_7$ is
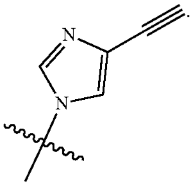 [SMILES: *n1cnc(C#C)c1]
In another embodiment, $R_7$ is
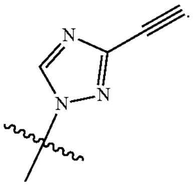 [SMILES: *n1cnc(C#C)n1]
In another embodiment, $R_7$ is
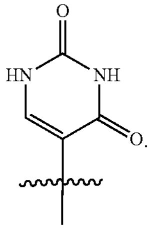 [SMILES: *c1c[nH]c(=O)[nH]c1=O]
In another embodiment, $R_7$ is
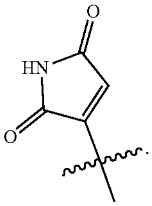 [SMILES: *C1=CC(=O)NC1=O]
In another embodiment, $R_7$ is
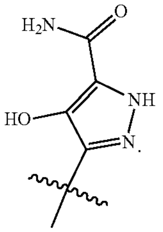
In another embodiment, $R_7$ is
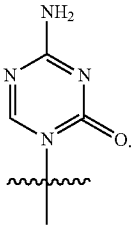
In another embodiment, $R_7$ is
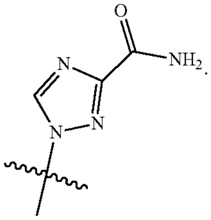 [SMILES: *n1cnc(C(N)=O)n1]
In another embodiment, $R_7$ is
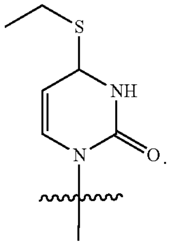 [SMILES: *N1C=CC(SCC)NC1=O]

In another embodiment, $R_7$ is

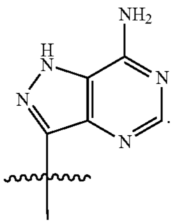 [SMILES: *c1n[nH]c2c(N)ncnc12]

In one embodiment, $A_3$ of $R_7$ is H, a halo or an amino. In another embodiment, $A_3$ is H. In another embodiment, $A_3$ is a halo. In another embodiment, $A_3$ is an amino.

In one embodiment, $A_4$ of $R_7$ is H, an amino, or an alkyl. In another embodiment, $A_4$ is H. In another embodiment, $A_4$ is an amino. In another embodiment, $A_4$ is an alkoxy. In another embodiment, $A_4$ is an alkyl.

In one embodiment, $A_5$ of $R_7$ is H, a halo, a hydroxy or an alkyne. In another embodiment, $A_5$ is H. In another embodiment, $A_5$ is a halo. In another embodiment, $A_5$ is a hydroxy. In another embodiment, $A_5$ is an alkyne. In one embodiment, $A_6$ of $R_7$ is H, an amino, or hydroxylamino. In another embodiment, $A_6$ is H. In another embodiment, $A_6$ is an amino. In another embodiment, $A_6$ is a hydroxylamino. In one embodiment, $A_7$ of $R_7$ is H or an amino. In another embodiment, $A_7$ is H. In another embodiment, $A_7$ is an amido. In one embodiment, $A_8$ of $R_7$ is an amino or an alkyl. In another embodiment, $A_8$ is an amino. In another embodiment, $A_8$ is an alkyl.

In one embodiment, if $R_1$ of Formula XVIB is

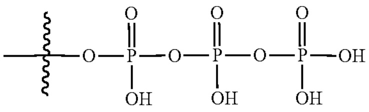 [SMILES: *OP(=O)(O)OP(=O)(O)OP(=O)(O)O]

and $R_7$ is

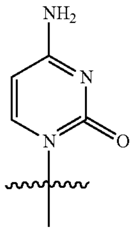

and $R_9$ is OH, then $R_6$ is not H. In one embodiment, if $R_1$ Formula XVIB is OH and $R_7$ is

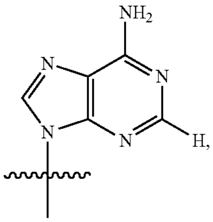

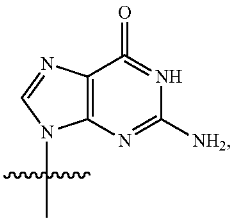

-continued

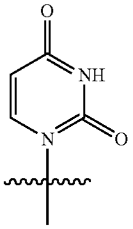 or 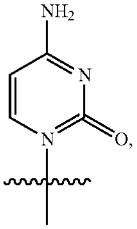

and $R_9$ is OH, then $R_6$ is not H.

In one embodiment, $R_{10}$ of a compound of Formula XVIIB is

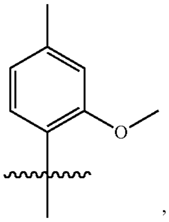 , 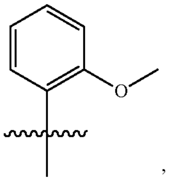 , 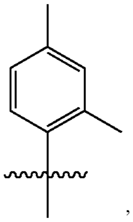 ,

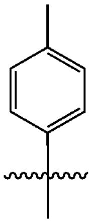 , 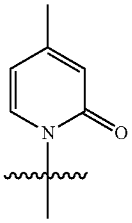 , 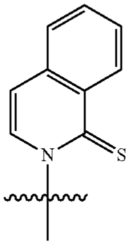 ,

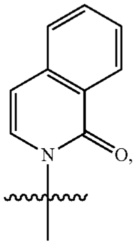 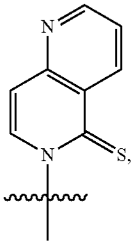 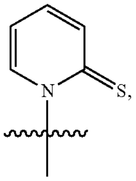

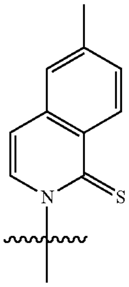 , 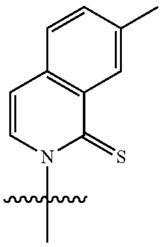 , or 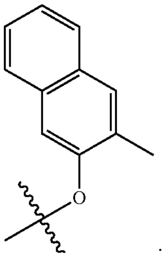 .

In another embodiment, $R_{10}$ is
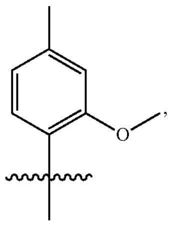 [SMILES: *c1ccc(C)cc1OC]
In another embodiment, $R_{10}$ is
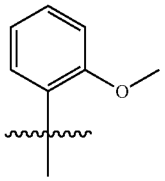 [SMILES: *c1ccccc1OC]
In another e embodiment, $R_{10}$ is
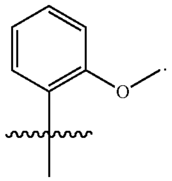 [SMILES: *c1ccccc1OC]
In another embodiment, $R_{10}$ is
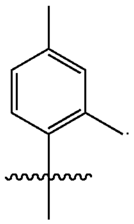 [SMILES: *c1ccc(C)cc1C]
In another embodiment, $R_{10}$ is
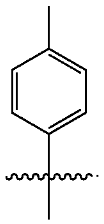 [SMILES: *c1ccc(C)cc1]
In another embodiment, $R_{10}$ is
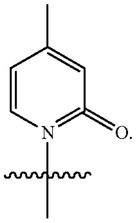
In another embodiment, $R_{10}$ is
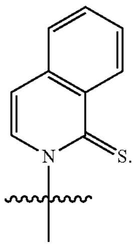 [SMILES: *n1ccc2ccccc2c1=O]
In another embodiment, $R_{10}$ is
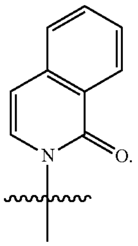
In another embodiment, $R_{10}$ is
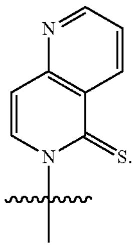
In another embodiment, $R_{10}$ is
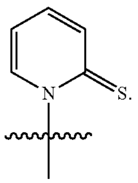

In another embodiment, $R_{10}$ is

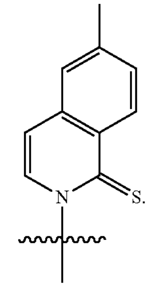

In one embodiment, $R_{10}$ is

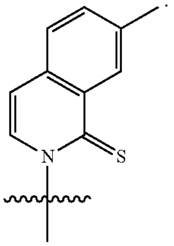 [SMILES: *n1ccc2ccc(C)cc2c1=S]

In another embodiment, $R_{10}$ is

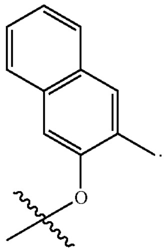 [SMILES: *Oc1cc2ccccc2cc1C]

As used herein, the term alkyl, used alone or as part of another group, refers, in one embodiment, to a "$C_1$ to $C_{18}$ alkyl" and denotes linear and branched, saturated or unsaturated (e.g., alkenyl, alkynyl) groups, the latter only when the number of carbon atoms in the alkyl chain is greater than or equal to two, and can contain mixed structures. Non-limiting examples are alkyl groups containing from 1 to 6 carbon atoms ($C_1$ to $C_6$ alkyls), or alkyl groups containing from 1 to 4 carbon atoms ($C_1$ to $C_4$ alkyls). Examples of saturated alkyl groups include, but are not limited to, methyl, ethyl, n-propyl, isopropyl, n-butyl, iso-butyl, sec-butyl, tert-butyl, amyl, tert-amyl and hexyl. Examples of alkenyl groups include, but are not limited to, vinyl, allyl, butenyl and the like. Examples of alkynyl groups include, but are not limited to, ethynyl, propynyl and the like. Similarly, the term "$C_1$ to $C_{12}$ alkylene" denotes a bivalent radical of 1 to 12 carbons.

The alkyl group can be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryls, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, alkylthio, arylthio, or alkylsulfonyl groups. Any substituents can be unsubstituted or further substituted with any one of these aforementioned substituents.

The term "haloalkyl" used herein alone or as part of another group, refers to, in some embodiments, to an alkyl group as defined above, which is substituted by one or more halogen atoms, e.g. by F, Cl, Br or I.

The term "alkoxy" used herein alone or as part of another group, refers to the —O-(alkyl) group, where the point of attachment is through the oxygen-atom and the alkyl group is as defined hereinbefore.

The term "alkyne" used herein alone or as part of another group, refers to an alkyl as defined above with at least one triple bond. The "alkyne" in some embodiment, refer to have 2 to 20 carbon atoms ($C_2$-$C_{18}$ alkyne). The Alkyne, in some embodiments, is unsubstituted. The Alkyne, in some embodiments, is substituted with one or more substituents selected from the group consisting of aryl, halogen, hydroxy, alkoxy, aryloxy, alkylaryloxy, heteroaryloxy, oxo, cycloalkyl, phenyl, heteroaryls, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, alkylthio, arylthio, or alkylsulfonyl groups. Any substituents can be unsubstituted or further substituted with any one of these aforementioned substituents.

"Alkenyl" is a hydrocarbon containing normal, secondary, tertiary or cyclic carbon atoms with at least one site of unsaturation, i.e., a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), 2 to 6 carbon atoms (i.e., $C_{2-6}$ alkenyl) or 2 to 4 carbon atoms (i.e., $C_2$-$C_4$ alkenyl). Examples of suitable alkenyl groups include, but are not limited to, ethenyl or vinyl (both having a structure $—CH{=}CH_2$), allyl ($CH_2CH{=}CH_2$), cyclopentenyl ($—C_5H_7$), and 5-hexenyl ($—CH_2CH_2CH_2CH_2CH{=}CH_2$).

"Alkynyl" is a hydrocarbon containing normal, secondary, tertiary or cyclic carbon atoms with at least one site of unsaturation, i.e., a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne), 2 to 6 carbon atoms (i.e., $C_2$-$C_6$ alkynyl), or 2 to 4 carbon atoms (i.e., $C_2$-$C_4$ alkynyl). Examples of suitable alkynyl groups include, but are not limited to, ethynyl or acetylenic ($—C{\equiv}CH$), propargyl ($—CH_2C—{=}CH$), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene ($—CH_2—$), 1,1-ethyl ($—CH(CH_3)—$), 1,2-ethyl ($—CH_2CH_2—$), 1,1-propyl ($—CH(CH_2CH_3)—$), 1,2-propyl ($—CH_2CH(CH_3)—$), 1,3-propyl ($—CH_2CH_2CH_2—$), 1,4-butyl ($—CH_2CH_2CH_2CH_2—$), and the like.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups such as halogen, alkyl, aryl, hydroxy, alkoxy, aryloxy, alkylaryloxy, heteroaryloxy, oxo, cycloalkyl, phenyl, heteroaryls, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, alkylthio, arylthio, alkylsulfonyl —OCN, —SCN, —N═C═O, —NCS, —NO, $—N_3$, $—OP(═O)(O)R^*)_2$, $—P(═O)(OR^*)_2$, $—P(═O)(O^-)_2$, $—P(═O)(OH)_2$, $—P(O)(OR^*)(O^-)$, —C(═O)R*, —C(═O)X, —C(S)R*, —C(S)OR*, —C(O)SR*, —C(S)SR*, —C(S)SR*, $—C(S)NR^*_2$, or $—C(═NR^*)NR^*_2$ groups, where each R* is independently H, alkyl, aryl, arylalkyl, a heterocycle, or a protecting group or prodrug moiety groups. Any substituents can be unsubstituted or further substituted with any one of these aforementioned substituents.

The term "heteroaryl" refers to an aromatic ring system containing from 5-14 member ring having at least one heteroatom in the ring. Non-limiting examples of suitable heteroatoms which can be included in the aromatic ring include oxygen, sulfur, phosphate and nitrogen. Non-limiting examples of heteroaryl rings include pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc. The heteroaryl group can be unsubstituted or substituted through available carbon atoms with one or more groups such as, halogen, alkyl, aryl, hydroxy, alkoxy, aryloxy, alkylaryloxy, heteroaryloxy, oxo, cycloalkyl, phenyl, heteroaryls, heterocyclyl, naphthyl, amino, amido, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, alkylthio, arylthio, alkylsulfonyl, —OCN, —SCN, —N═C═O, —NCS, —NO, $—N_3$, $—OP(═O)(OR^*)_2$, $—P(═O)(OR^*)_2$, $—P(═O)(O^-)_2$, $—P(═O)(OH)_2$, $—P(O)(OR^*)(O^-)$, —C(═O)R*, —C(O)X, —C(S)R*, —C(S)OR*, —C(O)SR*, —C(S)SR*, $—C(S)NR^*_2$ or $—C(═NR^*)NR^*_2$ groups, where each R* is independently H, alkyl, aryl, arylalkyl, a heterocycle, or a protecting group or prodrug moiety. Any substituents can be unsubstituted or further substituted with any one of these aforementioned substituents.

As used herein, the term "amino", used alone or as part of another group, refers to any primary, secondary, tertiary or quaternary amine each independently substituted with H, substituted or unsubstituted straight or branched $C_1$-$C_{10}$ alkyl, straight or branched $C_2$-$C_{10}$ alkenyl, straight or branched $C_2$-$C_{10}$ alkynyl, substituted or unsubstituted carbocyclyl, substituted or unsubstituted aryl, substituted or unsubstituted heterocyclyl, etc. In some embodiments, the primary, secondary and tertiary amines where the point of attachment is through the nitrogen-atom. In case of the secondary or tertiary amines, the substituting groups on the nitrogen may be the same or different. Nonlimiting types of amino include $—NH_2$, $—N(alkyl)_2$, —NH(alkyl), $—N(carbocyclyl)_2$, —NH(carbocyclyl), $—N(heterocyclyl)_2$, —NH(heterocyclyl), $—N(aryl)_2$, —NH(aryl), —N(alkyl)(aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with at least one alkyl group. Nonlimiting examples of amino groups include $—NH_2$, $—NH(CH_3)$, $—N(CH_3)_2$, $—NH(CH_2CH_3)$, $—N(CH_2CH_3)_2$, —NH(phenyl), $—N(phenyl)_2$, —NH(benzyl), $—N(benzyl)_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), $—N(alkylene-C(O)—OH)_2$, $—N(alkylene-C(O)—O-alkyl)_2$, etc.

The term "halogen" or "halo" as used herein refers to —Cl, —Br, —F, or —I groups.

As used herein, the term "hydroxylamino", used alone or as part of another group, refers, in one embodiment, to an amino group as defined above, which is substituted by one or more hydroxyl groups.

As used herein, the term "amido", used alone or as part of another group, refers, to the formula —C(═O)NRR' or —NHCO—R or —N(R)—C(O)—R, wherein R and R' are each individually is H or an $C_1$ to $C_{10}$ alkyl, aryl, cycloalkyl, heterocycle as defined above.

As used herein, the term "heterocyclic nitrogen based ring" refers to substituted or unsubstituted uracil or uracil derivative, substituted or unsubstituted cytosine or cytosine derivative, substituted or unsubstituted adenine or adenine derivative, substituted or unsubstituted guanine or guanine derivative, substituted or unsubstituted 5 to 6 member ring with between 1-3 nitrogen atoms, substituted or unsubstituted bicyclic rings with between 1-4 nitrogen atoms, substituted or unsubstituted fused rings with between 1-4 nitrogen atoms. The "heterocyclic nitrogen based ring" can be substituted with one or more groups such as halogen, hydroxy, alkoxy, aryloxy, alkylaryloxy, heteroaryloxy, aryl, oxo, cycloalkyl, phenyl, heteroaryls, heterocyclyl, naphthyl, amino, amido, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, alkylthio, arylthio, or alkylsulfonyl groups. Any substituents can be unsubstituted or further substituted with any one of these aforementioned substituents. Some of the "Heterocyclic nitrogen based ring" is exemplified herein as $R_7$.

As used herein, the term "side chain of an amino acid" refers to the side group of each amino acid, such as substituent that is specific to each amino acid, wherein the "side chain" is an organic substituent. The "side chain of an amino acid" comprises H refers to the side chain of Glycine, methyl refers to the side chain of Alanine, benzyl refers to the side chain of Phenylalanine, iso-propyl refers to the side chain of Valine, iso-butyl refers to the side chain of Leucine, sec-butyl refers to the side chain of Isoleucine, $—CH_2OH$ refers to the side chain of Serine,

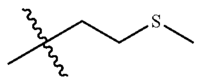

refers to the side chain of Methionine,

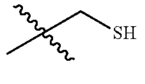 [SMILES: *CS]

refers to the side chain of Cysteine,

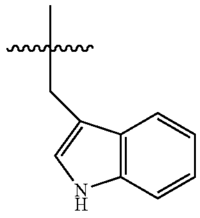 [SMILES: *Cc1c[nH]c2ccccc12]

refers to the side chain of Tryptophan,

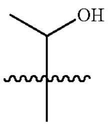 [SMILES: *C(C)O]

refers to the side chain of Threonine, —$CH_2CONH_2$ refers to the side chain of Asparagine,

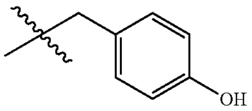 [SMILES: *Cc1ccc(O)cc1]

refers to the side chain of Tyrosine, —$CH_2COOH$ or $CH_2COO$— refers to the side chain of Aspartic acid, —$CH_2CH_2COOH$ or —$CH_2CH_2COO^-$ refers to the side chain of Glutamic acid, —$CH_2CH_2CONH_2$ refers to the side chain of Glutamine —$CH_2CH_2CH_2NH_2$ or —$CH_2CH_2CH_2NH_3^+$ refer to the side chain of Lysine,

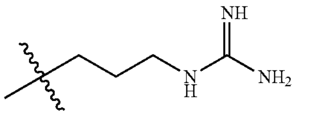 or

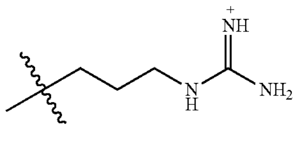

refer to the side chain of Arginine,

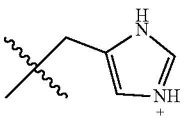 or 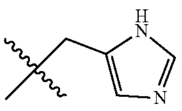

refer to the side chain of Histidine, —$CH_2CH_2CH_2$-connected to the N of the $R_1$ structure refer to the side chain of Proline, —$CH_2SeH$ refer to the side chain of Selenocysteine,

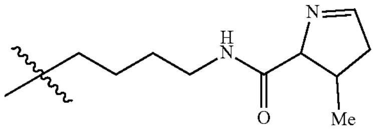 [SMILES: *CCCCNC(=O)C1N=CCC1C]

refer to the side chain of Pyrrolysine.

In one embodiment, the process for the preparation of compounds represented by the structure of Formula IB, Formula IIB, Formula IIIB, Formula IVB, Formula VB, Formula VB1, Formula VIB, Formula VIIB, Formula VIIIB, Formula IXB, Formula XB, Formula XIB, Formula XIIB, Formula XIIIB, Formula XIIIB1, Formula XIVB, Formula XIVB1, Formula XIVB2, Formula XIVB3, Formula XIVB4, Formula XIV5, Formula XVB, Formula XVB1, Formula XVB2, Formula XVB3, Formula XVB4, Formula XVB5, Formula XVB6, Formula XVIB, Formula XVIB1, Formula XVIB2, Formula XVIB3, Formula XVIB4, Formula XVIB5, Formula XVIB6, Formula XVIB7, Formula XVIB8, Formula XVIB9, Formula XVIB10, Formula XVIB11, Formula XVIB12, Formula XVIB13, Formula XVIB14, Formula XVIB15, Formula XVIB16, Formula XVIB17, Formula XVIB18, Formula XVIB19, Formula XVIB20, Formula XVIB21, Formula XVIB22, Formula XVIB23, Formula XVIB24, Formula XVIB25, Formula XVIB26, Formula XVIB27, Formula XVIB28, Formula XVIB29, Formula XVIB30, Formula XVIB31, Formula XVIB32, Formula XVIB33, Formula XVIIB, Formula XVIIIB, Formula XXB, Formula XIXB, Formula XXIB, Formula XXIIB, Formula XXXIIIB, Formula XXIVB, or Formula XXVB comprises reacting the corresponding substrate of each compound by any known process known in the art, wherein the corresponding substrate are represented in Table 1 and Table 2, and $R_1$ is OH,

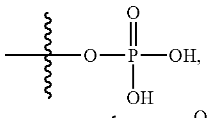 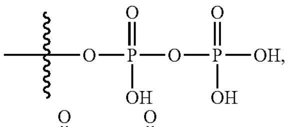

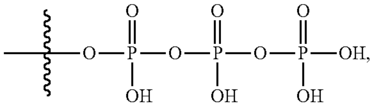

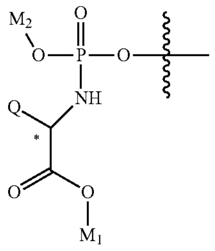, 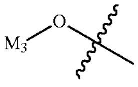,

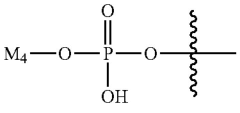, or 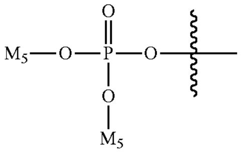;

Q is a side chain of an amino acid;

$M_1$ is an alkyl;

$M_2$ is an aryl, a substituted aryl, a heteroaryl or a substituted heteroaryl;

$M_3$ is

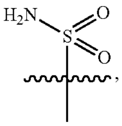, 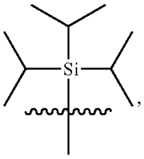, 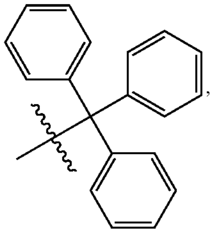, or 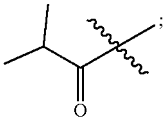;

$M_4$ is —($C_2$-$C_6$)alkyl-O—($C_{10}$-$C_{20}$)alkyl;

each $M_5$ is —$(CH_2)_n$—S—C(═O)—($C_1$-$C_8$)alkyl;

n is 1-4;

or $R_{11}$ is

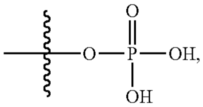, 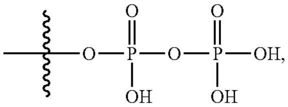, 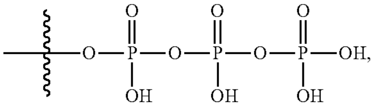, 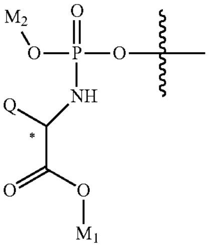, 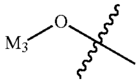, 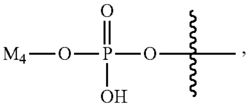, or 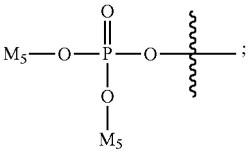;

$M_1$ is an alkyl;

$M_2$ is an aryl, a substituted aryl, a heteroaryl or a substituted heteroaryl;

$M_3$ is

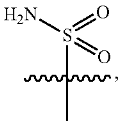, 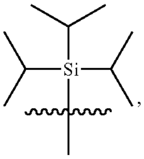, 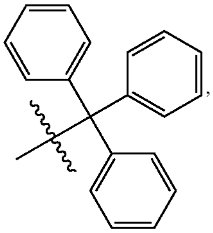, or

-continued

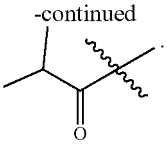.

$M_4$ is —($C_2$-$C_6$)alkyl-O—($C_{10}$-$C_{20}$)alkyl;

each $M_5$ is —$(CH_2)_n$—S—C(═O)—($C_1$-$C_8$)alkyl; and n is 1-4;

or $R_{21}$ is

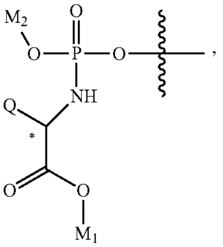, 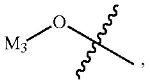, 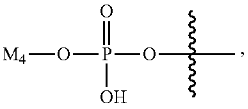, or 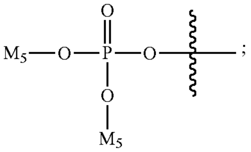;

Q is a side chain of an amino acid;

$M_1$ is an alkyl;

$M_2$ is an aryl, a substituted aryl, a heteroaryl or a substituted heteroaryl;

$M_3$ is

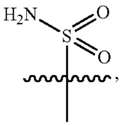, 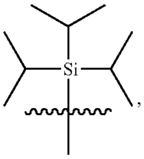, 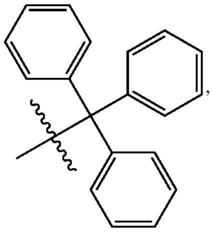, or 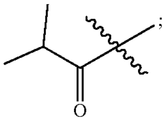;

$M_4$ is —($C_2$-$C_6$)alkyl-O—($C_{10}$-$C_{20}$)alkyl;

each $M_5$ is —$(CH_2)_n$—S—C(═O)—($C_1$-$C_8$)alkyl; and n is 1-4.

In another embodiment, the process comprises corresponding substrate wherein $R_1$ is

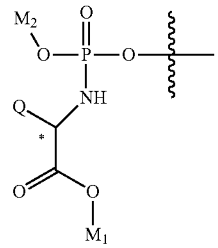
,
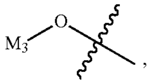
,
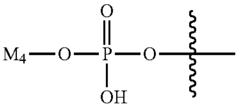
, or
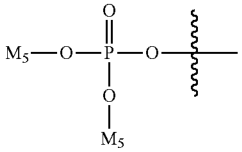
;

Q is a side chain of an amino acid;

$M_1$ is an alkyl;

$M_2$ is an aryl, a substituted aryl, a heteroaryl or a substituted heteroaryl;

$M_3$ is

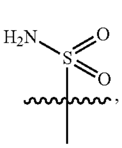
,
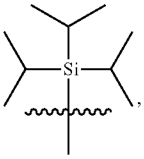
,
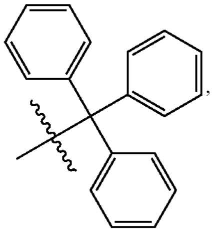
, or
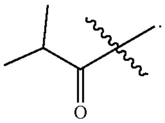
.

$M_4$ is —($C_2$-$C_6$)alkyl-O—($C_{10}$-$C_{20}$)alkyl;

each $M_5$ is —$(CH_2)_n$—S—C(═O)—($C_1$-$C_8$)alkyl;

n is 1-4.

In another embodiment, the process comprises corresponding substrate wherein $R_{11}$ is

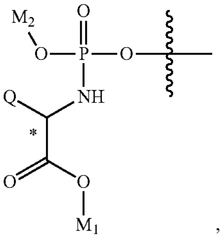
,
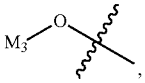
,
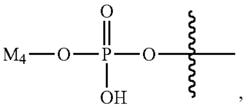
, or
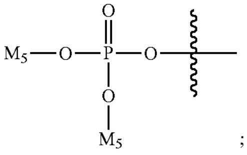
;

Q is a side chain of an amino acid; $M_1$ an alkyl;

$M_2$ is an aryl, a substituted aryl, a heteroaryl or a substituted heteroaryl; $M_3$ is

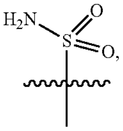
,
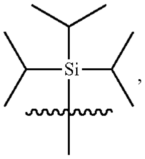
,
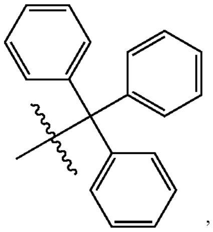
, or
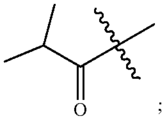
;

$M_4$ is —($C_2$-$C_6$)alkyl-O—($C_{10}$-$C_{20}$)alkyl; each $M_5$ is —$(CH_2)_n$—S—C(═O)—(C1-C8)alkyl; and n is 1-4

In another embodiment, the process comprises corresponding substrate wherein $R_{21}$ is

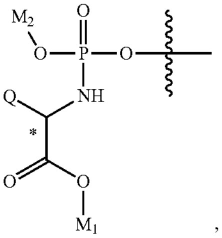
,
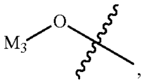
,
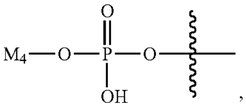
, or
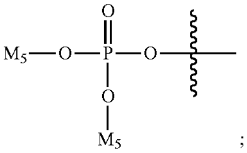
;

Q is a side chain of an amino acid;

$M_1$ is an alkyl;

$M_2$ is an aryl, a substituted aryl, a heteroaryl or a substituted heteroaryl;

$M_3$ is

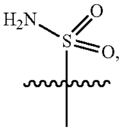
,
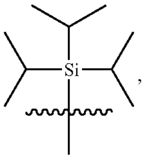
,
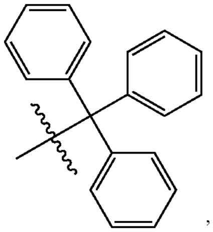
, or
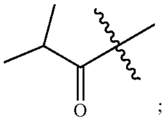
;

$M_4$ is —($C_2$-$C_6$)alkyl-O—($C_{10}$-$C_{20}$)alkyl;

each $M_5$ is —$(CH_2)_n$—S—C(═O)—($C_1$-$C_8$)alkyl; and n is 1-4.

In one embodiment, the process for the preparation of compounds represented by the structure of Formula IB, Formula IIB, Formula IIIB, Formula IVB, Formula VB, Formula VB1, Formula VIB, Formula VIIB, Formula VIIIB, Formula IXB, Formula XB, Formula XIB, Formula XIIB, Formula XIIIB, Formula XIIIB1, Formula XIVB, Formula XIVB1, Formula XIVB2, Formula XIVB3, Formula XIVB4, Formula XIV5, Formula XVB, Formula XVB1, Formula XVB2, Formula XVB3, Formula XVB4, Formula XVB5, Formula XVB6, Formula XVIB, Formula XVIB1, Formula XVIB2, Formula XVIB3, Formula XVIB4, Formula XVIB5, Formula XVIB6, Formula XVIB7, Formula XVIB8, Formula XVIB9, Formula XVIB10, Formula XVIB11, Formula XVIB12, Formula XVIB13, Formula XVIB14, Formula XVIB15, Formula XVIB16, Formula XVIB17, Formula XVIB18, Formula XVIB19, Formula XVIB20, Formula XVIB21, Formula XVIB22, Formula XVIB23, Formula XVIB24, Formula XVIB25, Formula XVIB26, Formula XVIB27, Formula XVIB28, Formula XVIB29, Formula XVIB30, Formula XVIB31, Formula XVIB32, Formula XVIB33, Formula XVIIB, Formula XVIIIB, Formula XXB, Formula XIXB, Formula XXIB, Formula XXIIB, Formula XXXIIIB, or Formula XXIVB, comprises reacting the corresponding substrate of each compound with pVip enzymes, wherein the corresponding substrate is described in Table 1 and Table 2 wherein $R_1$ of each corresponding substrate is OH,

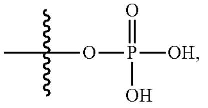
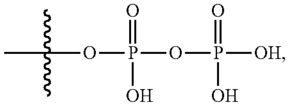
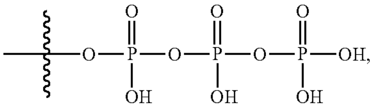

or $R_{11}$ is

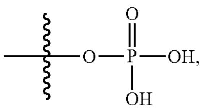
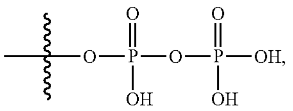
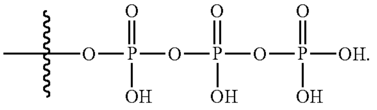

In some embodiments, the process is in vivo. In other embodiments, the process is in vitro. In another embodiment, R1 of the corresponding substrate is OH. In another embodiment, $R_1$ or $R_{11}$ of the corresponding substrate is

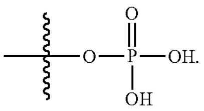 [SMILES: *OP(=O)(O)O]

In another embodiment, $R_1$ or $R_{11}$ of the corresponding substrate is

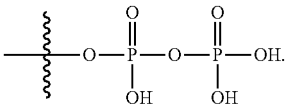 [SMILES: *OP(=O)(O)OP(=O)(O)O]

In another embodiment, $R_1$ or $R_{11}$ of the corresponding substrate is

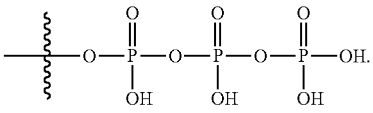 [SMILES: *OP(=O)(O)OP(=O)(O)OP(=O)(O)O]

In another embodiment, the method comprises introducing and expressing a nucleic acid construct comprising and expressing a pVip gene, then purifying the expressed the pVip protein, then using the purified pVip protein to produce a ddh or deoxy-ddh compound from non-natural substrates in vitro. In some embodiments, when the pVip synthesizes a ddh or deoxy-ddh compound, said ddh or deoxy-ddh compound is de-phosphorylated. In some embodiments, when the pVip synthesizes a ddh or deoxy-ddh compound, said ddh or deoxy-ddh compound is phosphorylated. In some embodiments, when the pVip synthesizes a ddh or deoxy-ddh compound, said ddh or deoxy-ddh compound is modified to include a protective chemical group at the $R_1$ or $R_{11}$ position in place of a hydroxyl or phosphate group(s).

As described above, ddh or deoxy-ddh compounds produced, for example from the non-natural substrates comprise a variant of the corresponding compounds lacking a 4' hydrogen and a 3' hydroxyl group. In another embodiment, the non-natural substrates are modified to have the 3' hydroxyl groups removed. In one embodiment, a ddh or deoxy-ddh compound comprises a dehydrated form of the corresponding substrate. In one embodiment, the dehydration positions are the 3' and 4' of the sugar molecule. In one embodiment, the sugar is a ribose. In another embodiment, the sugar is a deoxyribose. In one embodiment, a ddh or deoxy-ddh compound is in the 3'-deoxy-3',4'-didehydro (deoxy-ddh) form. In one embodiment, a ddh or deoxy-ddh compound is in the 3',4'-didehydro (ddh) form.

As described herein, a pVip may produce one or more kinds of a ddh or deoxy-ddh compound. In one embodiment, a pVip may produce one kind of a ddh or deoxy-ddh compound. In another embodiment, a pVip may produce multiple kinds of a ddh or deoxy-ddh compound analogs. In another embodiment, the DNA or RNA chain terminators, or anti-viral substances, anti-cancer, anti-tumor, or antibiotic produced by a pVip or synthesized using methods known in the art may not include a ribose or deoxy-ribose sugar.

In another embodiment, the present disclosure provides a method of producing a ddh or deoxy-ddh compound from non-natural substrates, the method comprising: (a) introducing a pVip, or a nucleic acid construct encoding a pVip into a cell, wherein the pVip produces a ddh or deoxy-ddh compound from non-natural substrates; and (b) purifying the ddh or deoxy-ddh compound from the cell. In one embodiment, the pVip has the sequence of any one of SEQ ID NOs:409-789 or a homologue thereof comprising at least 80% homology to the amino acid sequence set forth in any one of SEQ ID NOs:409-789. In another embodiment, the pVip is encoded by a pVip gene comprising one of the sequences of SEQ ID Nos:3-408 or a homologue thereof comprising at least 80% identity to any one of SEQ ID Nos:3-408. In one embodiment, when the pVip in the above method produces a ddh or deoxy-ddh compound, the method further comprises dephosphorylating the ddh or deoxy-ddh compound. In one embodiment, the above method further comprises introducing into the cell pVip co-factors, or pVip substrates, or any combination thereof.

In another embodiment, the present disclosure provides a method of producing a ddh or deoxy-ddh compound in vitro, the method comprising: (a) providing an isolated prokaryotic viperin homolog (pVip) in vitro; (b) mixing the isolated pVip with a pVip non-natural substrate and co-factors; (c) purifying the ddh or deoxy-ddh compound produced in step (b), thereby producing the ddh or deoxy-ddh compound, or a combination thereof. In one embodiment, the amino acid sequence of the pVip is set forth in any one of SEQ ID NOs:409-789 or a homologue thereof comprising at least 80% homology to any one of SEQ ID NOs:409-789. In another embodiment, the pVip is encoded by a pVip gene comprising the sequence of one of SEQ ID Nos:3-408 or a homologue thereof comprising at least 80% identity to any one of SEQ ID Nos:3-408.

TABLE 1
| Markush Substrates and Products | | | |
|---|---|---|---|
| A | Markush Substrates | B | Markush Products |
| IA | 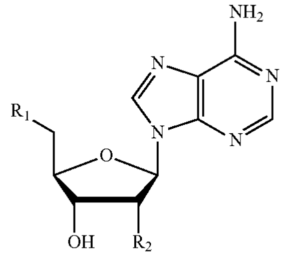 | IB 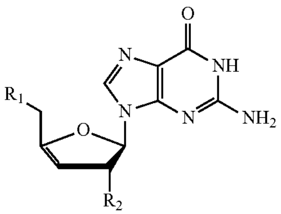 | $R_1$ = OH, 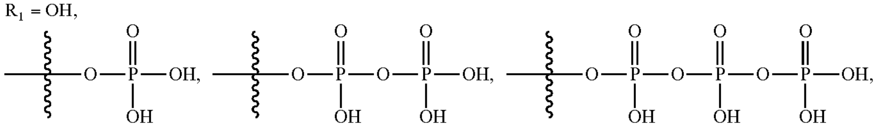 |
| IIA | 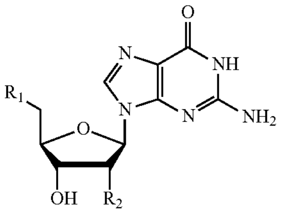 | IIB 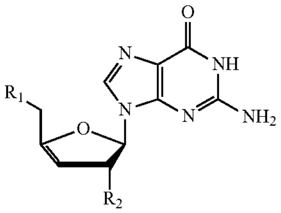 | 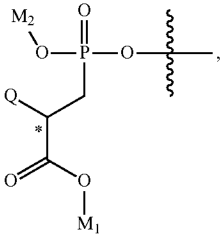, 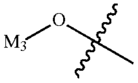, 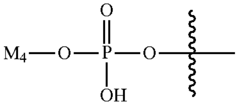, or 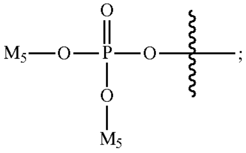; |
| IIIA | 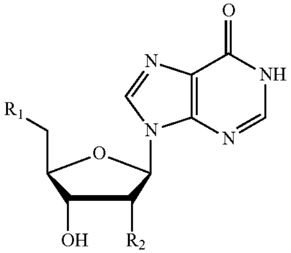 | IIIB 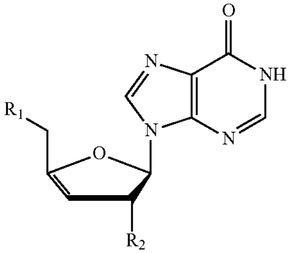 | Q is a side chain of an amino acid;<br>$M_1$ = an alkyl;<br>$M_2$ = an aryl, a substituted aryl, a heteroaryl or a substituted heteroaryl;<br>$M_3$ = 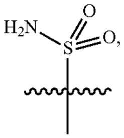 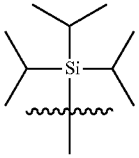, 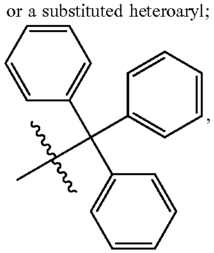, or 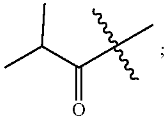; |

TABLE 1-continued
| Markush Substrates and Products | | | | |
|---|---|---|---|---|
| A | Markush Substrates | B | | Markush Products |
| IVA | 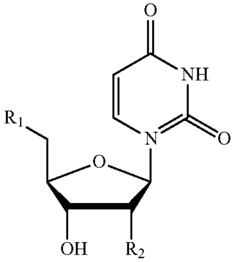 | IVB | 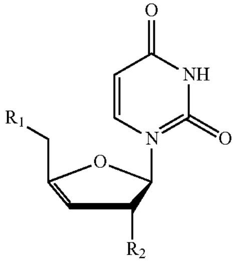 | $M_4$ is —($C_2$-$C_6$)alkyl-O—($C_{10}$-$C_{20}$)alkyl;<br>each $M_5$ is —$(CH_2)_n$—S—C(═O)—(C1-C8)alkyl;<br>n is 1-4;<br>$R_2$ = —OH or —O—COO-alkyl; and<br>wherein if $R_1$ is OH, then $R_2$ is —O—COO-alkyl. |
| VA | 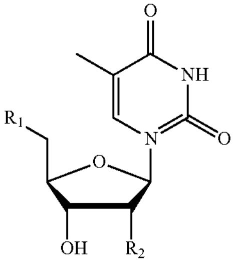 | VB | 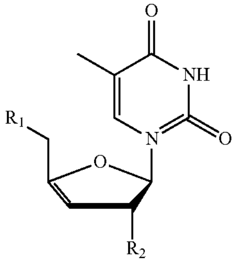 | |
| VIA | 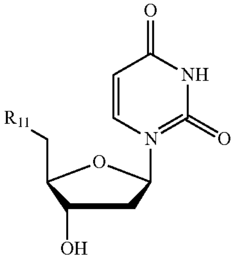 | VIB | 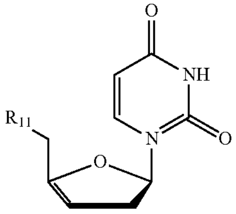 | $R_{11}$ =, 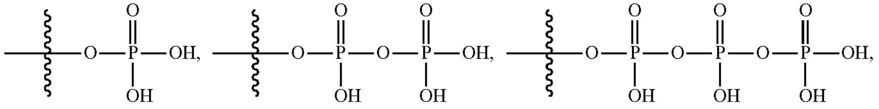 |

TABLE 1-continued
| Markush Substrates and Products | | | |
|---|---|---|---|
| A | Markush Substrates | B | Markush Products |
| VIIA | 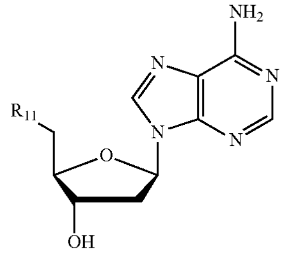 | VIIB | 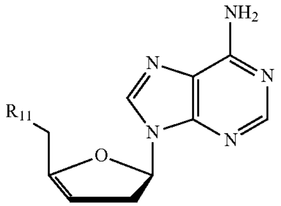 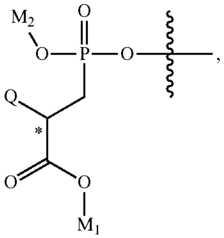, 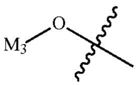, 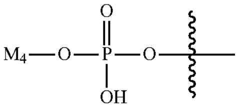, or 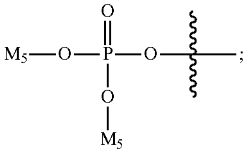; |
| VIIIA | 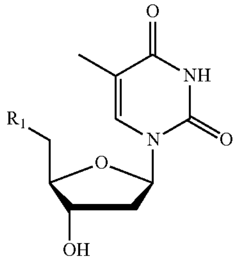 | VIIIB | 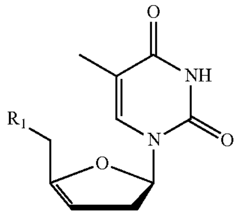 Q is a side chain of an amino acid;<br>$M_1$ = an alkyl;<br>$M_2$ = an aryl, a substituted aryl, a heteroaryl or a substituted heteroaryl;<br>$M_3$ = 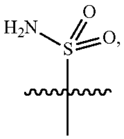 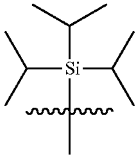, 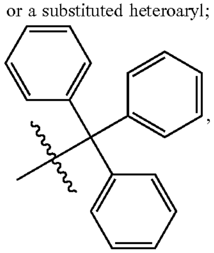, or 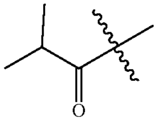;<br>$M_4$ is $-(C_2\text{-}C_6)$alkyl-O$-(C_{10}\text{-}C_{20})$alkyl;<br>each $M_5$ is $-(CH_2)_n-S-C(=O)-(C1\text{-}C8)$alkyl; and<br>n is 1-4 |

TABLE 1-continued

| Markush Substrates and Products | | | |
|---|---|---|---|
| A | Markush Substrates | B | Markush Products |
| IXA | 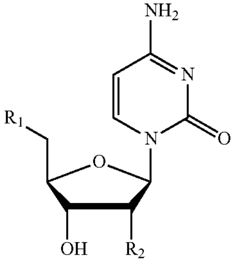 | IXB | 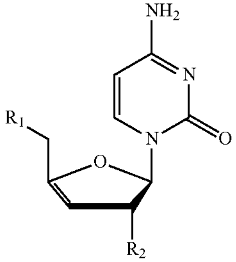 |

Markush Products:

$R_1$ = OH,

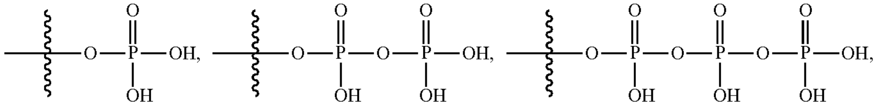

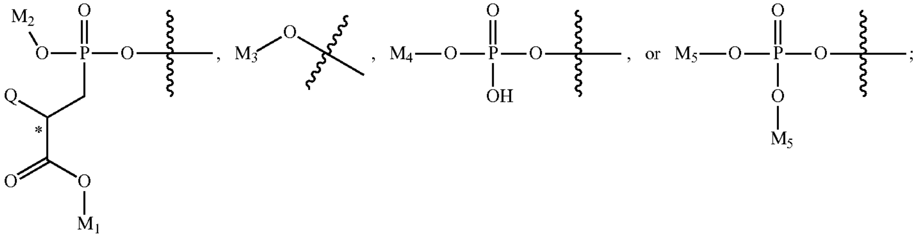

Q is a side chain of an amino acid; $M_1$ = an alkyl;
$M_2$ = an aryl, a substituted aryl, a heteroaryl or a substituted heteroaryl;

$M_3$ = 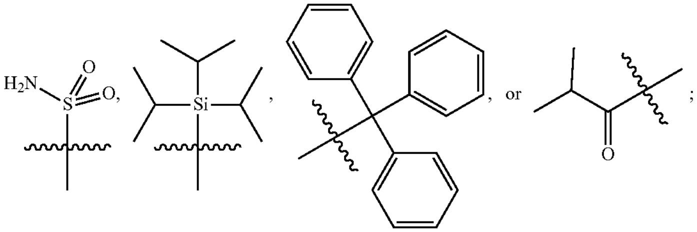

$M_4$ = —($C_2$-$C_6$)alkyl-O—($C_{10}$-$C_{20}$)alkyl;
each $M_5$ = —$(CH_2)_n$—S—C(═O)—($C_1$-$C_8$)alkyl;
n is 1-4
$R_2$ = —OH or —O—COO-alkyl; and wherein if $R_1$ is OH or

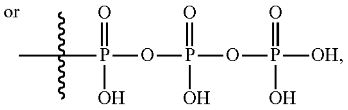

then $R_2$ is not OH

TABLE 1-continued
| Markush Substrates and Products | | | |
|---|---|---|---|
| A | Markush Substrates | B | Markush Products |
| XA | 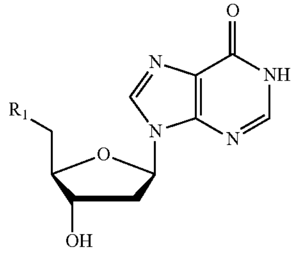 | XB | 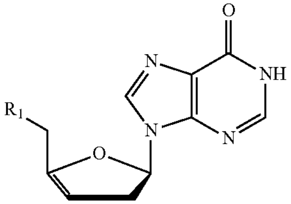 $R_1$ = OH, 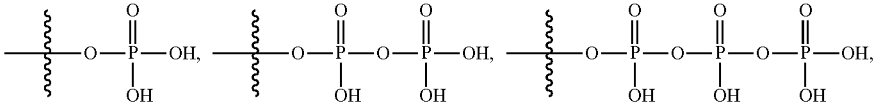 |
| XIA | 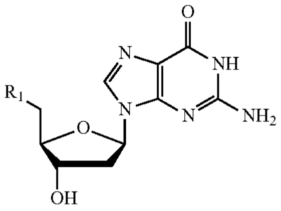 | XIB | 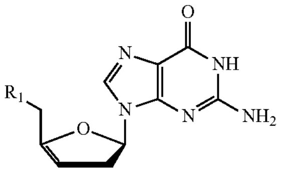 | 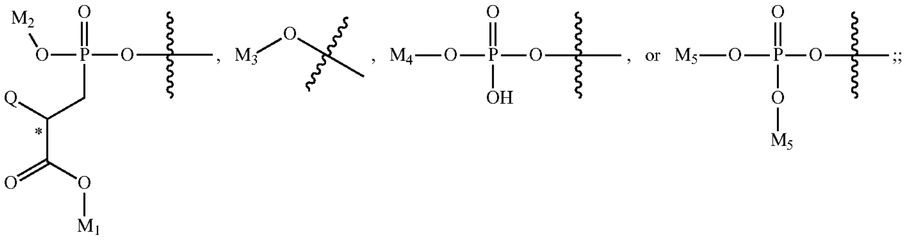 |
| XIIA | 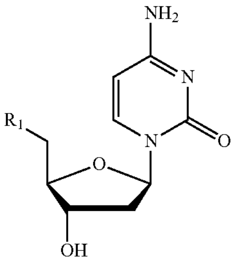 | XIIB | 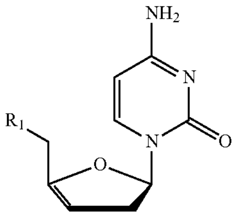 | $M_1$ = an alknyl;<br>$M_2$ = an aryl, a substituted aryl, a heteroaryl or a substituted heteroaryl;<br>$M_3$ = 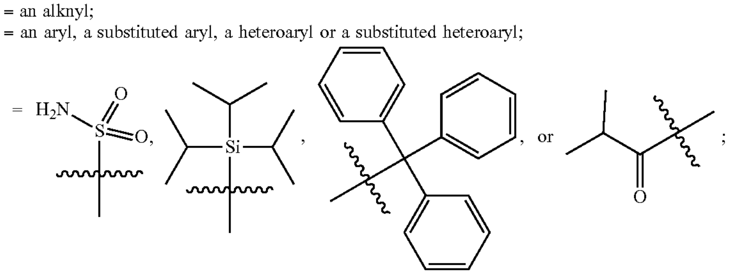<br>$M_4$ = —($C_2$-$C_6$)alkyl-O—($C_{10}$-$C_{20}$)alkyl;<br>each $M_5$ = —$(CH_2)_n$—S—C(═O)—($C_1$-$C_8$)alkyl;<br>n is 1-4; and<br>Q is a side chain of an amino acid; |

TABLE 1-continued

| Markush Substrates and Products | | | |
|---|---|---|---|
| A | Markush Substrates | B | Markush Products |
| XIIIA | 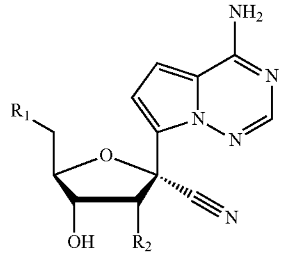 | XIIIB | 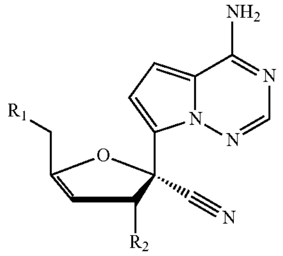 $R_1$ = OH,<br>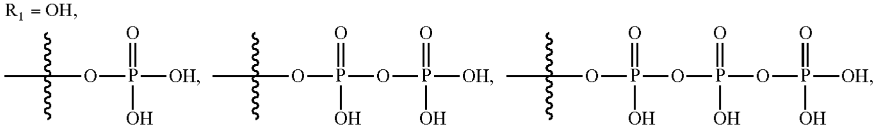<br>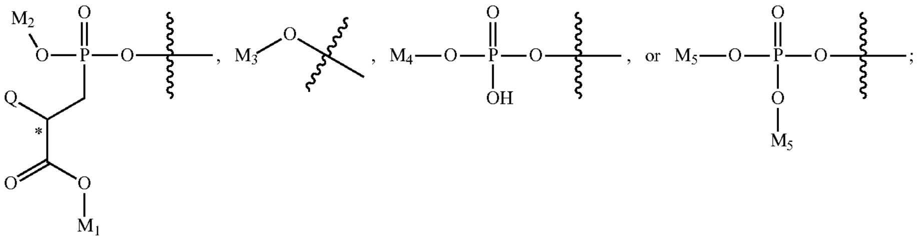<br>Q is a side chain of an amino acid;<br>$M_1$ = an alkyl;<br>$M_2$ = an aryl, a substituted aryl, a heteroaryl or a substituted heteroaryl;<br>$M_3$ = 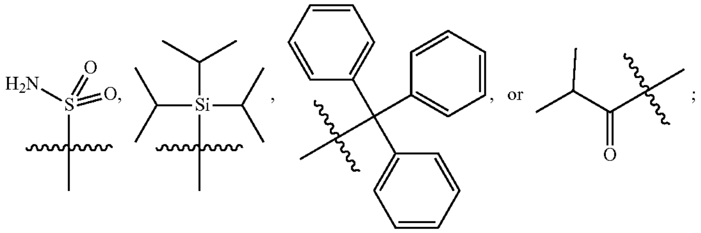<br>$M_4$ = —$(C_2\text{-}C_6)$alkyl-O—$(C_{10}\text{-}C_{20})$alkyl;<br>each $M_5$ = —$(CH_2)_n$—S—C(═O)—$(C_1\text{-}C_8)$alkyl;<br>n is 1-4; and<br>$R_2$ = —OH, —O—COO-alkyl |

TABLE 1-continued
| Markush Substrates and Products | | | |
|---|---|---|---|
| A | Markush Substrates | B | Markush Products |
| XIVA | 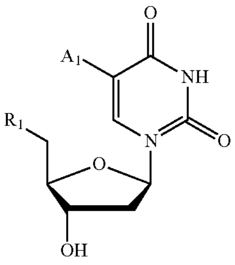 | XIVB 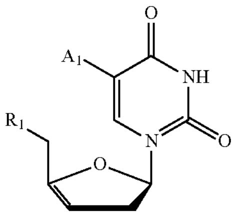 | $R_1$ = OH,<br>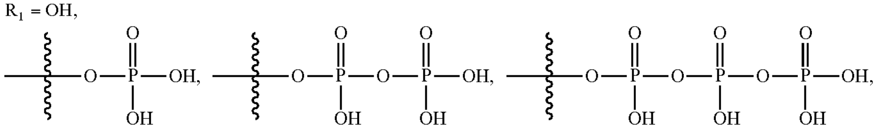<br>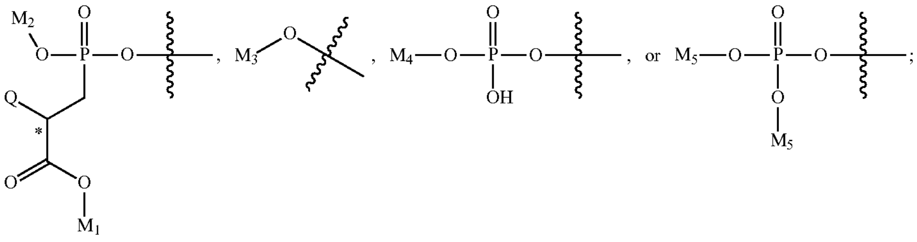<br>Q is a side chain of an amino acid;<br>$M_1$ = an alkyl; $M_2$ = an aryl, a substituted aryl, a heteroaryl or a substituted heteroaryl;<br>$M_3$ = 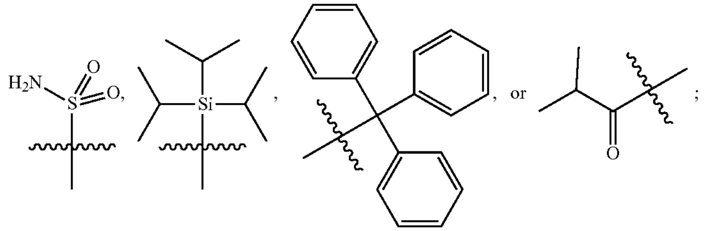<br>$M_4$ = $-(C_2-C_6)$alkyl-O$-(C_{10}-C_{20})$alkyl;<br>each $M_5$ = $-(CH_2)_n-S-C(=O)-(C_1-C_8)$alkyl;<br>n is 1-4; and<br>$A_1$ = a halo, a haloalkyl, an alkyl, 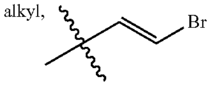 |

TABLE 1-continued
| Markush Substrates and Products | | | |
|---|---|---|---|
| A | Markush Substrates | B | Markush Products |
| XVA | 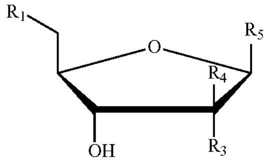 | XVB | 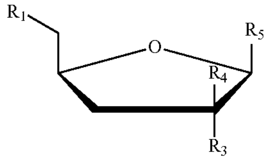 |
$R_1$ = OH,
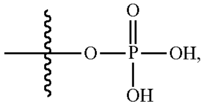 , 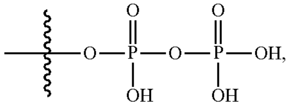 , 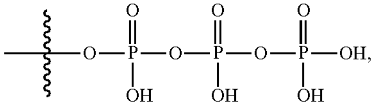 ,
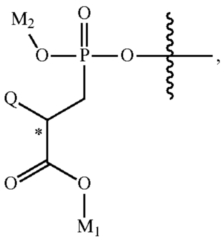 , 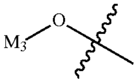 , 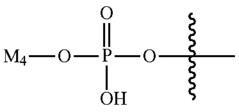 , or 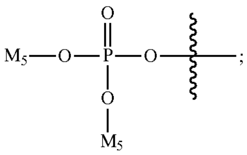 ;
Q is a side chain of an amino acid; $M_1$ = an alkyl; $M_2$ = an aryl, a substituted aryl, a heteroaryl or a substituted heteroaryl;
$M_3$ = 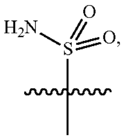 , 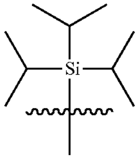 , 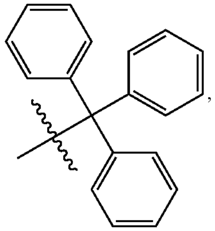 , or 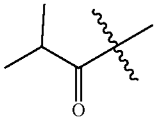 ;
$M_4$ = $-(C_2-C_6)$alkyl-O$-(C_{10}-C_{20})$alkyl;
each $M_5$ = $-(CH_2)_n-S-C(=O)-(C_1-C_8)$alkyl;
n is 1-4;
$R_4$ = H, a halo or an alkyl
$R_3$ = H, a halo, an alkoxy TABLE 1-continued
Markush Substrates and Products
| A | Markush Substrates | B | Markush Products |
| --- | --- | --- | --- |
| XVIA | 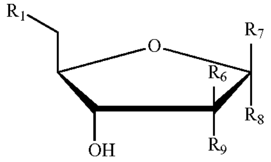 | XVIB | 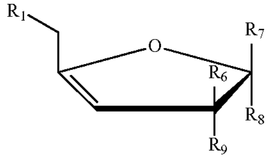 |
| | | | $R_5$ = 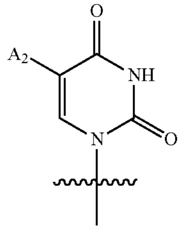 or 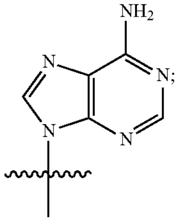; |
| | | | $A_2$ = H, a halo or alkyl; and wherein $R_3$ is not the same as $R_4$ |
| | | | $R_1$ = OH, 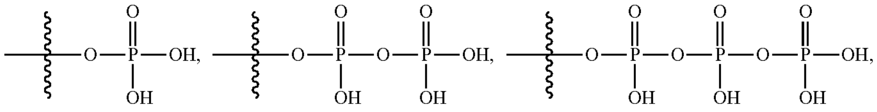 [SMILES: *OP(=O)(O)O ; *OP(=O)(O)OP(=O)(O)O ; *OP(=O)(O)OP(=O)(O)OP(=O)(O)O] |
| | | | 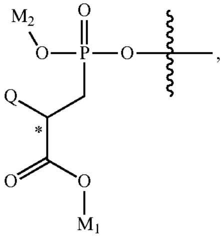, 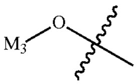, 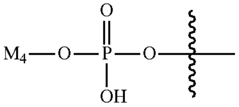, or 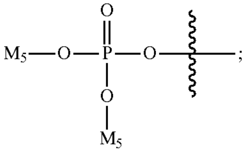; |
| | | | Q is a side chain of an amino acid; $M_1$ = an alkyl; $M_2$ = an aryl, a substituted aryl, a heteroaryl or a substituted heteroaryl; |
| | | | $M_3$ = 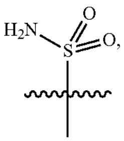, 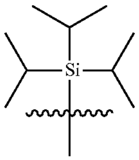, 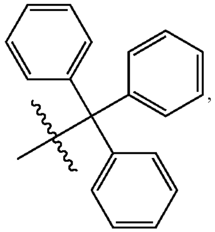, or 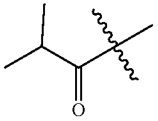; |

TABLE 1-continued

| Markush Substrates and Products | | | |
|---|---|---|---|
| A | Markush Substrates | B | Markush Products |
| | | | $M_4$ = —($C_2$-$C_6$)alkyl-O—($C_{10}$-$C_{20}$)alkyl;<br>each $M_5$ = —$(CH_2)_n$—S—C(═O)—($C_1$-$C_8$)alkyl;<br>n is 1-4;<br>$R_9$ = H, OH or —O—COO-alkyl<br>$R_6$ = H, Me, —CCH or OH<br>$R_8$ = H<br>$R_7$ = 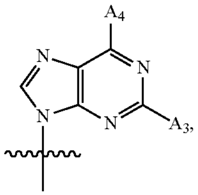 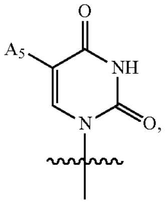 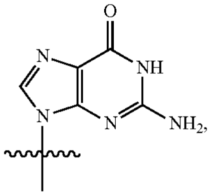 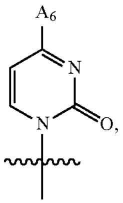 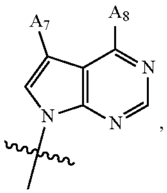 ,<br>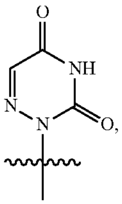 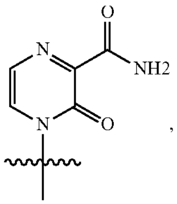 , 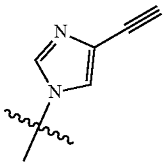 , 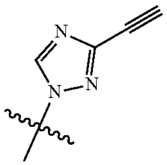 , 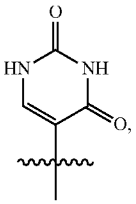 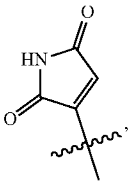 ,<br>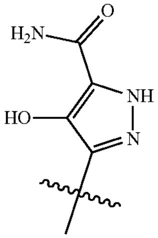 , 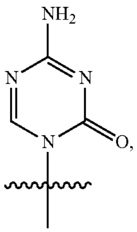 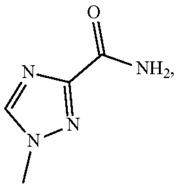 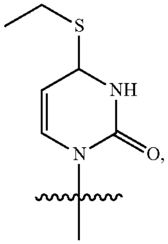 or 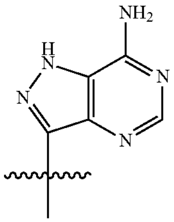<br>$A_3$ = H, a halo or an amino;<br>$A_4$ = H, an amino, an alkoxy, or an alkyl;<br>$A_5$ = H, a halo, a hydroxy or an alkyne;<br>$A_6$ = H, an amino or a hydroxylamino;<br>$A_7$ = H or an amido;<br>$A_8$ = an amino or an alkyl<br>wherein if $R_1$ is OH and is |

TABLE 1-continued
| Markush Substrates and Products | | | |
|---|---|---|---|
| A | Markush Substrates | B | Markush Products |
| | | | 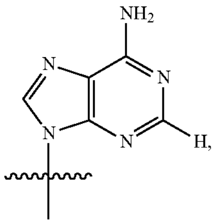 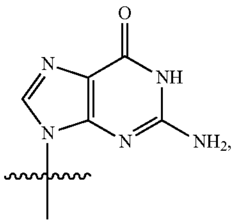 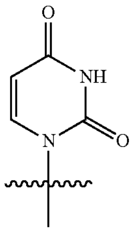 or 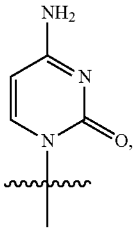 [SMILES: *n1ccc(N)nc1=O] and $R_9$ is OH then $R_6$ is not H; and wherein if $R_1$ is 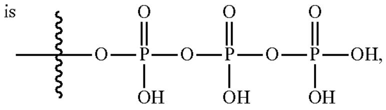 and $R_7$ is 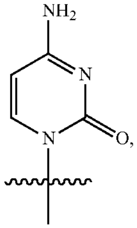 and $R_9$ is OH, then $R_6$ is not H. |
| XVIIA | 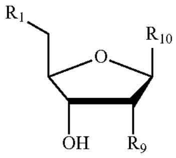 | XVIIB | 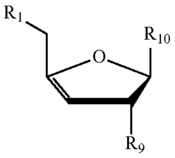 $R_1$ = OH, 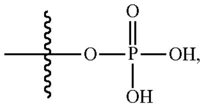 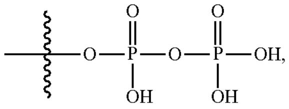 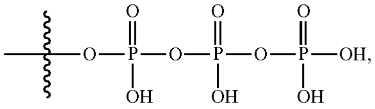 |

TABLE 1-continued
| Markush Substrates and Products | | | |
|---|---|---|---|
| A | Markush Substrates | B | Markush Products |
| | | | 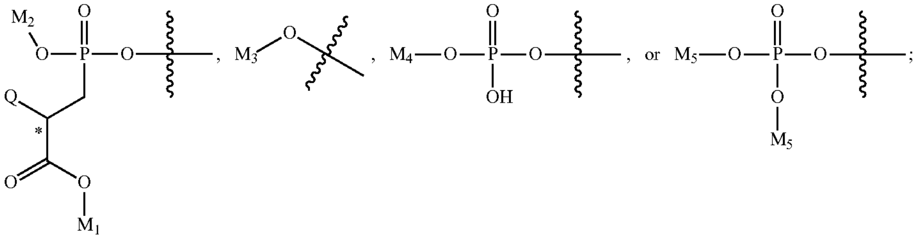<br>Q is a side chain of an amino acid; $M_1$ = an alkyl; $M_2$ = an aryl, a substituted aryl, a heteroaryl or a substituted heteroaryl;<br>$M_3$ = 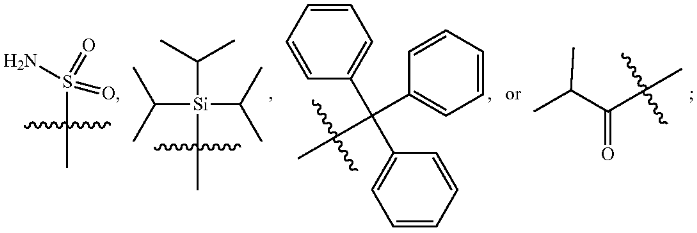 ;<br>$M_4$ = $-(C_2-C_6)$alkyl-O$-(C_{10}-C_{20})$alkyl;<br>each $M_5$ = $-(CH_2)_n-S-C(=O)-(C_1-C_8)$alkyl;<br>n is 1-4;<br>$R_9$ = H, OH or $-O-COO$-alkyl.<br>$R_{10}$ = 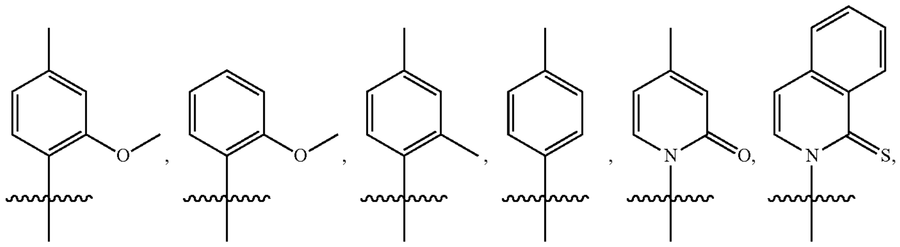 |

TABLE 1-continued
| Markush Substrates and Products | | | |
|---|---|---|---|
| A | Markush Substrates | B | Markush Products |
| | | | 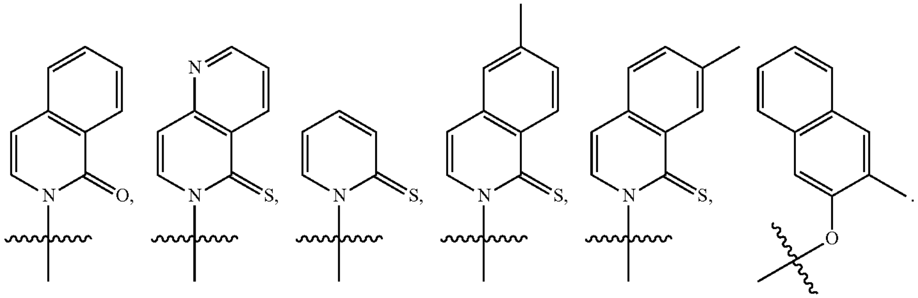 |
| XVIIIA | 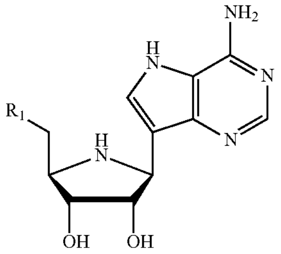 | XVIIIB 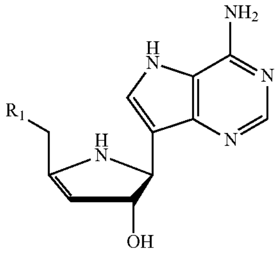 | $R_1$ = OH, 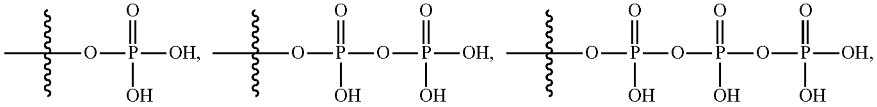 |
| XIXA | 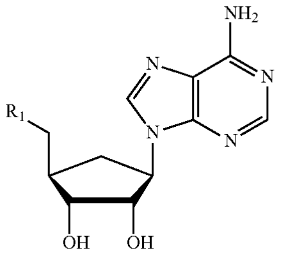 | XIXB 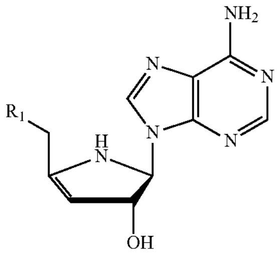 | 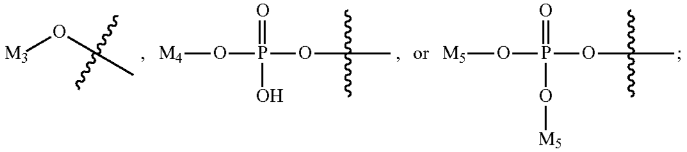 Q is a side chain of an amino acid; $M_1$ = an alkyl; $M_2$ = an aryl, a substituted aryl, a heteroaryl or a substituted heteroaryl; |

TABLE 1-continued
| Markush Substrates and Products | | | |
|---|---|---|---|
| A | Markush Substrates | B | Markush Products |
| XXA | 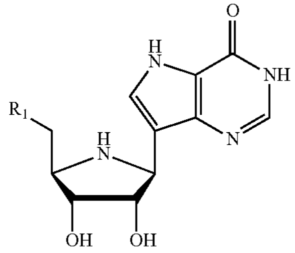 | XXB | 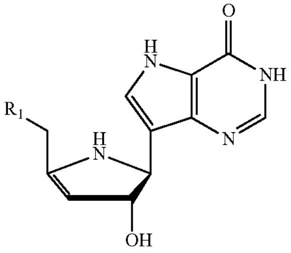 $M_3$ = 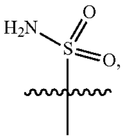, 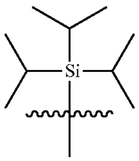, 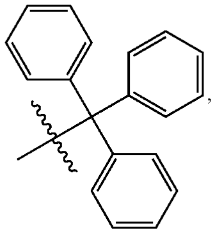, or 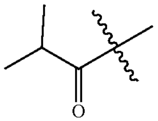. |
| XXIA | 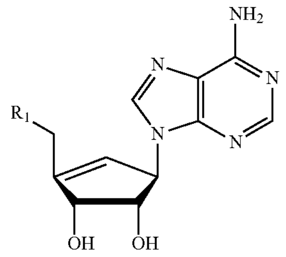 | XXIB | 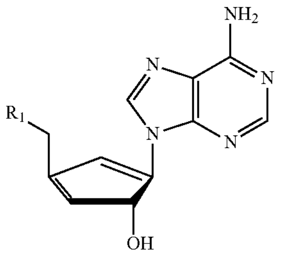 $M_4$ = —($C_2$-$C_6$)alkyl-O—($C_{10}$-$C_{20}$)alkyl;<br>each $M_5$ = —$(CH_2)_n$—S—C(═O)—($C_1$-$C_8$)alkyl;<br>n is 1-4. |
| XXIIA | 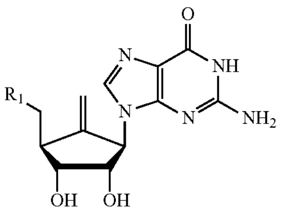 | XXIIB | 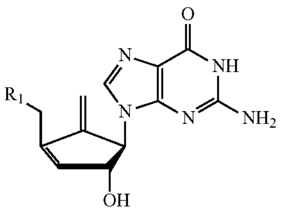 |
| XXIIIA | 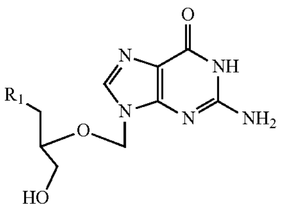 | XXIIIB | 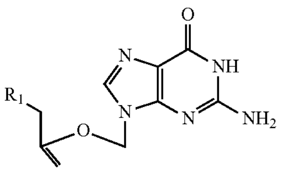 |

TABLE 1-continued
| Markush Substrates and Products | | | | |
|---|---|---|---|---|
| A | Markush Substrates | B | | Markush Products |
| XXIVA | 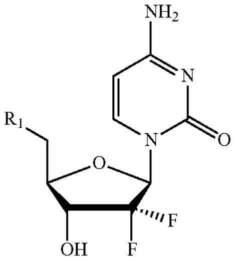 | XXIVB | 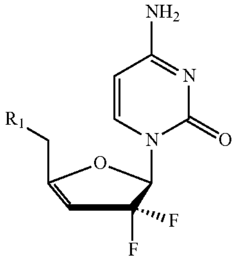 | $R_1$ = OH, 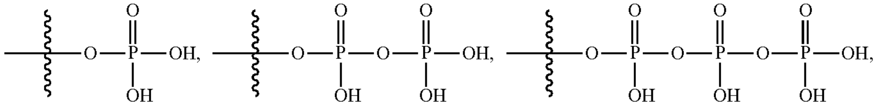 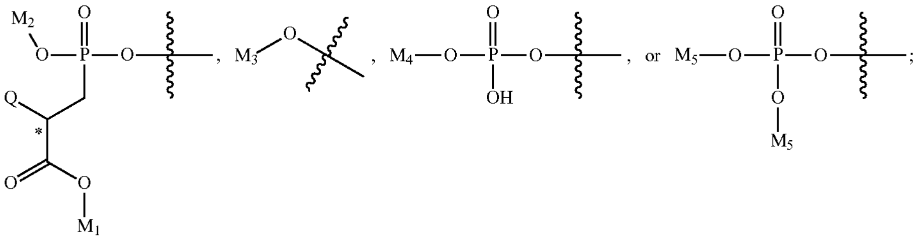 Q is a side chain of an amino acid; $M_1$ = an alkyl; $M_2$ = an aryl, a substituted aryl, a heteroaryl or a substituted heteroaryl; $M_3$ = 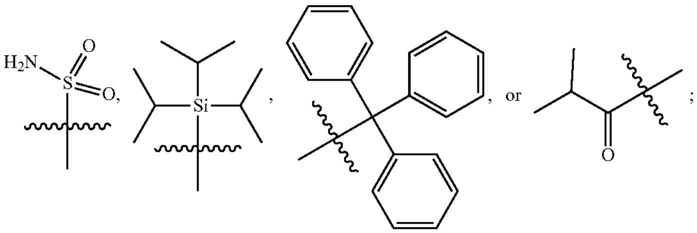 $M_4$ = —($C_2$-$C_6$)alkyl-O—($C_{10}$-$C_{20}$)alkyl; each $M_5$ is —$(CH_2)_n$—S—C(=O)—($C_1$-$C_8$)alkyl; and n is 1-4 |

TABLE 1-continued
| Markush Substrates and Products | | | |
|---|---|---|---|
| A | Markush Substrates | B | Markush Products |
| XXVA | 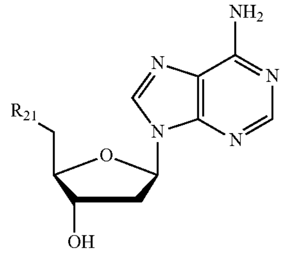 | XXVB | 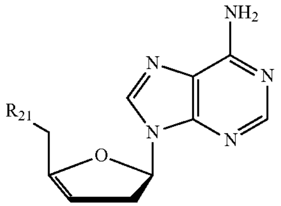 |
| | | | 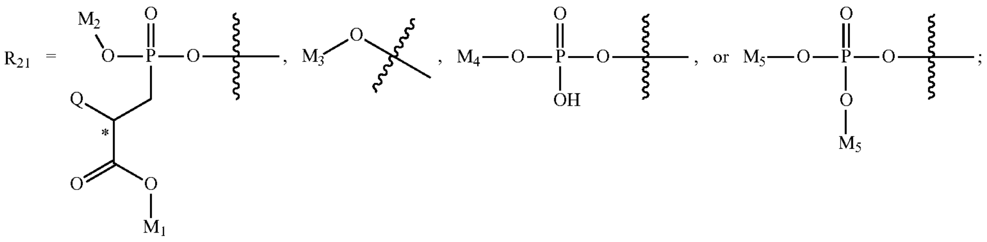 Q is a side chain of an amino acid; $M_1$ = an alkyl; $M_2$ = an aryl, a substituted aryl, a heteroaryl or a substituted heteroaryl; 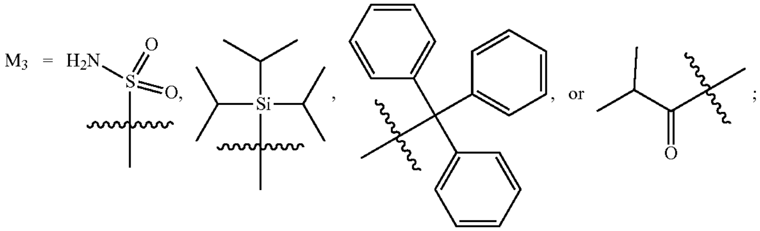 $M_4$ = $-(C_2\text{-}C_6)$alkyl-O$-(C_{10}\text{-}C_{20})$alkyl; each $M_5$ is $-(CH_2)_n-S-C(=O)-(C_1\text{-}C_8)$alkyl; and n is 1-4 |

TABLE 2
Substrate and product structures
| Substrate Name/A | Substrate Structure | Product Name/B (Formula #) | Product Structure | Markush group |
|---|---|---|---|---|
| 2'-C-methyladenosine | 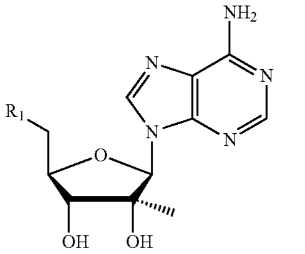 | XVIB1 | 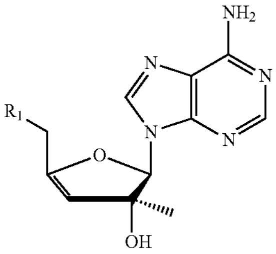 | XVIB |
| 2'-C-methylguanosine | 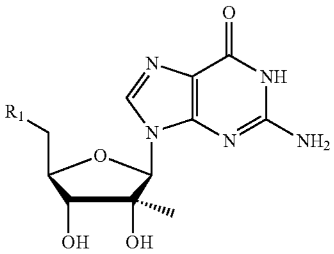 | XVIB2 | 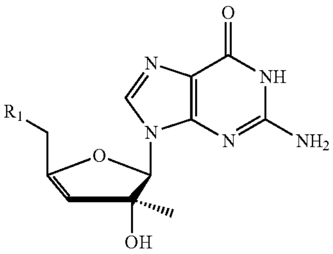 | XVIB |
| 2'-C-methyluridine | 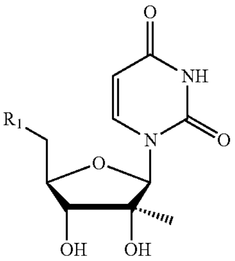 | XVIB3 | 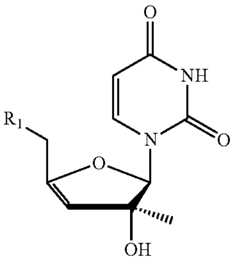 | XVIB |
| 2'-C-Methylcytidine | 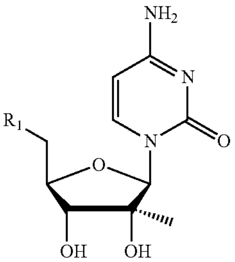 | XVIB4 | 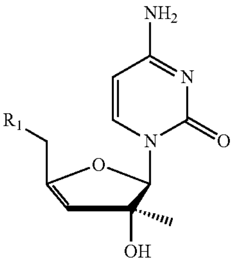 | XVIB |
| 2'-C-ethynyladenosine | 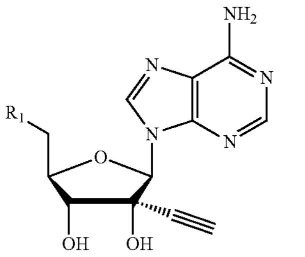 | XVIB5 | 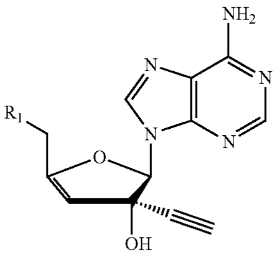 | XVIB |

TABLE 2-continued
| Substrate and product structures | | | | |
|---|---|---|---|---|
| Substrate Name/A | Substrate Structure | Product Name/B (Formula #) | Product Structure | Markush group |
| Cytarabine (ara-C) | 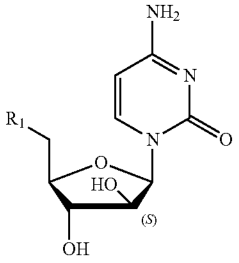 | XVIB6 | 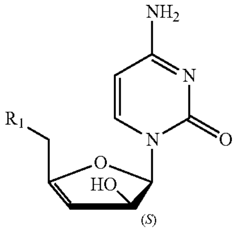 | XVIB |
| ara-A (vidarabine) | 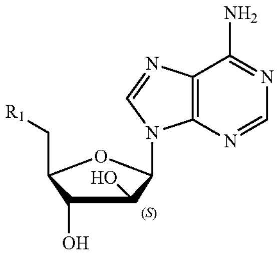 | XVIB7 | 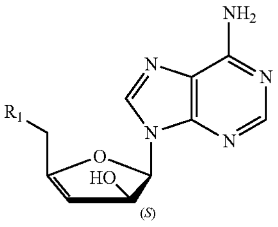 | XVIB |
| Gemcitabine hydrochloride | 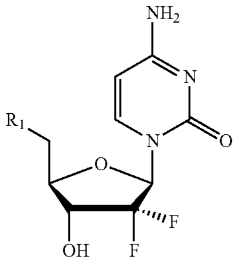 | XXVIB | 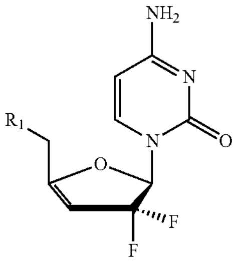 | XXVIB |
| 2'-Deoxy-2'-fluoro-2'-methyluridine | 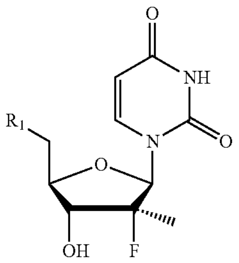 | XVB1 | 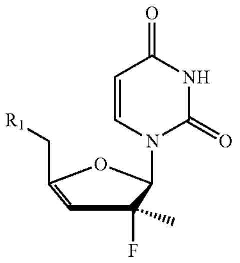 | XVB |
| 2'OMe-Uridine | 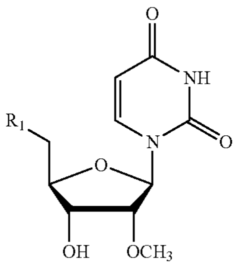 | XVB2 | 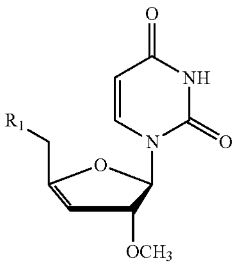 | XVB |

TABLE 2-continued

Substrate and product structures

| Substrate Name/A | Substrate Structure | Product Name/B (Formula #) | Product Structure | Markush group |
|---|---|---|---|---|
| 2'OMe-Adenosine | 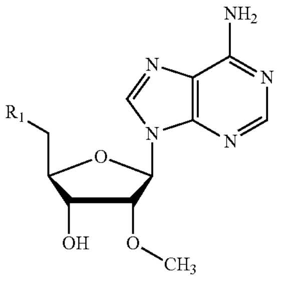 | XVB3 | 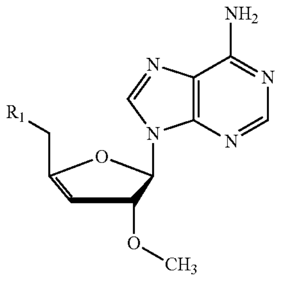 | XVB |
| T-1106 | 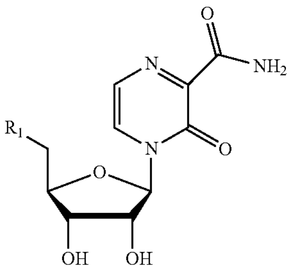 | XVIB8 | 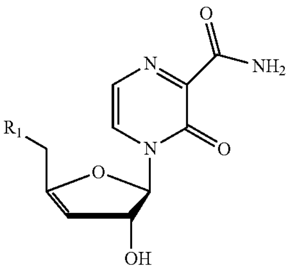 | XVIB |
| Fluorouridine 1-[(2R,3R,4S,5R)-3,4-dihydroxy-5-(hydroxymethyl) oxolan-2-yl]-5-fluoropyrimidine-2,4-dione | 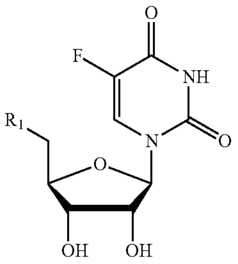 | 5-fluoro-1-((2R,3R)-3-hydroxy-5-(hydroxy methyl)-2,3-dihydrofuran-2-yl)pyrimidine-2,4(1H,3H)-dione XVIB9 | 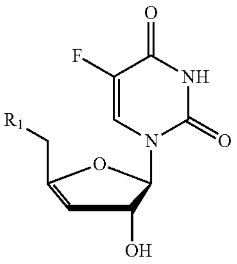 | XVIB |
| 5-Fluoro-deoxy-uridine | 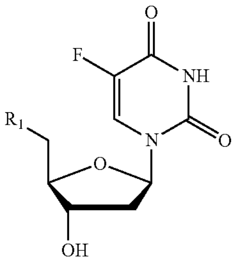 | XIVB1 | 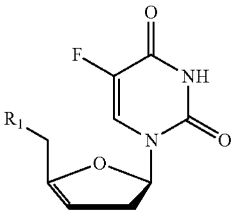 | XVIB |
| 3,4-dihydroxy-5-(hydroxymethyl) tetrahydrofuran-2-yl)-4-(hydroxyamino) pyrimidin-2(lH)-one | 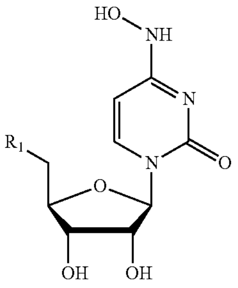 | XVIB10 | 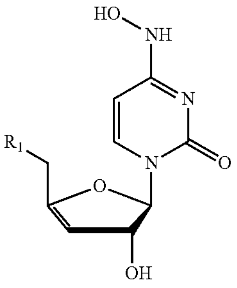 | XVIB |

TABLE 2-continued
| Substrate and product structures | | | | |
|---|---|---|---|---|
| Substrate Name/A | Substrate Structure | Product Name/B (Formula #) | Product Structure | Markush group |
| 6-Methyl-7-deazaadenosine | 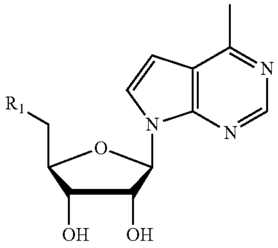 | XVIB11 | 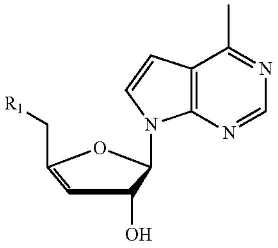 | XVIB |
| N6-(9-antranylmethyl) adenosine | 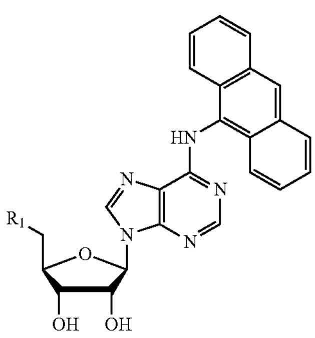 | XVIB12 | 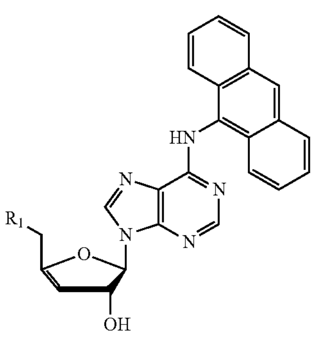 | XVIB |
| N6-(1-pyrenylmethyl) adenosine | 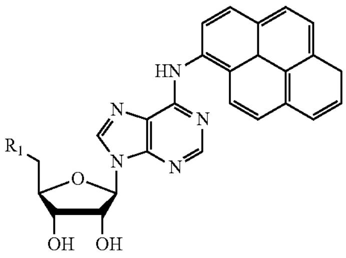 | XVIB13 | 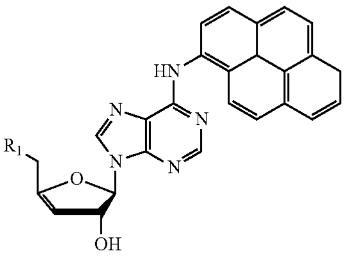 | XVIB |
| 5-(Perylen-3-yl)ethynyl-arabino-uridine | 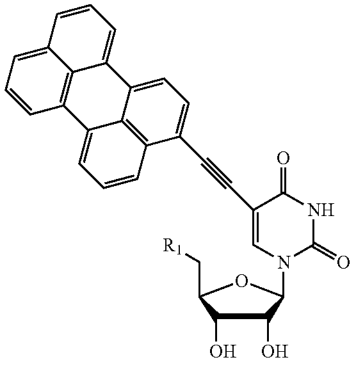 | XVIB14 | 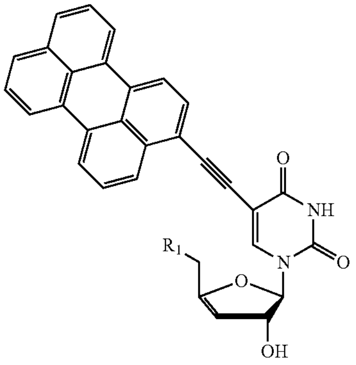 | XVIB |
| ETAR | 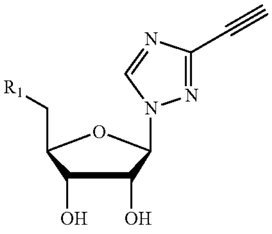 | XVIB15 | 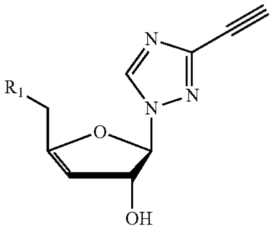 | XVIB |

TABLE 2-continued
| Substrate and product structures | | | | |
|---|---|---|---|---|
| Substrate Name/A | Substrate Structure | Product Name/B (Formula #) | Product Structure | Markush group |
| IM18 | 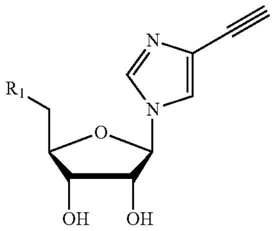 | XVIB16 | 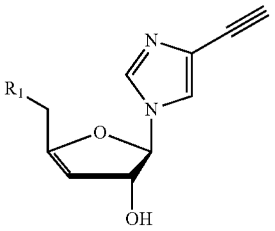 | XVIB |
| 6-Azauridine | 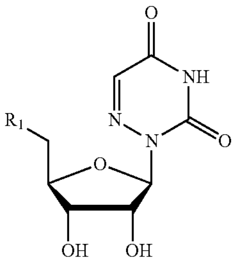 | XVIB17 | 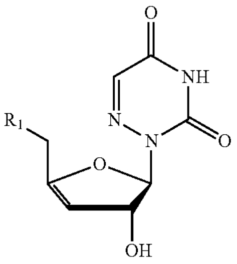 | XVIB |
| Zebularine | 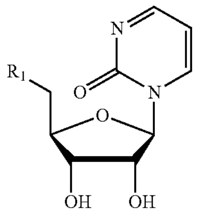 | XVIB18 | 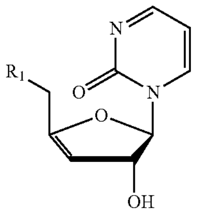 | XVIB |
| 5-Azacytidine | 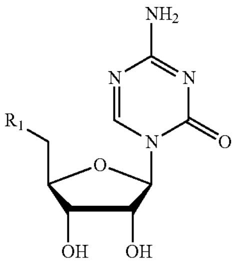 | XVIB19 | 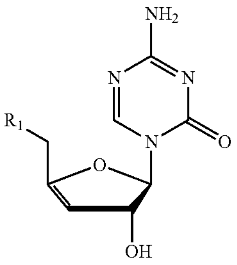 | XVIB |
| Ribavirin (Virazole) | 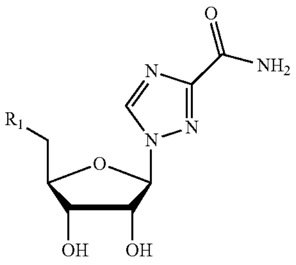 | XVIB20 | 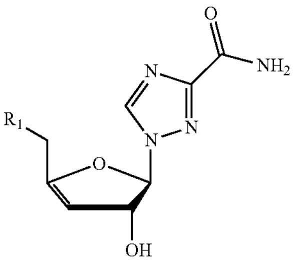 | XVIB |
| Formycin A | 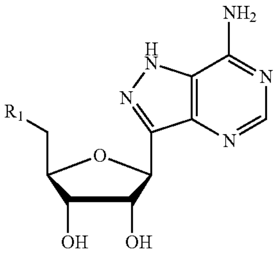 | XVIB21 | 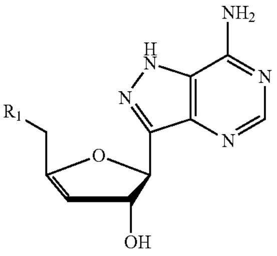 | XVIB |

TABLE 2-continued
Substrate and product structures
| Substrate Name/A | Substrate Structure | Product Name/B (Formula #) | Product Structure | Markush group |
|---|---|---|---|---|
| Pyrazofurin | 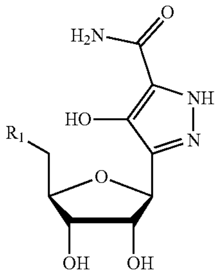 | XVIB22 | 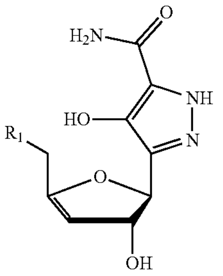 | XVIB |
| Pseudouridine | 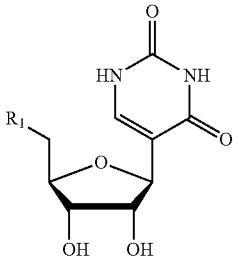 | XVIB23 | 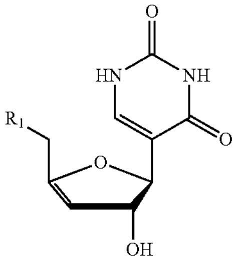 | XVIB |
| Showdomycin | 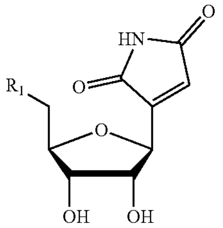 | XVIB24 | 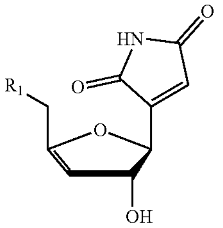 | XVIB |
| Idoxuridine | 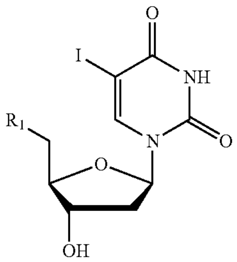 | XIVB2 | 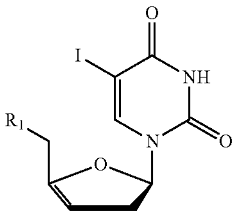 | XVIB |
| Trifluridine | 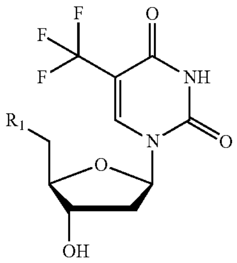 | XIVB3 | 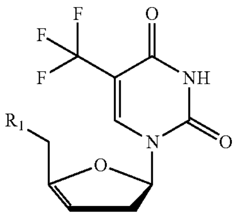 | XVIB |

TABLE 2-continued
Substrate and product structures
| Substrate Name/A | Substrate Structure | Product Name/B (Formula #) | Product Structure | Markush group |
|---|---|---|---|---|
| Brivudine | 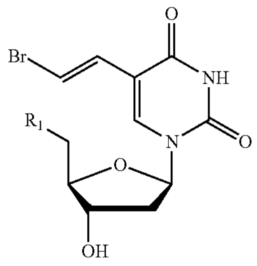 | XIVB4 | 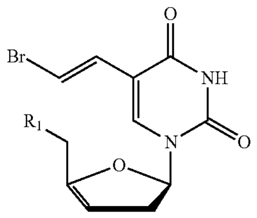 | XVIB |
| Acedurid | 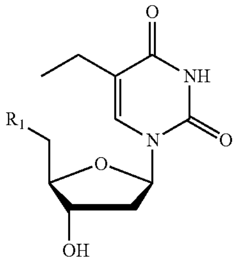 | XIVB5 | 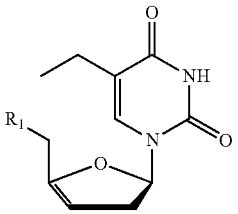 | XVIB |
| 5-Hydroxy-Uridine | 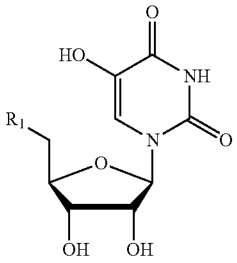 | XVIB25 | 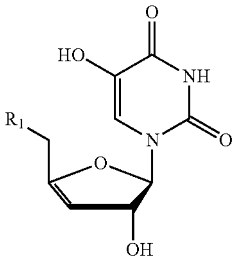 | XVIB |
| 5-Methyl-Uridine | 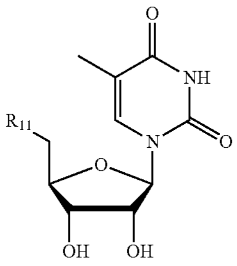 | VB1 | 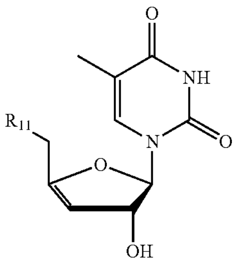 | VB |
| 4-Thio-i-propyl-Uridine | 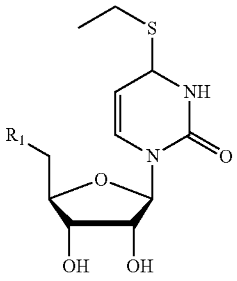 | XVIB26 | 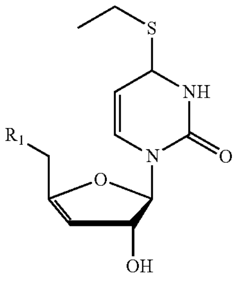 | XVIB |

TABLE 2-continued
| Substrate and product structures | | | | |
|---|---|---|---|---|
| Substrate Name/A | Substrate Structure | Product Name/B (Formula #) | Product Structure | Markush group |
| GS-441524 | 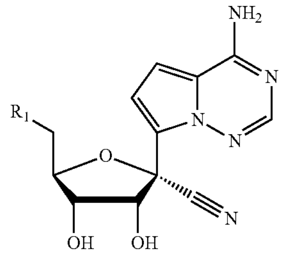 | XIIIB1 | 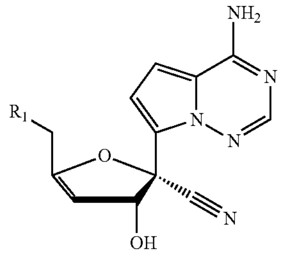 | XIIIB |
| Remdesvir-nucleoside | 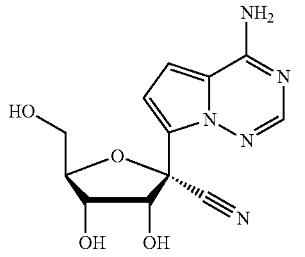 | Compound 101 | 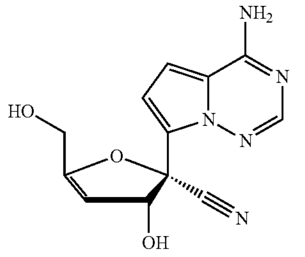 | |
| 7-Deaza-2'-C-methyl-adenosine | 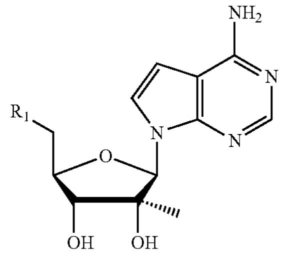 | XVIB27 | 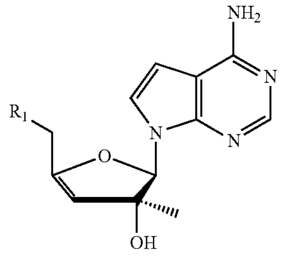 | XVIB |
| NITD008 | 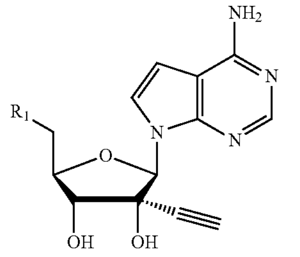 | XVIB28 | 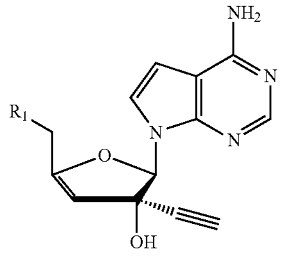 | XVIB |
| 2'-Deoxy-2'-fluoro-arabinofuranosyl nucleoside FIAU | 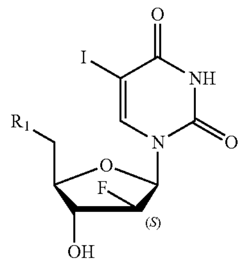 | XVB4 | 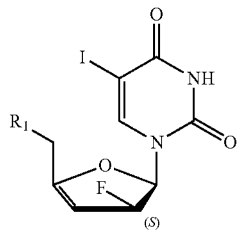 | XVB |

TABLE 2-continued

Substrate and product structures

| Substrate Name/A | Substrate Structure | Product Name/B (Formula #) | Product Structure | Markush group |
|---|---|---|---|---|
| 2'-Deoxy-2'-fluoro-arabinofuranosyl nucleoside FMAU | 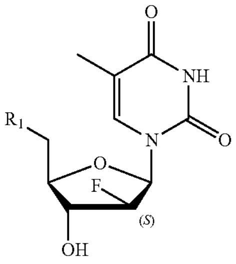 | XVB5 | 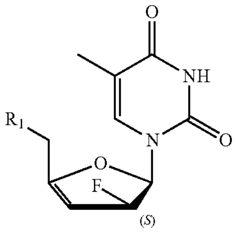 | XVB |
| 2'-Deoxy-2'-fluoro-arabinofuranosyl nucleoside FEAU | 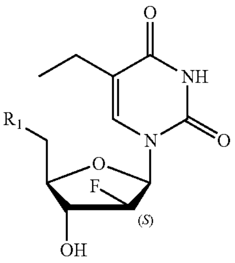 | XVB6 | 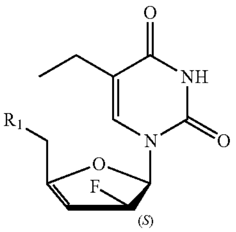 | XVB |
| Fludarabine (2-Fluoro-ara-Adenosine) | 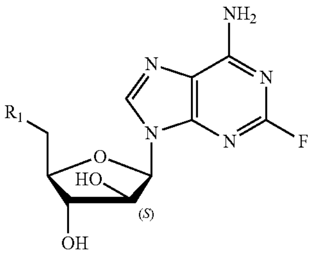 | XVIB29 | 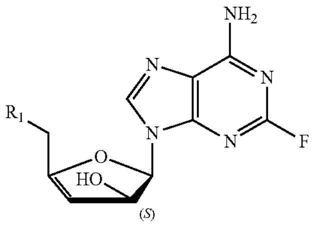 | XVIB |
| NITD449 | 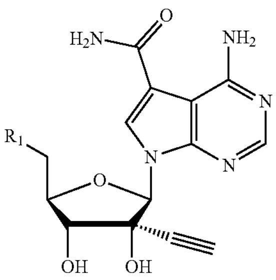 | XVIB30 | 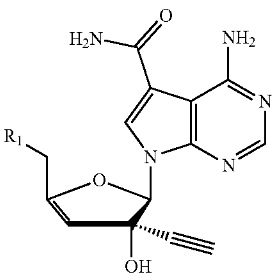 | XVIB |
| 2-(2-amino-6-methoxy-9H-purin-9-yl)-5-(hydroxymethyl)-3-methyltetrahydro-furan-3,4-diol | 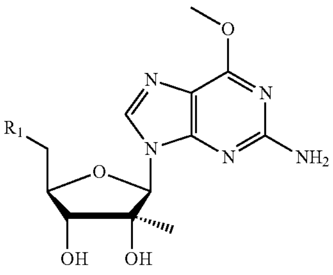 | XVIB31 | 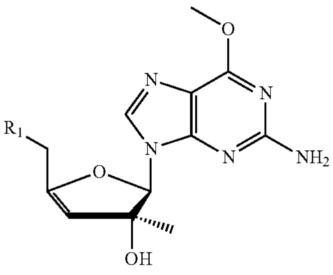 | XVIB |

TABLE 2-continued

Substrate and product structures

| Substrate Name/A | Substrate Structure | Product Name/B (Formula #) | Product Structure | Markush group |
|---|---|---|---|---|
| 3-fluoro-4-hydroxy-5-(hydroxymethyl)-3-methyltetrahydro-furan-2-yl)pyrimidine-2,4(1H,3H)-dione | 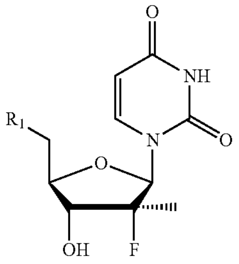 | XVB1 | 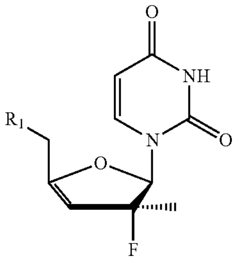 | XVB |
| 2-(6-(benzylamino)-9H-purin-9-yl)-5-(hydroxymethyl) tetrahydrofuran-3,4-diol | 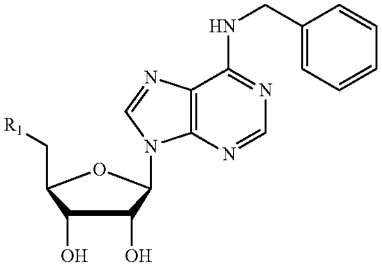 | XVIB32 | 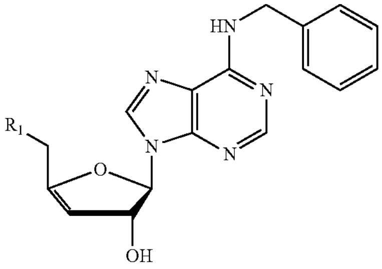 | XVIB |
| 3,4-dihydroxy-5-(hydroxymethyl) tetrahydrofuran-2-yl)-4-(hydroxyamino) pyrimidin-2(1H)-one | 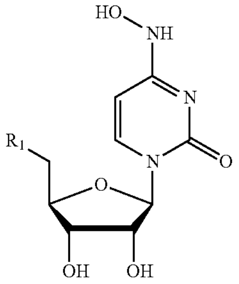 | XVIB33 | 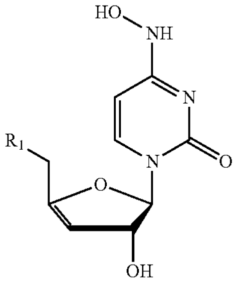 | XVIB |
| Ganciclovir | 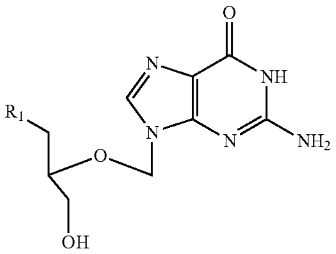 | XXIIIB | 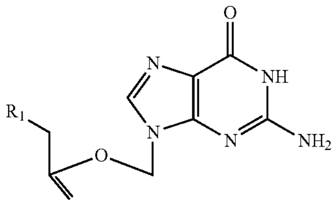 | XXIIIB |
| BCX4430 | 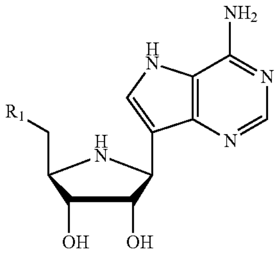 | XXIIIB | 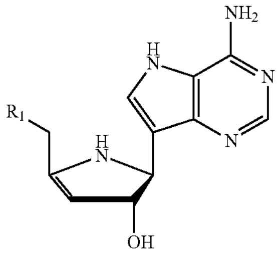 | XXIIIB |

TABLE 2-continued
Substrate and product structures
| Substrate Name/A | Substrate Structure | Product Name/B (Formula #) | Product Structure | Markush group |
|---|---|---|---|---|
| Aristeromycin | 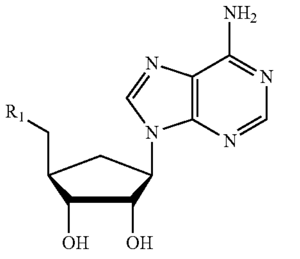 | XIXB | 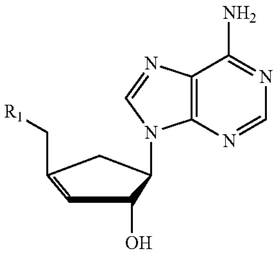 | XIXB |
| Forodesine | 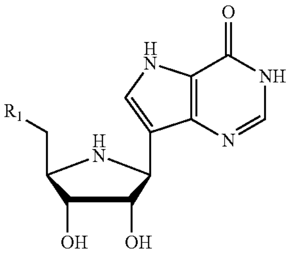 | XXB | 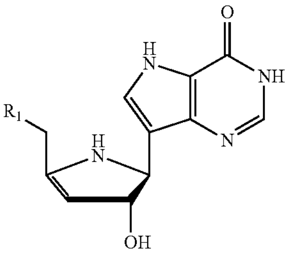 | XXB |
| Neplanocin A | 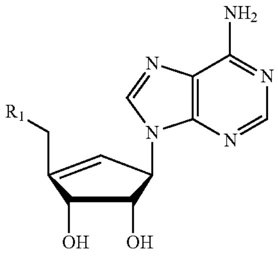 | XXIB | 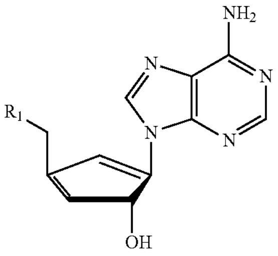 | XXIB |
| Entecavir | 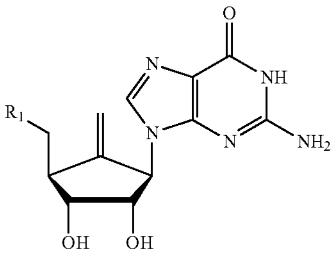 | XXIIIB | 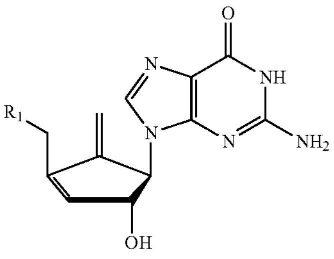 | XXIIIB |
| Telbivudine | 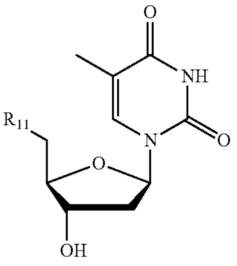 | VIIIB | 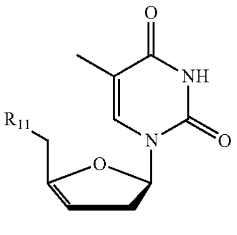 | VIIIB |

In some embodiments $R_1$ OH,

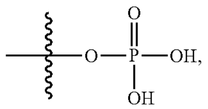 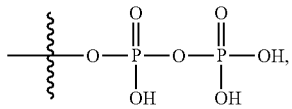

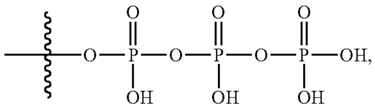

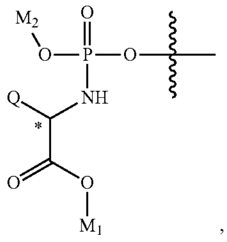

,

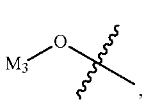

,

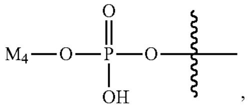

, or

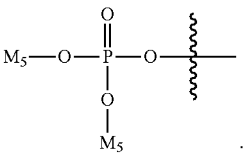

.

In some embodiments $R_{11}$ is OH,

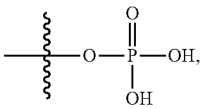 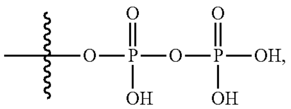

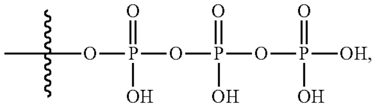

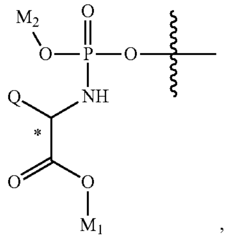

,

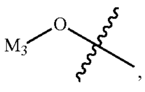

,

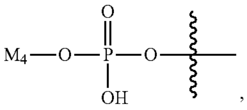

, or

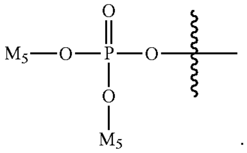

.

In one embodiment, Q of $R_1$ or $R_{11}$ is a side chain of an amino acid. In another embodiment, $M_1$ of $R_1$ or $R_{11}$ is an alkyl. In another embodiment, $M_2$ is of $R_1$ or $R_{11}$ an aryl, a substituted aryl, a heteroaryl or a substituted aryl. In another embodiment, $M_3$ of $R_1$ or $R_{11}$ is

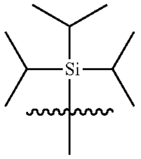

,

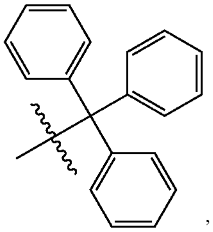

, or

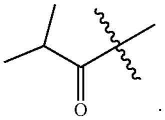

.

In another embodiment, $M_4$ of $R_1$ or $R_{11}$ is $-(C_2-C_6)$alkyl-O$-(C_{10}-C_{20})$alkyl. In another embodiment, $M_5$ of $R_1$ or $R_{11}$ is $-(CH_2)_n-S-C(=O)-(C_1-C_8)$alkyl. In one embodiment, n of $M_5$ is 1, 2, 3 or 4.

Pharmaceutical Compositions

In one embodiment, provided herein is a pharmaceutical composition comprising any one of the compounds disclosed herein. In one embodiment, provided herein is a pharmaceutical composition comprising one or more of the compounds disclosed herein. In one embodiment, provided herein is a pharmaceutical composition comprising any one of the compounds disclosed herein and a pharmaceutically acceptable carrier. In one embodiment, a pharmaceutical composition comprises a preparation of one or more of the ddh- or deoxy-ddh compounds, or prodrugs thereof, described herein with other chemical components, such as physiologically suitable carriers and excipients. The purpose of a pharmaceutical composition is to facilitate administration of a compound to an organism. In certain embodiments, a pharmaceutical composition provides the pharmaceutical dosage form of a drug.

In one embodiment, provided herein is a pharmaceutical composition comprising a compound represented by a the structure any one of the following compounds: Formula IB, Formula IIB, Formula IIIB, Formula IVB, Formula VB, Formula VB1, Formula VIB, Formula VIIB, Formula VIIIB, Formula IXB, Formula XB, Formula XIB, Formula XIIB, Formula XIIIB, Formula XIIIB1, Formula XIVB, Formula XIVB1, Formula XIVB2, Formula XIV3, Formula XIV4, Formula XIV5, Formula XVB, Formula XVB1, Formula XVB2, Formula XVB3, Formula XVB4, Formula XVB5, Formula XVB6, Formula XVIB, Formula XVIB1, Formula XVIB2, Formula XVIB3, Formula XVIB4, Formula XVIB5, Formula XVIB6, Formula XVIB7, Formula XVIB8, Formula XVIB9, Formula XVIB10, Formula XVIB11, Formula XVIB12, Formula XVIB13, Formula XVIB14, Formula XVIB15, Formula XVIB16, Formula XVIB17, Formula XVIB18, Formula XVIB19, Formula XVIB20, Formula XVIB21, Formula XVIB22, Formula XVIB23, Formula XVIB24, Formula XVIB25, Formula XVIB26, Formula XVIB27, Formula XVIB28, Formula XVIB29, Formula XVIB30, Formula XVIB31, Formula XVIB32, Formula XVIB33, Formula XVIIB, Formula XVIIIB, Formula XXB, Formula XIXB, Formula XXIB, Formula XXIIB, Formula XXXIIIB, Formula XXIVB, Formula XXVB or a combination thereof.

In one embodiment, provided herein is a pharmaceutical composition comprising a compound represented by the structure of Formula IB, Formula IB, Formula IIIB, Formula IVB, Formula VB, Formula VIB, Formula VIB, Formula VIIIB, Formula IXB, Formula XB, Formula XB, Formula XIIB, Formula XIIIB, Formula XIVB, Formula XVB, Formula XVIB, Formula XVIB, Formula XVIIIB, Formula XXB, Formula XIXB, Formula XXIB, Formula XXIB, Formula XXXIIB, Formula XXIVB, Formula XXVB or a combination thereof.

In one embodiment, provided herein is a pharmaceutical composition comprising a compound represented by the structure of Formula B, Formula IIB, Formula IIIB, Formula IVB, Formula VB, or a combination thereof.

In one embodiment, provided herein is a pharmaceutical composition comprising a compound represented by the structure of Formula B. In one embodiment, provided herein is a pharmaceutical composition comprising a compound represented by the structure of Formula IIB. In one embodiment, provided herein is a pharmaceutical composition comprising a compound represented by the structure of Formula IIIB. In one embodiment, provided herein is a pharmaceutical composition comprising a compound represented by the structure of Formula IVB. In one embodiment, provided herein is a pharmaceutical composition comprising a compound represented by the structure of Formula VB. In one embodiment, provided herein is a pharmaceutical composition comprising a compound represented by the structure of Formula VB1.

In one embodiment, provided herein is a pharmaceutical composition comprising a compound represented by the structure of Formula VIB, Formula VIIB, Formula VIIIB or a combination thereof. In one embodiment, provided herein is a pharmaceutical composition comprising a compound represented by the structure of Formula VIB. In one embodiment, provided herein is a pharmaceutical composition comprising a compound represented by the structure of Formula VIIB. In one embodiment, provided herein is a pharmaceutical composition comprising a compound represented by the structure of Formula VIIIB. In one embodiment, provided herein is a pharmaceutical composition comprising a compound represented by the structure of Formula IXB. In one embodiment, provided herein is a pharmaceutical composition comprising a compound represented by the structure of Formula XB, Formula XIB, Formula XIIB, or a combination thereof. In one embodiment, provided herein is a pharmaceutical composition comprising a compound represented by the structure of Formula XB. In one embodiment, provided herein is a pharmaceutical composition comprising a compound represented by the structure of Formula XIB. In one embodiment, provided herein is a pharmaceutical composition comprising a compound represented by the structure of Formula XIIB. In one embodiment, provided herein is a pharmaceutical composition comprising a compound represented by the structure of Formula XIIIB. In one embodiment, provided herein is a pharmaceutical composition comprising a compound represented by the structure of Formula XIIIB1.

In one embodiment, provided herein is a pharmaceutical composition comprising a compound represented by the structure of Formula XIVB. In one embodiment, provided herein is a pharmaceutical composition comprising a compound represented by the structure of Formula XIVB1, Formula XIVB2, Formula XIVB3, Formula XIVB4, Formula XIVB5, or a combination thereof. In one embodiment, provided herein is a pharmaceutical composition comprising a compound represented by the structure of Formula XIVB1. In one embodiment, provided herein is a pharmaceutical composition comprising a compound represented by the structure of Formula XIVB2. In one embodiment, provided herein is a pharmaceutical composition comprising a compound represented by the structure of Formula XIVB3. In one embodiment, provided herein is a pharmaceutical composition comprising a compound represented by the structure of Formula XIVB4. In one embodiment, provided herein is a pharmaceutical composition comprising a compound represented by the structure of Formula XIVB5.

In one embodiment, provided herein is a pharmaceutical composition comprising a compound represented by the structure of Formula XVB. In one embodiment, provided herein is a pharmaceutical composition comprising a compound represented by the structure of Formula XVB1, Formula XVB2, Formula XVB3, Formula XVB4, Formula XVB5, Formula XVB6, or a combination thereof. In one embodiment, provided herein is a pharmaceutical composition comprising a compound represented by the structure of Formula XVB1. In one embodiment, provided herein is a pharmaceutical composition comprising a compound represented by the structure of Formula XVB2. In one embodiment, provided herein is a pharmaceutical composition comprising a compound represented by the structure of Formula XVB3. In one embodiment, provided herein is a pharmaceutical composition comprising a compound represented by the structure of Formula XVB4. In one embodiment, provided herein is a pharmaceutical composition comprising a compound represented by the structure of Formula XVB5. In one embodiment, provided herein is a pharmaceutical composition comprising a compound represented by the structure of Formula XVB6.

In one embodiment, provided herein is a pharmaceutical composition comprising a compound represented by the structure of Formula XVIB. In one embodiment, provided herein is a pharmaceutical composition comprising a compound represented by the structure of Formula XVIB1, Formula XVIB2, Formula XVIB3, Formula XVIB4, Formula XVIB5, Formula XVIB6, Formula XVIB7, Formula XVIB8, Formula XVIB9, Formula XVIB10, Formula XVIB11, Formula XVIB12, Formula XVIB13, Formula XVIB14, Formula XVIB15, Formula XVIB16, Formula XVIB17, Formula XVIB18, Formula XVIB19, Formula XVIB20, Formula XVIB21, Formula XVIB22, Formula XVIB23, Formula XVIB24, Formula XVIB25, Formula XVIB26, Formula XVIB27, Formula XVIB28, Formula XVIB29, Formula XVIB30 Formula XVIB31, Formula XVIB32, Formula XVIB33, or a combination thereof.

In one embodiment, provided herein is a pharmaceutical composition comprising a compound represented by the structure of Formula XVIB1. In one embodiment, provided herein is a pharmaceutical composition comprising a compound represented by the structure of Formula XVIB2. In one embodiment, provided herein is a pharmaceutical composition comprising a compound represented by the structure of Formula XVIB3. In one embodiment, provided herein is a pharmaceutical composition comprising a compound represented by the structure of Formula XVIB4. In one embodiment, provided herein is a pharmaceutical composition comprising a compound represented by the structure of Formula XVIB5. In one embodiment, provided herein is a pharmaceutical composition comprising a compound represented by the structure of Formula XVIB6. In one embodiment, provided herein is a pharmaceutical composition comprising a compound represented by the structure of Formula XVIB7. In one embodiment, provided herein is a pharmaceutical composition comprising a compound represented by the structure of Formula XVIB8. In one embodiment, provided herein is a pharmaceutical composition comprising a compound represented by the structure of Formula XVIB9. In one embodiment, provided herein is a pharmaceutical composition comprising a compound represented by the structure of Formula XVIB10. In one embodiment, provided herein is a pharmaceutical composition comprising a compound represented by the structure of Formula XVIB11. In one embodiment, provided herein is a pharmaceutical composition comprising a compound represented by the structure of Formula XVIB12. In one embodiment, provided herein is a pharmaceutical composition comprising a compound represented by the structure of Formula XVIB13. In one embodiment, provided herein is a pharmaceutical composition comprising a compound represented by the structure of Formula XVIB14. In one embodiment, provided herein is a pharmaceutical composition comprising a compound represented by the structure of Formula XVIB15. In one embodiment, provided herein is a pharmaceutical composition comprising a compound represented by the structure of Formula XVIB16. In one embodiment, provided herein is a pharmaceutical composition comprising a compound represented by the structure of Formula XVIB17. In one embodiment, provided herein is a pharmaceutical composition comprising a compound represented by the structure of Formula XVIB18. In one embodiment, provided herein is a pharmaceutical composition comprising a compound represented by the structure of Formula XVIB19. In one embodiment, provided herein is a pharmaceutical composition comprising a compound represented by the structure of Formula XVIB20. In one embodiment, provided herein is a pharmaceutical composition comprising a compound represented by the structure of Formula XVIB21. In one embodiment, provided herein is a pharmaceutical composition comprising a compound represented by the structure of Formula XVIB22. In one embodiment, provided herein is a pharmaceutical composition comprising a compound represented by the structure of Formula XVIB23. In one embodiment, provided herein is a pharmaceutical composition comprising a compound represented by the structure of Formula XVIB24. In one embodiment, provided herein is a pharmaceutical composition comprising a compound represented by the structure of Formula XVIB25. In one embodiment, provided herein is a pharmaceutical composition comprising a compound represented by the structure of Formula XVIB26. In one embodiment, provided herein is a pharmaceutical composition comprising a compound represented by the structure of Formula XVIB27. In one embodiment, provided herein is a pharmaceutical composition comprising a compound represented by the structure of Formula XVIB28. In one embodiment, provided herein is a pharmaceutical composition comprising a compound represented by the structure of Formula XVIB29. In one embodiment, provided herein is a pharmaceutical composition comprising a compound represented by the structure of Formula XVIB30. In one embodiment, provided herein is a pharmaceutical composition comprising a compound represented by the structure of Formula XVIB31. In one embodiment, provided herein is a pharmaceutical composition comprising a compound represented by the structure of Formula XVIB32. In one embodiment, provided herein is a pharmaceutical composition comprising a compound represented by the structure of Formula XVIB33.

In one embodiment, provided herein is a pharmaceutical composition comprising a compound represented by the structure of Formula XVIIB.

In one embodiment, provided herein is a pharmaceutical composition comprising a compound represented by the structure of Formula XVIIIB, Formula XXB or a combination thereof.

In one embodiment, provided herein is a pharmaceutical composition comprising a compound represented by the structure of Formula XVIIB. In one embodiment, provided herein is a pharmaceutical composition comprising a compound represented by the structure of Formula XXB. In one embodiment, provided herein is a pharmaceutical composition comprising a compound represented by the structure of Formula XIXB. In one embodiment, provided herein is a pharmaceutical composition comprising a compound represented by the structure of Formula XXIB. In one embodiment, provided herein is a pharmaceutical composition comprising a compound represented by the structure of Formula XXIIB. In one embodiment, provided herein is a pharmaceutical composition comprising a compound represented by the structure of Formula XXIIIB. In one embodiment, provided herein is a pharmaceutical composition comprising a compound represented by the structure of Formula XXIVB. In one embodiment, provided herein is a pharmaceutical composition comprising a compound represented by the structure of Formula XXVB In one embodiment, provided herein is a pharmaceutical composition comprising at least two of the following compounds: Formula IB, Formula IIB, Formula IIIB, Formula IVB, Formula VB, Formula VB1, Formula VIB, Formula VIIB, Formula VIIIB, Formula IXB, Formula XB, Formula XIB, Formula XIIB, Formula XIIIB, Formula XIIIB1, Formula XIVB, Formula XIVB1, Formula XIVB2, Formula XIV3, Formula XIV4, Formula XIV5, Formula XVB, Formula XVB1, Formula XVB2, Formula XVB3, Formula XVB4, Formula XVB5, Formula XVB6, Formula XVIB, Formula XVIB1, Formula XVIB2, Formula XVIB3, Formula XVIB4, Formula XVIB5, Formula XVIB6, Formula XVIB7, Formula XVIB8, Formula XVIB9, Formula XVIB10, Formula XVIB11, Formula XVIB12, Formula XVIB13, Formula XVIB14, Formula XVIB15, Formula XVIB16, Formula XVIB17, Formula XVIB18, Formula XVIB19, Formula XVIB20, Formula XVIB21, Formula XVIB22, Formula XVIB23, Formula XVIB24, Formula XVIB25, Formula XVIB26, Formula XVIB27, Formula XVIB28, Formula XVIB29, Formula XVIB30, Formula XVIB31, Formula XVIB32, Formula XVIB33, Formula XVIB, Formula XVIIIB, Formula XXB, Formula XIXB, Formula XXIB, Formula XXIIB, Formula XXXIIIB, Formula XXIVB, or Formula XXVB.

In one embodiment, provided herein is a pharmaceutical composition comprising at least two of the following compounds: Formula B, Formula IIB, Formula IIIB, Formula IVB, Formula VB, Formula VIB, Formula VIIB, Formula VIIIB, Formula IXB, Formula XB, Formula XIB, Formula XIIB, Formula XIIIB, Formula XIIIB1, Formula XIVB, Formula XVB, Formula XVIB, Formula XVIB, Formula XVIIIB, Formula XXB, Formula XIXB, Formula XXIB, Formula XXIB, Formula XXXIIIB, Formula XXIVB, or Formula XXVB.

In one embodiment, provided herein is a pharmaceutical composition comprising at least two of the following compounds: Formula VB1. Formula XIIIB1, Formula XIVB1, Formula XIVB2, Formula XIV3, Formula XIV4, Formula XIV5, Formula XVB1, Formula XVB2, Formula XVB3, Formula XVB4, Formula XVB5, Formula XVB6, Formula XVIB1, Formula XVIB2, Formula XVIB3, Formula XVIB4, Formula XVIB5, Formula XVIB6, Formula XVIB7, Formula XVIB8, Formula XVIB9, Formula XVIB10, Formula XVIB11, Formula XVIB12, Formula XVIB13, Formula XVIB14, Formula XVIB15, Formula XVIB16, Formula XVIB17, Formula XVIB18, Formula XVIB19, Formula XVIB20, Formula XVIB21, Formula XVIB22, Formula XVIB23, Formula XVIB24, Formula XVIB25, Formula XVIB26, Formula XVIB27, Formula XVIB28, Formula XVIB29, Formula XVIB30, Formula XVIB31, Formula XVIB32 or Formula XVIB33.

In one embodiment, the pharmaceutical composition comprises ddh or deoxy-ddh compounds that are in a prodrug form as described herein, comprising a protective chemical group.

In some embodiments, a pharmaceutical composition comprises one or more of the compounds represented by the structures disclosed herein. In some embodiments, a pharmaceutical composition comprises any one of the compounds represented by the structures disclosed herein, and a pharmaceutically acceptable carrier. In some embodiments, a pharmaceutical composition comprises at least one of the compounds represented by the structures disclosed herein, and a pharmaceutically acceptable carrier. In some embodiments, a pharmaceutical composition comprises at least 2, 3, 4, etc, of the compounds represented by the structures disclosed herein, and a pharmaceutically acceptable carrier. In one embodiment, provided herein is a pharmaceutical composition comprising a compound represented by a the structure any one of the following compounds: Formula IB, Formula IIB, Formula IIIB, Formula IVB, Formula VB, Formula VB1, Formula VIB, Formula VIB, Formula VIIIB, Formula IXB, Formula XB, Formula XIB, Formula XIIB, Formula XIIIB, Formula XIIIB1, Formula XIVB, Formula XIVB1, Formula XIVB2, Formula XIV3, Formula XIV4, Formula XIV5, Formula XVB, Formula XVB1, Formula XVB2, Formula XVB3, Formula XVB4, Formula XVB5, Formula XVB6, Formula XVIB, Formula XVIB1, Formula XVIB2, Formula XVIB3, Formula XVIB4, Formula XVIB5, Formula XVIB6, Formula XVIB7, Formula XVIB8, Formula XVIB9, Formula XVIB10, Formula XVIB11, Formula XVIB12, Formula XVIB13, Formula XVIB14, Formula XVIB15, Formula XVIB16, Formula XVIB17, Formula XVIB18, Formula XVIB19, Formula XVIB20, Formula XVIB21, Formula XVIB22, Formula XVIB23, Formula XVIB24, Formula XVIB25, Formula XVIB26, Formula XVIB27, Formula XVIB28, Formula XVIB29, Formula XVIB30, Formula XVIB31, Formula XVIB32, Formula XVIB33, Formula XVIIB, Formula XVIIIB, Formula XXB, Formula XIXB, Formula XXIB, Formula XXIIB, Formula XXXIIIB, Formula XXIVB, or Formula XXVB, or a combination thereof, and a pharmaceutically acceptable carrier.

In some embodiments, a composition with an appropriate physiologically acceptable carrier may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients and/or suitable excipients such as salts, buffers and stabilizers may, but need not, be present within the composition. As used herein, the term "pharmaceutically acceptable carrier" may in some embodiments be used interchangeably with the terms "physiological carrier", "physiologically acceptable carrier", "pharmaceutically acceptable diluent" or "pharmaceutically acceptable excipient" having all the same qualities and meanings.

Administration of a pharmaceutical composition disclosed herein may be achieved by a variety of different routes, including oral, parenteral, nasal, intravenous, intradermal, subcutaneous or topical. In some embodiments, modes of administration depend upon the nature of the condition to be treated or prevented. In some embodiments, an amount that, following administration, reduces, inhibits, prevents or delays the progression and/or metastasis of a cancer is considered effective. In some embodiments, an amount that, following administration, reduces, inhibits, prevents or delays the progression of a viral infection or disease associated with a viral infection is considered effective. In some embodiments, an amount that, following administration, reduces, inhibits, prevents or delays the progression of a bacterial infection or disease associated with a bacterial infection is considered effective. In some embodiments, an amount that, following administration, reduces, inhibits, prevents or delays the progression of an immune disease or disorder is considered effective. In some embodiments, an amount that, following administration, reduces, inhibits, prevents or delays the progression of an autoimmune disease or disorder is considered effective. A skilled artisan would appreciate that the term "physiologically acceptable carrier, diluent or excipient", may in some embodiments be used interchangeably with the term "pharmaceutically acceptable carrier" having all the same means and qualities.

A pharmaceutical composition may be in the form of a solid or liquid. In some embodiments, the pharmaceutically acceptable carrier(s) are particulate, so that the compositions are, for example, in tablet or powder form. The pharmaceutically acceptable carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible pharmaceutically acceptable carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid pharmaceutically acceptable carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of a ddh- or deoxy-ddh-compound or prodrug thereof as herein disclosed, such that a suitable dosage will be obtained.

The pharmaceutical composition may be intended for topical administration, in which case the pharmaceutically acceptable carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredient or prodrug thereof (a ddh- or deoxy-ddh compound or prodrug thereof) may be encased in a gelatin capsule. The pharmaceutical composition in solid or liquid form may include an agent that binds to the ddh or deoxy-ddh compounds as disclosed herein, and thereby assists in the delivery of the compound. Suitable agents that may act in this capacity include monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises a ddh- or deoxy-ddh-compound or prodrug thereof as described herein, and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the ddh- or deoxy-ddh composition so as to facilitate dissolution or homogeneous suspension of ddh- or deoxy-ddh compound in the aqueous delivery system.

The compositions may be administered in a therapeutically effective amount, which will vary depending upon a variety of factors including the activity of the ddh- or deoxy-ddh compound employed; the metabolic stability and length of action of the ddh- or deoxy-ddh compound; the age, body weight, general health, sex, and diet of the patient; the mode and time of administration; the rate of excretion; the drug combination; the severity of the particular allergic or respiratory disorder or condition; and the subject undergoing therapy.

In some embodiments, a pharmaceutically acceptable carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens, phenols or cresols, mercurials, chlorobutanol, methyl and propyl p-hydroxybenzoic acid esters, thimerosal, benzalkonium chloride and benzethonium chloride); antioxidants (such as ascorbic acid and sodium bisulfite; methionine, sodium thiosulfate, platinum, catalase, citric acid, cysteine, thioglycerol, thioglycolic acid, thiosorbitol, butylated hydroxyanisol, butylated hydroxytoluene, and/or propyl gallate) and chelating agents (such as ethylenediaminetetraacetic acid (EDTA)); buffers (such as acetates, citrates and phosphates). If administered intravenously, suitable pharmaceutically acceptable carriers include physiological saline or phosphate buffered saline (PBS), and solutions containing thickening and solubilizing agents, such as glucose, polyethylene glycol, polypropylene glycol and mixtures thereof.

The compositions comprising a ddh- or deoxy-ddh compound as described herein, may be prepared with pharmaceutically acceptable carriers that protect the ddh- or deoxy-ddh compound against rapid elimination from the body, such as time release formulations or coatings. Such pharmaceutically acceptable carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

Prokaryotic Viperin Homologs (pVips)

In some embodiments, disclosed herein are prokaryotic viperin homologs (pVips). Viperin is a protein found in eukaryotic cells, usually localized in the endoplasmic reticulum where it is anchored via its N-terminal domain, though it is also found in other cell compartments. The presence of viperin in a cell was reported to inhibit replication of many DNAnd RNA viruses in the cell, viruses including by not limited to chikungunya, human cytomegalovirus (HCV), hepatitis C virus, dengue, West Nile virus, sindbis virus, influenza, HIV LAI strain, and others. Viperin expression can be induced by the release of inflammatory signals, such as IFN-γ. Viperin was reported to down-regulate the concentration of viral structural proteins essential for viral assembling and maturation.

In eukaryotes, viperin catalyzes the conversion of the nucleotide cytidine triphosphate (CTP) to 3'-deoxy-3',4'-didehydro-CTP (ddhCTP) via SAM-dependent radical mechanism. This RNA nucleotide analog lacks 4' hydrogen and the 3' hydroxyl group compared to CTP, and acts as a new type of polynucleotide chain terminator for viral RNA dependent polymerases. In vertebrate genomes, the kinase cytidylate monophosphate kinase 2 (CMPK2) is adjacent to the viperin. This kinase phosphorylates cytidine monophosphate (CMP) to CTP thus generating the substrate of vertebrate viperins. When tested as an anti-viral agent, 3'-deoxy-3',4'-didehydro-C (ddhC), was applied to cells, where it was phosphorylated by endogenous proteins producing ddhCTP, and directly inhibited replication of Zika virus in vivo.

In some embodiments, disclosed herein are prokaryotic enzymes showing sequence similarity to vertebrate viperin, and that produce modified nucleotides that function as anti-viral chain terminators. In some embodiments, disclosed herein are methods to identify such prokaryotic enzymes out of other prokaryotic enzymes that show sequence similarity to the vertebrate viperin but do not have anti-viral activities. In some embodiments, bacterial and archeal enzymes showing sequence or functional similarity to eukaryotic viperin are referred to herein as "prokaryotic viperin homologs" or "pVips".

While prokaryotic homologs of viperins share some sequence similarity with eukaryotic viperins, an initial similarity-based search revealed a very large number of enzymes. Only by using the method disclosed herein, it was possible to predict the defense score of these enzymes, and to reduce considerably the number of proteins to find true viperin homologs. The in vivo verification of the activity of such enzymes required a complex strategy to heterologously express enzymes in model organisms (including the use of a specific strains to increase iron-sulfur cluster production) and test them against a wide array of bacteriophages.

A skilled artisan would recognize that immune genes from eukaryotes, such a viperin gene, are expected to be different from immune genes in prokaryotes. This is corroborated, for example, by the almost absence of immune systems present in both eukaryotes and prokaryotes. Only the pAgo proteins have been described as being involved in both RNA interference in eukaryotes and plasmid restriction in prokaryotes. This stresses the unexpectedness to discover prokaryotic viperin homologs (pVips). The fact that no prokaryotic defense systems similar to the disclosed herein is known, i.e. a defense system comprising enzymes generating chain terminators, further highlights the unexpectedness of the of the present disclosure.

A skilled artisan will recognize that, in some embodiments, prokaryotes or prokaryotic cells comprise unicellular organisms lacking a membrane-restricted nucleus, mitochondria, or other eukaryotic-specific organelle. In some embodiments a prokaryote comprises one of Euryarchaeota, Proteobacteria, Firmicutes, Bacteriodetes, or cyanobacteria.

In some embodiments, a prokaryote comprises a microbial cell such as bacteria, e.g., Gram-positive or Gram-negative bacteria. In some embodiments, a bacteria comprise Gram-negative bacteria or Negativicutes that stain negative in Gram stain. In some embodiments, a bacteria comprises gram-positive bacteria, gram-negative bacteria, or archaea.

In some embodiments, Gram-negative bacteria can be *Acinetobacter calcoaceticus, Actinobacillus actinomycetemcomitans, Aeromonas hydrophila, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chlamydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Treponema carateum, Treponema pallidum, Treponema pallidum endemicum, Treponema pertenue, Veillonella* spp., *Vibrio cholerae, Vibrio vulnifcus, Yersinia enterocolitica*, or *Yersinia pestis.*

In some embodiments, the bacteria comprise gammaproteobacteria (e.g. *Escherichia coli, pseudomonas, vibrio* and *klebsiella*) or Firmicutes (belonging to class Negativicutes that stain negative in Gram stain).

In some embodiments, Gram-positive bacteria can be *Actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abcessus, Mycobacterium avium* complex, *Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B *streptococcus*), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *streptococcus*), *Streptococcus salivarius*, or *Streptococcus sanguis.*

In some embodiments, the bacteria can be from a species of *Escherichia, Shigella, Salmonella, Erwinia, Yersinia, Bacillus, Vibrio, Legionella, Pseudomonas, Neisseria, Bordetella, Helicobacter, Listeria, Agrobacterium, Staphylococcus, Streptococcus, Enterococcus, Clostridium, Corynebacterium, Mycobacterium, Treponema, Borrelia, Francisella, Brucella, Campylobacter, Klebsiella, Frankia, Bartonella, Rickettsia, Shewanella, Serratia, Enterobacter, Proteus, Providencia, Brochothrix*, or *Brevibacterium.*

In some embodiments, a prokaryote comprises archaea. In some embodiments, the archaea can be: *Archaeoglobi, Methanobacteria, Methanococci, Methanomicrobia, Methanopyri, Nanohaloarchaea, Thermococci, Thermoplasmata, Thermoprotei, Aeropyrum pernix, Cenarchaeum symbiosum, Haladaptatus paucihalophilus, Haloarcula quadrata, Halobacterium salinarum, Halobiforma haloterrestris, Haloferax larsenii, Haloferax volcanii, Haloquadratum*

*walsbyi, Halorubrum salsolis, Metallosphaera sedula, Methanobrevibacter curvatus, Methanobrevibacter cuticularis, Methanobrevibacter filiformis, Methanobrevibacter gottschalkii, Methanobrevibacter oralis, Methanobrevibacter smithii, Methanobrevibacter thaueri, Methanobrevibacter woesei, Methanobrevibacter wolinii, Methanocella paludicola, Methanococcoides methylutens, Methanogenium boonei, Methanogenium frigidum, Methanogenium marinum, Methanosarcinacetivorans, Methanosarcina thermophila, Methanosphaera stadtmaniae, Methanothrix soehngenii, Methylosphaera hansonii, Nanoarchaeum equitans, Palaeococcus helgesonii, Picrophilus oshimae, Picrophilus torridus, Pyrococcus abyssi, Pyrococcus furiosus, Pyrococcus horikoshii, Pyrococcus woesei, Pyrodictium abyssi, Pyrolobus fumarii, Saccharolobus shibatae, Salinirubellus salinus, Thermococcus alcaliphilus, Thermococcus barophilus, Thermococcus celer, Thermococcus chitonophagus, Thermococcus gammatolerans, Thermococcus hydrothermalis, Thermococcus kodakarensis, Thermococcus litoralis, Thermococcus profundus*, or *Thermococcus stetteri.*

In some embodiments, a pVip comprises a prokaryotic protein comprising an amino acid sequence homologous to the sequence of a vertebrate viperin, for example but not limited to NCBI accession NP_542388.2 (SEQ ID NO: 2) or SEQ ID NOs 826-828.

A skilled artisan will recognize that there are several methods that can be used to determine sequence homology and/or sequence identity. Such techniques are thoroughly explained in the literature. See, for example, "A survey of sequence alignment algorithms for next-generation sequencing", Li H et al. Brief Bioinform. 2010 September; 11(5): 473-83; or "Sequence Alignment" Altschul S F et al in Source Handbook of Discrete and Combinatorial Mathematics. 2017 Nov. 20.

In some embodiments, a pVip comprises an amino acid sequence comprising at least 10% sequence identity to eukaryotic viperin. In some embodiments, a pVip comprises an amino acid sequence comprising at least 20% sequence identity to eukaryotic viperin. In some embodiments, a pVip comprises an amino acid sequence comprising at least 25% sequence identity to eukaryotic viperin. In some embodiments, a pVip comprises an amino acid sequence comprising at least 30% sequence identity to eukaryotic viperin. In some embodiments, a pVip comprises an amino acid sequence comprising at least 35% sequence identity to eukaryotic viperin. In some embodiments, a pVip comprises an amino acid sequence comprising at least 40% sequence identity to eukaryotic viperin. In some embodiments, a pVip comprises an amino acid sequence comprising at least 45% sequence identity to eukaryotic viperin. In some embodiments, a pVip comprises an amino acid sequence comprising at least 50% sequence identity to eukaryotic viperin.

In some embodiments, a pVip comprises an amino acid sequence comprising at least 55% sequence identity to eukaryotic viperin. In some embodiments, a pVip comprises an amino acid sequence comprising at least 60% sequence identity to eukaryotic viperin. In some embodiments, a pVip comprises an amino acid sequence comprising at least 65% sequence identity to eukaryotic viperin. In some embodiments, a pVip comprises an amino acid sequence comprising at least 70% sequence identity to eukaryotic viperin. In some embodiments, a pVip comprises an amino acid sequence comprising at least 75% sequence identity to eukaryotic viperin. In some embodiments, a pVip comprises an amino acid sequence comprising at least 80% sequence identity to eukaryotic viperin. In some embodiments, a pVip comprises an amino acid sequence comprising at least 85% sequence identity to eukaryotic viperin. In some embodiments, a pVip comprises an amino acid sequence comprising at least 90% sequence identity to eukaryotic viperin. In some embodiments, a pVip comprises an amino acid sequence comprising at least 95% sequence identity to eukaryotic viperin. A skilled artisan would recognize that, in some embodiments, the terms "sequence identity" and "sequence homology" are used herein interchangeably having all the same qualities and meanings.

In some embodiments, a pVip comprises an amino acid sequence comprising between about 15% to about 25% sequence identity to eukaryotic viperin. In some embodiments, a pVip comprises an amino acid sequence comprising between about 25% to about 35% sequence identity to eukaryotic viperin. In some embodiments, a pVip comprises an amino acid sequence comprising between about 35% to about 45% sequence identity to eukaryotic viperin. In some embodiments, a pVip comprises an amino acid sequence comprising between about 45% to about 15% sequence identity to eukaryotic viperin. In some embodiments, a pVip comprises an amino acid sequence comprising between about 55% to about 65% sequence identity to eukaryotic viperin. In some embodiments, a pVip comprises an amino acid sequence comprising between about 65% to about 75% sequence identity to eukaryotic viperin. In some embodiments, a pVip comprises an amino acid sequence comprising between about 75% to about 85% sequence identity to eukaryotic viperin. In some embodiments, a eukaryotic viperin is a human viperin.

In some embodiments, pVips are clustered according to their homology across prokaryotic species into pVip clusters. In some embodiments, a defense score is calculated for a pVip cluster. In some embodiments, pVip clusters have a "defense score" above a pre-determined threshold. In some embodiments, a defense score above a pre-determined threshold is indicative that a cluster of genes comprises pVips. As used herein, "defense score" is a value computed for a cluster of homologous genes, that is useful in predicting whether the genes of said cluster have antiviral functions. The computation of defense scores is detailed in Doron, S. et al. Systematic discovery of antiphage pVips in the microbial pangenome. Science (80). 4120, eaar4120 (2018), and WO 2018/220616 A2, which are incorporated herein by reference. Briefly, the neighborhood of a gene of interest (+/−10 genes) is screened for known defense genes. In some embodiments, enrichment of known defense genes in the vicinity of genes of a cluster is a predictor that said genes of said cluster perform anti-viral functions.

In some embodiments, a defense score is calculated for a cluster of genes comprising homology to a viperin. In some embodiments, a defense score comprises a first score indicating the proportion of genes with defensive neighborhood, termed also "Score 1". In some embodiments a defense score comprises a second score indicating the average number of defense genes in the neighborhood of the genes of said cluster, termed also "Score 2". In some embodiments, a defense score comprises a Score 1 and a Score 2.

In some embodiments, the enrichment of known defense genes in the vicinity to the genes of a cluster predicts that the cluster comprises pVips. In some embodiments, enrichment of known defense genes in the vicinity of genes of the cluster can be calculated as statistically significant enrichment beyond the background expected by chance. In some embodiments, enrichment of known defense genes in the vicinity of genes of the cluster, or a Score 1, can be calculated as a fraction of the total genes in the cluster that are found in the vicinity of known defense genes, wherein this fraction is above the fraction expected by chance.

In some embodiments, a fraction of at least 40% of the genes of a cluster predicts that the cluster comprises pVips. In some embodiments, a fraction of at least 50% of the genes of a cluster predicts that the cluster comprises pVips. In some embodiments, a fraction of at least 75% of the genes of a cluster predicts that the cluster comprises pVips. In some embodiments, a fraction of at least 100% of the genes of a cluster predicts that the cluster comprises pVips.

In some embodiments, the average number of known defense genes in the vicinity of the genes of a cluster, or a Score 2, provides an additional support to the prediction that the cluster comprises pVips. In some embodiments, an average of at least 0.75, 1, 1.5, 2, 3, 4, or 5 known defense genes in the vicinity to the genes of a cluster predicts that the cluster comprises pVips. In some embodiments, an average of between 0.75 and 1 known defense genes in the vicinity to the genes of a cluster predicts that the cluster comprises pVips. In some embodiments, an average of between 1 and 2 known defense genes in the vicinity to the genes of a cluster predicts that the cluster comprises pVips. In some embodiments, an average of between 2 and 5 known defense genes in the vicinity to the genes of a cluster predicts that the cluster comprises pVips.

In some embodiments, a gene encoding a pVip is located in the vicinity of a gene encoding a nucleotide kinase. In some embodiments, proximity to a nucleotide kinase gene predicts that a gene of interest is a pVip. In some embodiments, said nucleotide kinase is selected from a group comprising a Cytidine/Uridine Monophosphate Kinase 2 (CMPK2), a cytidylate kinase, a thymidylate kinase, a guanylate kinase, and an adenylate kinase. In some embodiments, the substrate of the nucleotide kinases is a ribonucleoside or a ribonucleotide. In some embodiments, the substrate of the nucleoside kinases is a deoxy-ribonucleoside or a deoxy-ribonucleotide.

As described below, the pVips are found to have wider substrate promiscuity as compared to the eukaryotic Vips. Based on the substrate promiscuity of pVips as shown herein, it is expected that the pVips would act on various non-natural substrates and generate novel structural modifications on multiple nucleotide derivatives and other molecules.

Figure 13A:
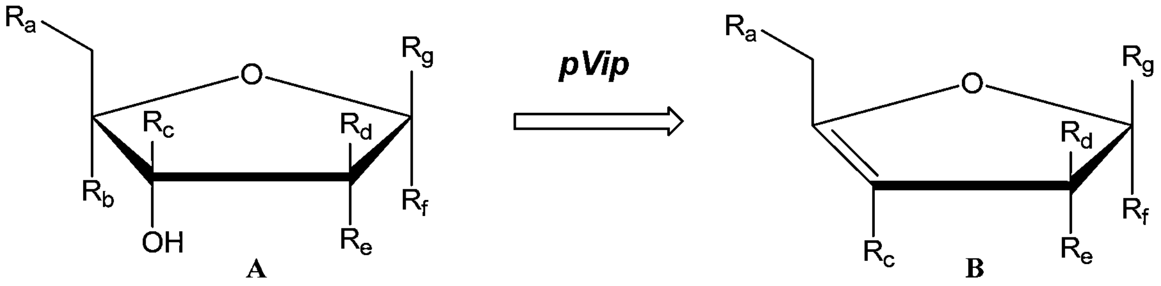
FIGS. 13A-13F are schematic representations of catalytic modifications of a diverse group of non-natural substrates by pVips. The 3' hydroxyl groups of the substrates are removed by pVips.
Figure 13A:
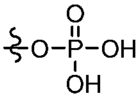
Figure 13A:
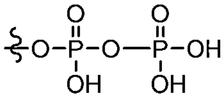
Figure 13A:
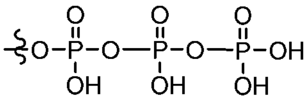
Figure 13B:
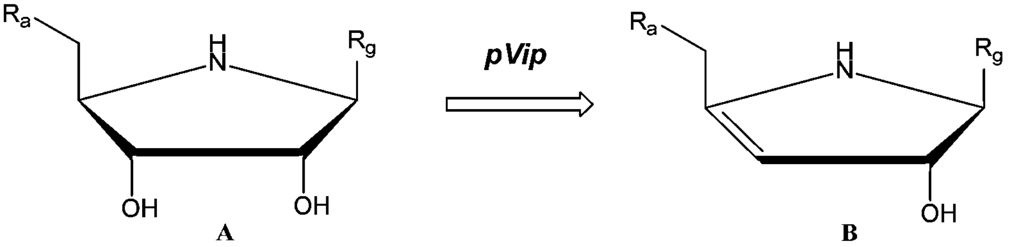
Figure 13C:
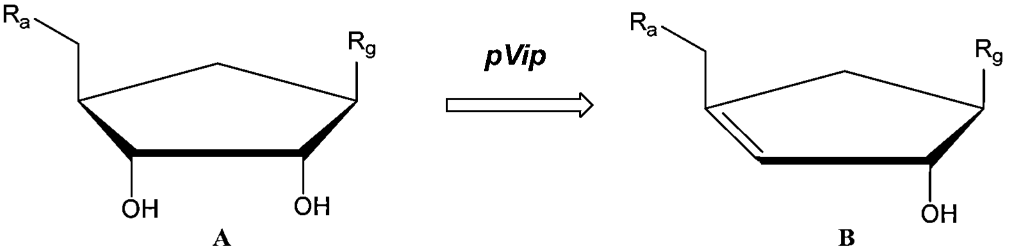
Figure 13D:
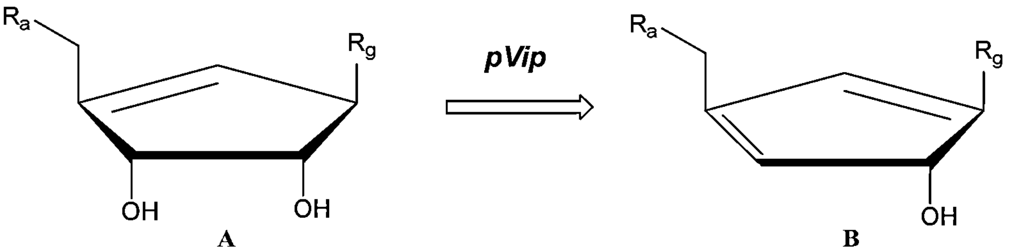
Figure 13E:
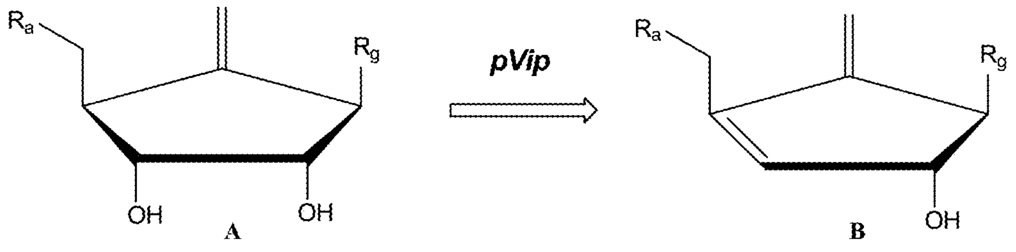
Figure 13F:
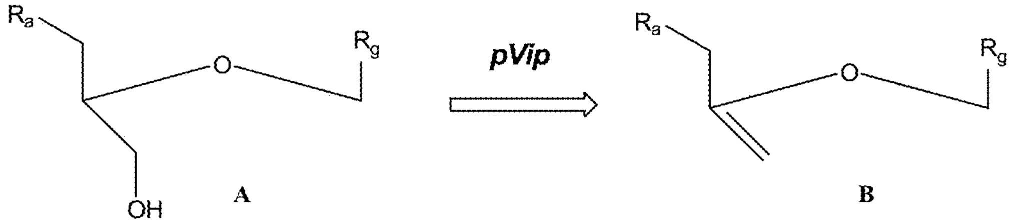

In one embodiment, the modification catalyzed by pVips on a non-natural substrate is the dehydration of the 3' carbon in the ribose moiety of a nucleotide derivatives (FIG. 13A). In one embodiment, the modification catalyzed by pVips on a non-natural substrate is the dehydration of the 3' carbon in the 5 member nitrogen based ring (FIG. 13B). In one embodiment, the modification catalyzed by pVips on a non-natural substrate is the dehydration of the 3' carbon in the 5 member carbon based ring) (FIGS. 13C, 13D and 13E). In one embodiment, the modification catalyzed by pVips on a non-natural substrate is the dehydration of the terminal hydroxyl group on an etheric chain (FIG. 13F).

In certain embodiments, the product produced is a ddh-compound. In certain embodiments, the product produced is a deoxy-ddh-compound. In one embodiment, the products generated from the non-natural substrates by the pVips provide novel therapeutic properties. In one embodiment, the pVips would be able to modify a large set of non-natural substrates as disclosed herein, and one or more of the products of these modifications are useful in treating various diseases, such as viral infection, bacterial infection, a bacterial associated disease, a virus-induced disease, an autoimmune disease, an immune disorder, or cancer, or a combination thereof.

In some embodiments, the non-natural substrates comprise the compounds represented by the structure of Formula IA, Formula IIA, Formula IIIA, Formula IVA, Formula VA, Formula VIA, Formula VIIA, Formula VIIIA, Formula IXA, Formula XA, Formula XIA, Formula XIIA, Formula XIIIA, Formula XIVA, Formula XVA, Formula XVIA, Formula XVIIA, Formula XVIIIA, Formula XIXA, Formula XXA, Formula XXIA, Formula XXIIA, Formula XXIIIA, Formula XXIVA, Formula XXVA, as disclosed in Table 1 and having the variants as listed therein.

In one embodiment, a non-natural substrate comprises a compound represented by the structure of Formula IA, as disclosed in Table 1 and having the variants as listed therein. In one embodiment, a non-natural substrate comprises a compound represented by the structure of Formula IIA, as disclosed in Table 1 and having the variants as listed therein. In one embodiment, a non-natural substrate comprises a compound represented by the structure of Formula IIIA, as disclosed in Table 1 and having the variants as listed therein. In one embodiment, a non-natural substrate comprises a compound represented by the structure of Formula IVA, as disclosed in Table 1 and having the variants as listed therein. In one embodiment, a non-natural substrate comprises a compound represented by the structure of Formula VA, as disclosed in Table 1 and having the variants as listed therein. In one embodiment, a non-natural substrate comprises a compound represented by the structure of Formula VIA, as disclosed in Table 1 and having the variants as listed therein. In one embodiment, a non-natural substrate comprises a compound represented by the structure of Formula VIIA, as disclosed in Table 1 and having the variants as listed therein. In one embodiment, a non-natural substrate comprises a compound represented by the structure of Formula VIIA, as disclosed in Table 1 and having the variants as listed therein. In one embodiment, a non-natural substrate comprises a compound represented by the structure of Formula IXA, as disclosed in Table 1 and having the variants as listed therein. In one embodiment, a non-natural substrate comprises a compound represented by the structure of Formula XA, as disclosed in Table 1 and having the variants as listed therein. In one embodiment, a non-natural substrate comprises a compound represented by the structure of Formula XIA, as disclosed in Table 1 and having the variants as listed therein. In one embodiment, a non-natural substrate comprises a compound represented by the structure of Formula XIIA, as disclosed in Table 1 and having the variants as listed therein. In one embodiment, a non-natural substrate comprises a compound represented by the structure of Formula XIIIA, as disclosed in Table 1 and having the variants as listed therein. In one embodiment, a non-natural substrate comprises a compound represented by the structure of Formula XIVA, as disclosed in Table 1 and having the variants as listed therein. In one embodiment, a non-natural substrate comprises a compound represented by the structure of Formula XVA, as disclosed in Table 1 and having the variants as listed therein. In one embodiment, a non-natural substrate comprises a compound represented by the structure of Formula XVIA, as disclosed in Table 1 and having the variants as listed therein. In one embodiment, a non-natural substrate comprises a compound represented by the structure of Formula XVIIA, as disclosed in Table 1 and having the variants as listed therein. In one embodiment, a non-natural substrate comprises a compound represented by the structure of Formula XVIIIA, as disclosed in Table 1 and having the variants as listed therein. In one embodiment, a non-natural substrate comprises a compound represented by the structure of Formula XIXA, as disclosed in Table 1 and having the variants as listed therein. In one embodiment, a non-natural substrate comprises a compound represented by the structure of Formula XXA, as disclosed in Table 1 and having the variants as listed therein. In one embodiment, a non-natural substrate comprises a compound represented by the structure of Formula XXIA, as disclosed in Table 1 and having the variants as listed therein. In one embodiment, a non-natural substrate comprises a compound represented by the structure of Formula XXIIA, as disclosed in Table 1 and having the variants as listed therein. In one embodiment, a non-natural substrate comprises a compound represented by the structure of Formula XXIIIA, as disclosed in Table 1 and having the variants as listed therein. In one embodiment, a non-natural substrate comprises a compound represented by the structure of Formula XXIVA, as disclosed in Table 1 and having the variants as listed therein. In one embodiment, a non-natural substrate comprises a compound represented by the structure of Formula XXVAs disclosed in Table 1 and having the variants as listed therein.

In some embodiments, the non-natural substrates comprise the compounds represented by the structure of 2'-C-methyladenosine, 2'-C-methylguanosine, 2'-C-methyluridine, 2'-C-Methylcytidine, 2'-C-ethynyladenosine, Cytarabine (ara-C), ara-A (vidarabine), Gemcitabine hydrochloride, 2'-Deoxy-2'-fluoro-2'-methyluridine, 2'OMe-Uridine, 2'OMe-Adenosine, T-1106, Fluorouridine, 1-[(2R,3R,4S,5R)-3,4-dihydroxy-5-(hydroxymethyl)oxolan-2-yl]-5-fluoropyrimidine-2,4-dione, 5-Fluoro-deoxy-uridine, 3,4-dihydroxy-5-(hydroxymethyl)tetrahydrofuran-2-yl)-4-(hydroxyamino)pyrimidin-2(1H)-one, 6-Methyl-7-deazaadenosine, N6-(9-antranylmethyl) adenosine, N6-(1-pyrenylmethyl) adenosine, 5-(Perylen-3-yl)ethynyl-arabino-uridine, ETAR, IM18, 6-Azauridine, Zebularine, 5-Azacytidine, Ribavirin (Virazole), Formycin A, Pyrazofurin, Pseudouridine, Showdomycin, Idoxuridine, Trifluridine, Brivudine, Acedurid, 5-Hydroxy-Uridine, 5-Methyl-Uridine, 4-Thio-i-propyl-Uridine, GS-441524, 7-Deaza-2'-C-methyl-adenosine, NITD008, 2'-Deoxy-2'-fluoro-arabinofuranosyl nucleoside, FIAU, 2'-Deoxy-2'-fluoro-arabinofuranosyl nucleoside, FMAU, 2'-Deoxy-2'-fluoro-arabinofuranosyl nucleoside, FEAU, Fludarabine (2-Fluoro-ara-Adenosine), NITD449, 2-(2-amino-6-methoxy-9H-purin-9-yl)-5-(hydroxymethyl)-3-methyltetrahydrofuran-3,4-diol, 3-fluoro-4-hydroxy-5-(hydroxymethyl)-3-methyltetrahydrofuran-2-yl)pyrimidine-2,4(1H,3H)-dione, 2-(6-(benzylamino)-9H-purin-9-yl)-5-(hydroxymethyl)tetrahydrofuran-3,4-diol, 3,4-dihydroxy-5-(hydroxymethyl) tetrahydrofuran-2-yl)-4-(hydroxyamino)pyrimidin-2(1H)-one, Ganciclovir, BCX4430, Aristeromycin, Forodesine, Neplanocin A, Entecavir, or Telbivudine, as disclosed in Table 2, wherein $R_1$ of each corresponding substrate is OH,

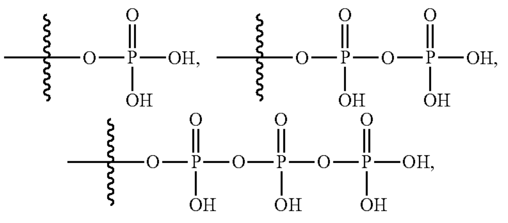

-continued

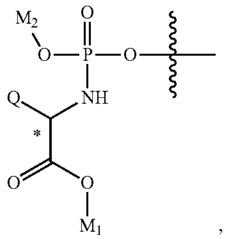

,

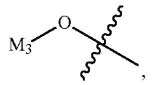

,

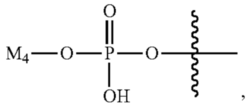

, or

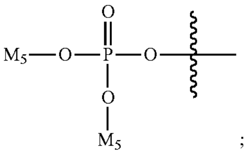

;

or $R_{11}$ is

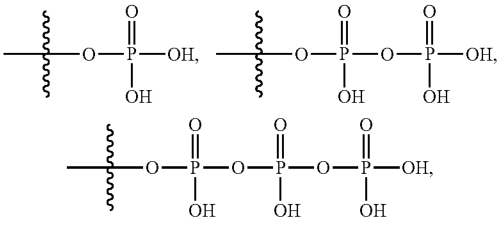

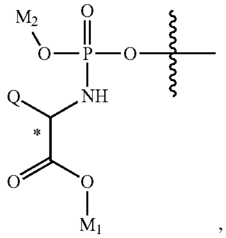

,

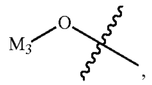

,

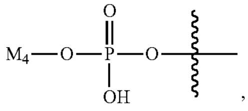

, or

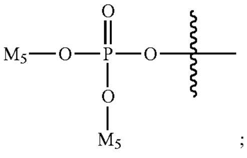

;

wherein Q of $R_1$ or $R_{11}$ is a side chain of an amino acid; $M_1$ of $R_1$ or $R_{11}$ is an alkyl;

$M_2$ of $R_1$ or $R_{11}$ is an aryl, a substituted aryl, a heteroaryl or a substituted heteroaryl;

$M_3$ of $R_1$ or $R_{11}$ is

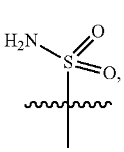

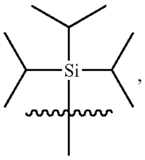

,

-continued

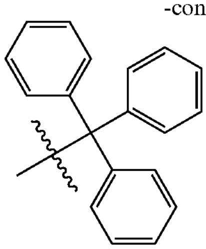

, or

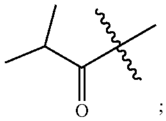

;

$M_4$ of $R_1$ or $R_{11}$ is —$(C_2$-$C_6)$alkyl-O—$(C_{10}$-$C_{20})$alkyl; each $M_5$ of $R_1$ or $R_{11}$ is —$(CH_2)_n$—S—C(═O)—$(C_1$-$C_8)$alkyl; and n of $M_5$ is 1-4.

In one embodiment, a non-natural substrate comprises a compound represented by the structure of 2'-C-methyladenosine. In one embodiment, a non-natural substrate comprises a compound represented by the structure of 2'-C-methylguanosine. In one embodiment, a non-natural substrate comprises a compound represented by the structure of 2'-C-methyluridine. In one embodiment, a non-natural substrate comprises a compound represented by the structure of 2'-C-Methylcytidine. In one embodiment, a non-natural substrate comprises a compound represented by the structure of 2'-C-ethynyladenosine. In one embodiment, a non-natural substrate comprises a compound represented by the structure of Cytarabine (ara-C). In one embodiment, a non-natural substrate comprises a compound represented by the structure of ara-A (vidarabine). In one embodiment, a non-natural substrate comprises a compound represented by the structure of Gemcitabine hydrochloride. In one embodiment, a non-natural substrate comprises a compound represented by the structure of 2'-Deoxy-2'-fluoro-2'-methyluridine. In one embodiment, a non-natural substrate comprises a compound represented by the structure of 2'OMe-Uridine. In one embodiment, a non-natural substrate comprises a compound represented by the structure of 2'OMe-Adenosine. In one embodiment, a non-natural substrate comprises a compound represented by the structure of T-1106. In one embodiment, a non-natural substrate comprises a compound represented by the structure of Fluorouridine. In one embodiment, a non-natural substrate comprises a compound represented by the structure of 1-[(2R,3R,4S,5R)-3,4-dihydroxy-5-(hydroxymethyl)oxolan-2-yl]-5-fluoropyrimidine-2,4-dione. In one embodiment, a non-natural substrate comprises a compound represented by the structure of 5-Fluoro-deoxy-uridine. In one embodiment, a non-natural substrate comprises a compound represented by the structure of 3,4-dihydroxy-5-(hydroxymethyl)tetrahydrofuran-2-yl)-4-(hydroxyamino) pyrimidin-2(1H)-one. In one embodiment, a non-natural substrate comprises a compound represented by the structure of 6-Methyl-7-deazaadenosine. In one embodiment, a non-natural substrate comprises a compound represented by the structure of N6-(9-antranylmethyl) adenosine. In one embodiment, a non-natural substrate comprises a compound represented by the structure of N6-(1-pyrenylmethyl) adenosine. In one embodiment, a non-natural substrate comprises a compound represented by the structure of 5-(Perylen-3-yl)ethynyl-arabino-uridine. In one embodiment, a non-natural substrate comprises a compound represented by the structure of ETAR. In one embodiment, a non-natural substrate comprises a compound represented by the structure of IM18. In one embodiment, a non-natural substrate comprises a compound represented by the structure of 6-Azauridine. In one embodiment, a non-natural substrate comprises a compound represented by the structure of Zebularine. In one embodiment, a non-natural substrate comprises a compound represented by the structure of 5-Azacytidine. In one embodiment, a non-natural substrate comprises a compound represented by the structure of Ribavirin (Virazole). In one embodiment, a non-natural substrate comprises a compound represented by the structure of Formycin A. In one embodiment, a non-natural substrate comprises a compound represented by the structure of Pyrazofurin. In one embodiment, a non-natural substrate comprises a compound represented by the structure of Pseudouridine. In one embodiment, a non-natural substrate comprises a compound represented by the structure of Showdomycin. In one embodiment, a non-natural substrate comprises a compound represented by the structure of Idoxuridine. In one embodiment, a non-natural substrate comprises a compound represented by the structure of Trifluridine. In one embodiment, a non-natural substrate comprises a compound represented by the structure of Brivudine. In one embodiment, a non-natural substrate comprises a compound represented by the structure of Acedurid. In one embodiment, a non-natural substrate comprises a compound represented by the structure of 5-Hydroxy-Uridine. In one embodiment, a non-natural substrate comprises a compound represented by the structure of 5-Methyl-Uridine. In one embodiment, a non-natural substrate comprises a compound represented by the structure of 4-Thio-i-propyl-Uridine. In one embodiment, a non-natural substrate comprises a compound represented by the structure of GS-441524. In one embodiment, a non-natural substrate comprises a compound represented by the structure of 7-Deaza-2'-C-methyl-adenosine. In one embodiment, a non-natural substrate comprises a compound represented by the structure of NITD008. In one embodiment, a non-natural substrate comprises a compound represented by the structure of 2'-Deoxy-2'-fluoro-arabinofuranosyl nucleoside. In one embodiment, a non-natural substrate comprises a compound represented by the structure of FIAU. In one embodiment, a non-natural substrate comprises a compound represented by the structure of 2'-Deoxy-2'-fluoro-arabinofuranosyl nucleoside. In one embodiment, a non-natural substrate comprises a compound represented by the structure of FMAU. In one embodiment, a non-natural substrate comprises a compound represented by the structure of 2'-Deoxy-2'-fluoro-arabinofuranosyl nucleoside. In one embodiment, a non-natural substrate comprises a compound represented by the structure of FEAU. In one embodiment, a non-natural substrate comprises a compound represented by the structure of Fludarabine (2-Fluoro-ara-Adenosine). In one embodiment, a non-natural substrate comprises a compound represented by the structure of NITD449. In one embodiment, a non-natural substrate comprises a compound represented by the structure of 2-(2-amino-6-methoxy-9H-purin-9-yl)-5-(hydroxymethyl)-3-methyltetrahydrofuran-3,4-diol. In one embodiment, a non-natural substrate comprises a compound represented by the structure of 3-fluoro-4-hydroxy-5-(hydroxymethyl)-3-methyltetrahydrofuran-2-yl)pyrimidine-2,4 (1H,3H)-dione. In one embodiment, a non-natural substrate comprises a compound represented by the structure of 2-(6-(benzylamino)-9H-purin-9-yl)-5-(hydroxymethyl)tetrahydrofuran-3,4-diol. In one embodiment, a non-natural substrate comprises a compound represented by the structure of 3,4-dihydroxy-5-(hydroxymethyl)tetrahydrofuran-2-yl)-4-(hydroxyamino)pyrimidin-2(1H)-one. In one embodiment, a non-natural substrate comprises a compound represented by the structure of Ganciclovir. In one embodiment, a non-natural substrate comprises a compound represented by the structure of BCX4430. In one embodiment, a non-natural substrate comprises a compound represented by the structure of Aristeromycin. In one embodiment, a non-natural substrate comprises a compound represented by the structure of Forodesine. In one embodiment, a non-natural substrate comprises a compound represented by the structure of Neplanocin A. In one embodiment, a non-natural substrate comprises a compound represented by the structure of Entecavir. In one embodiment, a non-natural substrate comprises a compound represented by the structure of Telbivudine. In some embodiments, for the non-natural substrates disclosed herein from Table 2, $R_1$ of each corresponding substrate is OH,

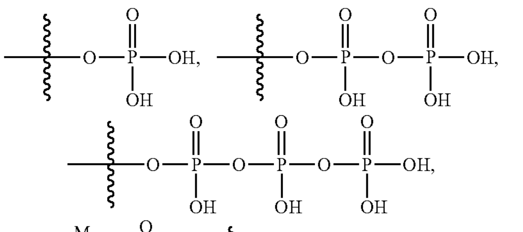

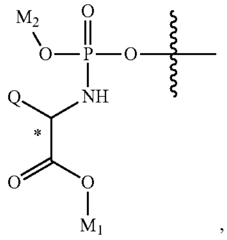

,

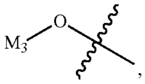

,

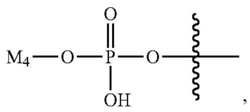

, or

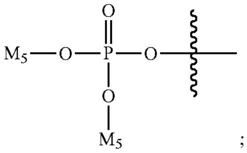

;

or $R_{11}$ is

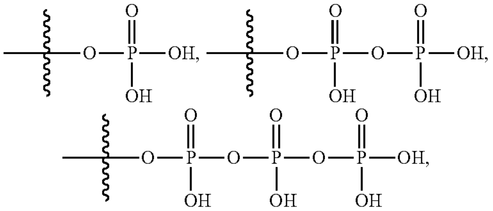

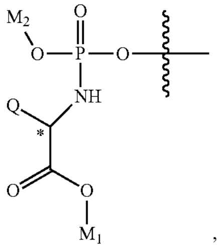

,

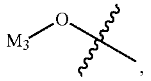

,

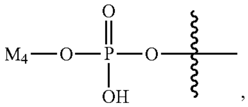

, or

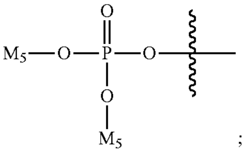

;

wherein Q of $R_1$ or $R_{11}$ is a side chain of an amino acid;

$M_1$ of $R_1$ or $R_{11}$ is an alkyl;

$M_2$ of $R_1$ or $R_{11}$ is an aryl, a substituted aryl, a heteroaryl or a substituted heteroaryl;

$M_3$ of $R_1$ or $R_{11}$ is

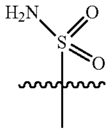

,

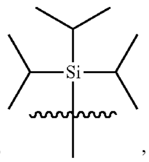

,

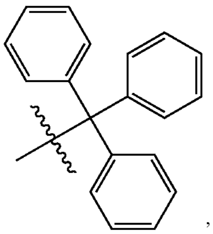

, or

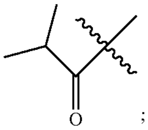

;

$M_4$ of $R_1$ or $R_{11}$ is $-(C_2-C_6)$alkyl-O$-(C_{10}-C_{20})$alkyl; each $M_5$ is $-(CH_2)_n-S-C(=O)-(C_1-C_8)$alkyl; and n of $M_5$ is 1-4

In some embodiment, any one of the above non-natural substrates can be modified by the pVips disclosed herein to generate ddh or deoxy-ddh compounds that can be used as DNA/RNA chain terminators. In some embodiments, these non-natural substrates are modified by the pVips to produce their 3',4'-didehydro (ddh) derivates. In other embodiments, these non-natural substrates are modified by the pVips to become the 3'-deoxy-3',4'-didehydro (deoxy-ddh) derivates.

In some embodiments, a pVip comprises any of the pVips provided in Table 3, Table 4, or Table 5 (Tables 3, 4, and 5 are provided below). In some embodiments, a pVip comprises an amino acid sequence having at least 80% sequence identity to any one of amino acid sequences of SEQ ID NOs: 409-789. In some embodiments, a pVip comprises any one of the amino acid sequences set forth in SEQ ID NOs: 409-789. In some embodiments, a pVip comprises an amino acid sequence with at least 20%, at least 30%, at least 40%, at least 50%, or at least 60% sequence identity to SEQ ID NO: 2. In some embodiments, a pVip comprises an amino acid sequence with at least 20%, at least 30%, at least 40%, at least 50%, or with at least 60% sequence identity to a vertebrate viperin.

TABLE 6

Examples of Protein and Gene Sequences of Eukaryotic Viperins

| SEQ ID No | description | NCBI Accession number |
|---|---|---|
| 1 | human viperin gene | AF442151.1 |
| 2 | human viperin protein | NP_542388.2 |
| 826 | rat viperin protein | NP_620236.1 |
| 827 | mouse viperin protein | NP_067359.2 |
| 828 | zebra fish viperin protein | NP_001020727.1 |

In some embodiments, the terms "prokaryotic viperin homolog", "pVip", "pVip protein", and "pVip polypeptide" may be used herein interchangeably having all the same qualities and meanings.

In some embodiments, a pVip comprises an amino acid sequence encoded by one of the polynucleotide sequences of SEQ ID NOs: 3-383. In some embodiments, a pVip comprises an amino acid sequence encoded by one of the polynucleotide sequences of SEQ ID NOs: 384-408. In some embodiments, a pVip comprises an amino acid sequence encoded by a polynucleotide sequence comprising at least 80% identity to a polynucleotide sequence selected from SEQ ID NOs: 3-383. In some embodiments, a pVip comprises an amino acid sequence encoded by a polynucleotide sequence comprising at least 80% identity to a polynucleotide sequence selected from SEQ ID NOs: 384-408.

In some embodiments, a pVip gene comprises a gene encoding a pVip. In some embodiments, a pVip gene comprises a gene encoding a pVip, wherein said pVip amino acid sequence is set forth in any one of SEQ ID NOs: 409-789. In some embodiments, said pVip gene comprises a sequence with at least 20%, at least 30%, at least 40%, at least 50%, at least 60%, or at least 70% to SEQ ID NO: 1.

In some embodiments, a pVip comprises a fragment or a functional domain of any one of SEQ ID NOs: 409-789.

pVips and viperins are radical-SAM enzymes that contain an iron sulfur cluster 4Fe-4S8. For such enzymes, the 4Fe-4S cluster is built by a complex of proteins and then carried into the apoenzyme making it an active holoenzyme. This metabolic step can require some specific interactions between the proteins that build the iron sulfur cluster and the pVip. Heterologous expression of iron-sulfur cluster enzymes such as viperins can thus be devoid of catalytic activity, if the cell in which the viperin is expressed does not express the iron sulfur clusters to high enough levels.

A skilled artisan would recognize that catalytic activity of metaloenzymes in heterologous hosts can be promoted by a number of strategies. For example, synthesis of iron sulfur cluster in the host can be promoted by deleting the regulator iscR in *E. coli*. Further, heterologous iron sulfur cluster operons can be expressed to promote iron sulfur cluster synthesis, for example by transfection with plasmids as pDB1282, which encodes the isc operon from *Azotobacter vinelandii*. A further strategy comprises expressing the protein in a more closely related organism from a phylogenetic point of view. Given the sensitivity to oxygen of iron-sulfur cluster proteins, growth in anaerobic conditions, as well as engineering electron transfer pathways into the host cells, are avenues that can also be followed to improve metaloenzymes activities. Further methods can be found, for example, in Shomar H, "Producing high-value chemicals in *Escherichia coli* through synthetic biology and metabolic engineering", ISBN number 978-90-8593-386-1.

Table 3, which is displayed at the end of this specification, shows 381 pVip genes, each with its correspondent IMG_id number, metagenome genome IMG_id number, genome or metagenome name, nucleic acid sequence, the clade to which it was clustered (see Example 2, and FIGS. 3A and 3B), and whether a kinase was found in its genomic neighborhood, and its SEQ ID NO. "IMG_id" refers to an identification number in the "Integrated Microbial Genomes and Metagenomes" database, https://img.jgi.doe.gov/.

Table 4, which is displayed at the end of this specification, shows 25 pVips experimentally shown to have anti-viral activity, each with its correspondent IMG_id number, metagenome or genome IMG_id number, genome or metagenome name, the codon-optimized sequence used for its expression (see Example 4), the clade to which it was clustered (see Example 2, and FIGS. 3A and 3B), whether a kinase was found in its genomic neighborhood, and its SEQ ID No.

Table 5, which is displayed at the end of this specification, shows 381 pVip proteins, each with its correspondent IMG_id number, metagenome or genome IMG_id number, genome or metagenome name, amino acid sequence, and SEQ ID No.

Nucleic Acid Constructs Encoding pVips

In some embodiments, disclosed herein is a nucleic acid construct encoding a pVip. In some embodiments, the pVip construct comprises any one of the pVip genes provided in Table 3 or Table 4. In some embodiments, the pVip construct comprises any one of SEQ ID NOs: 3-408. In some embodiments, the pVip construct comprises a nucleic acid sequence comprising at least 80% identity to one of SEQ ID NOs: 3-408. In some embodiments, a pVip construct comprises a fragment of any one of SEQ ID NOs: 409-789.

In some embodiments, provided herein is a nucleic acid construct encoding a pVip, said nucleic acid construct comprising a pVip gene and a non-naturally occurring regulatory element operably linked. In some embodiments, said regulatory element comprises a cis-acting regulatory element for directing expression of said pVip gene, a transmissible element for directing transfer of said pVip gene from one cell to another, or a recombination element for integrating said pVip gene into a genome of a cell transfected with said construct, or an element providing episomal maintenance of said construct within a cell transfected with said construct, or any combination thereof.

In some embodiment, the nucleic acid sequence of the regulatory element is from the same species of the pVip gene. In some embodiment, the nucleic acid sequence of the regulatory element is not from the same species as the pVip gene. In some embodiment, the nucleic acid sequence of the regulatory element is not from the donor species of the pVip gene. In some embodiment, when a host cell comprises a pVip gene, the nucleic acid sequence of the regulatory element is from the host species.

In some embodiments, cis-acting regulatory elements include those that direct constitutive expression of a nucleic acid sequence. In some embodiments, cis-acting regulatory elements comprise those that direct inducible expression of the nucleic acid sequence only under certain conditions.

Constitutive promoters suitable for use with some embodiments of the nucleic acid constructs disclosed herein are promoter sequences which are active under most environmental conditions and most types of cells such as those from the cytomegalovirus (CMV) and Rous sarcoma virus (RSV). Inducible promoters suitable for use with some embodiments of pVip constructs disclosed herein include, but are not limited to the tetracycline-inducible promoter (Zabala M, et al., Cancer Res. 2004, 64(8): 2799-804) or pathogen-inducible promoters. Such promoters include those from pathogenesis-related proteins (PR proteins), which are induced following infection by a pathogen.

A non-limiting example of a gene activator protein is the catabolite activator protein (CAP), which helps initiate transcription of the lac operon in *Escherichia coli* (Raibaud et al. (1984) Annu. Rev. Genet. 18:173). Regulated expression can therefore be either positive or negative, thereby either enhancing or reducing transcription. Other examples of positive and negative regulatory elements are well known in the art. Various promoters that can be included in the protein expression system include, but are not limited to, a T7/LacO hybrid promoter, a trp promoter, a T7 promoter, a lac promoter, and a bacteriophage lambda promoter.

Any suitable promoter can be used with the pVips disclosed herein, including the native promoter or a heterologous promoter. In some embodiments, the promoter is a naturally occurring pVip promoter. In some embodiments, the promoter is a non-naturally occurring, or a heterologous pVip promoter. Heterologous promoters can be constitutively active or inducible. A non-limiting example of a heterologous promoter is given in U.S. Pat. No. 6,242,194 to Kullen and Klaenhammer, which is incorporated herein in full. In some embodiments, the promoter comprises a pARA promoter. In some embodiments, the promoter comprises a pHypraspank promoter. In some embodiments, a pARA promoter is induced by arabinose. In some embodiments, a pHypraspank promoter is induced by IPTG.

Sequences encoding metabolic pathway enzymes provide particularly useful promoter sequences. Examples include promoter sequences derived from sugar metabolizing enzymes, such as galactose, lactose (lac) (Chang et al. (1987) Nature 198:1056), and maltose. Additional examples include promoter sequences derived from biosynthetic enzymes such as tryptophan (trp) (Goeddel et al. (1980) Nucleic Acids Res. 8:4057; Yelverton et al. (1981) Nucleic Acids Res. 9:731; U.S. Pat. No. 4,738,921; EPO Publication Nos. 36,776 and 121,775). The beta-lactamase (bla) promoter system (Weissmann, (1981) "The Cloning of Interferon and Other Mistakes," in Interferon 3 (ed. I. Gresser); bacteriophage lambda PL (Shimatake et al. (1981) Nature 292:128); the arabinose-inducible araB promoter (U.S. Pat. No. 5,028,530); and T5 (U.S. Pat. No. 4,689,406) promoter systems also provide useful promoter sequences. See also Balbas (2001) Mol. Biotech. 19:251-267, where *E. coli* expression systems are discussed.

In addition, synthetic promoters that do not occur in nature also function as bacterial promoters. For example, transcription activation sequences of one bacterial or phage promoter can be joined with the operon sequences of another bacterial or phage promoter, creating a synthetic hybrid promoter (U.S. Pat. No. 4,551,433). For example, the tac (Amann et al. (1983) Gene 25:167; de Boer et al. (1983) Proc. Natl. Acad. Sci. 80:21) and trc (Brosius et al. (1985) J. Biol. Chem. 260:3539-3541) promoters are hybrid trp-lac promoters comprised of both trp promoter and lac operon sequences that are regulated by the lac repressor. The tac promoter has the additional feature of being an inducible regulatory sequence. Thus, for example, expression of a coding sequence operably linked to the tac promoter can be induced in a cell culture by adding isopropyl-1-thio-β-D-galactoside (IPTG). Furthermore, bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The phage T7 RNA polymerase/promoter system is an example of a coupled promoter system (Studier et al. (1986) J. Mol. Biol. 189:113; Tabor et al. (1985) Proc. Natl. Acad. Sci. 82:1074). In addition, a hybrid promoter can also be comprised of a phage promoter and an *E. coli* operator region (EPO Publication No. 267,851).

The nucleic acid construct can additionally contain a nucleic acid sequence encoding the repressor or the inducer for that promoter. For example, an inducible construct can regulate transcription from the Lac operator (LacO) by expressing the nucleotide sequence encoding the LacI repressor protein. Other examples include the use of the lexA gene to regulate expression of pRecA, and the use of trpO to regulate ptrp. Alleles of such genes that increase the extent of repression (e.g., lacIq) or that modify the manner of induction (e.g., lambda CI857, rendering lambda pL thermo-inducible, or lambda CI+, rendering lambda pL chemo-inducible) can be employed.

In the construction of the construct, in some embodiments, the promoter is positioned approximately the same distance from the heterologous transcription start site as it is from the transcription start site in its natural setting. As is known in the art, however, some variation in this distance can be accommodated without loss of promoter function.

According to some embodiments, the nucleic acid construct includes a promoter sequence for directing transcription of the nucleic acid sequence in the cell in a constitutive or inducible manner. In some embodiments, the expression of the pVip genes disclosed herein can be transient or consistent, episomal or integrated into the chromosome of a host cell. According to some embodiments, the expression is on a transmissible genetic element.

The nucleic acid construct disclosed herein may further include additional sequences which render this construct suitable for replication and integration in prokaryotes, eukaryotes, or both (e.g., shuttle vectors). In some embodiments, the nucleic acid construct comprises a recombination element for integrating the pVip gene into the genome of a cell transfected with the construct. A skilled artisan would appreciate that the term "recombination element" encompasses a nucleic acid sequence that allows the integration of the polynucleotide in the genome of a cell (e.g. bacteria) transfected with the construct.

In some embodiments, the nucleic acid construct comprises an element providing episomal maintenance of said construct within a cell transfected with said construct.

In some embodiments, a construct may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

In some embodiments, the nucleic acid construct further comprises a transmissible element for directing transfer of said nucleic acid sequence from one cell to another. In some embodiments, a pVip gene is on a transmissible genetic element. In some embodiments, a pVip gene selected from a gene provided in Table 1, Table 2, or comprising any one of SEQ ID NOs: 3-408 is on a transmissible genetic element.

A skilled artisan would appreciate that the term "transmissible element" or "transmissible genetic element", which are interchangeably used, encompasses a polynucleotide that allows the transfer of the nucleic acid sequence from one cell to another, e.g. from one bacterium to another.

According to some embodiments, a transmissible genetic element comprises a conjugative genetic element or mobilizable genetic element. In some embodiments, a transmissible genetic element comprises a conjugative genetic element. In some embodiments, a transmissible genetic element comprises a mobilizable genetic element. The skilled artisan would appreciate that a "conjugative plasmid" encompasses a plasmid that is transferred from one cell (e.g. bacteria) to another during conjugation, and the term "mobilizable element" encompasses a transposon, which is a DNA sequence that can change its position within the genome.

In some embodiments, a nucleic acid construct disclosed herein comprises an expression vector. In some embodiments, an "expression vector" or a "vector", used interchangeably herein, comprises and expresses a pVip gene encoding a pVip disclosed herein. In some embodiments, expression comprises transient expression. In some embodiments, expression comprises constitutive expression. In some embodiments, expression is from an episomal nucleic acid sequence. In some embodiments, expression is from a nucleic acid sequence integrated into the chromosome of the cell. According to specific embodiments, the expression is on a transmissible genetic element.

In some embodiments, provided herein is a transmissible genetic element comprising a nucleic acid construct encoding a pVip. In some embodiments, disclosed herein is an expression vector comprising a nucleic acid construct encoding a pVip.

According to some embodiment, the nucleic acid construct comprises a plurality of cloning sites for ligating a nucleic acid sequence of a pVip gene, such that it is under transcriptional regulation of the regulatory elements.

Selectable marker genes that ensure maintenance of a construct in a host cell can also be included in the construct. In some embodiments, selectable markers include those which confer resistance to drugs such as ampicillin, chloramphenicol, erythromycin, kanamycin (neomycin), and tetracycline (Davies et al. (1978) Annu. Rev. Microbiol. 32:469). Selectable markers can also allow a cell to grow on minimal medium, or in the presence of toxic metabolite and can include biosynthetic genes, such as those in the histidine, tryptophan, and leucine biosynthetic pathways.

Other than containing the necessary elements for the transcription and translation of the inserted coding sequence, the expression construct of some embodiments can also include sequences engineered to enhance stability, production, purification, yield or toxicity of the expressed polypeptide. Where appropriate, the nucleic acid sequences may be optimized for increased expression in the transformed organism. For example, the nucleic acid sequences can be synthesized using preferred codons for improved expression.

Introduction of pVips into Cells

Various methods known within the art can be used to introduce a pVip into a cell. In some embodiments, introducing a pVip into a cell comprises introducing a pVip polypeptide into a cell. In some embodiments, introducing a pVip into a cell comprises introducing a nucleic acid construct encoding a pVip gene into a cell. Methods for introducing a nucleic acid construct or a polypeptide into a cell are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, natural or induced transformation, lipofection, electroporation and infection with recombinant viral vectors. In addition, see U.S. Pat. Nos. 5,464,764 and 5,487,992 for positive-negative selection methods, which are incorporated herein.

Introduction of nucleic acids by phage infection offers several advantages over other methods such as transformation, since higher transfection efficiency can be obtained due to the infectious nature of phages. These methods are especially useful for rendering bacteria more sensitive to phage attack for antibiotics purposes as further described hereinbelow.

It will be appreciated that a pVip can be introduced directly into the cell (e.g., bacterial cell) and not via recombinant expression to confer viral resistance. Thus, according to some embodiments, disclosed herein are isolated pVips or functional fragments thereof as described herein.

In some embodiments, a pVip can be introduced directly into the cell (e.g., bacterial cell) and not via recombinant expression, for example to confer viral resistance. In some embodiments, said pVip comprises a pVip provided in Table 5, or any of SEQ ID NOs: 409-789. In some embodiments, viral resistance comprises resistance to foreign nucleic acid invasion, to at least one phage infection, resistance to plasmid transformation, resistance to entry of a conjugative element, or any combination thereof.

In some embodiments, a pVip or a pVip gene is introduced into a cell together with co-factors. In some embodiments, these co-factors are needed for pVip proper functioning. In some embodiments, said co-factors comprise an s-adenosyl methionine. In some embodiments, said co-factors comprise the pVip specific substrate. In some embodiments, the specific substrate can be a non-natural substrate having any one of the structures of as disclosed herein, for example as provided in Table 1 and Table 2, or any combination thereof.

In some embodiments, the cell to which a pVip is introduced is a eukaryotic cell. In some embodiments, the eukaryotic cell is a tumor cell. In some embodiments, the cell to which a pVip is introduced is a prokaryotic cell, for example, a bacterium or achaea. In some embodiments, the bacterium is a gram-positive bacterium or a gram-negative bacterium.

Isolated Cells Comprising Prokaryotic Viperin Homologs (pVips)

In some embodiments, provided herein are isolated cells comprising an ectopic prokaryotic viperin homolog (pVip). In some embodiments, provided herein are cells genetically modified to express a pVip or a fragment thereof pVips have been described in detail herein. In some embodiments, a pVip comprises a pVip provided in Table 5, or any one of SEQ ID NOs: 409-789. In some embodiments, a pVip comprises an amino acid sequence with at least 80% homology to pVip provided in Table 5, or any one of SEQ ID NOs: 409-789. In some embodiments, the isolated cell comprises more than one pVip.

In some embodiments, the cell comprises an ectopic pVip gene. In some embodiments, the cell comprises one or more of the genes provided in Table 3, Table 4, or comprising one or more of SEQ ID NOs: 3-408. In some embodiment the cell comprises more than one ectopic pVip gene. In some embodiments, the cell comprises endogenous pVip co-factors. In some embodiments, pVip co-factors are ectopically provided.

In some embodiments, a cell is genetically modified to express a pVip gene. In some embodiments, a cell is genetically modified to express a combination of more than one pVip gene. In some embodiments, the cell comprises anti-phage, anti-plasmid, or anti-phage and anti-plasmid resistance provided by pVip genes. In some embodiments, multiple pVips are comprised in a single nucleic acid construct. In some embodiments, multiple pVips are comprised in multiple nucleic acid constructs.

In some embodiments, a cell (e.g., a bacterial cell) does not express an endogenous pVip. In some embodiments, the cell expresses an endogenous pVip which is different than the ectopically expressed pVip. In some embodiments, the cell expresses an endogenous pVip similar to the ectopically expressed pVip. In some embodiments, when an endogenous pVip is similar to the ectopically expressed pVip, expression of the ectopic pVip increases the concentration of said pVip in the cell.

Uses of Prokaryotic Viperin Homolog (pVip)

Structural elements, such as amino acid sequences of prokaryotic viperin homologs (pVips) have been described in detail above, as well as the genes that encode these pVips. Uses of pVips have been described above as well. Further details for uses of pVips is presented herein and exemplified in the Examples section below. In some embodiments, methods of using a pVip disclosed herein comprise use of a pVip, or a pVip gene. In some embodiments, the pVip comprises a pVip provided in Table 5, or any one of SEQ ID NOs: 409-789. In some embodiments, the pVip comprises an amino acid comprising at least 80% homology to a pVip provided in Table 5, or to any one of SEQ ID Nos: 409-789. In some embodiments, methods of use of pVip comprise use of a combination of pVips. In some embodiments, the pVips is encoded by a polynucleotide having at least 80% identity to a gene provided in Table 3, Table 4, or to any one of SEQ ID NOs: 3-408.

In some embodiments, the present disclosure provides methods of using ddh or deoxy-ddh compounds generated by the pVips from non-natural substrates disclosed herein. In some embodiments, methods of using these using ddh or deoxy-ddh compounds include methods of protecting eukaryotic cells from viral infection, methods for decreasing viral replication in eukaryotic cells, and methods of decreasing RNA transcription, for example for viruses with RNA genomes. In some embodiments, methods of using ddh or deoxy-ddh compounds disclosed herein include methods of increasing termination of DNA synthesis, methods of increasing termination of RNA synthesis, methods of decreasing proliferation in a cell, methods of conferring tumor resistance to a cell. In some embodiments, methods of using ddh or deoxy-ddh compounds disclosed herein include methods of treating an autoimmune disease, an immune disorder, or a disease or disorder associated with bacterial infection in a cell. In some embodiments, the cell is a eukaryotic cell. In some embodiment, the eukaryotic cell comprises a human cell.

In some embodiments, methods of using these using ddh or deoxy-ddh compounds described herein include, methods of treating a disease in a subject in need. In some embodiments, methods of using ddh or deoxy-ddh compounds described herein comprise treating a disease in a subject in need, wherein said disease comprises a virus-induced disease, a viral infection, a cancer or a tumor, an autoimmune disease, an immune disorder, or a disease or disorder associated with a bacterial infection, or any combination thereof. In some embodiments methods of using ddh or deoxy-ddh compounds described herein comprise treating a disease in a subject in need, wherein said disease comprises a virus-induced disease. In some embodiments methods of using ddh or deoxy-ddh compounds described herein comprise treating a disease in a subject in need, wherein said disease comprises a cancer or a tumor. In some embodiments methods of using ddh or deoxy-ddh compounds described herein comprise treating a disease in a subject in need, wherein said disease comprises an autoimmune disease. In some embodiments methods of using ddh or deoxy-ddh compounds described herein comprise treating a disease in a subject in need, wherein said disease comprises an immune disorder. In some embodiments methods of using ddh or deoxy-ddh compounds described herein comprise treating a disease in a subject in need, wherein said disease comprises a disease or disorder associated with a bacterial infection, or any combination thereof. In some embodiment, the subject in need is a human.

In some embodiments, a virus induced disease comprises a viral infection. In some embodiments, a viral induced disease comprises a viral infection, wherein said virus is selected from the group consisting of norovirus, rotavirus, hepatitis virus A, B, C, D, or E, rabies virus, West Nile virus, enterovirus, echovirus, coxsackievirus, herpes simplex virus (HSV), varicella-zoster virus, mosquito-borne viruses, arbovirus, St. Louis encephalitis virus, California encephalitis virus, lymphocytic choriomeningitis virus, human immunodeficiency virus (HIV), poliovirus, zika virus, rubella virus, cytomegalovirus (CMV), human papillomavirus (HPV), enteovirus D68, severe acute respiratory syndrome (SARS) coronavirus, Middle East respiratory syndrome coronavirus (MERS-CoV), SARS coronavirus 2 (SARS-CoV-2), Epstein-Barr virus (EBV), influenza virus, influenza virus A2, influenza virus B, influenza virus A(H1N1), respiratory syncytical virus (RSV), polyoma viruses, JC virus, BK virus, Tacaribe virus, Ebola virus, Dengue virus, and any combination thereof In some embodiments, the viral induced disease comprises COVID19 as a result of a SARS-CoV-2 infection. In some embodiments, the viral induced disease comprises infectious mononucleosis; non-malignant, premalignant, and malignant Epstein-Barr virus-associated lymphoproliferative diseases such as Burkitt lymphoma, hemophagocytic lymphohistiocytosis; Hodgkin's lymphoma; non-lymphoid malignancies such as gastric cancer and nasopharyngeal carcinoma; or conditions associated with human immunodeficiency virus such as hairy leukoplakia and central nervous system lymphomas, as a result of a EBV infection. In some embodiments, the viral induced disease occurs in an immunocompromised or immunosuppressed subject, as a result of a BK virus infection. In some embodiments, the viral induced disease occurs in an immunocompromised or immunosuppressed subject, as a result of a JC virus infection. In some embodiments, the viral induced disease comprises progressive multifocal leukoencephalopathy (PML), as a result of a JC virus infection.

In some embodiments, activity of the ddh- and deoxy-ddh compounds terminating polynucleotide chain synthesis confers viral resistance in a cell, wherein said cell is a eukaryotic cell. In some embodiments, the eukaryotic cell is a tumor cell, a cancer cell, or is a cell infected by a virus. Or foreign DNA.

A skilled artisan would appreciate that the while the ddh or deoxy-ddh compounds described herein may in certain embodiments be generated by the pVips described herein or homologs thereof from non-natural pVip substrates, in other embodiments, the ddh or deoxy-ddh compounds could be synthesized using chemical synthetic methods known in the art.

In one embodiment, methods of use of a pVip described herein include but are not limited to methods of producing modified nucleosides or modified nucleotides, methods for the discovery of nucleotide chain terminator molecules, methods to produce nucleotide analogs, methods to produce nucleoside analogs, methods to produce anti-viral compounds, and methods to produce antibiotic compounds. In some embodiments, the ddh or deoxy-ddh compounds are generated by the pVips from non-natural substrates having the substrate structures as described in detail herein, for example in Table 1 and Table 2 above.

In one embodiment, a ddh or deoxy-ddh compound is produced by the pVips from a non-natural substrate that is described in Table 1. In one embodiment, a ddh or deoxy-ddh compound is produced by the pVips from a non-natural substrates that is described in Table 2. In one embodiment, such ddh or deoxy-ddh compound is used in methods described herein. In one embodiment, such ddh or deoxy-ddh compound is used in methods described herein. In one embodiment, combinations of such ddh or deoxy-ddh compounds are used in methods described herein. In one embodiment, combinations of such ddh or deoxy-ddh compound are used in methods described herein. In one embodiment, a composition comprising 2 or more such ddh or deoxy-ddh compound are used. In one embodiment, a composition comprising 2 or more such ddh or deoxy-ddh compound are used. In one embodiment, a composition comprising 3 or more such ddh or deoxy-ddh compound are used. In one embodiment, a composition comprising 3 or more such ddh or deoxy-ddh compound are used.

In one embodiment, any one of the non-natural substrates described herein can be modified by the pVips to generate ddh or deoxy-ddh compound that can be used as DNA/RNA chain terminators or inhibitors These ddh or deoxy-ddh compound can be applied in the various methods of uses as described herein. In one embodiment, a pVip may produce one kind of ddh or deoxy-ddh compound from the non-natural substrates. In another embodiment, a pVip may produce multiple kinds of ddh or deoxy-ddh compounds from the non-natural substrates. For example, a pVip may produce two kinds of ddh or deoxy-ddh compounds, or a pVip may produce three kinds ddh or deoxy-ddh compounds, etc.

Methods for Treating a Disease

In one embodiment, the present disclosure provides a pharmaceutical composition comprising one or more ddh- or deoxy-ddh compounds as disclosed herein, for use in the treatment of a disease in a subject in need thereof. The ddh- or deoxy-ddh compounds may in certain embodiments, be used to treat a disease as a result of a viral infection. In some embodiments, the ddh- or deoxy-ddh compounds disclosed herein comprise antiviral activity. In one embodiment, the present disclosure provides a pharmaceutical composition comprising one or more compounds as disclosed herein, for use in the treatment of a disease in a subject in need thereof.

In some embodiments, the viral infection comprises infection by an RNA virus. In some embodiments, the viral infection comprises infection by a DNA virus.

The ddh- or deoxy-ddh compounds may in certain embodiments, be produced by a prokaryotic homolog of viperin (pVip) from non-natural substrates, wherein the pVip comprises the amino acid sequence of one of SEQ ID NOs:409-789. In another embodiment, the pVip comprises an amino acid having at least 80% homology to a pVip provided in Table 3, or having at least 80% homology to any one of SEQ ID NOs: 409-789. In some embodiments, the ddh- or deoxy-ddh compounds are produced synthetically using methods known in the art.

In one embodiment, the non-natural substrates, for example as described in detail herein, can have one of the structures of wherein the non-natural substrates each comprises 0, 1, 2, or 3 phosphate groups.

In some embodiments, a non-natural substrate comprises 0, 1, 2, or 3 phosphate groups. In some embodiments, a non-natural substrate comprises 0 phosphate groups. In some embodiments, a non-natural substrate comprises 1 phosphate group. In some embodiments, a non-natural substrate comprises 2 phosphate group. In some embodiments, a non-natural substrate comprises 3 phosphate group.

In some embodiments, the ddh- or deoxy-ddh compounds produced from the non-natural substrates comprise a variant of the corresponding ddh- or deoxy-ddh compounds lacking a 4' hydrogen and a 3' hydroxyl group. In some embodiments, a ddh- or deoxy-ddh compounds comprises 0, 1, 2, or 3 phosphate groups. In some embodiments, a ddh- or deoxy-ddh compound comprises 0 phosphate groups. In some embodiments, a ddh- or deoxy-ddh compound comprises 1 phosphate group. In some embodiments, a ddh- or deoxy-ddh compound comprises 2 phosphate group. In some embodiments, a ddh- or deoxy-ddh compound comprises 3 phosphate group.

In some embodiments provided herein is a ddh- or deoxy-ddh compound wherein the compound is represented by the structure of Formula IB, Formula IIB, Formula IIIB, Formula IVB, Formula VB, Formula VB1, Formula VIB, Formula VIIB, Formula VIIIB, Formula IXB, Formula XB, Formula XIB, Formula XIIB, Formula XIIIB, Formula XIIIB1, Formula XIVB, Formula XIVB1, Formula XIVB2, Formula XIV3, Formula XIV4, Formula XIV5, Formula XVB, Formula XVB1, Formula XVB2, Formula XVB3, Formula XVB4, Formula XVB5, Formula XVB6, Formula XVIB, Formula XVIB1, Formula XVIB2, Formula XVIB3, Formula XVIB4, Formula XVIB5, Formula XVIB6, Formula XVIB7, Formula XVIB8, Formula XVIB9, Formula XVIB10, Formula XVIB11, Formula XVIB12, Formula XVIB13, Formula XVIB14, Formula XVIB15, Formula XVIB16, Formula XVIB17, Formula XVIB18, Formula XVIB19, Formula XVIB20, Formula XVIB21, Formula XVIB22, Formula XVIB23, Formula XVIB24, Formula XVIB25, Formula XVIB26, Formula XVIB27, Formula XVIB28, Formula XVIB29, Formula XVIB30, Formula XVIB31, Formula XVIB32, Formula XVIB33, Formula XVIIB, Formula XVIIIB, Formula XXB, Formula XIXB, Formula XXIB, Formula XXIIB, Formula XXXIIIB, Formula XXIVB, or Formula XXVB for use in the treatment of a disease in a subject in need thereof.

In some embodiments, provided herein is a compound wherein the compound is represented by the structure of Formula IB, Formula IIB, Formula IIIB, Formula IVB, Formula VB, Formula VB1, Formula VIB, Formula VIIB, Formula VIIIB, Formula IXB, Formula XB, Formula XIB, Formula XIIB, Formula XIIIB, Formula XIIIB1, Formula XIVB, Formula XIVB1, Formula XIVB2, Formula XIV3, Formula XIV4, Formula XIV5, Formula XVB, Formula XVB1, Formula XVB2, Formula XVB3, Formula XVB4, Formula XVB5, Formula XVB6, Formula XVIB, Formula XVIB1, Formula XVIB2, Formula XVIB3, Formula XVIB4, Formula XVIB5, Formula XVIB6, Formula XVIB7, Formula XVIB8, Formula XVIB9, Formula XVIB10, Formula XVIB11, Formula XVIB12, Formula XVIB13, Formula XVIB14, Formula XVIB15, Formula XVIB16, Formula XVIB17, Formula XVIB18, Formula XVIB19, Formula XVIB20, Formula XVIB21, Formula XVIB22, Formula XVIB23, Formula XVIB24, Formula XVIB25, Formula XVIB26, Formula XVIB27, Formula XVIB28, Formula XVIB29, Formula XVIB30, Formula XVIB31, Formula XVIB32, Formula XVIB33, Formula XVIIB, Formula XVIIIB, Formula XXB, Formula XIXB, Formula XXIB, Formula XXIIB, Formula XXXIIIB, Formula XXIVB or Formula XXVB for use in the treatment of a disease comprises a virus-induced disease, a cancer, an autoimmune disease, an immune disorder, a bacterial associated disease or infection, or a combination thereof, in a subject in need thereof. In another embodiment, the disease is a virus-induced disease. In another embodiment, the disease is a cancer. In another embodiment, the disease is an autoimmune disease. In another embodiment, the disease is an immune disorder. In another embodiment, the disease is a bacterial associated disease.

In another embodiment, methods of use treat a disease comprising an infection. In another embodiment, methods of use disclosed herein treat COVID19 because of SARS-CoV-2 infection.

Subjects infected with EBV have an increased the risk for the development of several cancers and autoimmune diseases. Diseases associate with EBV infection included but are not limited to infectious mononucleosis, hemophagocytic lymphohistiocytosis, non-malignant or premalignant or malignant lymphoproliferative diseases such as Burkitt lymphoma, Hodgkin's lymphoma, non-lymphoid malignancies such as gastric cancer and nasopharyngeal carcinoma, hairy leukoplakia, central nervous system lymphomas, and multiple sclerosis. (See, Drosu et al., (2020) *Tenofovir prodrugs potently inhibit Epstein-Barr virus lytic DNA replication by targeting the viral DNA polymerase*. PNAS 117(22):12368-12374.) In some embodiment, methods of use disclosed herein treat an EBV infection-associated disease comprising infectious mononucleosis, hemophagocytic lymphohistiocytosis, non-malignant or premalignant or malignant lymphoproliferative diseases such as Burkitt lymphoma, Hodgkin's lymphoma, non-lymphoid malignancies such as gastric cancer and nasopharyngeal carcinoma, hairy leukoplakia, central nervous system lymphomas, and multiple sclerosis.

Double-stranded (ds) DNA virus infections often occur concomitantly in immunocompromised patients. In another embodiment, methods of use disclosed herein treat a viral induced disease occurring in an immunocompromised or immunosuppressed subject. In some embodiments, methods of use treat an immunocompromised patient infected with a BK virus, an adenovirus, a herpesvirus including Epstein-Barr virus, a poxvirus, or a polyoma virus including BK virus or JC virus (human polyomavirus 2)). Patients undergoing solid organ transplantation or allogeneic hematopoietic cell transplant (allo-HCT) are susceptible to viral infection, due to immunosuppressive environment created to support the transplant. In some embodiments, these patients are suffering from diseases including but not limited to nephropathy or hemorrhagic cystitis, etc. These transplant patients are particularly susceptible to dsDNA viral infections, for example EBV infections or polyoma viral infection including BKV and JCV infections.

In some embodiments, methods of treating disclosed herein, treat a disease associated with a dsDNA viral infection. In some embodiments, diseases associated dsDNA viral infections include diseases associated with a hematopoietic cell transplantation including nephropathy, hemorrhagic cystitis, etc.

In some embodiments, methods of use treat an immunosuppressed transplant patient, for example a subject undergoing a solid organ transplantation or a hematopoietic cell transplantation, wherein said patient has a dsDNA viral infection. In some embodiments, methods of use treat an immunosuppressed transplant patient, for example a subject undergoing a solid organ transplantation or a hematopoietic cell transplantation, wherein said patient has an EBV, BKV, herpes virus-6, adenovirus, CMV, or JCV infection. (See for example, Chemaly et al., (2019) *In vitro comparison of currently available and investigational antiviral agents against pathogenic human double-stranded DNA viruses: A systematic literature review*. Antiviral Research 163: 50-58.) In some embodiments, methods of use treat an immunosuppressed transplant patient with an EBV infection. In some embodiments, methods of use treat an immunosuppressed transplant patient with an BKV infection. In some embodiments, methods of use treat an immunosuppressed transplant patient with a herpes virus-6 infection. In some embodiments, methods of use treat an immunosuppressed transplant patient with an adenovirus infection. In some embodiments, methods of use treat an immunosuppressed transplant patient with a CMV infection. In some embodiments, methods of use treat an immunosuppressed transplant patient with a JCV infection.

In another embodiment, a disease treated by methods disclosed herein is caused by a viral infection, wherein the virus is selected from the group consisting of norovirus, rotavirus, hepatitis virus A, B, C, D, or E, rabies virus, West Nile virus, enterovirus, echovirus, coxsackievirus, herpes simplex virus (HSV), varicella-zoster virus, mosquito-borne viruses, arbovirus, St. Louis encephalitis virus, California encephalitis virus, lymphocytic choriomeningitis virus, human immunodeficiency virus (HIV), poliovirus, zika virus, rubella virus, cytomegalovirus, human papillomavirus (HPV), enteovirus D68, severe acute respiratory syndrome (SARS) coronavirus, Middle East respiratory syndrome coronavirus (MERS-CoV), SARS coronavirus 2 (SARS-CoV-2), Epstein-Barr virus (EBV), influenza virus, influenza virus A2, influenza virus B, influenza virus A(H1N1), respiratory syncytical virus (RSV), polyoma viruses, JC virus, BK virus, Tacaribe virus, Ebola virus, Dengue virus, and any combination thereof.

In another embodiment, the disease is caused by an EBV infection. In another embodiment, the disease is caused by a CMV infection. In another embodiment, the disease is caused by an BKV infection. In another embodiment, the disease is caused by an JCV infection. In another embodiment, the disease is caused by a SAR-CoV-2 infection.

In some embodiments provided herein is a pharmaceutical composition comprising a compound wherein the compound is represented by the structure of Formula IB, Formula IIB, Formula IIIB, Formula IVB, Formula VB, Formula VB1, Formula VIB, Formula VIIB, Formula VIIIB, Formula IXB, Formula XB, Formula XIB, Formula XIIB, Formula XIIIB, Formula XIIIB1, Formula XIVB, Formula XIVB1, Formula XIVB2, Formula XIV3, Formula XIV4, Formula XIV5, Formula XVB, Formula XVB1, Formula XVB2, Formula XVB3, Formula XVB4, Formula XVB5, Formula XVB6, Formula XVIB, Formula XVIB1, Formula XVIB2, Formula XVIB3, Formula XVIB4, Formula XVIB5, Formula XVIB6, Formula XVIB7, Formula XVIB8, Formula XVIB9, Formula XVIB10, Formula XVIB11, Formula XVIB12, Formula XVIB13, Formula XVIB14, Formula XVIB15, Formula XVIB16, Formula XVIB17, Formula XVIB18, Formula XVIB19, Formula XVIB20, Formula XVIB21, Formula XVIB22, Formula XVIB23, Formula XVIB24, Formula XVIB25, Formula XVIB26, Formula XVIB27, Formula XVIB28, Formula XVIB29, Formula XVIB30, Formula XVIB31, Formula XVIB32, Formula XVIB33, Formula XVIIB, Formula XVIIIB, Formula XXB, Formula XIXB, Formula XXIB, Formula XXIIB, Formula XXXIIIB, Formula XXIVB, or Formula XXVB or a combination thereof, for use in the treatment of a disease in a subject in need thereof.

In some embodiments provided herein is a pharmaceutical composition comprising a compound wherein the compound is represented by the structure of Formula IB, Formula IIB, Formula IIIB, Formula IVB, Formula VB, Formula VIB, Formula VIIB, Formula VIIIB, Formula IXB, Formula XB, Formula XIB, Formula XIIB, Formula XIIIB, Formula XIIIB1, Formula XIVB, Formula XIVB1, Formula XIVB2, Formula XIV3, Formula XIV4, Formula XIV5, Formula XVB, Formula VB1, Formula XVB1, Formula XVB2, Formula XVB3, Formula XVB4, Formula XVB5, Formula XVB6, Formula XVIB, Formula XVIB1, Formula XVIB2, Formula XVIB3, Formula XVIB4, Formula XVIB5, Formula XVIB6, Formula XVIB7, Formula XVIB8, Formula XVIB9, Formula XVIB10, Formula XVIB11, Formula XVIB12, Formula XVIB13, Formula XVIB14, Formula XVIB15, Formula XVIB16, Formula XVIB17, Formula XVIB18, Formula XVIB19, Formula XVIB20, Formula XVIB21, Formula XVIB22, Formula XVIB23, Formula XVIB24, Formula XVIB25, Formula XVIB26, Formula XVIB27, Formula XVIB28, Formula XVIB29, Formula XVIB30, Formula XVIB31, Formula XVIB32, Formula XVIB33, Formula XVIIIB, Formula XVIIIB, Formula XXB, Formula XIXB, Formula XXIB, Formula XXIIB, Formula XXXIIIB, Formula XXIVB, or Formula XXVB or a combination thereof, for use in the treatment of a disease comprises a virus-induced disease, a cancer, an autoimmune disease, an immune disorder, a bacterial associated disease or infection, or a combination thereof, in a subject in need thereof. In another embodiment, the disease is a virus-induced disease. In another embodiment, the disease is a cancer. In another embodiment, the disease is an autoimmune disease. In another embodiment, the disease is an immune disorder. In another embodiment, the disease is a bacterial associated disease. In another embodiment, the disease is an infection. In another embodiment, the disease is COVID19 caused by a SARS-CoV-2 infection. In another embodiment, the disease is caused by an EBV infection. In another embodiment, the disease is caused by a CMV infection. In another embodiment, the disease is caused by an BKV infection. In another embodiment, the disease is caused by an JCV infection.

In another embodiment, the disease is caused by a virus selected from the group consisting of norovirus, rotavirus, hepatitis virus A, B, C, D, or E, rabies virus, West Nile virus, enterovirus, echovirus, coxsackievirus, herpes simplex virus (HSV), varicella-zoster virus, mosquito-borne viruses, arbovirus, St. Louis encephalitis virus, California encephalitis virus, lymphocytic choriomeningitis virus, human immunodeficiency virus (HIV), poliovirus, zika virus, rubella virus, cytomegalovirus, human papillomavirus (HPV), enteovirus D68, severe acute respiratory syndrome (SARS) coronavirus, Middle East respiratory syndrome coronavirus (MERS-CoV), SARS coronavirus 2 (SARS-CoV-2), Epstein-Barr virus (EBV), influenza virus, influenza virus A2, influenza virus B, influenza virus A(H1N1), respiratory syncytical virus (RSV), polyoma viruses, JC virus, BK virus, Tacaribe virus, Ebola virus, Dengue virus, and any combination thereof.

In some embodiments, the methods of treating comprising use of a ddh- or deoxy-ddh compound disclosed herein, terminates polynucleotide chain synthesis in a cell.

As it is generally known in the art, in order to function as DNA or RNA chain terminators in vivo, a ddh- or deoxy ddh compound would have to be converted by one or more viral or cellular kinases into their 5'-triphosphate form before they can compete with the natural substrates (dNTPs for DNA synthesis and NTPs for RNA synthesis) in the DNA or RNA polymerization reaction. Thus, the "active metabolite" for the purpose of DNA or RNA chain termination is the ddh- or deoxy ddh compound in a 5'-triphosphate form. In other words, the products generated from the non-natural substrates by the pVips, or any other means, for example chemical synthesis, comprise active metabolites as DNA or RNA chain terminators, and these products or active metabolites are in 5'-triphosphate form. However, in order to administer these products or active metabolites to the cells and allow transport across cell membrane, these products or active metabolites need to be made into a form without a phosphate group.

In another embodiment, terminating polynucleotide chain synthesis increases termination of DNA chain synthesis, or increases termination of RNA chain synthesis, or a combination thereof. In another embodiment, terminating polynucleotide chain synthesis increases termination of DNA chain synthesis. In another embodiment, the terminating polynucleotide chain synthesis increases termination of RNA chain synthesis.

In some embodiments, these ddh or deoxy-ddh products or active metabolites thereof comprise a pro-drug functional group:

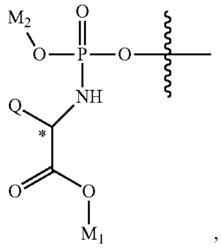

,

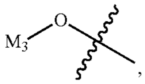

,

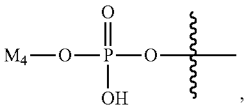

, or

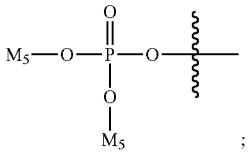

;

Q is a side chain of an amino acid; $M_1$ is an alkyl;

$M_2$ is an aryl, a substituted aryl, a heteroaryl or a substituted heteroaryl;

$M_3$ is

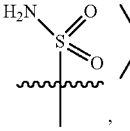

,

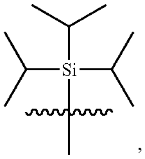

,

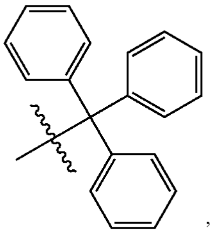

, or

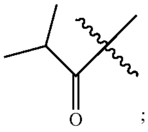

;

$M_4$ is $-(C_2\text{-}C_6)$alkyl-O$-(C_{10}\text{-}C_{20})$alkyl;

each $M_5$ is $-(CH_2)_n-S-C(=O)-(C_1\text{-}C_8)$alkyl; and n is 1-4 at the $R_1$, $R_{11}$ or $R_{21}$ positions.

In one embodiment, the above compositions comprising one or more ddh or deoxy-ddh compounds can be provided to the subject with additional active agents to achieve an improved therapeutic effect as compared to treatment with each agent by itself. In another embodiment, additional active agents can be anti-viral agents or anti-cancer drugs or antibiotics.

In another embodiment, the present disclosure provides a composition comprising one or more non-natural substrates of pVip for use in the treatment of a disease in a subject in need thereof. The subject has been or is concurrently treated to express the pVip. To express the pVip in the subject, the subject can be treated prior or concurrently with a composition comprising the pVip. Alternatively, the subject can be treated prior or concurrently with a composition comprising nucleotide sequences encoding the pVip. The non-natural substrates are recognized as substrates by a pVip that comprises the amino acid sequence of one of SEQ ID NOs:409-789. In another embodiment, the pVip comprises an amino acid having at least 80% homology to a pVip provided in Table 5, or having at least 80% homology to any one of SEQ ID NOs: 409-789. In one embodiment, the non-natural substrates have been described in detail herein.

In one embodiment, the non-natural substrates are administered to cells or a subject in a form that can enter the cells (e.g. non-phosphorylated form). Once inside the cells, these non-natural substrates can be converted (e.g. phosphorylation by one or more viral or cellular kinases) to a form that can be recognized as substrates by the pVip. pVip expressed in the cells would then convert these non-natural substrates to produce ddh or deoxy-ddh compounds that can inhibit DNA/RNA replication. In one embodiment, the non-natural substrates can be modified and administered in "prodrug" form as described above. In one embodiment, a prodrug comprises a non-natural substrate with a chemical structure that can be oxidized, reduced, aminated, deaminated, esterified, deesterified, alkylated, dealkylated, acylated, deacylated, phosphorylated, dephosphorylated, photolyzed, hydrolyzed, or other functional group change or conversion to produce the non-natural substrates that can be recognized by pVip as substrate, or produce the non-natural substrates that can be transported across cell membrane. In one embodiment, the non-natural substrate catalyzed by the pVip can be modified by adding a protective chemical group and thereby becoming a prodrug.

In one embodiment, the above composition comprising one or more non-natural substrates can be provided to the subject with additional active agents to achieve an improved therapeutic effect as compared to treatment with each agent by itself. In one embodiment, additional active agents can be anti-viral agents or anti-cancer drugs or antibiotics.

In another embodiment, the present disclosure provides a method of use of a composition, wherein the composition comprises one or more ddh or deoxy-ddh compounds as described herein, for use in the treatment of a disease in a subject in need thereof.

In one embodiment, the disease can be a virus-induced disease, a cancer or a tumor, an autoimmune disease, an immune disorder, or a disease or disorder associated with a bacterial infection, or a combination thereof.

In one embodiment, a viral infection is caused by viruses in the Baltimore classification Group I group of viruses: double-stranded DNA viruses (e.g. Adenoviruses, Herpesviruses including Epstein-Barr virus, Poxviruses, Polyoma viruses including BK virus and JC virus (human polyomavirus 2)). In another embodiment, the viral infection is caused by viruses in the Baltimore classification Group II group of viruses: single-stranded (or "sense") DNA viruses (e.g. Parvoviruses). In another embodiment, the viral infection is caused by viruses in the Baltimore classification Group III group of viruses: double-stranded RNA viruses (e.g. Reoviruses). In another embodiment, the viral infection is caused by viruses in the Baltimore classification Group IV group of viruses: single-stranded (sense) RNA viruses (e.g. Picornaviruses, Togaviruses, Coronavirus including SARS-CoV-2). In another embodiment, the viral infection is caused by viruses in the Baltimore classification Group V of viruses: single-stranded (antisense) RNA viruses (e.g. Orthomyxoviruses, Rhabdoviruses). In another embodiment, the viral infection is caused by viruses in the Baltimore classification Group VI group of viruses: single-stranded (sense) RNA viruses with DNA intermediate in life-cycle (e.g. Retroviruses). In another embodiment, the viral infection is caused by viruses in the Baltimore classification Group VII group of viruses: double-stranded DNA viruses with RNA intermediate in life-cycle (e.g. Hepadnaviruses).

In one embodiment, the virus-induced disease can be respiratory viral infection (e.g. common cold, seasonal influenzas), gastrointestinal viral infection, liver viral infection, nervous system viral infection, skin viral infection, sexually transmitted viral infection, placental viral infection, or fetal viral infection.

In one embodiment, examples of viral induced disease include, but are not limited to, gastroenteritis, keratoconjunctivitis, pharyngitis, croup, pharyngoconjunctival fever, pneumonia, cystitis (Adenovirus), Hand, foot and mouth disease, pleurodynia, aseptic meningitis, pericarditis, myocarditis (Coxsackievirus), infectious mononucleosis, Burkitt's lymphoma, Hodgkin's lymphoma, nasopharyngeal carcinoma (Epstein-Barr virus), acute hepatitis, chronic hepatitis, hepatic cirrhosis, hepatocellular carcinoma, herpes labialis, cold sores, gingivostomatitis in children, tonsillitis & pharyngitis in adults, skin vesicles, mucosal ulcers, oral and/or genital ulcers, Aseptic meningitis (Herpes simplex virus, type 2), Cytomegalic inclusion disease, liver, lung and spleen diseases in the newborn, congenital seizures in the newborn (Cytomegalovirus), Kaposi sarcoma, multicentric Castleman disease, primary effusion lymphoma (Human herpesvirus, type 8), AIDS (HIV), influenza, Reye syndrome (Influenza virus), measles, postinfectious encephalomyelitis (Measles virus), mumps, hyperplastic epithelial lesions (common, flat, plantar and anogenital warts, laryngeal papillomas, epidermodysplasia verruciformis), cervical carcinoma, squamous cell carcinomas (Human papillomavirus), bronchiolitis, common cold (Parainfluenza virus), poliomyelitis (Poliovirus), rabies, influenza-like syndrome, severe bronchiolitis with pneumonia (Respiratory syncytial virus), congenital rubella, German measles (Rubella virus), chickenpox, herpes zoster, Congenital varicella syndrome (Varicella-zoster virus).

In one embodiment, the disease is caused by one or more of the following viruses: norovirus, rotavirus, hepatitis virus A, B, C, D, or E, rabies virus, West Nile virus, enterovirus, echovirus, coxsackievirus, herpes simplex virus (HSV), varicella-zoster virus, mosquito-borne viruses, arbovirus, St. Louis encephalitis virus, California encephalitis virus, lymphocytic choriomeningitis virus, human immunodeficiency virus (HIV), poliovirus, zika virus, rubella virus, cytomegalovirus, human papillomavirus (HPV), enteovirus D68, severe acute respiratory syndrome (SARS) coronavirus, Middle East respiratory syndrome coronavirus (MERS-CoV), SARS coronavirus 2 (SARS-CoV-2), Epstein-Barr virus (EBV), influenza virus, influenza virus A2, influenza virus B, influenza virus A(H1N1), respiratory syncytical virus (RSV), polyoma viruses, JC virus, BK virus, Tacaribe virus, Ebola virus, and Dengue virus.

In one embodiment, the disease is COVID19 caused by SARS coronavirus 2. In one embodiment, the disease is the result of an EBV infection. In one embodiment, the disease is the results of an CMV infection In one embodiment, the disease is the result of an BKV infection. In one embodiment, the disease is the results of an JCV infection.

In one embodiment, the viral infection is caused by viruses of human or non-human origin. In some embodiments, the viral infection is caused by modified or unmodified viruses that originate from animals or any foreign organism, for example, infection caused by SARS coronavirus, SARS-CoV-2, etc.

In some embodiments, treating a viral infection comprises protecting an organism from foreign nucleic acid invasion. In some embodiments, treating a viral infection comprises decreasing viral nucleic acid replication.

In one embodiment, the above-described composition comprising one or more ddh or deoxy-ddh compounds generated by the pVips from non-natural substrates or synthesized using methods known in the art, can be used in the treatment of cancer or a tumor. Representative examples of cancer include, but are not limited to, carcinoma, sarcoma, lymphoma, leukemia, germ cell tumor, blastoma, chondrosarcoma, Ewing's sarcoma, malignant fibrous histiocytoma of bone, osteosarcoma, rhabdomyosarcoma, heart cancer, brain cancer, astrocytoma, glioma, medulloblastoma, neuroblastoma, breast cancer, medullary carcinoma, adrenocortical carcinoma, thyroid cancer, Merkel cell carcinoma, eye cancer, gastrointestinal cancer, colon cancer, gallbladder cancer, gastric (stomach) cancer, gastrointestinal carcinoid tumor, hepatocellular cancer, pancreatic cancer, rectal cancer, bladder cancer, cervical cancer, endometrial cancer, ovarian cancer, renal cell carcinoma, prostate cancer, testicular cancer, urethral cancer, uterine sarcoma, vaginal cancer, head cancer, neck cancer, nasopharyngeal carcinoma, hematopoetic cancer, Non-Hodgkin lymphoma, skin cancer, basal-cell carcinoma, melanoma, small cell lung cancer, non-small cell lung cancer, or any combination thereof.

In one embodiment, the above-described composition comprising one or more ddh or deoxy-ddh compounds generated by the pVips from non-natural substrates or synthesized using methods known in the art, can be used in the treatment of autoimmune disease. Representative examples of autoimmune disease include, but are not limited to, achalasia, amyloidosis, ankylosing spondylitis, anti-gbm/anti-tbm nephritis, antiphospholipid syndrome, arthritis, autoimmune angioedema, autoimmune encephalomyelitis, autoimmune hepatitis, autoimmune myocarditis, autoimmune oophoritis, autoimmune orchitis, autoimmune pancreatitis, autoimmune retinopathy, autoimmune urticaria, Behcet's disease, celiac disease, chagas disease, chronic inflammatory demyelinating polyneuropathy, Cogan's syndrome, congenital heart block, Crohn's disease, dermatitis, dermatomyositis, discoid lupus, Dressler's syndrome, endometriosis, fibromyalgia, fibrosing alveolitis, granulomatosis with polyangiitis, Graves' disease, Guillain-Barre syndrome, herpes gestationis, immune thrombocytopenic purpura, interstitial cystitis, juvenile arthritis, juvenile diabetes (type 1 diabetes), juvenile myositis, Kawasaki disease, Lambert-Eaton syndrome, lichen planus, lupus, Lyme disease, multiple sclerosis, myasthenia gravis, myositis, neonatal lupus, neutropenia, palindromic rheumatism, peripheral neuropathy, polyarteritis nodosa, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, reactive arthritis, retroperitoneal fibrosis, rheumatic fever, rheumatoid arthritis, sarcoidosis, Schmidt syndrome, scleritis, scleroderma, Sjögren's syndrome, thrombocytopenic purpura, type 1 diabetes, ulcerative colitis, uveitis, vasculitis, and vitiligo.

In one embodiment, the above-described composition comprising one or more ddh or deoxy-ddh compounds generated by the pVips from non-natural substrates or synthesized using methods known in the art, can be used in the treatment of immune disorders.

In one embodiment, the above-described composition comprising one or more ddh or deoxy-ddh compounds generated by the pVips from non-natural substrates or synthesized using methods known in the art, can be used in the treatment of bacterial infections and diseases or disorders associated with bacterial infections. Bacterial infections can be caused by numerous bacterial pathogens. In general, bacterial pathogens may be classified as either Gram-positive or Gram-negative pathogens. In some embodiments, the ddh or deoxy-ddh compounds described herein may comprise effective activity against either a Gram-positive bacterium or a Gram-negative bacteria, or both. In some embodiments, the ddh or deoxy-ddh compounds described herein comprise a broad-spectrum antibiotic activity. For example, but not limited to, in some embodiments, a bacterial infection may be the result of infection from a *Streptococcus pneumoniae; Staphylococcus aureus; Haemophilus influenza, Myoplasma* species, or *Moraxella catarrhalis.*

In some embodiments, disclosed herein is a method for treating a disease in a subject in need thereof, the method comprising administering to said subject In some embodiments, disclosed herein is a method for treating a disease in a subject in need thereof, the method comprising administering to said subject a composition comprising a nucleic acid construct comprising pVip gene. In some embodiments, disclosed herein is a method for treating a disease in a subject in need thereof, the method comprising administering to said subject a composition comprising a nucleic acid construct comprising pVip gene and a non-natural substrate as described herein. In some embodiments, disclosed herein is a method for treating a disease in a subject in need thereof, the method comprising administering to said subject a composition comprising a cell comprising a pVip gene. In some embodiments, disclosed herein is a method for treating a disease in a subject in need thereof, the method comprising administering to said subject a composition comprising a cell comprising a pVip gene, wherein administering further includes providing a non-natural substrate as described herein. In some embodiments, a non-natural substrate is provided following administration of a composition comprising a nucleic acid construct comprising a pVip gene or a cell comprising a pVip gene. The later administration of the non-natural substrate provides a window of time for the medical professional to access expression of the pVip gene prior to administration of the non-natural substrate.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Determination of a therapeutically effective amount is well within the capability of those skilled in the art. For any preparation used in the methods disclosed herein, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

The amount of a composition to be administered will, of course, be dependent on e.g. the subject being treated, the severity of the affliction, the manner of administration, the judgment of the prescribing physician, etc.

In another embodiment, terminating polynucleotide chain synthesis confers viral resistance to said cell.

In another embodiment, the cell is a eukaryotic cell. In another embodiment, said eukaryotic cell is a tumor cell, or is infected by a virus or a foreign DNA. In another embodiment, said eukaryotic cell is a tumor cell. In another embodiment, said eukaryotic cell is infected by a virus or a foreign DNA.

In some embodiments, the cell in which termination of polynucleotide chain synthesis is desired is a eukaryotic cell. In some embodiments, the eukaryotic cell is a tumor cell.

In some embodiments, termination of polynucleotide chain synthesis confers viral resistance to a cell. In some embodiments, termination of polynucleotide chain synthesis decreases DNA replication in a cell. In some embodiments, termination of polynucleotide chain synthesis decreases RNA transcription in a cell.

In one embodiment, the present disclosure provides a method of terminating polynucleotide chain synthesis in a cell, the method comprises contacting the cell with a composition comprising one or more ddh or deoxy-ddh compounds. In one embodiment, the present disclosure provides a method of terminating polynucleotide chain synthesis in a cell, the method comprises contacting the cell with a composition comprising one or more ddh or deoxy-ddh compounds comprising a protective chemical group. In one embodiment, the present disclosure provides a method of terminating polynucleotide chain synthesis in a cell, the method comprises contacting the cell with a composition comprising one or more ddh or deoxy-ddh compounds that are derived from products produced by a prokaryotic homolog of viperin (pVip) or by synthetic methods known in the art from non-natural substrates, wherein the pVip comprises the amino acid sequence of one of SEQ ID NOs:409-789. In one embodiment, the pVip comprises an amino acid having at least 80% homology to a pVip provided in Table 5, or having at least 80% homology to any one of SEQ ID NOs: 409-789. In one embodiment, the non-natural substrates for the pVips have been described in detail herein.

In one embodiment, the ddh or deoxy-ddh compounds can be applied in a prodrug form as described above. Various forms of ddh or deoxy-ddh compounds can be applied as described herein, for example, a compound is in the 3'-deoxy-3',4'-didehydro (ddh) form. In one embodiment, the ddh or deoxy-ddh compound can be administered to the cells in the form that can enter the cells (e.g. non-phosphorylated form). Once inside the cells, these nucleoside analogs can be converted by one or more viral or cellular kinases to the active form that can inhibit DNA/RNA replication.

In another embodiment, the present disclosure provides a method of terminating polynucleotide chain synthesis in a cell, the method comprising contacting the cell with a composition comprising one or more non-natural substrates of prokaryotic homolog of viperin (pVip). The cell has been or is concurrently treated to express the pVip. To express the pVip in the cell, the cell can be treated prior or concurrently with a composition comprising the pVip.

Alternatively, the cell can be treated prior or concurrently with a composition comprising nucleotide sequences encoding the pVip. The non-natural substrates are recognized as substrates by a pVip that comprises the amino acid sequence of one of SEQ ID NOs:409-789. In one embodiment, the pVip comprises an amino acid having at least 80% homology to a pVip provided in Table 3, or having at least 80% homology to any one of SEQ ID NOs: 409-789. In one embodiment, the non-natural substrates for the pVips have been described in detail herein. In one embodiment, the method is carried out in vitro.

In one embodiment, the non-natural substrates are administered to cells in a form that can enter the cells (e.g. nucleoside form, or non-phosphorylated form). Once inside the cells, these non-natural substrates can be converted (e.g. phosphorylation by one or more viral or cellular kinases) to a form that can be recognized as substrates by the pVip. pVip expressed in the cells would then convert these non-natural substrates to produce nucleotide/nucleoside analogs that can inhibit DNA/RNA replication. In one embodiment, the non-natural substrates can be modified and administered in "prodrug" form as described above. In one embodiment, the non-natural substrate catalyzed by the pVip can be modified by adding a protective chemical group and thereby becoming a prodrug.

In some embodiments, the cell in which termination of polynucleotide chain synthesis is desired is a eukaryotic cell. In some embodiments, the eukaryotic cell is a tumor cell or a cancer cell.

In some embodiments, termination of polynucleotide chain synthesis confers viral resistance to a cell. In some embodiments, termination of polynucleotide chain synthesis decreases DNA replication in a cell. In some embodiments, termination of polynucleotide chain synthesis decreases RNA transcription in a cell.

In some embodiments, termination of polynucleotide chain synthesis comprises increased termination of DNA chain synthesis. In some embodiments, termination of polynucleotide chain synthesis comprises increased termination of RNA chain synthesis. In some embodiments, termination of polynucleotide chain synthesis decreases proliferation of a cell. In some embodiments, termination of polynucleotide chain synthesis comprises an anti-tumor activity.

In some embodiments, terminating polynucleotide chain synthesis in a cell comprises reducing polynucleotide chain synthesis in a cell by at least 1%, by at least 2%, by at least 3%, by at least 4%, by at least 5%, by at least 6%, by at least 7%, by at least 8%, by at least 9%, by at least 10%, by at least 20%, by at least 30%, by at least 40%, by at least 50%, by at least 60%, by at least 70%, by at least 80%, by at least 90%, or by 100%.

In some embodiments, terminating polynucleotide chain synthesis in a cell comprises reducing viral DNA replication. In some embodiments, terminating polynucleotide chain synthesis in a cell comprises reducing viral RNA chain synthesis. In some embodiments, terminating polynucleotide chain synthesis in a cell comprises reducing viral DNA or RNA chain synthesis without modifying DNA replication of the host cell.

In some embodiments, terminating polynucleotide chain synthesis in a cell comprises reducing eukaryotic DNA replication. In some embodiments, the eukaryotic cell is a tumor cell.

In some embodiments, terminating polynucleotide chain synthesis in a cell comprises reducing polynucleotide chain synthesis in a cell by between about 0% and about 10%, between about 10% and about 20%, between about 20% and about 30%, between about 30% and about 40%, between about 40% and about 50%, between about 50% and about 60%, between about 60% and about 70%, between about 70% and about 80%, between about 80% and about 90%, or between about 90% and about 100%.

In some embodiments, provided herein is a method for treating a disease wherein the method comprises administration of a pharmaceutical composition described herein.

In some embodiments, provided herein is a method for treating a disease wherein the method comprises administration of a compound described herein.

Methods of Protecting a Cell from Viral Infection

In some embodiments, disclosed herein is a method of protecting a cell from viral infection, said method comprising a step of introducing into said cell a prokaryotic viperin homolog (pVip), or a pVip gene. In some embodiments, a method of protecting a cell from viral infection comprises a step of introducing into said cell a pVip gene selected from a gene provided in Table 3, Table 4, or comprising any one of SEQ ID NOs: 3-408. In some embodiments, a method of protecting a cell from viral infection comprises a step of introducing into said cell a pVip gene encoding for a protein with an amino acid sequence of one of those provided in Table 5, or comprising any one of SEQ ID NOs: 409-789. In another embodiment, the pVip comprises an amino acid having at least 80% homology to a pVip provided in Table 5, or having at least 80% homology to any one of SEQ ID NOs: 409-789.

In some embodiments, a method of protecting a cell from viral infection comprises a step of introducing into said cell a composition comprising one or more ddh or deoxy-ddh compounds, or prodrug forms thereof, as described herein, which may be generated by the pVips from the non-natural substrates described herein or as synthesized using methods known in the art. In some embodiments, the cell comprises a human cell. In some embodiments, the cell comprises a tumor cell or a cancer cell. In some embodiments, the cell has been infected by a virus. In one embodiment, the non-natural substrates are modified by the pVips to have the 3' hydroxyl groups removed. In another embodiment, these non-natural substrates are modified by the pVips to become the 3'-deoxy-3',4'-didehydro (ddh) derivates. In some embodiments, the ddh or deoxy-ddh compounds are modified to have the 3' hydroxyl groups removed. In some embodiments, the ddh or deoxy-ddh compounds that are modified become the 3'-deoxy-3',4'-didehydro (ddh) derivates. In one embodiment, the ddh or deoxy-ddh compounds are modified to include a protective chemical group, wherein the modified compound comprises a prodrug. In some embodiments, the viral infection comprises infection with a phage. In some embodiments, the viral infection comprises infection with a virus. Examples of viruses or viral infections have been described above.

As used herein the term "about" refers to +10%. As used herein, the singular form "a", "an" and "the" include plural references unless the context clearly dictates otherwise. For example, the term "a compound" or "at least one compound" may include a plurality of compounds, including mixtures thereof.

Throughout this application, various embodiments are disclosed that may be presented in a range format. It should be understood that the description in range format is merely for convenience and brevity and should not be construed as an inflexible limitation on the scope. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

EXAMPLES

Reference is now made to the following examples, which together with the above descriptions illustrate some embodiments in a non-limiting fashion.

Generally, the nomenclature used herein, and the laboratory procedures utilized, include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are well known in the art and are provided for the convenience of the reader. All the information contained therein is incorporated herein by reference.

Example 1—Materials and Methods

Bacterial Strains and Growth Conditions

*Escherichia coli* strains (MG1655, Keio ΔiscR, DH5α) were grown in LB or LB agar at 37° C. unless mentioned otherwise. Whenever applicable, media were supplemented with ampicillin (100 $\mu gml^{-1}$), kanamycin (50 $\mu gml^{-1}$) or tetracycline (10 $ugmL^{-1}$) to ensure the maintenance of plasmids. *Bacillus subtilis* strain BEST7003 and its derivatives were grown in LB or LB agar at 37° C. Whenever applicable, media were supplemented with spectinomicin (100 $\mu gml^{-1}$). Expression from pAr and pHypraspank promoters was induced by the addition of respectively arabinose (0.2%) or IPTG (1 mM).

Plasmids and Strain Construction pVip genes were codon optimized and synthetized by Twist Bioscience (pVips 6-10, and 12) or by Genscript (all other pVips). Synthetized pVip are shown in Table 2. Each candidate sequence was cloned in two plasmids: pDR111 and pBad/His A (Thermofisher, Catalog number 43001). For pVips 6-12, PCR fragments were joined using Gibson Assembly®. The primers used in these experiments are shown in Table 5. For other candidates, cloning was performed by Genscript. Candidate pVip plasmids were first cloned and propagated in DH5α. pBad/HisA derivatives were further transformed in relevant strains (MG1655, Keio ΔiscR). pDR111 derivatives were integrated in the amyE locus of the BEST strains. pAGG encodes a GFP under a T7 promoter and a module with T7 lyzozyme to limit the leakiness of RNAP in strain BL21-DE3. The pAGG plasmid was obtained through two consecutives Gibbson assemblies, the first to generate pAG (insert pDR111 primers OG630, OG631, vector pACYc, primers OG629, OG628) and then a second to generate pAGG (insert pLysS primers AB55, AB56, vector pAG, primers AB53, AB54) (Table 7).

TABLE 7

Primers

| Name | SEQ ID NO: |
|---|---|
| AB_Vip1-gibbson_coli_vector_F | 790 |
| AB_Vip2-gibbson_coli_vector_R | 791 |
| AB_Vip3-gibbson_coli_insert_F | 792 |
| AB_Vip4-gibbson_coli_insert_R | 793 |
| AB_Vip5-res_coli_vector_F | 794 |
| AB_Vip6-res_coli_vector_R | 795 |
| AB_Vip7-gibbson_subtilis_vector_F | 796 |
| AB_Vip8-gibbson_subtilis_vector_R | 797 |
| AB_Vip19-gibbson_subtilis_insert_pVip6_F | 798 |
| AB_Vip20-gibbson_subtilis_insert_pVip6_R | 799 |
| AB_Vip21-gibbson_subtilis_insert_pVip7_F | 800 |
| AB_Vip22-gibbson_subtilis_insert_pVip7_R | 801 |
| AB_Vip23-gibbson_subtilis_insert_pVip8_F | 802 |
| AB_Vip24-gibbson_subtilis_insert_pVip8_R | 803 |

TABLE 7-continued

Primers

| Name | SEQ ID NO: |
|---|---|
| AB_Vip25-gibbson_subtilis_insert_pVip9_F | 804 |
| AB_Vip26-gibbson_subtilis_insert_pVip9_R | 805 |
| AB_Vip27-gibbson_subtilis_insert_pVip10_F | 806 |
| AB_Vip28-gibbson_subtilis_insert_pVip10_R | 807 |
| AB_Vip31-gibbson_subtilis_insert_pVip12_F | 808 |
| AB_Vip32-gibbson_subtilis_insert_pVip12_R | 809 |
| AB_Vip37-sequencing_primer_coli_1 | 810 |
| AB_Vip38-sequencing_primer_coli_2 | 811 |
| AB_Vip39-sequencing_primer_subtilis_1 | 812 |
| AB_Vip40-sequencing_primer_subtilis_2 | 813 |
| AB_Vip41-pVip_control_coli_vector_F | 814 |
| AB_Vip42-pVip_control_coli_vector_R | 815 |
| AB_Vip43-pVip_control_coli_insert_F | 816 |
| AB_Vip44-pVip_control_coli_insert_R | 817 |
| AB53 | 818 |
| AB54 | 819 |
| AB55 | 820 |
| AB56 | 821 |
| OG628 | 822 |
| OG629 | 823 |
| OG630 | 824 |
| OG631 | 825 |

Phage Propagation

Phages were propagated on either *E. coli* MG1655, *E. coli* MG1655 F+ or *B. subtilis* BEST7003 using the plate lysate method as described in Fortier, L. C. et al. Phage Production and Maintenance of Stocks, Including Expected Stock Lifetimes; in "Bacteriophages: Methods and Protocols, Vol 1: Isolation, Characterization, and Interactions" (eds. Clokie, M. R. J. & Kropinski, A. M.) 203-219 (Humana Press, 2009). Lysate titer was determined using the small drop plaque assay method as described in Kropinski et al. Enumeration of Bacteriophages by Double Agar Overlay Plaque Assay; in "Bacteriophages: Methods and Protocols, Volume 1: Isolation, Characterization, and Interactions" (eds. Clokie, M. R. J. & Kropinski, A. M.) 69-76 (Humana Press, 2009). Phages used in this study are presented in Table 8.

TABLE 8

Phages used in these experiments

| Phage | Host | Taxonomy | Accession number |
|---|---|---|---|
| SBSphi28-4 | *B. subtilis* | Siphoviridae | N/A |
| SP82G | *B. subtilis* | Myoviridae | N/A |
| phi105 | *B. subtilis* | Siphoviridae | HM072038.1 |
| SPP1 | *B. subtilis* | Siphoviridae | NC_004166.2 |
| Phi3T | *B. subtilis* | Siphoviridae | KY030782.1 |
| SPBeta | *B. subtilis* | Siphoviridae | AF020713.1 |
| SPR | *B. subtilis* | Siphoviridae | N/A |
| Rho14 | *B. subtilis* | Siphoviridae | N/A |
| SPO1 | *B. subtilis* | Myoviridae | NC_011421.1 |
| phi29 | *B. subtilis* | Podoviridae | NC_011048.1 |
| SBSphiC | *B. subtilis* | Myoviridae | LT960610.1 |
| SBSphiJ | *B. subtilis* | Myoviridae | LT960608.1 |
| SECphi18 | *E. coli* | Siphoviridae | LT960609.1 |
| SECphi27 | *E. coli* | Siphoviridae | LT961732.1 |
| SEC32-2 | *E. coli* | Siphoviridae | N/A |
| Lambda_VIR | *E. coli* | Siphoviridae | NC_001416.1 |
| SECphi17 | *E. coli* | Microviridae | LT960607.1 |
| SECphi6_1 | *E. coli* | Siphoviridae | N/A |
| P1 | *E. coli* | Myoviridae | AF234172.1 |
| T2 | *E. coli* | Myoviridae | LC348380.1 |
| T4 | *E. coli* | Myoviridae | AF158101.6 |
| T5 | *E. coli* | Siphoviridae | AY543070.1 |
| T6 | *E. coli* | Myoviridae | MH550421.1 |
| T7 | *E. coli* | Podoviridae | NC_001604.1 |

Plaque Assays

Plaque assays were performed as previously described in Kropinski, A M et al. Enumeration of Bacteriophages by Double Agar Overlay Plaque Assay. in Bacteriophages: Methods and Protocols, Volume 1: Isolation, Characterization, and Interactions (eds. Clokie, M. R. J. & Kropinski, A. M.) 69-76 (Humana Press, 2009). doi:10.1007/978-1-60327-164-6_7. Bacteria from overnight cultures were mixed with MMB agar (LB+0.1 mM MnCl2+5 mM MgCl2+5 mM CaCl2)+0.5% agar), and serial dilutions of phage lysate in MMB agar were dropped on top of them. After the drops dried up, plates were incubated overnight at room temperature for *B. subtilis* phages and for *E. coli* phages SECphi6, SECphi17, SECphi18, SECphi27, SECphi32, and T7, or at 37° C. for *E. coli* phages P1, T2, T4, T5, T6, λvir, Qbeta, M13, Fd, and MS2. Efficiency of plating (EOP) was measured by performing small drop plaque assay with the same phage lysate on control and induced bacteria, and comparing the ratio of plaque formation.

Liquid Infection Assays

Bacteria were grown for one hour at 37° C. Inducer (arabinose or IPTG) was added and cells were incubated one hour at room temperature. Cells were infected with phages within 96-well plates. OD was monitored using Tecan Plate reader.

Example 2—Sequence Homology-Based Discovery of Prokaryotic Homologs of Viperins Search for Viperin Homologs in Prokaryotic Genomes The human viperin protein sequence (NCBI accession NP_542388.2 (SEQ ID NO: 2)) was used as a seed for a MMseqs search (v6-f5a1c, default parameters, 3 iterations) on the IMG database (https://img.jgi.doe.gov/downloaded October 2017, 38183 genomes). MMseqs (Many-against-Many sequence searching) is a software suite for fast and deep clustering and searching of large datasets. MMseqs is open-source software available at https://github.com/soedinglab/MMseqs. The search yielded 2150 hits, that show between 25%-41% sequence identity to the human viperin. Genes with an e-value higher than $10^{-5}$ were discarded, leaving 1724 genes. This dataset was clustered using MMseqs (v6-f5a1c, default parameter, coverage 60%, sensitivity 7.5) and redundancy was removed resulting in 17 clusters, among which 5 clusters had more than 10 genes (Table 1). For each cluster, defense scores were computed as described in Doron, S. et al. Systematic discovery of antiphage pVips in the microbial pangenome. Science (80). 4120, eaar4120 (2018).

Some of these bacterial and archaeal genes distantly homologous to the human viperin may function in anti-phage activities in prokaryotes. However, it was not trivial to predict which of these homologs is indeed an anti-phage gene. In prokaryotes, genes involved in anti-viral function co-localize on the genome forming "defense islands". Enrichment next to known defense genes can be a predictor that this group of genes performs anti-viral functions. Briefly, neighborhood of the selected gene (+/−10 genes) was screened for known defense genes. A first score corresponds to the proportion of genes in the cluster which exhibit at least one defense gene in its neighborhood. A second score corresponds to the average number of defense genes found in the neighborhood of the genes of the cluster. Only one of viperin-homolog clusters obtained showed high propensity for being enriched next to known defense systems (Table 7). Manual examination of the genomic context of genes of this cluster confirmed the presence of many known anti-phage defense genes in its vicinity (FIG. 1). This cluster (of 134 genes) showed high defense scores (0.602 and 1.687 respectively), and was selected for further analysis. Given that the online IMG database is constantly growing (31242 additional genomes since the download on October 2017), additional candidate prokaryotic viperin homologs (pVips) were searched manually using the "top IMG homologs" function in IMG. This added 84 genes to the cluster. Finally, a MMseqs search using genes of this cluster as seeds was performed on a metagenomes database (downloaded from IMG in October 2017, comprising 9769 metagenomes altogether, scaffolds with less than 21 genes were removed). Hits were filtered to cover at least 200a and hit at least 20 target genes from the pVip cluster. This added 163 genes, resulting in a total of 381 pVips (Table 3 and Table 5).

Table 9 below shows clusters (sized at least 10 genes) of hits of homologs search. The first column indicates the number of genes in the cluster. Second and third columns show defense scores (proportion of genes in the cluster with known anti-phage defense genes in their vicinity; average number of known defense genes in neighborhood).

TABLE 9

Clusters of genes retrieved in the homology-based search

| | Number of genes | Proportion of genes with defensive neighborhood (score 1) | Average number of Defense Genes in neighborhood (score 2) |
|---|---|---|---|
| Cluster 1 | 855 | 0.061 | 0.094 |
| Cluster 2 | 134 | 0.602 | 1.687 |
| Cluster 3 | 54 | 0.2 | 0.32 |
| Cluster 4 | 21 | 0.077 | 0.077 |
| Cluster 5 | 17 | 0.077 | 0.077 |

Example 3—Diversity of pVips

Figure 2:
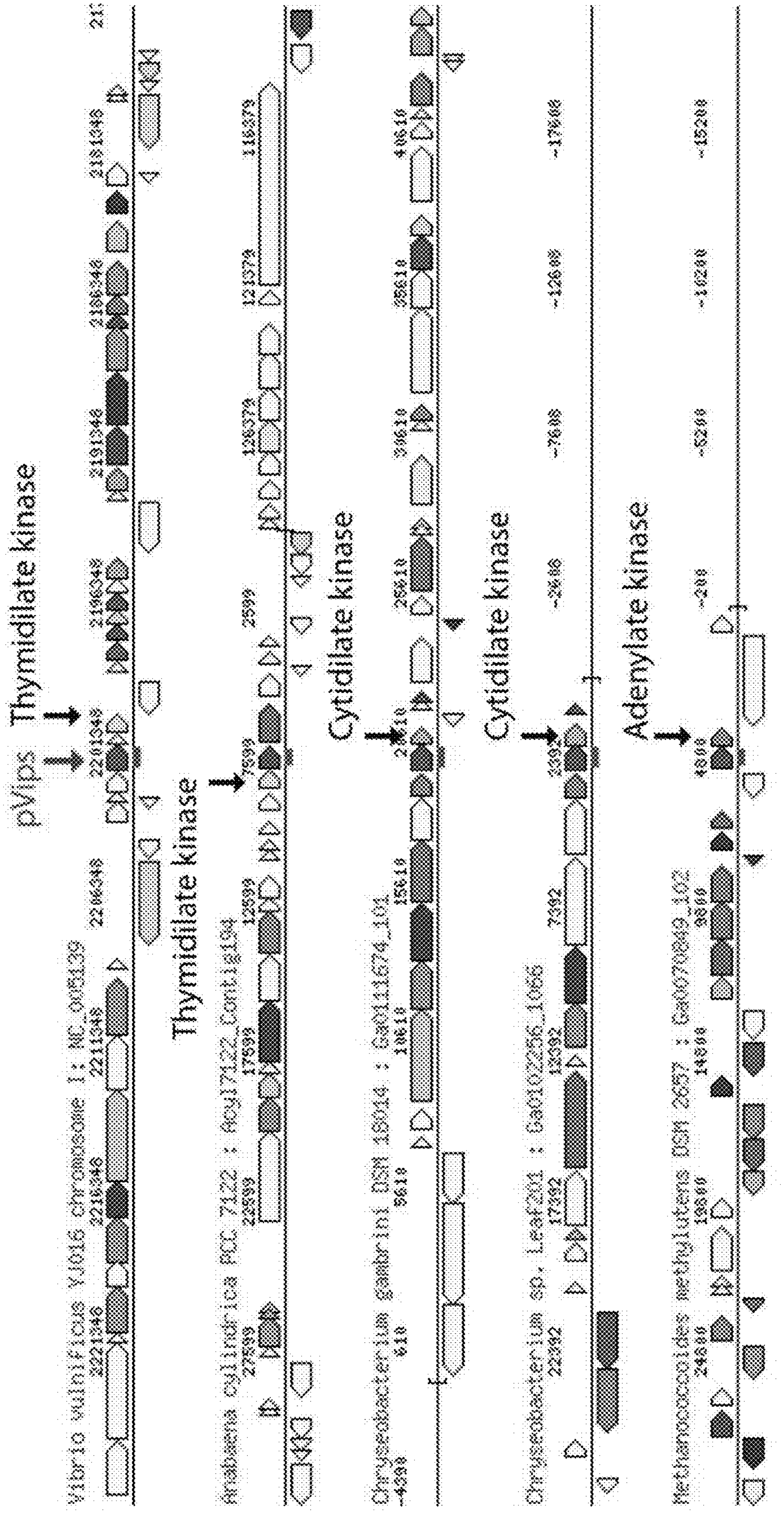
FIG. 2 shows an embodiment of the genomic neighborhood of pVip genes. The presence of diverse kinases, predicted to supply nucleotide substrates to the pVip, is observed in the neighborhood of pVip genes. pVip genes are represented in red. Black arrows point at genes annotated as nucleotide kinases.

Examination of the genomic context of pVips revealed the presence of nucleoside kinases or nucleotide kinases in their vicinity, an observation reminiscent of the organization of the human system, in which viperin is located close to CMPK2 (FIG. 2). In vertebrates, CMPK2 phosphorylates cytidine monophosphate (CMP) to generate cytidine triphosphate (CTP), which is the viperin substrate that is converted by the viperin to ddhCTP. The adjacent kinases might therefore be indicative of the potential substrate of the nearby viperin. In total, 15% of the pVips encode a kinase in their neighborhood. Some pVip-associated kinases are annotated as cytidylate kinase pointing at a potentially identical substrate as CMPK2, namely that the substrate of these pVips is predicted to be CTP. However, many other pVips are found next to nucleoside kinases or nucleotide kinases annotated as thymidylate, guanylate or adenylate kinases (FIG. 2). This suggests that the substrate of some pVips may be nucleotides other than CTP, and that they can thus generate new chain terminators that were not described previously. For example, pVips found next to thymidylate or guanylate kinases may generate ddhUTP or ddhGTP or derivatives thereof. Moreover, some of these kinases are annotated as kinases of deoxy-nucleosides or deoxy-nucleotides, namely the DNA form of the nucleoside or nucleotide rather than the RNA form that is modified by the eukaryotic viperins. In this case, the relevant pVips can generate deoxy form of ddh nucleosides or nucleotides, leading to new DNA chain terminator molecules rather than RNA chain terminator molecules.

Figure 3A:
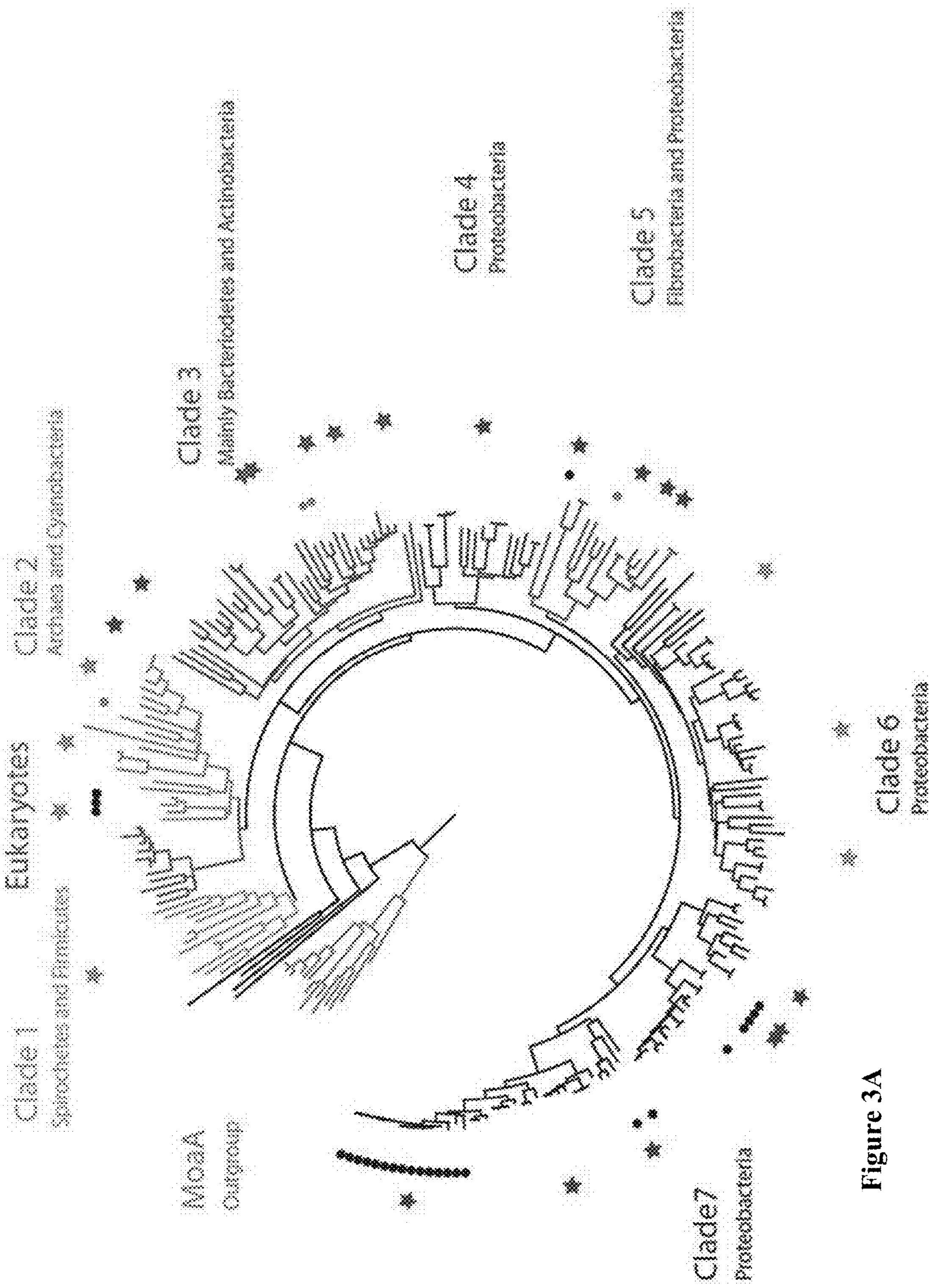
FIGS. 3A-3B show phylogenetic trees of pVip genes.

The sequences of pVips are highly diverse with on average 37% identity at the protein level when compared to one another. pVips were found in 94 genera of diverse phyla including Euryarchaeota, Proteobacteria, Firmicutes, and Bacteriodetes. To better understand this diversity and phylogenetic relationship with eukaryotic viperins, a phylogenetic tree of the protein family was built (FIG. 3A).

The Molybdenum cofactor biosynthesis protein (MoaA) is known to be a structural homolog of Viperin, but MoaA does not participate in defense against viruses and does not generate antiviral chain terminator nucleotide analogs (Santamaria-Araujo J A et al. (2004) J Biol Chem. 279(16): 15994-9; Fenwick M K et al. (2017) Proc Natl Acad Sci USA. 114(26):6806-6811). Hence, the MoaA gene can be used as an outgroup for phylogenetic analyses. Eukaryotic sequences of viperins were chosen to represent a diversity of species for the tree building and are provided in attached files. Prokaryotic viperins, eukaryotic viperins and MoaA sequences were aligned using mafft (v7.402, default parameters). The tree was computed with IQ-TREE multicore v.1.6.5 under model LG+I+G4. This model gave the lowest Bayesian Information Criterion (BIC) among all models available for both trees (option -m TEST in IQ-TREE). 1000 ultra-fast bootstraps were made in order to evaluate node support (options -bb 1000 -wbtl in IQ-TREE). Phylogenetic trees figures were designed using ITOL.

It was found that pVips are grouped in 7 major clades (FIG. 3A) that partly correspond to major prokaryotic phyla. For example, clade 2 encompasses many archaeand cyanobacteria versions while clades 5, 6, 7 mainly encode pVips from Proteobacteria. Interestingly, all eukaryotic viperins are found in one clade within the tree, with a closest common ancestor with pVips from clade 2. This specific place of eukaryotic viperins in the pVip tree suggests that the evolutionary origin of all eukaryotic viperins was a pVip from clade 2. This also means that pVips encode higher diversity than eukaryotic viperins, suggesting again that pVips would produce a variety of polynucleotide chain terminators other than ddhCTP. While some clades encode exclusively one type of kinases, like clade 7 (thymidylate kinases) some encode diverse kinases like clade 5 (both thymidylate and adenylate) (FIG. 3A).

Figure 3B:
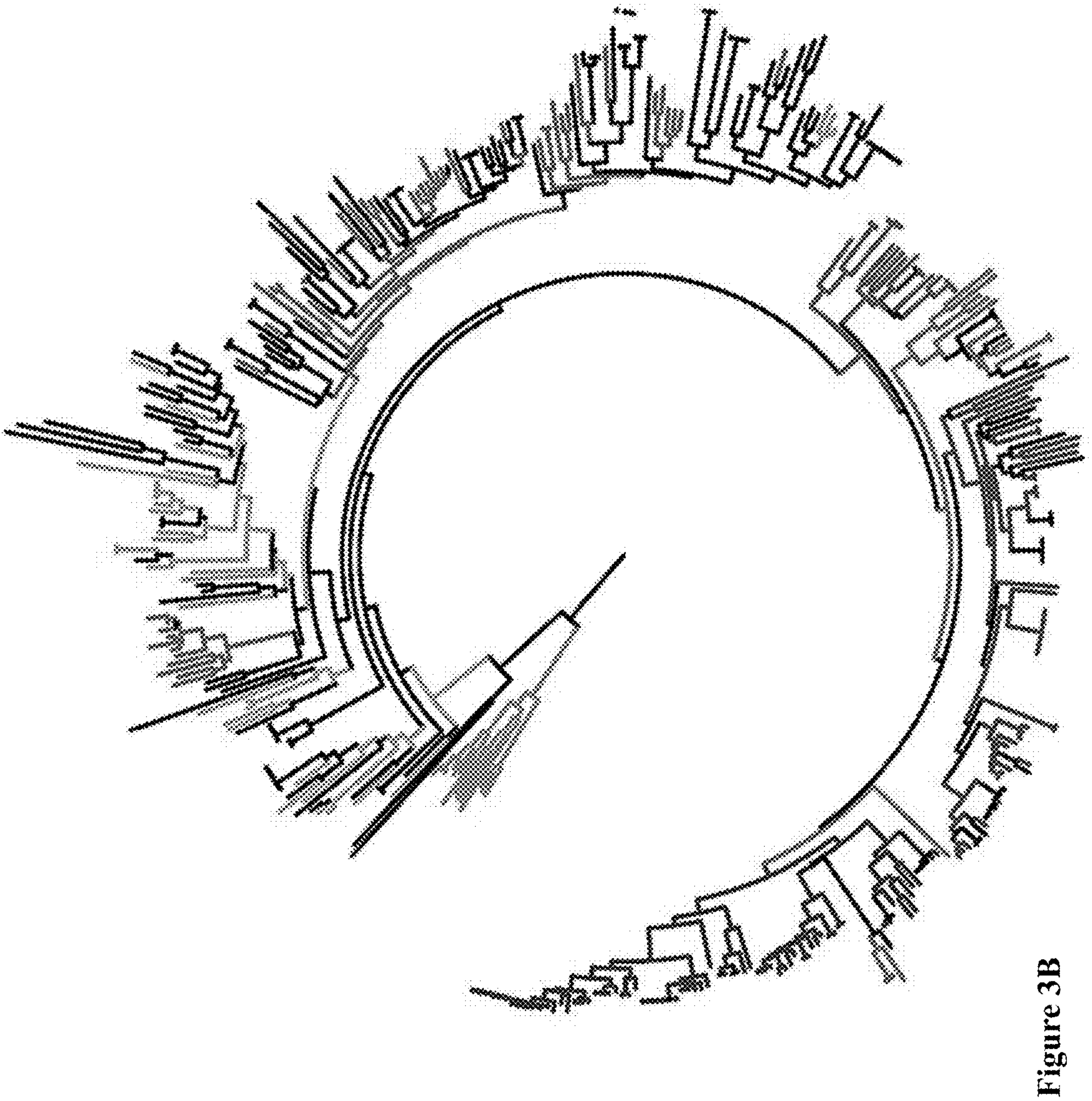

To fully capture the diversity of this protein family, homologs search was extended to metagenomes. Sequences from the initial cluster were used as a seed for a MMseqs search on a database of 9769 metagenomes that were downloaded from IMG in October 2017 as described in Example 2. This search added, after filtering (coverage of at least 200a and hit at least 20 target genes from the pVips cluster), 163 sequences to the pVips dataset yielding 381 homologs in total. These additional 163 pVips identified within metagenomes also had a high propensity to be found next to known defense genes (85 of the 163, 52%), suggesting that these set of genes also functions in antiviral defense. A second phylogenetic tree was built that includes the pVips from isolate genomes as well as these 163 additional genes (FIG. 3B). Sequences found in metagenomes do not change the topology of the initial tree, with still seven major clades and eukaryotic viperins being embedded in one of the prokaryotic clades. These observations suggest that the dataset of 381 pVips is representative of the diversity of the protein family.

Altogether, these results indicate the existence of a diverse family of pVips. While quite rare among microbial genomes, they are present in phylogenetically very distant organisms suggesting an ancient evolutionary origin. Their genomic context is indicative of a potential anti-viral activity. Presence of nearby nucleoside kinases or nucleotide kinases with diverse predicted substrates suggest a diversity of substrates and subsequently of products generated by the pVips which are predicted to be other than the known ddhCTP produced by the eukaryotic viperins.

Example 4—pVips Provide Anti-Viral Activity In Vivo

Figure 4:
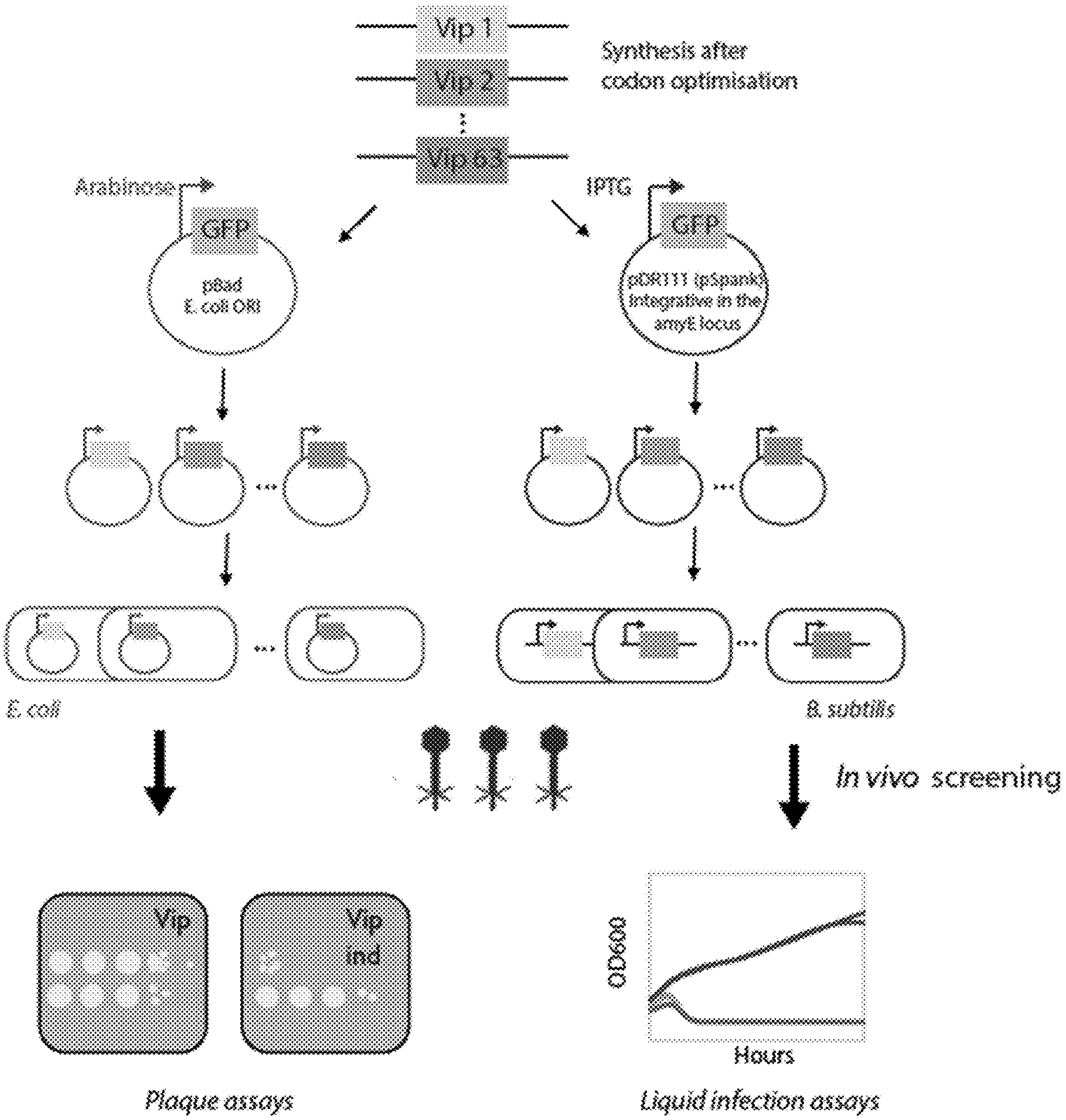
FIG. 4 shows the experimental approach used for functional validation of pVips. pVip gene candidates were synthetized and cloned in two different vectors under inducible promoters. *E. coli* and *B. subtilis* bacteria were transfected with these vectors and then tested for viral resistance against a collection of phages. Anti-viral activity of pVips was assessed in two types of assays: solid plaque assays and liquid infection assays.
Figure 5A:
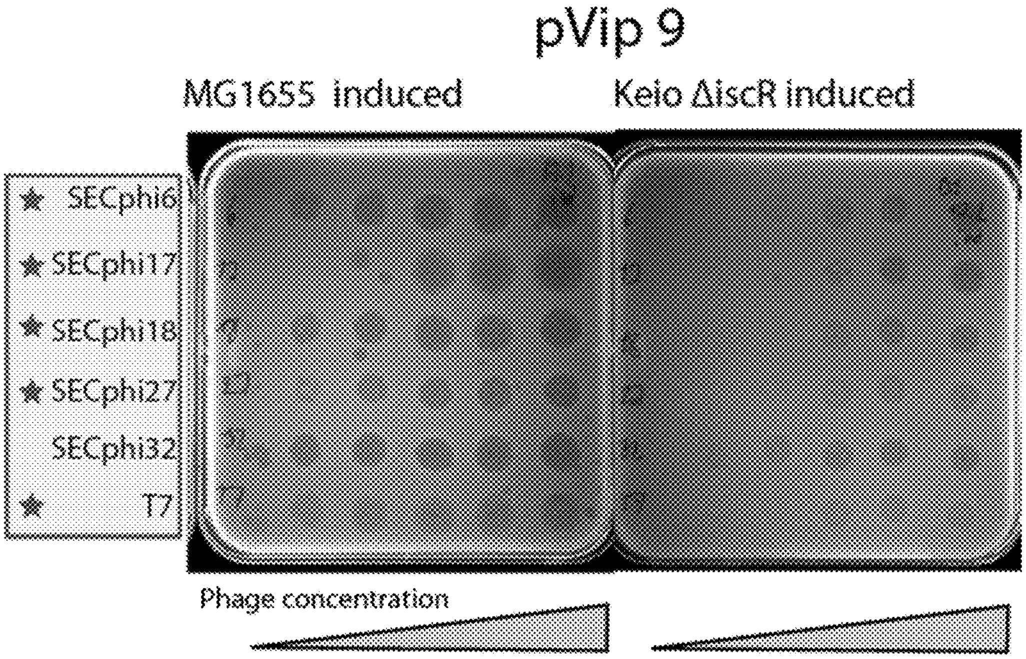
FIGS. 5A-5B show that a strain with a knockout in the iscR gene (Keio ΔiscR) rescues pVips activity in vivo.
Figure 5B:
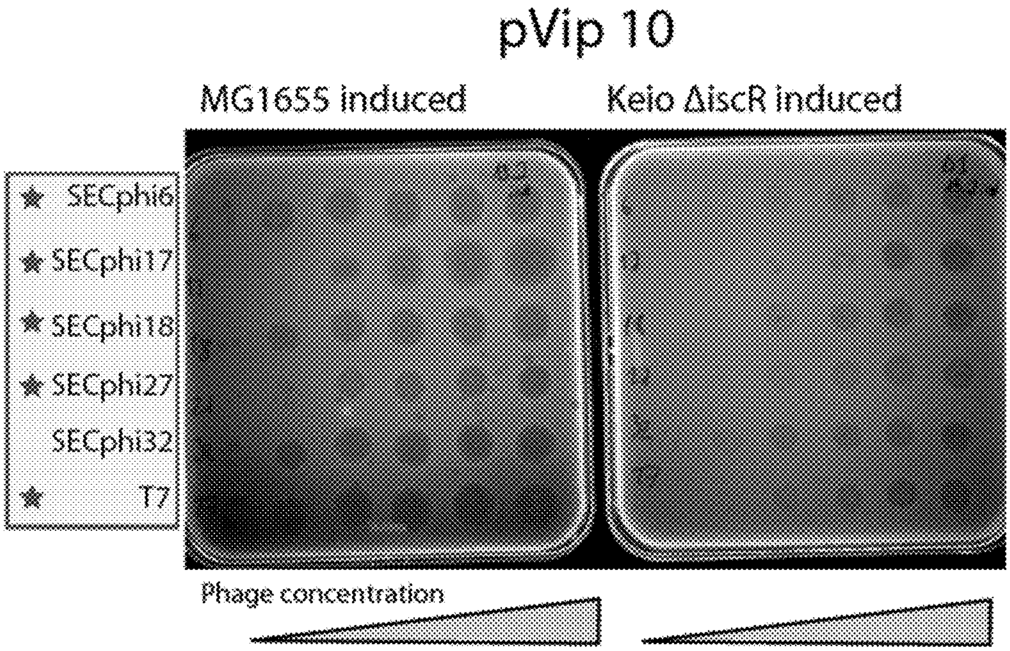
Figure 6A:
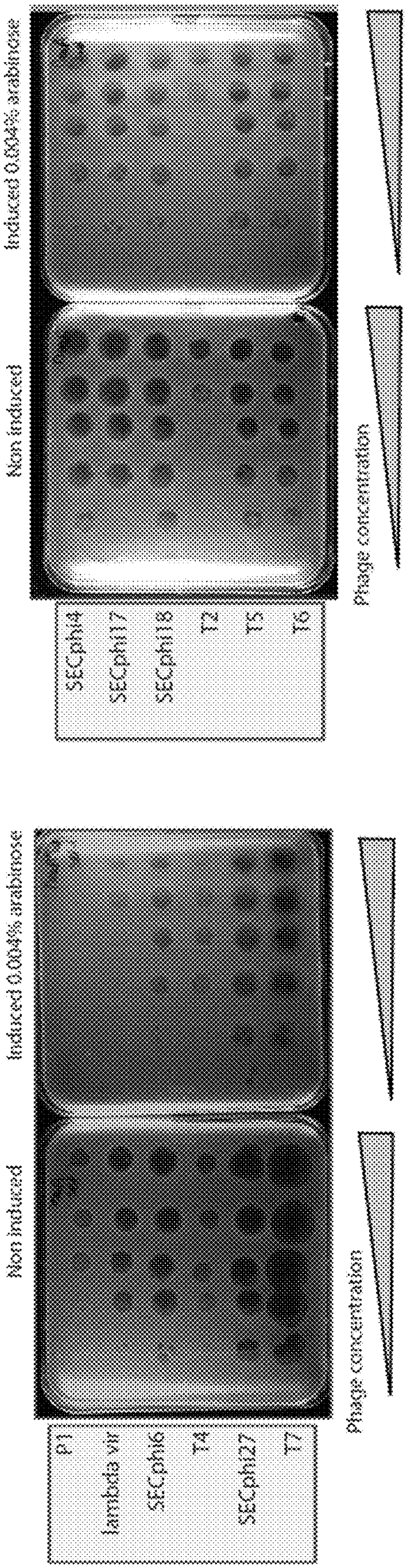
FIGS. 6A-6Z show plaque assays of multiple pVips cloned and expressed in Keio ΔiscR colonies indicating in vivo anti-viral activity of the pVips. Shown are plaque assays in which pVip expression was either non induced or induced by adding 0.004% arabinose, as indicated. Colonies were challenged with the following phages: P1, lambda vir, SECPhi6, T4, SECPhi27, T7, SECPhi4, SECPhi17, SECPhi18, T2, T5, and T6 as indicated. Phages were diluted from $10^{-1}$ to $10^{-6}$ of the original stock. Star indicates phages for which activity of pVip was observed.
Figure 6B:
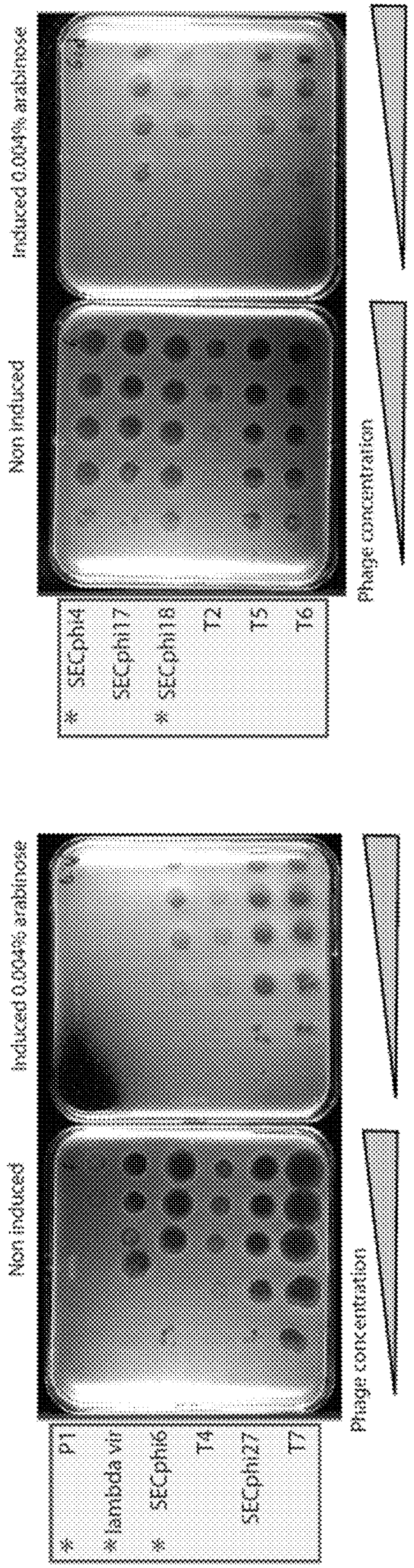
Figure 6C:
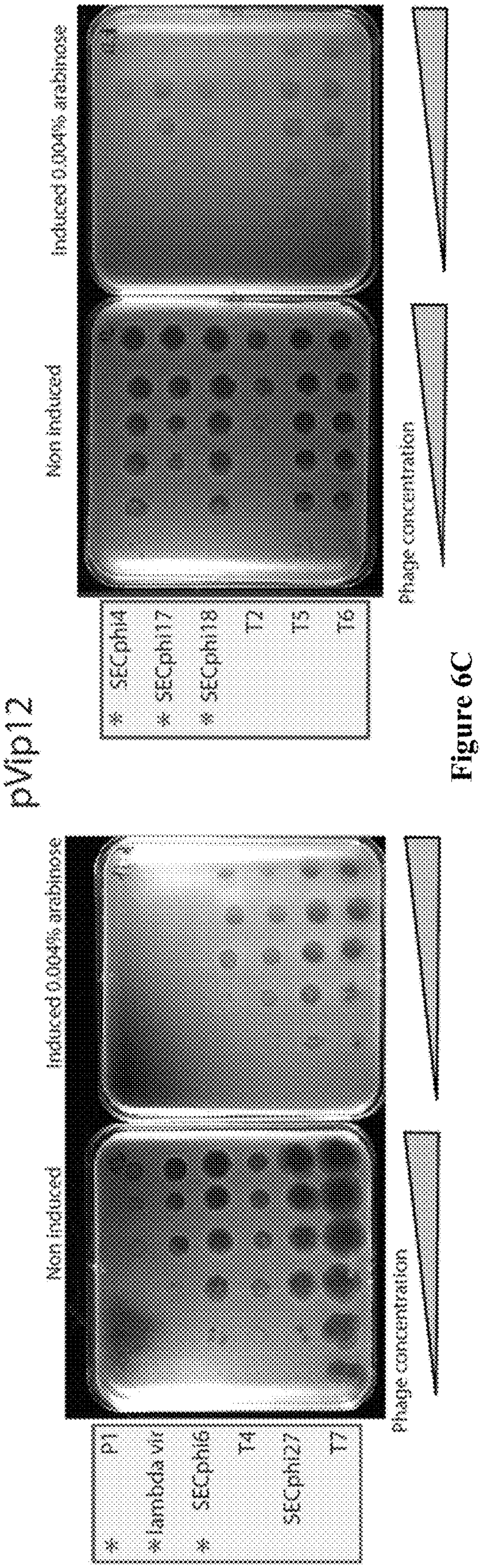
Figure 6D:
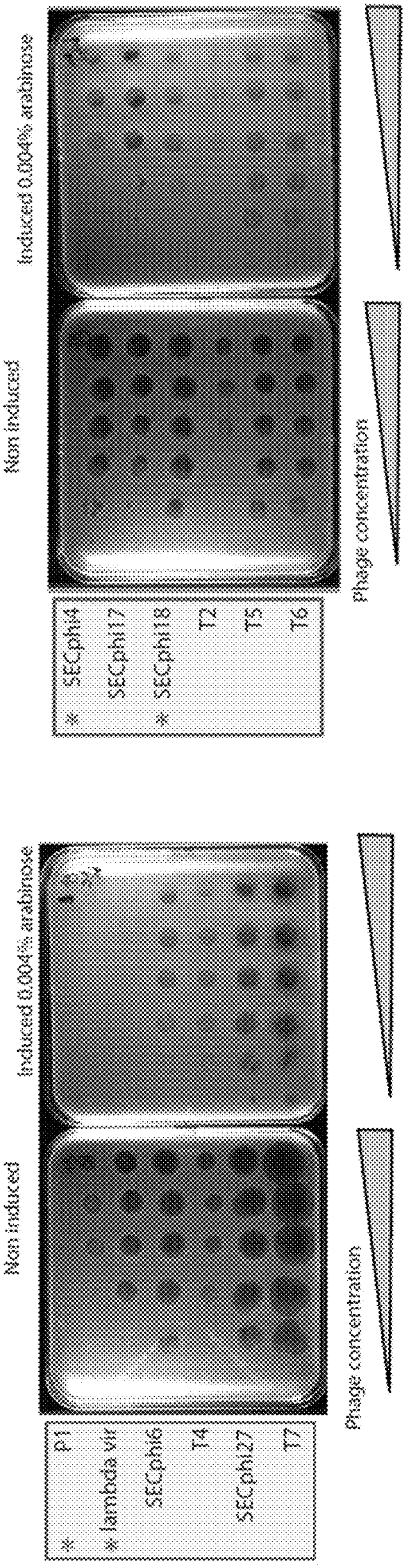
Figure 6E:
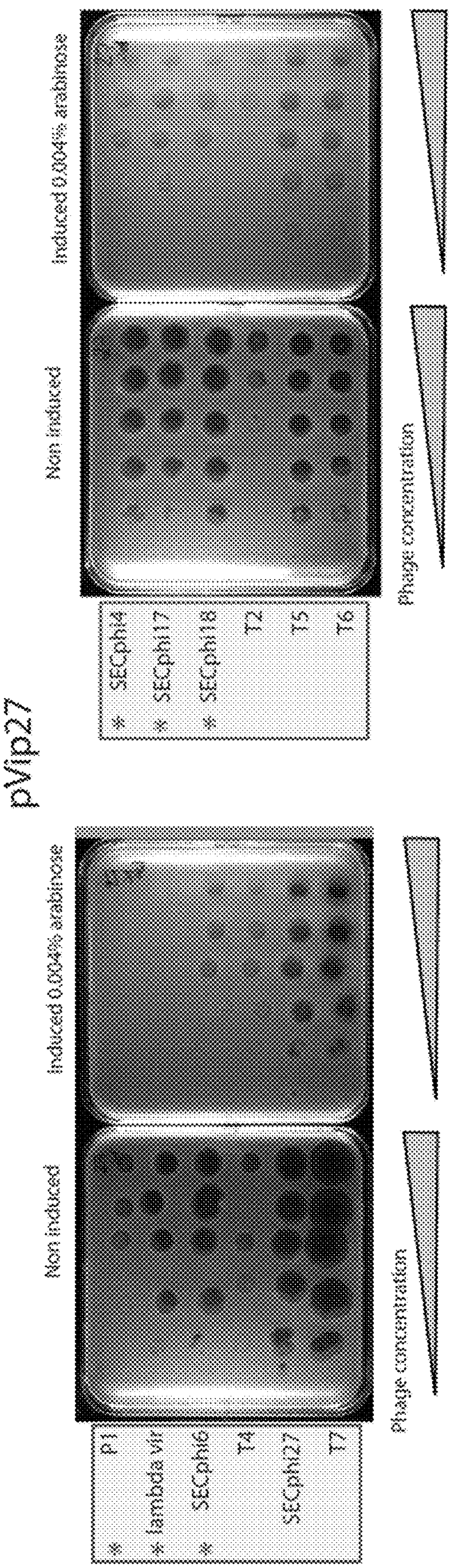
Figure 6F:
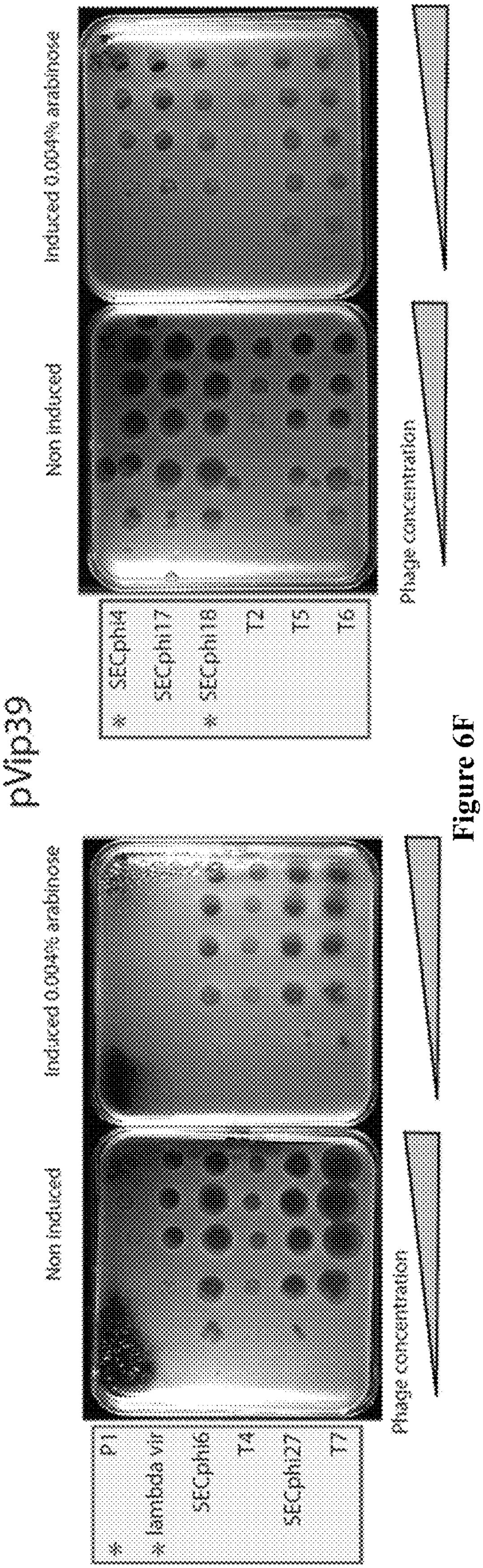
Figure 6G:
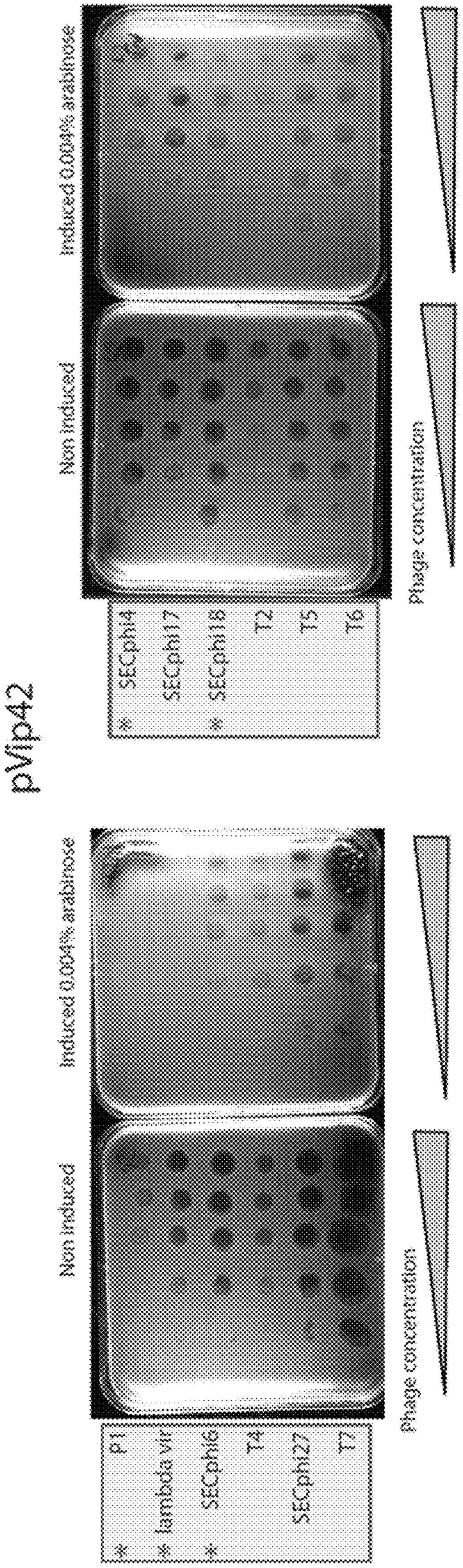
Figure 6H:
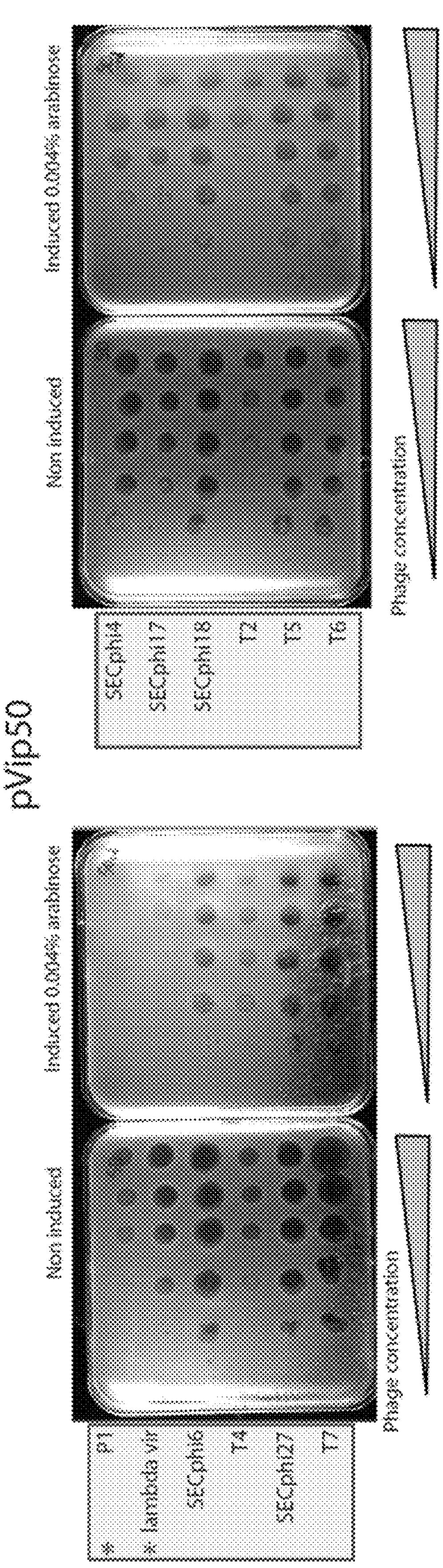
Figure 6I:
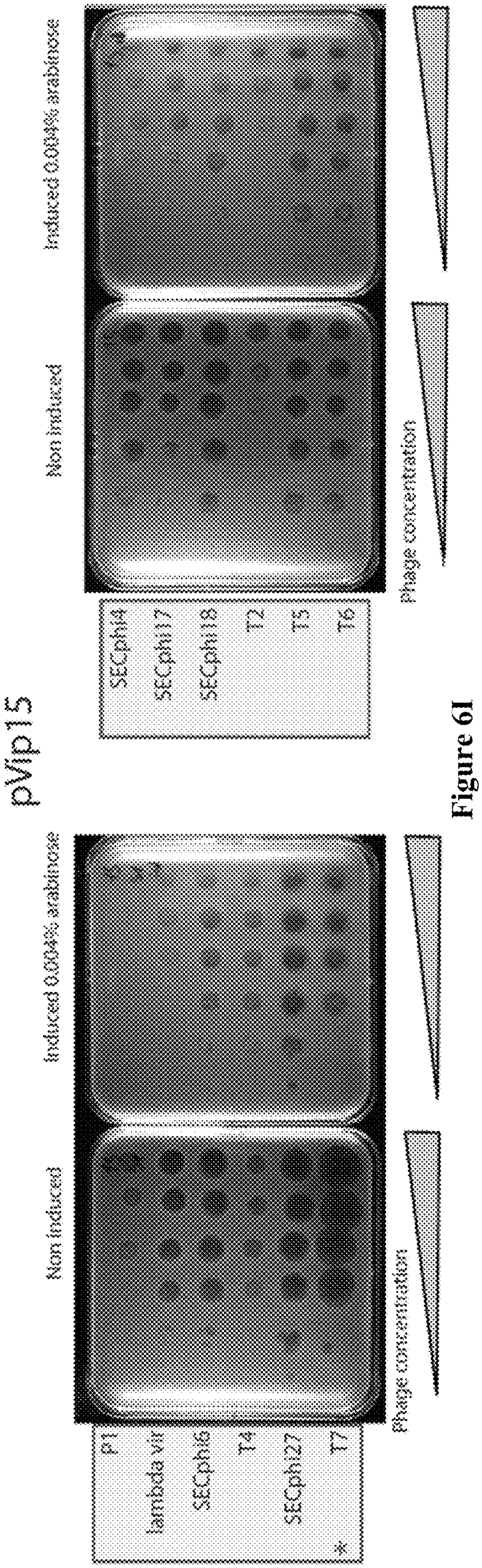
Figure 6J:
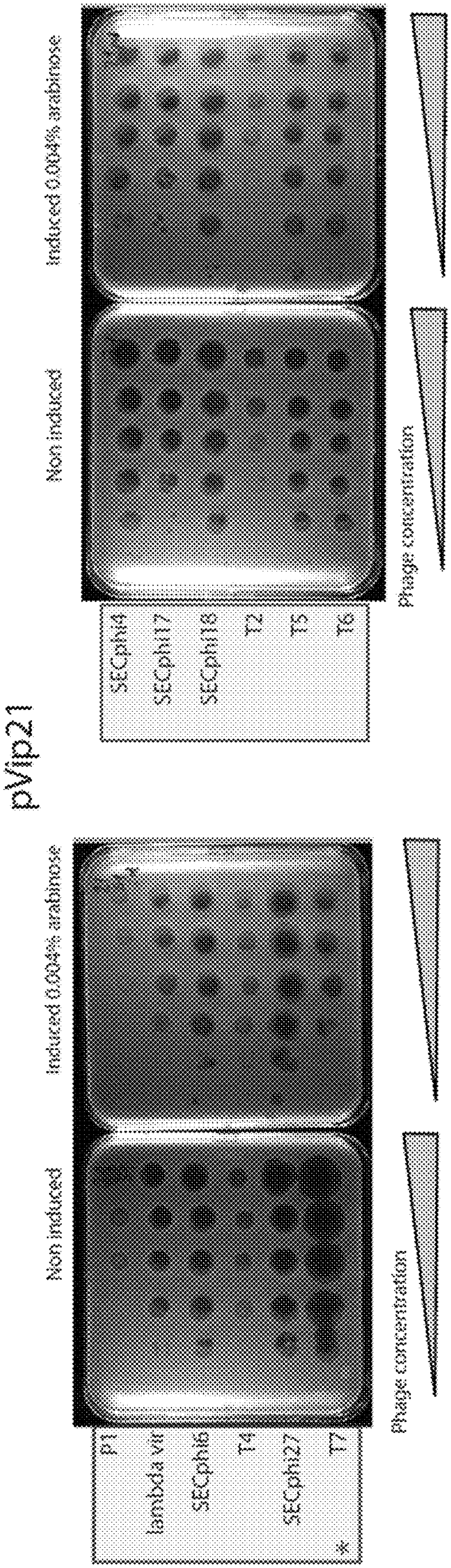
Figure 6K:
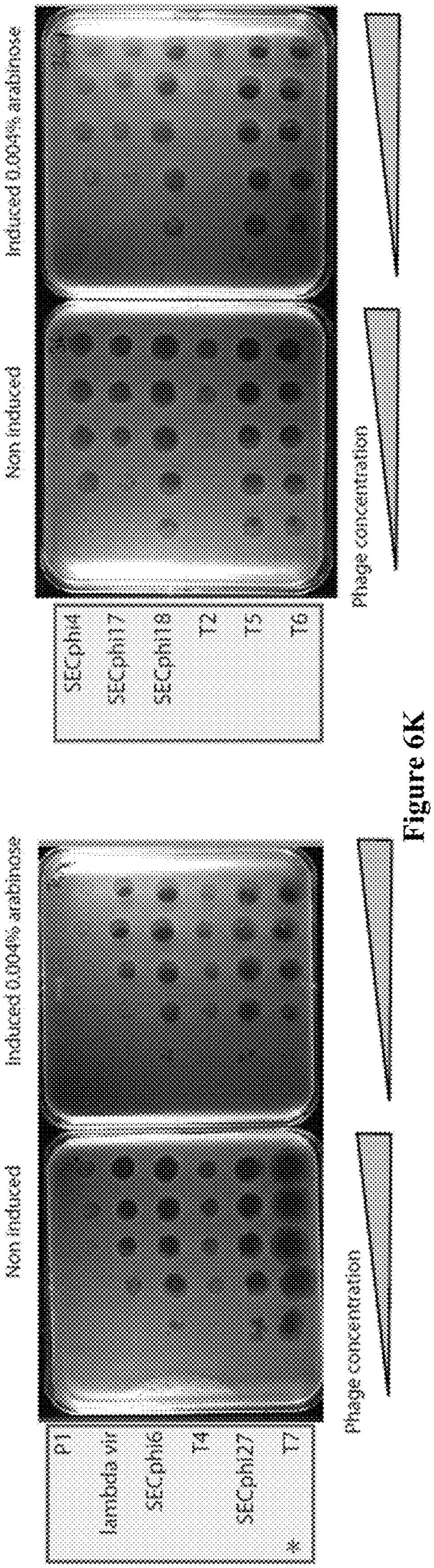
Figure 6L:
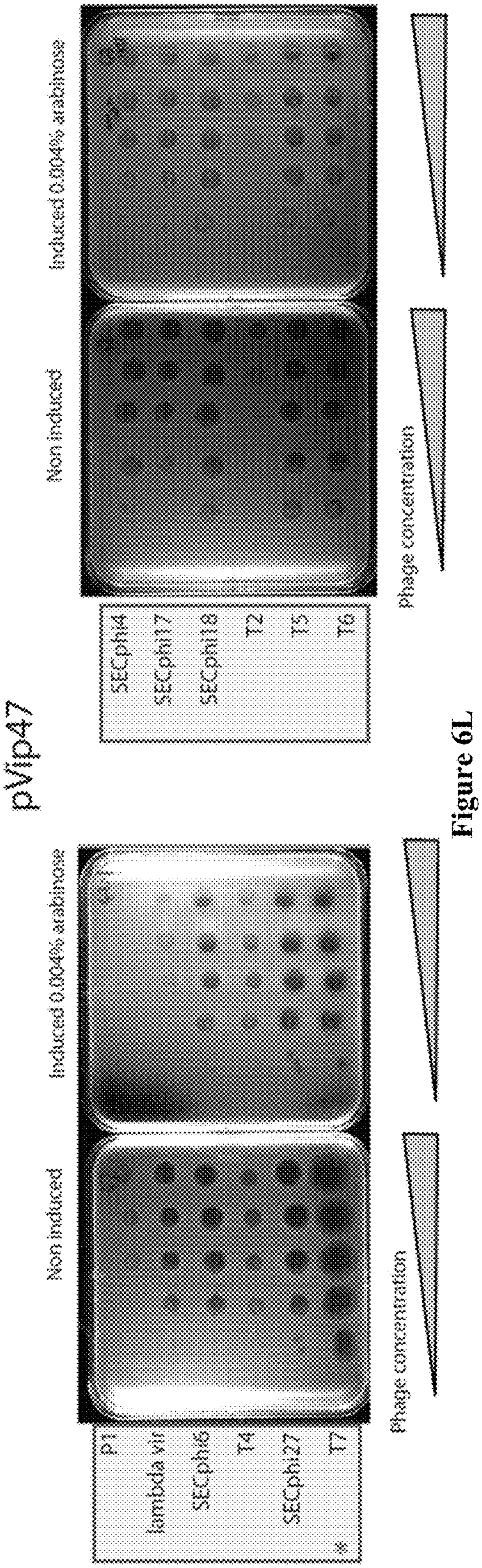
Figure 6M:
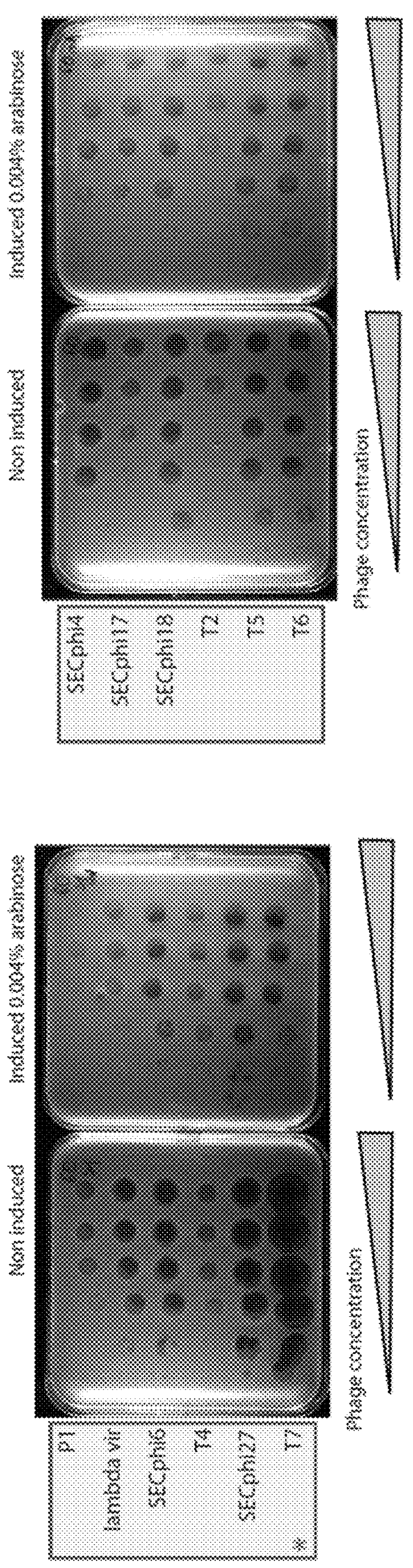
Figure 6N:
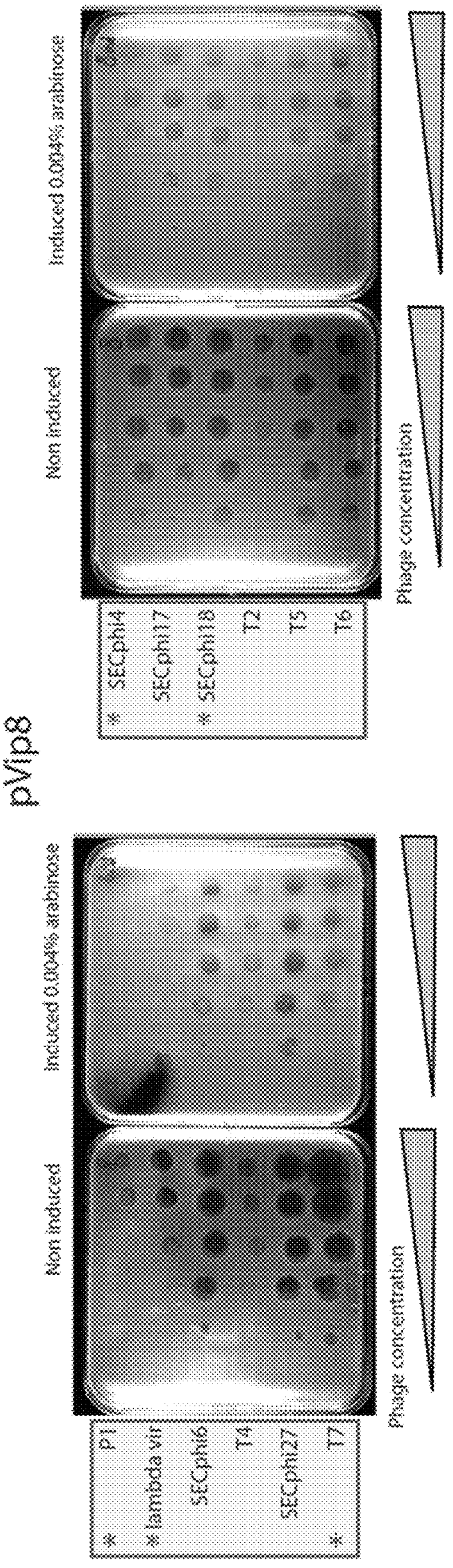
Figure 6O:
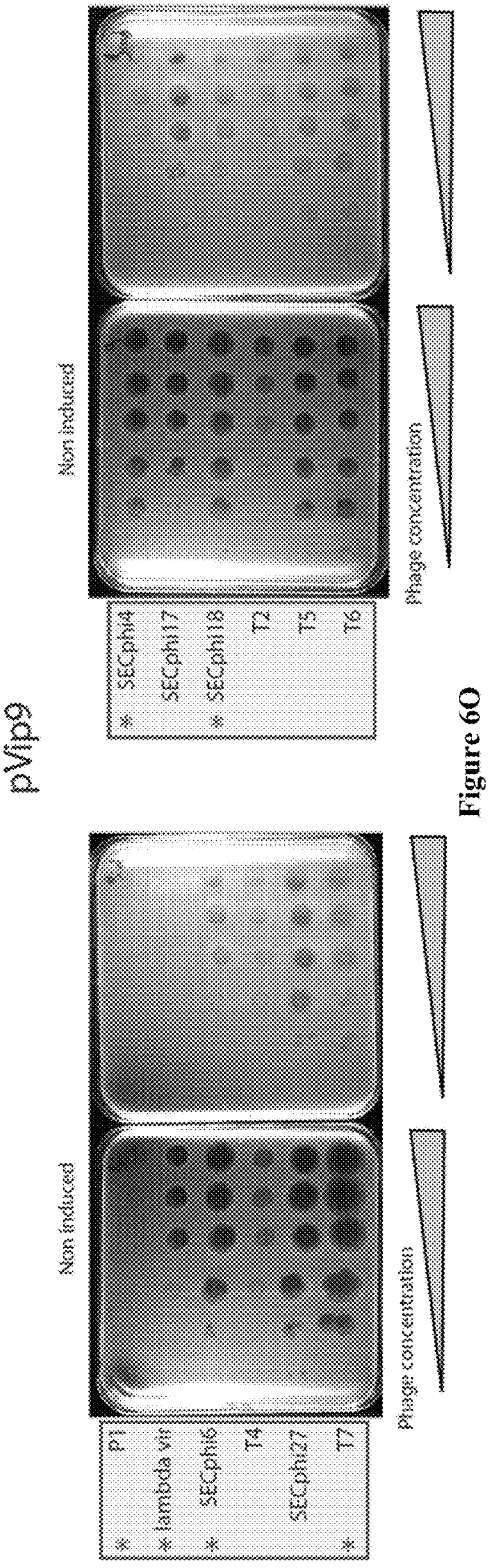
Figure 6P:
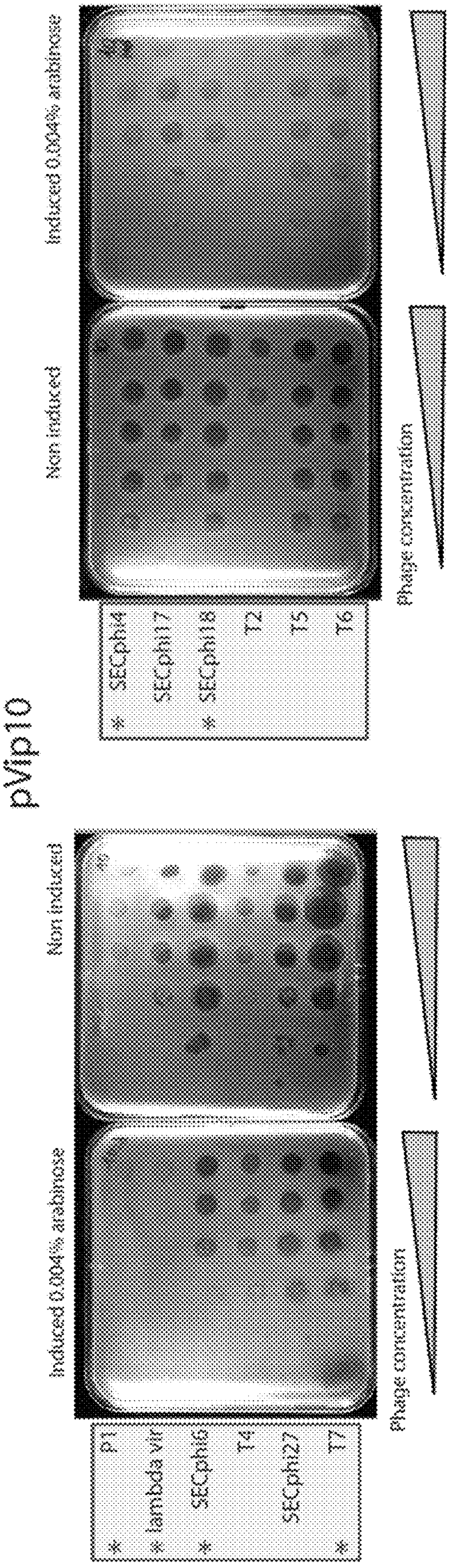
Figure 6Q:
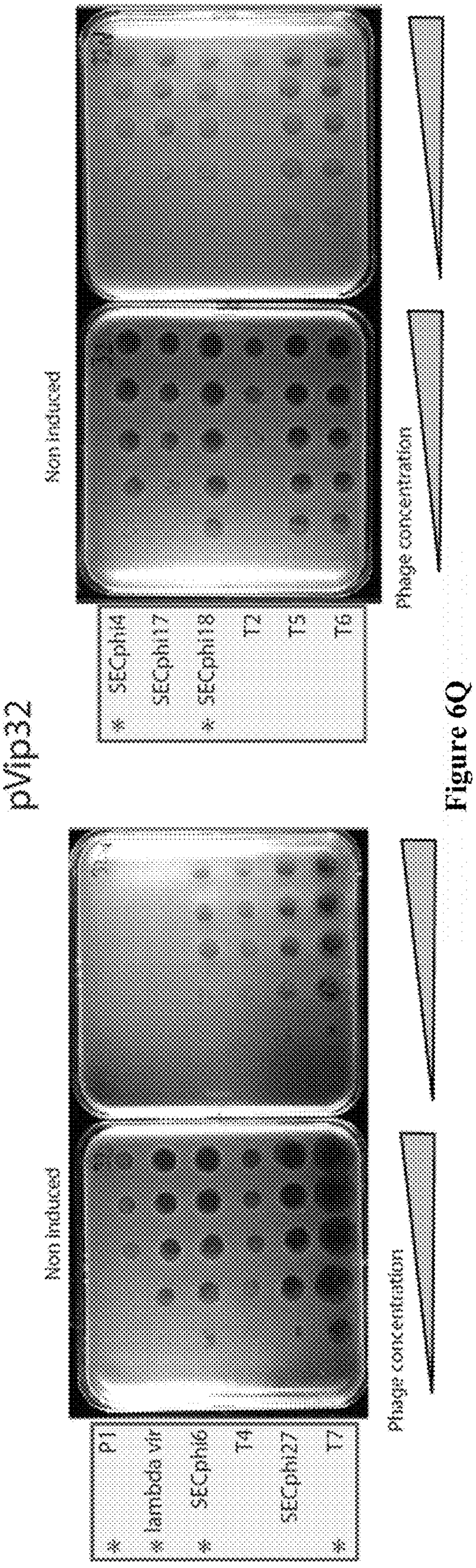
Figure 6R:
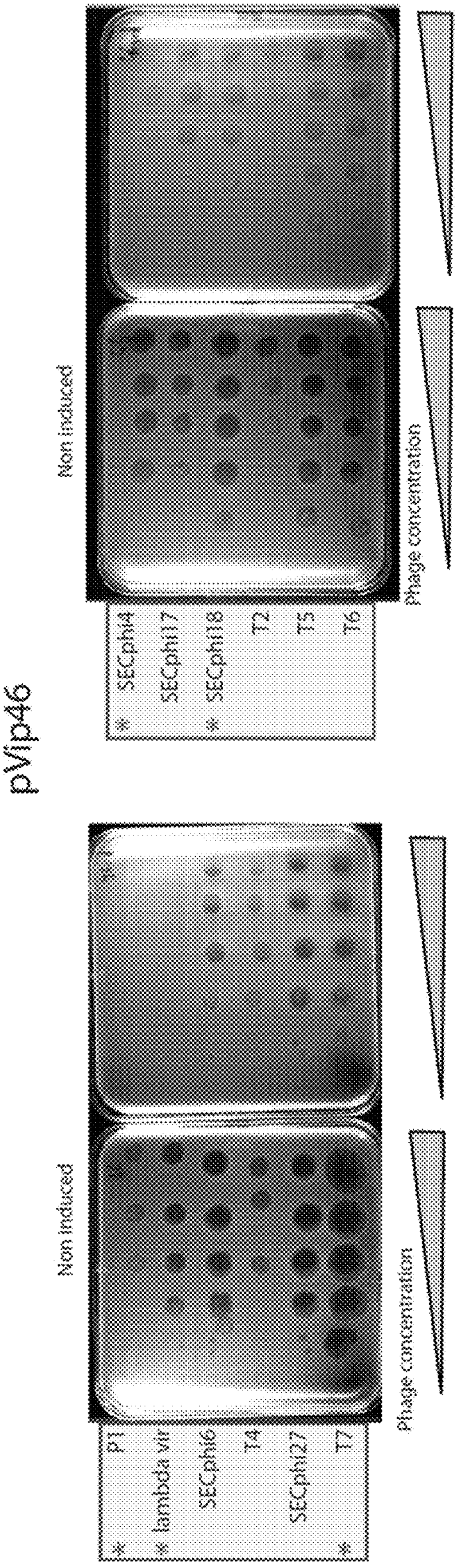
Figure 6S:
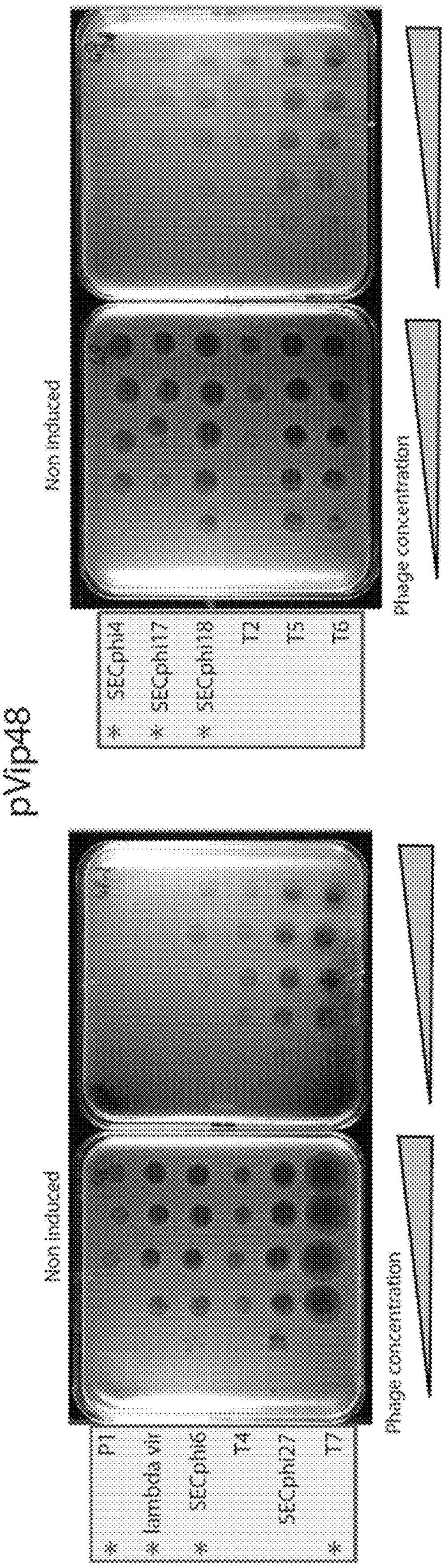
Figure 6T:
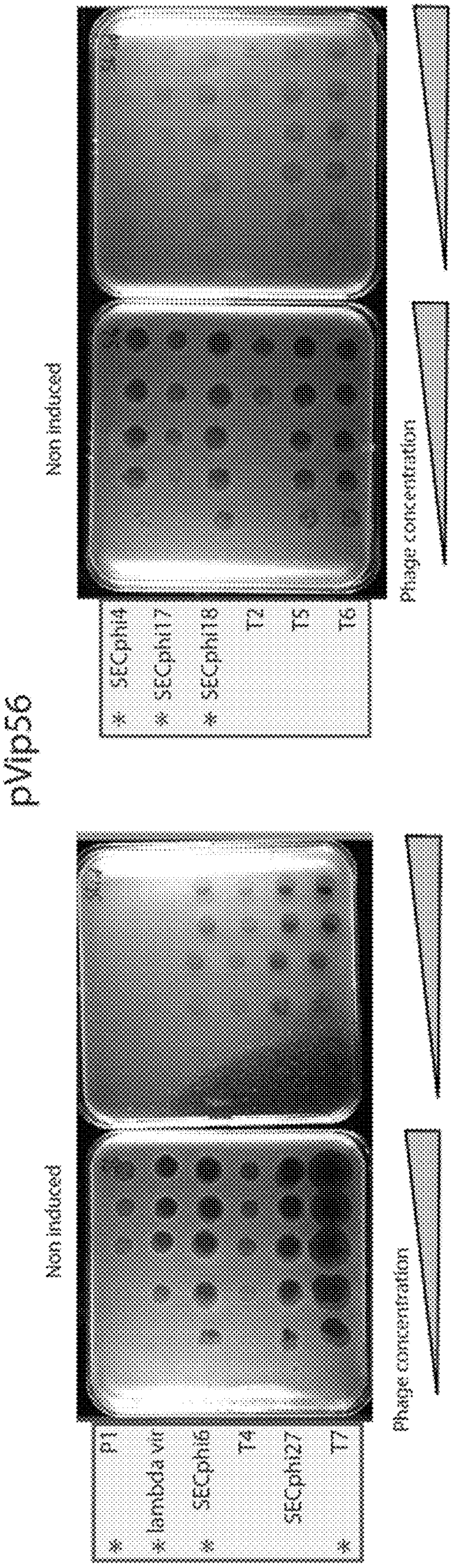
Figure 6U:
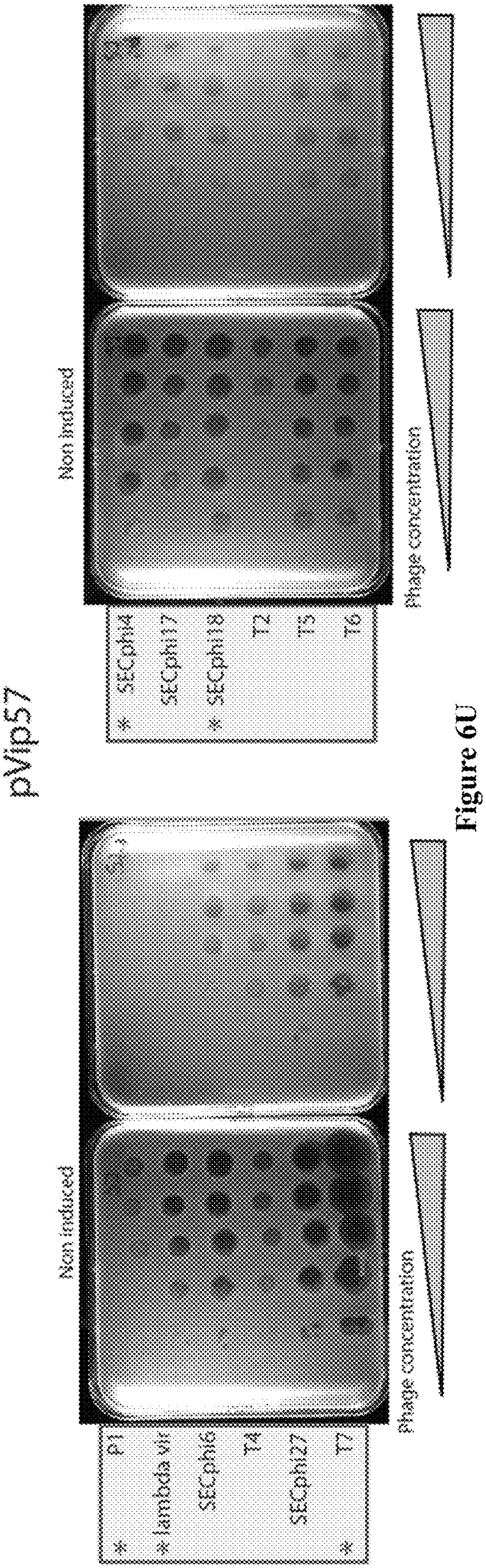
Figure 6V:
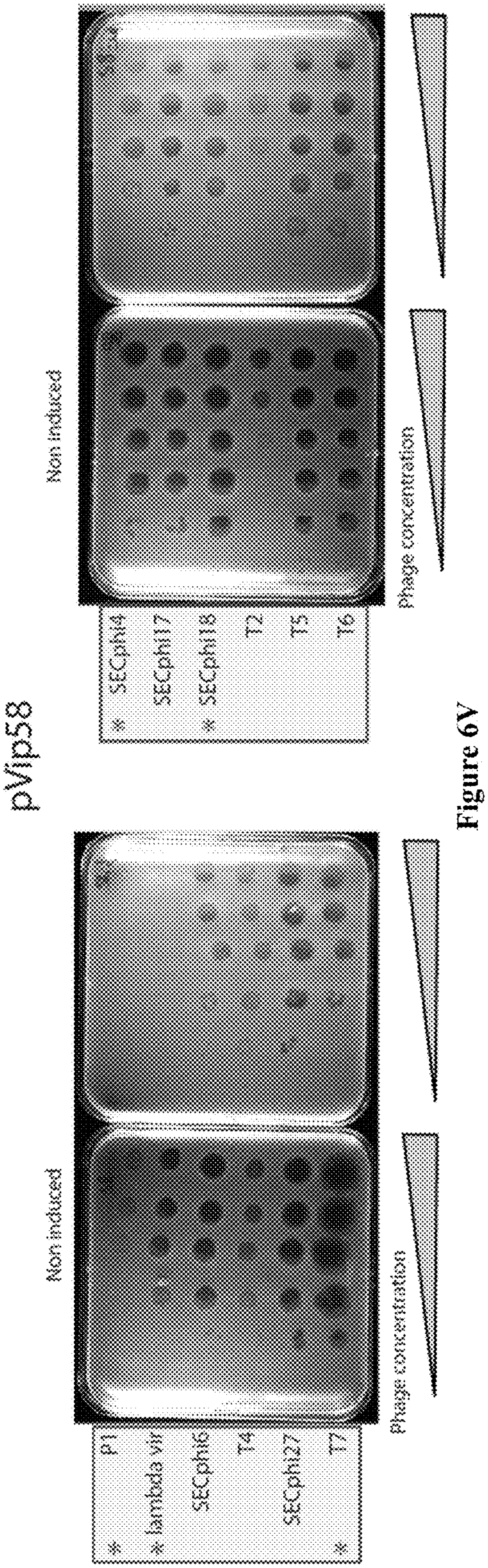
Figure 6W:
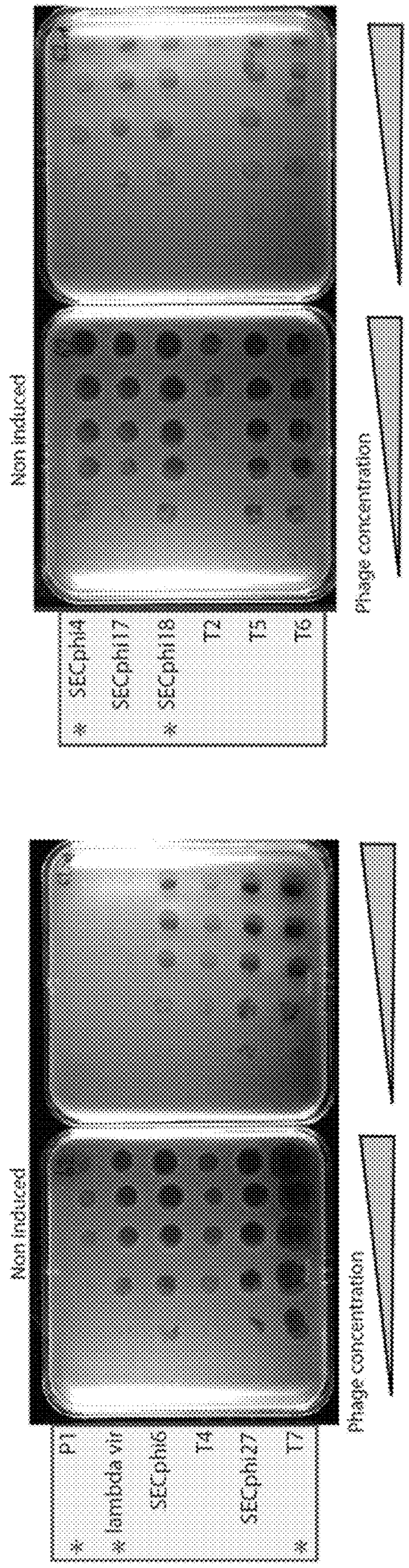
Figure 6X:
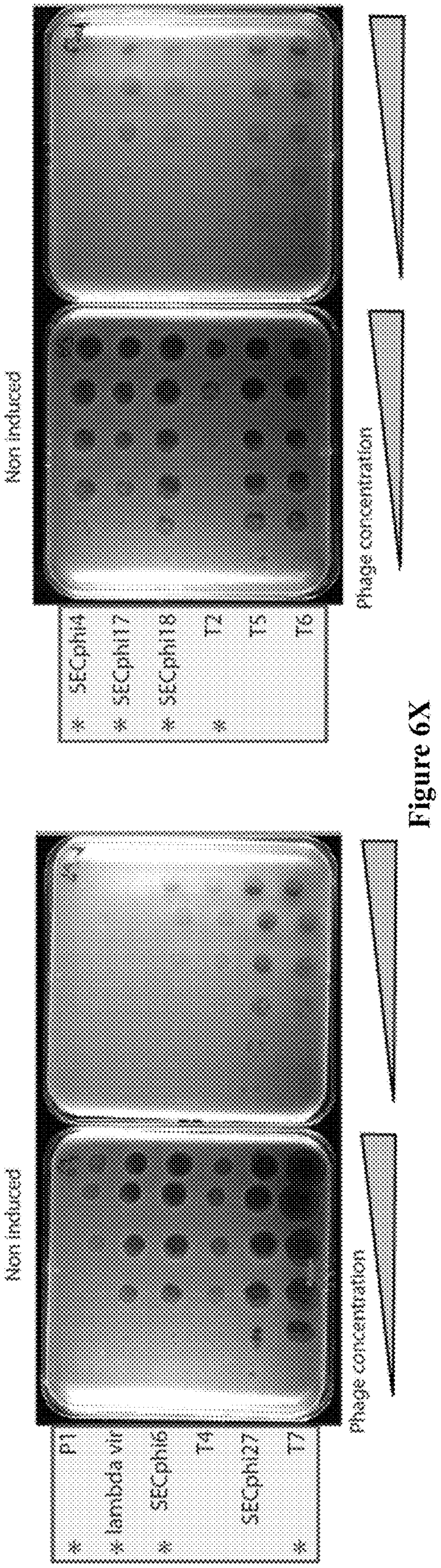
Figure 6Y:
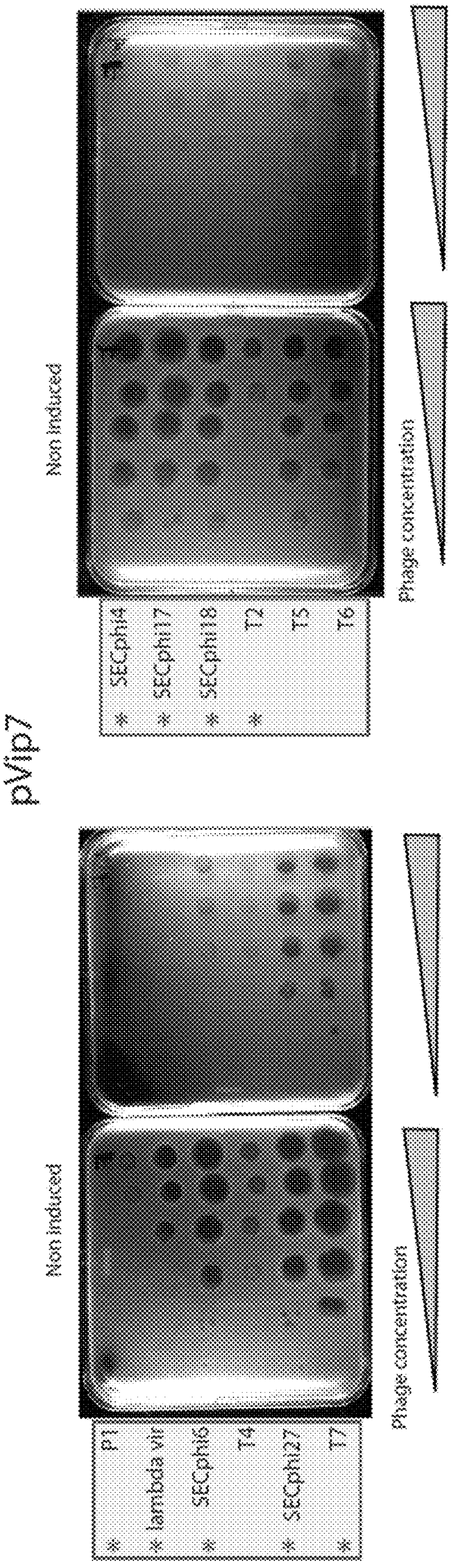
Figure 6Z:
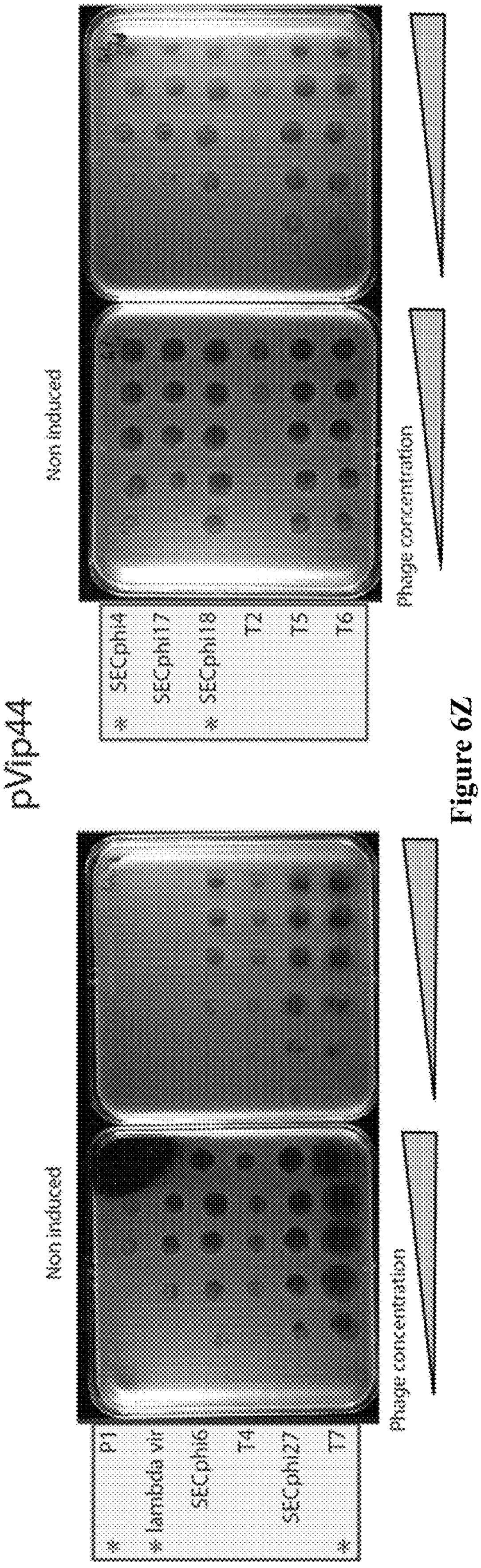

The objective of this study was testing whether prokaryotic homologs of viperins (pVips) provide defense against bacteriophages in vivo. 25 genes that span across the pVip phylogenetic tree were selected to assess activity of diverse representatives of the family. MoaA from *E. coli*, structurally similar to viperins but with a demonstrated function in metabolism and not in antiviral activity, was used as a negative control. The sequences of these genes were codon optimized for expression in lab bacteria (*E. coli*), resulting in the codon-optimized sequences presented in (SEQ ID NOs: 384-408), and cloned in vectors for *E. coli* and *B. subtilis* under the control of inducible promoters (pAra for *E. coli*, pHypraspank for *B. subtilis*) to avoid potential toxicity effects (FIG. 4).

pVips, as well as eukaryotic viperins, are Radical-SAM enzymes that contain an iron sulfur cluster 4Fe-4S. For such enzymes, the 4Fe-4S cluster is built by a complex of proteins and then carried into the apoenzyme making it an active holoenzyme. This metabolic step can require some specific interactions between the proteins that build the iron sulfur cluster and the protein that receive it, in this case the pVip. Heterologous expression of iron-sulfur cluster enzymes such as viperins can thus lead to loss of catalytic activity, if the cell in which the viperin is expressed does not express the iron sulfur clusters to high enough levels.

Some of the tested pVip candidates could be inactive in vivo in *E. coli* or in *B. subtilis* because of this limitation. Several strategies have been employed to circumvent this issue for other iron-sulfur cluster proteins, such as the expression of an exogenous set of genes responsible for iron sulfur cluster formation or the endogenous overexpression of the iron sulfur cluster metabolism genes of *E. coli* through deletion of the endogenous repressor of these genes, iscR, in *E. coli*. In the current study we used the second approach, and pVips were cloned into an *E. coli* strain from the Keio collection deleted for iscR. As a control, *E. coli* Keio ΔiscR were transfected with MoaA.

To test if pVips have antiviral activities, their expression (as well as the expression of the MoaA control) was induced with 0.004% arabinose. A reduction in plaque numbers as compared to MoaA control was observed for the 25 pVips including pVip6, pVip7, pVip8, pVip9, pVip10, pVip12, pVip15, pVip19, pVip21, pVip27, pVip32, pVip34, pVip39, pVip42, pVip44, pVip46, pVip47, pVip48, pVip50, pVip56, pVip57, pVip58, pVip60, pVip62, and pVip63 provided defense against phages in the strain Keio ΔiscR (FIGS. 5A and 5B, FIGS. 6A-6Z, Table 4, and Table 10). Phages P1, lambda vir, T7, SecPhi4, SecPhi6, SecPhi17, and SecPhi18 were found susceptible to pVips. At least one viperin from each major clade of the protein family characterized showed activity against phages (FIG. 3A, Table 4 and Table 10). Three main defense phenotypes were observed for the different pVips: strong activity against T7 only (FIGS. 6I-6M), strong activity against P1 and lambda but not T7 (FIGS. 6B-6H) and strong activity against P1, lambdand T7 (FIGS. 6N-6Z). While clades 1, 2 and 6 seem to encode pVips with strong activity against P1 and lambda but not against T7, pVips with strong activity against T7 only are restricted to clade 3, and pVips with strong activity against P1, lambdand T7 are found in clades 3, 4, 5, and 7 (FIG. 3A). Given the homology with the eukaryotic viperins, it was hypothesized that the mechanism of defense involved synthesis of small anti-viral molecules, most probably chain terminators. These different phenotypes against the same phages suggest the existence of several different pVip products. These products could be, for example, nucleotide analogs other than ddhCTP; deoxy versions of ddh nucleotides; or other chain terminator nucleotide analogs.

Table 10 shows candidate pVips that were found to be active in protecting *E. coli* bacteria against phage infection

TABLE 10 pVips found to protect bacteriagainst phage infection

| pVip_number | IMG gene identifier | Genome name | Clade |
|---|---|---|---|
| 6 | 2624749465 | *Selenomonas ruminatium* S137 | 1 |
| 7 | 2739066738 | *Fibrobacter* sp. UWT3 | 5 |
| 8 | 2521798317 | *Psychrobacter lutiphocae* DSM 21542 | 4 |
| 9 | 2574301464 | *Vibrio porteresiae* DSM 19223 | 7 |
| 10 | 2720695169 | *Vibrio vulnificus* ATL 6-1306 | 7 |
| 12 | 2698137626 | *Ruegeria intermedia* DSM 29341 | 6 |
| 15 | 646713396 | *Coraliomargaritakajimensis* DSM 45221 | 3 |
| 19 | 2506475787 | *Methanoplanus limicola* M3, DSM 2279 | 2 |
| 21 | 2515428782 | *Lewinella persica* DSM 23188 | 3 |
| 27 | 2574506394 | *Desulfovibrio senezii* DSM 8436 | 6 |
| 32 | 2609132705 | *Phormidium* sp. OSCR GFM (version 2) | 5 |
| 34 | 2619892213 | Cryomorphaceae bacterium EBPR_Bin_135 | 3 |
| 39 | 2634960437 | Burkholderiales-76 (UID4002) | 6 |
| 42 | 2639213731 | *Planktothricoides* sp. SR001 | 2 |
| 44 | 2648875132 | *Chondromyces crocatus* Cm c5 | 3 |
| 46 | 2649993803 | *Photobacterium swingsii* CAIM 1393 | 7 |
| 47 | 2651203508 | *Flammeovirga pacifica* WPAGA1 | 3 |
| 48 | 2651490945 | *Vibrio crassostreae* J5-19 | 7 |
| 50 | 2661858798 | Methanogenic archaeon ISO4-H5 | 2 |
| 56 | 2701115162 | *Fibrobacter* sp. UWH6 | 5 |
| 57 | 2718503187 | *Flavobacterium lacus* CGMCC 1.12504 | 3 |
| 58 | 2721736750 | *Pseudoalteromonas ulvae* TC14 | 7 |
| 60 | 2733913669 | *Lacinutrix* sp. JCM 13824 | 3 |
| 62 | 2743907592 | Fibrobacteria bacterium GUT31IN01_31 | 5 |
| 63 | 2744633848 | *Pseudoalteromonas* sp. XI10 | 7 |

Example 5—pVips Provide Defense in *B. subtilis*

Figure 7A:
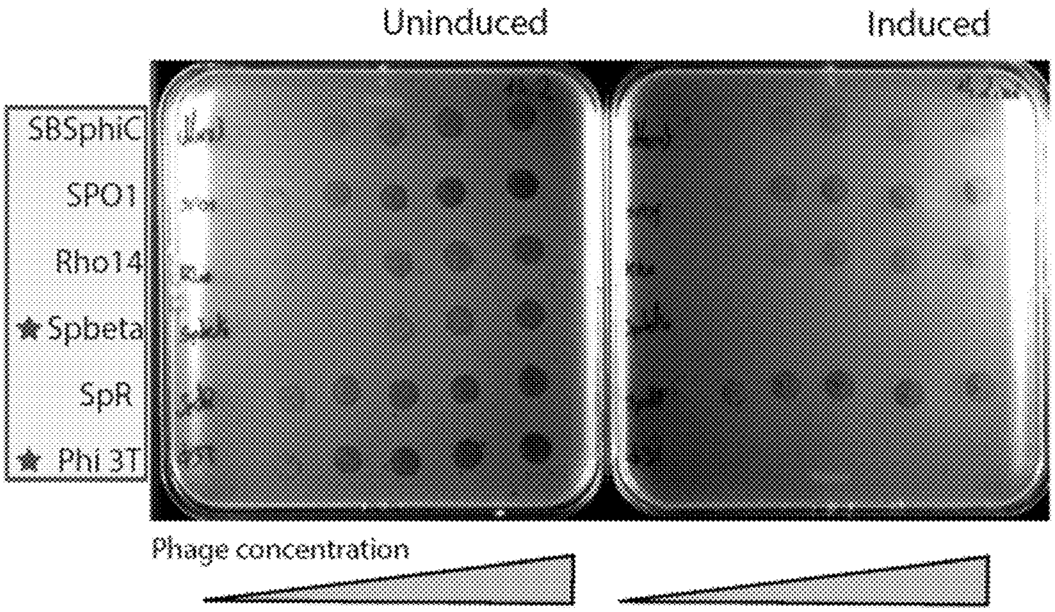
FIGS. 7A-7B show in vivo anti-viral activity of pVip7 in *B. subtilis*.
Figure 7B:
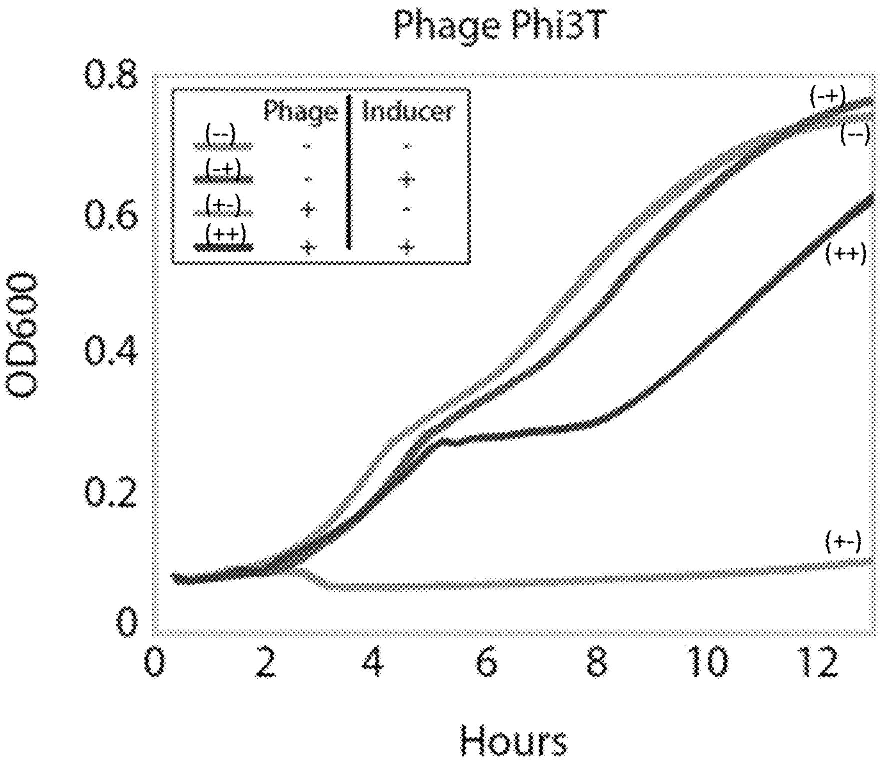

Next it was tested if pVips could provide anti-viral activity in bacteria other than *E. Coli*. We cloned pVip7 from *Fibrobacter* sp. UWT3 in *Bacillus subtilis* BEST7003 and tested it against an array of 12 different phages (detailed in Example 1).

pVip7 showed protection in *B. subtilis* against two phages: phi3T and spbeta (FIG. 7A). They both belong to the spBeta group of phages (Siphovridae). Protection against these two phages was very strong (more than 10,000 fold, which is the limit of detection of the assay used). Protection against phi3 T was confirmed with liquid infection assays, where the population in which the pVip expression was induced fully survived the phage infection, while the non-induced collapsed due to phage infection (FIG. 7B). Temperature was found to be another important parameter. While pVip7 was fully active at 25° C. in *B. subtilis*, it did not show a strong defense phenotype at 37° C. in liquid assays.

Example 6—T7 RNA Polymerase is Susceptible to Some of the Products of pVips

Figure 8A:
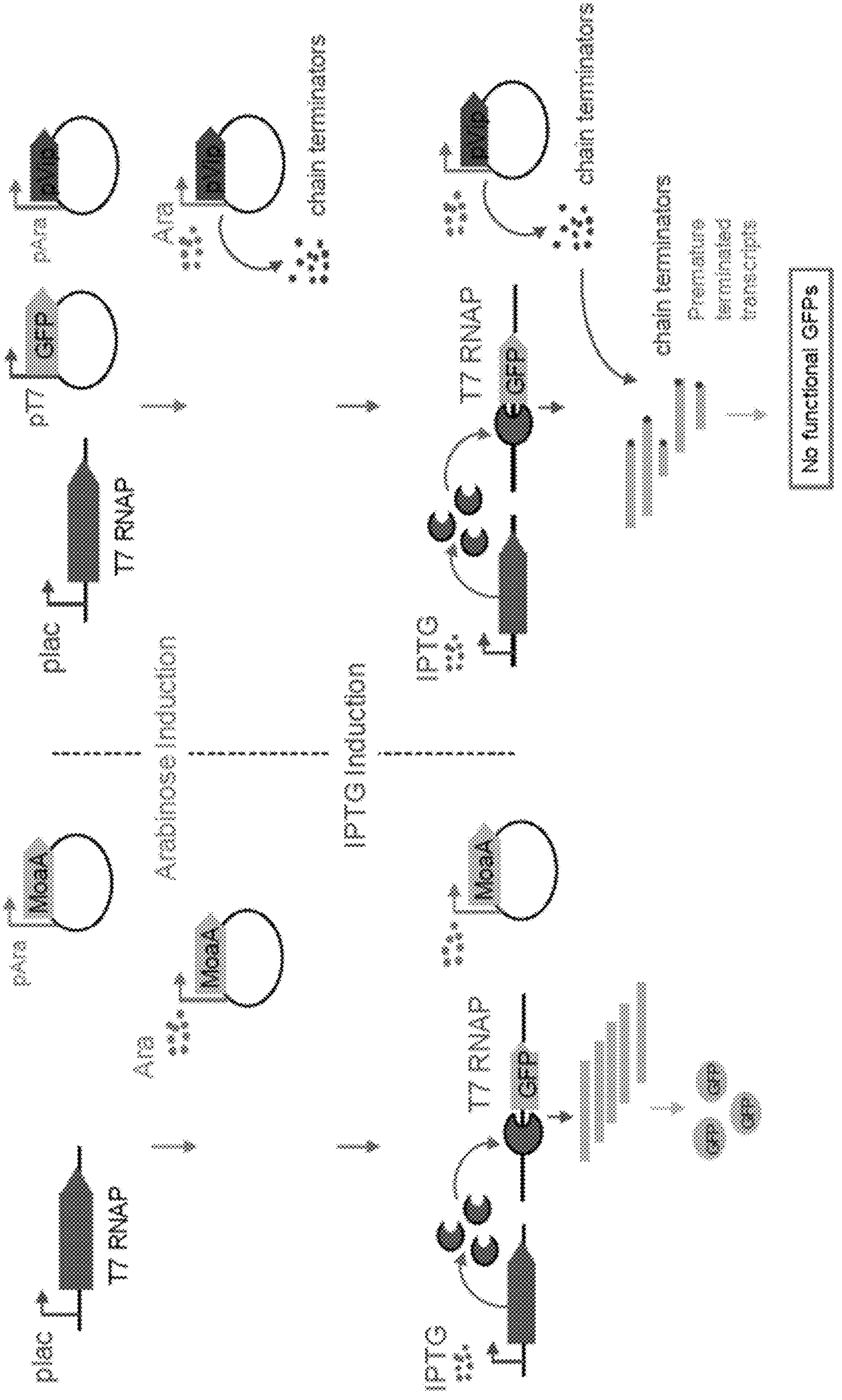
FIGS. 8A-8G shows T7 RNA polymerase (RNAP) susceptibility to pVips products.
Figure 8B:
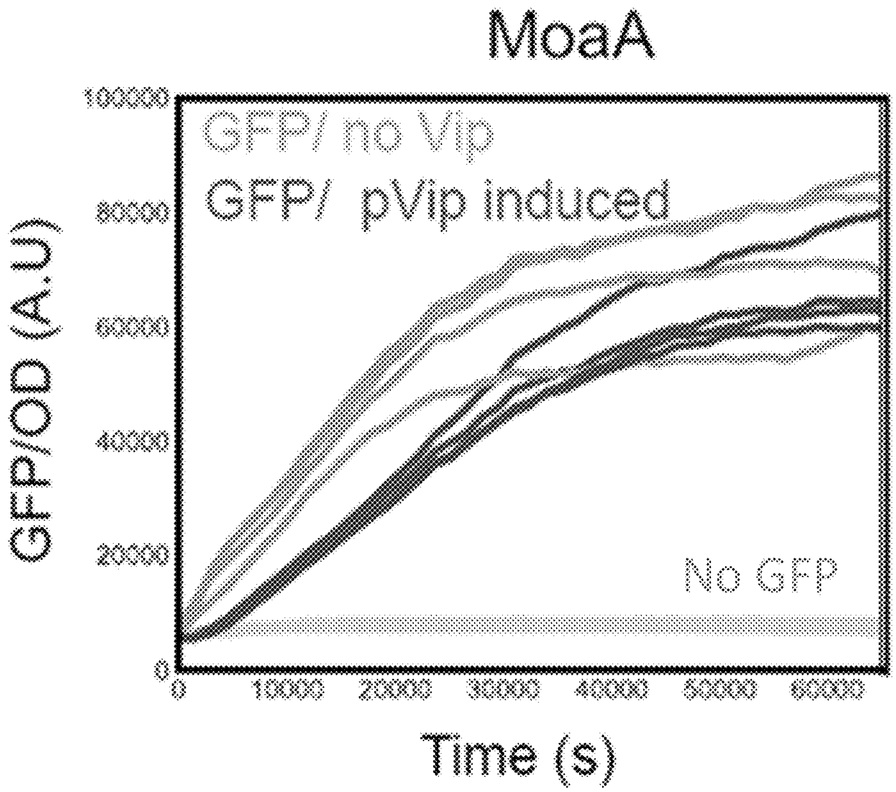
Figure 8C:
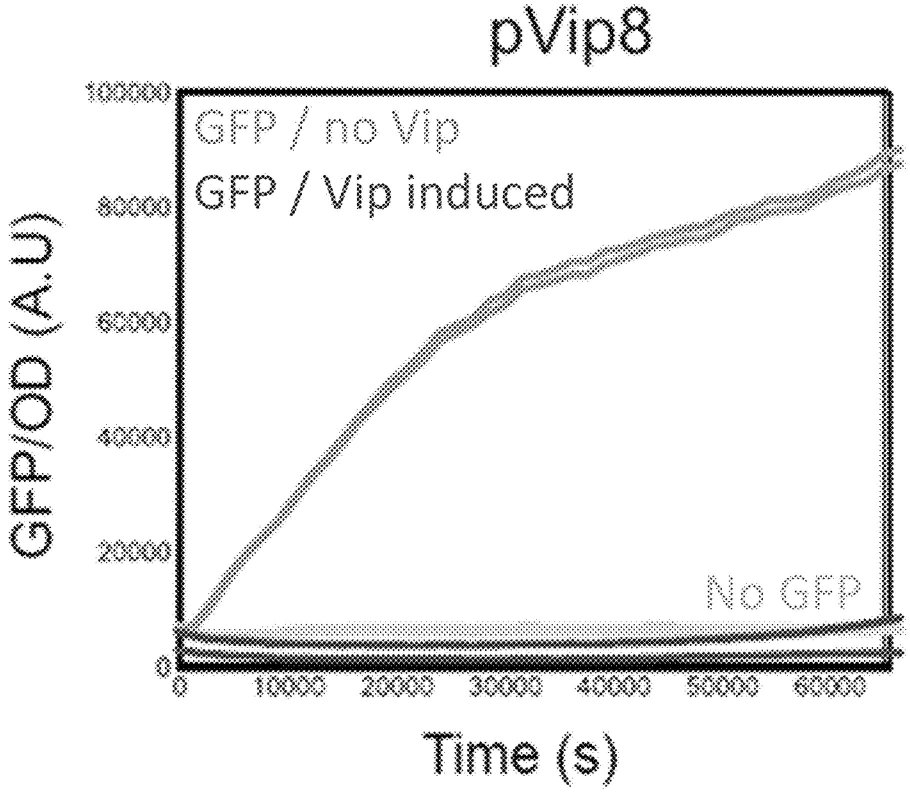
Figure 8D:
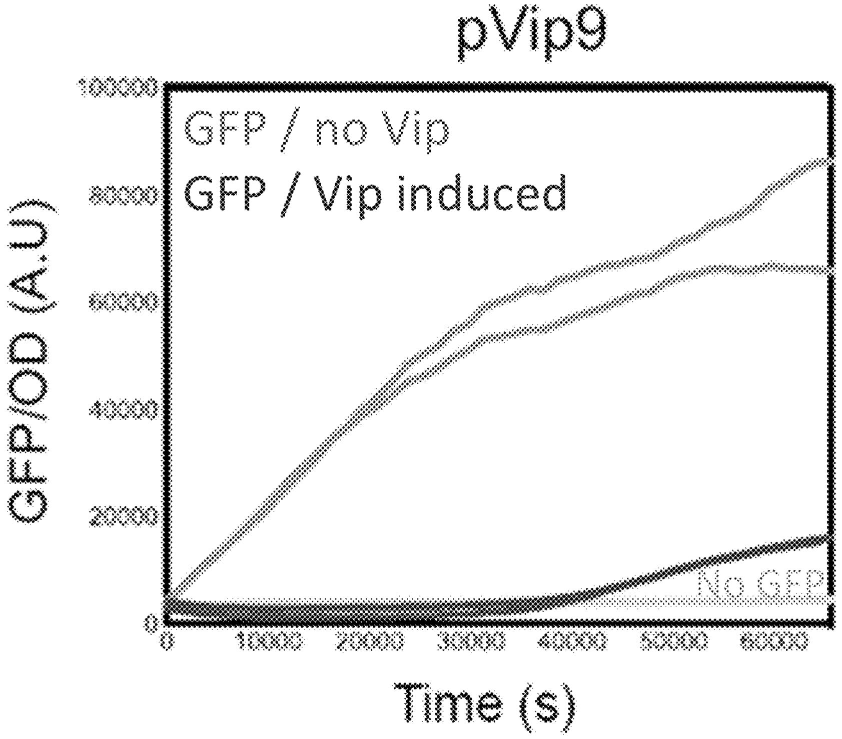
Figure 8E:
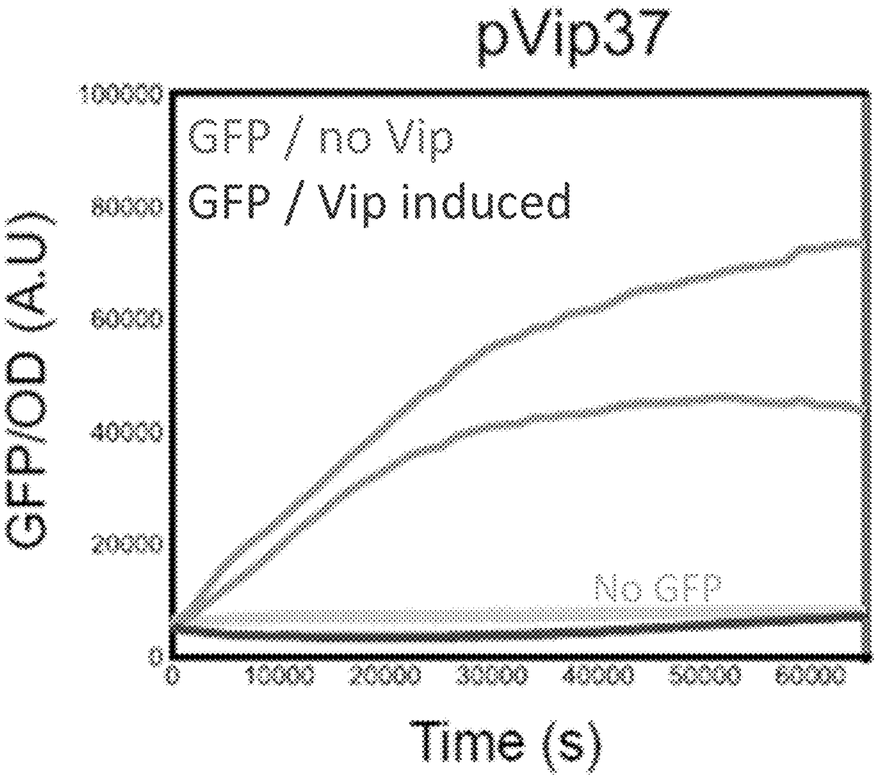
Figure 8F:
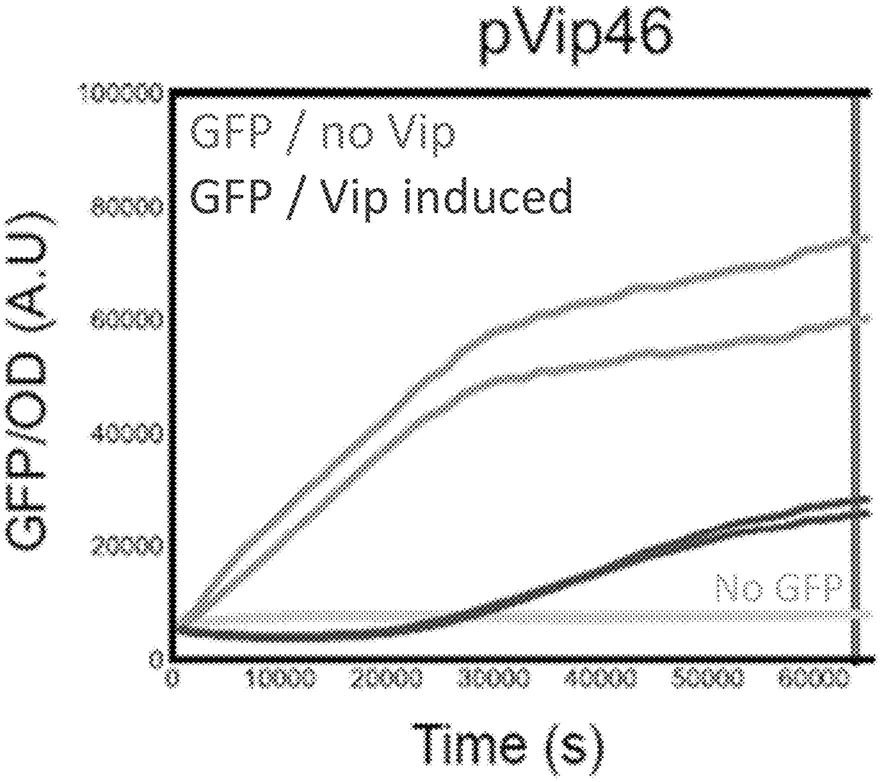
Figure 8G:
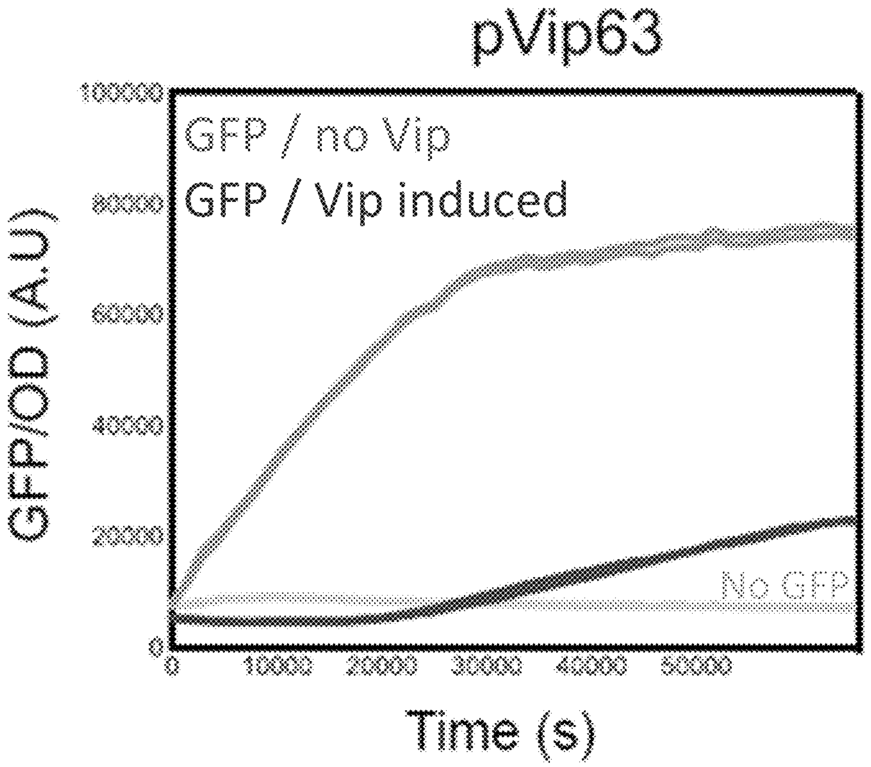

Given that some pVips provide defense against phage T7, it was hypothesized that T7 polymerase-dependent RNA synthesis might be affected by the nucleotide chain terminators produced by pVips. Therefore, it was tested if expression of a reporter gene (GFP) by the T7 polymerase was impacted by different pVips activities To do so, a collection of strains derivatives of BL21-DE3, which encodes a T7 RNA polymerase (RNAP) under the control of a lac promoter, was created. The derivative strains bore the reporter plasmid pAGG encoding a GFP under the control of T7 promoter, and a module with T7 lyzozyme to limit basal expression of T7 RNAP. Further derivative strains bore a pVip candidate under the control of arabinose promoter. In these constructs, the T7 RNA polymerase is induced by the addition of IPTG, thus activating the T7 promoter and inducing GFP transcription. We hypothesized that upon arabinose addition, pVips would be expressed inducing synthesis of polynucleotide chain terminators, which would terminate GFP transcription prematurely (FIG. 8A).

Cells were grown to OD600 0.1 overnight and pVips were induced by addition of arabinose 0.02%. After 45 minutes T7 RNAP expression was induced by addition of IPTG 0.01 mM (FIG. 8A). GFP and OD were monitored with a plate reader (Tecan, Switzerland).

It was observed that induction of pVip8, pVip9, pVip37, pVip46, and pVip63 prevented or substantially inhibited the expression of GFP by T7 polymerase (FIGS. 8B-8G). However, co-expression of MoaA, which is structurally similar to pVip, did not inhibit GFP expression. This suggests that the pVip product inhibits T7-RNAP-dependent expression of GFP by a chain terminator that interrupts the nascent GFP mRNA.

Example 7—Production of New Chain Terminators

The pVips disclosed herein can be used in order to produce chain terminators, including (but not limited to) ddhUTP, ddhATP, ddhGTP, ddhCTP, ddh-deoxy-GTP, and ddh-deoxy-ATP, ddh-deoxy-TTP, and ddh-deoxy-CTP. For this, the pVip protein would first be expressed in a heterologous expression system (e.g., in bacteria such a *E. coli* or *B. subtilis*, or in a eukaryotic expression system). Then, the expressed pVip will be purified, and then supplied with the necessary cofactors (e.g., s-adenosyl methionine) and the substrate (e.g., CTP, TTP etc, depending on the substrate of the specific pVip).

The pVip will produce the chain terminator, which will then be purified from the reaction and used for the proper application. Example 4 shows the importance of iron sulfur cluster metabolism for expression of functional pVips. Therefore, protein expression for pVips should be performed in strains such as ΔiscR or that contain plasmids like pDB1282, that encodes the iscR operon from *Azotobacter vinelandii*, or in another strain that allows expression of iron-sulfur cluster genes. Given the sensitive nature of iron sulfur cluster enzymes to oxygen, protein purification should preferentially be performed in anaerobic conditions.

While nucleotide analogs are actual chain terminators in vivo, nucleoside analogs, which is the version without phosphate groups, are the molecules generally used as drugs. The phosphate groups of the nucleotides may prevent entry to the cell due to its charge. Once nucleoside analogs enter the cells, they can be phosphorylated by endogenous enzymes or enzymes of the phage, and thus generate the cognate nucleotide analogs. Such an approach was used to show the efficiency of ddhC as an anti-viral molecule by Gizzi, A. S. et al. A naturally occurring antiviral ribonucleotide encoded by the human genome. Nature 558, 610-614 (2018). Upon entry to the cell, ddhC is phosphorylated to become ddhCTP and provides anti-viral activity against for example Zika virus. Similarly, cognate nucleoside analogs to the modified nucleotides produced by the pVips may be for example (but not limited to): ddhT, ddh-deoxy-G, ddh-deoxy-A, etc. Chemical strategies can be used to synthetize such types of nucleosides and could be applied to obtain these molecules.

Example 8—pVips and Products Thereof

Examples 1-6 reveal the existence of anew family of prokaryotic anti-viral genes, pVips. A homology-based search in 69425 prokaryotic genomes followed by a detailed and quantitative analysis of gene neighborhoods allowed to discriminate potential anti-viral genes among a wider family of radical-SAM enzymes. The pVips family was further enriched with similar genes extracted from a database of 9769 metagenomes. The analysis of the evolutionary history of pVips and the eukaryotic viperin (a known anti-viral enzyme which produces ddhCTP, a chain terminator) suggests that eukaryotic viperins has evolutionarily originated from pVips and represent only a small fraction of the diversity of the protein family. Furthermore, the analysis of pVip accessory genes (nucleoside kinases or nucleotide kinases) suggests the existence of diverse substrate for the pVips, suggesting a diversity of pVips chain terminator products.

An experimental approach to screen active pVips in vivo was developed. After selection, codon optimization and synthesis of diverse pVips, strains encoding pVips were screened against a diverse collection of phages. It was found that the use of a specific strain of *E. coli*, where iron sulfur cluster auxiliary genes are more highly expressed, greatly improves pVips activity.

Products of the pVip enzymes may include nucleotide analogs or nucleoside analogs. These can include, for example, ddhUTP, ddhGTP, ddhATP, ddhCTP, ddh-deoxy-GTP, ddh-deoxy-ATP, ddh-deoxy-TTP, ddh-deoxy-CTP, as well as modified versions of these modified nucleotides that can be used as new anti-viral or anti-tumor drugs functioning as DNA or RNA chain terminators.

Example 9—pVips Produce Diverse Anti-Viral Molecules

Material and Methods

Cell Lysates Preparation

Overnight cultures of Keio ΔiscR encoding pVips, MoaA or the human viperin were diluted 1:100 in 100 ml LB medium and grown at 37° C. (250 r.p.m.) for 1 hour and 45 minutes. The expression of viperin or MoaA was induced by the addition of arabinose (final concentration 0.2%) and cells were further incubated at 37° C. (250 r.p.m.) for one hour. Cells were then centrifuged at 3,900 g for 10 min at 4° C. and samples kept on ice throughout the cell lysate preparation. Pellets were resuspended in 600 μl PBS buffer containing 100 mM sodium phosphate (pH 7.4). The resuspended pellet was supplemented with 1 μl of hen-lysozyme (Merck) (final hen-lysozyme concentration of 10 μg/ml). The resuspended cells were then mixed with Lysing matrix B (MP) beads and cells were disrupted mechanically using a FastPrep-24 bead-beater device (MP) (2 cycles of 40 s, 6 m $s^{-1}$, at 4° C.). Cell lysates were then centrifuged at 12,000 g for 10 min at 4° C. and the supernatant was loaded onto a 3-kDa filter Amicon Ultra-0.5 centrifugal filter unit (Merck) and centrifuged at 14,000 g for 30 min at 4° C. The resulting flow-through, containing substances smaller than 3 kDa, was used as the lysate sample for evaluating the presence of ddh nucleotides by LC-MS.

Detection of Ddh-Nucleotides

Sample analysis was carried out by MS-Omics (Vedbok, Denmark) as follows. Samples where diluted 1:1 in 10 mM ammonium acetate in 90% acetonitrile. The analysis was carried out using a UHPLC system (Vanquish, Thermo Fisher Scientific, US) coupled with a high-resolution quadrupole-orbitrap mass spectrometer (Q Exactive™ HF Hybrid Quadrupole-Orbitrap, Thermo Fisher Scientific). An electrospray ionization interface was used as ionization source. Analysis was performed in positive ionization mode. The UPLC was performed using a slightly modified version of a previously described protocol. Peak areas were extracted using Compound Discoverer 2.0 (Thermo Scientific).

Quantification of 3'-deoxy-3',4'-didehydro cytidine (ddhC)

The 3'-deoxy-3',4'-didehydro cytidine molecule was synthesized by Jena Bioscience (Jena, Germany) and was used as a standard for ddC quantification in cell lysates using LC-MS. Sample analysis was carried out by MS-Omics (Vedbok, Denmark) as follows. Samples were diluted 1:1 in 10 mM ammonium formate and 0.1% formic acid in ultra-pure water. The analysis was carried out using the LC-MS setup described above. An electrospray ionization interface was used as ionization source performed in positive ionization mode. The UHPLC method is based on Waters Application note 2011, 720004042en (Waters Corporation, Milford, US). Peak areas of 3'-deoxy-3',4'-didehydrocytidine (ddhC) were extracted using Trace Finder™ Version 4.1 (Thermo Fisher Scientific, US) and quantified using an external calibration with the standard.

Results

Figure 10:
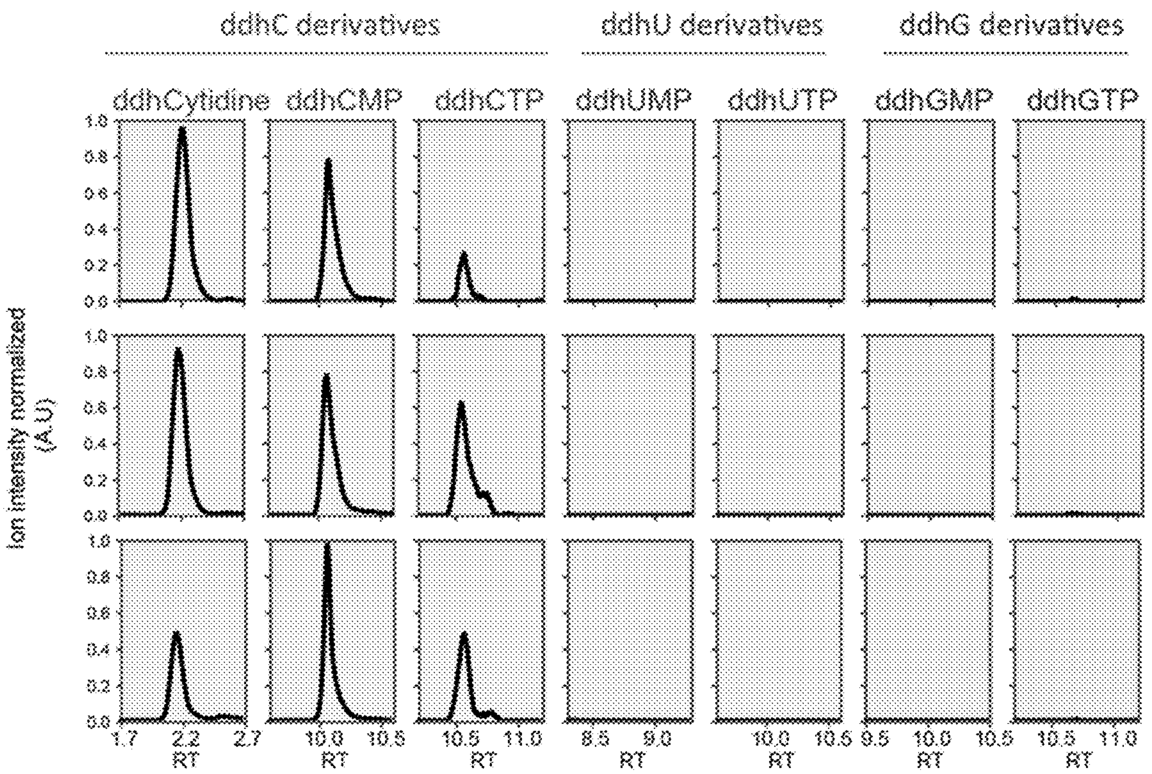
FIG. 10 shows detection of ddhCTP and ddhCTP derivatives in cell lysates from an *E. coli* strain expressing the human viperin. Extracted ion chromatogram for singly charged masses corresponding to ddhC (m/z 226.08223, retention time (RT) of 2.2 minutes), ddhCMP (m/z 306.04856, RT 9.7), ddhCTP (m/z 465.98122, RT 11.1), ddhUMP (m/z 307.03258, RT 8.7), ddhUTP (m/z 466.96524, RT 9.5), ddhGMP (m/z 266.08838, RT 9.8), and ddhGTP (m/z 505.98737, RT 10.6). X-axis depicts RT in minutes. Y axis, normalized ion intensity (arbitrary units). Normalization was performed on all human viperin and MoaA samples, with maximal value set to 1.0. Three biological replicates are presented.
Figure 12:
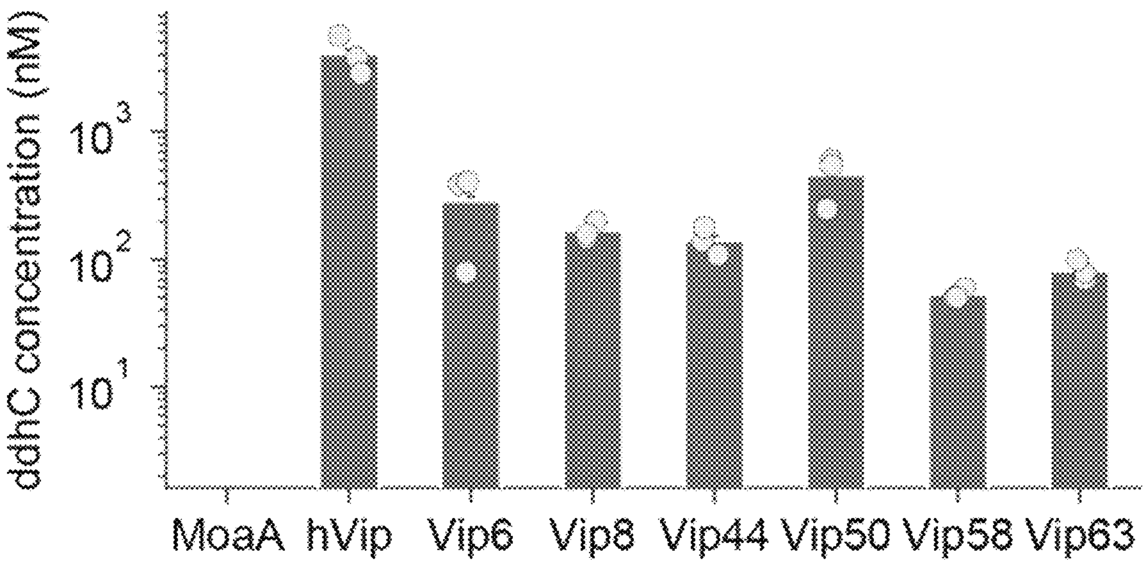
FIG. 12 shows quantification of ddh cytidine in lysates of cells expressing pVips. Detection and quantification of ddhC was performed using LC-MS with a synthesized chemical standard. For MoaA, the measurement was under the limit of detection. Bar graph represents average of three replicates, with individual data points overlaid.

The animal viperin catalyzes the production of ddhCTP. Whether pVips produce ddhCTP and/or other types of modified nucleotides was examined. For this, pVips were expressed in *E. coli* and the fraction of small molecules was extracted from the cell lysates, presuming that the pVip-produced molecule would be present in that fraction. These lysates were analyzed with liquid chromatography followed by mass spectrometry (LC-MS) using an untargeted approach. As a positive control, cell lysates from cells expressing the human viperin protein were similarly analyzed. As expected, a compound conforming with the mass of ddhCTP was readily detected in lysates from cells expressing the human viperin but not in the negative control lysates that were derived from MoaA-expressing cells (FIG. 10). Additional compounds found in the human viperin sample matched the masses of ddh-cytidine (ddhC) and ddh-cytidine monophosphate (CMP), possibly derived from natural decay of ddhCTP as also known to occur for CTP in neutral or acidic pH. Analysis of fragment ions using MS-MS further supported that the identified masses are ddhCTP, ddhCMP and ddhC with additional confirmation attained by subjecting synthesized ddhC standard to MS-MS analysis (FIG. 12). These results confirm that the human viperin actively produces ddhCTP when expressed in *E. coli*, explaining its observed anti-phage activity.

Figure 9A:
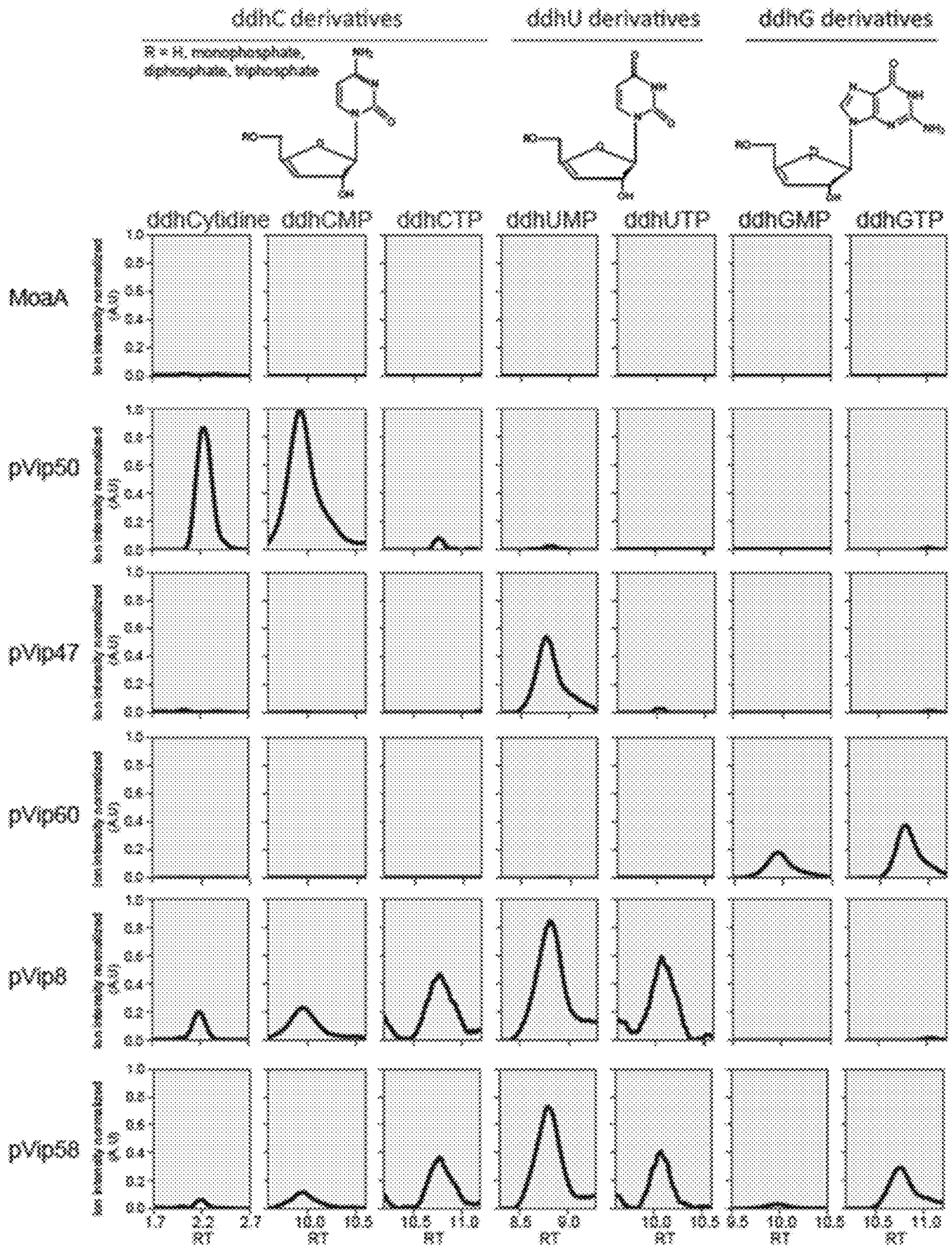
FIGS. 9A-9B show pVips produce a variety of modified ribonucleotides.
Figure 9B:
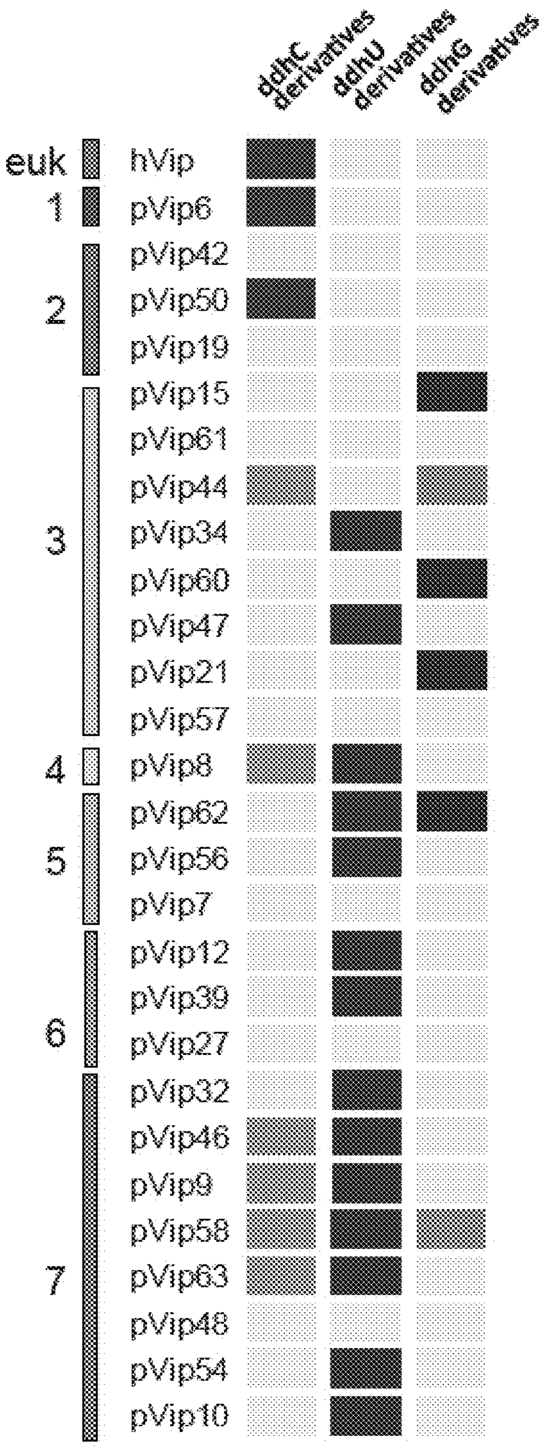
Figure 11:
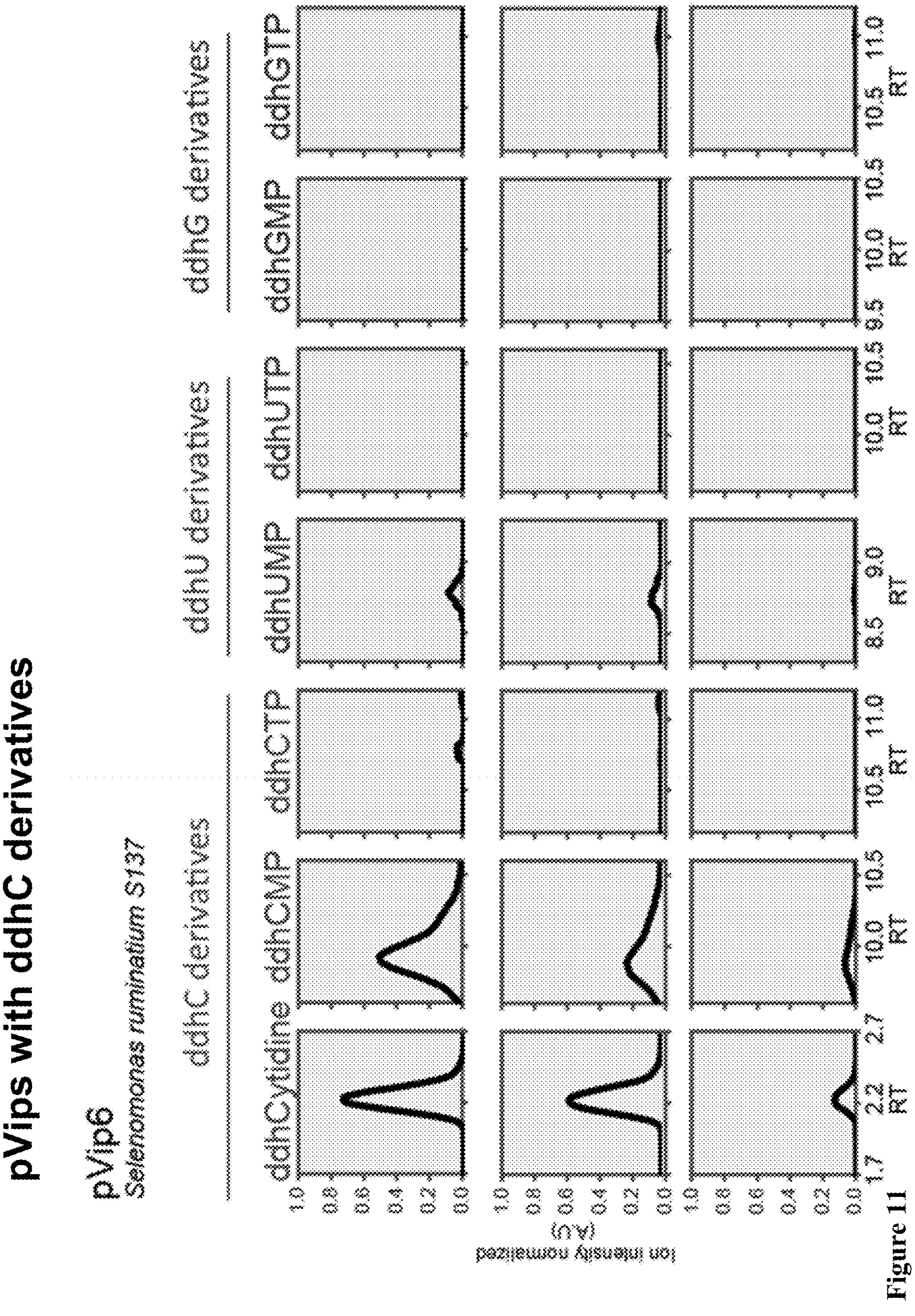
FIG. 11 shows detection of ddh nucleotides in lysates of cells that express pVips. Extracted ion chromatogram for singly charged masses corresponding to ddhC (m/z 226.08223, retention time (RT) of 2.2 minutes), ddhCMP (m/z 306.04856, RT 9.7), ddhCTP (m/z 465.98122, RT 11.1), ddhUMP (m/z 307.03258, RT 8.7), ddhUTP (m/z 466.96524, RT 9.5), ddhGMP (m/z 266.08838, RT 9.8), and ddhGTP (m/z 505.98737, RT 10.6). X-axis depicts RT in minutes. Y axis, normalized ion intensity (arbitrary units). Normalization was performed on all pVips and MoaA samples, with maximal value set to 1.0. Three biological replicates are presented for each pVip.
Figure 11:
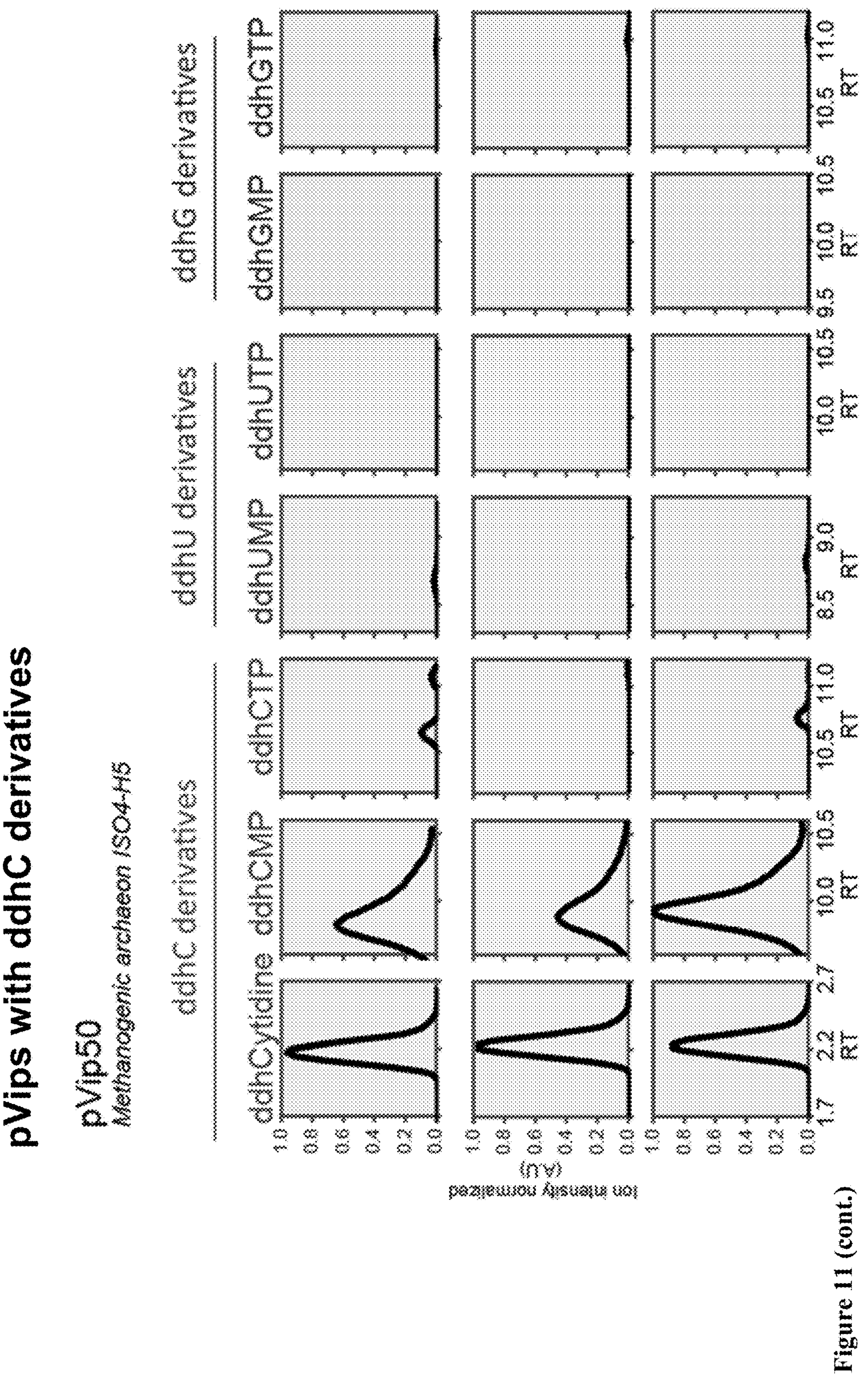

The small molecule fractions from lysates of cells expressing 27 pVips that were found to have an anti-phage activity were then analyzed. Derivatives of ddhCTP were detected by LC-MS in the lysate of pVip50, a protein derived from a methanogenic archaeon that belongs to clade 2 of the pVips tree, verifying that pVips are indeed functional homologs of the human viperin that produce similar antiviral molecules. Moreover, other masses that were markedly enriched in the lysates of cells expressing pVips and absent from the negative control lysate were also examined. For several of the pVips it was found masses that conform with 3'-deoxy-3',4'-didehydro-guanosine-triphosphate (ddhGTP) and 3'-deoxy-3',4'-didehydro-guanosine-diphosphate (ddhGDP), and for other pVips other molecules were found with masses matching 3'-deoxy-3',4'-didehydro-uridine triphosphate (ddhUTP) and 3'-deoxy-3',4'-didehydro-uridine monophosphate (ddhUMP) (FIGS. 9A and 9B, FIG. 11). These results suggest that pVips produce new types of antiviral ribonucleotides that were not observed before in nature.

For most of the pVips, predicted derivatives of a single modified nucleotide were observed in the lysate (either ddhCTP, ddhGTP or ddhUTP). However, seven of the pVips were found to produce derivatives of multiple ddh ribonucleotides. For example, in lysates derived from pVip8-expressing cells, it was found both ddhCTP and ddhUTP, and in lysates from pVip58 cells, ddhCTP, ddhUTP, ddhGTP and their derivatives were detected (FIG. 11). These results suggest that throughout evolution some pVips may have become more promiscuous and can modify more than one ribonucleotide to its ddh antiviral form. Presumably such pVips may have an advantage when encountering phages that can overcome one of these antiviral molecules but not the other two.

For seven of the tested pVips, no ddh nucleotide or its derivatives were detected in the cell lysates, despite a clear antiviral activity conferred by these pVips (FIG. 9A). It is possible that these pVips produce a different antiviral molecule that could not have been detected via the LC-MS protocol, or, alternatively, that these pVips have evolved to confer defense by another mechanism of action that does not involve production of antiviral molecules.

The identity of the molecules produced by the various pVips is largely consistent with their phylogenetic relatedness. pVips from clades 4-7 were predicted to produce ddhUTP, with some of these also producing additional ddh ribonucleotides. In clade 1 and clade 2, which resides together with the eukaryotic viperins on the same superclade, certain pVips were found to produce ddhCTP. Clade 3 includes pVips that were predicted to generate either ddhGTP or ddhUTP (FIG. 9B).

Example 10—Anti-Viral Activities of ddh-Compounds

The present example examines the antiviral activities for ddhC (compound AB21650), ddhU (compound AB21649) and ddhG (compound AB21651).

The compounds were tested against a panel of 17 viruses: adenovirus-5 (Ad5), acaribe virus (TCRV), Rift Valley fever virus (RVFV), SARS-CoV, dengue virus-2 (DV-2), Japanese encephalitis virus (JEV), Powassan virus (POWV), West Nile virus (WNV), Yellow fever virus (YFV), Zika virus, Influenza(H1N1), Influenza(H5N1), Influenza B, RSV, poliovirus-1 (POV-1), enterovirus-68 (EV-68), and Venezuelan equine encephalitis virus (VEEV). Cell types used were A549 for Ad5; Vero E6 for TCRV; Huh7 for DV-2 and YFV; BHK-21 for POWV; RD for EV-68; MA-104 for RSV; MDCK for influenza viruses; and Vero 76 for all other viruses.

The compounds were solubilized in DMSO to prepare a 400 mM stock solution. The compounds were then serially diluted using eight half-log dilutions in test medium (MEM supplemented with 2% FBS and 50 μg/mL gentamicin) so that the starting (high) test concentration was 2 mM. Each dilution was added to 5 wells of a 96-well plate with 80-100% confluent cells. Three wells of each dilution were infected with virus, and two wells remained uninfected as toxicity controls. Six wells were infected and untreated as virus controls, and six wells were uninfected and untreated as cell controls. The viruses were prepared to achieve the lowest possible multiplicity of infection (MOI) that would yield >80% cytopathic effect (CPE) within 3-7 days. Positive control compounds were tested in parallel for each virus tested. Plates infected with EV-68 were incubated at 33±2° C., 5% $CO_2$; all other plates were incubated at 37±2° C., 5% $CO_2$.

On day 3-7 post-infection, once untreated virus control wells reached maximum CPE, the plates were stained with neutral red dye for approximately 2 hours (±15 minutes). Supernatant dye was removed and the wells were rinsed with PBS, and the incorporated dye was extracted in 50:50 Sorensen citrate buffer/ethanol for >30 minutes and optical density was read on a spectrophotometer at 540 nm. Optical densities were converted to percent of cell controls and normalized to the virus control, then the concentration of test compound required to inhibit CPE by 50% ($EC_{50}$) was calculated by regression analysis. The concentration of compound that would cause 50% cell death in the absence of virus was similarly calculated ($CC_{50}$). The selective index (SI) is the $CC_{50}$ divided by $EC_{50}$.

The results are shown in Table 11. It is found that ddhG exhibits antiviral activity against Influenza (H1N1) and Influenza (H5N1); ddhU exhibits antiviral activity against Influenza B and Influenza (H1N1 and H5N1); ddhC exhibits some activity against enterovirus EV-68.

TABLE 11

In vitro antiviral activity of AB21650 (ddhC), AB21651 (ddhG), and AB21649 (ddhU).

| | | AB21650 | | | AB21651 | | | AB21649 | | | Positive Control | | |
|---|---|---|---|---|---|---|---|---|---|---|---|---|---|
| | Positive Control | $EC_{50}$ | $CC_{50}$ | SI | $EC_{50}$ | $CC_{50}$ | SI | $EC_{50}$ | $CC_{50}$ | SI | $EQ_{50}$ | $CC_{50}$ | SI |
| Ad5 | 2-3 Dideoxycytidine | >2 | >2 | 0 | >2 | >2 | 0 | >2 | >2 | 0 | 1.8 | >100 | >56 |
| TCRV | Ribavirin | >2 | >2 | 0 | >2 | >2 | 0 | >1.2 | 1.2 | 0 | 13 | 820 | 63 |
| RVFV | Ribavirin | >2 | >2 | 0 | >2 | >2 | 0 | >1.1 | 1.1 | 0 | 14 | 870 | 62 |
| SARS-CoV | M128533 | >2 | >2 | 0 | >2 | >2 | 0 | >1.5 | 1.5 | 0 | 0.075 | >100 | >1300 |
| SARS-CoV-2 | M128533 | >2 | >2 | 0 | >2 | >2 | 0 | >2 | >2 | 0 | 0.33 | >100 | >300 |
| DV-2 | Infergen | >2 | >2 | 0 | >2 | >2 | 0 | >2 | >2 | 0 | 0.13 | >10 | >77 |
| JEV | Infergen | >2 | >2 | 0 | >2 | >2 | 0 | >1.7 | 1.7 | 0 | 0.043 | >10 | >230 |
| POWV | Infergen | >2 | >2 | 0 | >2 | >2 | 0 | >2 | >2 | 0 | 0.0051 | >10 | >2000 |
| WNV | Infergen | >2 | >2 | 0 | >2 | >2 | 0 | >1.4 | 1.4 | 0 | 0.12 | >10 | >83 |
| YFV | infergen | >2 | >2 | 0 | >2 | >2 | 0 | >2 | >2 | 0 | 0.012 | >10 | >830 |
| VEEV | infergen | >2 | >2 | 0 | >2 | >2 | 0 | >1.1 | 1.1 | 0 | 0.17 | >10 | >59 |
| Zika | NITD008 | >2 | >2 | 0 | >2 | >2 | 0 | >1.5 | 1.5 | 0 | 1.8 | 44 | 24 |
| influenza A(H1N1) | Ribavirin | >2 | >2 | 0 | 0.44 | >2 | >4.5 | 0.56 | 1.4 | 2.5 | 4.6 | >1000 | >220 |
| influenza A(H5N1) | Ribavirin | >2 | >2 | 0 | 1.3 | >2 | >1.5 | 0.8 | 1.3 | 1.6 | 1.8 | >1000 | >560 |
| influenza B | Ribavirin | >2 | >2 | 0 | >2 | >2 | 0 | 0.31 | 1.3 | 4.2 | 1.4 | >1000 | >710 |
| RSV | Ribavirin | >2 | >2 | 0 | >2 | >2 | 0 | >1.9 | 1.9 | 0 | 7.3 | 42 | 5.8 |
| POV-1 | Enviroxime | >2 | >2 | 0 | >2 | >2 | 0 | >1.0 | 1.0 | 0 | 0.0095 | 3.3 | 350 |
| EV-68 | Pirodavir | 0.91 | 1.8 | 2 | >1.1 | 1.1 | 0 | >0.39 | 0.39 | 0 | 0.039 | 4.3 | 110 |

Units are in mM for test compounds, ng/mL for Infergen™, and µg/mL for all other positive control compounds $EC_{50}$: 50% effective antiviral concentration $CC_{50}$: 50% cytotoxic concentration of compound without virus added

SI = $CC_{50}/EC_{50}$

M128533 positive control is Z-Leu-Gln(NMe2)-FMK (Zhang et al. (2006) J. Med. Chem. 2006, 49, 1198-1201).

Example 11—Synthesis of Novel Synthetic Nucleotide Analogs

Figure 14:
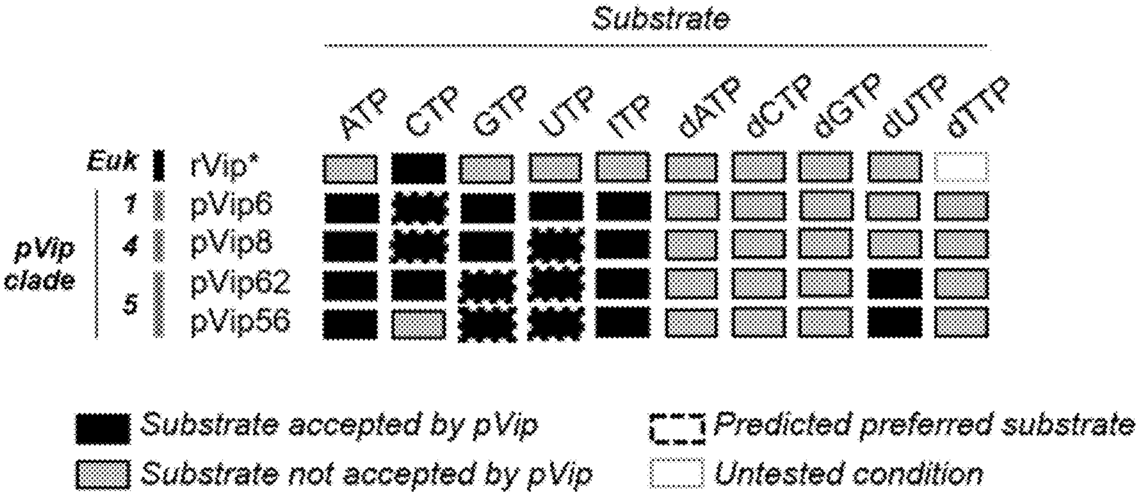
FIG. 14 presents results showing pVips display broad substrate promiscuity. Each pVip was screened against a set of substrates and 5'-dA production was measure by HPLC. Black boxes depict reactions in which enhanced 5'-dA production by at least 2-fold was observed compared to control reactions (without substrate or dithionite), indicating substrate activation. Grey boxes represent negative reactions where the positive and negative control display similar 5'-dA levels. Outlined boxed indicate predicted pVip natural substrates from products detected in lysates overexpressing each pVip. White boxes depict untested conditions. * denotes results from Gizzi et al., (2018) *A naturally occurring antiviral ribonucleotide encoded by the human genome*. Nature 558, 610-614.

To test whether pVips can modify substrates that are non-natural to their native activities in vivo, the catalytic activities of pVips against a battery of substrates were explored by performing in vitro enzymatic assays with purified enzymes. The results show that pVips accept multiple nucleotides as substrates in vitro and catalyze the production of 3'-deoxy-3',4'-didehydro forms of ATP, GTP, CTP, UTP and ITP, as well deoxy-UTP, even when these products are not produced by these enzymes in vivo. For example, pVip6 was shown in vivo to generate the product ddhCTP; but in vitro, it also produces ddhUTP, ddhATP, ddhGTP and ddhITP (FIG. 14). These results show that pVips, as opposed to eukaryotic viperins, are promiscuous enzymes that can perform their enzymatic activities (removal of the OH from the 3' carbon) on multiple different substrates.

In addition to the previous identified products—ddhCTP, ddhUTP and ddhGTP—the production of three novel nucleotide analogs by pVips was detected in vitro: ddhATP, ddhITP and ddhdUTP. These results demonstrate that pVips can produce a wide range of nucleotide analogs and display a wider substrate promiscuity as compared to eukaryotic homologues.

Based on the proven substrate promiscuity of pVips, it is predicted that these enzymes would generate novel structural modifications on multiple non-natural nucleotide derivatives and other molecules. In one embodiment, the modification done by pVips is the dehydration of the 3' carbon in the ribose moiety of the nucleotide, and these non-natural products of pVips could confer novel therapeutic properties. In one embodiment, the pVips would be able to modify a large set of non-natural nucleotides as disclosed herein, and one or more of the products of these modifications could have potential therapeutic properties. For instance, pVips could be harnessed to generate 3'-deoxy-3',4'-didehydro variants (see FIG. 13) of existing synthetic nucleotide analogs such as Ribavirin, 6-Azauridine, Gemcitabine or Remdesivir. Moreover, given the observed pVips promiscuity, it is predicted that these enzymes could catalyze other types of nucleotide modifications—other than the 3'-dehydroxylation—leading to the generation of additional novel analogs.

The utilization of pVips to modify clinically relevant non-natural nucleotide analogs could lead to the discovery of new compounds with improved therapeutic properties that display, for instance, enhanced antiviral/anti-tumoral/antibacterial potency, reduced toxicity, or improved bioconversion and pharmacokinetic properties. Moreover, given the advantages that bio-based production methods offer over chemical synthesis methods—which are time-consuming, costly and polluting—the enzymatic generation of non-natural nucleotide analogs using pVips could accelerate the discovery and production of novel therapeutic variants as well as their deployment to the clinic.

Materials and Methods

Strains and Growth Conditions

*E. coli* strains BL21 (NEB®) and BL21-ΔiscR were used for protein production and strain DH10β (NEB®) for molecular cloning. Unless otherwise noted, all *E. coli* strains were grown in LB medium supplemented with antibiotics kanamycin (25 µg/mL), ampicillin (50 µg/mL) or chloramphenicol (17.5 µg/mL) when appropriate for selective plasmid propagation. The strain BL21-ΔiscR was constructed from *E. coli* BL21 by knocking out the chromosomal iscR gene through P1 transduction using phages propagated from the Keio ΔiscR strain, followed by several rounds of kanamycin selection. Successful deletion of iscR was verified by PCR and sequencing.

Plasmid Construction

All plasmids were constructed using Gibson assembly in *E. coli* DH10β. Codon-optimized pVip genes were amplified by PCR from pAB_Vip expression vectors (Sorek lab) and cloned into the aTc-inducible expression vector pASG-IBA143 (IBA Lifesciences) for fusion of a Twin-Strep-Tag® to the C terminus of the pVips. To construct the suf operon expression vector "pSuf", the complete operon (sufABCDSE) amplified from *E. coli* MG1655 genomic DNAnd the arabinose expression system from pAB_Vip vectors were cloned into the pACYC-184 (NEB®) backbone. The resulting expression vector is arabinose-inducible and contains a chloramphenicol resistance cassette as well as a p15A origin of replication.

Protein Expression

BL21-ΔiscR or BL21 pSuf cells freshly transformed with plasmids encoding the tagged pVips were used. Transformants were grown overnight on selective LB agar plates at 37° C. Individual colonies of engineered strains were picked into 5 mL selective LB medium and incubated overnight with shaking at 37° C. From overnight cultures, protein production cultures were seeded at an initial OD600 of ~0.06 either in 1-2 L of selective LB medium or in 1-2 L of selective M9 medium supplemented with 4 g $L^{-1}$ D-glucose. Cultures were incubated at 37° C. with shaking. Cultures of strains carrying the pSuf vector were supplemented with 100 μM $FeCl_3$, 100 μM L-cysteine and induced with 0.2% arabinose at $OD_{600}$=0.2-0.3. For all cultures, pVip expression was induced with 50 ng per mL aTc when $OD_{600}$ reached 0.6-0.8. BL21-ΔiscR strains were also supplemented with 100 μM $FeCl_3$, 100 μM L-cysteine at $OD_{600}$=0.6-0.8. After induction with aTc, cultures grown in LB were incubated at 37° C. with shaking for 3-4 h and pellets were harvested by centrifugation. After induction with aTc, cultures grown in $M_9$ were placed at 4° C. for 1 h, pellets were harvested by centrifugation after incubation overnight at 18° C. with shaking. Pellets were stored at −20° C.

Protein Purification

Frozen cell pellets were thawed, resuspended in lysis buffer (50 mM Tris HCl, 500 mM NaCl, 5 mM dithiothreitol (DTT), 0.5 M arginine, and 20% glycerol), and sonicated with a Branson Sonifier (15 sec ON, 45 sec OFF, 10 min total ON, 30% amplitude) on ice. Lysates were subjected to centrifugation for 30 min at 17,000 g and 4° C. (Avanti J-20 XP centrifuge; JA-25.50 rotor). The lysate was loaded onto a StrepTactin Superflow High Capacity (50% suspension; IBA #2-1208-025) column previously equilibrated with 20 column volumes of Buffer W (100 mM Tris-HCl pH 8, 300 mM NaCl, 5 mM DTT, 10% glycerol). The column was washed twice with 10 column volumes of Buffer W and eluted with buffer E (50 mM Tris-HCl pH 8, 300 mM NaCl, 5 mM DTT, 2.5 mM desthiobiotin, 20% glycerol). The presence of the pVip proteins in the resulting fractions was confirmed by SDS-PAGE. Purified proteins were frozen in liquid nitrogen and stored at −80° C.

Protein Reconstitution

Purified protein solutions were thawed on ice and introduced into in a customized MBraun anaerobic chamber maintained at <0.1 ppm oxygen. All subsequent steps were performed in anaerobic conditions at 12° C. Proteins were incubated for 1 hour with 50 mM DTT with gentle shaking. Protein solutions were supplemented with 8-fold molar excess $Fe(NH_4)_2(SO_4)_2$, incubated for 15 min with gentle shaking, followed by adding 8-fold molar excess of Na2S droplet by droplet. After incubation for 3-4 h to overnight with slow shaking, the reconstituted pVips were transferred to the Reaction Buffer (50 mM HEPES pH 7.5, 150 mM KCl, 5 mM DTT, 20% Glycerol) using PD-10 desalting columns (GE Healthcare) and concentrated using an Amicon Ultra centrifugal 10 kDa filter (Merck) to a final protein concentration of 20-50 μM. Proteins were then flash-freezed with liquid nitrogen and stored at −80° C.

Enzymatic Assay

Reactions were performed in a total volume of 100 μL containing: 20-50 μM protein in Reaction buffer, 2 mM S-Adenosyl methionine (SAM), 1 mM of nucleotide substrate, and 5 mM sodium dithionite. Reactions were carried out inside the anaerobic chamber maintained at <0.1 ppm oxygen. Reaction mixtures without dithionite were incubated at 37° C. for 5 minutes. A 10 μL aliquot was removed from the reaction mixture (sample before reaction). Reactions were then initiated with sodium dithionite and incubated at 37° C. for 1-2 h. After incubation, samples were taken out of the anaerobic chamber and stored at −80° C. until analysis.

HPLC Method

High-performance liquid chromatography (HPLC) with detection of UV absorbance (280 nm wavelength) was conducted at 23° C. with a constant flow of 0.5 mL per minute. The mobile phase was composed of solvent A (0.1% formic acid, 5% methanol) and solvent B (100% acetonitrile). Samples in volume of 1 μL were fed onto an Agilent Eclipse Plus C18 RRHD column equilibrated with 100% solvent A. Samples were separated with a gradient from 0% to 5% of solvent B in 0.5 min, followed by a gradient from 5% to 20% for 1.5 min, then from 20% to 50% solvent B for 1 min, and then held at 50% solvent B for 0.5 min before returning to 0% solvent B for equilibration for 5.5 min. Quantification of 5'-dA in reaction samples was performed using a standard curves generated with 5'dA purchased from Sigma-Aldrich.

LC-MS Method

LC-MS measurements were performed with a Thermo Scientific Q Exactive Orbitrap mass spectrometry system equipped with a Dionex Ultimate 3000 UHPLC system. The software Thermo Xcalibur was used for instrument control and data processing. Prior to analysis, 10 μL of samples from enzymatic assays were mixed with 40 μL of acetonitrile: methanol organic mixture (5:3 v/v ratio). The mixtures were vortexed, centrifuged at 17,000 g for 2 min and 3 μL of supernatant were injected onto an SeQuant® ZIC®-pHILIC 5 μm polymeric 100×2.1 mm HPLC column. The mobile phase was composed of 20 mM ammonium carbonate pH 9.5 (solvent A) and 100% acetonitrile (solvent B). Samples were separated using a constant flow rate of 0.2 mL/min, 80% solvent B was held for 2 min, followed by a gradient from 80% to 20% of solvent B for 15 min, before immediately returning to 80% solvent B for equilibration for 9 min. Data analysis was performed using the Thermo Scientific FreeStyle software.

In Vitro Production of 3'-deoxy-3',4'-didehydro-GTP

To obtain sufficient amounts of ddhGTP for MS/MS analysis, enzymatic reactions were performed in a total volume of 1 ml containing: 113 mM pVip56, 2 mM SAM, 2 mM GTP and 5 mM dithionite in Reaction Buffer. Reactions were carried out in anaerobic conditions as previously described and incubated at 37° C. for 3 hours. To remove the protein, 10K centrifugal filters were used. The flow through was diluted 2-fold into cold 10 mM ammonium bicarbonate buffer pH 9.0 (buffer A), then loaded onto Capto™ HiRes Q 5/50 (GE Healthcare) pre-equilibrated with buffer A. The column was washed with 25 mL of buffer And elution was performed using linear elution gradient (100 mL) of 200 mM to 800 mM ammonium bicarbonate, pH 9. The purified product was lyophilized and resuspended in water prior LC-MS analysis.

Results

The substrate selectivity and catalytic potential of pVips were investigated by performing in vitro biochemical studies with purified enzymes from different clades. To this purpose, vectors were constructed for overexpressing the 27 codon-optimized pVips of interest with a Strep II-tag fused to their C-terminus. Individual tagged pVips were overexpressed in *E. coli* and purified by Strep II-tag affinity purification. After reconstitution of the enzyme's [4Fe-4S] cluster, the ability of each pVip to catalyze reductive cleavage of SAM into 5'-deoxyadenosine (5'-dA) was measured in the presence of a specific substrate. Enhanced 5'-dA production under reducing conditions is a characteristic indicator of substrate activation of radical SAM enzymes, and widely employed for substrate identification. Each pVip was screened against a set of substrate candidates corresponding to most members of the natural nucleotide triphosphate pool: ribonucleotides (ATP, GTP, UTP, CTP, ITP) and deoxyribonucleotides (dATP, dGTP, dUTP, dCTP, dTTP). For each pVip, the production of 5'-dA was measured in the presence of a substrate, as compared to control reactions without nucleotide or activating reducing agent (condition before reaction).

Figure 15A:
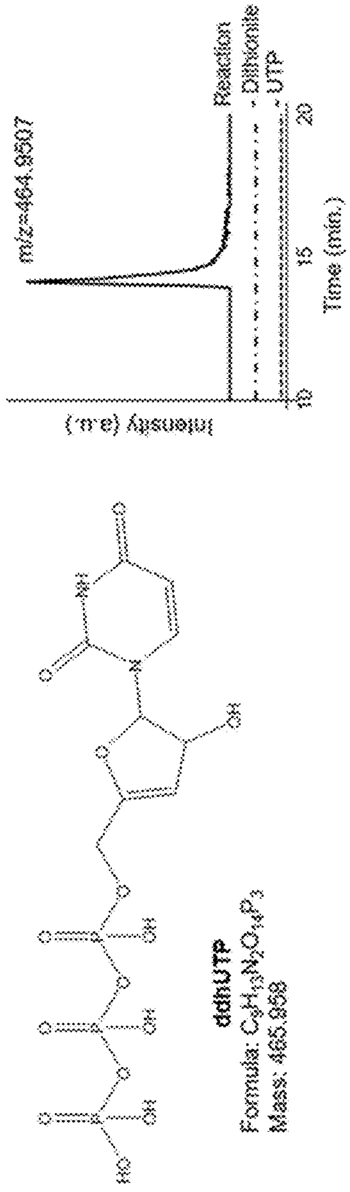
FIGS. 15A-15B shows LC-MS analysis indicating that pVips catalyze the conversion of UTP into ddhUTP.
Figure 15B:
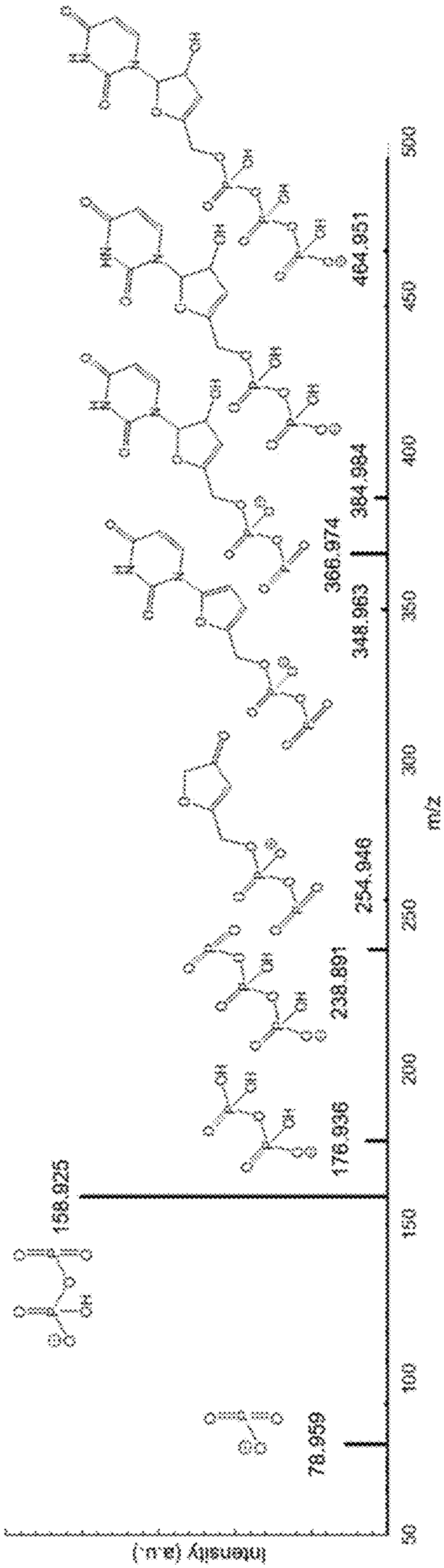
Figure 16A:
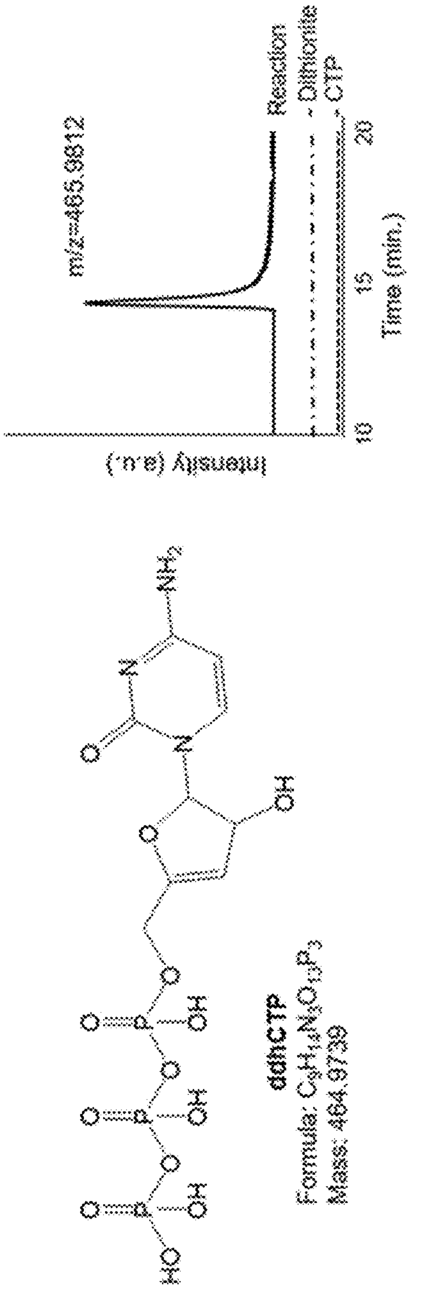
FIGS. 16A-16B shows LC-MS analysis indicating that pVips catalyze the conversion of CTP into ddhCTP.
Figure 16B:
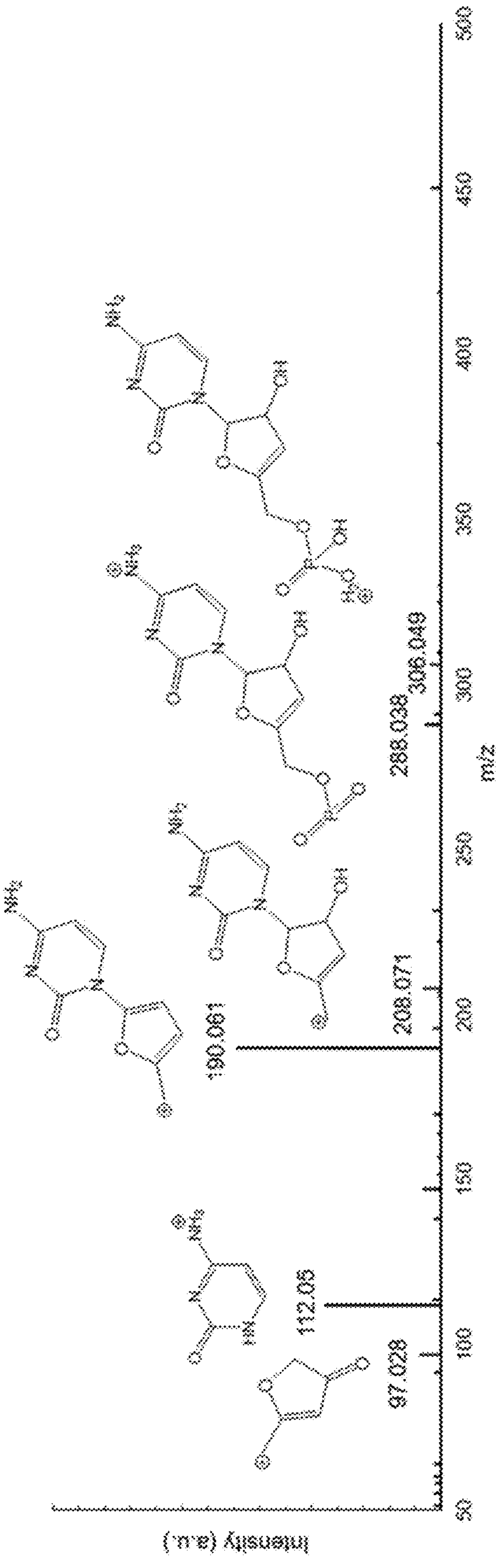
Figure 17A:
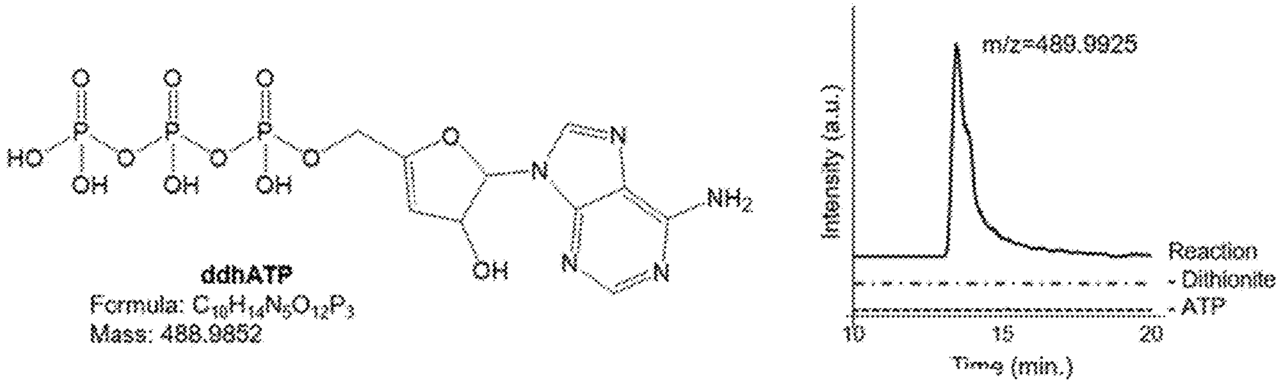
FIGS. 17A-17B shows LC-MS analysis indicating that pVips catalyze the conversion of ATP into ddhATP.
Figure 17B:
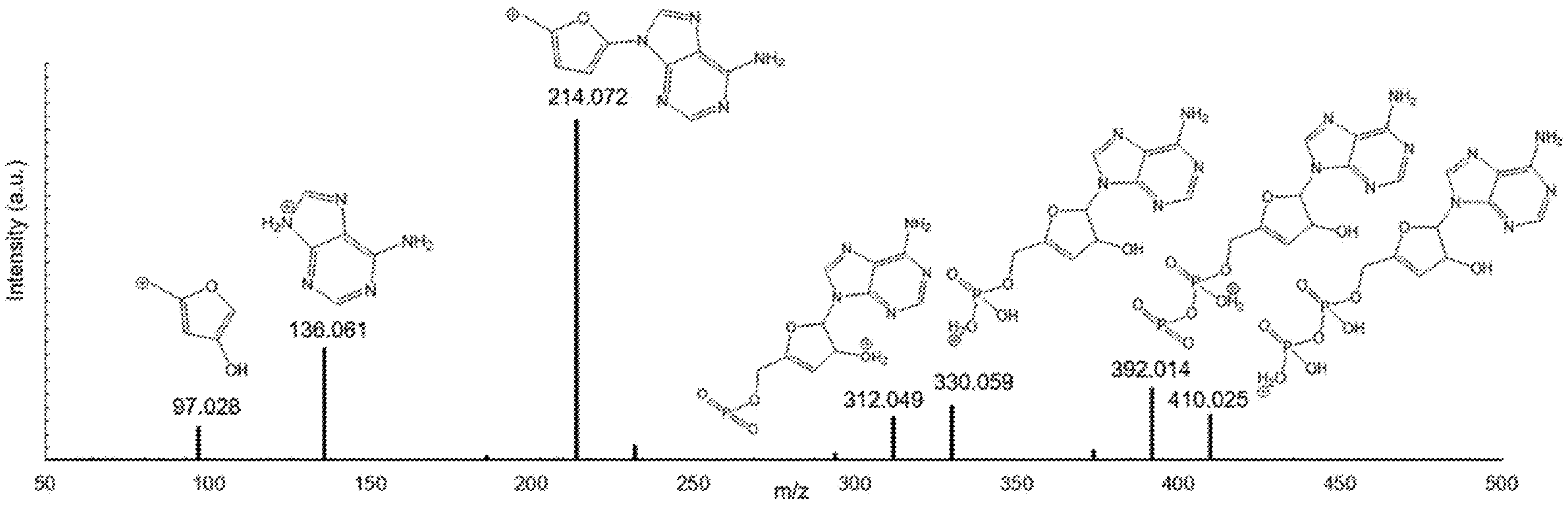
Figure 18A:
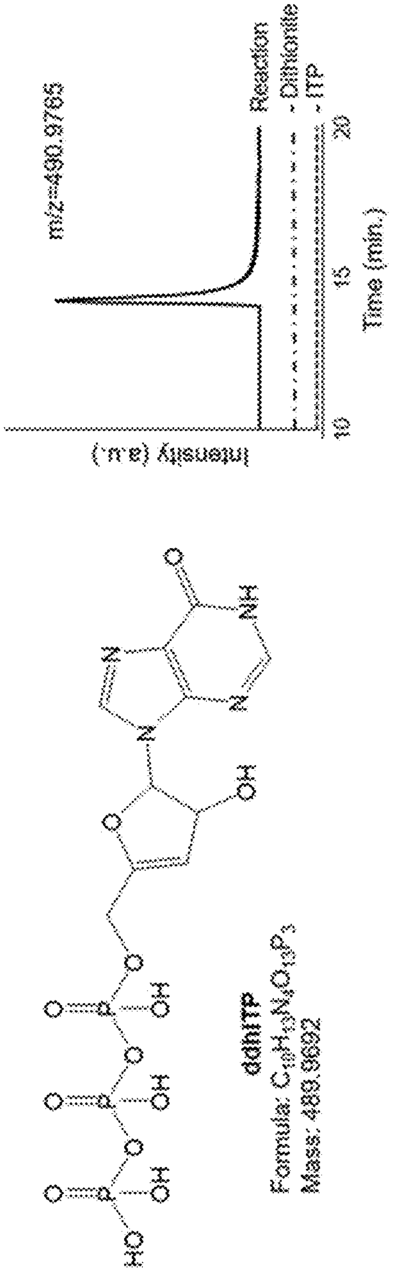
FIGS. 18A-18B shows LC-MS analysis indicating that pVips catalyze the conversion of ITP into ddhITP.
Figure 18B:
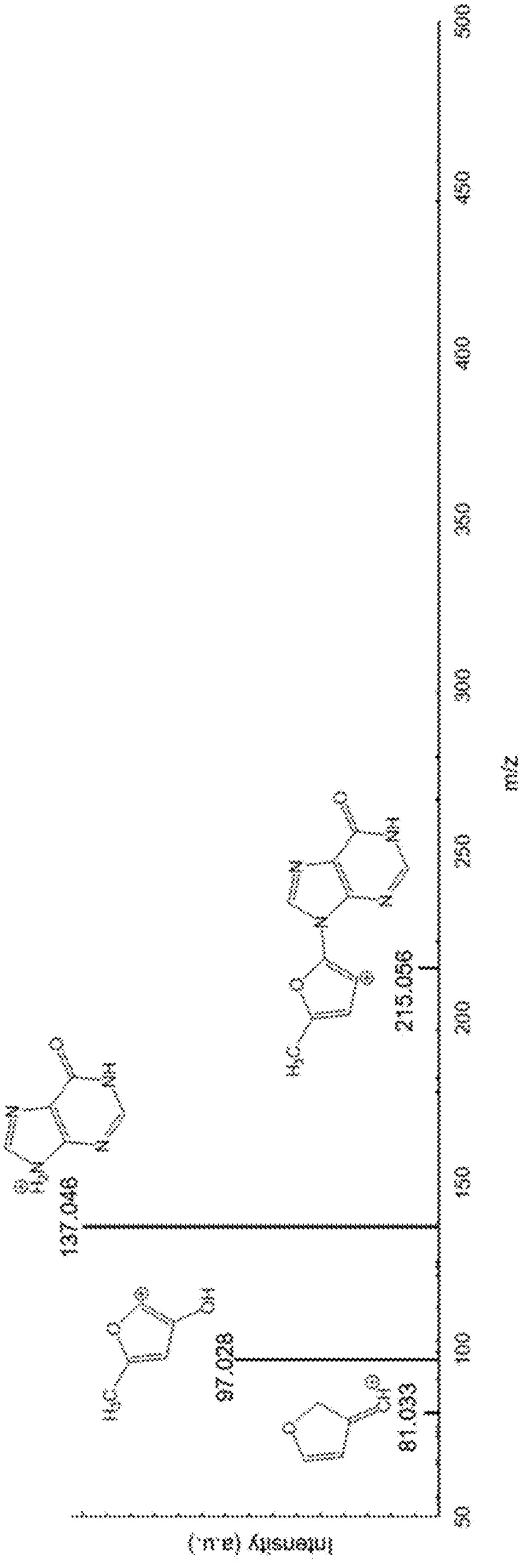
Figure 19A:
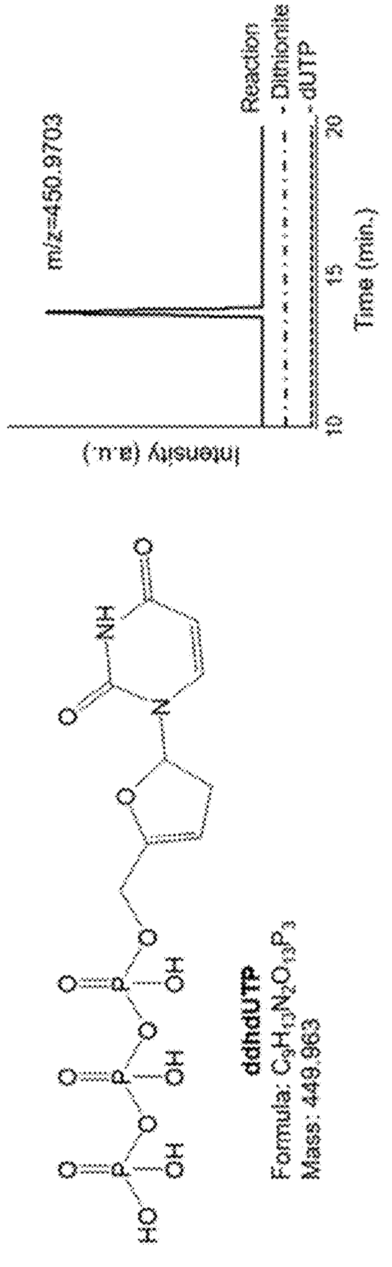
FIGS. 19A-19B shows LC-MS analysis indicating that pVips catalyze the conversion of dUTP into ddhdUTP.
Figure 19B:
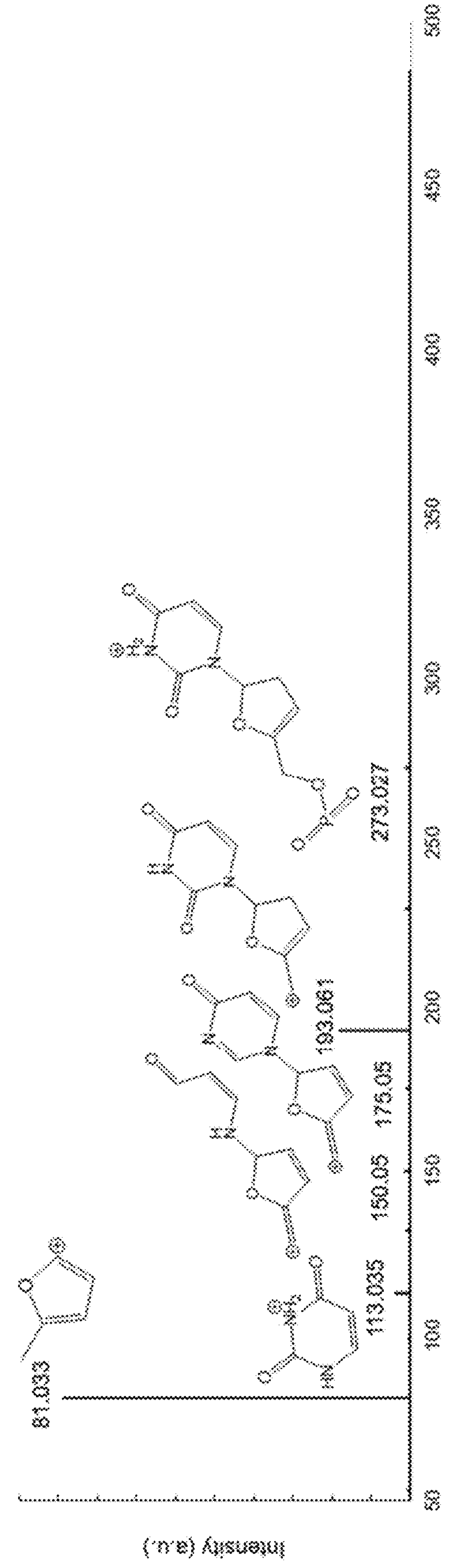
Figure 20A:
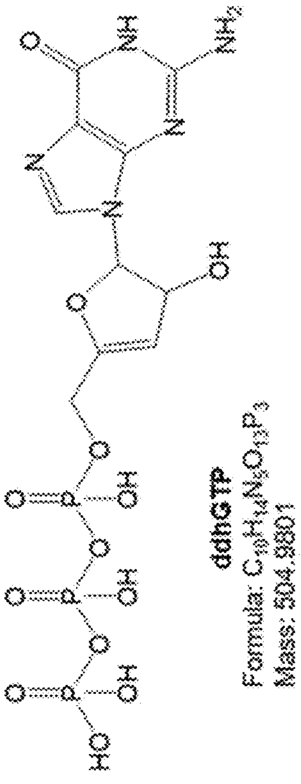
FIGS. 20A-20B shows LC-MS analysis indicating that pVips catalyze the conversion of GTP into ddhGTP.
Figure 20A:
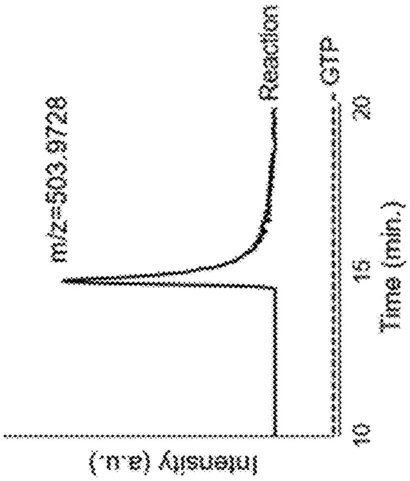
Figure 20B:
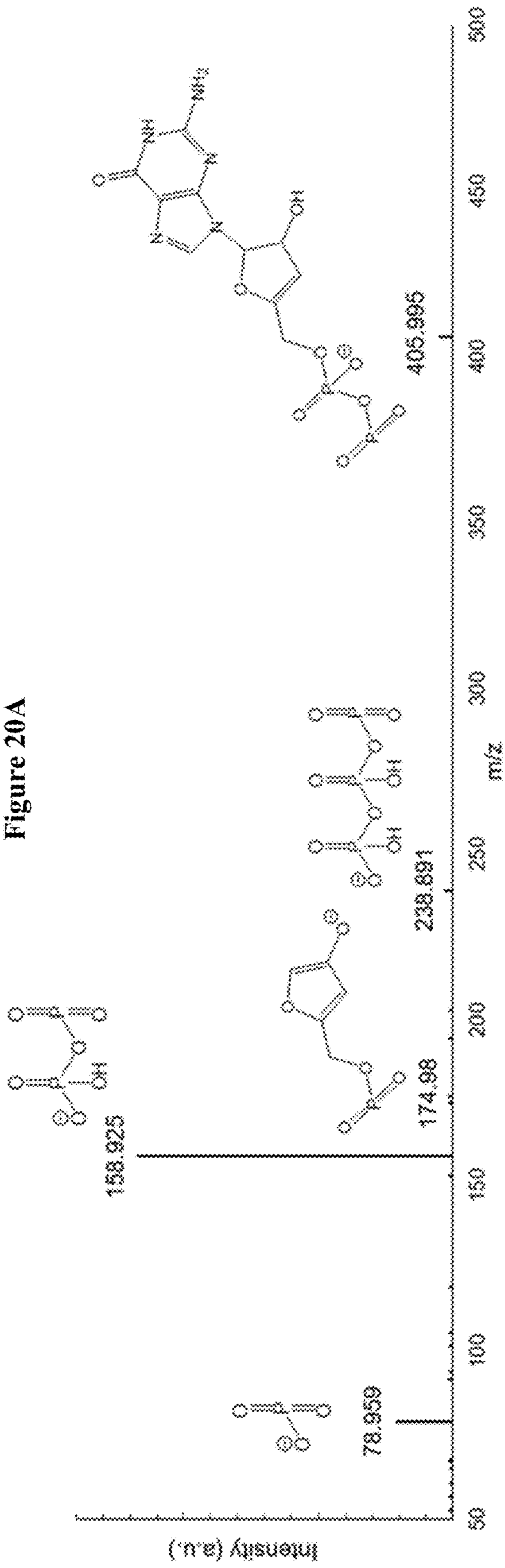

It was found that pVips from different evolutionary clades accept up to 6 natural nucleotides (ATP, CTP, GTP, ITP, UTP and dUTP) as substrates (FIG. 14). Furthermore, the reaction samples were analyzed by LC-MS in order to identify the products generated by the pVips. It was first confirmed that pVips catalyze the generation of a product with a mass that conforms to that of 3'-deoxy-3',4'-didehydro-nucleotides (ddhNTPs). The production of ddhUTP (FIGS. 15A-15B), ddhCTP (FIGS. 16A-16B), ddhATP (FIGS. 17A-17B), ddhITP (FIGS. 18A-18B) and ddhdUTP (FIGS. 19A-19B), and ddhGTP (FIGS. 20A-20B) by the pVips was further supported by the fragmentation spectrum of ions obtained via MS-MS, which displays masses corresponding to potential structures obtained from ddhNTPs.

The data reveal that pVips display, in vitro, a wider substrate range than the one predicted by in vivo analysis (see FIG. 14). For instance, only derivatives of ddhCTP were detected in lysates derived from pVip6-expressing cells (clade 1), suggesting that this enzyme could only catalyze the transformation of CTP. However, enzymatic assays presented herein demonstrate that CTP, UTP, ATP, GTP and ITP can all act as substrates. In the same manner, in vitro assays with pVip56 and pVip62 from clade 5, as well as pVip8 from clade 4, revealed that these enzymes accept more nucleotide substrates than reported by previous in vivo data. In conclusion, these in vitro results reveal that the substrate specificity of pVips is greater than the one reported for any other Viperin homologue from eukaryotic organisms.

Overall, the data presented herein demonstrate that pVips exhibit uniquely broad substrate promiscuity and catalyze in vitro the production of 3'-deoxy-3',4'-didehydro-variants of diverse natural nucleotide substrates. It was also shown that purified pVips can produce new molecules that were not described before, e.g. the production of the novel compounds ddhATP, ddhITP and ddhdUTP. These novel non-natural nucleotide analogs generated by pVips could hold new antiviral/anti-tumoral/antibacterial properties that can be harnessed to develop new therapies.

Example 12—Antiviral Assessment of Nucleoside Analogs

Objective: The objective of this study was to test ddh- and ddh-deoxy-compounds against Herpes simplex virus 1 (HSV-1), Human cytomegalovirus (HCMV), Epstein-Barr virus (EBV), BK virus (BKV), and JC virus (JCV).

Methods:

Table 12 sets forth the compounds tested.

TABLE 12 ddh- and ddh-deoxy-Compounds

| Name | MW | Amt |
|---|---|---|
| SATE-ddhU Compound 4 | 594.64 | 5.4 mg |
| SATE-ddhC Compound 6 | 593.65 | 4.3 mg |
| SATE-ddhG Compound 2 | 633.67 | 4.7 mg |
| SATE-ddhA Compound 1 | 617.68 | 4.4 mg |
| SATE-ddhI Compound 3 | 618.88 | 4.9 mg |
| SATE-ddhdeoxyU Compound 5 | 578.15 | 9.5 mg |

All compounds were solubilized by adding DMSO to each, based on quantities and molecular weights specified to achieve a final 30 mM concentration. These stocks were stored at 20° C. The working test compound solutions (1.5 mM) were prepared by diluting the 30 mM DMSO stocks 1:20 in warmed MEM+2% FBS. Positive and negative control drugs were prepared with working solutions at 1.5 and 1.0 mM in MEM+20% FBS.

Cells were infected with given virus and cultured in the presence of ddh- and ddh-deoxy compounds or controls. Cell viability was analyzed using a commercial assay according to the manufacturer's instructions (Promega, USA; CellTiter-Glo® Luminescent Cell Viability Assay), in cells infected with HSV-1, HCMV, EBV, BKV, or JCV.

Cells culture and virus strains. Human foreskin fibroblast (HFF) cells prepared from human foreskin tissue were obtained. The tissue was incubated at 4° C. for 4 h in Clinical Medium consisting of minimum essential media (MEM) with Earl's salts supplemented with 10% fetal bovine serum (FBS) (Hyclone, Inc. Logan UT), L-glutamine, fungizone, and vancomycin. Tissue is then placed in phosphate buffered saline (PBS), minced, rinsed to remove the red blood cells, and resuspended in trypsin/EDTA solution. The tissue suspension is incubated at 37° C. and gently agitated to disperse the cells, which are collected by centrifugation. Cells are resuspended in 4 ml Clinical Medium and placed in a 25 cm2 flask and incubated at 37° C. in a humidified $CO_2$ incubator for 24 h. The media is then replaced with fresh Clinical Medium and the cell growth is monitored daily until a confluent monolayer has formed. The HFF cells are then expanded through serial passages in standard growth medium of MEM with Earl's salts supplemented with 10% FBS, L-glutamine, penicillin, and gentamycin. The cells are passaged routinely and used for assays at or below passage 10. COS7 and C-33 A, Guinea Pig Lung, and Mouse embryo fibroblast cells were obtained from ATCC and maintained in standard growth medium of MEM with Earl's salts supplemented with 10% FBS, L-glutamine, penicillin, and gentamycin.

Akata cells were kindly provided by John Sixbey (Louisiana State University, Baton Rouge, LA). BCBL-1 cells were obtained through the NIH AIDS Research and Reference Reagent Program, Division of AIDS, NIAID, NIH. Molt-3 cells were obtained from Scott Schmid at the Centers for Disease Control and Prevention, Atlanta, GA. Lymphocytes were maintained routinely in RPMI 1640 (Mediatech, Inc., Herndon, VA) with 10% FBS, L-glutamine and antibiotics and passaged twice a week.

The E-377 strain of HSV-1 was a gift of Jack Hill (Burroughs Wellcome). The HCMV strain AD169, HSV-2 strain G, AdV5 strain Adenoid 75, GP CMV strain 11211 and MCMV strain were obtained from the American Type Culture Collection (ATCC, Manassas, VA). The Copenhagen strain of VACV and Brighton strain, CPXV were kindly provided by John W. Huggins (Department of Viral Therapeutics, Virology Division, United States Army Medical Research Institute of Infections Disease). VZV, strain Ellen, the BK virus Gardner strain and JC virus MAD4 strain were obtained from the ATCC. Akata cells latently infected with EBV were obtained from John Sixbey. The Z29 strain of HHV-6B was a gift of Scott Schmid at the Centers for Disease Control and Prevention, Atlanta GA. HHV-8 was obtained as latently infected BCBL-1 cells through the NIH AIDS Research and Reference Reagent Program.

Antiviral Assays: Each experiment that evaluated the antiviral activity of the compounds included both positive and negative control compounds to ensure the performance of each assay. Concurrent assessment of cytotoxicity was also performed for each study in the same cell line and with the same compound exposure (see below).

CPE assays for HSV-1, HSV-2, VZV, HCMV, MCMV, GPCMV, AdV, VACV, CPXV Assays were performed in monolayers as described (Hartline C B, Keith K A, Eagar J, Harden E A, Bowlin T L, Prichard M N. Antiviral Res. 2018. A standardized approach to the evaluation of antivirals against DNA viruses: Orthopox-, adeno-, and herpesviruses. November; 159:104-112). Briefly, cells were seeded in 384 well plates and incubated for 24 h to allow the formation of confluent monolayers. Dilutions of test drug were prepared directly in the plates and the monolayers infected at a predetermined MOI based on virus used. After incubation, cytopathology was determined by the addition of CellTiter-Glo (CTG) reagent. Concentrations of test compound sufficient to reduce CPE by 50% (EC50) or decrease cell viability by 50% (CC50) were interpolated using standard methods in Microsoft excel.

Plaque reduction assays for HSV-1, HSV-2, VZV, HCMV, MCMV, GPCMV, VACV, CPXV. Monolayers of HFF cells were prepared in six-well plates and incubated at 37° C. for 2 d to allow the cells to reach confluency. Media was then aspirated from the wells and 0.2 ml of virus was added to each of three wells to yield 20-30 plaques in each well. The virus was allowed to adsorb to the cells for 1 h and the plates were agitated every 15 minutes. Compounds were diluted in assay media consisting of MEM with Earl's salts supplemented with 2% FBS, L-glutamine, penicillin, and gentamycin. Diluted drug was added to duplicate wells and the plates were incubated for various times, depending on the virus used. For HSV-1 and -2, the monolayers were then stained with 1% crystal violet in 20% methanol and the unbound dye removed by washing with $dH_2O$. For all other assays, the cell monolayer was stained with 1% Neutral Red solution for 4 h then the stain was aspirated and the cells were washed with PBS. For all assays, plaques were enumerated using a stereomicroscope and the concentration of compound that reduced plaque formation by 50% ($EC_{50}$) was interpolated from the experimental data.

Yield reduction assays for HSV-1, HSV-2, HCMV, VACV, CPXV and AdV. Monolayers of HFF cells were prepared in 96-well plates and incubated at 37° C. for 1 d to allow the cells to reach confluency. Media was then aspirated from the wells and cells infected at a high MOI. At 1 h following infection, the inocula were removed and the monolayers rinsed with fresh media. Compounds were then diluted in assay media consisting of MEM with Earl's salts supplemented with 2% FBS, L-glutamine, penicillin, and gentamycin. Drug dilutions were added to the wells and the plates were incubated for various times, depending on the virus used and represents a single replication cycle for the virus. A duplicate set of dilutions were also performed but remained uninfected to serve as a cytotoxicity control and received equal compound exposure. Supernatants from each of the infected wells were subsequently titered in a TCID50 assay to quantify the progeny virus. For the cytotoxicity controls, cytotoxicity was assed using CTG according to the manufacturer's suggested protocol. For all assays, the concentration of compound that reduced virus titer by 90% ($EC_{90}$) was interpolated from the experimental data.

Assays for EBV, HHV-6B, and HHV-8. Assays for EBV, HHV-6B and HHV-8 were performed by methods we reported previously (Keith K A, Hartline C B, Bowlin T L, Prichard M N. Antiviral Res. 2018. A standardized approach to the evaluation of antivirals against DNA viruses: Polyomaviruses and lymphotropic herpesviruses). Akata cells were induced to undergo a lytic infection with 50 μg/ml of a goat anti-human IgG antibody. Experimental compounds were diluted within plates; the cells were added and incubated for 72 h. For HHV-6 assays, compounds were serially diluted plates then uninfected Molt-3 cells were added to each well. Infection was initiated by adding HHV-6B infected Molt-3 cells, at a ratio of approximately 1 infected cell for every 10 uninfected cells. Assay plates were incubated for seven days at 37° C. Assays for HHV-8 were performed in BCBL-1 cells. Similar plates were initiated without virus induction/addition and used for measuring cytotoxicity by the addition of CTG. For all assays, the replication of the virus was assessed by the quantification of viral DNA by PCR. Compound concentrations sufficient to reduce genome copy number by 50% were calculated from experimental datas well as compound cytotoxicity.

Assays for BK virus and JC virus. Primary assays for BKV and JCV were performed by methods we reported previously (Keith et al. 2018; ibid). For BKV, compound dilutions were prepared in plates containing cells, subsequently infected and incubated for 7 d. Total DNA was prepared and genome copy number was quantified by real time PCR (Leung A Y, Suen C K, Lie A K, Liang R H, Yuen K Y, Kwong Y L. Quantification of polyoma BK viruria in hemorrhagic cystitis complicating bone marrow transplantation. Blood. 2001; 98(6):1971-8). Plasmid pMP526 serves as the DNA standard for quantification purposes. Compounds that were positive in this assay were confirmed in a similar assay in 96-well plates according to established laboratory protocols with the compounds added 1 h post infection to identify compounds that inhibit early stages of replication including adsorption and penetration. Genome copy number was determined by methods described above.

Primary evaluation of compounds against JC virus were also performed by methods similar to those for BK virus primary assays but were done in COS7 cells and utilized the 1-4 strain of JCV in COS7 cells. Viral DNA was quantified using PCR. Secondary assays against JCV were also performed in COS7 cells by methods similar to those for BK virus to identify compounds that inhibited adsorption or penetration of the virus.

Assays for HPV

Primary assay: An HPV11 replicon assay was developed and expresses the essential E1 and E2 proteins from the native promoter. The E2 origin binding protein interacts with the virus origin of replication and recruits the E1 replicative helicase which unwinds the DNA and helps to recruit the cellular DNA replication machinery (including DNA polymerases, type I and type II topoisomerases, DNA ligase, single-stranded DNA binding proteins, proliferating cell nuclear antigen). The replication complex then drives the amplification of the replicon which can be assessed by the expression of a destabilized NanoLuc reporter gene carried on the replicon. In this assay, the replicon (pMP619) is transfected into C-33 A cells grown as monolayers in 384-well plates. At 48 h post transfection, the enzymatic activity of the destabilized NanoLuc reporter is assessed with NanoGlo reagent. The reference compound for this assay is PMEG and its EC50 value is within the prescribed range of 2-9.2 μM and is similar to a compound as reported previously (Beadle J R, Valiaeva N, Yang G, Yu J H, Broker T R, Aldern K A, et al. Synthesis and Antiviral Evaluation of Octadecyloxyethyl Benzyl 9-[(2-Phosphonomethoxy) ethyl]guanine (ODE-Bn-PMEG), a Potent Inhibitor of Transient HPV DNAmplification. J Med Chem. 2016; 59(23): 10470-8).

Results:

There were no problems with solubility of the compounds in DMSO or in MEM+2% FBS. For each assay using virus infected cells, the concentrations of ddh- and ddh-deoxy-compounds ranged from 0.048-150 μM (HSV-1; HCMV; EBV (also tested drug concentrations of 0.032-100); BKV; and JCV). Similarly, control drug concentration ranged from 0.048-150 μM. The results are presented in Tables 13 and 14 below:

Assay Against Epstein-Barr Virus (EBV)

| | Strain | Cell Line | Incubation | Assay Name |
|---|---|---|---|---|
| EBV | Akata | Akata | 3 d | Quantitative Polymerase Chain Reaction (DNA)/Cell Titer-Glo (Toxicity) |

TABLE 13

Effect of ddh- and ddh-deoxy-compounds in cells infected with EBV

| Drug | Activity | $EC_{50}$ | $EC_{90}$ | $CC_{50}$ | $SI_{50}$ | $SI_{90}$ |
|---|---|---|---|---|---|---|
| CDV | — | 9.23 | 29.89 | >100.00 | >11 | >3 |
| TNV | — | 45.76 | >150.00 | >150.00 | >3 | 1 |
| SATE-ddhU Compound 4 | NA | >30.00 | >30.00 | 108.58 | <4 | <4 |
| SATE-ddhC Compound 6 | MOD | 18.76 | >30.00 | 123.78 | 7 | <4 |
| SATE-ddhG Compound 2 | HI | 2.98 | >30.00 | 105.71 | 35 | <4 |
| SATE-ddhA Compound 1 | MOD | 12.89 | 26.79 | 55.82 | 4 | 2 |
| SATE-ddhI Compound 3 | MOD | 18.75 | 81.93 | >150.00 | >8 | >2 |
| SATE-ddhdeoxyU Compound 5 | NA | 79.81 | >150.00 | >150.00 | >2 | 1 |

CDV—Cidofovir - positive control, TNV—Tenofovir - negative control, NA (Not Active) $SI_{50}$ = 0-3.9, MOD (Moderately Active) $SI_{50}$ = 4-9.9, HI (Highly Active) $SI_{50}$ = ≥10.

Assay Against BK Virus (BKV)

| | Strain | Cell Line | Incubation | Assay Name |
|---|---|---|---|---|
| BKV | Gardner | HFF | 7 d | Quantitative Polymerase Chain Reaction (DNA)/Cell Titer-Glo (Toxicity) |

TABLE 14

Effect of ddh- and ddh-deoxy-compounds in cells infected with BKV

| Drug | Activity | $EC_{50}$ | $EC_{90}$ | $CC_{50}$ | $SI_{50}$ | $SI_{90}$ |
|---|---|---|---|---|---|---|
| CDV | — | 4.30 | 24.05 | >150.00 | >35 | >6 |
| TNV | — | >150.00 | >150.00 | >150.00 | 1 | 1 |
| SATE-ddhU Compound 4 | LO | 21.28 | >150.00 | >150.00 | >7 | 1 |
| SATE-ddhC Compound 6 | NA | 96.04 | >150.00 | >150.00 | >2 | 1 |
| SATE-ddhG Compound 2 | HI | 5.32 | 5.86 | >150.00 | >28 | >26 |
| SATE-ddhA Compound 1 | NA | >30.00 | >30.00 | 89.65 | <3 | <3 |
| SATE-ddhI Compound 3 | NA | 115.28 | >150.00 | >150.00 | >1 | 1 |
| SATE-ddhdeoxyU Compound 5 | NA | 111.30 | >150.00 | >150.00 | >1 | 1 |

CDV—Cidofovir - positive control, TNV—Tenofovir - negative control, NA (Not Active) $SI_{50}$ = 0-3.9, LO (Slightly Active) $SI_{50}$ = 4-9.9, MOD (Moderately Active) $SI_{50}$ = 10-19.9, HI (Highly Active) $SI_{50}$ = ≥20.

Summary: SATE-ddhC (Compound 6), SATE-ddhA (Compound 1), and SATE-ddhI (Compound 3) were moderately active against EBV. SATE-ddhG was highly active against both EBV and BK virus.

Example 13—In Vitro Antiviral Activity Against Influenza Viruses

Objective: The objective of this study was to test ddh- and ddh-deoxy-compounds against influenza viruses including SARS-CoV-2, MERS-CoV, Influenza(H1N1)pdm09, Influenza B, RSV, A2, Enterovirus-68, Tacaribe virus, and Dengue virus.

Methods: Compounds tested included SATE-ddhU (Compound 4), SATE-ddhC (Compound 6), SATE-ddhG (Compound 2), SATE-ddhA (Compound 1), and SATE-ddhI (Compound 3). These compounds were tested against a panel of viruses including SARS-CoV-2 (USA-WA1/2020), MVERSCoV (EMC), influenza/California/07/2009 (H1N1) pdm09, Influenza B/Florida/4/2006 (Yamagata), enterovirus-68 (EV-68, US/DY/14-18953), respiratory syncytial virus (RSV, A2), Tacaribe virus (TCRV, TRVL-11573), and dengue virus-2 (DENV-2, New Guinea C). For SARS-CoV-2 and MVERS-CoV, Vero 76 cells were used, and test media was MEM supplemented with 2% FBS and 50 μg/mL gentamicin. MDCK cells were used for influenza viruses and test media was MEM supplemented with 10 IU/mL trypsin, 1 μg/mL EDTA, and gentamicin. MA-104 cells were used for RSV and test media was MEM with 5% FBS and gentamicin. RD cells were used for EV68 and test media was MEM with 2% FBS, 25 μg/mL MgC12, and gentamicin. Vero cells were used for TCRV and test media was MEM with 2% FBS and gentamicin. Huh7 cells were used for DENV and test media was MEM with 5% FBS and gentamicin.

SATE-ddhU (Compound 4), SATE-ddhC (Compound 6), SATE-ddhG (Compound 2), SATE-ddhA (Compound 1), and SATE-ddhI (Compound 3) were in powder form. Compounds were solubilized in DMSO to prepare 200 mM stock solutions. Compounds were then serially diluted using eight half-log dilutions in test medium so that the starting (high) test concentration was 100 μM for EV-68 and MERS-CoV and 1000 μM for all other viruses.

Each dilution was added to 5 wells of a 96-well plate with 60-100% confluent cells. Three wells of each dilution were infected with virus, and two wells remained uninfected as toxicity controls. Six wells were infected and untreated as virus controls, and six wells were uninfected and untreated as cell controls. Viruses were prepared to achieve the lowest possible multiplicity of infection (MOI) that would yield >80% cytopathic effect (CPE) within 3-6 days. A positive control compound was tested in parallel for each virus tested.

Plates were incubated at 37±2° C. and 5% $CO_2$ for all viruses except EV-68, which was incubated at 33±2° C. and 5% $CO_2$.

On day 3-6 post-infection, once untreated virus control wells reached maximum CPE, plates were stained with neutral red dye for approximately 2 hours (±15 minutes). Supernatant dye was removed and wells rinsed with PBS, and the incorporated dye was extracted in 50:50 Sorensen citrate buffer/ethanol for >30 minutes and the optical density was read on a spectrophotometer at 540 nm. Optical densities were converted to percent of cell controls and normalized to the virus control, then the concentration of test compound required to inhibit CPE by 50% ($EC_{50}$) was calculated by regression analysis. The concentration of compound that would cause 50% cell death in the absence of virus was similarly calculated ($CC_{50}$). The selective index (SI) is the $CC_{50}$ divided by $EC_{50}$.

Results:

In vitro antiviral results are shown in Tables 15-19. SATE-ddhU (Compound 4) was active against SARS-CoV-2 (SI=3.5). SATE-ddhU (Compound 4), SATE-ddhC (Compound 6), SATE-ddhG (Compound 2), SATE-ddhA (Compound 1), SATE-ddhI (Compound 3) were not active against the other viruses tested. The positive control compounds performed as expected (Table 20).

TABLE 15

In vitro antiviral activity of SATE-ddhU (Compound 4), against a panel of viruses

| | Positive | SATE-ddhU | | |
|---|---|---|---|---|
| Virus | Control | EC50 | CC50 | SI50 |
| SARS-CoV-2 | Z-LEU-GLN(NME2)-FMK | 22 | 76 | 3.5 |
| MERS-CoV | Z-LEU-GLN(NME2)-FMK | >100 | >100 | 0 |
| Influenza(H1N1) | Ribavirin | >560 | 560 | 0 |
| Influenza B | Ribavirin | >560 | 560 | 0 |
| EV-68 | Enviroxime | >100 | >100 | 0 |
| RSV | Ribavirin | >180 | 180 | 0 |
| TCRV | Ribavirin | >170 | 170 | 0 |
| DENV-2 | Infergen | >160 | 160 | 0 |

Units are in gM
EC50: 50% effective antiviral concentration
CC50: 50% cytotoxic concentration of compound without virus added
SI = CC50/EC50

TABLE 16

In vitro antiviral activity of SATE-ddhC (Compound 6), against a panel of viruses

| | Positive | SATE-ddhC | | |
|---|---|---|---|---|
| Virus | Control | EC50 | CC50 | SI |
| SARS-CoV-2 | Z-LEU-GLN(NME2)-FMK | >410 | 410 | 0 |
| MERS-CoV | Z-LEU-GLN(NME2)-FMK | >100 | >100 | 0 |
| Influenza(H1N1) | Ribavirin | >550 | 550 | 0 |
| Influenza B | Ribavirin | >1000 | >1000 | 0 |
| EV-68 | Enviroxime | >100 | >100 | 0 |
| RSV | Ribavirin | >540 | 540 | 0 |
| TCRV | Ribavirin | >210 | 210 | 0 |
| DENV-2 | Infergen | >71 | 71 | 0 |

Units are in gM
EC50: 50% effective antiviral concentration
CC50: 50% cytotoxic concentration of compound without virus added
SI = CC50/EC50

TABLE 17

In vitro antiviral activity of SATE-ddhG Compound 2 against a panel of viruses

| | Positive | SATE-ddhG | | |
|---|---|---|---|---|
| Virus | Control | EC50 | CC50 | SI |
| SARS-CoV-2 | Z-LEU-GLN(NME2)-FMK | >1000 | >1000 | 0 |
| MERS-CoV | Z-LEU-GLN(NME2)-FMK | >100 | >100 | 0 |
| Influenza(H1N1) | Ribavirin | >1000 | >1000 | 0 |
| Influenza B | Ribavirin | >1000 | >1000 | 0 |
| EV-68 | Enviroxime | >83 | 83 | 0 |
| RSV | Ribavirin | >1000 | >1000 | 0 |
| TCRV | Ribavirin | >610 | 610 | 0 |
| DENV-2 | Infergen | >150 | 150 | 0 |

Units are in gM
EC50: 50% effective antiviral concentration
CC50: 50% cytotoxic concentration of compound without virus added
SI = CC50/EC50

TABLE 18

In vitro antiviral activity of SATE-ddhA Compound 1 against a panel of viruses

| | Positive | SATE-ddhA | | |
|---|---|---|---|---|
| Virus | Control | EC50 | CC50 | SI50 |
| SARS-CoV-2 | Z-LEU-GLN(NME2)-FMK | >49 | 49 | 0 |
| MERS-CoV | Z-LEU-GLN(NME2)-FMK | >100 | >100 | 0 |
| Influenza(H1N1) | Ribavirin | >180 | 180 | 0 |
| Influenza B | Ribavirin | >180 | 180 | 0 |
| EV-68 | Enviroxime | >2 | 2 | 0 |
| RSV | Ribavirin | >170 | 170 | 0 |
| TCRV | Ribavirin | >58 | 58 | 0 |
| DENV-2 | Infergen | >14 | 14 | 0 |

Units are in gM
EC50: 50% effective antiviral concentration
CC50: 50% cytotoxic concentration of compound without virus added
SI = CC50/EC50

TABLE 19

| In vitro antiviral activity of SATE-ddhI Compound 3 against a panel of viruses | | | | |
|---|---|---|---|---|
| | Positive | SATE-ddhI | | |
| Virus | Control | EC50 | CC50 | SI50 |
| SARS-CoV-2 | Z-LEU-GLN(NME2)-FMK | >530 | 530 | 0 |
| MERS-CoV | Z-LEU-GLN(NME2)-FMK | >100 | >100 | 0 |
| Influenza(H1N1) | Ribavirin | >1000 | >1000 | 0 |
| Influenza B | Ribavirin | >1000 | >1000 | 0 |
| EV-68 | Enviroxime | >100 | >100 | 0 |
| RSV | Ribavirin | >1000 | >1000 | 0 |
| TCRV | Ribavirin | >900 | 900 | 0 |
| DENV-2 | Infergen | >150 | 150 | 0 |

Units are in gM for test compounds; gg/mL Ribavirin, Z-LEU-GLN(NME2)-FMK, and Enviroxime; and ng/mL for Infergen
EC50: 50% effective antiviral concentration
CC50: 50% cytotoxic concentration of compound without virus added
SI = CC50/EC50

TABLE 20

| In vitro antiviral activity of positive controls against a panel of viruses | | | | |
|---|---|---|---|---|
| | Positive | Positive Control | | |
| Virus | Control | EC50 | CC50 | SI50 |
| SARS-CoV-2 | Z-LEU-GLN(NME2)-FMK | 0.089 | >100 | >1100 |
| MERS-CoV | Z-LEU-GLN(NME2)-FMK | 8 | >100 | >13 |
| Influenza(H1N1) | Ribavirin | 7.6 | >1000 | >130 |
| Influenza B | Ribavirin | 7.7 | >1000 | >130 |
| EV-68 | Enviroxime | 0.12 | 5.5 | 46 |
| RSV | Ribavirin | 19 | 310 | 16 |
| TCRV | Ribavirin | 5.3 | >1000 | >190 |
| DENV-2 | Infergen | 0.045 | >10 | >220 |

Units are jug/mL Ribavirin, Z-LEU-GLN(NME2)-FMK, and Enviroxime; and ng/mL for Infergen
EC50: 50% effective antiviral concentration
CC50: 50% cytotoxic concentration of compound without virus added
SI = CC50/EC50

Example 14—In Vitro Antiviral Activity Against SARS-CoV-2

Objective: The objective of this study was to test ddh-compounds SATE-ddhU (Compound 4) and SATE-ddhC (Compound 6) against SARS-CoV-2.

Methods:

SARS-CoV-2 (USA-WA1/2020) stocks were prepared by growing virus in Vero 76 cells. Test media was MEM supplemented with 2% FBS and 50 μg/mL gentamicin.

SATE-ddhU (Compound 4) and SATE-ddhC (Compound 6) were in powder form. The compounds were solubilized in DMSO to prepare a 200 mM stock solution. The compounds were then serially diluted using eight half-log dilutions in test medium so that the starting (high) test concentration was 100 μM. Each dilution was added to 5 wells of a 96-well plate with 80-100% confluent cells. Three wells of each dilution were infected with virus, and two wells remained uninfected as toxicity controls. Six wells were infected and untreated as virus controls, and six wells were uninfected and untreated as cell controls. SARS-CoV-2 was prepared to achieve the lowest possible multiplicity of infection (MOI) that would yield >80% cytopathic effect (CPE) within 5 days. A positive control compound was tested in parallel for each virus tested. Plates were incubated at 37±2° C. and 5% $CO_2$.

The test was set up as described above in two replicates. For one test, all media was removed from plates and replaced with fresh compound on day 1 and 2 post-infection (p.i.). The plates were stained on day 3 p.i. as described below. For the second test, media was not replaced daily, but the plate was stained and virus yield reduction (VYR) assay was performed as described below on day 2 p.i.

On day 3 p.i., once untreated virus control wells reached maximum CPE, plates were stained with neutral red dye for approximately 2 hours (±15 minutes). Supernatant dye was removed and wells rinsed with PBS, and the incorporated dye was extracted in 50:50 Sorensen citrate buffer/ethanol for >30 minutes and the optical density was read on a spectrophotometer at 540 nm. Optical densities were converted to percent of cell controls and normalized to the virus control, then the concentration of test compound required to inhibit CPE by 50% ($EC_{50}$) was calculated by regression analysis. The concentration of compound that would cause 50% cell death in the absence of virus was similarly calculated ($CC_{50}$). The selective index (SI) is the $CC_{50}$ divided by $EC_{50}$.

For VYR, the supernatant fluid from each compound concentration was collected on day 2 p.i., before neutral red staining (3 wells pooled) and tested for virus titer using a standard endpoint dilution CCID50 assay and titer calculations using the Reed-Muench (1948) equation. The concentration of compound required to reduce virus yield by 1 log 10 (EC90) was calculated by regression analysis.

Results:

In vitro antiviral results are shown in Table 21. SATE-ddhU (Compound 4) was active against SARS-CoV-2 when media was replaced with fresh compound daily (SI>6.7, Table 21).

The positive control compound performed as expected.

TABLE 21

| In vitro antiviral activity of SATE-ddhU against SARS-CoV-2 when compound was replenished daily. | | | |
|---|---|---|---|
| Compound | EC50 | CC50 | SI50 |
| SATE-ddhU | 15 | >100 | >6.7 |
| Z-LEU-GLN(NME2)-FMK | 0.38 | >100 | >260 |

Units are in pM for test compound and pg/mL for Z-LEU-GLN(NME2)-FMK
EC50: 50% effective antiviral concentration
CC50: 50% cytotoxic concentration of compound without virus added
SI = CC50/EC50

Example 15—Experimental Procedures for the Synthesis of Compounds
Objective: To synthesize embodiments of prodrug compounds disclosed herein.
Synthetic Approach for Compounds 5, 13 and 11
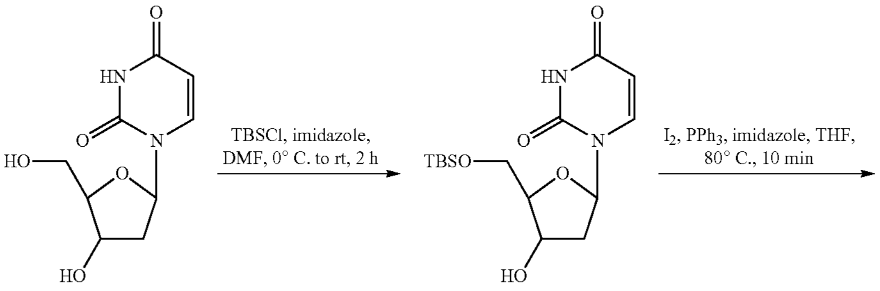
7
8
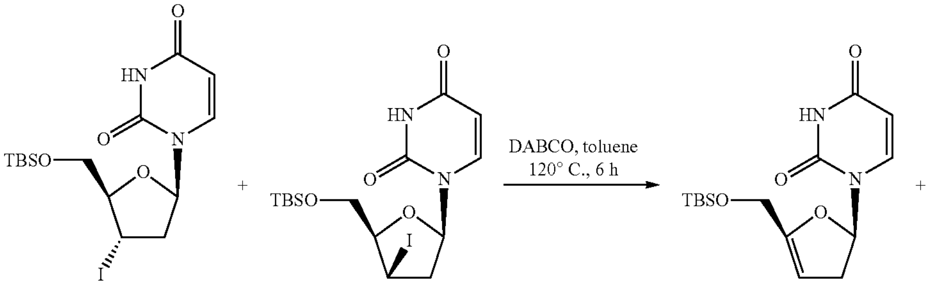
9′
9
10
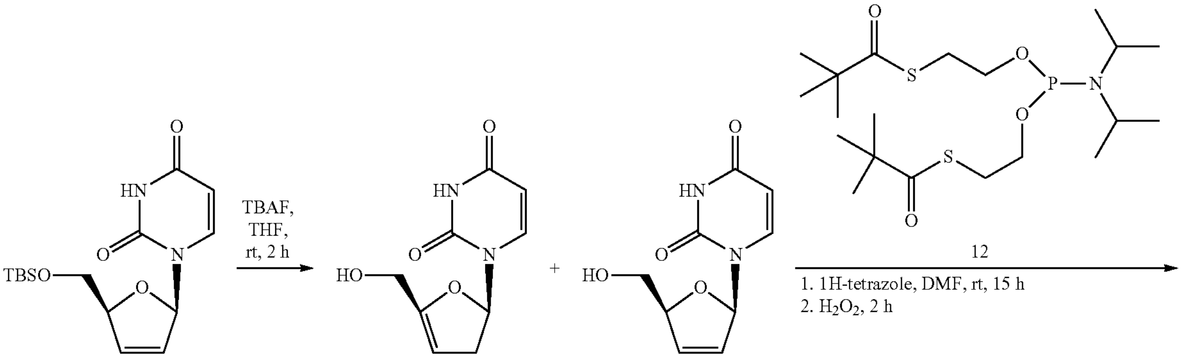
10′
11
AB23028
17 mg
obtained by Prep-HPLC
MeCN-H2O
11′
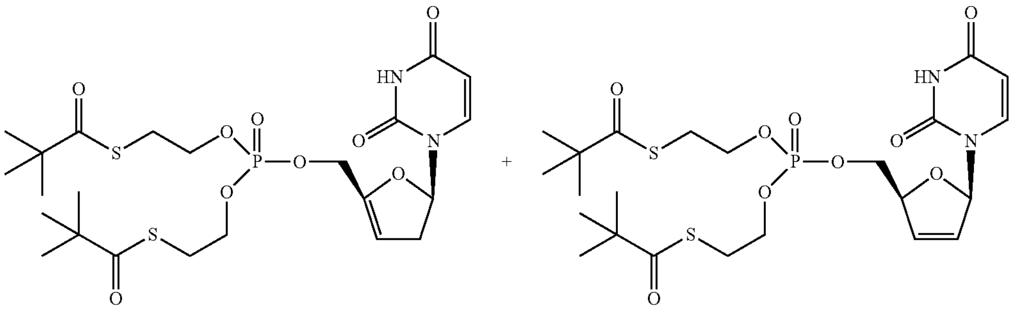
5
AB23026
45 mg shipped
13
AB23027
19 mg shipped
obtained by Prep-HPLC MeCN-H2O Procedure General Procedure for the Preparation of Compound 8

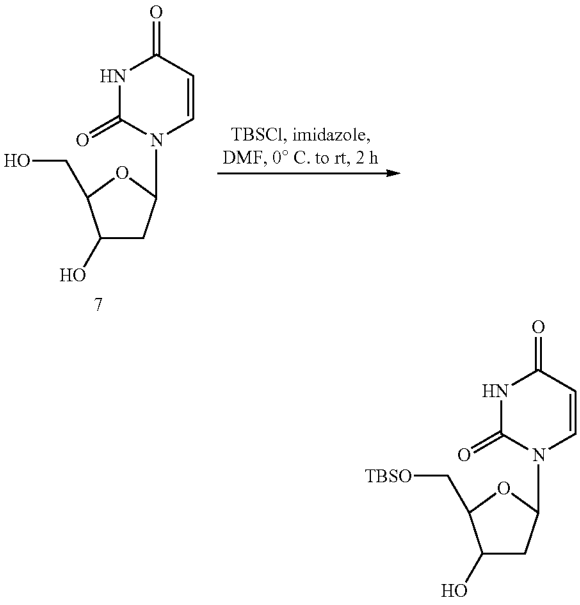

7

8

To a solution of compound 7 (10.0 g, 43.8 mmol, 1.0 eq) in dry DMF (100 mL) at 0° C. was added imidazole (14.9 g, 219 mmol, 5.0 eq) and TBSCl (9.9 g, 65.7 mmol, 1.5 eq) sequentially. The mixture was allowed to warm to room temperature. After being stirred at room temperature for 2 h, the mixture was poured into water and extracted with EtOAc. After evaporation of the solvent, the residue was purified by flash column chromatography (dichloromethane/methanol, 10/1) to afford 8 (14.5 g, 97%) as a white solid.

General Procedure for the Preparation of Compound 9 and 9'

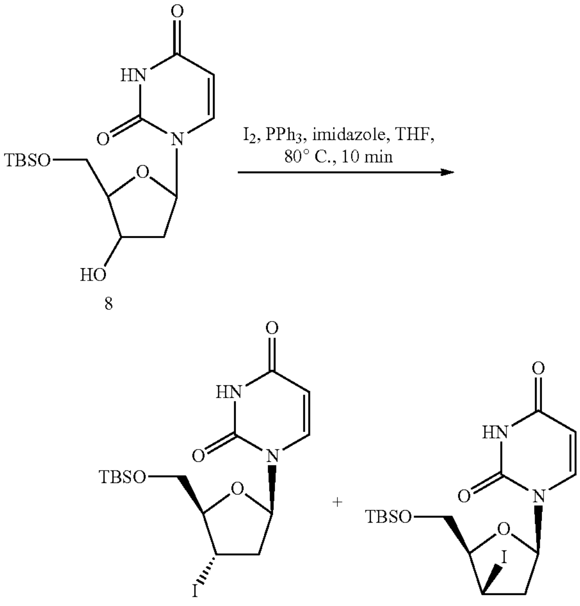

8

9'

9

To a solution of compound 8 (5.4 g, 15.8 mmol, 1.0 eq) in dry THF (100 mL) at room temperature was added imidazole (2.15 g, 31.6 mmol, 2.0 eq), $PPh_3$ (6.2 g, 23.7 mmol, 1.5 eq) and $I_2$ (6.0 g, 23.7 mmol, 1.5 eq) sequentially. Then the mixture was heated to 80° C. After being stirred at 80° C. for 10 min, the reaction mixture was cooled to room temperature, quenched with saturated aqueous $Na_2S_2O_3$ and extracted with EtOAc. The organic layer was further washed with saturated aqueous $Na_2HCO_3$ and water. After evaporation of the solvent, the residue was purified by flash column chromatography (petroleum ether/EtOAc, 1/1) to afford 9 and 9' (3.29 g) as white foams.

General Procedure for the Preparation of Compound 10 and 10'

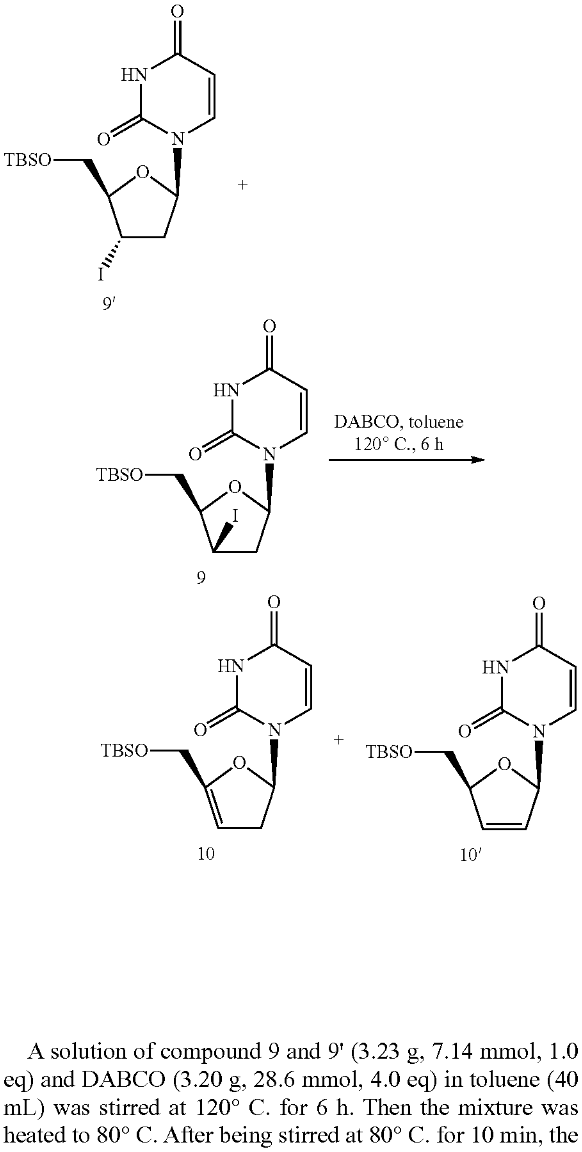

9'

9

10

10'

A solution of compound 9 and 9' (3.23 g, 7.14 mmol, 1.0 eq) and DABCO (3.20 g, 28.6 mmol, 4.0 eq) in toluene (40 mL) was stirred at 120° C. for 6 h. Then the mixture was heated to 80° C. After being stirred at 80° C. for 10 min, the reaction mixture was cooled to room temperature, quenched with saturated aqueous $NH_4Cl$ and extracted with EtOAc. The organic layer was further washed with saturated aqueous $NaHCO_3$ and water. After evaporation of the solvent, the residue was purified by flash column chromatography (petroleum ether/EtOAc, 1/1) to afford and (1.61 g, 10/10'=2:1 determined by H-NMR) as white foams.

General Procedure for the Preparation of Compound 11 and 11'

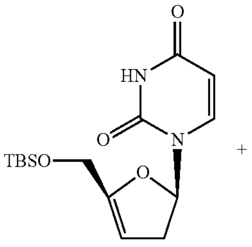

10

+

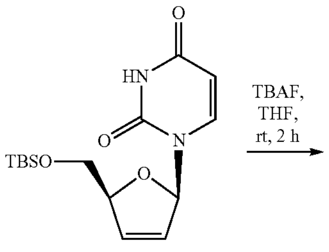

10′

-continued

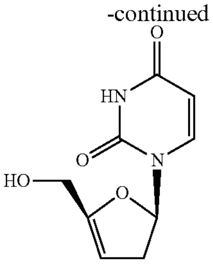

11

AB23028

17 mg obtained by Prep-HPLC

MeCN-$H_2O$

+

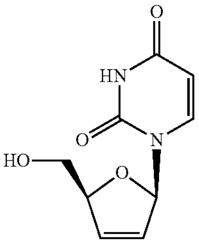

11′

A solution of compound 10 and 10' (3.2 g, 9.86 mmol, 1.0 eq) and TBAF (1.0 M, 19.7 mL, 2.0 eq) in dry THF (20 mL) was stirred at room temperature for 2 h. Then the reaction mixture was poured into water, extracted with EtOAc, and concentrated. After a crude purification with flash column chromatography, the residue was further purified by Biotage to afford crude 11 and 11' (2.38 g) as white foams. The crude product (11 and 11', 0.40 g) was further purified on reverse phase HPLC (MeCN—$H_2O$) to afford 11 (17 mg) as a white solid.

TLC: Dichloromethane/Methanol, 10/1

$R_f$ (Compound 10/10')=0.95

$R_f$ (Product 11/11')=0.5

LC-MS: 233.00 $[M+Na]^+$ $^1H$ NMR (400 MHz, $D_2O$) δ 7.62 (d, J=8.1 Hz, 1H), 6.67 (d, J=9.4 Hz, 1H), 5.87 (d, J=7.9 Hz, 1H), 5.21 (s, 1H), 4.30-4.12 (m, 2H), 3.28 (dd, J=17.3, 9.6 Hz, 1H), 2.76 (d, J=17.7 Hz, 1H).

General Procedure for the Preparation of Compound 5 and 13

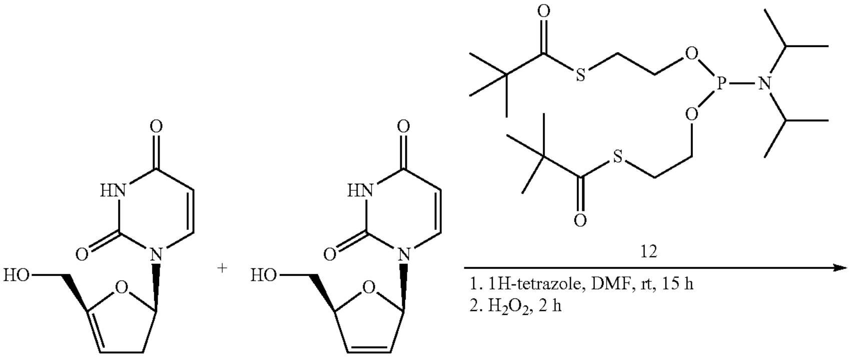

12

11 11′

-continued

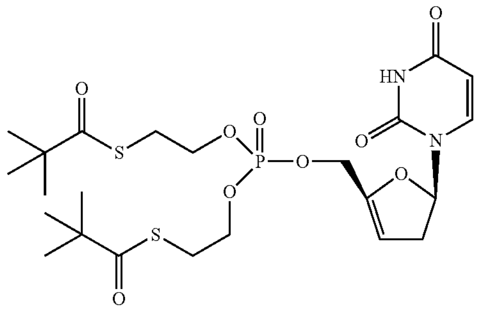

+

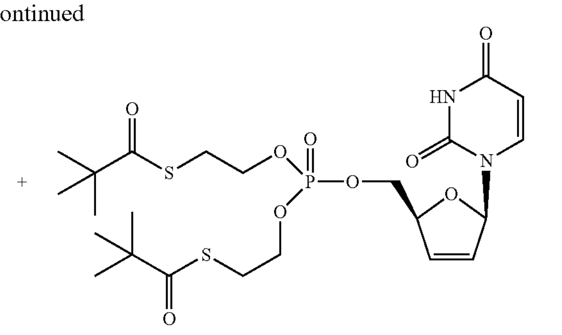

5
AB23026
45 mg shipped

13
AB23027
19 mg shipped obtained by Prep-HPLC MeCN-H2O

To a solution of alcohols 11 and 11' (0.40 g, 1.90 mmol, 1.0 eq) in dry DMF (20 mL) was added 1H-tetrazole (0.27 g, 3.80 mmol, 2.0 eq) and 12 (1.72 g, 3.80 mmol, 2.0 eq) sequentially. The mixture was stirred at room temperature for 15 h. The reaction was cooled to 0° C. and hydrogen peroxide (30% in water, 1.91 mL, 19.0 mmol, 10.0 eq) was added. After stirring for 0.5 h, the mixture was purified by Prep-HPLC to afford 5 (45 mg, 4%) and 13 (19 mg, 1.7%) as white solids.

TLC: Dichloromethane/Methanol, 20/1

$R_f$ (Compound 11/11')=0.1

$R_f$ (Product 5/13)=0.5

5:

LC-MS: 579.10[M+H]$^+$ $^1$H NMR (400 MHz, $CDCl_3$) δ 9.20 (s, 1H), 7.34 (d, J=7.4 Hz, 1H), 6.74 (d, J=6.3 Hz, 1H), 5.78 (d, J=7.4 Hz, 1H), 5.23 (s, 1H), 4.64 (br, 2H), 4.10 (d, J=5.7 Hz, 4H), 3.30 (dd, J=16.0, 9.9 Hz, 1H), 3.12 (br, 4H), 2.65 (d, J=17.2 Hz, 1H), 1.22 (s, 18H).

$^{31}$P NMR (162 MHz, $CDCl_3$) δ −1.78.

13: LC-MS: [M+H]$^+$ 579.10

$^1$H NMR (399 MHz, $CDCl_3$) δ 8.45 (s, 1H), 7.51 (d, J=8.0 Hz, 1H), 7.02 (s, 1H), 6.37 (d, J=5.1 Hz, 1H), 5.92 (d, J=4.6 Hz, 1H), 5.75 (d, J=8.0 Hz, 1H), 5.01 (s, 1H), 4.26 (br, 2H), 4.09 (dd, J=13.6, 6.6 Hz, 4H), 3.12 (br, 4H), 1.23 (s, 18H).

$^{31}$P NMR (162 MHz, $CDCl_3$) δ −1.60.

Synthetic Approach for Compounds 20 and 18

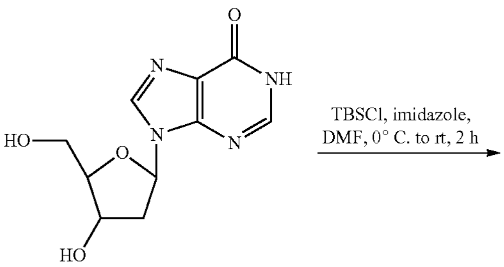

14

-continued

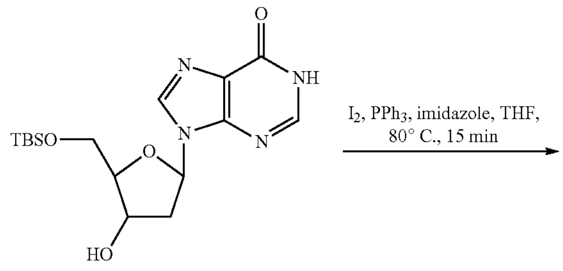

15

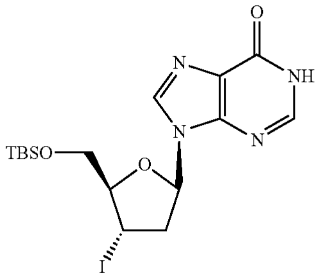

+

16′

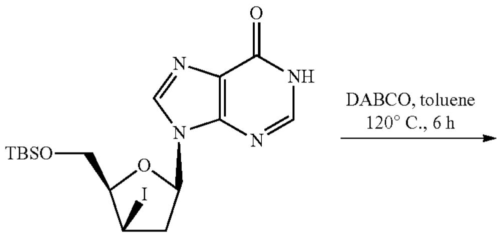

16

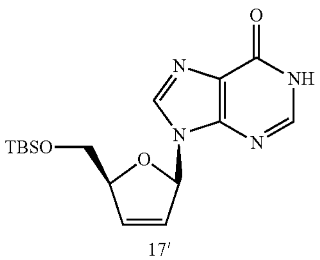

+

17′
trace P17′

-continued

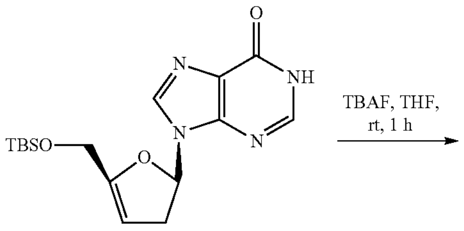

17

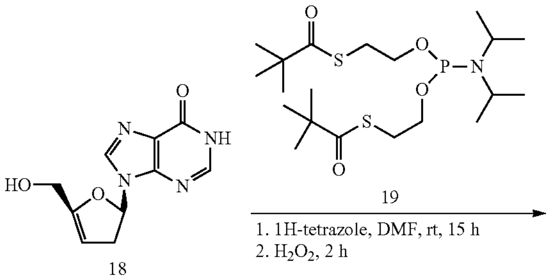

18
AB23030
32 mg shipped
obtained by Prep-HPLC
MeCN-$H_2O$

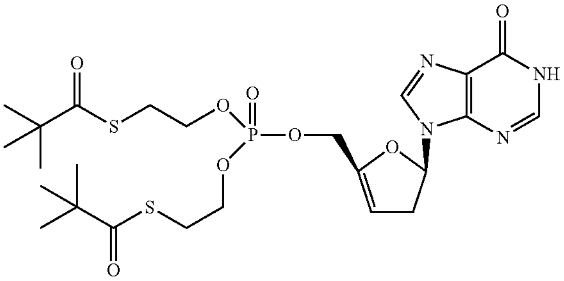

20
AB23029
208 mg shipped
obtained by Prep-HPLC
MeCN-$H_2O$

Procedure

General Procedure for the Preparation of Compound 15

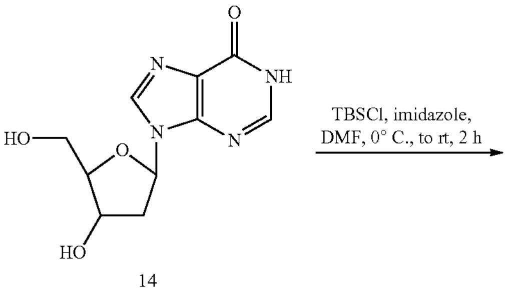

14

-continued

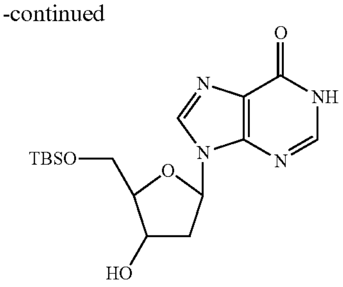

15

To a solution of compound 14 (10.0 g, 39.6 mmol, 1.0 eq) in dry DMF (100 mL) at 0° C. was added imidazole (13.5 g, 198 mmol, 5.0 eq) and TBSCl (8.96 g, 59.4 mmol, 1.5 eq) sequentially. The mixture was allowed to warm to room temperature. After being stirred at room temperature for 2 h, the mixture was poured into water and extracted with EtOAc. After evaporation of the solvent, the residue was purified by flash column chromatography (dichloromethane/methanol, 10/1) to afford 15 (12.8 g, 88%) as a white solid.

General Procedure for the Preparation of Compound 16 and 16'

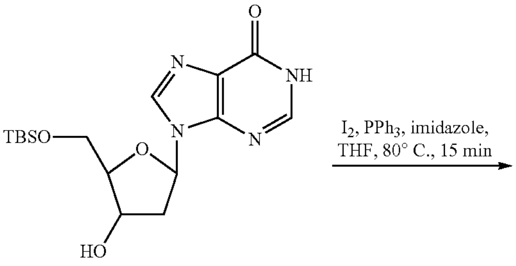

15

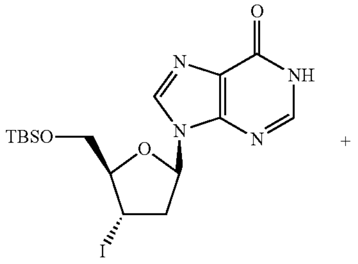

16'

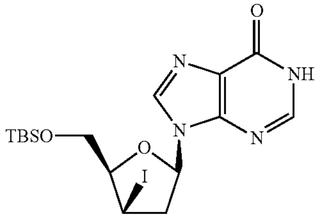

16

To a solution of compound 15 (7.58 g, 20.7 mmol, 1.0 eq) in dry THF (100 mL) at room temperature was added imidazole (2.82 g, 41.4 mmol, 2.0 eq), $PPh_3$ (8.16 g, 31.1 mmol, 1.5 eq) and $I_2$ (7.89 g, 31.1 mmol, 1.5 eq) sequentially. Then the mixture was heated to 80° C. After being stirred at 80° C. for 15 min, the reaction mixture was cooled to room temperature, quenched with saturated aqueous $Na_2S_2O_3$ and extracted with EtOAc. The organic layer was further washed with saturated aqueous $Na_2HCO_3$ and water. After evaporation of the solvent, the residue was purified by flash column chromatography (petroleum ether/EtOAc, 1/1) to afford 16 and 16' (5.97 g) as white foams.

General Procedure for the Preparation of Compound 17 and 17'

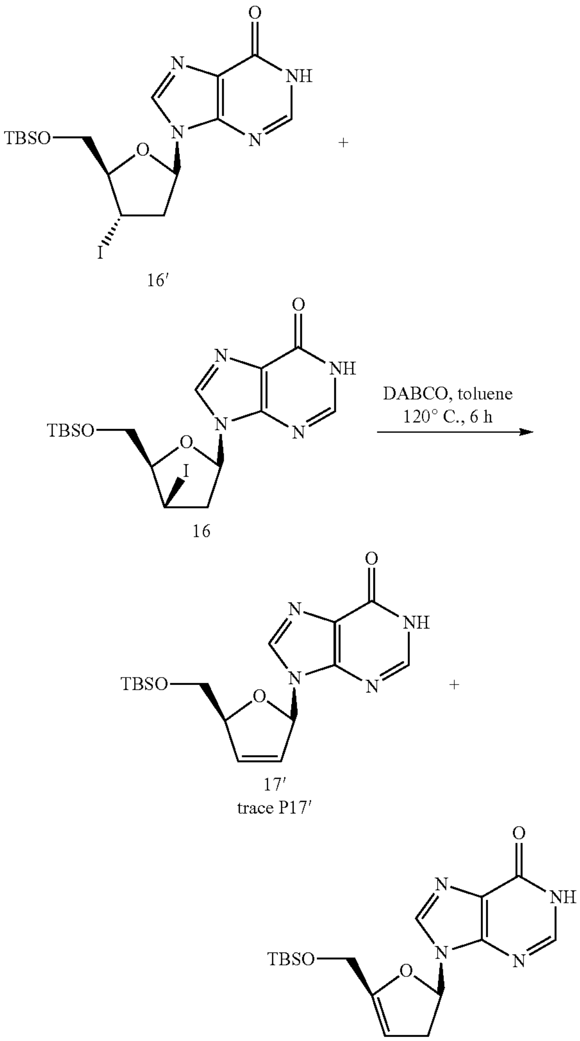

16'

16

17'
trace P17'

17

A solution of compound 16 and 16' (5.97 g, 12.5 mmol, 1.0 eq) and DABCO (5.61 g, 50.0 mmol, 4.0 eq) in toluene (40 mL) was stirred at 120° C. for 6 h. Then the reaction mixture was cooled to room temperature, quenched with saturated aqueous $NH_4Cl$ and extracted with EtOAc. The organic layer was further washed with saturated aqueous $NaHCO_3$ and water. After evaporation of the solvent, the residue was purified by flash column chromatography (petroleum ether/EtOAc, 1/1) to afford main product 17 and including trace product 17' (2.38 g) as white foams.

General Procedure for the Preparation of Compound 18

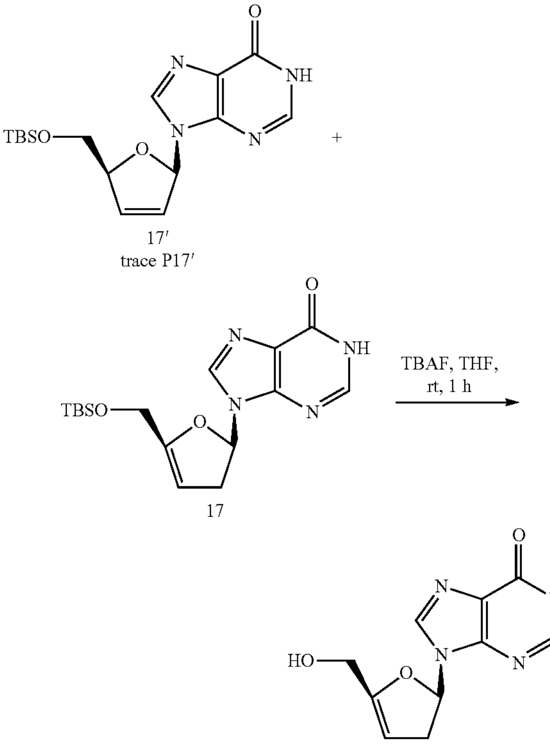

17'
trace P17'

17

18
AB23030
32 mg shipped
obtained by Prep-HPLC
MeCN-$H_2O$

A solution of compound 17 (2.38 g, 6.82 mmol, 1.0 eq) and TBAF (1.0 M, 13.6 mL, 2.0 eq) in dry THF (20 mL) was stirred at room temperature for 1 h. Then the reaction mixture was poured into water, extracted with EtOAc, and concentrated. After a crude purification with flash column chromatography, the residue was further purified by Biotage to afford 18 (0.3 g, 18%) as a white solid. Another crude product 18 (0.30 g) was further purified on reverse phase HPLC (MeCN—$H_2O$) to afford 18 (32 mg) as a white solid.

TLC: Dichloromethane/Methanol, 10/1

$R_f$ (Compound 17)=0.95

$R_f$ (Product 18)=0.5

LC-MS: 235.15 $[M+H]^+$ $^1H$ NMR (400 MHz, $D_2O$) δ 8.26 (s, 1H), 8.22 (s, 1H), 6.85 (d, J=7.6 Hz, 1H), 5.34 (s, 1H), 4.20 (s, 2H), 3.43 (dd, J=17.6, 9.0 Hz, 1H), 3.10 (d, J=17.5 Hz, 1H).

General Procedure for the Preparation of Compound 20

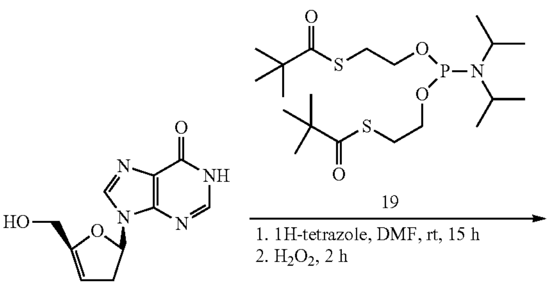

19

18

-continued

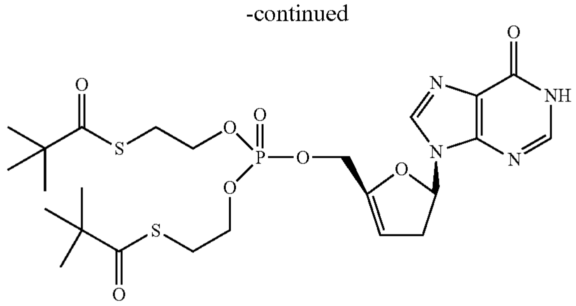

20
AB23029
208 mg shipped
obtained by Prep-HPLC
MeCN-$H_2O$

To a solution of alcohol 18 (0.30 g, 1.28 mmol, 1.0 eq) in dry DMF (20 mL) was added 1H-tetrazole (0.18 g, 2.56 mmol, 2.0 eq) and 19 (1.16 g, 2.56 mmol, 2.0 eq) sequentially. The mixture was stirred at room temperature for 15 h. The reaction was cooled to 0° C. and hydrogen peroxide (30% in water, 1.28 mL, 12.8 mmol, 10.0 eq) was added. After stirring for 0.5 h, the mixture was purified by Prep-HPLC to afford 20 (208 mg, 27%) as a white solid.

TLC: Dichloromethane/Methanol, 20/1

$R_f$ (Compound 18)=0.1

$R_f$ (Product 20)=0.5

LC-MS: 603.15 $[M+H]^+$ $^1H$ NMR (400 MHz, $CDCl_3$) δ 12.38 (br, 1H), 8.09 (s, 1H), 8.00 (s, 1H), 6.82 (d, J=5.4 Hz, 1H), 5.36 (s, 1H), 4.66 (d, J=9.0 Hz, 2H), 4.23-3.99 (m, 4H), 3.44 (dd, J=16.8, 8.7 Hz, 1H), 3.13 (q, J=6.8 Hz, 4H), 3.05 (d, J=17.9 Hz, 1H), 1.22 (s, 18H).

$^{31}P$ NMR (162 MHz, $CDCl_3$) δ −1.74.

Synthetic Approach for Compound 26

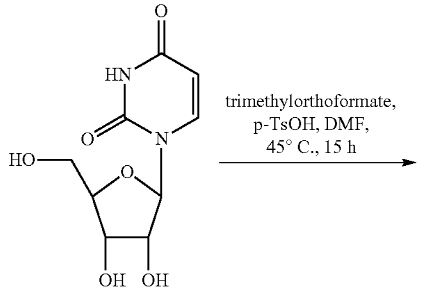

21

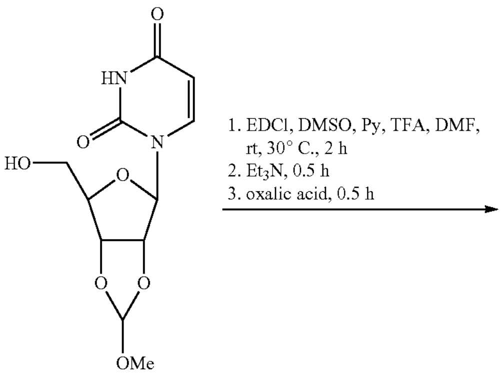

22

-continued

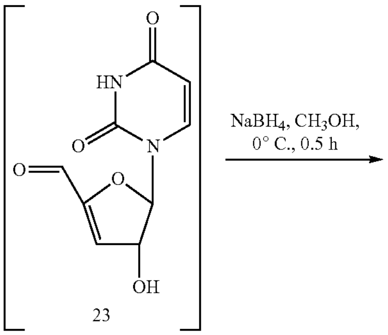

23

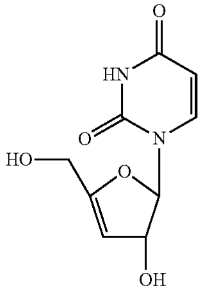

24

+

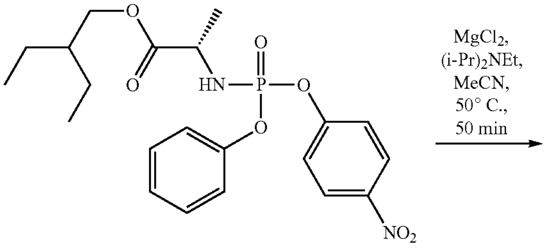

25

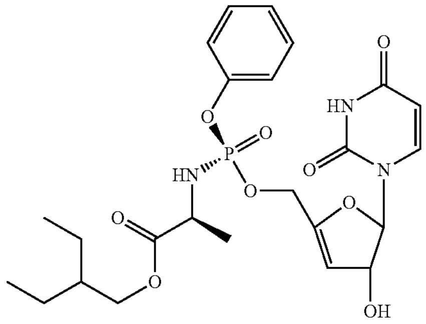

26
218 mg
obtained by Prep-HPLC
MeCN-$H_2O$

Synthetic Approach for Compound 33
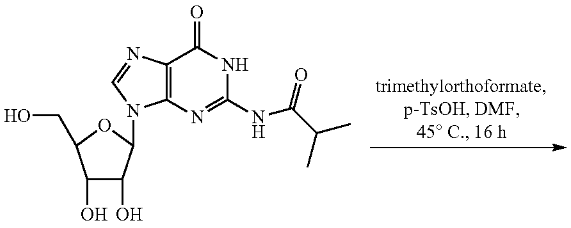
27
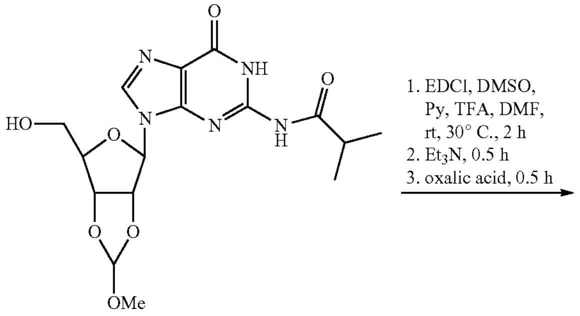
28
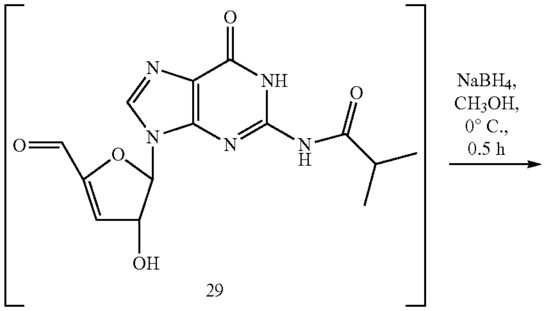
29
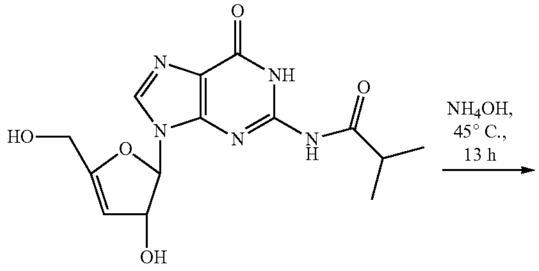
30
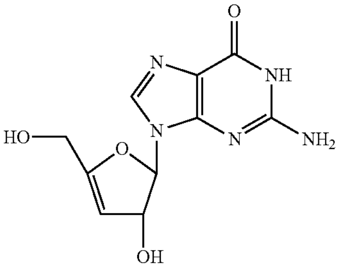
31
+
-continued
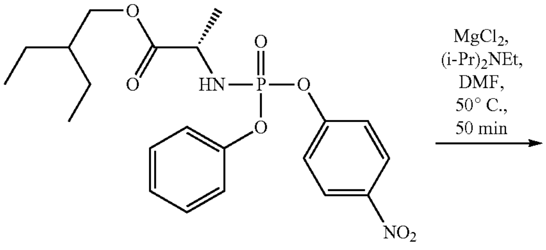
32
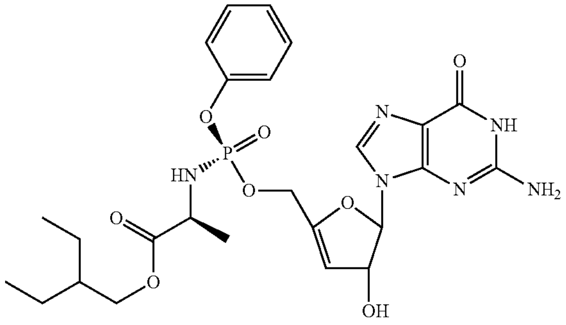
33
273 mg
obtained by Prep-HPLC
$MeCN-H_2O$
AB23032
Synthetic Approach for Compound 40
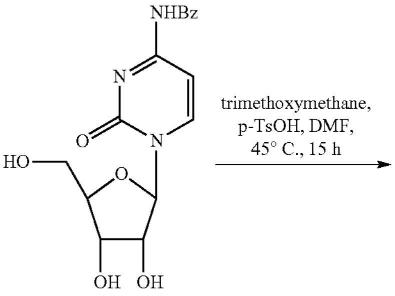
34
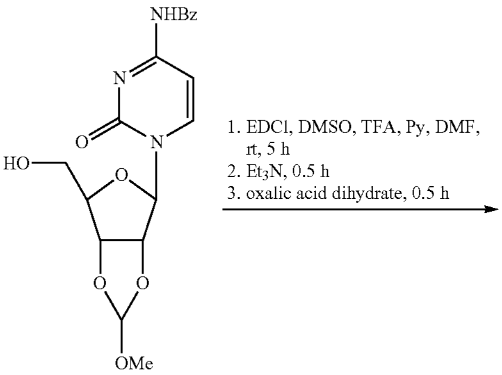
35

-continued

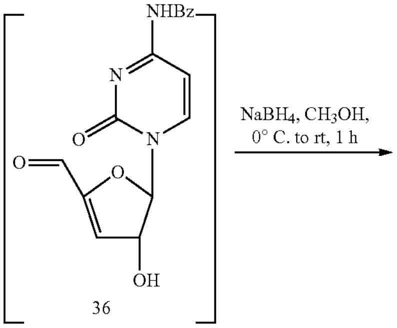

36

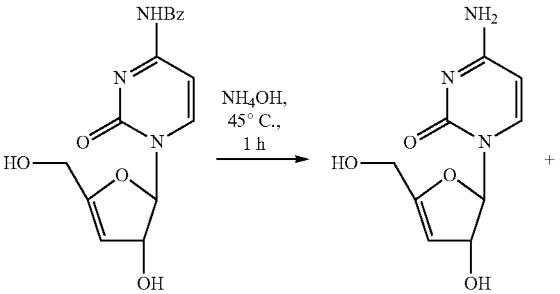

37

38

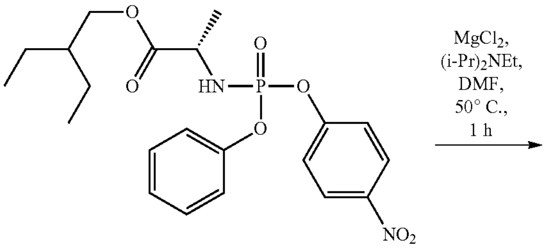

39

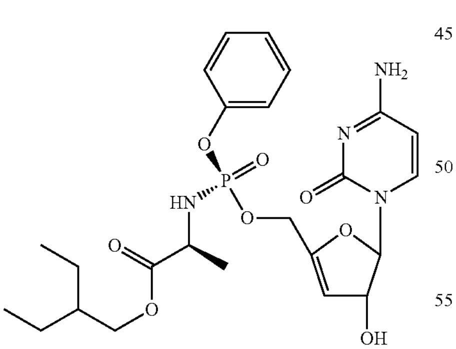

40

21 mg obtained by Prep-HPLC

MeCN-$H_2O$

AB23033

Procedure

General Procedure for the Preparation of Compound 26

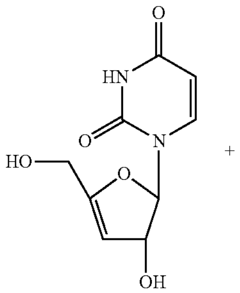

24

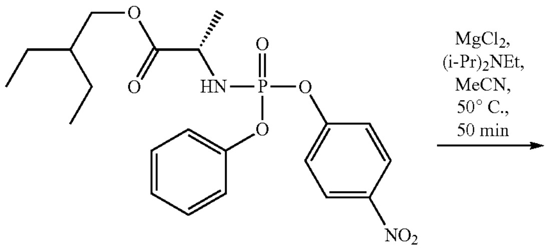

25

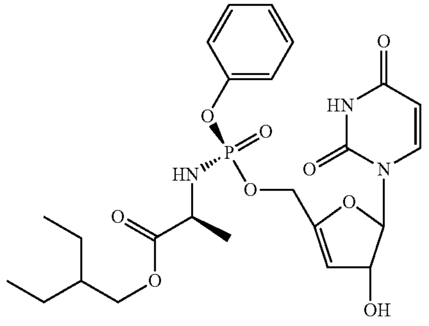

26

218 mg obtained by Prep-HPLC

MeCN-$H_2O$

AB23031

To a solution of compound 24 (0.77 g, 3.40 mmol, 1.0 eq) in MeCN (60 mL) at room temperature was added 25 (1.84 g, 4.08 mmol, 1.2 eq) and $MgCl_2$ (0.32 g, 3.40 mmol, 1.0 eq) sequentially. Then the mixture was heated to 50° C. for 10 min, and N,N-diisopropylethylamine (1.40 mL, 8.50 mmol, 2.5 eq) was added. After being stirred at 50° C. for another 50 min, the reaction mixture was cooled to room temperature, quenched with diluted HCl (1 M) and extracted with EtOAc. The organic layer was further washed with saturated aqueous $Na_2HCO_3$ and water. After evaporation of the solvent, the residue was purified by flash column chromatography (dichloromethane/methanol, 20/1) and further purified by prep-HPLC (MeCN—$H_2O$) to afford 26 (218 mg, 12%) as a white solid.

TLC: Dichloromethane/Methanol, 20/1

$R_f$ (Compound 24)=0.1

$R_f$ (Product 26)=0.5

LC-MS: 538.15 $[M+H]^+$ $^1H$ NMR (400 MHz, $CDCl_3$) δ 9.19 (br, 1H), 7.32 (d, J=7.5 Hz, 2H), 7.19 (dd, J=25.7, 8.0 Hz, 5H), 6.28 (s, 1H), 5.70 (d, J=8.0 Hz, 1H), 5.34 (s, 1H), 4.89 (s, 1H), 4.70 (d, J=8.2 Hz, 2H), 4.21-3.93 (m, 4H), 3.78 (s, 1H), 1.55-1.48 (m, 1H), 1.40-1.25 (m, 7H), 0.88 (t, J=7.2 Hz, 6H).

$^{31}P$ NMR (162 MHz, $CDCl_3$) δ 2.41.

General Procedure for the Preparation of Compound 33

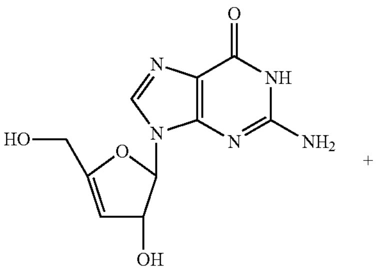

31

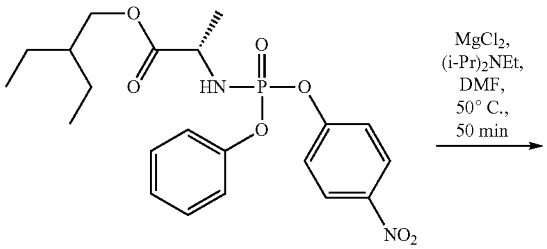

32

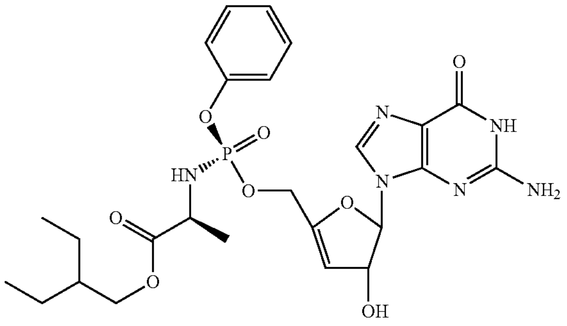

33
273 mg
obtained by Prep-HPLC
MeCN-H2O
AB23032

To a solution of compound 31 (0.65 g, 2.45 mmol, 1.0 eq) in DMF (20 mL) at room temperature was added 32 (1.32 g, 2.94 mmol, 1.2 eq) and $MgCl_2$ (0.23 g, 2.45 mmol, 1.0 eq) sequentially. Then the mixture was heated to 50° C. for 10 min, and N,N-diisopropylethylamine (1.01 mL, 6.13 mmol, 2.5 eq) was added. After being stirred at 50° C. for another 50 min, the reaction mixture was cooled to room temperature, quenched with diluted HCl (1 M) and extracted with EtOAc. The organic layer was further washed with saturated aqueous $Na_2HCO_3$ and water. After evaporation of the solvent, the residue was purified by flash column chromatography (dichloromethane/methanol, 20/1) and further purified by prep-HPLC (MeCN—$H_2O$) to afford 33 (273 mg, 19%) as a white solid.

TLC: Dichloromethane/Methanol, 20/1

$R_f$ (Compound 31)=0.1

$R_f$ (Product 33)=0.5

LC-MS: 577.15 $[M+H]^+$ $^1H$ NMR (400 MHz, DMSO-d6) δ 10.69 (s, 1H), 7.66 (s, 1H), 7.33 (t, J=7.3 Hz, 2H), 7.18-7.14 (m, 3H), 6.55 (s, 2H), 6.11-6.07 (m, 2H), 5.85 (d, J=5.5 Hz, 1H), 5.41-5.38 (m, 1H), 5.11 (s, 1H), 4.59 (d, J=6.9 Hz, 2H), 4.04-3.75 (m, 3H), 1.51-1.34 (m, 1H), 1.23 (q, J=13.1 Hz, 7H), 0.80 (t, J=7.2 Hz, 6H).

$^{31}P$ NMR (162 MHz, DMSO-d6) δ 3.49.

General Procedure for the Preparation of Compound 40

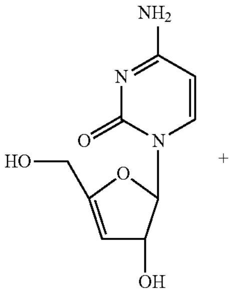

38

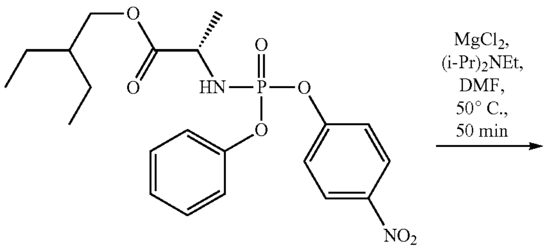

39

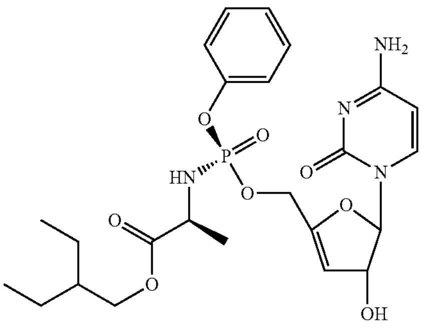

40
21 mg
obtained by Prep-HPLC
MeCN-H2O
AB23033

To a solution of compound 38 (0.51 g, 2.26 mmol, 1.0 eq) in DMF (20 mL) at room temperature was added 39 (1.22 g, 2.71 mmol, 1.2 eq) and $MgCl_2$ (0.22 g, 2.26 mmol, 1.0 eq) sequentially. Then the mixture was heated to 50° C. for 10 min, and N,N-diisopropylethylamine (0.93 mL, 5.65 mmol, 2.5 eq) was added. After being stirred at 50° C. for another 50 min, the reaction mixture was cooled to room temperature, quenched with diluted HCl (1 M) and extracted with EtOAc. The organic layer was further washed with saturated aqueous $Na_2HCO_3$ and brine. After evaporation of the solvent, the residue was purified by flash column chromatography (dichloromethane/methanol, 20/1) and further purified by prep-HPLC (MeCN—$H_2O$) to afford 40 (21 mg, 1.7%) as a white solid.

TLC: Dichloromethane/Methanol, 20/1

$R_f$ (Compound 38)=0.1

$R_f$ (Product 40)=0.5

LC-MS: 537.15 $[M+H]^+$ $^1H$ NMR (400 MHz, DMSO-d6) δ 7.36-7.34 (m, 3H), 7.21-7.20 (m, 5H), 6.21 (s, 1H), 6.15-6.09 (m, 1H), 5.72 (t,

J=7.1 Hz, 1H), 5.28 (s, 1H), 4.71 (s, 1H), 4.60 (d, J=6.9 Hz, 2H), 4.07-3.76 (m, 3H), 1.44 (s, 1H), 1.24 (d, J=6.8 Hz, 9H), 0.81 (t, J=7.0 Hz, 6H).
$^{31}P$ NMR (162 MHz, DMSO-d6) δ 3.47.
Synthetic Approach for Compounds 49 and 47
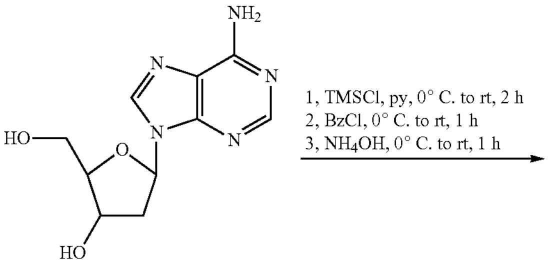
41
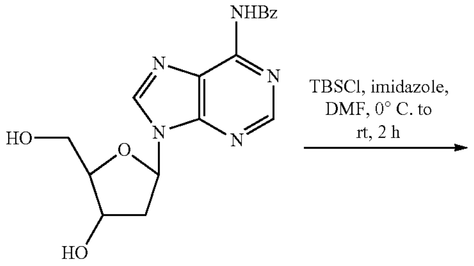
42
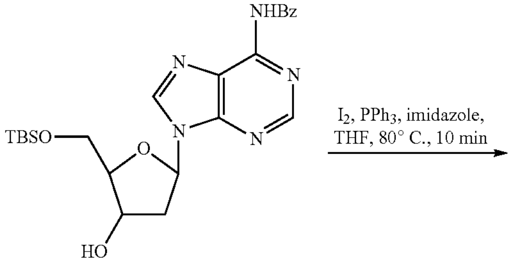
43
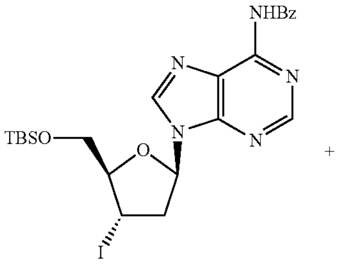
44′
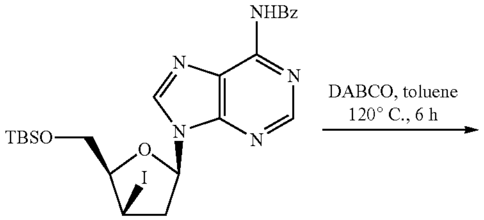
44
-continued
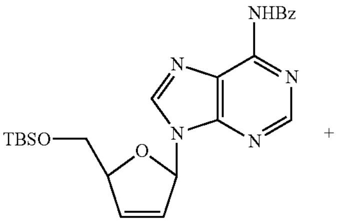
45′
trace P45′
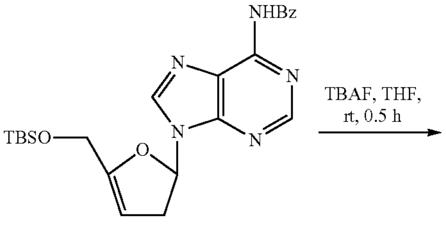
45
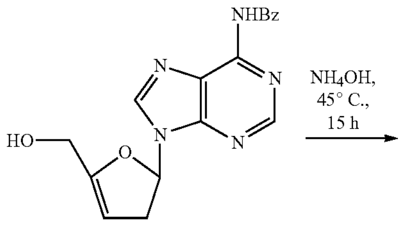
46
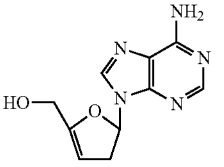
47
AB23035
11.7 mg + 22.3 mg
obtained by Prep-HPLC
MeCN-H2O
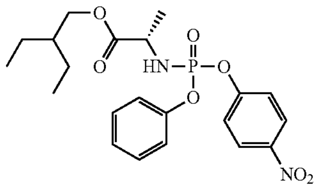
48
MgCl2, (i-Pr)2NEt,
DMF, 50° C., 1 h
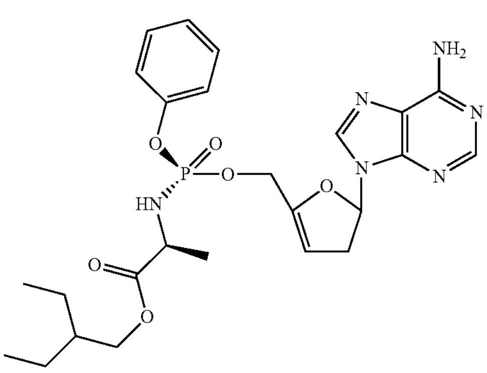
49
AB23034
102 mg + 215 mg
obtained by Prep-HPLC
MeCN-H2O Procedure General Procedure for the Preparation of Compound 42

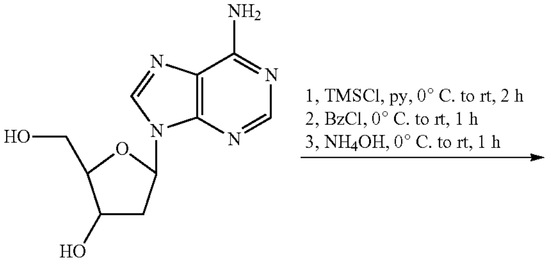

41

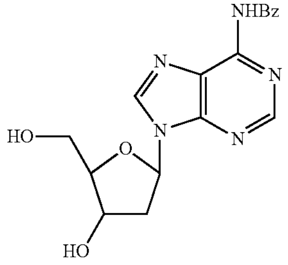

42

To a solution of compound 41 (11.0 g, 43.8 mmol, 1.0 eq) in pyridine (160 mL) at 0° C. was added TMSCl (27.8 mL, 219 mmol, 5.0 eq). The mixture was allowed to warm to room temperature. After being stirred at room temperature for 2 h, BzCl (5.56 mL, 48.2 mmol, 1.1 eq) was added to the reaction mixture at 0° C. After being stirred at room temperature for another 1 h, $H_2O$ (40 mL) and $NH_4OH$ (80 mL) was added to the reaction mixture at 0° C. After being stirred at room temperature for one more 1 h, the mixture was poured into water and extracted with EtOAc. After evaporation of the solvent, the residue was purified by flash column chromatography (dichloromethane/methanol, 9/1) to afford 42 (7.47 g, 48%) as a white solid.

General Procedure for the Preparation of Compound 43

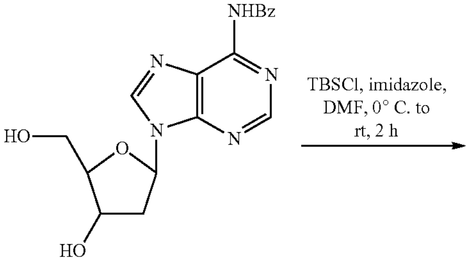

42

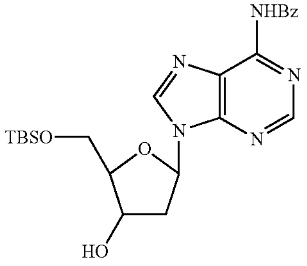

43

To a solution of compound 42 (6.78 g, 19.1 mmol, 1.0 eq) in dry DMF (100 mL) at 0° C. was added imidazole (6.50 g, 95.5 mmol, 5.0 eq) and TBSCl (4.32 g, 28.7 mmol, 1.5 eq) sequentially. The mixture was allowed to warm to room temperature. After being stirred at room temperature for 15 h, the mixture was poured into water and extracted with EtOAc. After evaporation of the solvent, the residue was purified by flash column chromatography (dichloromethane/methanol, 10/1) to afford 43 (7.17 g, 80%) as a white solid.

General Procedure for the Preparation of Compound 44 and 44'

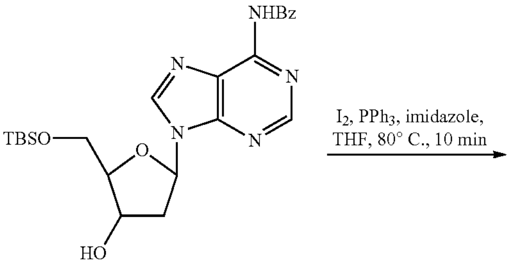

43

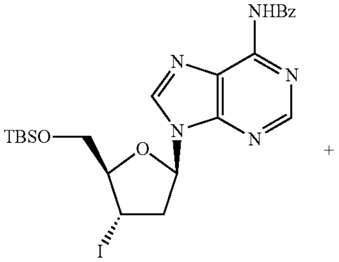

44'

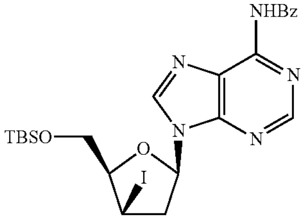

44

To a solution of compound 43 (5.18 g, 11.0 mmol, 1.0 eq) in dry THF (100 mL) at room temperature was added imidazole (1.50 g, 22.0 mmol, 2.0 eq), $PPh_3$ (4.32 g, 16.5 mmol, 1.5 eq) and $I_2$ (4.17 g, 16.5 mmol, 1.5 eq) sequentially. Then the mixture was heated to 80° C. After being stirred at 80° C. for 10 min, the reaction mixture was cooled to room temperature, quenched with saturated aqueous $Na_2S_2O_3$ and extracted with EtOAc. The organic layer was further washed with saturated aqueous $Na_2HCO_3$ and water. After evaporation of the solvent, the residue was purified by flash column chromatography (petroleum ether/EtOAc, 1/1) to afford 4 and 44' (5.74 g) as white foams.

General Procedure for the Preparation of Compound 45 and 45'

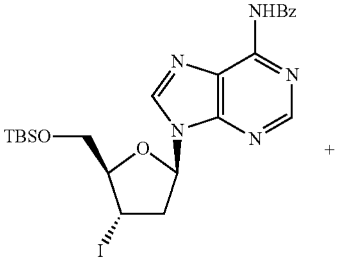

44'

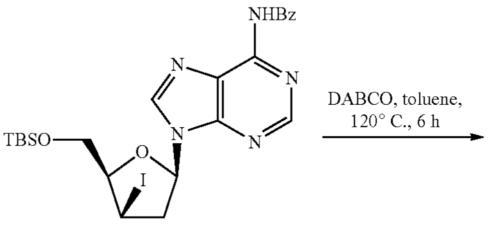

44

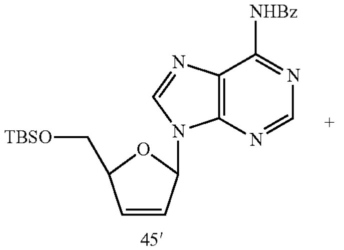

45'

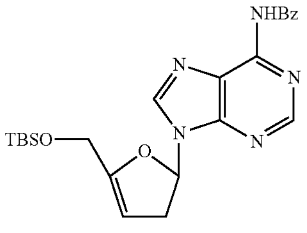

45

A solution of compound 44 and 44' (7.88 g, 13.6 mmol, 1.0 eq) and DABCO (6.10 g, 54.4 mmol, 4.0 eq) in toluene (60 mL) was stirred at 120° C. for 6 h. Then the reaction mixture was cooled to room temperature, quenched with saturated aqueous $NH_4Cl$ and extracted with EtOAc. The organic layer was further washed with saturated aqueous $NaHCO_3$ and water. After evaporation of the solvent, the residue was purified by flash column chromatography (dichloromethane/methanol, 20/1) to afford crude product 45 (3.45 g) including trace product 45' as white foams.

General Procedure for the Preparation of Compound 46

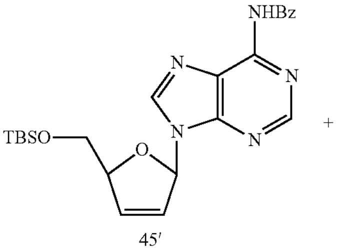

45'
trace product

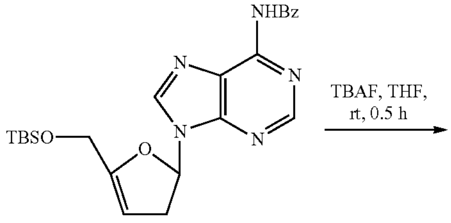

45

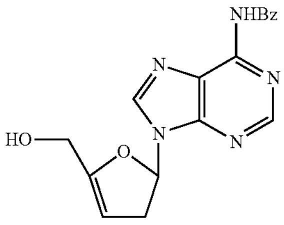

46

A solution of compound 45 (3.45 g, 7.64 mmol, 1.0 eq) and TBAF (1.0 M, 15.3 mL, 2.0 eq) in dry THF (20 mL) was stirred at room temperature for 1 h. Then the reaction mixture was poured into water, extracted with EtOAc, and concentrated. After evaporation of the solvent, the residue was purified by flash column chromatography (dichloromethane/methanol, 20/1) to afford crude product 46 (2.51 g) as a white foam.

General Procedure for the Preparation of Compound 47

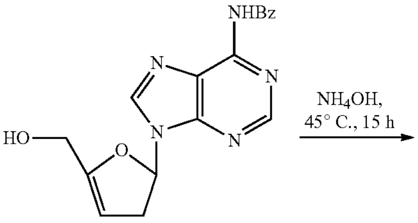

46

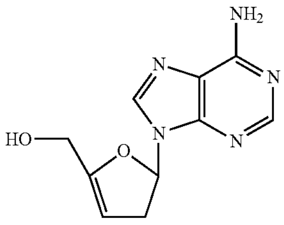

47
AB23035
11.7 mg + 22.3 mg
obtained by Prep-HPLC
MeCN-H2O

A solution of 46 (2.51 g, 7.44 mmol, 1.0 eq) in $NH_4OH$ (20 mL) was stirred at 45° C. for 15 h. The result mixture was concentrated under reduced pressure, the residue was purified by Biotage to afford 47 (0.69 g, 40%) as a white solid. Another crude product 47 (0.12 g) was further purified on reverse phase HPLC (MeCN—$H_2O$) to afford 47 (34 mg) as a white solid.

TLC: Dichloromethane/Methanol, 5/1

$R_f$ (Compound 46)=0.95

$R_f$ (Product 47)=0.5

LC-MS: 234.05 $[M+H]^+$ $^1H$ NMR (400 MHz, DMSO-d6) δ 8.17 (d, J=7.2 Hz, 2H), 7.31 (s, 2H), 6.76 (d, J=6.0 Hz, 1H), 5.11 (d, J=17.6 Hz, 2H), 3.96 (s, 2H), 3.22 (d, J=9.3 Hz, 1H), 3.07 (d, J=16.6 Hz, 1H).

General Procedure for the Preparation of Compound 49 (AB23034)

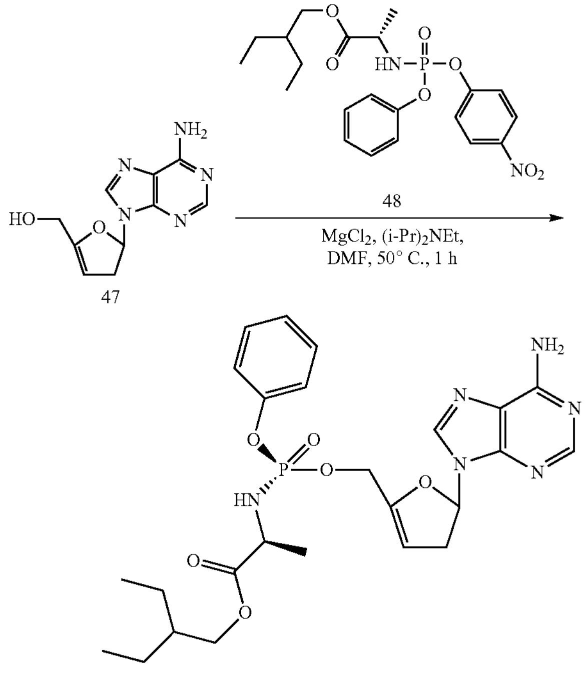

47

48

49
AB23034
102 mg + 215 mg
obtained by Prep-HPLC
MeCN-H2O

To a solution of compound 47 (0.57 g, 2.44 mmol, 1.0 eq) in DMF (20 mL) at room temperature was added 48 (1.32 g, 2.93 mmol, 1.2 eq) and $MgCl_2$ (0.23 g, 2.44 mmol, 1.0 eq) sequentially. Then the mixture was heated to 50° C. for 10 min, and N,N-diisopropylethylamine (1.01 mL, 6.10 mmol, 2.5 eq) was added. After being stirred at 50° C. for another 50 min, the reaction mixture was cooled to room temperature, quenched with diluted HCl (1 M) and extracted with EtOAc. The organic layer was further washed with saturated aqueous $Na_2HCO_3$ and brine. After evaporation of the solvent, the residue was purified by flash column chromatography (dichloromethane/methanol, 20/1) and further purified by prep-HPLC (MeCN—$H_2O$) to afford 49 (317 mg, 24%) as a white solid.

TLC: Dichloromethane/Methanol, 20/1

$R_f$ (Compound 47)=0.1

$R_f$ (Product 49)=0.5

LC-MS: 545.30 [M+H]+

$^1H$ NMR (400 MHz, DMSO-d6) δ 8.17 (d, J=9.3 Hz, 2H), 7.46-7.24 (m, 4H), 7.14 (d, J=7.3 Hz, 3H), 6.79 (d, J=5.5 Hz, 1H), 6.14-5.97 (m, 1H), 5.33 (s, 1H), 4.56 (s, 1H), 3.90 (d, J=5.5 Hz, 1H), 3.84 (d, J=5.7 Hz, 1H), 3.13 (d, J=17.4 Hz, 1H), 1.39 (d, J=6.0 Hz, 1H), 1.23 (t, J=8.9 Hz, 7H), 0.78 (t, J=7.3 Hz, 6H).

$^{31}P$ NMR (162 MHz, DMSO) δ 3.47.

Synthetic Approach for Compounds 56 and 56'

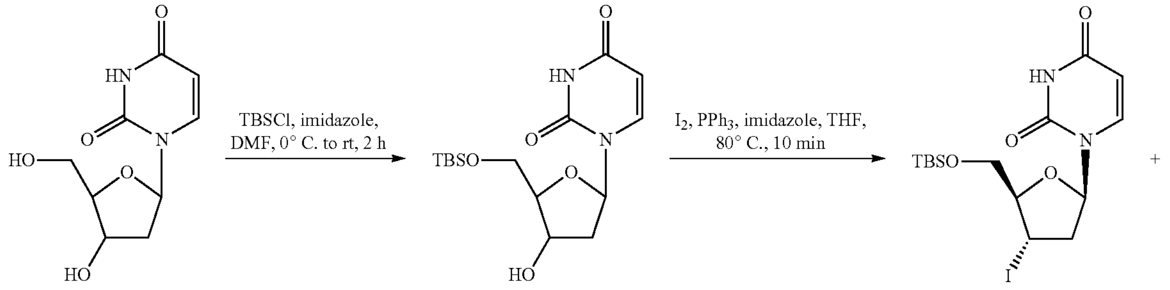

50 51 52'

-continued
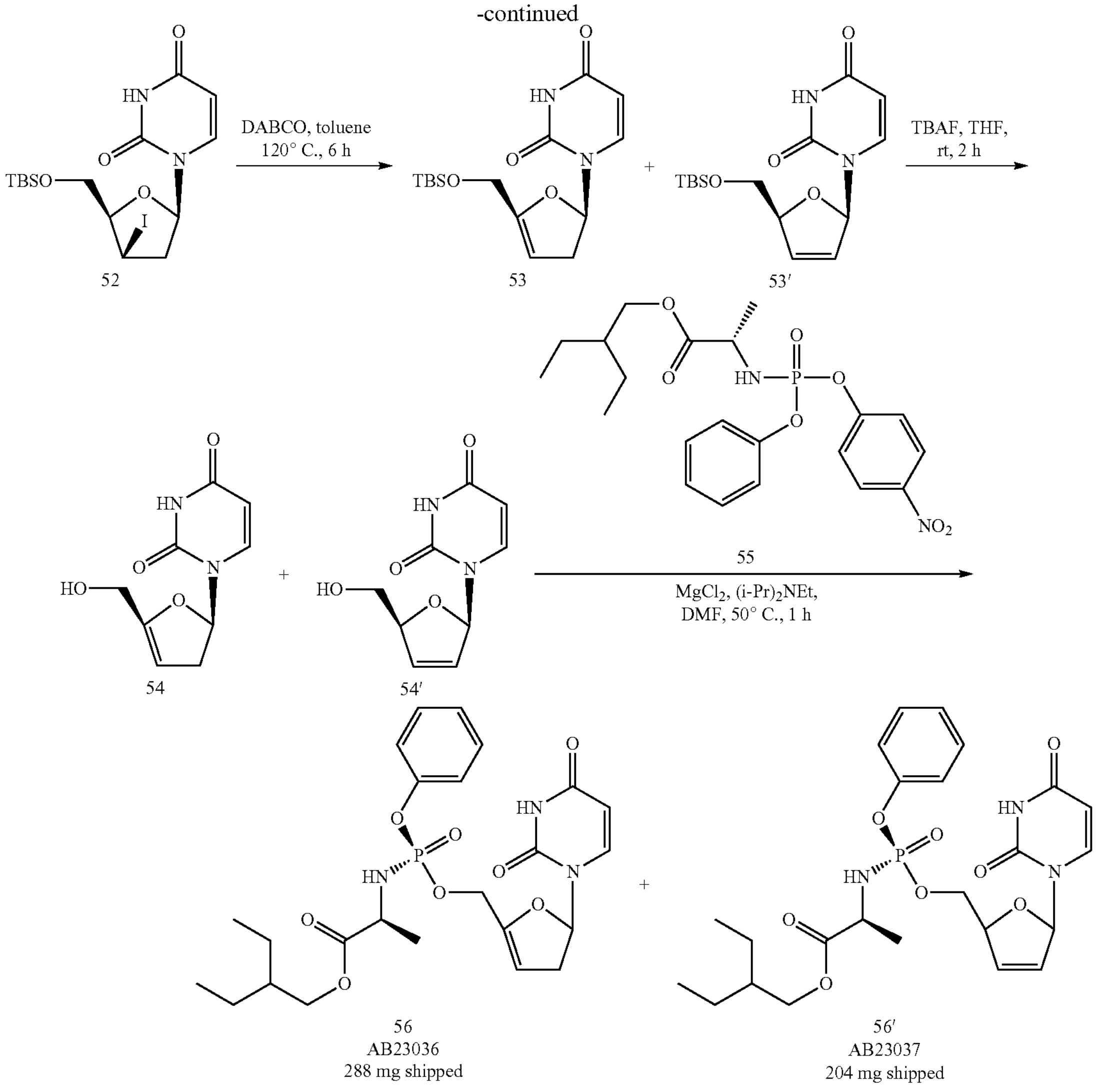
52
53
53′
55
54
54′
56
AB23036
288 mg shipped
56′
AB23037
204 mg shipped
obtained by Prep-HPLC MeCN-H2O
Procedure
General Procedure for the Preparation of Compound 7 and Compound 7'
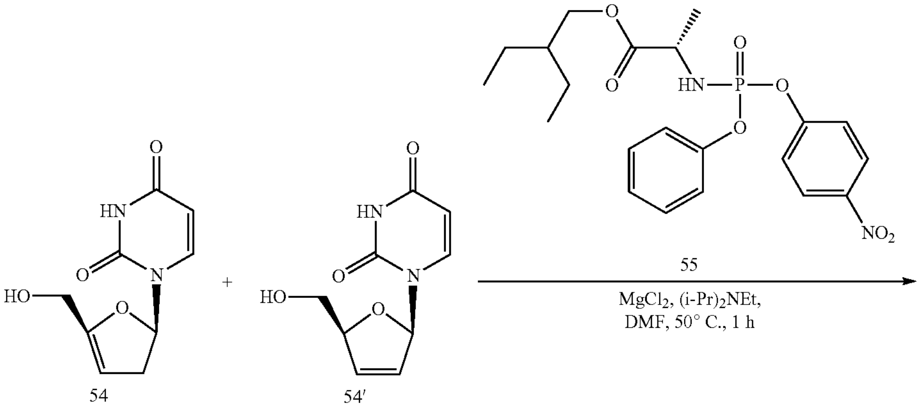
55
54
54′

-continued

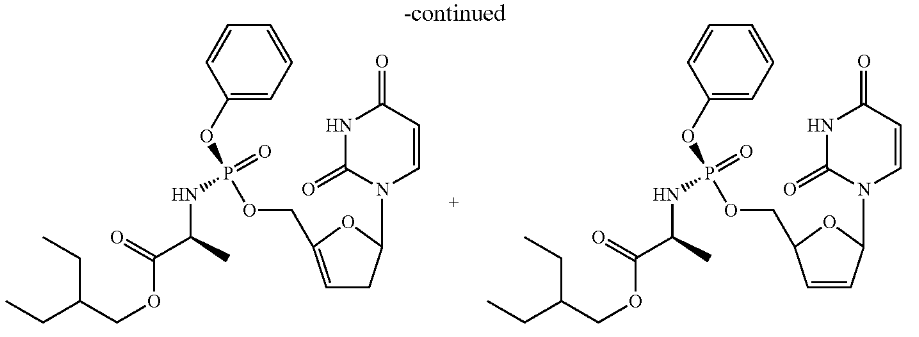

56
AB23036
288 mg shipped

56'
AB23037
204 mg shipped obtained by Prep-HPLC MeCN-H2O

To a solution of alcohols 54 and 54' (0.48 g, 2.28 mmol, 1.0 eq) in DMF (20 mL) at room temperature was added 55 (1.23 g, 2.74 mmol, 1.2 eq) and $MgCl_2$ (0.22 g, 2.28 mmol, 1.0 eq) sequentially. Then the mixture was heated to 50° C. for 10 min, and N,N-diisopropylethylamine (0.94 mL, 5.70 mmol, 2.5 eq) was added. After being stirred at 50° C. for another 50 min, the reaction mixture was cooled to room temperature, quenched with diluted HCl (1 M) and extracted with EtOAc. The organic layer was further washed with saturated aqueous $Na_2HCO_3$ and water. After evaporation of the solvent, the residue was purified by flash column chromatography (dichloromethane/methanol, 20/1) and further purified by prep-HPLC (MeCN—$H_2O$) to afford 56 (288 mg, 24%) as a yellow solid and 56' (204 mg, 17%) as a yellow solid.

TLC: Dichloromethane/Methanol, 20/1

$R_f$ (Compound 54)=0.1

$R_f$ (Product 56/56')=0.5

56:

LC-MS: 522.15 $[M+H]^+$ $^1H$ NMR (400 MHz, DMSO-d6) δ 11.41 (s, 1H), 7.37 (dd, J=16.9, 8.0 Hz, 3H), 7.18 (dd, J=13.6, 7.4 Hz, 3H), 6.58 (d, J=6.2 Hz, 1H), 6.09 (t, J=11.5 Hz, 1H), 5.60 (d, J=8.0 Hz, 1H), 5.23 (s, 1H), 4.57 (d, J=7.1 Hz, 2H), 4.00-3.83 (m, 3H), 3.16 (dd, J=16.9, 9.6 Hz, 1H), 2.66 (d, J=17.4 Hz, 1H), 1.52-1.38 (m, 1H), 1.36-1.14 (m, 7H), 0.82 (t, J=7.3 Hz, 6H).

$^{31}P$ NMR (162 MHz, DMSO) δ 3.45.

56':

LC-MS: 522.15 $[M+H]^+$ $^1H$ NMR (400 MHz, DMSO-d6) δ 11.36 (s, 1H), 7.45 (d, J=7.9 Hz, 1H), 7.35 (d, J=7.4 Hz, 2H), 7.19 (d, J=7.2 Hz, 3H), 6.82 (s, 1H), 6.39 (d, J=4.4 Hz, 1H), 6.13-5.93 (m, 2H), 5.45 (d, J=8.1 Hz, 1H), 4.96 (s, 1H), 4.14 (s, 2H), 4.04-3.74 (m, 3H), 1.44 (s, 1H), 1.36-1.13 (m, 8H), 0.82 (t, J=7.2 Hz, 7H).

$^{31}P$ NMR (162 MHz, DMSO-d6) δ 3.60.

Synthetic Approach for Compound 63

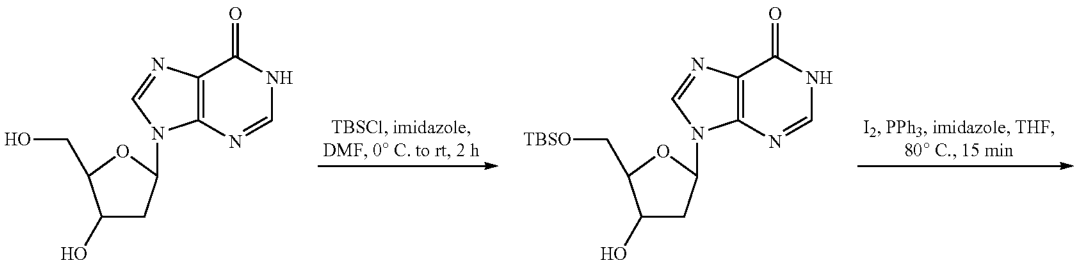

57

58

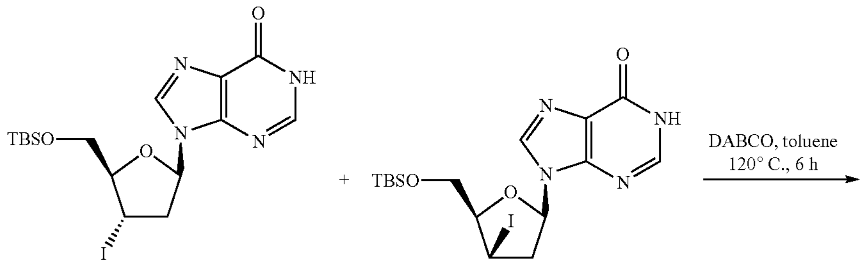

59'

59

-continued
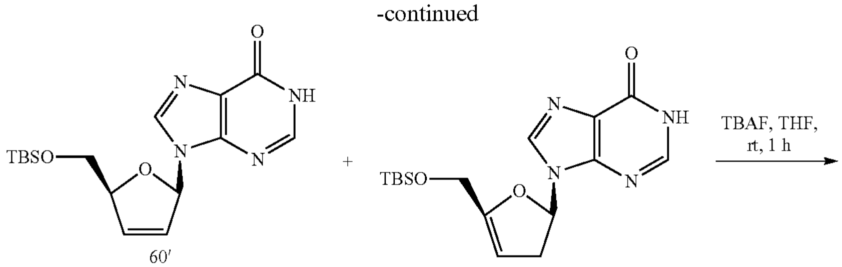
60'
trace P4'
60
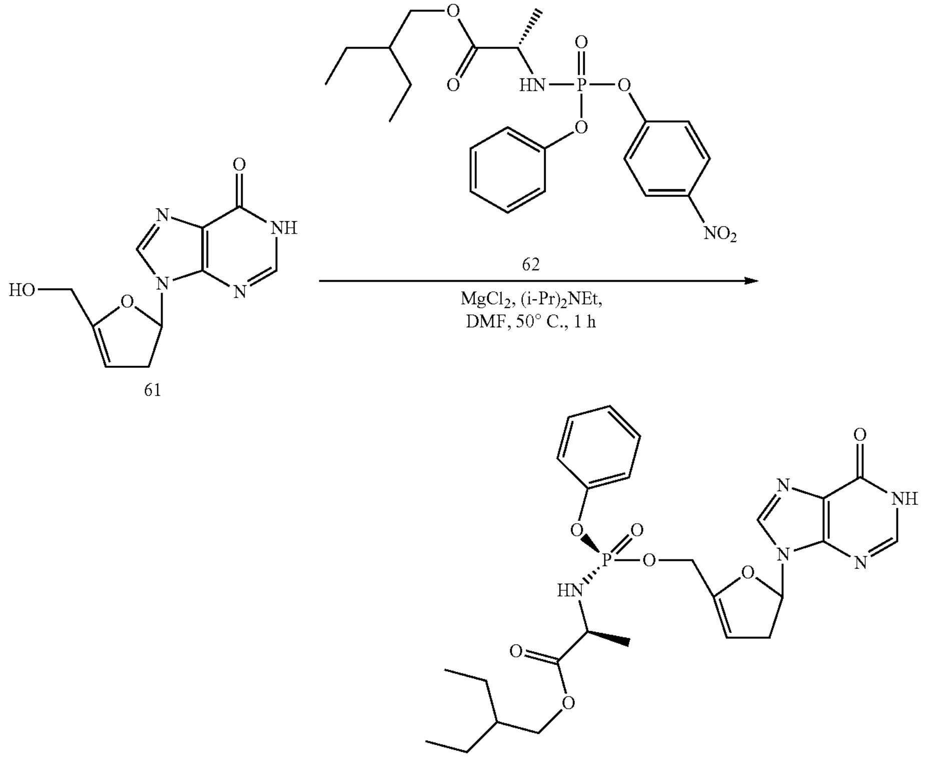
62
61
63
AB23038
374 mg
obtained by HPLC MeCN-H2O
Procedure
General Procedure for the Preparation of Compound 63
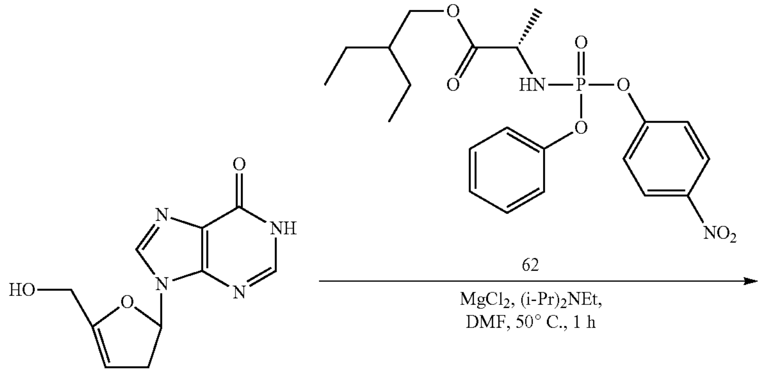
62
61

-continued

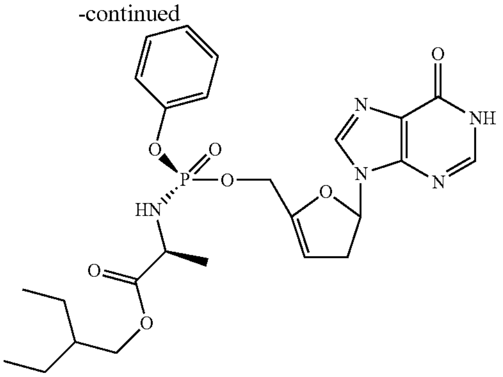

63
AB23038
374 mg
obtained by HPLC MeCN-H2O

To a solution of alcohol 61 (0.60 g, 2.56 mmol, 1.0 eq) in DMF (20 mL) at room temperature was added 62 (1.38 g, 3.07 mmol, 1.2 eq) and $MgCl_2$ (0.24 g, 2.56 mmol, 1.0 eq) sequentially. Then the mixture was heated to 50° C. for 10 min, and N,N-diisopropylethylamine (1.06 mL, 6.40 mmol, 2.5 eq) was added. After being stirred at 50° C. for another 50 min, the reaction mixture was cooled to room temperature, quenched with diluted HCl (1 M) and extracted with EtOAc. The organic layer was further washed with saturated aqueous $Na_2HCO_3$ and water. After evaporation of the solvent, the residue was purified by flash column chromatography (dichloromethane/methanol, 20/1) and further purified by Prep-HPLC (MeCN—$H_2O$) to afford 63 (374 mg, 27%) as a white solid.

TLC: Dichloromethane/Methanol, 20/1

$R_f$ (Compound 61)=0.1

$R_f$ (Product 63)=0.5

LC-MS: 546.15 $[M+H]^+$ $^1H$ NMR (400 MHz, DMSO-d6) δ 12.42 (s, 1H), 8.11 (d, J=20.9 Hz, 2H), 7.32 (t, J=7.1 Hz, 2H), 7.15 (d, J=6.9 Hz, 4H), 6.77 (d, J=6.1 Hz, 1H), 6.05 (t, J=11.5 Hz, 1H), 5.34 (s, 1H), 4.56 (br, 2H), 4.05-3.71 (m, 3H), 3.08 (d, J=16.6 Hz, 1H), 1.41 (s, 1H), 1.22 (d, J=6.5 Hz, 7H), 0.79 (t, J=6.7 Hz, 6H).

$^{31}P$ NMR (162 MHz, DMSO-d6) δ 3.47.

Example 16—Liver S9 Stability and Plasma Stability Determinations

Objective: To examine the stability and half-life of ddh-test compounds and metabolites thereof.

Methods: Test Compound Working Solutions:

| Compound | MW | Stock Conc. (mM) | Metabolite |
|---|---|---|---|
| AB23039 (compound 104; Formula IVB) | 588.70 | 10 | AB21649 (compound 24; Formula IVB) |
| AB23040 (compound 103; Formula IIB) | 627.70 | 10 | AB21651 (compound 31; Formula IIB) |

Liver S9 Working Solutions

| | | | Test compound = | 3 | |
|---|---|---|---|---|---|
| | | | Working solution Vol. = | 2623.5 | μL |
| Species | Liver S9 stock Conc. (mg/mL) | Liver S9 stock Vol. (μL) | Working solution Conc. (mg/mL) | Final Conc. in incubation (mg/mL) | Phosphate buffer Vol. (μL) |
| Human | 20 | 83 | 0.629 | 0.5 | 2541 |
| Rat | 20 | 83 | 0.629 | 0.5 | 2541 |

Results:

TABLE 22

| | Human | | | Rat | | |
|---|---|---|---|---|---|---|
| Compound | $T_{1/2}$ (min) | In vitro $CL_{int}$ (μL/min/mg protein) | $CL_{hep}$ (mL/min/kg) | $T_{1/2}$ (min) | In vitro $CL_{int}$ (μL/min/mg protein) | $CL_{hep}$ (mL/min/kg) |
| AB23039 | 264.7 | 5.2 | 9.1 | 347.1 | 4.0 | 14.3 |
| AB23040 | 198.7 | 7.0 | 10.6 | 237.1 | 5.8 | 18.7 |
| Dextromethorphan | 94.0 | 14.7 | 14.3 | 58.8 | 23.6 | 37.2 |

TABLE 23

| Peak area ratio measured for parent and its Metabolite: | | | | | | | |
|---|---|---|---|---|---|---|---|
| | | Human Peak area ratio | | | | | |
| | | With NADPH | | | | Without NADPH | |
| Compound | Analyst | 0 min | 15 min | 60 min | 180 min | 0 min | 180 min |
| AB23039 | AB23039 | 3.92E−01 | 3.41E−01 | 3.09E−01 | 2.34E−01 | 3.84E−01 | 3.28E−01 |
| | AB21649 | 0.00E+00 | 0.00E+00 | 0.00E+00 | 0.00E+00 | 0.00E+00 | 0.00E+00 |
| AB23040 | AB23040 | 1.29E−01 | 1.33E−01 | 1.05E−01 | 7.13E−02 | 1.31E−01 | 8.41E−02 |
| | AB21651 | 7.04E−04 | 1.03E−03 | 1.50E−03 | 3.03E−03 | 6.17E−04 | 3.06E−03 |
| | | Rat Peak area ratio | | | | | |
| | | With NADPH | | | | Without NADPH | |
| Compound | Analyst | 0 min | 15 min | 60 min | 180 min | 0 min | 180 min |
| AB23039 | AB23039 | 4.30E−01 | 3.61E−01 | 3.25E−01 | 2.81E−01 | 3.76E−01 | 3.27E−01 |
| | AB21649 | 0.00E+00 | 0.00E+00 | 0.00E+00 | 0.00E+00 | 0.00E+00 | 0.00E+00 |
| AB23040 | AB23040 | 1.37E−01 | 1.16E−01 | 1.11E−01 | 7.68E−02 | 1.20E−01 | 8.34E−02 |
| | AB21651 | 7.08E−04 | 6.93E−04 | 7.68E−04 | 1.30E−03 | 6.03E−04 | 2.39E−03 |

TABLE 24

| Stability without NADPH | | | | |
|---|---|---|---|---|
| | Stability (Yes/No) | | $T_{1/2}$ (min) | |
| Compound | Human | Rat | Human | Rat |
| AB23039 | Yes | Yes | — | — |
| AB23040 | No | No | 281.52 | 342.91 |

Summary Plasma Stability

| | $T_{1/2}$ (min) | |
|---|---|---|
| Compound | Human | Rat |
| AB23039 | >559.1 | >559.1 |
| AB23040 | >559.1 | >559.1 |
| Propantheline | 16.8 | — |
| Diltiazem | — | 124.8 |

Peak Area Ratio Measured for Parent and Metabolite in Plasma Stability Measurements.

| | | Human Peak area ratio | | | | Rat Peak area ratio | | | |
|---|---|---|---|---|---|---|---|---|---|
| Compound | Analyst | 0 min | 15 min | 60 min | 180 min | 0 min | 15 min | 60 min | 180 min |
| AB23039 | AB23039 | 3.13E−01 | 3.19E−01 | 3.08E−01 | 3.15E−01 | 3.11E−01 | 2.91E−01 | 2.98E−01 | 3.03E−01 |
| | AB21649 | 0.00E+00 | 0.00E+00 | 0.00E+00 | 0.00E+00 | 0.00E+00 | 2.76E−03 | 2.85E−03 | 3.08E−03 |
| AB23040 | AB23040 | 6.76E−02 | 6.03E−02 | 5.81E−02 | 6.50E−02 | 7.25E−02 | 7.28E−02 | 8.13E−02 | 7.58E−02 |
| | AB21651 | 5.52E−04 | 4.09E−04 | 5.47E−04 | 3.83E−04 | 8.33E−04 | 1.22E−03 | 1.02E−03 | 5.08E−04 |

Example 17—Analysis of Biochemical Activities of Ddh Compounds

Objective: To examine Remdesivir (AB2570) and ddh-Remdesivir (AB23046; compound 101), and triphosphate analogs thereof, for antiviral activities, for example but not limited to nucleotide incorporation and inhibition of RNA-Dependent RNA polymerase (RdRp) activity as they relate with SARS-CoV-2 and components thereof.

Methods:

Nsp12 Protein Expression and Purification

SARS-CoV-2 nsp12 gene (amino acid 4393-5324 Uniprot: P0DTD1) was synthesized de novo by GenScript (Nanjing, China) and constructed onto pET28A vector between BamHI and XhoI sites. Nsp12 expressed with a C-terminal 6 His-tag in BL21 (DE3) at 37° C. 2.5 mM $MgCl_2$ and 0.1 mM $ZnSO_4$ were supplemented in the culture during induction with 0.25 mM of IPTG. After 2 hours, cells were harvested and lysed by Branson sonifier in buffer containing 50 mM Tris pH 7.5, 500 mM NaCl, 1 mM $MgCl_2$, 20% glycerol, 5 mM BME and 25 mM imidazole. After centrifugation at 4000 rpm, Nsp12 was purified by Ni-Sepharose resin (GE Healthcare) using 20-mL gravity-flow column. Nsp12 was eluted at 200 mM imidazole and fractions were combined, concentrated and diluted with buffer containing 20 mM HEPES pH 7.5, 150 mM NaCl, 1 mM $MgCl_2$, 20% glycerol, 1 mM Tris(2-carboxyethyl) phosphine and stored at −80° C. The protein concentration was determined by A280 using the extinction coefficient calculated with ProtParam.

Nsp7 and Nsp8 Protein Expression and Purification

SARS-CoV-2 nsp8 gene (nucleotide 12092-12685, strain, GenBank: MN908947.3) and SARS-CoV-2 nsp7 gene (nucleotide 11846-12091, GenBank: MN908947.3) were synthesized de novo by GenScript (Nanjing, China) and cloned into a pET28A vector. Nsp7 and 8 were expressed with N-terminal 6 His-tag in BL21 (DE3) at 37° C. and induced with 0.5 mM of IPTG for 2 hours. Next, cells were harvested and lysed by Branson sonifier in buffer containing 50 mM Tris pH 7.5, 500 mM NaCl and 25 mM imidazole. Cell extract was clarified by centrifugation at 4000 rpm for 10 min at 4° C. Both proteins were purified by Nickel-affinity chromatography followed by ion-exchange chromatography (using HisTrap FF and Superdex 200 increase 10/300 GL columns, respectively, GE Healthcare). After first column peak fractions were combined, concentrated to 1 mM and injected onto second column in a buffer containing 20 mM HEPES pH 7.5, 150 mM NaCl, 5 mM Glycerol and 1 mM Tris(2-carboxyethyl)phosphine. Peaks were combined and concentrated to 500 mM and stored at −80° C. The protein concentration was determined by A280 using the extinction coefficient calculated with ProtParam.

Expression and Purification of Mitochondrial RNA Polymerase (POLRMT)

POLRMT D141 gene (amino acids 142-1230, GenBank: AAH98387.1) was synthesized by GenScript ((Nanjing, China) and cloned into a pET28A vector. POLRMT D141 was expressed with N-terminal 6 His-tag in BL21 (DE3) at 18° C. and induced with 0.25 mM of IPTG for 18 hours. On the next day, cells were harvested and lysed by Branson sonifier in buffer containing 50 mM Tris pH 7.5, 500 mM NaCl, 1 mM $MgCl_2$, 20% glycerol, 5 mM BME. After centrifugation at 4000 rpm, Nsp12 was purified by Ni-Sepharose resin (GE Healthcare) using 20-mL gravity-flow column. After elution at 250 mM imidazole, fractions were combined and concentrated then diluted with buffer containing 50 mM Tris pH 8, 500 mM NaCl, 20% glycerol, 10 mM BME, 500 mM EDTA and stored at −80° C. The protein concentration was determined by A280 using the extinction coefficient calculated with ProtParam.

Expression and Purification of Primase/Polymerase Protein Isoform 1 (PrimPol)

PrimPol gene (amino acids 2-559, GenBank: NP_001332824.1) was synthesized by GenScript (Nanjing, China) and cloned into a pET28A vector. PrimPol was expressed with N-terminal 6 His-tag in BL21 (DE3) at 18° C. and induced with 0.5 mM of IPTG for 24 hours. On the next day, cells were harvested and lysed by Branson sonifier in buffer containing 50 mM Tris pH 7.5, 500 mM NaCl, 1 mM $MgCl_2$, 20% glycerol, 5 mM BME. After centrifugation at 4000 rpm, Nsp12 was purified by Ni-Sepharose resin (GE Healthcare) using 20-mL gravity-flow column. After elution at 250 mM imidazole, fractions were combined and concentrated then diluted with buffer containing 50 mM Tris pH 8, 500 mM NaCl, 20% glycerol, 10 mM BME, 500 mM EDTA and stored at −80° C. The protein concentration was determined by A280 using the extinction coefficient calculated with ProtParam.

Primer and Template Annealing for SARS-Cov2 RdRp Polymerization

To generate RNA primer-template complexes for primer extension assay of SARS-Cov-2 RdRp, 1 mM fluorescently (Cy5.5) labeled RNA primer and 10 mM unlabeled RNA template (Table 1) were mixed in 50 mM NaCl in nuclease-free water, incubated at 98° C. for 10 min and slowly cooled to room temperature. The annealed primer and template complexes (P/Ts) were stored at −20° C. before use in primer extension assays.

Primer Extension Assay

Primer extension assay was performed. In brief, P/Ts were prepared by annealing Cy5/5 labeled RNA primer and unlabeled RNA template (described above). Primer extension reaction was performed in a 10 mL reaction mixture containing reaction buffer (20 mM HEPES pH 7.5, 5 mM MgCl2, 10 mM DTT, 0.01% Tween 20 and 1 kU/ml RNase Inhibitor), 200 nM P/T and 2 mM Nsp12 and Nsp8, and 10 mM Nsp7. The reaction was initiated by addition of rNTP at a final concentration of 100 mM, followed by incubation for 1 hour at 37° C. Reactions were quenched by addition of 20 mL of stopping solution (8M Urea, 90 mM Tris base, 29 mM Taurine, 10 mM EDTA, 0.02% SDS, 0.1% bromophenol blue). The quenched samples were denaturated at 95° C. for 10 min and primer extensions products were separated using 15% denaturing polyacrylamide gel electrophoresis (Urea-PAGE) in TTE buffer (90 mM Tris base, 29 mM Taurine, 0.5 mM EDTA). Gels were scanned using ChemiDoc MP imaging system (Bio-Rad, California, USA).

Analysis of Chain Termination Ability of Nucleotide Analogs

Nucleotide analog incorporation assay was performed using same concentrations as described above in primer extension assay reactions: 200 nM P/T and 2 mM Nsp12 and Nsp8, and 10 mM Nsp7. Reaction started with addition of the natural rNTP (the first nucleotide to be incorporated) and tested nucleotide analog (the second nucleotide to be incorporated) and incubated for 30 min at 37° C. before addition stopping solution. For chain termination assay: Incorporation of nucleotide analogs was performed as described above and then two natural rNTP (third and fourth nucleotide to be incorporated) were added to the reaction mixture and samples were incubated at 37° C. for another 30 min before addition stopping solution. The quenched samples were denatured at 95° C. for 10 min and primer extensions products were separated using 15% denaturing polyacrylamide gel electrophoresis (Urea-PAGE) as described above. After electrophoresis gels were scanned using ChemiDoc MP imaging system.

SARS-Cov2 RdRp Inhibition Assay

In reaction mixture containing 20 mM HEPES pH 7.5, 5 mM MgCl2, 10 mM DTT, 0.01% Tween 20, 1 kU/ml RNase Inhibitor, 200 nM P/T, 2 mM Nsp12 and Nsp8 and 10 mM Nsp7 was incubated with natural nucleotide (first nucleotide to be incorporated) for 30 min at 37° C. After first incorporation, nucleotide analogs were added using 12-step serial dilution in 2- and 5-fold increments and preincubated at 30° C. for 10 min. The reaction was initiated with addition of 50 mM of natural rNTP at 30° C. for 30 min and quenched with stopping solution. The quenched samples were treated as described above and gels were scanned using ChemiDoc MP imaging system. The images were analyzed and quantified using ImageLab™ software (Bio-Rad, California, USA).

Inhibition of Human Mitochondrial RNA Polymerase (POLRMT)

To generate RNA primer-DNA template complexes for inhibition assay of mitochondrial RNA polymerases (POLRMP), 10 mM fluorescently (Cy5.5) labeled RNA primer and 10 mM unlabeled DNA template were mixed in 50 mM NaCl in nuclease-free water, incubated at 95° C. for 5 min and slowly cooled to room temperature. The annealed primer and template complexes (P/Ts) were stored at −20° C. before use in primer extension assays. Reaction mixtures contained 50 mM Tris-HCl pH 7.5, 100 mM NaCl, 2.5 mM MgCl2, 2 mM DTT, 0.05 mg/ml BSA, 1 mM primer-template and 1 mM of POLRMT. Enzyme was preincubated with the P/T at 37° C. for 10 min and nucleotide analogs were added using 10-step serial dilution in 2- and 5-fold increments followed immediately by addition of 100 mM of rNTP. All samples were incubated for 30 min at 30° C. Reaction mixtures were quenched and treated as described above. The images were analyzed and quantified using ImageLab™ software (Bio-Rad, California, USA).

Inhibition of Mitochondrial DNA Polymerase (POLG1)

Inhibition assay of POLG1 was conducted in the similar manner as described above except that the concentration of POLG1 was modified to 100 nM and the incubation temperature to 37° C.

Inhibition of Primase/Polymerase Protein Isoform 1 (PrimPol)

Inhibition assay of PrimPol was conducted in the similar manner as described in the paragraph above except that the concentration of PrimPol was 1 mM, the incubation time—one hour and temperature −25° C.

Single Nucleotide Incorporation by Mitochondrial DNA Polymerase (POLG1)

A mixture of buffer 50 mM Tris-HCl pH 7.5, 100 mM NaCl, 2.5 mM MgCl2, 2 mM DTT, 0.05 mg/ml BSA, 200 nM P6/T6 or P6/T7 (Table 1) and 100 nM POLG1 was preincubated at 37° C. for 5 min. The reaction was started by addition 100 mM of dGTP/dUTP (depending on the template in use) for 30 min at 30° C. For the next step, 500 mM of NTP analog was added at 37° C. and 10 uL of reaction was removed and quenched with stopping solution at 0, 2, 5, 10, 20, 30, 60 and 90 m. The quenched samples were denaturated at 95° C. for 10 mi and primer extensions products were separated using 1500 denaturing polyacrylamide gel electrophoresis (Urea-PAGE) in TTE buffer (90 mM Tris base, 29 mM Taurine, 0.5 mM EDTA).

IMPDH Inhibitor Screening Assay

IMPDH inhibition screening assay kit was purchased for BioVision (California, USA).

TABLE 25

RNA and DNA oligonucleotides used in this study.

| Oligo | Sequence |
|---|---|
| P1 | Cy5.5-5'-GUCAUUCUCCUAAGAAGCUAUUAAAAUCAC-3' |
| P6 | Cy5.5-5'-UUUUGCCGCGCC-3' |
| P9 | Cy5.5-5'-TTTTGCCGCGCC-3' |
| *T2 | 5'-AUUAUUGC**U**AGUGAUUUUAAUAGCUUCUUAGGAGAAUGAC-3' |
| T3 | 5'-AUUAUUGU**C**AGUGAUUUUAAUAGCUUCUUAGGAGAAUGAC-3' |
| T4 | 5'-AUUAUUGC**A**UGUGAUUUUAAUAGCUUCUUAGGAGAAUGAC-3' |
| dT1 | 5'-GGGAATGCA**T**GGCGCGGC-3' |
| dT2 | 5'-GGGAATCAT**G**GGCGCGGC-3' |
| dT3 | 5'-GGGAATGTA**C**GGCGCGGC-3' |
| dT4 | 5'-GGGAATTGC**A**GGCGCGGC-3' |
| dT6 | 5'-GCAAATTAGTGGT**A**CCGGCGCGGC-3' |
| dT7 | 5'-GCAAATTAGTGGT**C**AAGGCGCGGC-3' |

*Bold and underlined nucleotides indicate position for the incorporation of the natureal rNTP/dNTP or NTP analog.

Results:

Expression, Purification, and Activity Measurements of SARS-Cov2 Nsp12-Nsp7-Nsp8

Figure 21:
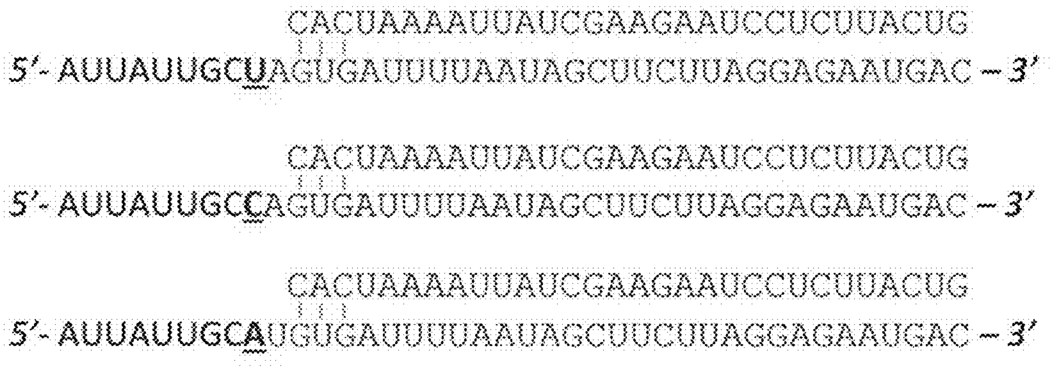
FIG. 21. RNA-primes RNA templates. Bold and underlined nucleotides indicate position for the incorporation of the natural rNTP/dNTP or NTP analog.
Figure 22A:
FIGS. 22A-22E. Nsp12 and nsp8-7 concentration optimization. Analysis of the primer extension activity in the condition of different concentrations of nsp12 and nsp8-7. Serial dilutions of nsp12 are indicated on the top of the gels.
Figure 22B:
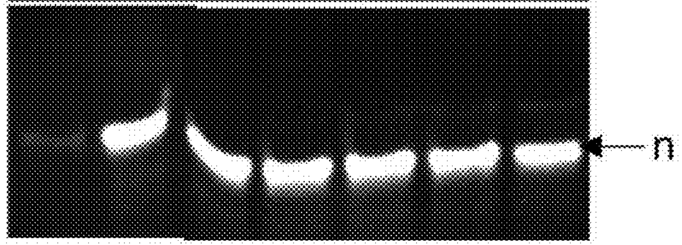
Figure 22C:
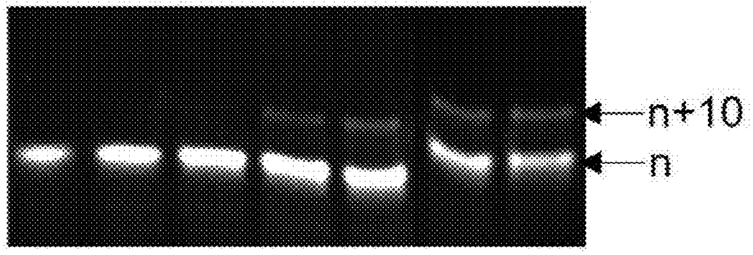
Figure 22D:
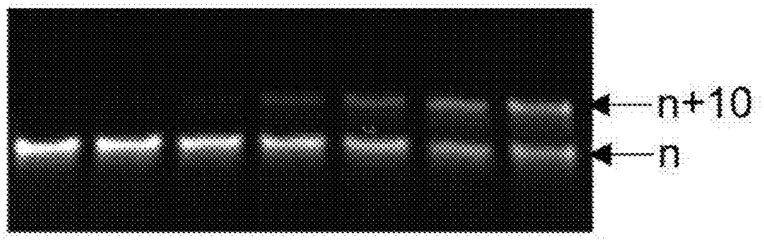
Figure 22E:
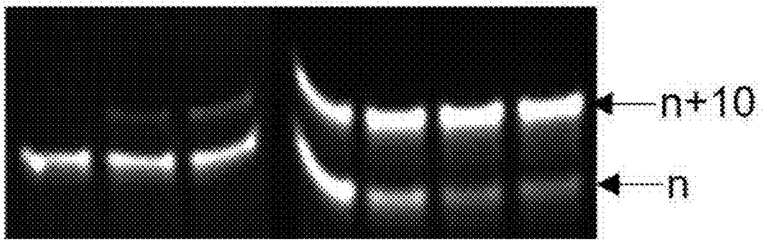

Nsp12, Nsp7, and Nsp8 were successfully expressed and purified from *E. coli*. The functional nsp12-nap8-nsp7 complex was assembled by simply mixing nsp12, nsp7 and nsp8 together in vitro as described before. For activity measurements of purified complex, a recently developed a primer extension assay was used employing an RNA template (40-mer RNA corresponding to sequence of 3'-end of SARS-Cov2 RNA genome) and a fluorescently labeled RNA primer (30-mer) (Table 25). In this report, three RNA templates (Table 25, T2-T4) were used to form three different P1/T scaffolds (FIG. 21) for testing incorporation of different nucleotide analogs.

Figure 23A:
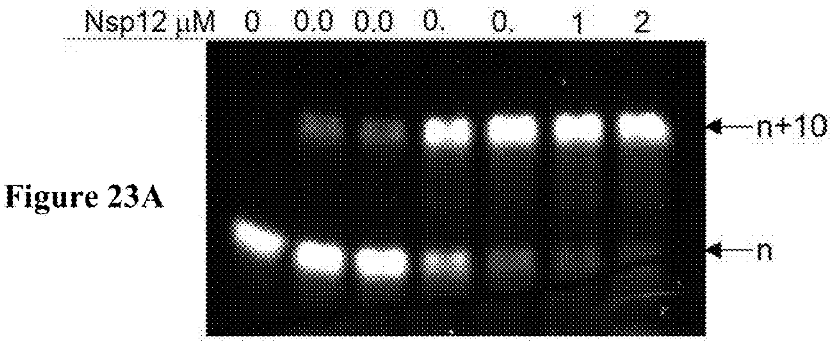
FIGS. 23A-23B. Nsp12 and nsp8-7 concentration optimization. Analysis of the primer extension activity in the condition of different concentrations of nsp12 and nsp8-7. Serial dilutions of nsp12 are indicated on the top of the gels.
Figure 23B:
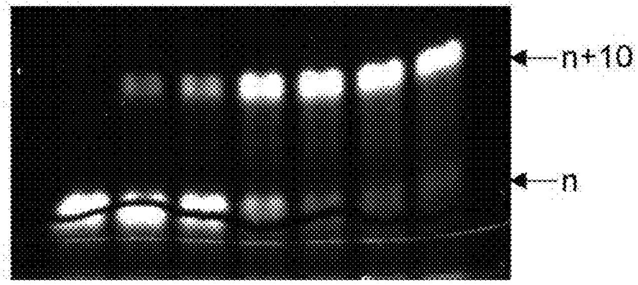

For optimal nsp7-nsp8-nsp12 concentrations we used an enzyme dilution assay with different concentrations of proteins. The results showed that nsp12 alone did not possess any RNA synthesis ability (FIG. 22). Maximum activity was observed in the in the presence of all components with following concentration ratio: 10 mM nsp7, 2 mM nsp8 and nsp12 (FIGS. 23A-23B).

Figure 24:
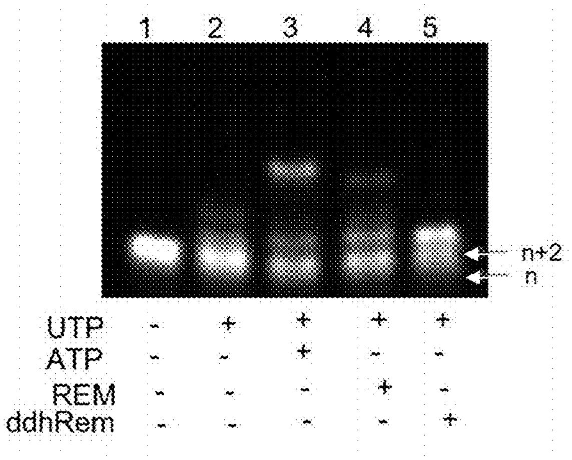
FIG. 24. Incorporation of REM and ddhREM in primer extension assay catalyzed by SARS-CoV-2 RdRp. Reaction products from SARS-Cov2 RdRp-catalyzed incorporation of ATP and its analogs.
Figure 25:
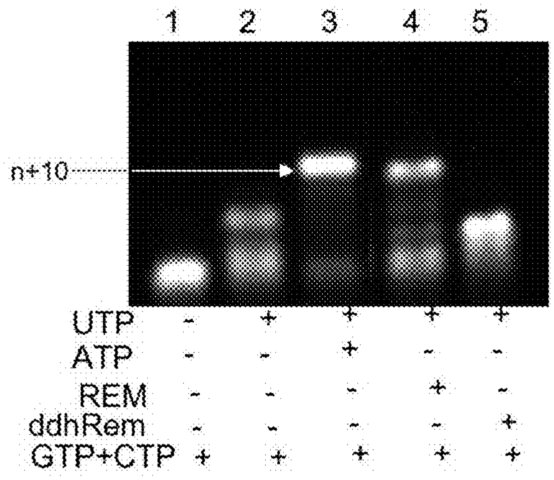
FIG. 25. Chain termination effect of REM and ddhREM in primer extension assay catalyzed by SARS-CoV-2 RdRp. Analysis of the chain termination abilities of the ATP analogs.
Figure 26C:
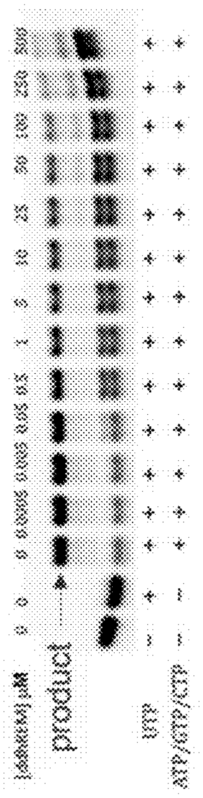
FIGS. 26A-26D. Inhibition of SARS-Cov2 RdRp by REM-TP and ddhREM-TP.
Figure 26D:
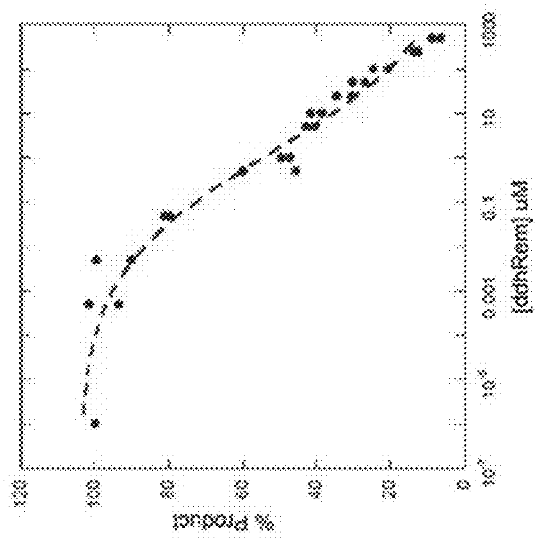
Figure 26A:
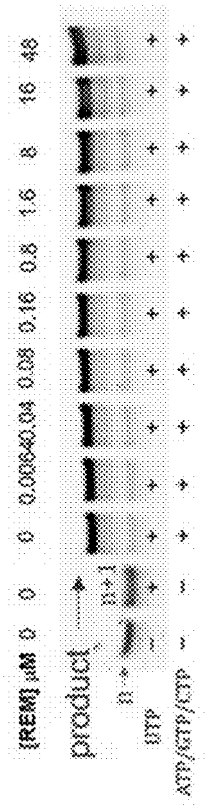
Figure 26B:
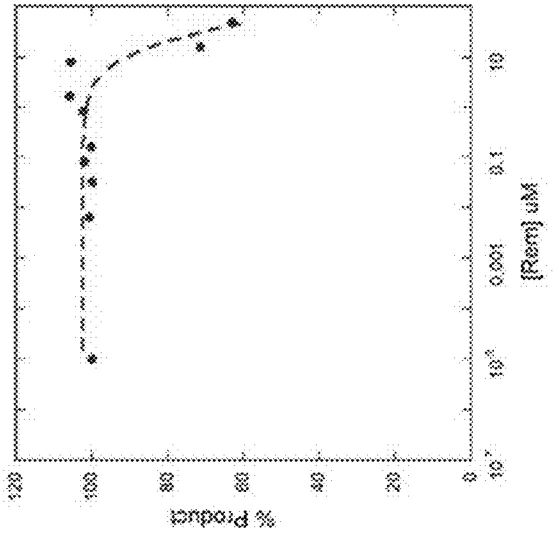

Nucleotide Incorporation of Remdesivir-TP (REM-TP) and ddhRemdesivir (ddhREM-TP) by SARS-Cov2 RdRp It was shown that REM-Triphosphate (REM-TP) can incorporate into RNA and this incorporation causes delayed chain termination. Here, the incorporation of ddhREM-TP was evaluated and compared with incorporation of REM-TP into 30-mer P1/T2 template (Table 25) that was designed for testing ATP analogs. P1/T2 template requires first incorporation of UTP and second incorporation of ATP analog, in this case—REM-TP and ddhREM-TP. The results showed that REM-TP and ddhREM-TP incorporated into RNA as ATP analogs at concentration of 100 uM (FIG. 24, lane 4 and 5). After addition GTP and CTP (third and fourth nucleotides to be incorporated), if incorporation of ATP analog leads to chain termination, the band will not extend. Incorporation of REM-TP did not cause chain termination while ddhREM-TP caused termination of RNA synthesis, since the elongation continued to the position of n+10 (FIG. 25, Lane 4 and 5).

Inhibition of SARS-Cov2 RdRp by REM-TP and ddhREM-TP

To interrogate the inhibitory effect of ddhREM-TP versus REM-TP, half-maximal inhibitory concentration (IC50) ddhREM-TP and REM-TP was calculated against RdRp. As summarized in Table 26, IC50 of ddhREM-TP was 1.32±0.42 mM while IC50 of REM was 65±21 mM (FIG. 26). These results indicate that ddhREM-TP with its mechanism of chain termination is a potent inhibitor of RNA replication of SARS-Cov2 RdRp while REM-TP shows inhibitory effect only in high concentrations.

TABLE 26

Inhibition of SARS-Cov2 RdRp mad human polymerases by NTP analogs

| Enzyme | REM-TP IC50 (mM) | ddhREM-TP IC50 (mM) | ddhUTP IC50 (mM) | ddhGTP IC50 (mM) |
|---|---|---|---|---|
| SARS-Cov2 RdRp | 65 ± 0.42 | 1.32 ± 0.42 | 1.9 ± 0.1 | 0.29 ± 0.07 |
| POLRMT | >200[a] | >600 | >150 | ND |
| POLG1 | >200[a] | >250 | >250 | ND |
| PrimPol | | >250 | >250 | ND |

[a]Taken from the literature.

Nucleotide Incorporation and Inhibition of SARS-Cov2 RdRp by ddhUTP and ddhGTP

Figure 27A:
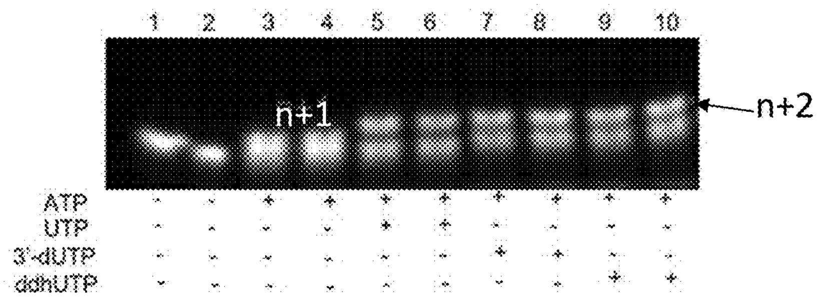
FIGS. 27A-27B Analysis of incorporation and chain termination effect of ddhUTP in primer extension assay catalyzed by SARS-CoV-2 RdRp.
Figure 28A:
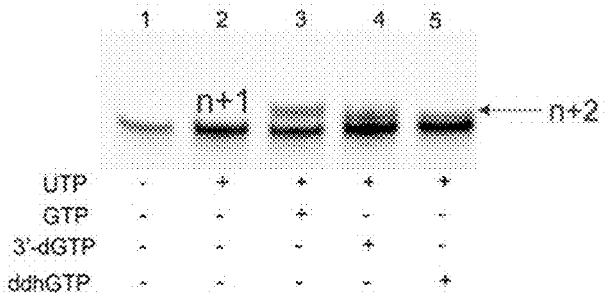
FIGS. 28A-28B. Analysis of incorporation and chain termination effect of ddhGTP in primer extension assay catalyzed by SARS-CoV-2 RdRp.

To test the incorporation of ddhUTP and ddhGTP, 30-mer P1/T4 template for UTP analogs incorporation and 30-mer P1/T3 for GTP analogs incorporation were used (Table 25). P1/T4 template requires first incorporation of ATP and second incorporation of UTP analog. P1/T3 template requires first incorporation of UTP and second incorporation of GTP analogs. The results showed that ddhUTP incorporated onto RNA as UTP analog at concentration of 100 mM (FIG. 27A, lane 9 and 10). The incorporation of the natural nucleotide and known chain terminator—3'-deoxyuracil triphosphate (3'-dUTP) that was used as a positive control, demonstrated the same level of incorporation as ddhUTP (FIG. 27A, lane 5-6 and 7-8). Likewise, ddhGTP also incorporates onto RNA as GTP analog at the same concentration (FIG. 28A, lane 5) the same as natural nucleotide and its positive control, 3'-dGTP (FIG. 28A, lane 3 and 4).

Figure 27B:
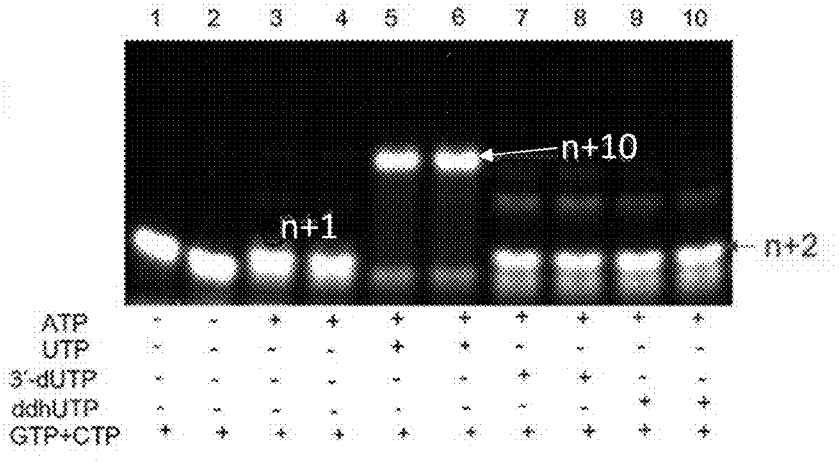
Figure 28B:
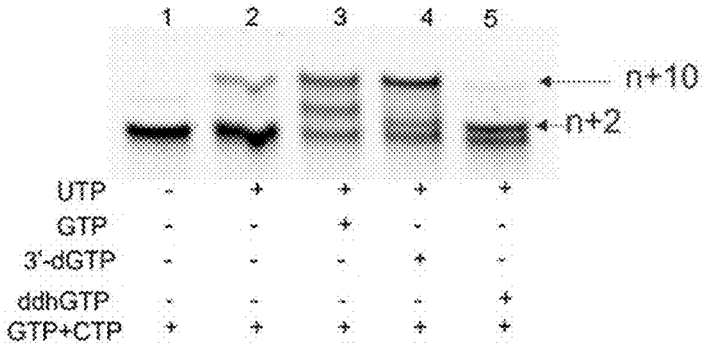
Figure 29A:
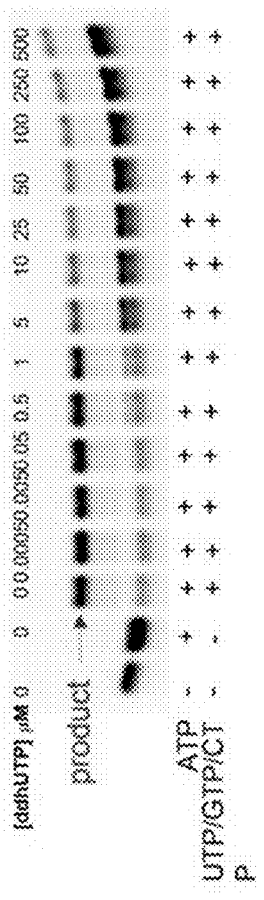
FIGS. 29A-29D. Inhibition of SARS-Cov2 RdRp by ddhUTP and ddhGTP.
Figure 29B:
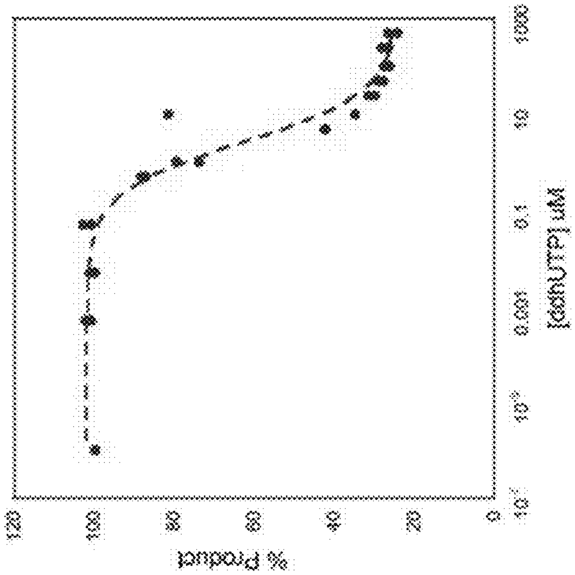
Figure 29C:
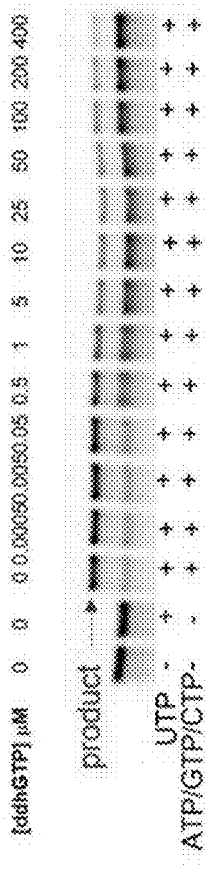
Figure 29D:
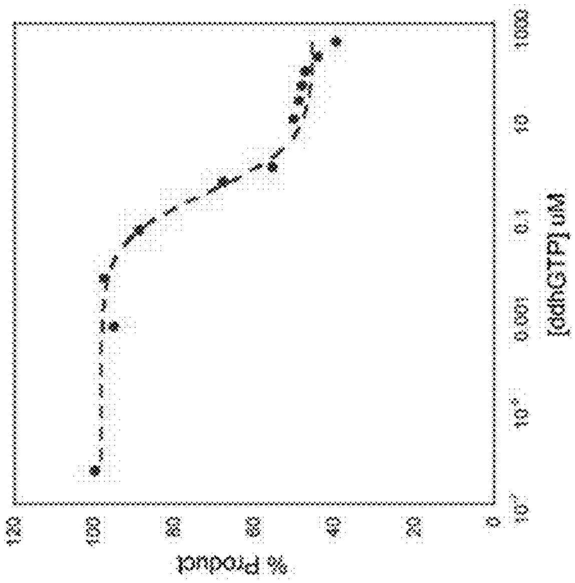

After incorporation of natural nucleotide, the addition of GTP and CTP (third and fourth nucleotides to be incorporated), proceeds RNA elongation up to 10th position. However, the incorporation of ddhUTP and ddhGTP caused chain termination of RNA synthesis, similarly as canonical chain terminator, 3'-dUTP and 3'-dGTP (FIG. 27B, lanes 7-10 and FIG. 28B lanes 4, 5). Both ddh nucleotides were able to terminate the polymerization of RNA at concentration of 100 mM.

ddhUTP and ddhGTP inhibitory effect on SARS-Cov2 RdRp was analyzed by calculating the half-maximal inhibitory concentration (IC50) of ddhUTP and ddhGTP against RdRp. IC50 of 1.9±0.1 and 0.29±0.07 mM for ddhUTP and ddhGTP, respectively (Table 26, FIG. 29) indicates that both compounds are a potent inhibitors of RNA replication of SARS-Cov2 RdRp.

Inhibition of Human DNA and RNA Polymerases

Figure 30A:
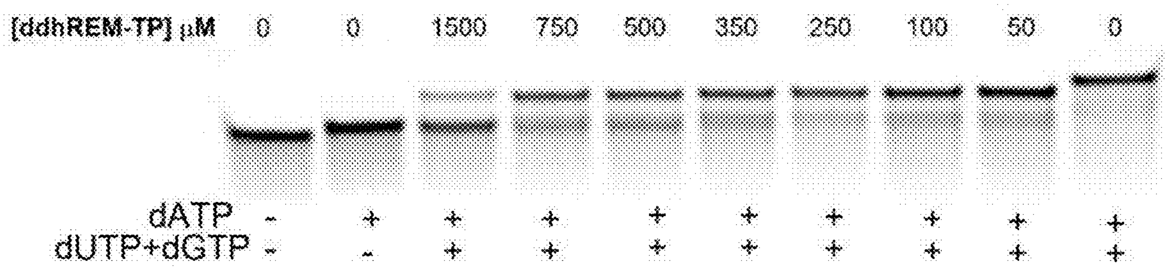
FIGS. 30A-30B. Inhibition of POLRMT by ddhREM-TP.
Figure 30B:
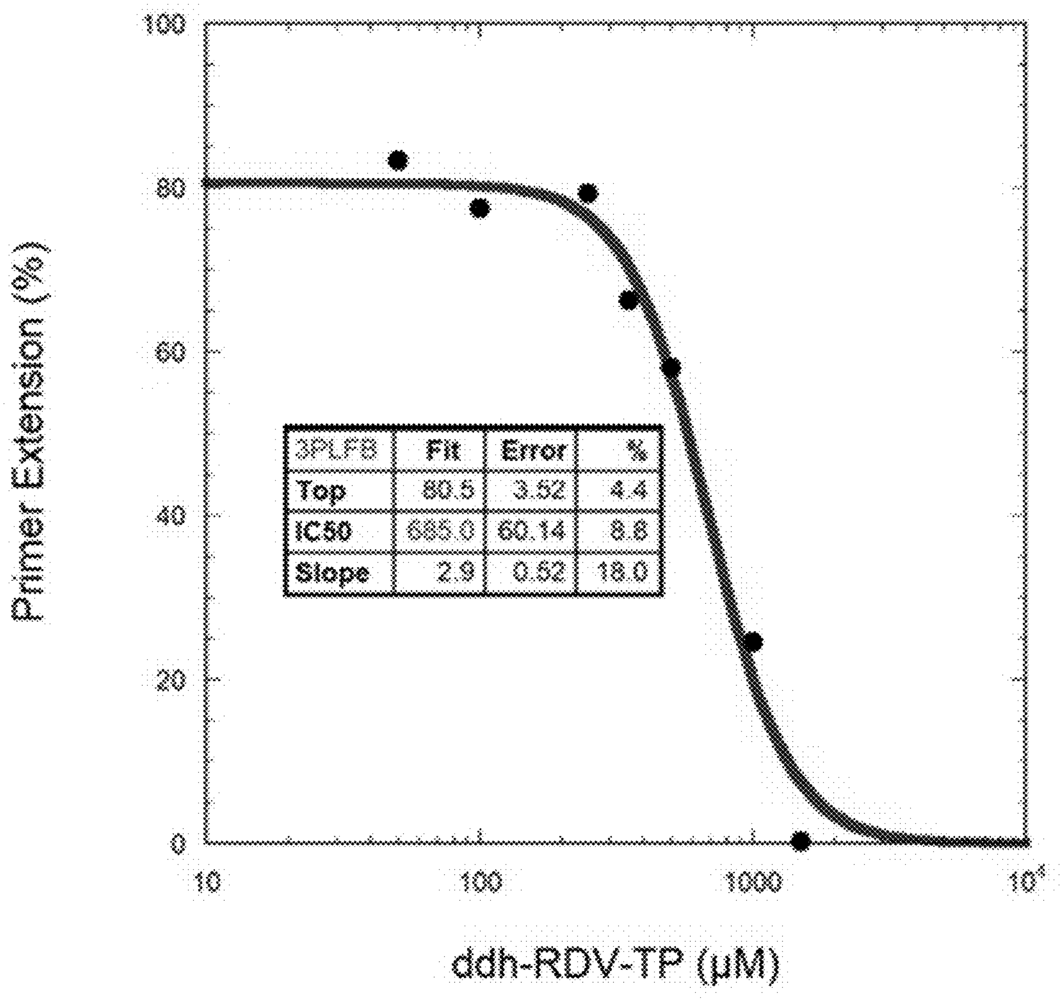
Figure 31A:
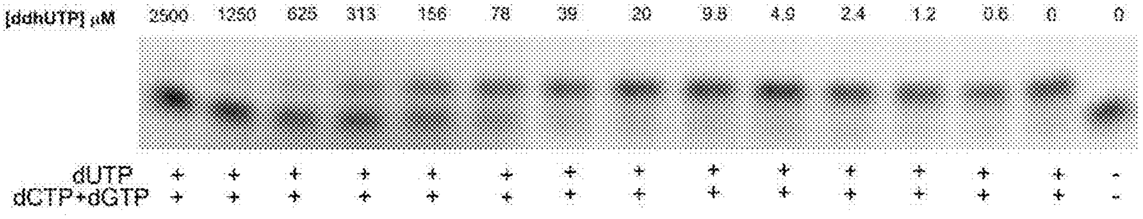
FIGS. 31A-31B. Inhibition of POLRMT by ddhUTP.
Figure 31B:
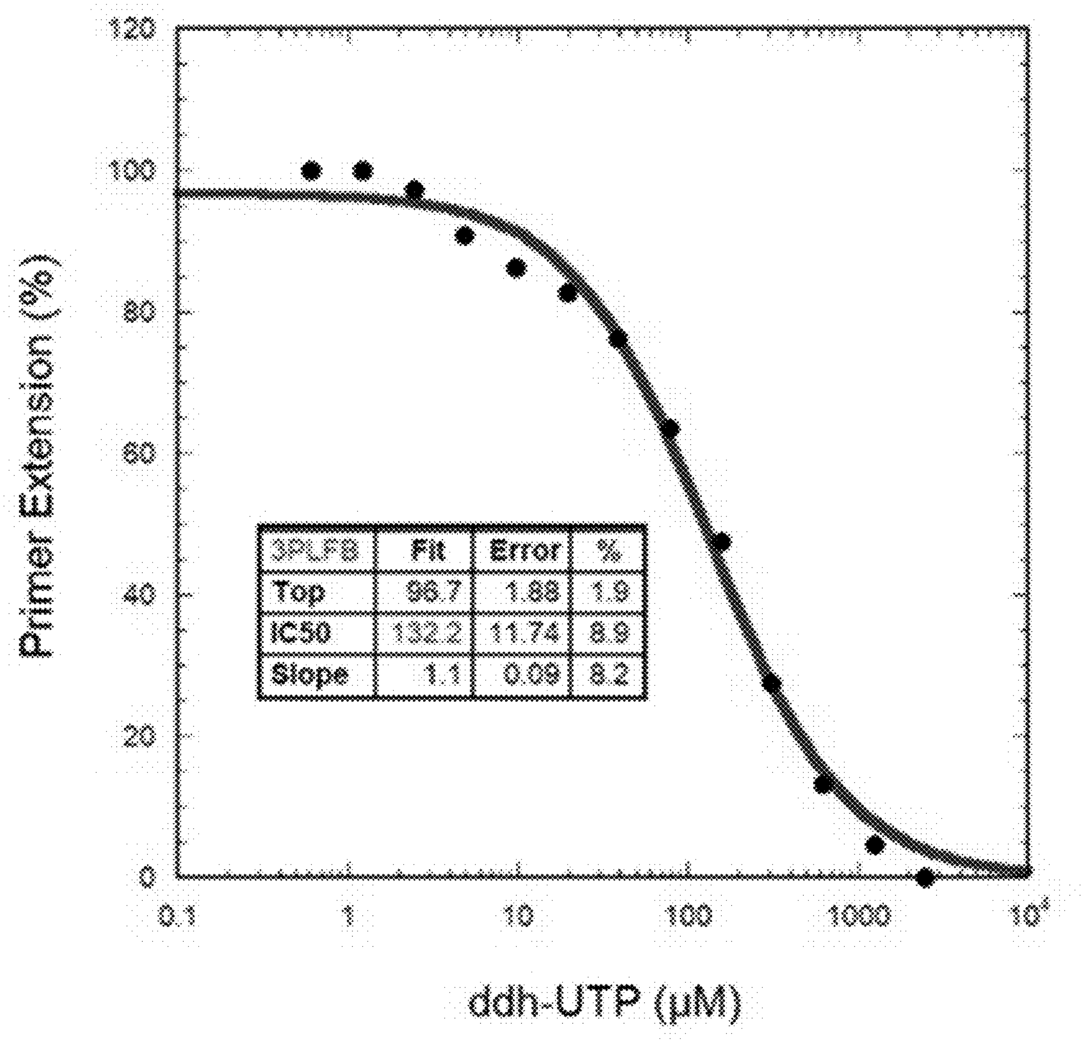
Figure 32A:
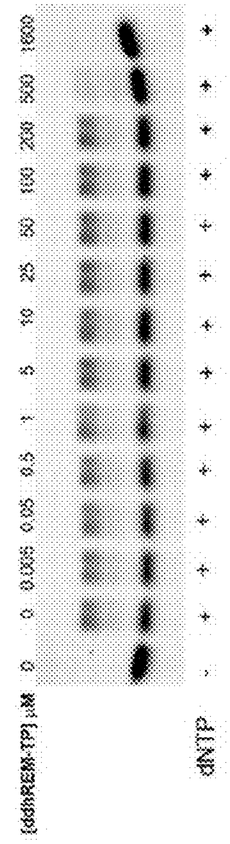
FIGS. 32A-32D. Inhibition of POLG1 by ddhREM-TP and ddhUTP.
Figure 32B:
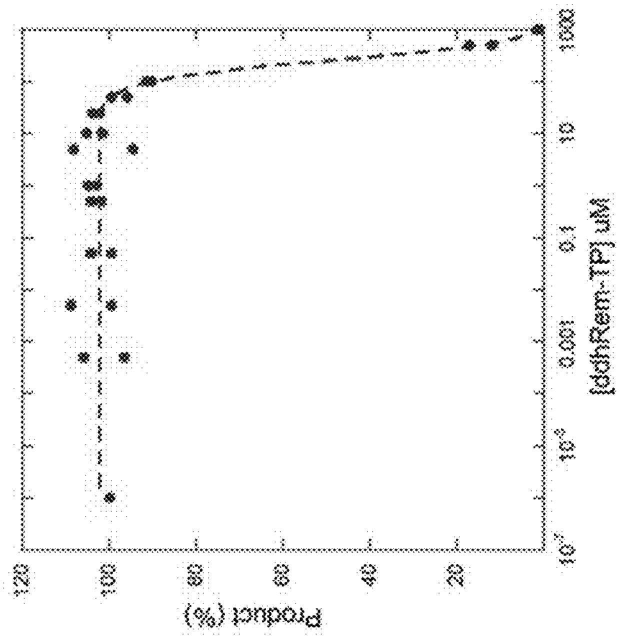
Figure 32C:
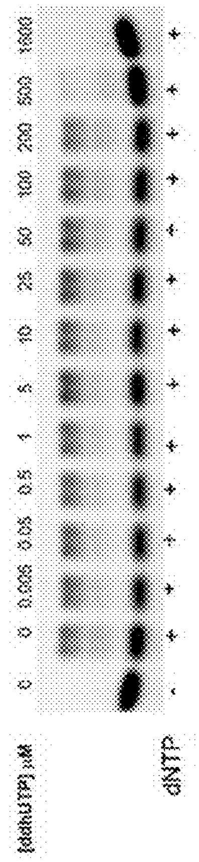
Figure 32D:
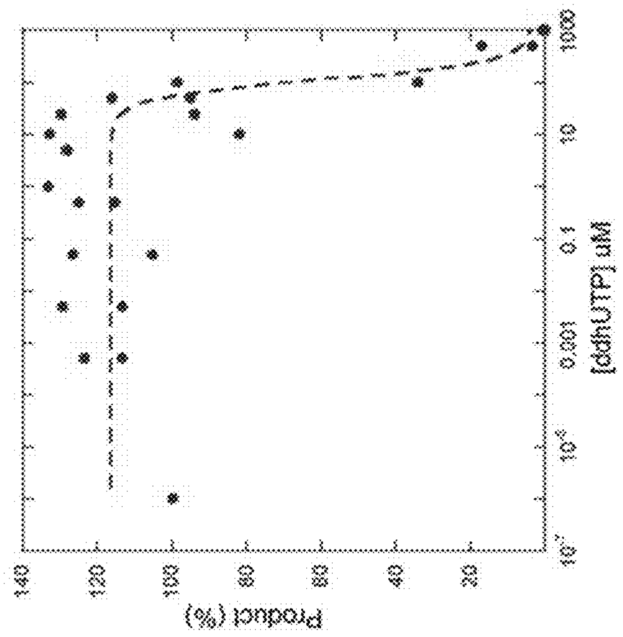
Figure 33A:
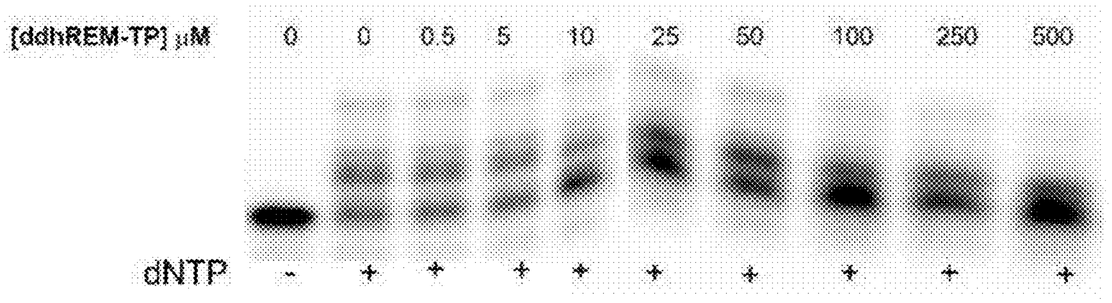
FIGS. 33A-33B. Inhibition of PrimPol by ddhREM-TP and ddhUTP.
Figure 33B:
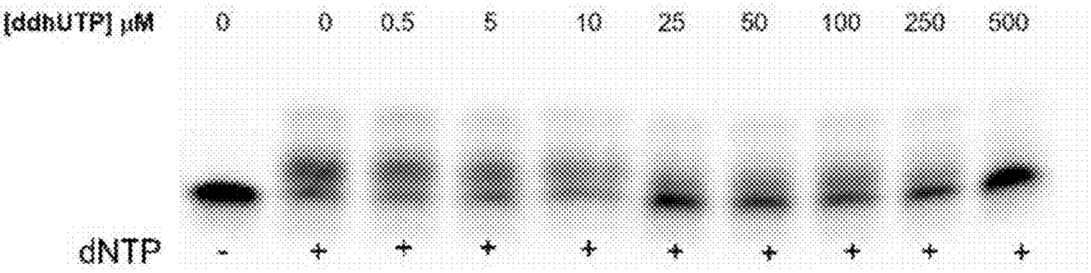

To assess the potential for off-target effect we tested the inhibition effect of potent inhibitors—ddhREM-TP and ddhUTP with the potential molecular targets of toxicity—POLG1, POLRMT and PrimPol. For ddhREM-TP toxicity, P6/dT1 primer/template complex requires $1^{st}$ incorporation of analog—and then $2^{nd}$ and $3^{rd}$ incorporation of UTP and GTP. For ddhUTP toxicity, P6/dT4 primer/template complex requires $1^{st}$ incorporation of analog—and then $2^{nd}$ and $3^{rd}$ incorporation of GTP and CTP. FIGS. 30-31 show that none of the ddh analogs inhibited POLRMT in concentration of 100 mM with IC50 of >200 mM. FIGS. 32 and 33 demonstrate inhibitory effect of POLG1 and PrimPol, respectively by ddhREM-TP and ddhUTP (Table 26). These results indicate that ddhREM-TP and ddhUTP are poor substrates for POLG1, POLRMT and PrimPol.

Figure 34A:
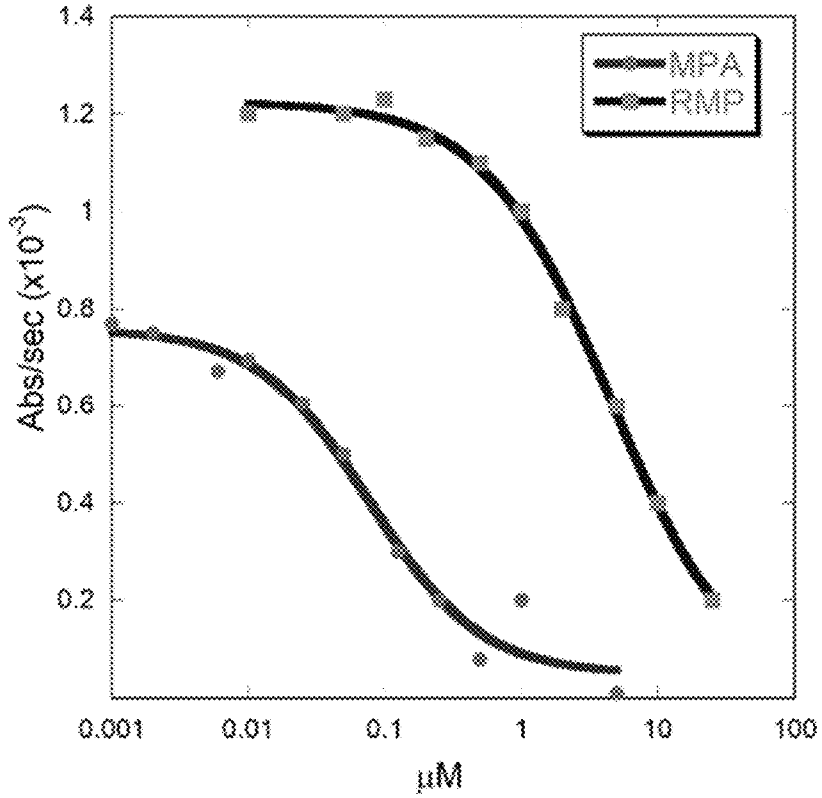
FIGS. 34A-34B. Inhibition of IPDH by ddhUMP and ddhGMP.
Figure 34B:
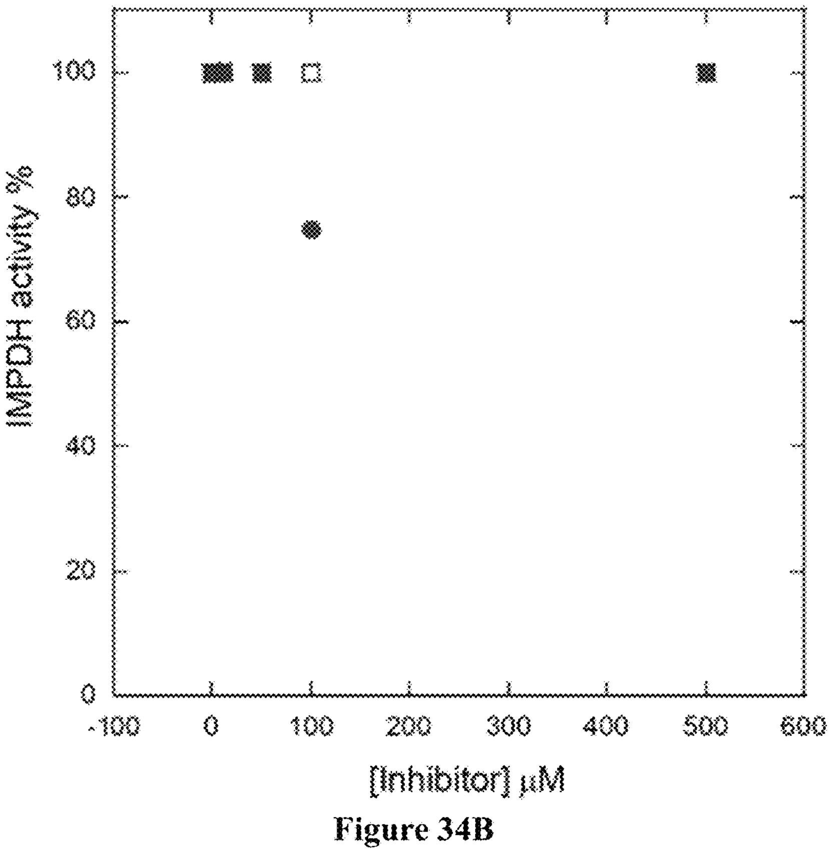

Human Inosine-5'-Monophosphate Dehydrogenase 2 (IMPDH2) Inhibitor Screening Assay IMPDH2 is a rate-limiting enzyme in de novo guanine nucleotide biosynthesis. IMPDH2 oxidizes inosine 5'-monophosphate (IMP) to xanthine 5'-monophopshate (XMP) using NAD as a cofactor. This enzyme is critical in cell growth and recognized as a validated target of some antiviral agents. Here, the goal was to examine if monophosphates metabolites of ddhUTP and ddhGTP can bind IMPDH and block its activity. To test the inhibitory effect of ddhUMP and ddhGMP toward IMPDH a BioVision IMPDH inhibitor screening assay was used, where IMP oxidized by IMPDH producing series of intermediates, which react with the probe to generated colorimetric signal (OD 450 nm). The signal is directly proportional to the IMPDH activity. Mycophenolic acid (MPA), a known IMPDH inhibitor was used as a positive control. Ribavirin 5'-monophosphate (RMP), that also known as IMPDH inhibitor that inhibits viral DNA and RNA replication through guanosine triphosphate synthesis was used as another positive control and antiviral agent. MPA and RMP demonstrated strong inhibition of IMPDH with IC50 of 76±10 nM and 2.6±1.8 uM, respectively (FIG. 34A). ddhUMP and ddhGMP both failed decrease IMPDH activity–IC50>1 mM (FIG. 34B). These results indicates that monophosphate form of ddhUTP and ddhGTP do not inhibit IMPDH at concentration that were used here.

Example 18—Antiviral Activity of ddh-Compounds in hCMV Assay

Objective: To examine the anti-hCMV activity of ddh-Compounds: AB21649 (compound 24; Formula IVB), AB23031 (compound 26; Formula IVB), AB23039 (compound 104; Formula IVB); AB21651 (compound 31; Formula IB), AB23032 (compound 33; Formula IIB), and AB23040 (compound 103; Formula IIB).

Methods:

HCMV Plaque Reduction Assay

General Description of HCMV Plaque Reduction Assay

MRC-5 cells were seeded at $1\times10^5$ cells/well in 24 well plates using MRC-5 growth medium. The plates were incubated overnight at 37° C. and 5% $CO_2$. The following day, media is aspirated and approximately 100 plaque forming units (pfu) of HCMV AD169 is added to 21 wells of each plate in a volume of 200 μL of assay medium (MRC-5 growth medium containing 2% FBS rather than 10% FBS). The remaining three wells of each plate serve as cellular control wells and receive 200 μL of assay medium without virus. The virus is allowed to adsorb onto the cells for 1 hr at 37° C. and 5% CO2.

Compounds were prepared by diluting them in assay medium containing 0.5% Methylcellulose. After the incubation period, 1 mL of each drug dilution is added to triplicate wells of a plate (without aspirating the virus inoculum). Assay medium (without drug) containing 0.5% Methylcellulose is added to the three cell control wells and to three virus control wells on each plate. Table 27 represents the standard plate format for evaluating the efficacy of compounds at 6 (triplicate) concentrations using a representative high-test concentration of 100 μM.

TABLE 27

Plate Format for Human Cytomegalovirus Plaque Reduction Assays Triplicate (6 dilutions)

| | 1 | 2 | 3 | 4 | 5 | 6 |
|---|---|---|---|---|---|---|
| A | | Cell Control | | | Virus Control | |
| B | Drug 1 | Drug 1 | Drug 1 | Drug 1 | Drug 1 | Drug 1 |
| C | High Test | 32 μM | 10 μM | 3.2 μM | 1.0 μM | Low-Test |
| D | 100 μM | | | | | 0.32 μM |

The plates were incubated for 6 days to allow for plaque formation. Cultures were examined microscopically, and compound precipitation and toxicity were noted. The media is then aspirated from the wells and the cells were fixed and stained using 20% Methanol containing Crystal Violet. Plaques were enumerated by microscopic inspection and the data is plotted as percent of virus control.

MRC-5 Cell Culture (ATCC CCL-171)

MRC-5 cells (Embryonal lung fibroblast, diploid, male, Human) were obtained from the American Type Culture Collection (ATCC, Rockville, Maryland) and were grown in Dulbecco's Modified Eagle's Medium DMEM) supplemented with 10% fetal bovine serum (FBS), 0.1 mM nonessential amino acids, 1.0 mM sodium pyruvate, 2.0 mM L-Glutamine, 100 units/ml Penicillin and 100 μg/ml Streptomycin ("MRC-5 growth medium"). Cells were sub-cultured twice a week at a split ratio of 1:2 using standard cell culture techniques.

HCMV Strain AD169 (ATCC VR-538)

HCMV Strain AD169 was obtained from the ATCC. Virus stocks were prepared by infecting approximately 80% confluent monolayers of MRC-5 cells at a minimal multiplicity of infection in MRC-5 growth medium containing a reduced FBS concentration (2%). Monolayers were incubated at 37° C. and 5% CO2 until 90-95% viral cytopathic effect (CPE) was observed (6 days). Culture medium was then collected from the cells, centrifuged at low speed to remove cellular debris, aliquoted in 1 ml volumes and frozen/stored at −80° C. as stock virus. The virus titer of the stock was determined by infecting MRC-5 cells with serial dilutions of the stock virus using an overlay medium. Plaques were enumerated in the cultures where the dilutions of virus allowed for the formation of individual plaques and the titer was determined based upon the number of plaques counted, the dilution of virus used and the volume of virus used to infect the cells.

MRC-5 Cytotoxicity Assay

MRC-5 cells were seeded at 1×104 cells per well in 96 well plates using MRC-5 growth medium. The plates were incubated overnight at 37° C. and 5% CO2. The following day, compounds were prepared in assay medium. Growth medium is removed from the plates and replaced with the prepared test compounds. Each dilution of compound is tested in triplicate. Each toxicity plate contains the necessary cell control and compound color controls. Table 28 represents the standard plate format for evaluating toxicity of compounds at 6 (triplicate) concentrations using a representative high-test concentration of 100 µM.

TABLE 28

Plate Format for Human Cytomegalovirus Cytotoxicity Assays Triplicate (6 dilutions)

| | 1 | 2 | 3 | 4 | 5 | 6 | 7 | 8 | 9 | 10 | 11 | 12 |
|---|---|---|---|---|---|---|---|---|---|---|---|---|
| A | | | | | | Reagent Background Control Wells (Media plus MTS, no cells) | | | | | | |
| B | Color 1 100 µM | | Drug 1 Tox High-Test 100 µM | | | Drug 2 Tox High-Test 100 µM | | | Drug 3 Tox High-Test 100 µM | | Cell Control | Reagent Background Control |
| C | Color 1 32 µM | | Tox 1 32 µM | | | Tox 2 32 µM | | | Tox 3 32 µM | | | Wells (Media plus |
| D | Color 1 10 µM | | Tox 1 10 µM | | | Tox 2 10 µM | | | Tox 3 10 µM | | | MTS, no cells) |
| E | Color 1 3.2 µM | | Tox 1 3.2 µM | | | Tox 2 3.2 µM | | | Tox 3 3.2 µM | | | |
| F | Color 1 1.0 µM | | Tox 1 1.0 µM | | | Tox 2 1.0 µM | | | Tox 3 1.0 µM | | | |
| G | Color 1 0.32 µM | | Drug 1 Tox Low-Test 0.32 µM | | | Drug 2 Tox Low-Test 0.32 µM | | | Drug 3 Tox Low-Test 0.32 µM | | | |
| H | Color 1 100 µM | Color 2 32 µM | Color 2 10 µM | Color 2 3.2 µM | Color 2 1.0 µM | Color 2 0.32 µM | Color 2 100 µM | Color 2 32 µM | Color 2 10 µM | Color 2 3.2 µM | Color 2 1.0 µM | Color 2 0.32 µM |

Cells labeled as "Tox 1", "Tox 2", "Tox 3" = Cells + Drug 1 Drug 2, or Drug 3, respectively (toxicity tested in triplicate)

Cells labeled as "Color 1" "Color 2", or "Color 3" = Media + Drug 1, Drug 2, or Drug 3, respectively, (colormetric background, no cells)

After a six day incubation period, cell viability is determined using CellTiter 96 Aqueous One Solution (Promega Corporation). This solution contains MTS (3-(4,5-dimethylthiazol-2-yl)-5-(3-carboxymethoxyphenyl)-2-(4-sulfophenyl)-2H-tetrazolium) which is converted by viable cells into an intensely colored formazan product. The solution is added to the wells of the 96 well plate in a volume resulting in a final 10% concentration (volume:volume) in each well.

Plates were incubated for an additional 4 hours at 37° C. Adhesive plate sealers were used in place of the lids, the sealed plates were inverted several times to mix the soluble formazan product and the plate is read spectrophotometrically at 490 and 650 nm with a Molecular Device Spectra-Max i3 plate reader. In addition to MTS dye reduction, the visual cytotoxicity of each concentration of test compound is visually assessed directly on the plates used for plaque assay. In this case, the appearance of cells in wells that contain both test article and virus were compared to the appearance of cells in the virus control. Visual cytotoxicity (tox) is scored as follows: 0=0% tox, 1=monolayer is disturbed, 2=monolayer is up to 50% gone, 3=significant loss of monolayer, and 4=100% tox (no cells).

Data Analysis

The minimum inhibitory drug concentration that reduces plaque formation by 50% ($EC_{50}$) and the minimum drug concentration that inhibits cell growth by 50% ($CC_{50}$) were calculated. A selectivity index (SI) for each active compound is determined by dividing the $CC_{50}$ by the $EC_{50}$.

Results:

TABLE 29 hCMV assay (MRC5 cells, AD169 strain of hCMV)

| Test Article | $EC_{50}$ (µM) | $CC_{50}$ (µM) | Selectivity Index ($CC_{50}/EC_{50}$) |
|---|---|---|---|
| AB21649 | >100 | >100 | N/A |
| AB23031 | >100 | >100 | N/A |
| AB23039 | 18.1 | 42.2 | 2.33 |
| AB21651 | >100 | >100 | N/A |
| AB23032 | >100 | >100 | N/A |

TABLE 29-continued hCMV assay (MRC5 cells, AD169 strain of hCMV)

| Test Article | $EC_{50}$ (µM) | $CC_{50}$ (µM) | Selectivity Index ($CC_{50}/EC_{50}$) |
|---|---|---|---|
| AB23040 | 22.1 | >100 | >4.52 |
| Ganciclovir | 7.36 | >100 | >13.6 |

Plaque assay, 6-days duration

Summary: The data presented above for AB23039 (Hostetler prodrug of ddhU) and AB23040 (Hostetler prodrug of ddhG) indicate that these ddh-compounds show impressive antiviral activity against hCMV.

Example 19—Antiviral Assessment of Natural Nucleoside Analogs

Objective: To examine the antiviral (JCV, and hCMV) activity, and effects on HFF and MOLT-3 proliferation of ddh-Compounds: AB23031 (compound 26; Formula IVB), AB23039 (compound 104; Formula IVB); AB23032 (compound 33; Formula IB), and AB23040 (compound 103; Formula IIB).

Methods:

Compounds were solubilized by adding DMSO to each, based on quantities and molecular weights specified to achieve a final 30 mM concentration. These stocks were stored at −20° C. There were no problems with solubility of the compounds in DMSO.

The working test compound solutions (1.5; 1.0 mM) were prepared by diluting the DMSO stocks in warmed MEM+20% FBS. There were no problems with solubility of the compounds in 2% MEM.

Positive and negative control drugs were prepared as per usual with working solutions at 1.5 and 1.0 mM in MEM+2% FBS.

Cell Proliferation Assay—Human Foreskin Fibroblast (HFF) Cells

HFF cells were seeded in 6-well plates at a concentration of $2.5\times10^4$ cells per well. The plates were incubated for 24 h and the media removed prior to adding compound dilutions in growth media. The cells were incubated for 72 h at 37° C., then the cells were removed with trypsin/EDTA and viable cells in duplicate wells were enumerated with a Coulter Counter. Average cell number in untreated control cultures was used to calculate the concentration of compound sufficient to reduce cell number by 50% ($IC_{50}$).

Cell Proliferation Assay—Human Lymphoblastoid MOLT-3 Cells

Drug dilutions were prepared in a 384 well spheroid plate as per usual. MOLT-3 cells were dispensed into each well at a concentration of $2.0\times10^3$ cells per well and the plate was incubated for 7 d at 37° C. After incubation, CellTiter-Glo was added and the relative light units determined using a luminometer. The concentration of compound sufficient to reduce cell number by 50% was calculated as the $CC_{50}$.

Secondary JCV Assay

COS7 cells in MEM with 10% FBS were plated into 96 well plates and incubated overnight in a $CO_2$ incubator. The media was then removed and replaced with 2% MEM. Drugs at the appropriate starting concentrations were added and then serially diluted 1:3 for 12 dilutions. Virus or media, for toxicity determinations, was then added and the plates incubated for 7 days. After 7 days, the DNA was extracted and quantified by qPCR using the primers and probes previously given for JC virus. $EC_{50}$ and $EC_{90}$ values were then calculated.

Secondary JCV Results

Test drug concentration 0.001-100 μM.

Control drug concentration 0.001-100 μM.

| Drug | Activity | $EC_{50}$ | $EC_{90}$ | $CC_{50}$ | $SI_{50}$ | $SI_{90}$ |
|---|---|---|---|---|---|---|
| AB23031 | NA | 93.82 | >100.00 | >100.00 | >1 | 1 |
| AB23032 | NA | >100.00 | >100.00 | >100.00 | 1 | 1 |
| AB23039 | MOD | 3.07 | 9.44 | 46.77 | 15 | 5 |
| AB23040 | HI | 0.37 | 18.55 | 31.28 | 85 | 2 |

NA (Not Active) $SI_{50}$ = 0-3.9
LO (Slightly Active) $SI_{50}$ = 4-9.9
MOD (Moderately Active) $SI_{50}$ = 10-19.9
HI (Highly Active) $SI_{50}$ = ≥20

Summary:

Proliferation assays were performed using AB23039 and AB23040 in human foreskin fibroblast (TIFF) cells and human lyphoblastoid MOLT-3 cells (4 assays total). AB23039 showed no inhibition of cell growth at the highest concentration tested ($IC_{50}$=>100 μM) in the proliferation assay using HFF cells (Fialuridine yielded $IC_{50}$=2.40 μM). The same was noted for this compound at the highest concentration tested ($CC_{50}$=>150 μM) in the proliferation assay using MOLT-3 cells. AB23040 yielded values of 65.90 μM and 112.04 μM in the HFF proliferation and the MOLT-3 assay, respectively. Positive and negative controls drugs performed as expected in these assays (positive control CDV yielded $CC_{50}$ of 101.21 μM and negative control TNV yielded $CC_{50}$>150 μM).

Proliferation assays were performed using AB23031 (compound 26; Formula IVB) in human foreskin fibroblast (HFF) cells and human lyphoblastoid MOLT-3 cells (2 assays total). AB23031 showed no inhibition of cell growth at the highest concentration tested ($IC_{50}$=>100 μM) in the proliferation assay using HFF cells (Fialuridine yielded $IC_{50}$=2.90 μM), but yielded a $CC_{50}$ of 55.40 μM in the MOLT-3 cells (positive control CDV yielded $CC_{50}$ of 97.05 μM and negative control TNV yielded $CC_{50}$>150 μM).

Secondary testing results against JCV demonstrate moderate (AB23039) and high (AB23040) antiviral activity for these compounds, as well as a measure of toxicity for each: AB23039—$CC_{50}$=46.77 μM; AB23040—$CC_{50}$=31.28 μM in COS7 cells.

Example 20—Antiviral Assessment of Natural Nucleoside Analogs

Objective: To examine compounds AB23039 (compound 104; Formula IVB) and AB23040 (compound 103; Formula IB)) in primary assays against BK virus (BKV) and JC virus (JCV). Brincidofovir (BCV) was added as an additional positive control drug to be used against all of the viruses tested in the primary assays.

Methods:

Compound AB23039 (compound 104; Formula IVB) was solubilized by adding DMSO, based on quantities and molecular weights specified to achieve a final 30 mM concentration. The stock was stored at −20° C. AB23040 was solubilized to a final 25 mM DMSO stock concentration and was also stored at −20° C. after use.

There were no problems with solubility of the compounds in DMSO.

The working test compound solutions (1.5 mM) were prepared by diluting the DMSO stocks in warmed MEM+2% FBS.

There were no problems with solubility of the compounds in 2% MEM.

Positive and negative control drugs were prepared as per usual with working solutions at 1.5, 1.0 and 0.1 mM in MEM+2% FBS.

See Example 20 above.

Results:

Primary Assay Results

BK Virus (BKV)

Test Drug Concentration: 0.048-150 μM.

Control Drug Concentration: 0.048-150; 0.003-10 μM.

TABLE 30

BKV Assay Results

| Drug | Activity | $EC_{50}$ | $EC_{90}$ | $CC_{50}$ | $SI_{50}$ | $SI_{90}$ |
|---|---|---|---|---|---|---|
| COV | — | 0.22 | 25.63 | >150.00 | >682 | >26 |
| TNV | — | 28.82 | >150.00 | >150.00 | >5 | 1 |
| BCV | — | 0.06 | 0.39 | >10.00 | >167 | >26 |
| AB23039 | HI | 0.86 | 7.76 | 90.90 | 106 | 12 |
| AB23040 | LO | 4.97 | >6.00 | 25.12 | 5 | <4 |

NA (Not Active) $SI_{50}$ = 0-3.9
LO (Slightly Active) $SI_{50}$ = 4-9.9
MOD (Moderately Active) $SI_{50}$ = 10-19.9
HI (Highly Active) $SI_{50}$ = ≥20

JC Virus (JCV)

Test Drug Concentration: 0.048-150 μM.

Control Drug Concentration: 0.048-150; 0.003-10 μM.

TABLE 31

JCV Assay Results

| Drug | Activity | $EC_{50}$ | $EC_{90}$ | $CC_{50}$ | $SI_{50}$ | $SI_{90}$ |
|---|---|---|---|---|---|---|
| CDV | — | 5.66 | 106.69 | >150.00 | >27 | >1 |
| TNV | — | >150.05 | >150.00 | >150.00 | 1 | 1 |
| BCV | — | 0.74 | 1.85 | 9.25 | 12 | 5 |
| AB23039 | HI | 0.21 | 23.40 | 71.79 | 342 | 3 |
| AB23040 | LO | 8.85 | 27.98 | 80.71 | 9 | 3 |

NA (Not Active) $SI_{50}$ = 0-3.9
LO (Slightly Active) $SI_{50}$ = 4-9.9
MOD (Moderately Active) $SI_{50}$ = 10-19.9
HI (Highly Active) $SI_{50}$ = ≥20

Summary:

All primary assays have been performed, with AB23039 exhibiting high activity against BK and JC viruses. Low activity was noted for AB23040 against both BK and JC viruses. As expected, BCV was active against all viruses in the appropriate test range with high or moderate activity.

Example 21—Antiviral Assessment of Natural Nucleoside Analogs

Objective: To examine three compounds: AB23031 (compound 26; Formula IVB), AB23032 (compound 33; Formula IIB), and AB23036 (compound 56; Formula VIB) in primary assays against compounds against Human cytomegalovirus (hCMV) and BK virus (BKV).

Methods:

All compounds were solubilized by adding DMSO to each, based on quantities and molecular weights specified to achieve a final 30 mM concentration. These stocks were stored at −20° C. There were no problems with solubility of the compounds in DMSO.

The working test compound solutions (1.5 mM) were prepared by diluting the 30 mM DMSO stocks 1:20 in warmed MEM+20% FBS. There were no problems with solubility of the compounds in 2% MEM.

Positive and negative control drugs were prepared as per usual with working solutions at 1.5 and 1.0 mM in MEM+2% FBS.

Viral assays were performed as described above.

Results:

Human Cytomegalovirus (hCMV)

Test Drug Concentration: 0.048-150 μM.

Control Drug Concentration: 0.048-150 μM.

TABLE 32 hCMV Assay Results

| Drug | Activity | $EC_{50}$ | $EC_{90}$ | $CC_{50}$ | $SI_{50}$ | $SI_{90}$ |
|---|---|---|---|---|---|---|
| GCV | — | 0.19 | >150.00 | >150.00 | >785 | 1 |
| TNV | — | >150.00 | >150.00 | >150.00 | 1 | 1 |
| AB23031 | HI | 0.15 | >150.00 | >150.00 | >1034 | 1 |
| AB23032 | NA | >150.00 | >150.00 | >150.00 | 1 | 1 |
| AB23036 | NA | >150.00 | >150.00 | >150.00 | 1 | 1 |

NA (Not Active) $SI_{50}$ = 0-3.9
LO (Slightly Active) $SI_{50}$ = 4-9.9
MOD (Moderately Active) $SI_{50}$ = 10-19.9
HI (Highly Active) $SI_{50}$ = ≥20

BK Virus (BKV)

Test Drug Concentration: 0.048-150 μM.

Control Drug Concentration: 0.048-150 μM.

TABLE 33

BKV Assay Results

| Drug | Activity | $EC_{50}$ | $EC_{90}$ | $CC_{50}$ | $SI_{50}$ | $SI_{90}$ |
|---|---|---|---|---|---|---|
| CDV | — | 4.62 | 106.45 | >150.00 | >32 | >1 |
| TNV | — | >150.00 | >150.00 | >150.00 | 1 | 1 |
| AB23031 | HI | 5.12 | >150.00 | >150.00 | >29 | 1 |
| AB23032 | NA | 77.21 | 149.16 | >150.00 | >2 | >1 |
| AB23036 | NA | 108.88 | >150.00 | >150.00 | >1 | 1 |

NA (Not Active) $SI_{50}$ = 0-3.9
LO (Slightly Active) $SI_{50}$ = 4-9.9
MOD (Moderately Active) $SI_{50}$ = 10-19.9
HI (Highly Active) $SI_{50}$ = ≥20

Summary:

No toxicity was detected in all 3 compounds. AB23031 is highly active against hCMV and BKV.

Example 22—Synthetic Approach for AB23040 (Compound 103; Formula IIB)

Objective: To provide a synthetic scheme for compound 103

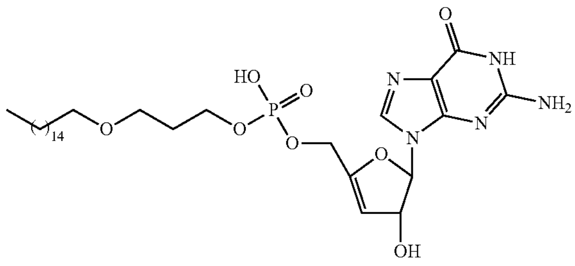

Scheme
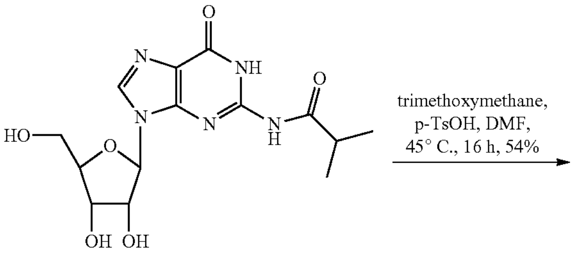
1
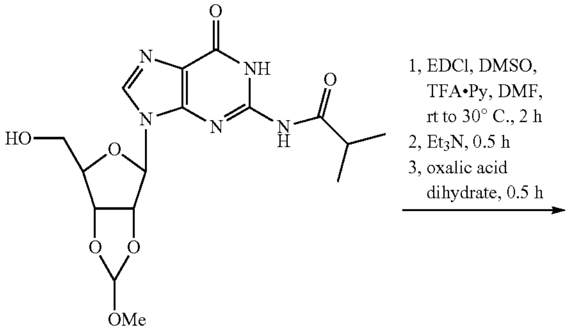
2
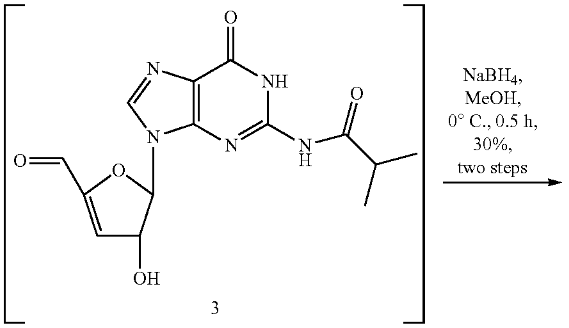
3
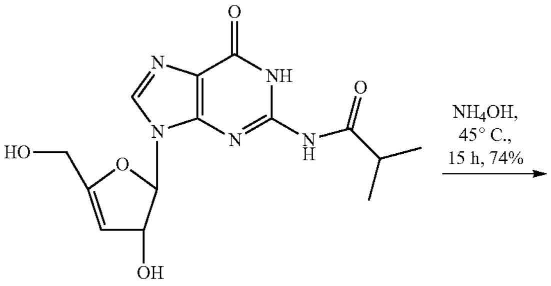
4
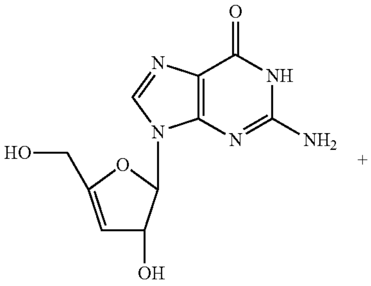
5
-continued
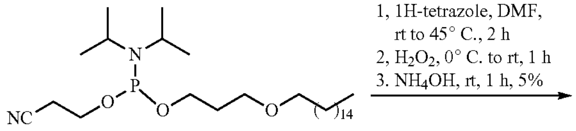
6
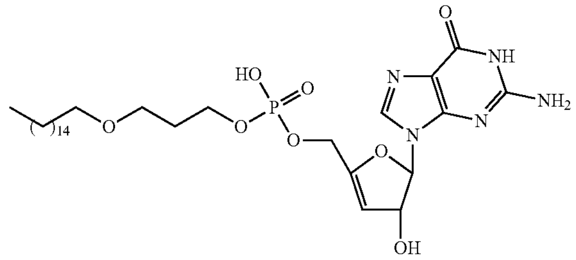 [SMILES: CCCOCCCOP(=O)(O)OCC1=CC(O)C(n2cnc3c(=O)[nH]c(N)nc32)O1]
7
200 mg
AB23040
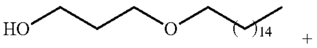
8
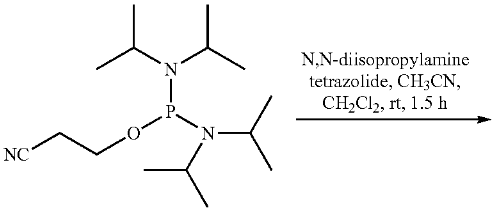
9
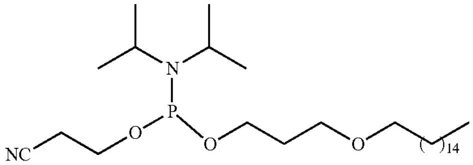
6
Procedure
General Procedure for the Preparation of Compound 2:
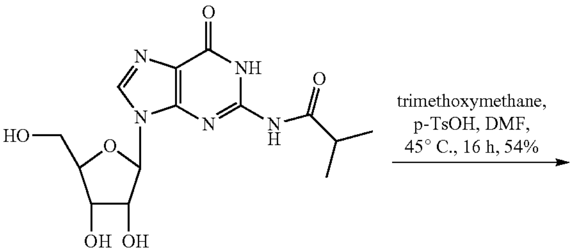
1

-continued

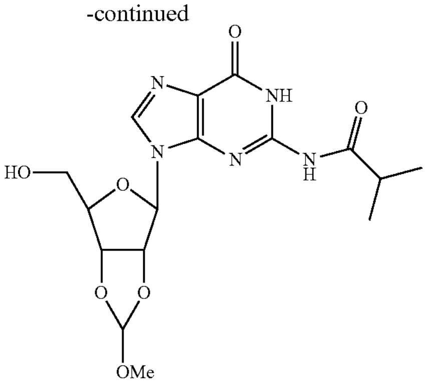

2

To a solution of compound 1 (50 g, 0.14 mol, 1.0 eq) in dry DMF (120 mL) was added trimethoxymethane (154.2 mL, 1.4 mol, 10.0 eq) and p-TsOH (24.2 g, 0.14 mol, 1.0 eq) sequentially. The mixture was stirred at 45° C. for 15 h. The mixture was quenched with Amberlyst® A-21 and triethylamine. After the evaporation of the solvent, the residue was purified by flash column chromatography (dichloromethane: methanol, 9:1) to afford compound 2 (30 g, 54%) as a white foam.

General Procedure for the Preparation of Compound 3

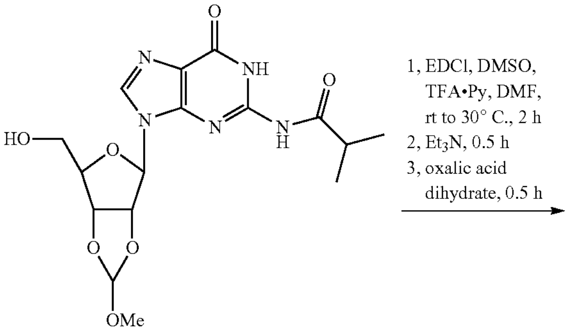

2

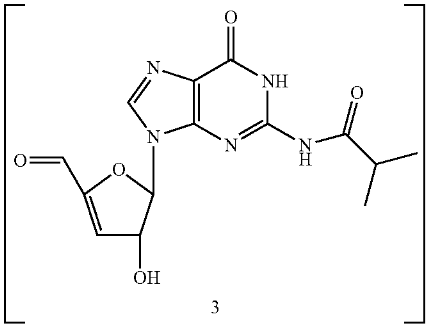

3

To a solution of 2 (30 g, 75.9 mmol, 1.0 eq) in dry DMF (180 mL) was added dimethyl sulfoxide (32.3 mL, 455.4 mmol, 6.0 eq), EDCI (43.7 g, 227.7 mmol, 3.0 eq) and TFA·py (7.32 g, 37.95 mmol, 0.5 eq) sequentially. The mixture was stirred at 30° C. for 2 h. Then triethylamine (42.2 mL, 303.6 mmol, 4.0 eq) was added to the reaction mixture, after stirring for 0.5 h, oxalic acid dihydrate (19.1 g, 151.8 mmol, 2.0 eq) was added. After stirring for another 30 min at room temperature, the mixture was concentrated under reduce pressure and purified by chromatography over silica gel (dichloromethane/methanol, 50/1 to 10/1) to afford crude compound 3 (40 g) as a yellow solid, which was used for the next step directly without further purification.

General Procedure for the Preparation of Compound 4

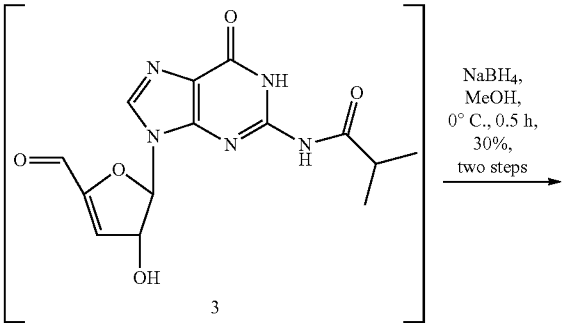

3

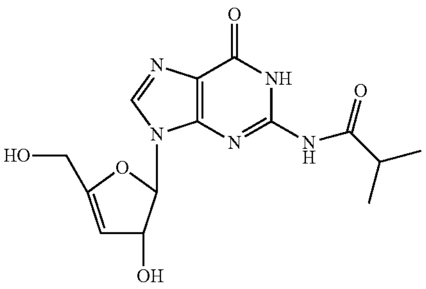

4

The crude compound 3 (40 g, 120.1 mmol, 1.0 eq) was dissolved in methanol (200 mL). The reaction mixture was cooled to 0° C. and $NaBH_4$ (2.27 g, 60.05 mmol, 0.50 eq) was added. After stirring at 0° C. for 1 h, the result mixture was quenched with diluted aqueous $NH_4Cl$ (5 M, 20 mL). After evaporation of the solvent, the residue was purified by a flash column chromatography (dichloromethane/methanol, 8/1) to afford 4 (7.5 g, 30%, two steps) as a white solid.

General Procedure for the Preparation of Compound 5

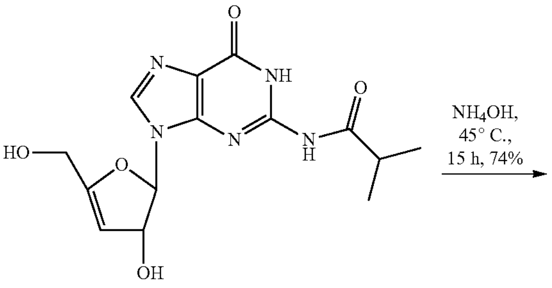

4

-continued

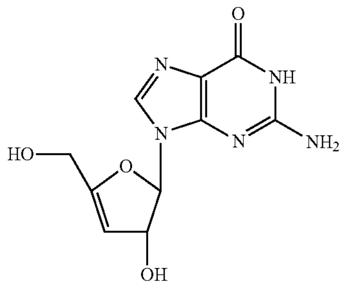

5

A solution of 4 (7.5 g, 22.3 mmol, 1.0 eq) in $NH_4OH$ (100 mL) was stirred at 45° C. for 13 h. The result mixture was concentrated under reduced pressure, the residue was purified by triturated with methanol to afford 5 (4.4 g, 74%) as white solid.

$^1H$ NMR (400 MHz, DMSO-d6) δ 9.22 (s, 1H), 7.60 (s, 1H), 6.53 (s, 2H), 6.00 (d, J=2.4 Hz, 1H), 5.66 (d, J=4.9 Hz, 1H), 5.26-5.12 (m, 2H), 5.02 (s, 1H), 3.97 (s, 2H).

General Procedure for the Preparation of Compound 6

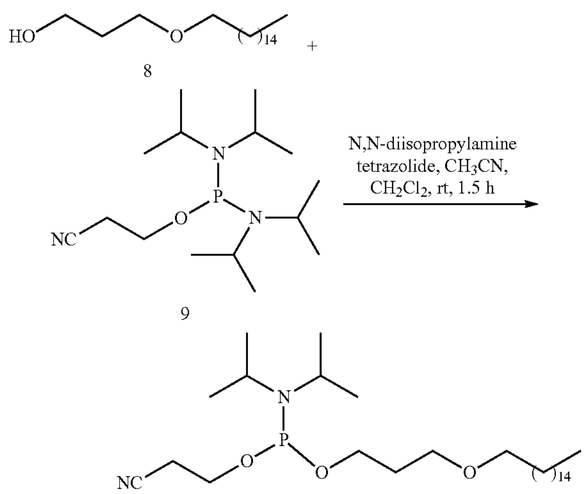

8

9

6

A mixture of 3-(hexadecyloxy)propan-1-ol (8 μg, 26.6 mmol) and N,N-diisopropylammonium tetrazolide (3.06 g, 17.8 mmol) was coevaporated with DCM-acetonitrile mixture (50:50, 10 mL) 3 times. To the dried mixture in DCM (50 mL) was added compound 9 (17.9 ml, 56.4 mmol). After being stirred for 1 hour at room temperature, methanol (5 mL) was added and stirred for 15 minutes. Then the reaction was concentrated under vacuum; diluted with 10% TEA solution in EtOAc (300 mL) and washed with 10% $NaHCO_3$ solution (2×100 mL) and water (2×100 mL); dried over anhydrous $Na_2SO_4$; filtered and evaporated. The crude product was purified with column chromatography using petroleum ether:EtOAc:TEA (10:1:0.05) to afford compound 6 (11 g, 82%) as a pale yellow oil.

General Procedure for the Preparation of Compound AB23040

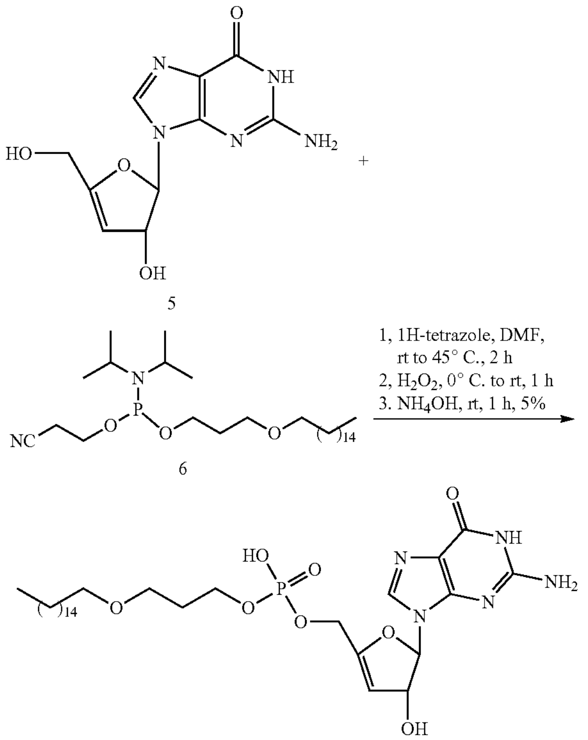

5

6

7

200 mg

AB23040

To a solution of 5 (1.77 g, 6.6 mmol, 1.0 eq) in dry DMF (50 mL) was added 1H-tetrazole (0.93 g, 13.2 mmol, 2.0 eq) and compound 6 (3.3 g, 6.6 mmol, 1.0 eq) sequentially. The mixture was stirred at 45° C. for 2 h. The reaction mixture was cooled to 0° C. and $H_2O_2$ (30%, 10 mL) was added. Then the reaction mixture was allowed to warm to room temperature. After stirring for 1 h, $NH_4OH$ (10 mL) was added. After stirring for another 1 h at room temperature, the residue was purified by reverse-phase flash chromatography (C18, using a 5%→60%~90% gradient of ACN in water) and further purified with reverse phase HPLC (ACN and water). After lyophilization of the desired fractions, the desired product AB23040 was obtained as a white solid (0.20 g, 5%).

LC-MS: 628.30 $[M+H]^+$

HPLC: Ret Time 8.629 min; Purity @ 220 nm, 99.4%, @254 nm, 100.0%.

$^1H$ NMR (400 MHz, $CD_3OD$) δ 7.74 (s, 1H), 6.24 (d, J=2.1 Hz, 1H), 5.46-5.42 (m, 1H), 5.10 (br, 1H), 4.47 (d, J=6.9 Hz, 2H), 3.94 (q, J=6.3 Hz, 2H), 3.59-3.48 (m, 3H), 3.40 (dd, J=14.2, 7.4 Hz, 3H), 3.22 (s, 1H), 3.12 (s, 1H), 2.70 (s, 2H), 2.29 (s, 1H), 2.21 (s, 1H), 1.91-1.81 (m, 2H), 1.58-1.47 (m, 3H), 1.33-1.28 (m, 40H), 0.90 (t, J=6.7 Hz, 4H).

$^{31}P$ NMR (162 MHz, $CD_3OD$) δ 0.47.

Example 23—In Vitro Stability of AB23039 (Compound 104; Formula IVB), AB23040 (Compound 103; Formula IB) in Hepatic Subcellular Fractions and Plasma from Rat and Human Objective: To examine the stability of AB23039 (compound 104; Formula IVB), AB23040 (compound 103; Formula IB), and Brincidofovir (BCV), a lipid prodrug of an antiviral acyclic phosphonate cidofovir, as a comparator in vitro in hepatic S9 fractions (S9) and plasma from human, and rat. The S9 stability assay is used to detect activity of hydrolytic enzymes like esterases, phosphatases, etc. NADPH is a cofactor for CYP450 oxidative enzymes and helps to differentiate between oxidative and hydrolytic metabolism. The rate of the hepatic and plasma metabolism is essential for predicting preclinical and human pharmacokinetics and potential toxicity.

Methods:

Reagents

Shanghai TianChem, ACROS and Sigma-Aldrich provided all chemicals. Mixed-gender pooled human plasma was purchased from GEMINI, male SD rat plasma was purchased from BIOIVT. Human S9 was purchased from Xenotech, rat S9 was purchased from RILD. Internal Standard/Quench (IS/Q) used to stop reactions in S9 incubations and plasma was 5/10 ng/mL (terfenadine/tolbutamide) in acetonitrile.

Metabolic Stability in Hepatic S9 Fractions and Plasma

The studies were performed at BioDuro-Sundia Shanghai Discovery Lab (report number PTN-FFS-PK-20210501-01V2) (7).

S9 Stability 1.5 μL of 200 μM working solution of test compounds was added to 238.5 μL of S9 working solution in phosphate buffer (0.629 mg/mL) and gently mixed. The mix was pre-incubated at 37° C. for 5 min and the reaction started by adding 60 μL NADPH 5 mM working solution in phosphate buffer. At each time point: 0, 15, 60 and 180 min, 30 μL reaction mixture was removed and mixed with 300 μL quenching solution (100% ACN). For no NADPH samples, 60 μL phosphate buffer was added instead of NADPH. At time points 0 and 180 min, 30 μL reaction mixture was removed and mixed with 300 μL of the quenching solution. The mix was vortexed vigorously for 1 min and centrifuged at 4,000 rpm at 4° C. for 15 min. 100 μL of the supernatant was removed and mixed with 100 μL distilled water for LC-MS/MS analysis.

Plasma Stability

Plasma was pre-warmed at 37° C. water bath for 15 min. 1.5 μL of 200 μM working compound solution of test compound was added into 398 μL of plasma and mixed well. 30 μL of reaction mixture was removed at each time point (0, 15, 60 and 180 min) and mixed with 300 μL of quenching solution. Samples were centrifuged at 4,000 rpm for 15 min at 4° C. 100 μL of the supernatant was removed and mixed with 100 μL distilled water for LC-MS/MS analysis as described below.

Liquid Chromatography—Mass Spectrometry

Quantification of BCV, AB23039 and AB23040, was performed by analyte/internal standard peak area ratios measured on API 4000/5000 tandem triple quadrupole mass spectrometers coupled to a chromatography system. Table 34 shows the MS conditions were used.

TABLE 34

Mass Spectrometry Conditions

| Compound | Ionization mode | MRM |
|---|---|---|
| AB23039 | ESI, negative | 587.200/379.100 |
| AB21649 | ESI, negative | 225.037/111.000 |
| AB23040 | ESI, negative | 626.200/132.600 |
| AB21651 | ESI, positive | 266.028/135.200 |
| AB23060 | ESI, positive | 562.300/261.800 |
| AB23061 | ESI, negative | 277.918/234.900 |

TABLE 34-continued

The following HPLC conditions used were:

1. BCV: Kinetex 2.6 m, C18, 100 Å column (2.1 mm×30 mm) with mobile phase A: 0.1% formic acid in H2O, mobile phase B: 0.1% formic acid in ACN, gradient 0% to 100% B in 1.5 min. The flow rate was 0.8 mL/min and the injection volume was 5 μL.
2. AB23061: ACQUITY UPLC HSS T3 1.8 μm (2.1 mm×50 mm) with mobile phase A: 0.05% formic acid with NH4OAC in H2O, mobile phase B: 0.1% formic acid in ACN, gradient 0% to 100% B in 1.5 min. The flow rate was 0.8 mL/min and the injection volume was 5 μL.
3. AB21649 & AB21651: Atlantis HILIC Silica 5 μm (2.1×100 mm) with mobile phase A: 0.05% formic acid with NH4OAC in H2O and mobile phase B: 0.1% formic acid in ACN, gradient 0% to 100% B in 1.5 min. The flow rate was 0.8 mL/min and the injection volume was 5 μL.
4. AB23039 & AB23040: ACE Excel 5 C4 (2.1 mm×30 mm) with mobile phase A: 5 mM NH4OAC with 0.05% formic acid in H2O, mobile phase B: 0.1% formic acid in ACN, run time 1.5 min. The flow rate was 0.8 mL/min and the injection volume was 5 μL.

Data Analysis

Stabilities in S9 fractions and plasma were determined by following the rate of disappearance of BCV, AB23039 and AB23040. Data (% of parent remaining) were plotted on a semi log scale and fitted using an exponential fit:

$$C_t = C_0 \cdot e^{-K \cdot t}, \text{ where}$$

$C_t$ % of parent remaining at time=t $C_0$ % of parent remaining at time=0 t time

K First order elimination rate constant with the half-life (T1/2) calculated as ln(2)/K The intrinsic hepatic clearance was calculated as follows (J Pharmacol Exp Ther. 1997, 283 (1): 46-58):

$$CL_{int} = K \cdot V \cdot Y/P, \text{ where}$$

$CL_{int}$ Intrinsic hepatic clearance (L/hr/kg body weight)

V Incubation volume (L)

Y S9 protein abundance (mg protein/kg body weight)

P Mass of S9 protein in the incubation (mg)

Values used for calculation of the intrinsic hepatic clearance were V=0.0003 L, Y=466.5 mg/kg (human) and 726 mg/kg (rat) and P=0.15 mg (Obach R S, et al., J Pharmacol Exp Ther. 1997, 283 (1): 46-58; Nishimuta H, et al., Drug Metab Dispos. 2014, 42: 1522-1531; Davies B, Morris T. Pharm. Res, 1993, 10, 1093). Hepatic clearance values ($CL_{hep}$) were then predicted using the well-stirred liver model and extraction values ($E_h$) were calculated from hepatic blood flow in each species ($Eh=CL_{hep}/Q_h$).

Results:

The metabolic stability of BCV, AB23039 and AB23040 was assessed in hepatic S9 fractions obtained from human and rat. Table 35 shows the T1/2, calculated predicted hepatic clearance, and hepatic extraction ratios for human and rat. Table 36 shows the stability of AB23039, AB23040, and BCV in human and rat plasma.

TABLE 35

Stability of AB23039, AB23040, and BCV in Human and Rat Hepatic S9 Fractions (mean, N = 2)

| | Human | | | Rat | | |
|---|---|---|---|---|---|---|
| Compound | $T_{1/2}$ (min) | $CL_{hep}$ (mL/min/kg) | $E_h$ (%) | $T_{1/2}$ (min) | $CL_{hep}$ (mL/min/kg) | $E_h$ (%) |
| AB23039 | 265 | 9.1 | 44 | 347 | 14.3 | 26 |
| AB23040 | 199 | 10.6 | 24 | 237 | 18.7 | 21 |
| BCV | 246 | 9.5 | 31 | 461 | 11.5 | 16 |

TABLE 36

Stability of AB23039, AB23040, and BCV in Human and Rat Plasma (mean, N = 2)

| | $T_{1/2}$ (h) | |
|---|---|---|
| Compound | Human | Rat |
| AB23039 | >9.3 | >9.3 |
| AB23040 | >9.3 | >9.3 |
| BCV | >9.3 | >9.3 |

Summary: Hydrolytic stability of all prodrugs in hepatic S9 is moderate in both rat and human hepatic. Between the compounds, AB23040 is the least stable, which is confirmed by some ddH-Guanosine formation, AB23039 is the most stable. The prodrugs demonstrated 2-5-fold decrease in stability with added NADPH indicating oxidative metabolism, likely of the lipid prodrug moiety (likely β-oxidation of saturated straight-chain fatty acids). The hepatic extraction ratios indicate potential moderate liver metabolism. However, since the metabolism is likely to occur on the cleavable lipid moiety, further investigation would be needed to determine an impact on the potency of the intracellular prodrugs. From these results, AB23039 and AB23040 are expected to demonstrate the hepatic and plasma metabolism similar to BCV.

Example 24—Pharmacokinetics and Selected Tissue Distribution of AB23040 (Compound 103; Formula IIB) in Rats Objective: To examine the pharmacokinetics and tissue distribution of AB23040 (compound 103; Formula IVB) and Brincidofovir (BCV), in rats administered intravenously and orally.

Methods:

AB23040 (compound 103; Formula IIB) and Brincidofovir (BCV) were dosed intravenously via a 2-h infusion at 10 mg/kg and orally (PO) at 10 mg/kg in male Sprague-Dawley rats. The concentrations of both compounds were measured in plasma, brain, lung, liver, and kidney tissues with an LC/MS/MS method. The concentrations of a tentative major metabolites of AB23040 and BCV, AB21651 (compound 31; Formula IIB; ddhG) and Cidofovir (CDV), formed in plasma and selected tissues were also measured.

Figure 35A:
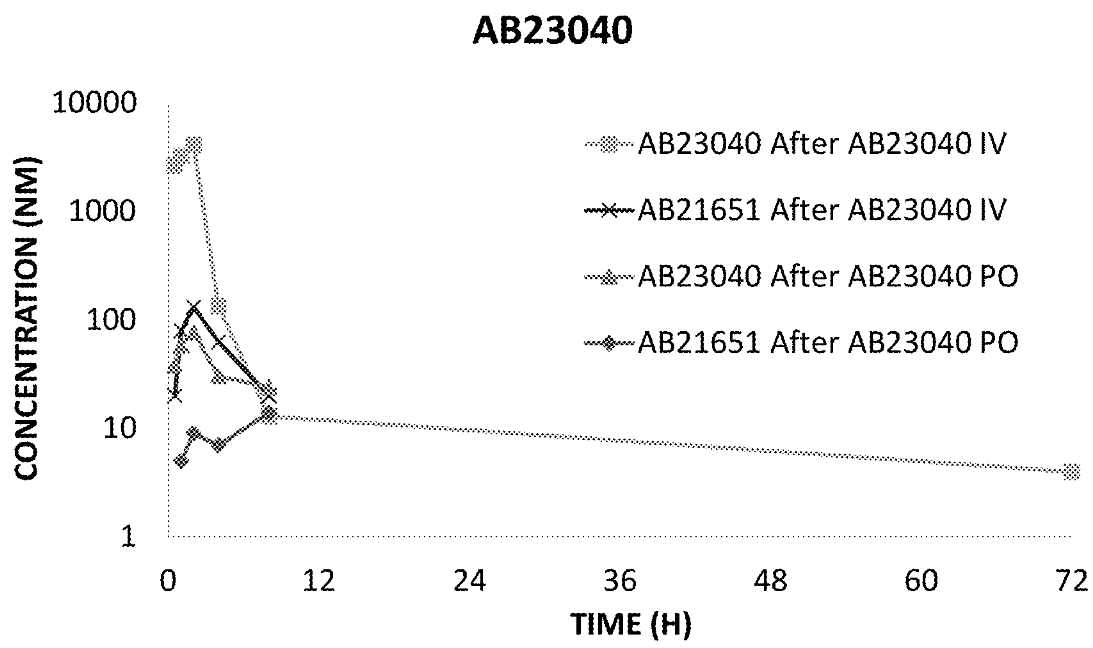
FIGS. 35A-35B. Concentration-time profiles of AB23040 and Brincidofovir (BCV) in plasma, following an IV infusion and PO dose at 10 mg/kg in rats.
Figure 35B:
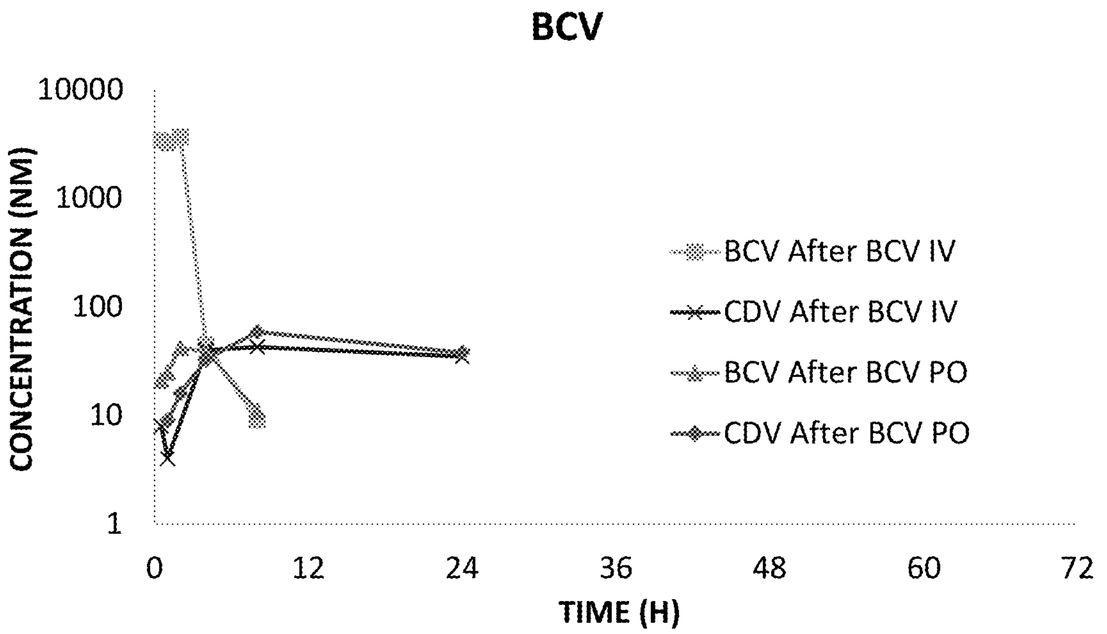
Figure 36A:
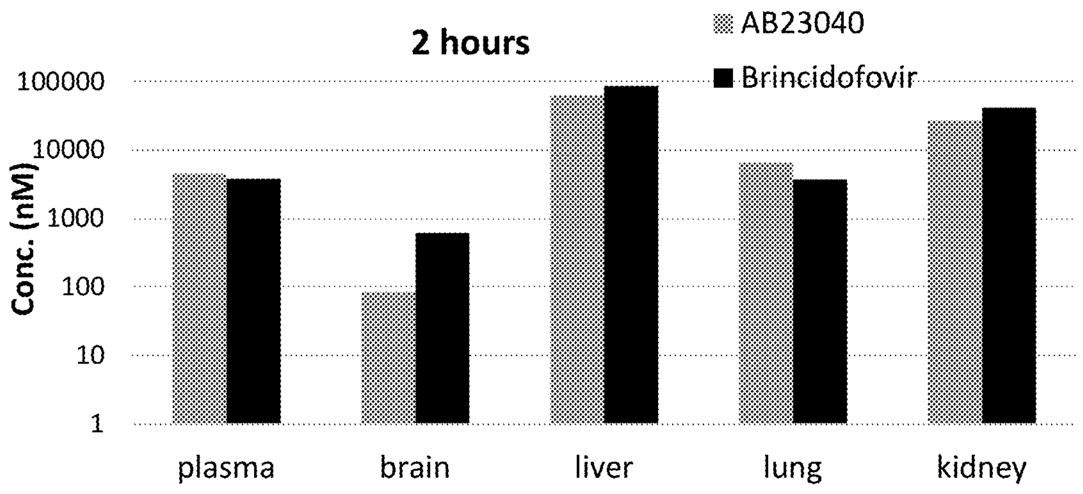
FIGS. 36A-36C. Concentrations of AB23040 and Brincidofovir (BCV) in selected tissues after an IV and PO dose at 10 mg/kg in rats.
Figure 36B:
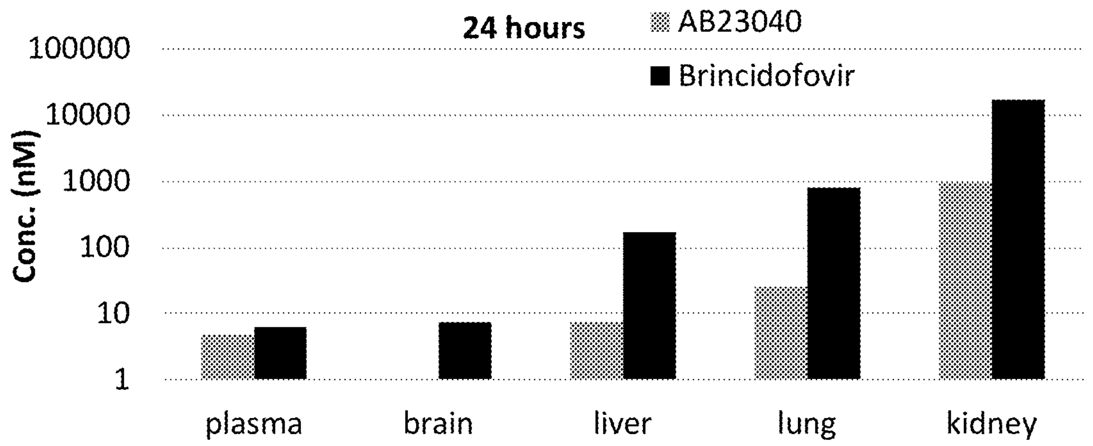
Figure 36C:
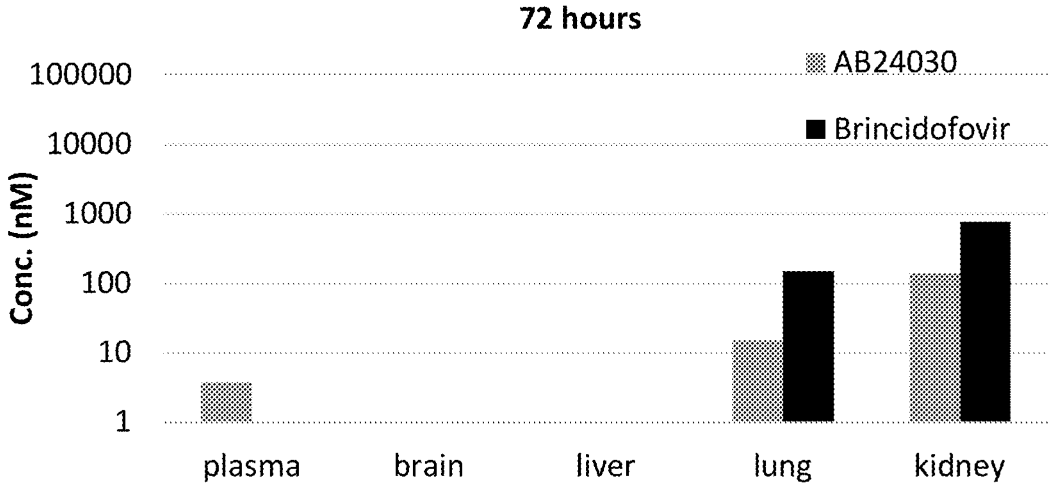

Results:

The plasma PK parameters for AB23040 and BCV for IV and PO doses are summarized in Tables 37-38. Tables 39-40 show plasma concentrations of AB23040 and BCV and their respective metabolites in individual animals. Table 41-42 compare concentrations of AB23040 and BCV and their respective metabolites in brain, liver, lung, and kidney tissues. The plasma concentrations-time profiles of AB23040 and BCV are shown in FIGS. 35A-B. FIGS. 36A-C show comparative tissue levels of AB23040 and BCV at different time points.

Both AB23040 and BCV were well-tolerated in the current study with no adverse events (AE) reported. Following the IV infusion, plasma concentrations for both AB23040 and BCV declined rapidly with t1/2 of less than 1 h and were accompanied by sequential appearance of smaller amounts of their respective metabolites AB21651 and CDV. Following PO doses, the bioavailability for both AB23040 and BCV was low, 4 and 11% respectively (FIGS. 35A-B, Tables 37-40). BCV appeared to almost quantitatively convert into its metabolite CDV. AB23040 produced smaller amount of AB21651. However, considering similar PK profiles for AB23040 and BCV, it is possible that another major metabolite, not followed in this study, was present, likely 5' monophosphate metabolite of AB21651.

The tissue distribution pattern was generally similar for AB23040 and BCV and their respective metabolites, with the concentrations higher for BCV and CDV, in all tissues (FIGS. 36A-C, Tables 41-42). The tissue concentrations rapidly declined for both compounds. It is known that BCV is rapidly taken up by cells followed by conversion into cidofovir and other polar metabolites including the active triphosphate. It is possible that AB23040 follows a similar pathway because it produces more metabolites not measured in this study.

TABLE 37

PK parameters for AB23040 and BCV in plasma after an IV dose at 10 mg/kg in rats

| | AB23040 | | | BCV | | |
|---|---|---|---|---|---|---|
| Animal | Rat #1 | Rat #2 | Mean | Rat #1 | Rat #2 | Mean |
| $t_{1/2}$ (h) | 0.8 | 0.8 | 0.8 | 0.8 | 0.8 | 0.8 |
| Terminal $t_{1/2}$ (h) | NA | 37 | 37 | NA | NA | ND |
| $t_{max}$ (h) | 2.0 | 2.0 | 2.0 | 2.0 | 0.50 | 1.3 |
| $C_{max}$ (nM) | 3,648 | 4,493 | 4,070 | 3,759 | 3,563 | 3,661 |
| $AUC_{last}$ (nM × h) | 9,117 | 12,212 | 10,664 | 8,979 | 9,034 | 9,007 |
| $AUC_{Inf}$ (nM × h) | 9,128 | 12,466 | 10,797 | 9,005 | 9,057 | 9,031 |
| $V_{ss}$ (L/kg) | 1.2 | 5.6 | 3.4 | 3.7 | 3.3 | 3.5 |
| CL (L/kg) | 1.7 | 1.3 | 1.5 | 2.0 | 2.0 | 2.0 |
| $MRT_{Inf}$ (h) | 0.7 | 4.4 | 2.5 | 1.9 | 1. | 1.8 |

TABLE 38

PK parameters for AB23040 and BCV in plasma after a PO dose at 10 mg/kg in rats

| Animal | AB23040 | | | BCV | | |
|---|---|---|---|---|---|---|
| Animal | Rat #7 | Rat #8 | Mean | Rat #7 | Rat #8 | Mean |
| $t_{1/2}$ (h) | 1.1 | 4.1 | 2.6 | 4.2 | 4.4 | 4.3 |
| Terminal $t_{1/2}$ (h) | 17 | 8.1 | 12.5 | ND | ND | ND |
| $t_{max}$ (h) | 2.0 | 2.0 | 2.0 | 4.0 | 2.0 | 3.0 |
| $C_{max}$ (nM) | 110 | 44 | 77 | 141 | 214 | 178 |
| $AUC_{last}$ (nM × h) | 387 | 246 | 316 | 1,172 | 916 | 1,044 |
| $AUC_{Inf}$ (nM × h) | 503 | 448 | 476 | 1,200 | 933 | 1,067 |
| $MRT_{Inf}$ (h) | 5.2 | 9.7 | 7.5 | 6.9 | 4.4 | 5.6 |
| F (%) | 4.7 | 4.1 | 4.4 | 12.2 | 9.5 | 10.9 |

TABLE 39

Concentrations of AB23040 and BCV and their respective metabolites AB21651 and CDV formed in plasma, following an IV infusion in rats

| | Plasma Concentration, nM | | | |
|---|---|---|---|---|
| | AB23040 10 mg/kg IV | | BCV 10 mg/kg IV | |
| Time, h | AB23040 | AB21651 | BCV | CDV |
| 0.5 | 2,668 | 20 | 3,400 | 8 |
| 1 | 3,258 | 79 | 3,205 | 4 |
| 2 | 4,070 | 131 | 3,659 | BLQ |
| 4 | 133 | 63 | 45 | 40 |
| 8 | 13 | 20 | 9 | 43 |

TABLE 39-continued

Concentrations of AB23040 and BCV and their respective metabolites AB21651 and CDV formed in plasma, following an IV infusion in rats

| | Plasma Concentration, nM | | | |
|---|---|---|---|---|
| | AB23040 10 mg/kg IV | | BCV 10 mg/kg IV | |
| Time, h | AB23040 | AB21651 | BCV | CDV |
| 24 | 5 | BLQ | 6 | 37 |
| 72 | 4 | BLQ | BLQ | BLQ |

TABLE 40

Concentrations of AB23040 and BCV and their respective metabolites AB21651 and CDV formed in plasma, following a PO dose in rats

| | Plasma Concentration, nM | | | |
|---|---|---|---|---|
| | AB23040 10 mg/kg PO | | BCV 10 mg/kg PO | |
| Time, h | AB23040 | AB21651 | BCV | CDV |
| 0.5 | 38 | BLQ | 21 | BLQ |
| 1 | 58 | 5 | 25 | 9 |
| 2 | 77 | 9 | 42 | 16 |
| 4 | 30.4 | 7 | 39 | 33 |
| 8 | 24 | 14 | 11 | 59 |
| 24 | BLQ | BLQ | BLQ | 38 |
| 72 | BLQ | BLQ | BLQ | BLQ |

TABLE 41

Concentrations of AB23040 and its metabolite AB21651 formed in selected tissues after an IV and PO dose at 10 mg/kg in rats

| | Tissue Concentration, nM | | | | | | | |
|---|---|---|---|---|---|---|---|---|
| | IV infusion | | | | | | PO | |
| | 2 h | | 24 h | | 72 h | | 24 h | |
| Tissue | AB23040 | AB21651 | AB23040 | AB21651 | AB23040 | AB21651 | AB23040 | AB21651 |
| Brain | 85 | 10 | BLQ | BLQ | BLQ | BLQ | BLQ | BLQ |
| Liver | 63,325 | 4,015 | 7 | BLQ | BLQ | BLQ | 25 | 5 |
| Lung | 6,456 | 196 | 25 | BLQ | 15 | BLQ | 14 | BLQ |
| Kidney | 27,600 | 2,545 | 952 | 35 | 140 | BLQ | 84 | 12 |

TABLE 42

Concentrations of BCV and its metabolite CDV formed in selected tissues after an IV and PO dose at 10 mg/kg in rats

| | Tissue Concentration, nM | | | | | | | |
|---|---|---|---|---|---|---|---|---|
| | IV infusion | | | | | | PO | |
| | 2 h | | 24 h | | 72 h | | 24 h | |
| Tissue | BCV | CDV | BCV | CDV | BCV | CDV | BCV | CDV |
| Brain | 615 | 20 | 7 | 47 | BLQ | BLQ | BLQ | BLQ |
| Liver | 87,313 | 12,361 | 168 | 5,948 | BLQ | 674 | 204 | 4,891 |
| Lung | 3,715 | 288 | 792 | 649 | 151 | 456 | 75 | 114 |
| Kidney | 41,652 | 1,890 | 16,884 | 6,216 | 774 | 816 | 1,541 | 4,945 |

TABLE 3

| pVip Genes | | | |
|---|---|---|---|
| SEQ ID NO | IMG ID | pVip # | Metagenome genome IMG ID |
| 3 | 2624749465 | 6 | 2623620517 |
| 4 | 2739066738 | 7 | 2738541339 |
| 5 | 2521798317 | 8 | 2521172648 |
| 6 | 2574301464 | 9 | 2574179732 |
| 7 | 2720695169 | 10 | 2718218250 |
| 8 | 2698137626 | 12 | 2695420938 |
| 9 | 646713396 | 15 | 646564524 |
| 10 | 2506475787 | 19 | 2506381025 |
| 11 | 2515428782 | 21 | 2515154070 |
| 12 | 2574506394 | 27 | 2574179788 |
| 13 | 2609132705 | 32 | 2608642208 |
| 14 | 2619892213 | 34 | 2619618891 |
| 15 | 2634960437 | 39 | 2634166261 |
| 16 | 2639213731 | 42 | 2636416084 |
| 17 | 2648875132 | 44 | 2648501185 |
| 18 | 2649993803 | 46 | 2648501459 |
| 19 | 2651203508 | 47 | 2648501771 |
| 20 | 2651490945 | 48 | 2648501840 |
| 21 | 2661858798 | 50 | 2660238307 |
| 22 | 2701115162 | 56 | 2700988679 |
| 23 | 2718503187 | 57 | 2718217692 |
| 24 | 2721736750 | 58 | 2718218507 |
| 25 | 2733913669 | 60 | 2731957952 |
| 26 | 2743907592 | 62 | 2740892545 |
| 27 | 2744633848 | 63 | 2744054527 |
| 28 | 2695043264 | 1 | 2693429896 |
| 29 | 2684559953 | 2 | 2681813561 |
| 30 | 2507146842 | 3 | 2506783068 |
| 31 | 2632766730 | 11 | 2630968672 |
| 32 | 2744653400 | 13 | 2744054531 |
| 33 | 2654783232 | 14 | 2654587543 |
| 34 | 2504625218 | 17 | 2504557017 |
| 35 | 2506474236 | 18 | 2506381025 |
| 36 | 2509664214 | 20 | 2509601008 |
| 37 | 2518436022 | 22 | 2518285547 |
| 38 | 2522341593 | 23 | 2522125098 |
| 39 | 2524269675 | 24 | 2524023156 |
| 40 | 2525334630 | 25 | 2524614668 |
| 41 | 2557036911 | 26 | 2556921023 |
| 42 | 2574517928 | 28 | 2574179790 |
| 43 | 2582805913 | 29 | 2582580599 |
| 44 | 2582946381 | 30 | 2582580664 |
| 45 | 2596421479 | 31 | 2595698251 |
| 46 | 2618018523 | 33 | 2617270916 |
| 47 | 2631333032 | 36 | 2630968323 |
| 48 | 2632937107 | 37 | 2630968711 |
| 49 | 2633985761 | 38 | 2630968972 |
| 50 | 2635314107 | 40 | 2634166348 |
| 51 | 2637497700 | 41 | 2636415666 |
| 52 | 2641427518 | 43 | 2639762959 |
| 53 | 2649163162 | 45 | 2648501251 |
| 54 | 2651585264 | 49 | 2648501863 |
| 55 | 2665950188 | 51 | 2663763173 |
| 56 | 2674184607 | 52 | 2671180787 |
| 57 | 2684813341 | 53 | 2684622550 |
| 58 | 2693697599 | 54 | 2693429564 |
| 59 | 2694112273 | 55 | 2693429660 |
| 60 | 2728147792 | 59 | 2724679805 |
| 61 | 2741341560 | 61 | 2740891962 |
| 62 | 2741409035 | 64 | 2740891993 |
| 63 | 2504129180 | 65 | 2503982047 |
| 64 | 637160692 | 66 | 637000327 |
| 65 | 637364324 | 67 | 637000336 |
| 66 | 637468954 | 68 | 637000337 |
| 67 | 637586319 | 69 | 637000206 |
| 68 | 637752529 | 70 | 637000204 |
| 69 | 639797708 | 71 | 639633052 |
| 70 | 640805406 | 72 | 640753033 |
| 71 | 640830189 | 73 | 640753049 |
| 72 | 641096015 | 74 | 640963011 |
| 73 | 641147750 | 75 | 640963027 |
| 74 | 641288534 | 76 | 641228507 |
| 75 | 643461066 | 77 | 643348574 |
| 76 | 646369858 | 78 | 646311927 |

TABLE 3-continued

| pVip Genes | | | |
|---|---|---|---|
| SEQ ID NO | IMG ID | pVip # | Metagenome genome IMG ID |
| 77 | 646419713 | 79 | 646311963 |
| 78 | 647622404 | 80 | 647533121 |
| 79 | 649804297 | 81 | 649633054 |
| 80 | 650410387 | 82 | 650377991 |
| 81 | 650419199 | 83 | 650377942 |
| 82 | 650463340 | 84 | 650377984 |
| 83 | 650537321 | 85 | 650377925 |
| 84 | 650742368 | 86 | 650716002 |
| 85 | 650921542 | 87 | 650716044 |
| 86 | 2501733929 | 88 | 2501651210 |
| 87 | 2502233141 | 89 | 2502171154 |
| 88 | 2509552219 | 90 | 2509276055 |
| 89 | 2512440669 | 91 | 2512047059 |
| 90 | 2519473577 | 92 | 2519103099 |
| 91 | 2519473579 | 93 | 2519103099 |
| 92 | 2519484486 | 94 | 2519103103 |
| 93 | 2519815572 | 95 | 2519103180 |
| 94 | 2521802859 | 96 | 2521172649 |
| 95 | 2522303848 | 97 | 2522125086 |
| 96 | 2524107537 | 98 | 2524023060 |
| 97 | 2525610838 | 99 | 2524614740 |
| 98 | 2525930338 | 100 | 2524614816 |
| 99 | 2528325157 | 101 | 2528311002 |
| 100 | 2531202617 | 102 | 2529293096 |
| 101 | 2532381218 | 103 | 2531839141 |
| 102 | 2532646932 | 104 | 2531839206 |
| 103 | 2538932271 | 105 | 2537561856 |
| 104 | 2540642849 | 106 | 2540341105 |
| 105 | 2540668036 | 107 | 2540341115 |
| 106 | 2540825991 | 108 | 2540341170 |
| 107 | 2541039228 | 109 | 2540341248 |
| 108 | 2541315631 | 110 | 2541046975 |
| 109 | 2546450678 | 111 | 2545824694 |
| 110 | 2546738312 | 112 | 2545824767 |
| 111 | 2547718745 | 113 | 2547132187 |
| 112 | 2551476655 | 114 | 2551306039 |
| 113 | 2551491916 | 115 | 2551306042 |
| 114 | 2551562099 | 116 | 2551306058 |
| 115 | 2551596444 | 117 | 2551306067 |
| 116 | 2553401559 | 118 | 2551306520 |
| 117 | 2553886541 | 119 | 2551306646 |
| 118 | 2558097217 | 120 | 2556921621 |
| 119 | 2559286049 | 121 | 2558860239 |
| 120 | 2559416375 | 122 | 2558860277 |
| 121 | 2562001279 | 123 | 2561511079 |
| 122 | 2563081558 | 124 | 2562617115 |
| 123 | 2563230595 | 125 | 2562617155 |
| 124 | 2565569616 | 126 | 2563367142 |
| 125 | 2565702223 | 127 | 2563367170 |
| 126 | 2566542256 | 128 | 2565956643 |
| 127 | 2566736970 | 129 | 2565956698 |
| 128 | 2569938648 | 130 | 2568526421 |
| 129 | 2574423613 | 131 | 2574179766 |
| 130 | 2574578667 | 132 | 2574179802 |
| 131 | 2577747326 | 133 | 2576861245 |
| 132 | 2577787495 | 134 | 2576861258 |
| 133 | 25804401517 | 135 | 2579778656 |
| 134 | 25810324187 | 136 | 2579778800 |
| 135 | 2581542389 | 137 | 2579778918 |
| 136 | 2582293224 | 138 | 2579779100 |
| 137 | 2582959978 | 139 | 2582580668 |
| 138 | 2583671671 | 140 | 2582580861 |
| 139 | 2584203718 | 141 | 2582580995 |
| 140 | 2585240392 | 142 | 2582581301 |
| 141 | 2587265930 | 143 | 2585427937 |
| 142 | 2589217693 | 144 | 2588253911 |
| 143 | 2597063350 | 145 | 2596583606 |
| 144 | 2600497862 | 146 | 2600254970 |
| 145 | 2600833866 | 147 | 2600255071 |
| 146 | 2609594859 | 148 | 2609459643 |
| 147 | 2609930410 | 149 | 2609459764 |
| 148 | 2611345001 | 150 | 2609460080 |
| 149 | 2611749855 | 151 | 2609460164 |
| 150 | 2612132826 | 152 | 2609460245 |

TABLE 3-continued pVip Genes

| SEQ ID NO | IMG ID | pVip # | Metagenome genome IMG ID |
|---|---|---|---|
| 151 | 2617465221 | 153 | 2617270765 |
| 152 | 2617538802 | 154 | 2617270789 |
| 153 | 2619647987 | 155 | 2619618818 |
| 154 | 2619760352 | 156 | 2619618853 |
| 155 | 2620549291 | 157 | 2619619052 |
| 156 | 2621169600 | 158 | 2619619266 |
| 157 | 2623278845 | 159 | 2622736530 |
| 158 | 2632746825 | 160 | 2630968667 |
| 159 | 2642232622 | 161 | 2639763156 |
| 160 | 2644760915 | 162 | 2643221740 |
| 161 | 2645912334 | 163 | 2645727543 |
| 162 | 2647434260 | 164 | 2645727892 |
| 163 | 2649993012 | 165 | 2648501459 |
| 164 | 2651793160 | 166 | 2648501913 |
| 165 | 2652273697 | 167 | 2651869653 |
| 166 | 2654809173 | 168 | 2654587547 |
| 167 | 2658339966 | 169 | 2657245169 |
| 168 | 2667505054 | 170 | 2663763602 |
| 169 | 2667963948 | 171 | 2667527390 |
| 170 | 2668144532 | 172 | 2667527434 |
| 171 | 2668847476 | 173 | 2667527626 |
| 172 | 2672407511 | 174 | 2671180348 |
| 173 | 2674782375 | 175 | 2671180928 |
| 174 | 2677278474 | 176 | 2675903261 |
| 175 | 2682061458 | 177 | 2681812894 |
| 176 | 2684092807 | 178 | 2681813425 |
| 177 | 2688794699 | 179 | 2687453440 |
| 178 | 2693209812 | 180 | 2690316327 |
| 179 | 2694949528 | 181 | 2693429874 |
| 180 | 2700499480 | 182 | 2698536835 |
| 181 | 2701140257 | 183 | 2700988686 |
| 182 | 2701911183 | 184 | 2700989248 |
| 183 | 2705695255 | 185 | 2703719122 |
| 184 | 2706043000 | 186 | 2703719236 |
| 185 | 2712662546 | 187 | 2711768198 |
| 186 | 2714077658 | 188 | 2713896747 |
| 187 | 2719376594 | 189 | 2718217925 |
| 188 | 2719498267 | 190 | 2718217953 |
| 189 | 2719828580 | 191 | 2718218033 |
| 190 | 2722236530 | 192 | 2721755284 |
| 191 | 2727845415 | 193 | 2724679709 |
| 192 | 2728971251 | 194 | 2728369061 |
| 193 | 2729066335 | 195 | 2728369080 |
| 194 | 2730169305 | 196 | 2728369366 |
| 195 | 2731232863 | 197 | 2728369654 |
| 196 | 2735939253 | 198 | 2734482289 |
| 197 | 2740266671 | 199 | 2739367982 |
| 198 | 2741408272 | 200 | 2740891993 |
| 199 | 2742412079 | 201 | 2740892189 |
| 200 | 2742415354 | 202 | 2740892190 |
| 201 | 2743908240 | 203 | 2740892545 |
| 202 | 2751139676 | 204 | 2747843223 |
| 203 | 2752652723 | 205 | 2751185612 |
| 204 | 2753090639 | 206 | 2751185737 |
| 205 | 2753093587 | 207 | 2751185738 |
| 206 | 2753363234 | 208 | 2751185801 |
| 207 | 2753367132 | 209 | 2751185802 |
| 208 | 2753371117 | 210 | 2751185803 |
| 209 | 2753755176 | 211 | 2751185895 |
| 210 | 2758508848 | 212 | 2757320913 |
| 211 | 2758538137 | 213 | 2757320982 |
| 212 | 2758668677 | 214 | 2758568024 |
| 213 | 2766104288 | 215 | 2765235962 |
| 214 | 2770832229 | 216 | 2767802753 |
| 215 | 2558444101 | 217 | 2558309039 |
| 216 | 2620552401 | 218 | 2619619052 |
| 217 | 2620553354 | 219 | 2619619052 |
| 218 | 2671326339 | 220 | 2671180039 |
| 219 | 2722096198 | 221 | 2721755233 |
| 220 | 2725246328 | 222 | 2724679053 |
| 221 | 2049941002 assembled LHMISPF__00252280 | 223 | 2049941002 |
| 222 | 2061766007 assembled__HiSeq__03538890 | 224 | 2061766007 |

TABLE 3-continued pVip Genes

| SEQ ID NO | IMG ID | pVip # | Metagenome genome IMG ID |
|---|---|---|---|
| 223 | 2061766007 assembled__HiSeq__08062520 | 225 | 2061766007 |
| 224 | 2061766007 assembled__HiSeq__12004210 | 226 | 2061766007 |
| 225 | 2061766007 assembled__HiSeq__13805260 | 227 | 2061766007 |
| 226 | 2061766007 assembled__HiSeq__17035850 | 228 | 2061766007 |
| 227 | 2061766007 assembled__HiSeq__22354030 | 229 | 2061766007 |
| 228 | 3300000553 assembled TBL__comb47__HYPO-DRAFT__1000031312 | 230 | 3300000553 |
| 229 | 3300000558 assembled Draft__1000017819 | 231 | 3300000558 |
| 230 | 3300000558 assembled Draft__1020415419 | 232 | 3300000558 |
| 231 | 3300000568 assembled Draft__1000864417 | 233 | 3300000568 |
| 232 | 3300000970 assembled BBAY66__100003029 | 234 | 3300000970 |
| 233 | 3300001102 assembled BBAY67__1000022226 | 235 | 3300001102 |
| 234 | 3300001200 assembled BBAY65__1000011634 | 236 | 3300001200 |
| 235 | 3300001348 assembled JGI20154J14316__1000097623 | 237 | 3300001348 |
| 236 | 3300001450 assembled JGI24006J15134__1000007033 | 238 | 3300001450 |
| 237 | 3300001450 assembled JGI24006J15134__1000007151 | 239 | 3300001450 |
| 238 | 3300001598 assembled EMG__100002329 | 240 | 3300001598 |
| 239 | 3300001749 assembled JGI24025J20009__1000044120 | 241 | 3300001749 |
| 240 | 3300001750 assembled JGI24023J19991__100005742 | 242 | 3300001750 |
| 241 | 3300001835 assembled shallow__100084433 | 243 | 3300001835 |
| 242 | 3300002119 assembled JGI20170J26628__1000030318 | 244 | 3300002119 |
| 243 | 3300002165 assembled JGI24527J20359__100014812 | 245 | 3300002165 |
| 244 | 3300002180 assembled JGI24724J26744__1000065020 | 246 | 3300002180 |
| 245 | 3300002219 assembled SCADCLC__1000381914 | 247 | 3300002219 |
| 246 | 3300002219 assembled SCADCLC__1000709320 | 248 | 3300002219 |
| 247 | 3300002220 assembled MLSBCLC__100183129 | 249 | 3300002220 |
| 248 | 3300002220 assembled MLSBCLC__1002228019 | 250 | 3300002220 |
| 249 | 3300002462 assembled JGI24702J35022__1000091311 | 251 | 3300002462 |
| 250 | 3300002518 assembled JGI25134J35505__1000001183 | 252 | 3300002518 |
| 251 | 3300002835 assembled B570J40625__1000006467 | 253 | 3300002835 |
| 252 | 3300003765 assembled Ga0056911__100030025 | 254 | 3300003765 |
| 253 | 3300003767 assembled Ga0056908__1000061101 | 255 | 3300003767 |
| 254 | 3300004166 assembled Ga0066427__100005916 | 256 | 3300004166 |
| 255 | 3300004173 assembled Ga0066412__100001438 | 257 | 3300004173 |
| 256 | 3300004173 assembled Ga0066412__100011719 | 258 | 3300004173 |
| 257 | 3300004178 assembled Ga0066410__100009118 | 259 | 3300004178 |
| 258 | 3300004197 assembled Ga0066420__100001947 | 260 | 3300004197 |

TABLE 3-continued pVip Genes

| SEQ ID NO | IMG ID | pVip # | Metagenome genome IMG ID |
|---|---|---|---|
| 259 | 3300004197 assembled Ga0066420_100010317 | 261 | 3300004197 |
| 260 | 3300004202 assembled Ga0066418_100009418 | 262 | 3300004202 |
| 261 | 3300004203 assembled Ga0066419_100000529 | 263 | 3300004203 |
| 262 | 3300004203 assembled Ga0066419_100003817 | 264 | 3300004203 |
| 263 | 3300004230 assembled Ga0066452_100000937 | 265 | 3300004230 |
| 264 | 3300004250 assembled Ga0066472_1000237 | 266 | 3300004250 |
| 265 | 3300004253 assembled Ga0066464_100004618 | 267 | 3300004253 |
| 266 | 3300004253 assembled Ga0066464_100006643 | 268 | 3300004253 |
| 267 | 3300004806 assembled Ga0007854_100000246 | 269 | 3300004806 |
| 268 | 3300005080 assembled Ga0069611_1000016445 | 270 | 3300005080 |
| 269 | 3300005124 assembled Ga0070424_1100226 | 271 | 3300005124 |
| 270 | 3300005125 assembled Ga0070411_1062712 | 272 | 3300005125 |
| 271 | 3300005144 assembled Ga0068711_100038117 | 273 | 3300005144 |
| 272 | 3300005286 assembled Ga0065721_1000460410 | 274 | 3300005286 |
| 273 | 3300005326 assembled Ga0074195_10008286 | 275 | 3300005326 |
| 274 | 3300005531 assembled Ga0070738_1000151042 | 276 | 3300005531 |
| 275 | 3300005588 assembled Ga0070728_1000021436 | 277 | 3300005588 |
| 276 | 3300005588 assembled Ga0070728_1000125023 | 278 | 3300005588 |
| 277 | 3300005589 assembled Ga0070729_10000081117 | 279 | 3300005589 |
| 278 | 3300005589 assembled Ga0070729_1000129613 | 280 | 3300005589 |
| 279 | 3300005609 assembled Ga0070724_1000012829 | 281 | 3300005609 |
| 280 | 3300005609 assembled Ga0070724_1000028613 | 282 | 3300005609 |
| 281 | 3300005609 assembled Ga0070724_1000048517 | 283 | 3300005609 |
| 282 | 3300005675 assembled Ga0074424_10021430 | 284 | 3300005675 |
| 283 | 3300005915 assembled Ga0075122_100007968 | 285 | 3300005915 |
| 284 | 3300005920 assembled Ga0070725_1000012429 | 286 | 3300005920 |
| 285 | 3300005920 assembled Ga0070725_1000027223 | 287 | 3300005920 |
| 286 | 3300005920 assembled Ga0070725_100003449 | 288 | 3300005920 |
| 287 | 3300005986 assembled Ga0075152_1000034111 | 289 | 3300005986 |
| 288 | 3300006056 assembled Ga0075163_1000220113 | 290 | 3300006056 |
| 289 | 3300006104 assembled Ga0007882_1000004313 | 291 | 3300006104 |
| 290 | 3300006104 assembled Ga0007882_1000014836 | 292 | 3300006104 |
| 291 | 3300006182 assembled Ga0075033_10000633 | 293 | 3300006182 |
| 292 | 3300006226 assembled Ga0099364_100017018 | 294 | 3300006226 |
| 293 | 3300006243 assembled Ga0099348_1001723 | 295 | 3300006243 |
| 294 | 3300006417 assembled Ga0069787_1004128015 | 296 | 3300006417 |
| 295 | 3300006417 assembled Ga0069787_1005605520 | 297 | 3300006417 |
| 296 | 3300006417 assembled Ga0069787_1005688918 | 298 | 3300006417 |
| 297 | 3300006417 assembled Ga0069787_1021696324 | 299 | 3300006417 |
| 298 | 3300006417 assembled Ga0069787_1113807921 | 300 | 3300006417 |
| 299 | 3300006736 assembled Ga0098033_1000001464 | 301 | 3300006736 |
| 300 | 3300006738 assembled Ga0098035_100006013 | 302 | 3300006738 |
| 301 | 3300006789 assembled Ga0098054_10000219 | 303 | 3300006789 |
| 302 | 3300006790 assembled Ga0098074_100033128 | 304 | 3300006790 |
| 303 | 3300006810 assembled Ga0070754_1000007993 | 305 | 3300006810 |
| 304 | 3300006879 assembled Ga0079226_100011884 | 306 | 3300006879 |
| 305 | 3300006927 assembled Ga0098034_100013824 | 307 | 3300006927 |
| 306 | 3300006929 assembled Ga0098036_100012625 | 308 | 3300006929 |
| 307 | 3300006987 assembled Ga0098063_100010810 | 309 | 3300006987 |
| 308 | 3300006988 assembled Ga0098064_10002211 | 310 | 3300006988 |
| 309 | 3300007344 assembled Ga0070745_100033022 | 311 | 3300007344 |
| 310 | 3300007346 assembled Ga0070753_100014333 | 312 | 3300007346 |
| 311 | 3300007462 assembled Ga0099934_110520 | 313 | 3300007462 |
| 312 | 3300007485 assembled Ga0099929_1008119 | 314 | 3300007485 |
| 313 | 3300007516 assembled Ga0105050_1000139429 | 315 | 3300007516 |
| 314 | 3300007640 assembled Ga0070751_1000004111 | 316 | 3300007640 |
| 315 | 3300007961 assembled Ga0079305_100003992 | 317 | 3300007961 |
| 316 | 3300007963 assembled Ga0110931_100009625 | 318 | 3300007963 |
| 317 | 3300008050 assembled Ga0098052_10001839 | 319 | 3300008050 |
| 318 | 3300008050 assembled Ga0098052_100026416 | 320 | 3300008050 |
| 319 | 3300008224 assembled Ga0105350_100000945 | 321 | 3300008224 |
| 320 | 3300009093 assembled Ga0105240_100005042 | 322 | 3300009093 |
| 321 | 3300009169 assembled Ga0105097_1000009945 | 323 | 3300009169 |
| 322 | 3300009175 assembled Ga0073936_1000120334 | 324 | 3300009175 |
| 323 | 3300009415 assembled Ga0115029_100184931 | 325 | 3300009415 |
| 324 | 3300009419 assembled Ga0114982_10001831 | 326 | 3300009419 |
| 325 | 3300009488 assembled Ga0114925_1000023517 | 327 | 3300009488 |
| 326 | 3300009488 assembled Ga0114925_100003506 | 328 | 3300009488 |
| 327 | 3300009508 assembled Ga0115567_1000068222 | 329 | 3300009508 |
| 328 | 3300009512 assembled Ga0115003_100022198 | 330 | 3300009512 |
| 329 | 3300009546 assembled Ga0099799_100233 | 331 | 3300009546 |
| 330 | 3300009669 assembled Ga0116148_10010742 | 332 | 3300009669 |
| 331 | 3300009779 assembled Ga0116152_100003906 | 333 | 3300009779 |
| 332 | 3300009788 assembled Ga0114923_1000042134 | 334 | 3300009788 |

TABLE 3-continued

| pVip Genes | | | |
|---|---|---|---|
| SEQ ID NO | IMG ID | pVip # | Metagenome genome IMG ID |
| 333 | 3300009838 assembled Ga0116153_100010806 | 335 | 3300009838 |
| 334 | 3300010028 assembled Ga0134115_1006245 | 336 | 3300010028 |
| 335 | 3300010160 assembled Ga0114967_100001146 | 337 | 3300010160 |
| 336 | 3300010162 assembled Ga0131853_1000011621 | 338 | 3300010162 |
| 337 | 3300010162 assembled Ga0131853_1000234120 | 339 | 3300010162 |
| 338 | 3300010162 assembled Ga0131853_1000511220 | 340 | 3300010162 |
| 339 | 3300010270 assembled Ga0129306_100025163 | 341 | 3300010270 |
| 340 | 3300010313 assembled Ga0116211_100026028 | 342 | 3300010313 |
| 341 | 3300010373 assembled Ga0134128_1000050820 | 343 | 3300010373 |
| 342 | 3300010379 assembled Ga0136449_1000153745 | 344 | 3300010379 |
| 343 | 3300010396 assembled Ga0134126_1000011835 | 345 | 3300010396 |
| 344 | 3300010430 assembled Ga0118733_10000149451 | 346 | 3300010430 |
| 345 | 3300010430 assembled Ga0118733_10000158731 | 347 | 3300010430 |
| 346 | 3300010430 assembled Ga0118733_10000628422 | 348 | 3300010430 |
| 347 | 3300012103 assembled Ga0136578_1000209 | 349 | 3300012103 |
| 348 | 3300012533 assembled Ga0138256_1000042615 | 350 | 3300012533 |
| 349 | 3300012950 assembled Ga0163108_1000095519 | 351 | 3300012950 |
| 350 | 3300012979 assembled Ga0123348_1000024225 | 352 | 3300012979 |
| 351 | 3300012983 assembled Ga0123349_1000049625 | 353 | 3300012983 |
| 352 | 3300013088 assembled Ga0163200_1000002129 | 354 | 3300013088 |
| 353 | 3300013092 assembled Ga0163199_1000006211 | 355 | 3300013092 |
| 354 | 3300013131 assembled Ga0172373_100005744 | 356 | 3300013131 |
| 355 | 3300014491 assembled Ga0182014_100007864 | 357 | 3300014491 |
| 356 | 3300014499 assembled Ga0182012_100003757 | 358 | 3300014499 |
| 357 | 3300017795 assembled Ga0189288_1022816 | 359 | 3300017795 |
| 358 | 3300017798 assembled Ga0189289_1026116 | 360 | 3300017798 |
| 359 | 3300017805 assembled Ga0189287_100018226 | 361 | 3300017805 |
| 360 | 3300017990 assembled Ga0180436_1000345026 | 362 | 3300017990 |
| 361 | 3300018018 assembled Ga0187886_100041240 | 363 | 3300018018 |
| 362 | 3300018018 assembled Ga0187886_100069122 | 364 | 3300018018 |
| 363 | 3300018033 assembled Ga0187867_1000087624 | 365 | 3300018033 |
| 364 | 3300018038 assembled Ga0187855_1000057816 | 366 | 3300018038 |
| 365 | 3300018042 assembled Ga0187871_100009711 | 367 | 3300018042 |
| 366 | 3300018080 assembled Ga0180433_1001105911 | 368 | 3300018080 |

TABLE 3-continued

| pVip Genes | | | |
|---|---|---|---|
| SEQ ID NO | IMG ID | pVip # | Metagenome genome IMG ID |
| 367 | 3300018428 assembled Ga0181568_1000115027 | 369 | 3300018428 |
| 368 | 3300018475 assembled Ga0187907_1000663212 | 370 | 3300018475 |
| 369 | 3300018475 assembled Ga0187907_100078053 | 371 | 3300018475 |
| 370 | 3300018475 assembled Ga0187907_1000859111 | 372 | 3300018475 |
| 371 | 3300018493 assembled Ga0187909_1000543313 | 373 | 3300018493 |
| 372 | 3300018494 assembled Ga0187911_1000586113 | 374 | 3300018494 |
| 373 | 3300018494 assembled Ga0187911_1001224520 | 375 | 3300018494 |
| 374 | 3300018495 assembled Ga0187908_1000576413 | 376 | 3300018495 |
| 375 | 3300018495 assembled Ga0187908_1000603814 | 377 | 3300018495 |
| 376 | 3300018495 assembled Ga0187908_100073603 | 378 | 3300018495 |
| 377 | 3300018878 assembled Ga0187910_1000693112 | 379 | 3300018878 |
| 378 | 3300018878 assembled Ga0187910_1000711113 | 380 | 3300018878 |
| 379 | 3300018878 assembled Ga0187910_100083003 | 381 | 3300018878 |
| 380 | 3300018878 assembled Ga0187910_1000906015 | 382 | 3300018878 |
| 381 | 3300019373 assembled Ga0187895_100043618 | 383 | 3300019373 |
| 382 | 3300019457 assembled Ga0193932_1007821 | 384 | 3300019457 |
| 383 | 3300019750 assembled Ga0194000_100000539 | 385 | 3300019750 |

TABLE 4

| pVip-Encoding Polynucleotides | |
|---|---|
| SEQ ID NO | pVip number |
| 384 | 6 |
| 385 | 7 |
| 386 | 8 |
| 387 | 9 |
| 388 | 10 |
| 389 | 12 |
| 390 | 15 |
| 391 | 19 |
| 392 | 21 |
| 393 | 27 |
| 394 | 32 |
| 395 | 34 |
| 396 | 39 |
| 397 | 42 |
| 398 | 44 |
| 399 | 46 |
| 400 | 47 |
| 401 | 48 |
| 402 | 50 |
| 403 | 56 |
| 404 | 57 |
| 405 | 58 |
| 406 | 60 |
| 407 | 62 |
| 408 | 63 |

TABLE 5 pVip Proteins

| SEQ ID NO | IMG id | pVip # | Clade | Metagenome genome IMG ID | Genome Metagenome Name | Kinase |
|---|---|---|---|---|---|---|
| 409 | 2624749465 | 6 | 1 | 2623620517 | *Selenomonas ruminatium* S137 | No |
| 410 | 2739066738 | 7 | 5 | 2738541339 | *Fibrobacter* sp. UWT3 | No |
| 411 | 2521798317 | 8 | 4 | 2521172648 | *Psychrobacter lutiphocae* DSM 21542 | No |
| 412 | 2574301464 | 9 | 7 | 2574179732 | *Vibrio porteresiae* DSM 19223 | Yes |
| 413 | 2720695169 | 10 | 7 | 2718218250 | *Vibrio vulnificus* ATL 6-1306 | Yes |
| 414 | 2698137626 | 12 | 6 | 2695420938 | *Ruegeria intermedia* DSM 29341 | No |
| 415 | 646713396 | 15 | 3 | 646564524 | *Coraliomargaritakajimensis* DSM 45221 | No |
| 416 | 2506475787 | 19 | 2 | 2506381025 | *Methanoplanus limicola* M3, DSM 2279 | No |
| 417 | 2515428782 | 21 | 3 | 2515154070 | *Lewinella persica* DSM 23188 | No |
| 418 | 2574506394 | 27 | 6 | 2574179788 | *Desulfovibrio senezii* DSM 8436 | No |
| 419 | 2609132705 | 32 | 5 | 2608642208 | *Phormidium* sp. OSCR GFM (version 2) | Yes |
| 420 | 2619892213 | 34 | 3 | 2619618891 | Cryomorphaceae bacterium EBPR_Bin_135 | No |
| 421 | 2634960437 | 39 | 6 | 2634166261 | Burkholderiales-76 (UID4002) | No |
| 422 | 2639213731 | 42 | 2 | 2636416084 | *Planktothricoides* sp. SR001 | Yes |
| 423 | 2648875132 | 44 | 3 | 2648501185 | *Chondromyces crocatus* Cm c5 | No |
| 424 | 2649993803 | 46 | 7 | 2648501459 | *Photobacterium swingsii* CAIM 1393 | Yes |
| 425 | 2651203508 | 47 | 3 | 2648501771 | *Flammeovirga pacifica* WPAGA1 | No |
| 426 | 2651490945 | 48 | 7 | 2648501840 | *Vibrio crassostreae* J5-19 | No |
| 427 | 2661858798 | 50 | 2 | 2660238307 | Methanogenic archaeon ISO4-H5 | No |
| 428 | 2701115162 | 56 | 5 | 2700988679 | *Fibrobacter* sp. UWH6 | No |
| 429 | 2718503187 | 57 | 3 | 2718217692 | *Flavobacterium lacus* CGMCC 1.12504 | No |
| 430 | 2721736750 | 58 | 7 | 2718218507 | *Pseudoalteromonas ulvae* TC14 | No |
| 431 | 2733913669 | 60 | 3 | 2731957952 | *Lacinutrix* sp. JCM 13824 | No |
| 432 | 2743907592 | 62 | 5 | 2740892545 | Fibrobacteria bacterium GUT31 IN01_31 | No |
| 433 | 2744633848 | 63 | 6 | 2744054527 | *Pseudoalteromonas* sp. XI10 | Yes |
| 434 | 2695043264 | 1 | 3 | 2693429896 | *Lutibacter oricola* DSM 24956 | No |
| 435 | 2684559953 | 2 | 3 | 2681813561 | *Chryseobacterium gambrini* DSM 18014 | Yes |
| 436 | 2507146842 | 3 | 2 | 2506783068 | *Methanofollis liminatans* GKZPZ, DSM 4140 | No |
| 437 | 2632766730 | 11 | 7 | 2630968672 | *Shewanella baltica* OS678 | No |
| 438 | 2744653400 | 13 | 6 | 2744054531 | *Marinobacter* sp. YWL01 | No |
| 439 | 2654783232 | 14 | 6 | 2654587543 | *Pseudomonas nitroreducens* B | No |
| 440 | 2504625218 | 17 | 7 | 2504557017 | *Marinomonas* sp GOBB3-320 | No |
| 441 | 2506474236 | 18 | 2 | 2506381025 | *Methanoplanus limicola* M3, DSM 2279 | No |
| 442 | 2509664214 | 20 | 2 | 2509601008 | *Methanomethylovorans hollandica* DSM 15978 | No |
| 443 | 2518436022 | 22 | 3 | 2518285547 | *Pelobacter carbinolicus* Bd1, GraBd1 | No |
| 444 | 2522341593 | 23 | 5 | 2522125098 | *Tolumonas lignilytica* BRL6-1 | No |
| 445 | 2524269675 | 24 | 4 | 2524023156 | *Conchiformibius kuhniae* DSM 17694 | No |
| 446 | 2525334630 | 25 | 2 | 2524614668 | *Methanocorpusculum bavaricum* DSM 4179 | No |
| 447 | 2557036911 | 26 | 7 | 2556921023 | *Pseudoalteromonas* sp. H105 PacBio methylation | No |
| 448 | 2574517928 | 28 | 7 | 2574179790 | *Endozoicomonas numazuensis* DSM 25634 | No |
| 449 | 2582805913 | 29 | 3 | 2582580599 | Composite genome from Lake Mendota Epilimnion pan-assembly MEint.metabat.6813 | No |
| 450 | 2582946381 | 30 | 3 | 2582580664 | Composite genome from Trout Bog Hypolimnion pan-assembly TBhypo.metabat.2746 | No |
| 451 | 2596421479 | 31 | 3 | 2595698251 | *Kibdelosporangium aridum* DSM 43828 | No |
| 452 | 2618018523 | 33 | 6 | 2617270916 | *Marinobacter zhejiangensis* CGMCC 1.7061 | No |

TABLE 5-continued pVip Proteins

| SEQ ID NO | IMG id | pVip # | Clade | Metagenome genome IMG ID | Genome Metagenome Name | Kinase |
|---|---|---|---|---|---|---|
| 453 | 2631333032 | 36 | 7 | 2630968323 | *Nitrincola* sp. A-D6 | No |
| 454 | 2632937107 | 37 | 7 | 2630968711 | *Shewanella* sp. cp20 | No |
| 455 | 2633985761 | 38 | 2 | 2630968972 | *Methanococcoides methylutens* DSM 2657 | Yes |
| 456 | 2635314107 | 40 | 3 | 2634166348 | *Actinomadura echinospora* DSM 43163 | No |
| 457 | 2637497700 | 41 | 7 | 2636415666 | *Photobacterium leiognathi mandapamensis* KNH6 | No |
| 458 | 2641427518 | 43 | 6 | 2639762959 | Actinobacteria bacterium OK074 | No |
| 459 | 2649163162 | 45 | 7 | 2648501251 | *Moritella viscosa* 06/09/139 | Yes |
| 460 | 2651585264 | 49 | 6 | 2648501863 | *Aeromonas caviae* CECT 4221 | No |
| 461 | 2665950188 | 51 | 6 | 2663763173 | *Legionella santicrucis* SC-63-C7 | No |
| 462 | 2674184607 | 52 | 6 | 2671180787 | *Pseudomonas stutzeri* C2 | No |
| 463 | 2684813341 | 53 | 6 | 2684622550 | *Aquabacterium parvum* B6 | No |
| 464 | 2693697599 | 54 | 7 | 2693429564 | *Vibrio metoecus* YB4D01 | No |
| 465 | 2694112273 | 55 | 4 | 2693429660 | *Helicobacter bilis* Missouri | No |
| 466 | 2728147792 | 59 | 6 | 2724679805 | *Shimia sagamensis* DSM 29734 | No |
| 467 | 2741341560 | 61 | 3 | 2740891962 | Marine group II.A Euryarchaeotarchaeon SCGC AG-487__M08 (contamination screened) | No |
| 468 | 2741409035 | 64 | 2 | 2740891993 | Candidatus Heimdallarchaeotarchaeon LC__3 | No |
| 469 | 2504129180 | 65 | 2 | 2503982047 | *Anabaena cylindrica* PCC 7122 | Yes |
| 470 | 637160692 | 66 | 1 | 637000327 | *Treponema denticola*TCC 35405 | No |
| 471 | 637364324 | 67 | 7 | 637000336 | *Vibrio vulnificus* CMCP6 | Yes |
| 472 | 637468954 | 68 | 7 | 637000337 | *Vibrio vulnificus* YJ016 | Yes |
| 473 | 637586319 | 69 | 7 | 637000206 | Photobacterium profundum SS9 | Yes |
| 474 | 637752529 | 70 | 3 | 637000204 | *Pelobacter carbinolicus* Bd1, GraBd1 | No |
| 475 | 639797708 | 71 | 7 | 639633052 | *Psychromonas ingrahamii* 37 | No |
| 476 | 640805406 | 72 | 7 | 640753033 | *Marinomonas* sp. MWYL1 | No |
| 477 | 640830189 | 73 | 7 | 640753049 | *Shewanella baltica* OS185 | No |
| 478 | 641096015 | 74 | 4 | 640963011 | *Beggiatoa* sp. PS | No |
| 479 | 641147750 | 75 | 6 | 640963027 | *Marinobacter algicola* DG893 | No |
| 480 | 641288534 | 76 | 7 | 641228507 | *Shewanella baltica* OS195 | No |
| 481 | 643461066 | 77 | 7 | 643348574 | *Shewanella baltica* OS223 | No |
| 482 | 646369858 | 78 | 5 | 646311927 | *Fibrobacter succinogenes* S85 | No |
| 483 | 646419713 | 79 | 3 | 646311963 | *Thermomonospora curvata* DSM 43183 | No |
| 484 | 647622404 | 80 | 4 | 647533121 | Campylobacterales sp. GD 1 | No |
| 485 | 649804297 | 81 | 4 | 649633054 | *Helicobacter felis* CS1, ATCC 49179 | No |
| 486 | 650410387 | 82 | 6 | 650377991 | *Marinobacter adhaerens* HP15 | No |
| 487 | 650419199 | 83 | 5 | 650377942 | *Fibrobacter succinogenes* S85 | No |
| 488 | 650463340 | 84 | 7 | 650377984 | *Vibrio furnissii* 2510/74, NCTC 11218 | No |
| 489 | 650537321 | 85 | 1 | 650377925 | *Coprococcus catus* GD/7 | No |
| 490 | 650742368 | 86 | 6 | 650716002 | *Acidiphilium multivorum* AIU301 | No |
| 491 | 650921542 | 87 | 3 | 650716044 | *Lacinutrix* sp. 5H-3-7-4 | No |
| 492 | 2501733929 | 88 | 7 | 2501651210 | Photobacterium profundum 3TCK | Yes |
| 493 | 2502233141 | 89 | 2 | 2502171154 | Thermoplasmatales archaeon BRNA1 | No |
| 494 | 2509552219 | 90 | 1 | 2509276055 | *Treponema saccharophilum* PB, DSM 2985 | No |
| 495 | 2512440669 | 91 | 4 | 2512047059 | *Haemophilus haemolyticus* M21621 | No |
| 496 | 2519473577 | 92 | 2 | 2519103099 | *Methanolobus psychrophilus* R15 | No |
| 497 | 2519473579 | 93 | 2 | 2519103099 | *Methanolobus psychrophilus* R15 | No |
| 498 | 2519484486 | 94 | 1 | 2519103103 | *Brachyspira pilosicoli* B2904 | No |
| 499 | 2519815572 | 95 | 6 | 2519103180 | *Curvibacter lanceolatus* ATCC 14669 | No |

TABLE 5-continued

| pVip Proteins | | | | | | |
|---|---|---|---|---|---|---|
| SEQ ID NO | IMG id | pVip # | Clade | Metagenome genome IMG ID | Genome Metagenome Name | Kinase |
| 500 | 2521802859 | 96 | 6 | 2521172649 | *Rheinheimera perlucida* DSM 18276 | No |
| 501 | 2522303848 | 97 | 1 | 2522125086 | *Succinimonas amylolytica* DSM 2873 | No |
| 502 | 2524107537 | 98 | 7 | 2524023060 | *Ferrimonas kyonanensis* DSM 18153 | No |
| 503 | 2525610838 | 99 | 6 | 2524614740 | *Pseudomonas stutz*eri MF28 | No |
| 504 | 2525930338 | 100 | 5 | 2524614816 | *Halodesulfovibrio aestuarii* DSM 10141 | No |
| 505 | 2528325157 | 101 | 6 | 2528311002 | *Comamonas testosteroni* ZNC0007 | No |
| 506 | 2531202617 | 102 | 4 | 2529293096 | *Sulfurimonas gotlandica* GDI | No |
| 507 | 2532381218 | 103 | 4 | 2531839141 | *Kingella kingae* PYKK081 | No |
| 508 | 2532646932 | 104 | 6 | 2531839206 | *Thauera* sp. 63 | No |
| 509 | 2538932271 | 105 | 1 | 2537561856 | *Brachyspira hampsonii* 30446 | No |
| 510 | 2540642849 | 106 | 2 | 2540341105 | *Methanoculleus bourgensis* MS2 | No |
| 511 | 2540668036 | 107 | 2 | 2540341115 | Candidatus *Methanomethylophilus alvus* Mx1201 | No |
| 512 | 2540825991 | 108 | 3 | 2540341170 | *Pseudodesulfovibrio piezophilus* C1TLV30 | No |
| 513 | 2541039228 | 109 | 1 | 2540341248 | *Ruminococcus flavefaciens* AE3010 | No |
| 514 | 2541315631 | 110 | 1 | 2541046975 | *Treponema* medium ATCC 700293 | No |
| 515 | 2546450678 | 111 | 6 | 2545824694 | *Marinobacter santoriniensis* NKSG1 | No |
| 516 | 2546738312 | 112 | 7 | 2545824767 | *Bacteriovorax* sp. DB6_IX | Yes |
| 517 | 2547718745 | 113 | 4 | 2547132187 | *Acinetobacter* sp. MDS7A | No |
| 518 | 2551476655 | 114 | 7 | 2551306039 | *Vibrio harveyi* ZJ0603 | No |
| 519 | 2551491916 | 115 | 7 | 2551306042 | *Vibrio* genomosp. F10 ZF-129 | No |
| 520 | 2551562099 | 116 | 7 | 2551306058 | *Vibrio splendidus* 12E03 | No |
| 521 | 2551596444 | 117 | 7 | 2551306067 | *Vibrio rumoiensis* 1S-45 | No |
| 522 | 2553401559 | 118 | 7 | 2551306520 | *Aliivibrio logei* ATCC 35077 | No |
| 523 | 2553886541 | 119 | 7 | 2551306646 | *Vibrio harveyi* AOD131 | No |
| 524 | 2558097217 | 120 | 4 | 2556921621 | *Acinetobacter towneri* DSM 14962 | No |
| 525 | 2559286049 | 121 | 1 | 2558860239 | *Spiroplasma culicicola*ES-1 | No |
| 526 | 2559416375 | 122 | 1 | 2558860277 | *Treponema primitia* ZAS-1 | No |
| 527 | 2562001279 | 123 | 1 | 2561511079 | *Selenomonas* sp. FC4001 | No |
| 528 | 2563081558 | 124 | 3 | 2562617115 | *Myxococcus hansupus* DSM 436 | No |
| 529 | 2563230595 | 125 | 4 | 2562617155 | *Helicobacter bilis* ATCC 43879 | No |
| 530 | 2565569616 | 126 | 7 | 2563367142 | *Vibrio halioticoli* NBRC 102217 | No |
| 531 | 2565702223 | 127 | 4 | 2563367170 | *Helicobacter bilis* WiWa | No |
| 532 | 2566542256 | 128 | 4 | 2565956643 | *Acinetobacter parvus* NIPH 1103 | No |
| 533 | 2566736970 | 129 | 4 | 2565956698 | *Acinetobacter towneri* DSM 14962 | No |
| 534 | 2569938648 | 130 | 7 | 2568526421 | *Vibrio parahaemolyticus* TUMSAT_H10_S6 | Yes |
| 535 | 2574423613 | 131 | 3 | 2574179766 | *Thiomonas* sp. FB-Cd, DSM 25617 | No |
| 536 | 2574578667 | 132 | 5 | 2574179802 | *Sulfitobacter mediterraneus* KCTC 32188 | No |
| 537 | 2577747326 | 133 | 7 | 2576861245 | *Vibrio parahaemolyticus* VIP4-0444 | Yes |
| 538 | 2577787495 | 134 | 7 | 2576861258 | *Pseudoalteromonas haloplanktis* TB25 | No |
| 539 | 25804401517 | 135 | 7 | 2579778656 | *Pseudoalteromonas haloplanktis* AC163 | No |
| 540 | 25810324187 | 136 | 7 | 2579778800 | *Vibrio metoecus* PPCK-2014 | No |
| 541 | 2581542389 | 137 | 7 | 2579778918 | *Vibrio harveyi* E385 | No |
| 542 | 2582293224 | 138 | 7 | 2579779100 | *Vibrio parahaemolyticus* VIP4-0430 | Yes |
| 543 | 2582959978 | 139 | 3 | 2582580668 | Composite genome from Trout Bog Hypolimnion pan-assembly TBhypo.metabat.3004 | No |
| 544 | 2583671671 | 140 | 7 | 2582580861 | *Pseudoalteromonas* sp. TAE56 | No |
| 545 | 2584203718 | 141 | 7 | 2582580995 | *Vibrio parahaemolyticus* TUMSAT_DE2_S2 | Yes |
| 546 | 2585240392 | 142 | 6 | 2582581301 | *Janthinobacterium* sp. RA13 | No |

TABLE 5-continued pVip Proteins

| SEQ ID NO | IMG id | pVip # | Clade | Metagenome genome IMG ID | Genome Metagenome Name | Kinase |
|---|---|---|---|---|---|---|
| 547 | 2587265930 | 143 | 7 | 2585427937 | *Pseudoalteromonas* sp. 520P1 | No |
| 548 | 2589217693 | 144 | 3 | 2588253911 | *Chondromyces apiculatus* DSM 436 | No |
| 549 | 2597063350 | 145 | 5 | 2596583606 | *Fibrobacter succinogenes elongatus* HM2 | No |
| 550 | 2600497862 | 146 | 6 | 2600254970 | *Pseudomonas* sp. 1-7 | No |
| 551 | 2600833866 | 147 | 7 | 2600255071 | *Vibrio ezurae* NBRC 102218 | No |
| 552 | 2609594859 | 148 | 6 | 2609459643 | *Janthinobacterium* sp. OK676 | No |
| 553 | 2609930410 | 149 | 6 | 2609459764 | *Marinobacter* sp. ES.048 | No |
| 554 | 2611345001 | 150 | 3 | 2609460080 | *Hyalangium minutum* DSM 14724 | No |
| 555 | 2611749855 | 151 | 6 | 2609460164 | *Acidithiobacillus thiooxidans Licanantay* | No |
| 556 | 2612132826 | 152 | 6 | 2609460245 | *Delftia tsuruhatensis* 391 | No |
| 557 | 2617465221 | 153 | 6 | 2617270765 | *Marinobacter mobilis* CGMCC 1.7059 | No |
| 558 | 2617538802 | 154 | 3 | 2617270789 | *Flavobacterium omnivorum* CGMCC 1.2747 | No |
| 559 | 2619647987 | 155 | 7 | 2619618818 | *Pseudidiomarina donghaiensis* CGMCC 1.7284 | No |
| 560 | 2619760352 | 156 | 6 | 2619618853 | Betaproteobacteria sp. genome_bin_13 | No |
| 561 | 2620549291 | 157 | 3 | 2619619052 | Unclassified Chloroflexi bacterium bin152 | No |
| 562 | 2621169600 | 158 | 7 | 2619619266 | *Photobacterium phosphoreum* ANT220 | Yes |
| 563 | 2623278845 | 159 | 6 | 2622736530 | *Roseovarius lutimaris* DSM 28463 | No |
| 564 | 2632746825 | 160 | 3 | 2630968667 | *Nonlabens ulvanivorans* JCM 19297 | No |
| 565 | 2642232622 | 161 | 6 | 2639763156 | *Aeromonas sobria* CECT 4245 | No |
| 566 | 2644760915 | 162 | 3 | 2643221740 | *Chryseobacterium* sp. Leaf201 | Yes |
| 567 | 2645912334 | 163 | 7 | 2645727543 | *Aeromonas tecta* CECT 7082 | No |
| 568 | 2647434260 | 164 | 6 | 2645727892 | *Comamonas testosteroni* KF712 | No |
| 569 | 2649993012 | 165 | 7 | 2648501459 | *Photobacterium swingsii* CAIM 1393 | No |
| 570 | 2651793160 | 166 | 6 | 2648501913 | *Pseudomonas nitroreducens* DPB | No |
| 571 | 2652273697 | 167 | 6 | 2651869653 | *Rubrivivax* sp. AAP121 | No |
| 572 | 2654809173 | 168 | 6 | 2654587547 | *Achromobacter spanius* CGMCC9173 | No |
| 573 | 2658339966 | 169 | 2 | 2657245169 | *Methanoculleus* sp. EBM-46 | No |
| 574 | 2667505054 | 170 | 6 | 2663763602 | *Pseudomonas hussainii* JCM 19513 | No |
| 575 | 2667963948 | 171 | 3 | 2667527390 | *Fabibacter pacificus* CGMCC 1.12402 | No |
| 576 | 2668144532 | 172 | 6 | 2667527434 | *Pseudomonas oryzae* KCTC 32247 | No |
| 577 | 2668847476 | 173 | 7 | 2667527626 | *Vibrio parahaemolyticus* S164 | Yes |
| 578 | 2672407511 | 174 | 7 | 2671180348 | *Vibrio tritonius* AM2 | Yes |
| 579 | 2674782375 | 175 | 7 | 2671180928 | *Vibrio parahaemolyticus* CFSAN007447 | Yes |
| 580 | 2677278474 | 176 | 2 | 2675903261 | *Anabaena* sp. 4-3 | Yes |
| 581 | 2682061458 | 177 | 6 | 2681812894 | *Sphaerotilus natans* ATCC 13338 | No |
| 582 | 2684092807 | 178 | 2 | 2681813425 | *Methanoculleus* sp. MAB1 | No |
| 583 | 2688794699 | 179 | 6 | 2687453440 | *Aeromonas veronii* TH0426 | No |
| 584 | 2693209812 | 180 | 7 | 2690316327 | *Vibrio parahaemolyticus* S165 | Yes |
| 585 | 2694949528 | 181 | 3 | 2693429874 | *Olleya namhaensis* DSM 28881 | No |
| 586 | 2700499480 | 182 | sp | 2698536835 | Microgenomates bacterium JGI CrystG Apr02-3-G15 (contamination screened) | No |
| 587 | 2701140257 | 183 | 5 | 2700988686 | *Fibrobacter* sp. UWH9 | No |
| 588 | 2701911183 | 184 | 7 | 2700989248 | *Vibrio parahaemolyticus* CFSAN007448 | Yes |
| 589 | 2705695255 | 185 | 5 | 2703719122 | unclassified Deltaproteobacteria bin 1 | No |
| 590 | 2706043000 | 186 | 5 | 2703719236 | *Fibrobacter* sp. UWB7 | No |
| 591 | 2712662546 | 187 | 6 | 2711768198 | *Arsukibacterium ikkense* GCM72 | No |
| 592 | 2714077658 | 188 | 7 | 2713896747 | *Vibrio alginolyticus* V2 | No |
| 593 | 2719376594 | 189 | 7 | 2718217925 | *Alteromonas* sp. Mex14 | No |

TABLE 5-continued

| pVip Proteins | | | | | | |
|---|---|---|---|---|---|---|
| SEQ ID NO | IMG id | pVip # | Clade | Metagenome genome IMG ID | Genome Metagenome Name | Kinase |
| 594 | 2719498267 | 190 | 6 | 2718217953 | *Marinobacter salinus* Hb8 | No |
| 595 | 2719828580 | 191 | 3 | 2718218033 | *Lutibacter* sp. LPB0138 | No |
| 596 | 2722236530 | 192 | 6 | 2721755284 | Gammaproteobacteria bacterium GWF2_41_13 | No |
| 597 | 2727845415 | 193 | 3 | 2724679709 | *Saccharicrinis carchari* DSM 27040 | No |
| 598 | 2728971251 | 194 | 7 | 2728369061 | *Aliivibrio wodanis* CL7 | No |
| 599 | 2729066335 | 195 | 6 | 2728369080 | *Dechloromonas denitrificans* ATCC BAA-841 | No |
| 600 | 2730169305 | 196 | 3 | 2728369366 | *Tenacibaculum* sp. LPB0136 | No |
| 601 | 2731232863 | 197 | 7 | 2728369654 | *Vibrio* sp. JCM 19061 | Yes |
| 602 | 2735939253 | 198 | 5 | 2734482289 | *Sulfitobacter mediterraneus* DSM 12244 | No |
| 603 | 2740266671 | 199 | 5 | 2739367982 | Oceanospirillales bacterium JGI 01_G13_750m (contamination screened) | No |
| 604 | 2741408272 | 200 | 2 | 2740891993 | Candidatus Heimdallarchaeotarchaeon LC_3 | No |
| 605 | 2742412079 | 201 | 6 | 2740892189 | *Marinobacter* sp. EN3 | No |
| 606 | 2742415354 | 202 | 4 | 2740892190 | *Acinetobacter* sp. COS3 | No |
| 607 | 2743908240 | 203 | 5 | 2740892545 | Fibrobacteria bacterium GUT31 IN01_31 | Yes |
| 608 | 2751139676 | 204 | 6 | 2747843223 | *Janthinobacterium* sp. 64 | No |
| 609 | 2752652723 | 205 | 2 | 2751185612 | Bacteroidales bacterium Bact_07 | No |
| 610 | 2753090639 | 206 | 7 | 2751185737 | *Salinivibrio* sp. DV | No |
| 611 | 2753093587 | 207 | 7 | 2751185738 | *Salinivibrio* sp. BNH | No |
| 612 | 2753363234 | 208 | 7 | 2751185801 | *Aliivibrio* sp. 1S128 | Yes |
| 613 | 2753367132 | 209 | 7 | 2751185802 | *Aliivibrio* sp. 1S165 | No |
| 614 | 2753371117 | 210 | 7 | 2751185803 | *Aliivibrio* sp. 1S175 | No |
| 615 | 2753755176 | 211 | 4 | 2751185895 | *Haemophilus quentini* MP1 | No |
| 616 | 2758508848 | 212 | 6 | 2757320913 | *Diaphorobacter polyhydroxybutyrativorans* SL-205 | No |
| 617 | 2758538137 | 213 | 3 | 2757320982 | *Winogradskyella* sp. PC-19 | No |
| 618 | 2758668677 | 214 | 2 | 2758568024 | *Thermococcus siculi* RG-20 | No |
| 619 | 2766104288 | 215 | 4 | 2765235962 | *Neisseria* sp. 10023 | No |
| 620 | 2770832229 | 216 | 3 | 2767802753 | *Cystobacter ferrugineus* Cbfe23 | No |
| 621 | 2558444101 | 217 | sp | 2558309039 | *Megasphaera elsdenii* T81 | Yes |
| 622 | 2620552401 | 218 | 3 | 2619619052 | Unclassified Chloroflexi bacterium bin152 | No |
| 623 | 2620553354 | 219 | 3 | 2619619052 | Unclassified Chloroflexi bacterium bin152 | No |
| 624 | 2671326339 | 220 | sp | 2671180039 | *Streptomyces rubidus* CGMCC 4.2026 | No |
| 625 | 2722096198 | 221 | sp | 2721755233 | Nitrospirae bacterium GWD2_57_9 | No |
| 626 | 2725246328 | 222 | 7 | 2724679053 | *Photobacterium kishitanii* 201212X | Yes |
| 627 | 2049941002 assembled LHMISPF 00252280 | 223 | 3 | 2049941002 | Sinkhole freshwater microbial communities from Lake Huron, US, Sample 419 (*) (MER-FS) (assembled) | |
| 628 | 2061766007 assembled_HiSeq_03538890 | 224 | 2 | 2061766007 | Bovine rumen microbial communities fromthe University of Illinois at Urbana-Champaign, USA, that are switchgrass associated - Sample 470 (*) (MER-FS) (assembled) | |
| 629 | 2061766007 assembled_HiSeq_08062520 | 225 | 5 | 2061766007 | Bovine rumen microbial communities fromthe University of Illinois at Urbana-Champaign, USA, that are switchgrass associated - Sample 470 (*) (MER-FS) (assembled) | |
| 630 | 2061766007 assembled_HiSeq_12004210 | 226 | 2 | 2061766007 | Bovine rumen microbial communities fromthe University of Illinois at Urbana-Champaign, USA, that are switchgrass associated - Sample 470 (*) (MER-FS) (assembled) | |
| 631 | 2061766007 assembled_HiSeq_13805260 | 227 | 1 | 2061766007 | Bovine rumen microbial communities fromthe University of Illinois at Urbana-Champaign, USA, that are switchgrass associated - Sample 470 (*) (MER-FS) (assembled) | |

TABLE 5-continued pVip Proteins

| SEQ ID NO | IMG id | pVip # | Clade | Metagenome genome IMG ID | Genome Metagenome Name | Kinase |
|---|---|---|---|---|---|---|
| 632 | 2061766007 assembled_HiSeq_17035850 | 228 | 5 | 2061766007 | Bovine rumen microbial communities fromthe University of Illinois at Urbana-Champaign, USA, that are switchgrass associated - Sample 470 (*) (MER-FS) (assembled) | |
| 633 | 2061766007 assembled_HiSeq_22354030 | 229 | 1 | 2061766007 | Bovine rumen microbial communities fromthe University of Illinois at Urbana-Champaign, USA, that are switchgrass associated - Sample 470 (*) (MER-FS) (assembled) | |
| 634 | 3300000553 assembled TBL_comb47_HYPO-DRAFT_1000031312 | 230 | 1 | 3300000553 | Trout Bog Lake May 28, 2007 Hypolimnion (Trout Bog Lake Combined Assembly 47 Hypolimnion Samples, August 2012 Assem) (*) (MER-FS) (assembled) | |
| 635 | 3300000558 assembled Draft_1000017819 | 231 | 6 | 3300000558 | Wastewater microbial communities from Syncrude, Ft. McMurray, Alberta - West In Pit SyncrudeMLSB2011 (*) (MER-FS) (assembled) | |
| 636 | 3300000558 assembled Draft_1020415419 | 232 | 2 | 3300000558 | Wastewater microbial communities from Syncrude, Ft. McMurray, Alberta - West In Pit SyncrudeMLSB2011 (*) (MER-FS) (assembled) | |
| 637 | 3300000568 assembled Draft_1000864417 | 233 | 2 | 3300000568 | Tailings pond microbial communities from Northern Alberta -Short chain hydrocarbon degrading methanogenic enrichment culture SCADC: (*) (MER-FS) (assembled) | |
| 638 | 3300000970 assembled BBAY66_100003029 | 234 | 3 | 3300000970 | Macroalgal surface ecosystem from Botany Bay, Sydney, Australia - BBAY66 (*) (MER-FS) (assembled) | |
| 639 | 3300001102 assembled BBAY67_1000022226 | 235 | 3 | 3300001102 | Macroalgal surface ecosystem from Botany Bay, Sydney, Australia - BBAY67 (*) (MER-FS) (assembled) | |
| 640 | 3300001200 assembled BBAY65_1000011634 | 236 | 3 | 3300001200 | Macroalgal surface ecosystem from Botany Bay, Sydney, Australia - BBAY65 (*) (MER-FS) (assembled) | |
| 641 | 3300001348 assembled JGI20154J14316_1000097623 | 237 | 2 | 3300001348 | Pelagic Microbial community sample from North Sea - COGITO 998_met_04 (*) (MER-FS) (assembled) | |
| 642 | 3300001450 assembled JGI24006J15134_1000007033 | 238 | 6 | 3300001450 | Marine viral communities from the Pacific Ocean - LP-53 (*) (MER-FS) (assembled) | |
| 643 | 3300001450 assembled JGI24006J15134_1000007151 | 239 | 6 | 3300001450 | Marine viral communities from the Pacific Ocean - LP-53 (*) (MER-FS) (assembled) | |
| 644 | 3300001598 assembled EMG_100002329 | 240 | sp | 3300001598 | Elephant fecal microbiome from Asian Elephant in Hamburg Zoo, Germany (*) (MER-FS) (assembled) | |
| 645 | 3300001749 assembled JGI24025J20009_1000044120 | 241 | 7 | 3300001749 | Oil polluted marine microbial communities from Coal Oil Point, Santa Barbara, California, USA - Sample 3 (*) (MER-FS) (assembled) | |
| 646 | 3300001750 assembled JGI24023J19991_100005742 | 242 | 3 | 3300001750 | Oil polluted marine microbial communities from Coal Oil Point, Santa Barbara, California, USA - Sample 1 (*) (MER-FS) (assembled) | |
| 647 | 3300001835 assembled shallow_100084433 | 243 | 7 | 3300001835 | Hydrothermal vent plume microbial communities from the Mid Cayman Rise - Shallow Sites - gte4kb (*) (MER-FS) (assembled) | |
| 648 | 3300002119 assembled JGI20170J26628_1000030318 | 244 | 1 | 3300002119 | *Nasutitennes corniger* P3 segment microbial communities from Max Planck Institute, Germany - Nc150P3 (*) (MER-FS) (assembled) | |
| 649 | 3300002165 assembled JGI24527J20359_100014812 | 245 | 7 | 3300002165 | Marine viral communities from the Subarctic Pacific Ocean - LP-52 (*) (MER-FS) (assembled) | |
| 650 | 3300002180 assembled JGI24724J26744_1000065020 | 246 | 3 | 3300002180 | Oil polluted marine microbial communities from Coal Oil Point, Santa Barbara, California, USA - Sample 7 (*) (MER-FS) (assembled) | |
| 651 | 3300002219 assembled SCADCLC_1000381914 | 247 | 6 | 3300002219 | Tailings pond microbial communities from Northern Alberta -Short chain hydrocarbon degrading methanogenic enrichment culture SCADC: (*) (MER-FS) (assembled) | |
| 652 | 3300002219 assembled SCADCLC_1000709320 | 248 | 2 | 3300002219 | Tailings pond microbial communities from Northern Alberta -Short chain hydrocarbon degrading methanogenic enrichment culture SCADC: (*) (MER-FS) (assembled) | |

TABLE 5-continued

| SEQ ID NO | IMG id | pVip # | Clade | Metagenome genome IMG ID | Genome Metagenome Name | Kinase |
|---|---|---|---|---|---|---|
| pVip Proteins | | | | | | |
| 653 | 3300002220 assembled MLSBCLC__100183129 | 249 | 6 | 3300002220 | Wastewater microbial communities from Syncrude, Ft. McMurray, Alberta - West In Pit SyncrudeMLSB2011 (*) (MER-FS) (assembled) | |
| 654 | 3300002220 assembled MLSBCLC__1002228019 | 250 | 2 | 3300002220 | Wastewater microbial communities from Syncrude, Ft. McMurray, Alberta - West In Pit SyncrudeMLSB2011 (*) (MER-FS) (assembled) | |
| 655 | 3300002462 assembled JGI24702J35022__1000091311 | 251 | 2 | 3300002462 | Termite gut P4 segment microbial communities from Max Planck Institute, Germany - Th196 (*) (MER-FS) (assembled) | |
| 656 | 3300002518 assembled JGI25134J35505__1000001183 | 252 | 6 | 3300002518 | Marine viral communities from the Pacific Ocean - ETNP__6__100 (*) (MER-FS) (assembled) | |
| 657 | 3300002835 assembled B570J40625__1000006467 | 253 | 3 | 3300002835 | Freshwater microbial communities from Lake Mendota, WI - (Lake Mendota Combined Ray assembly, ASSEMBLY__DATE=20140605) (*) (MER-FS) (assembled) | |
| 658 | 3300003765 assembled Ga0056911__100030025 | 254 | 3 | 3300003765 | Wastewater treatment Type I *Accumulibacter* community from EBPR Bioreactor in Madison, WI, USA - Reactor 2__5/13/2013__DNA (*) (MER-FS) (assembled) | |
| 659 | 3300003767 assembled Ga0056908__1000061101 | 255 | 3 | 3300003767 | Wastewater treatment Type I *Accumulibacter* community from EBPR Bioreactor in Madison, WI, USA - Reactor 1__10/4/2010__DNA (*) (MER-FS) (assembled) | |
| 660 | 3300004166 assembled Ga0066427__100005916 | 256 | 3 | 3300004166 | Freshwater sediment methanotrophic microbial communities from Lake Washington under simulated oxygen tension - Sediment Metagenome 39__LOW7 (*) (MER-FS) (assembled) | |
| 661 | 3300004173 assembled Ga0066412__100001438 | 257 | 3 | 3300004173 | Freshwater sediment methanotrophic microbial communities from Lake Washington under simulated oxygen tension - Sediment Metagenome 16 LOW5 (*) (MER-FS) (assembled) | |
| 662 | 3300004173 assembled Ga0066412__100011719 | 258 | 3 | 3300004173 | Freshwater sediment methanotrophic microbial communities from Lake Washington under simulated oxygen tension - Sediment Metagenome 16__LOW5 (*) (MER-FS) (assembled) | |
| 663 | 3300004178 assembled Ga0066410__100009118 | 259 | 3 | 3300004178 | Freshwater sediment methanotrophic microbial communities from Lake Washington under simulated oxygen tension - Sediment Metagenome 14__LOW5 (*) (MER-FS) (assembled) | |
| 664 | 3300004197 assembled Ga0066420__100001947 | 260 | 3 | 3300004197 | Freshwater sediment methanotrophic microbial communities from Lake Washington under simulated oxygen tension - Sediment Metagenome 28__LOW6 (*) (MER-FS) (assembled) | |
| 665 | 3300004197 assembled Ga0066420__100010317 | 261 | 3 | 3300004197 | Freshwater sediment methanotrophic microbial communities from Lake Washington under simulated oxygen tension - Sediment Metagenome 28__LOW6 (*) (MER-FS) (assembled) | |
| 666 | 3300004202 assembled Ga0066418__100009418 | 262 | 3 | 3300004202 | Freshwater sediment methanotrophic microbial communities from Lake Washington under simulated oxygen tension - Sediment Metagenome 26__LOW6 (*) (MER-FS) (assembled) | |
| 667 | 3300004203 assembled Ga0066419__100000529 | 263 | 3 | 3300004203 | Freshwater sediment methanotrophic microbial communities from Lake Washington under simulated oxygen tension - Sediment Metagenome 27__LOW6 (*) (MER-FS) (assembled) | |
| 668 | 3300004203 assembled Ga0066419__100003817 | 264 | 3 | 3300004203 | Freshwater sediment methanotrophic microbial communities from Lake Washington under simulated oxygen tension - Sediment Metagenome 27__LOW6 (*) (MER-FS) (assembled) | |
| 669 | 3300004230 assembled Ga0066452__100000937 | 265 | 6 | 3300004230 | Freshwater sediment methanotrophic microbial communities from Lake Washington under simulated oxygen tension - Sediment Metagenome 76__LOW10 (*) (MER-FS) (assembled) | |
| 670 | 3300004250 assembled Ga0066472__1000237 | 266 | 6 | 3300004250 | Freshwater sediment methanotrophic microbial communities from Lake Washington under simulated oxygen tension - Sediment Metagenome 106__HOW12 (*) (MER-FS) (assembled) | |

TABLE 5-continued

| pVip Proteins | | | | | | |
|---|---|---|---|---|---|---|
| SEQ ID NO | IMG id | pVip # | Clade | Metagenome genome IMG ID | Genome Metagenome Name | Kinase |
| 671 | 3300004253 assembled Ga0066464_100004618 | 267 | 6 | 3300004253 | Freshwater sediment methanotrophic microbial communities from Lake Washington under simulated oxygen tension - Sediment Metagenome 94_HOW11 (*) (MER-FS) (assembled) | |
| 672 | 3300004253 assembled Ga0066464_100006643 | 268 | 6 | 3300004253 | Freshwater sediment methanotrophic microbial communities from Lake Washington under simulated oxygen tension - Sediment Metagenome 94_HOW11 (*) (MER-FS) (assembled) | |
| 673 | 3300004806 assembled Ga0007854_100000246 | 269 | 3 | 3300004806 | Freshwater microbial communities from Crystal Bog, Wisconsin, USA - CBH12Aug08 (*) (MER-FS) (assembled) | |
| 674 | 3300005080 assembled Ga0069611_1000016445 | 270 | 3 | 3300005080 | Combined Assembly of Gp0111534, Gp0111535, Gp0111536, Gp0111537, Gp0111539, Gp0111540, Gp0111541, Gp0111542, Gp0111543 (*) (MER-FS) (assembled) | |
| 675 | 3300005124 assembled Ga0070424_1100226 | 271 | 3 | 3300005124 | Active sludge cell enrichment microbial communities from Klosterneuburg, Austria - *Nitrospira* DOME DR08B08 (*) (MER-FS) (assembled) | |
| 676 | 3300005125 assembled Ga0070411_1062712 | 272 | 3 | 3300005125 | Active sludge cell enrichment microbial communities from Klosterneuburg, Austria - *Nitrosomonas* DOME CR02B12 (*) (MER-FS) (assembled) | |
| 677 | 3300005144 assembled Ga0068711_100038117 | 273 | 2 | 3300005144 | Enrichment culture microbial communities from Arthur Kill intertidal strait, New Jersey, USA, that are MTBE-degrading - MTBE-AKM (Arthur Kill Methanogenic) MetaG (*) (MER-FS) (assembled) | |
| 678 | 3300005286 assembled Ga0065721_1000460410 | 274 | 6 | 3300005286 | Mesophilic microbial community from rice straw/compost enrichment Sample: eDNA_1 (*) (MER-FS) (assembled) | |
| 679 | 3300005326 assembled Ga0074195_10008286 | 275 | 2 | 3300005326 | Bioremediated contaminated groundwater from EPA Superfund site, New Mexico - Sample HSE6-23 (*) (MER-FS) (assembled) | |
| 680 | 3300005531 assembled Ga0070738_1000151042 | 276 | 3 | 3300005531 | Surface soil microbial communities from Centralia Pennsylvania, which are recovering from an underground coalmine fire - Coalmine Soil_Cen12_06102014_R2 (*) (MER-FS) (assembled) | |
| 681 | 3300005588 assembled Ga0070728_1000021436 | 277 | 3 | 3300005588 | Marine sediment microbial communities from the Atlantic coast under amendment with organic carbon and nitrate - tdDd47.1 (*) (MER-FS) (assembled) | |
| 682 | 3300005588 assembled Ga0070728_1000125023 | 278 | 3 | 3300005588 | Marine sediment microbial communities from the Atlantic coast under amendment with organic carbon and nitrate - tdDd47.1 (*) (MER-FS) (assembled) | |
| 683 | 3300005589 assembled Ga0070729_10000081117 | 279 | 3 | 3300005589 | Marine sediment microbial communities from the Atlantic coast under amendment with organic carbon and nitrate - tdDd47.2 (*) (MER-FS) (assembled) | |
| 684 | 3300005589 assembled Ga0070729_1000129613 | 280 | 3 | 3300005589 | Marine sediment microbial communities from the Atlantic coast under amendment with organic carbon and nitrate - tdDd47.2 (*) (MER-FS) (assembled) | |
| 685 | 3300005609 assembled Ga0070724_1000012829 | 281 | 7 | 3300005609 | Marine sediment microbial communities from the Atlantic coast under amendment with organic carbon and nitrate - tdDd00.1 (*) (MER-FS) (assembled) | |
| 686 | 3300005609 assembled Ga0070724_1000028613 | 282 | 3 | 3300005609 | Marine sediment microbial communities from the Atlantic coast under amendment with organic carbon and nitrate - tdDd00.1 (*) (MER-FS) (assembled) | |
| 687 | 3300005609 assembled Ga0070724_1000048517 | 283 | 3 | 3300005609 | Marine sediment microbial communities from the Atlantic coast under amendment with organic carbon and nitrate - tdDd00.1 (*) (MER-FS) (assembled) | |
| 688 | 3300005675 assembled Ga0074424_10021430 | 284 | 3 | 3300005675 | Enhanced biological phosphorus removal bioreactor viral communities from the University of Queensland, Australia - SBR4-V90806 Phage Sequencing (*) (MER-FS) (assembled) | |
| 689 | 3300005915 assembled Ga0075122 100007968 | 285 | 2 | 3300005915 | Saline lake microbial communities from Ace Lake, Antarctica - Antarctic Ace Lake Metagenome 02UKB (*) (MER-FS) (assembled) | |
| 690 | 3300005920 assembled Ga0070725 1000012429 | 286 | 7 | 3300005920 | Marine sediment microbial communities from the Atlantic coast under amendment with organic carbon and nitrate - tdDd00.2 (*) (MER-FS) (assembled) | |
| 691 | 3300005920 assembled Ga0070725 1000027223 | 287 | 3 | 3300005920 | Marine sediment microbial communities from the Atlantic coast under amendment with organic carbon and nitrate - tdDd00.2 (*) (MER-FS) (assembled) | |

TABLE 5-continued

| pVip Proteins | | | | | | |
|---|---|---|---|---|---|---|
| SEQ ID NO | IMG id | pVip # | Clade | Metagenome genome IMG ID | Genome Metagenome Name | Kinase |
| 692 | 3300005920 assembled Ga0070725 100003449 | 288 | 3 | 3300005920 | Marine sediment microbial communities from the Atlantic coast under amendment with organic carbon and nitrate - tdDd00.2 (*) (MER-FS) (assembled) | |
| 693 | 3300005986 assembled Ga0075152_1000034111 | 289 | 3 | 3300005986 | Wastewater effluent complex algal communities from Wisconsin, to seasonally profile nutrient transformation and Carbon sequestration - JI Jun. 11, 2014 C2 DNA (*) (MER-FS) (assembled) | |
| 694 | 3300006056 assembled Ga0075163_1000220113 | 290 | 3 | 3300006056 | Wastewater effluent complex algal communities from Wisconsin, to seasonally profile nutrient transformation and Carbon sequestration - JI Oct. 23, 2014 1A DNA (*) (MER-FS) (assembled) | |
| 695 | 3300006104 assembled Ga0007882_1000004313 | 291 | 3 | 3300006104 | Freshwater microbial communities from Crystal Bog, Wisconsin, USA - CBH12Aug09.1 (*) (MER-FS) (assembled) | |
| 696 | 3300006104 assembled Ga0007882_1000014836 | 292 | 3 | 3300006104 | Freshwater microbial communities from Crystal Bog, Wisconsin, USA - CBH12Aug09.1 (*) (MER-FS) (assembled) | |
| 697 | 3300006182 assembled Ga0075033_10000633 | 293 | 6 | 3300006182 | Synthetic microbial communities from Ohio, USA - SynthPrep_5_END_DS10_MetaG (*) (MER-FS) (assembled) | |
| 698 | 3300006226 assembled Ga0099364_100017018 | 294 | 3 | 3300006226 | Termite gut P3 segment microbial communities from Max Planck Institute, Germany - Th196 (*) (MER-FS) (assembled) | |
| 699 | 3300006243 assembled Ga0099348_1001723 | 295 | 4 | 3300006243 | Human buccal mucosa microbial communities from NIH, USA - visit 2, subject 370425937 (*) (MER-FS) (assembled) | |
| 700 | 3300006417 assembled Ga0069787_1004128015 | 296 | 3 | 3300006417 | Combined Assembly of Gp0110018, Gp0110022, Gp0110020 (*) (MER-FS) (assembled) | |
| 701 | 3300006417 assembled Ga0069787_1005605520 | 297 | 3 | 3300006417 | Combined Assembly of Gp0110018, Gp0110022, Gp0110020 (*) (MER-FS) (assembled) | |
| 702 | 3300006417 assembled Ga0069787_1005688918 | 298 | 6 | 3300006417 | Combined Assembly of Gp0110018, Gp0110022, Gp0110020 (*) (MER-FS) (assembled) | |
| 703 | 3300006417 assembled Ga0069787_1021696324 | 299 | 3 | 3300006417 | Combined Assembly of Gp0110018, Gp0110022, Gp0110020 (*) (MER-FS) (assembled) | |
| 704 | 3300006417 assembled Ga0069787_1113807921 | 300 | 3 | 3300006417 | Combined Assembly of Gp0110018, Gp0110022, Gp0110020 (*) (MER-FS) (assembled) | |
| 705 | 3300006736 assembled Ga0098033_1000001464 | 301 | 6 | 3300006736 | Marine viral communities from the Subarctic Pacific Ocean - 1_ETSP_OMZ_AT15124 metaG (*) (MER-FS) (assembled) | |
| 706 | 3300006738 assembled Ga0098035_100006013 | 302 | 6 | 3300006738 | Marine viral communities from the Subarctic Pacific Ocean - 3_ETSP_OMZ_AT15126 metaG (*) (MER-FS) (assembled) | |
| 707 | 3300006789 assembled Ga0098054_10000219 | 303 | 6 | 3300006789 | Marine viral communities from the Subarctic Pacific Ocean - 16_ETSP_OMZ_AT15313 metaG (*) (MER-FS) (assembled) | |
| 708 | 3300006790 assembled Ga0098074_100033128 | 304 | 6 | 3300006790 | Marine viral communities from the Gulf of Mexico - 32_GoM_OMZ_CsCl metaG (*) (MER-FS) (assembled) | |
| 709 | 3300006810 assembled Ga0070754_1000007993 | 305 | 3 | 3300006810 | Aqueous microbial communities from the Delaware River and Bay under freshwater to marine salinity gradient to study organic matter cycling in a time-series - Viral MetaG DEL_Sep_01 (*) (MER-FS) (assembled) | |
| 710 | 3300006879 assembled Ga0079226_100011884 | 306 | 3 | 3300006879 | Agricultural soil microbial communities from Georgia to study Nitrogen management - Poultry litter 2014 (*) (MER-FS) (assembled) | |
| 711 | 3300006927 assembled Ga0098034_100013824 | 307 | 6 | 3300006927 | Marine viral communities from the Subarctic Pacific Ocean - 2_ETSP_OMZ_AT15125 metaG (*) (MER-FS) (assembled) | |
| 712 | 3300006929 assembled Ga0098036_100012625 | 308 | 6 | 3300006929 | Marine viral communities from the Subarctic Pacific Ocean - 4_ETSP_OMZ_AT15127 metaG (*) (MER-FS) (assembled) | |
| 713 | 3300006987 assembled Ga0098063_100010810 | 309 | 6 | 3300006987 | Marine viral communities from the Gulf of Mexico - 24_WHOI_OMZ metaG (*) (MER-FS) (assembled) | |

TABLE 5-continued

| pVip Proteins | | | | | | |
|---|---|---|---|---|---|---|
| SEQ ID NO | IMG id | pVip # | Clade | Metagenome genome IMG ID | Genome Metagenome Name | Kinase |
| 714 | 3300006988 assembled Ga0098064_10002211 | 310 | 6 | 3300006988 | Marine viral communities from the Gulf of Mexico - 24B_WHOI_OMZ_CsCl metaG (*) (MER-FS) (assembled) | |
| 715 | 3300007344 assembled Ga0070745_100033022 | 311 | 7 | 3300007344 | Aqueous microbial communities from the Delaware River and Bay under freshwater to marine salinity gradient to study organic matter cycling in a time-series - Viral MetaG DEL_Mar_4 (*) (MER-FS) (assembled) | |
| 716 | 3300007346 assembled Ga0070753_100014333 | 312 | 7 | 3300007346 | Aqueous microbial communities from the Delaware River and Bay under freshwater to marine salinity gradient to study organic matter cycling in a time-series - Viral MetaG DEL_Aug_31 (*) (MER-FS) (assembled) | |
| 717 | 3300007462 assembled Ga0099934_110520 | 313 | 3 | 3300007462 | Active sludge microbial communities from Klosterneuburg, Austria - Klosterneuburg WWTP active sludge D35_HANv2 (*) (MER-FS) (assembled) | |
| 718 | 3300007485 assembled Ga0099929_1008119 | 314 | 3 | 3300007485 | Active sludge microbial communities from Klosterneuburg, Austria - Klosterneuburg WWTP active sludge D02_HANv2 (*) (MER-FS) (assembled) | |
| 719 | 3300007516 assembled Ga0105050_1000139429 | 315 | 3 | 3300007516 | Freshwater microbial communities from Lake Fryxell liftoff mats and glacier meltwater in Antarctica - FRY-01 (*) (MER-FS) (assembled) | |
| 720 | 3300007640 assembled Ga0070751_1000004111 | 316 | 7 | 3300007640 | Aqueous microbial communities from the Delaware River and Bay under freshwater to marine salinity gradient to study organic matter cycling in a time-series - Viral MetaG DEL_Aug_28 (*) (MER-FS) (assembled) | |
| 721 | 3300007961 assembled Ga0079305_100003992 | 317 | 2 | 3300007961 | Deep subsurface shale carbon reservoir microbial communities from Ohio, USA - LMS_cellobiose_enrichment (*) (MER-FS) (assembled) | |
| 722 | 3300007963 assembled Ga0110931_100009625 | 318 | 6 | 3300007963 | Marine viral communities from the Subarctic Pacific Ocean - 4_ETSP_OMZ_AT15127 metaG (version 2) (*) (MER-FS) (assembled) | |
| 723 | 3300008050 assembled Ga0098052_10001839 | 319 | 6 | 3300008050 | Marine viral communities from the Subarctic Pacific Ocean - 15_ETSP_OMZ_AT15312 metaG (*) (MER-FS) (assembled) | |
| 724 | 3300008050 assembled Ga0098052_100026416 | 320 | 3 | 3300008050 | Marine viral communities from the Subarctic Pacific Ocean - 15_ETSP_OMZ_AT15312 metaG (*) (MER-FS) (assembled) | |
| 725 | 3300008224 assembled Ga0105350_100000945 | 321 | 3 | 3300008224 | Methane-oxidizing microbial communities from mesocosms in the Hudson Canyon - EN1E Hudson Canyon (*) (MER-FS) (assembled) | |
| 726 | 3300009093 assembled Ga0105240_100005042 | 322 | 3 | 3300009093 | Corn rhizosphere microbial communities from Kellogg Biological Station, Michigan, USA - KBS C5-4 metaG (*) (MER-FS) (assembled) | |
| 727 | 3300009169 assembled Ga0105097_1000009945 | 323 | 3 | 3300009169 | Freshwater sediment microbial communities from Prairie Pothole Lake near Jamestown, North Dakota, USA - PPLs Lake P7 Core (1) Depth 10-12 cm May 2015 (*) (MER-FS) (assembled) | |
| 728 | 3300009175 assembled Ga0073936_1000120334 | 324 | 3 | 3300009175 | Freshwater lake bacterial and archeal communities from Alinen Mustajarvi, Finland, to study Microbial Dark Matter (Phase II) - Alinen Mustajarvi 5m metaG (*) (MER-FS) (assembled) | |
| 729 | 3300009415 assembled Ga0115029_100184931 | 325 | 3 | 3300009415 | Marine algal microbial communities from Sidmouth, United Kingdom - Sidmouth_Asex1 metaG (*) (MER-FS) (assembled) | |
| 730 | 3300009419 assembled Ga0114982_10001831 | 326 | 3 | 3300009419 | Subsurface microbial communities from deep shales in Ohio, USA - Utica-3 well 1 S input2 FT (*) (MER-FS) (assembled) | |
| 731 | 3300009488 assembled Ga0114925_1000023517 | 327 | 2 | 3300009488 | Deep subsurface microbial communities from Indian Ocean to uncover new lineages of life (NeLLi) - Sumatra_00607 metaG (*) (MER-FS) (assembled) | |
| 732 | 3300009488 assembled Ga0114925_100003506 | 328 | 2 | 3300009488 | Deep subsurface microbial communities from Indian Ocean to uncover new lineages of life (NeLLi) - Sumatra_00607 metaG (*) (MER-FS) (assembled) | |
| 733 | 3300009508 assembled Ga0115567_1000068222 | 329 | 7 | 3300009508 | Pelagic marine microbial communities from North Sea - COGITO_mtgs_120412 (*) (MER-FS) (assembled) | |
| 734 | 3300009512 assembled Ga0115003_100022198 | 330 | 3 | 3300009512 | Marine microbial communities from western Arctic Ocean - ArcticOcean_MG_CB11_88 (*) (MER-FS) (assembled) | |

TABLE 5-continued

| pVip Proteins | | | | | | |
|---|---|---|---|---|---|---|
| SEQ ID NO | IMG id | pVip # | Clade | Metagenome genome IMG ID | Genome Metagenome Name | Kinase |
| 735 | 3300009546 assembled Ga0099799__100233 | 331 | 3 | 3300009546 | Marine eukaryotic communities from CALCOFI LINE 67, Pacific Ocean - CN11__C50__N6__SortLC__1 (*) (MER-FS) (assembled) | |
| 736 | 3300009669 assembled Ga0116148__10010742 | 332 | 3 | 3300009669 | Active sludge microbial communities of municipal wastewater-treating anaerobic digesters from USA - AD__UKC055__MetaG (*) (MER-FS) (assembled) | |
| 737 | 3300009779 assembled Ga0116152__100003906 | 333 | 3 | 3300009779 | Active sludge microbial communities of municipal wastewater-treating anaerobic digesters from Hong Kong - AD__UKC119__MetaG (*) (MER-FS) (assembled) | |
| 738 | 3300009788 assembled Ga0114923__1000042134 | 334 | 2 | 3300009788 | Deep subsurface microbial communities from Indian Ocean to uncover new lineages of life (NeLLi) - Sumatra__00157__metaG (*) (MER-FS) (assembled) | |
| 739 | 3300009838 assembled Ga0116153__100010806 | 335 | 6 | 3300009838 | Active sludge microbial communities of municipal wastewater-treating anaerobic digesters from USA - AD__UKC028__MetaG (*) (MER-FS) (assembled) | |
| 740 | 3300010028 assembled Ga0134115__1006245 | 336 | 3 | 3300010028 | Active sludge microbial communities from wastewater treatment plant in Klosterneuburg, Austria - C35__LANv3 (*) (MER-FS) (assembled) | |
| 741 | 3300010160 assembled Ga0114967__100001146 | 337 | 3 | 3300010160 | Freshwater microbial communities from Lake Montjoie, Canada to study carbon cycling - M__130628__MF__MetaG (*) (MER-FS) (assembled) | |
| 742 | 3300010162 assembled Ga0131853__1000011621 | 338 | 3 | 3300010162 | Termite gut microbial communities from Petit-Saut, French Guiana - Lab288P1 metaG (version 2) (*) (MER-FS) (assembled) | |
| 743 | 3300010162 assembled Ga0131853__1000234120 | 339 | 3 | 3300010162 | Termite gut microbial communities from Petit-Saut, French Guiana - Lab288P1 metaG (version 2) (*) (MER-FS) (assembled) | |
| 744 | 3300010162 assembled Ga0131853__1000511220 | 340 | 3 | 3300010162 | Termite gut microbial communities from Petit-Saut, French Guiana - Lab288P1 metaG (version 2) (*) (MER-FS) (assembled) | |
| 745 | 3300010270 assembled Ga0129306__100025163 | 341 | 1 | 3300010270 | Capybara group fecal microbial communities from Wisconsin, USA - P827 metagenome (*) (MER-FS) (assembled) | |
| 746 | 3300010313 assembled Ga0116211__100026028 | 342 | 6 | 3300010313 | Hot spring microbial communities from South Africa to study Microbial Dark Matter (Phase II) - Sagole hot spring metaG (*) (MER-FS) (assembled) | |
| 747 | 3300010373 assembled Ga0134128__1000050820 | 343 | 3 | 3300010373 | Terrestrial soil microbial communities with excess Nitrogen fertilizer from Kellogg Biological Station, Michigan, USA - KB3-175-4 (*) (MER-FS) (assembled) | |
| 748 | 3300010379 assembled Ga0136449__1000153745 | 344 | 2 | 3300010379 | Sb__50d combined assembly (*) (MER-FS) (assembled) | |
| 749 | 3300010396 assembled Ga0134126__1000011835 | 345 | 3 | 3300010396 | Terrestrial soil microbial communities with excess Nitrogen fertilizer from Kellogg Biological Station, Michigan, USA - KB3-175-2 (*) (MER-FS) (assembled) | |
| 750 | 3300010430 assembled Ga0118733__10000149451 | 346 | 3 | 3300010430 | Marine sediment microbial communities from Gulf of Thailand under amendment with organic carbon and nitrate - JGI co-assembly of 8 samples (*) (MER-FS) (assembled) | |
| 751 | 3300010430 assembled Ga0118733__10000158731 | 347 | 6 | 3300010430 | Marine sediment microbial communities from Gulf of Thailand under amendment with organic carbon and nitrate - JGI co-assembly of 8 samples (*) (MER-FS) (assembled) | |
| 752 | 3300010430 assembled Ga0118733__10000628422 | 348 | 3 | 3300010430 | Marine sediment microbial communities from Gulf of Thailand under amendment with organic carbon and nitrate - JGI co-assembly of 8 samples (*) (MER-FS) (assembled) | |
| 753 | 3300012103 assembled Ga0136578__1000209 | 349 | 6 | 3300012103 | Saline lake microbial communities from Deep lake, Antarctica - Metagenome #190 (*) (MER-FS) (assembled) | |
| 754 | 3300012533 assembled Ga0138256__1000042615 | 350 | 6 | 3300012533 | Active sludge microbial communities from wastewater in Klosterneuburg, Austria - KNB2014incub__MG (*) (MER-FS) (assembled) | |
| 755 | 3300012950 assembled Ga0163108__1000095519 | 351 | 3 | 3300012950 | Marine microbial communities from the Central Pacific Ocean - Fk160115 155m metaG (*) (MER-FS) (assembled) | |
| 756 | 3300012979 assembled Ga0123348__1000024225 | 352 | 5 | 3300012979 | Fecal eukaryotic communities from dung pellets of Tule Elk in California, USA - Elk Dung B1 Day 1 Metagenome (*) (MER-FS) (assembled) | |

TABLE 5-continued

| pVip Proteins | | | | | | |
|---|---|---|---|---|---|---|
| SEQ ID NO | IMG id | pVip # | Clade | Metagenome genome IMG ID | Genome Metagenome Name | Kinase |
| 757 | 3300012983 assembled Ga0123349__1000049625 | 353 | 5 | 3300012983 | Fecal eukaryotic communities from dung pellets of Tule Elk in California, USA - Elk Dung C2 Day 2 Metagenome (*) (MER-FS) (assembled) | |
| 758 | 3300013088 assembled Ga0163200__1000002129 | 354 | 6 | 3300013088 | Freshwater microbial communities from Powell Lake, British Columbia, Canada to study Microbial Dark Matter (Phase II) - PL__2010__200m (*) (MER-FS) (assembled) | |
| 759 | 3300013092 assembled Ga0163199__1000006211 | 355 | 6 | 3300013092 | Freshwater microbial communities from Powell Lake, British Columbia, Canada to study Microbial Dark Matter (Phase II) - PL__2010__150m (*) (MER-FS) (assembled) | |
| 760 | 3300013131 assembled Ga0172373__100005744 | 356 | 3 | 3300013131 | Freshwater microbial communities from Kabuno Bay, South-Kivu, Congo ? kab__092012__10m (*) (MER-FS) (assembled) | |
| 761 | 3300014491 assembled Ga0182014__100007864 | 357 | 2 | 3300014491 | Permafrost microbial communities from Stordalen Mire, Sweden - 612S2D metaG (*) (MER-FS) (assembled) | |
| 762 | 3300014499 assembled Ga0182012__100003757 | 358 | 3 | 3300014499 | Permafrost microbial communities from Stordalen Mire, Sweden - 612S2S metaG (*) (MER-FS) (assembled) | |
| 763 | 3300017795 assembled Ga0189288__1022816 | 359 | 6 | 3300017795 | Marine microbial communities from the Costa Rica Dome - UW105 mini metaG (*) (MER-FS) (assembled) | |
| 764 | 3300017798 assembled Ga0189289__1026116 | 360 | 6 | 3300017798 | Marine microbial communities from the Costa Rica Dome - UW106 mini metaG (*) (MER-FS) (assembled) | |
| 765 | 3300017805 assembled Ga0189287__100018226 | 361 | 6 | 3300017805 | Marine microbial communities from the Costa Rica Dome - UW86 mini metaG (*) (MER-FS) (assembled) | |
| 766 | 3300017990 assembled Ga0180436__1000345026 | 362 | 3 | 3300017990 | Hypersaline lake sediment archaeal communities from the Salton Sea, California, USA - SS__3__S__2 metaG (*) (MER-FS) (assembled) | |
| 767 | 3300018018 assembled Ga0187886__100041240 | 363 | 2 | 3300018018 | Peatland microbial communities from SPRUCE experiment site at the Marcell Experimental Forest, Minnesota, USA - June2016WEW__20__150 (*) (MER-FS) (assembled) | |
| 768 | 3300018018 assembled Ga0187886__100069122 | 364 | 2 | 3300018018 | Peatland microbial communities from SPRUCE experiment site at die Marcell Experimental Forest, Minnesota, USA - June2016WEW__20__150 (*) (MER-FS) (assembled) | |
| 769 | 3300018033 assembled Ga0187867__1000087624 | 365 | 3 | 3300018033 | Peatland microbial communities from SPRUCE experiment site at the Marcell Experimental Forest, Minnesota, USA - June2016WEW__13__10 (*) (MER-FS) (assembled) | |
| 770 | 3300018038 assembled Ga0187855__1000057816 | 366 | 3 | 3300018038 | Peatland microbial communities from SPRUCE experiment site at the Marcell Experimental Forest, Minnesota, USA - June2016WEW__8__10 (*) (MER-FS) (assembled) | |
| 771 | 3300018042 assembled Ga0187871__100009711 | 367 | 3 | 3300018042 | Peatland microbial communities from SPRUCE experiment site at the Marcell Experimental Forest, Minnesota, USA - June2016WEW__16__10 (*) (MER-FS) (assembled) | |
| 772 | 3300018080 assembled Ga0180433__1001105911 | 368 | 3 | 3300018080 | Hypersaline lake sediment archaeal communities from the Salton Sea, California, USA - SS__1__D__1 metaG (*) (MER-FS) (assembled) | |
| 773 | 3300018428 assembled Ga0181568__1000115027 | 369 | 3 | 3300018428 | Coastal salt marsh microbial communities from the Groves Creek Marsh, Skidaway Island, Georgia - 101404AT metaG (megahit assembly) (*) (MER-FS) (assembled) | |
| 774 | 3300018475 assembled Ga0187907__1000663212 | 370 | 1 | 3300018475 | Goat fecal pellet fungal communities from Santa Barbara, California, USA ? pellet 1 (*) (MER-FS) (assembled) | |
| 775 | 3300018475 assembled Ga0187907__100078053 | 371 | 1 | 3300018475 | Goat fecal pellet fungal communities from Santa Barbara, California, USA ? pellet 1 (*) (MER-FS) (assembled) | |
| 776 | 3300018475 assembled Ga0187907__1000859111 | 372 | 1 | 3300018475 | Goat fecal pellet fungal communities from Santa Barbara, California, USA ? pellet 1 (*) (MER-FS) (assembled) | |

TABLE 5-continued

| pVip Proteins | | | | | | |
|---|---|---|---|---|---|---|
| SEQ ID NO | IMG id | pVip # | Clade | Metagenome genome IMG ID | Genome Metagenome Name | Kinase |
| 777 | 3300018493 assembled Ga0187909__1000543313 | 373 | 1 | 3300018493 | Goat fecal pellet fungal communities from Santa Barbara, California, USA ? pellet 3 (*) (MER-FS) (assembled) | |
| 778 | 3300018494 assembled Ga0187911__1000586113 | 374 | 1 | 3300018494 | Goat fecal pellet fungal communities from Santa Barbara, California, USA ? diluted pellet 2 (*) (MER-FS) (assembled) | |
| 779 | 3300018494 assembled Ga0187911__1001224520 | 375 | 1 | 3300018494 | Goat fecal pellet fungal communities from Santa Barbara, California, USA ? diluted pellet 2 (*) (MER-FS) (assembled) | |
| 780 | 3300018495 assembled Ga0187908__1000576413 | 376 | 1 | 3300018495 | Goat fecal pellet fungal communities from Santa Barbara, California, USA ? pellet 2 (*) (MER-FS) (assembled) | |
| 781 | 3300018495 assembled Ga0187908__1000603814 | 377 | 1 | 3300018495 | Goat fecal pellet fungal communities from Santa Barbara, California, USA ? pellet 2 (*) (MER-FS) (assembled) | |
| 782 | 3300018495 assembled Ga0187908__100073603 | 378 | 1 | 3300018495 | Goat fecal pellet fungal communities from Santa Barbara, California. USA ? pellet 2 (*) (MER-FS) (assembled) | |
| 783 | 3300018878 assembled Ga0187910__1000693112 | 379 | 1 | 3300018878 | Goat fecal pellet fungal communities from Santa Barbara, California, USA ? diluted pellet 1 (*) (MER-FS) (assembled) | |
| 784 | 3300018878 assembled Ga0187910__1000711113 | 380 | 1 | 3300018878 | Goat fecal pellet fungal communities from Santa Barbara, California, USA ? diluted pellet 1 (*) (MER-FS) (assembled) | |
| 785 | 3300018878 assembled Ga0187910__100083003 | 381 | 1 | 3300018878 | Goat fecal pellet fungal communities from Santa Barbara, California, USA ? diluted pellet 1 (*) (MER-FS) (assembled) | |
| 786 | 3300018878 assembled Ga0187910__1000906015 | 382 | sp | 3300018878 | Goat fecal pellet fungal communities from Santa Barbara, California, USA ? diluted pellet 1 (*) (MER-FS) (assembled) | |
| 787 | 3300019373 assembled Ga0187895__100043618 | 383 | 1 | 3300019373 | Goat fecal pellet enrichment culture fungal communities from Isla Vista, California, USA - Alfalfa, Gen0, Rep 3 (*) (MER-FS) (assembled) | |
| 788 | 3300019457 assembled Ga0193932__1007821 | 384 | sp | 3300019457 | Sorted cell/s from Southern Trench hydrothermal vent microbial mat, Guaymas Basin, Mexico ? 6X__4868__18__01 (*) (MER-FS) (assembled) | |
| 789 | 3300019750 assembled Ga0194000__100000539 | 385 | 1 | 3300019750 | Sediment microbial communities from the Broadkill River, Lewes, Delaware, United States ? FLT__6-7__MG (*) (MER-FS) (assembled) | |

While certain features disclosed have been illustrated and described herein, many modifications, substitutions, changes, and equivalents will now occur to those of ordinary skill in the art. It is, therefore, to be understood that the appended claims are intended to cover all such modifications and changes as fall within the true spirit of the compounds and methods of use disclosed herein.

SEQUENCE LISTING

The patent contains a lengthy sequence listing. A copy of the sequence listing is available in electronic form from the USPTO web site (https://seqdata.uspto.gov/docdetail?docId=US12466849B2). An electronic copy of the sequence listing will also be available from the USPTO upon request and payment of the fee set forth in 37 CFR 1.19(b)(3).

What is claimed is:

1. A compound represented by the structure of Formula IIB:

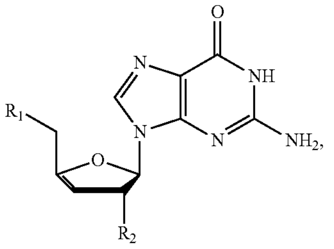

or Formula IVB:

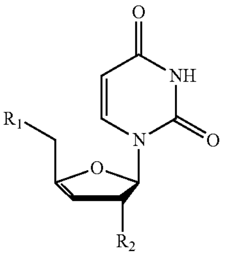

wherein $R_1$ is

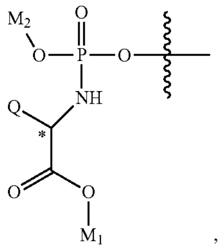

,

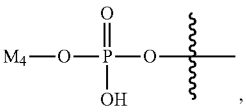

, or

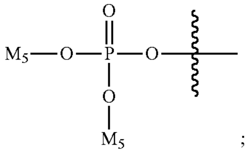

;

Q is a side chain of an amino acid;

$M_1$ is an alkyl;

$M_2$ is an aryl, a substituted aryl, a heteroaryl or a substituted heteroaryl;

$M_4$ is $-(C_2\text{-}C_6)$alkyl-O$-(C_{10}\text{-}C_{20})$alkyl;

each $M_5$ is $-(CH_2)_n-S-C(=O)-(C_1\text{-}C_8)$alkyl;

n is 1-4; and $R_2$ is —OH.

2. The compound of claim 1, wherein said compound has the structure of

Compound 2

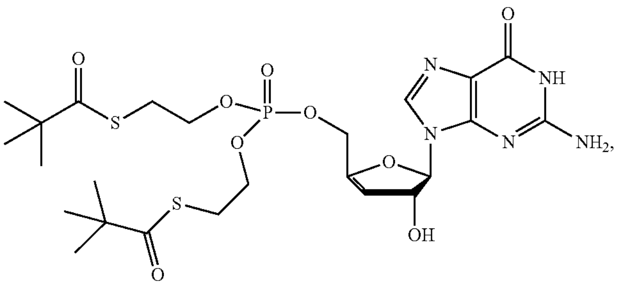

-continued
Compound 4
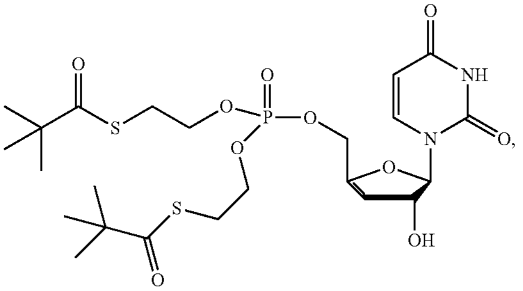
Compound 103
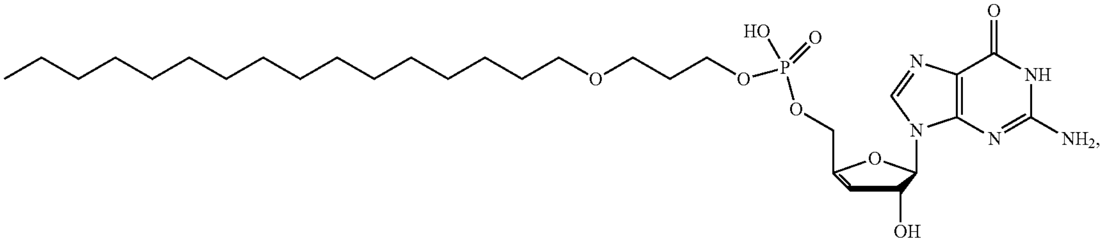
Compound 104
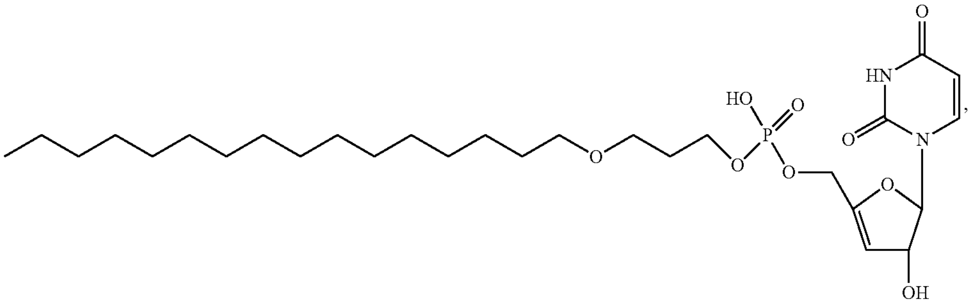
Compound 33
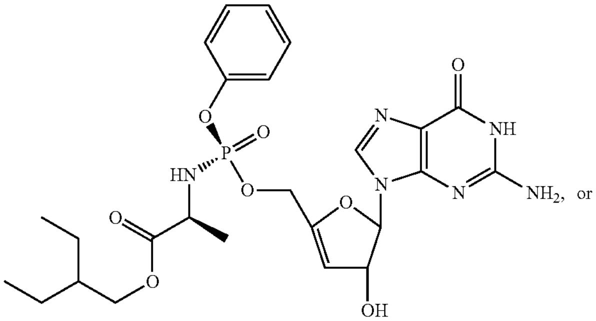
Compound 26
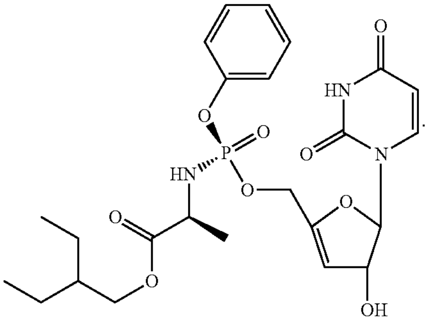

3. The compound of claim 2, wherein said compound has the structure of

Compound 2

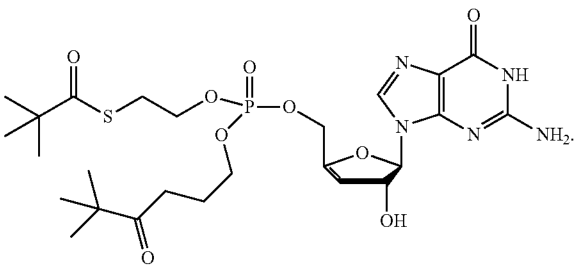

4. The compound of claim 2, wherein said compound has the structure of

Compound 4

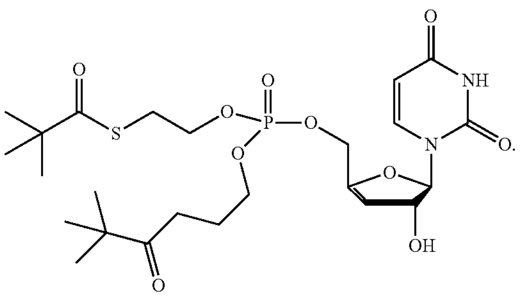

5. The compound of claim 2, wherein said compound has the structure of

Compound 103

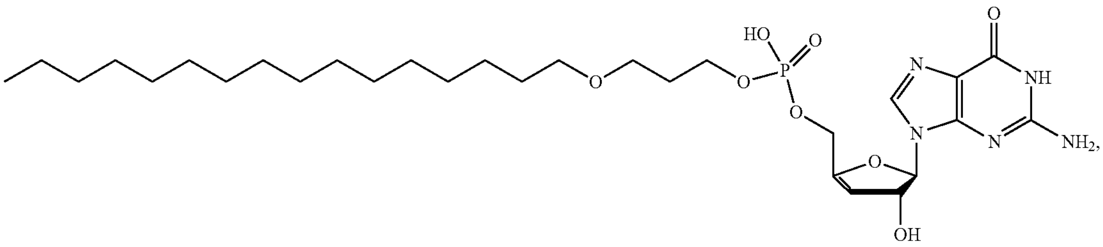

6. The compound of claim 2, wherein said compound has the structure of

Compound 104

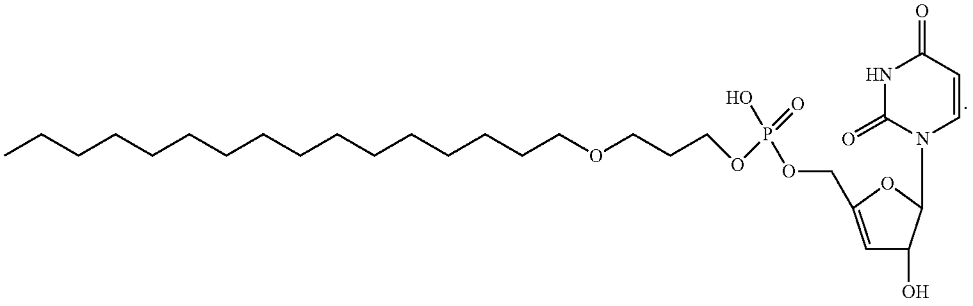

7. The compound of claim 2, wherein said compound has the structure of

Compound 33

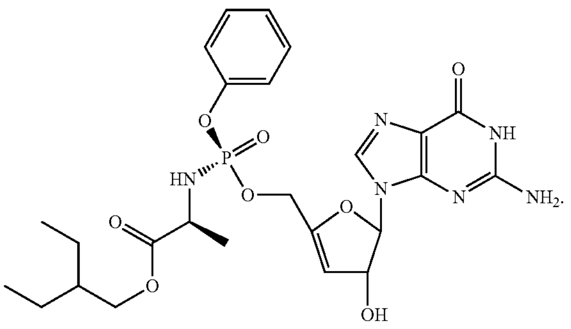

8. The compound of claim 2, wherein said compound has the structure of

Compound 26

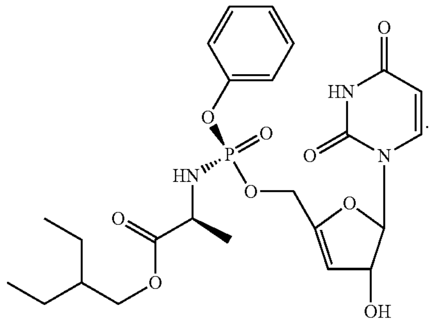

9. A pharmaceutical composition comprising one or more compounds of claim 2.

10. A pharmaceutical composition comprising at least two of the compounds of claim 2.

11. The pharmaceutical composition of claim 9, wherein said composition comprises a pharmaceutically acceptable carrier.

12. A method of treating a disease caused by cytomegalovirus in a subject in need thereof, comprising administering to the subject a composition comprising Compound 103

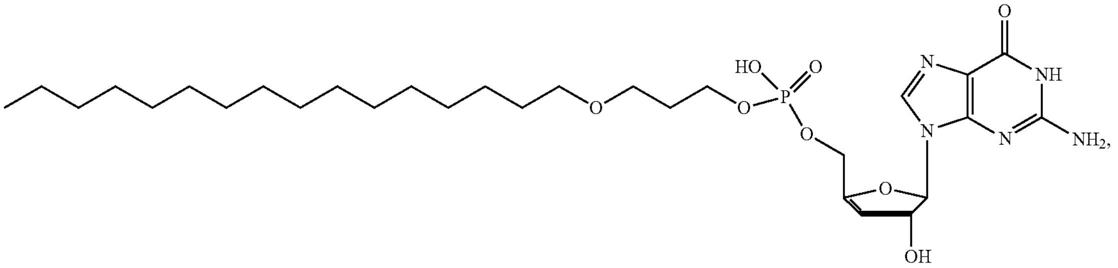

Compound 104

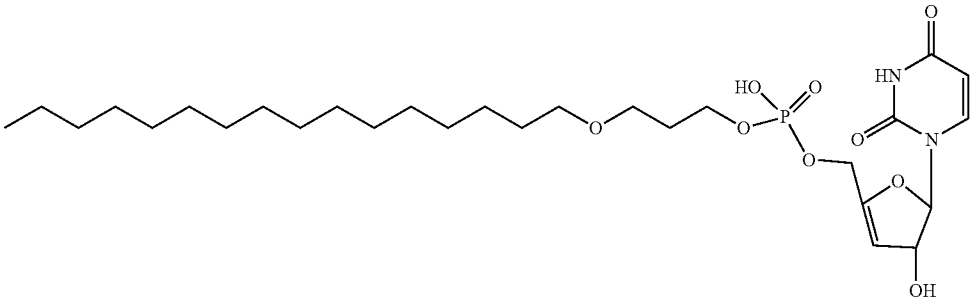

, or

Compound 26

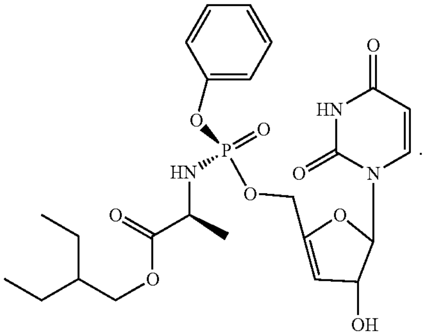

13. The method of claim 12, wherein said method terminates polynucleotide chain synthesis in a cell.

14. The method of claim 13, wherein said terminating polynucleotide chain synthesis increases termination of DNA chain synthesis, or increases termination of RNA chain synthesis, or a combination thereof.

15. A method of treating a disease caused by JC virus in a subject in need thereof, comprising administering to the subject a composition comprising Compound 103

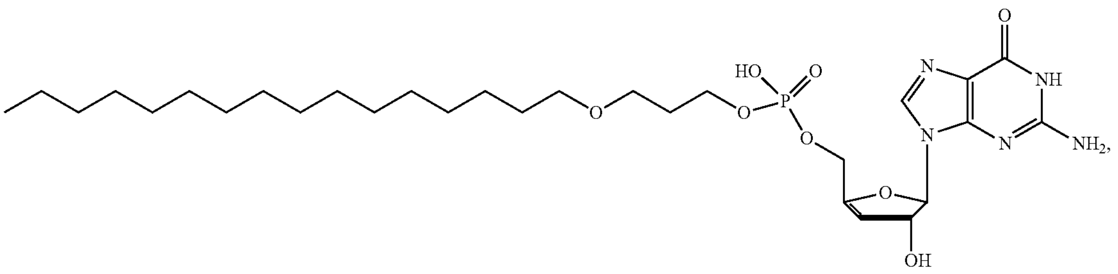

Compound 104

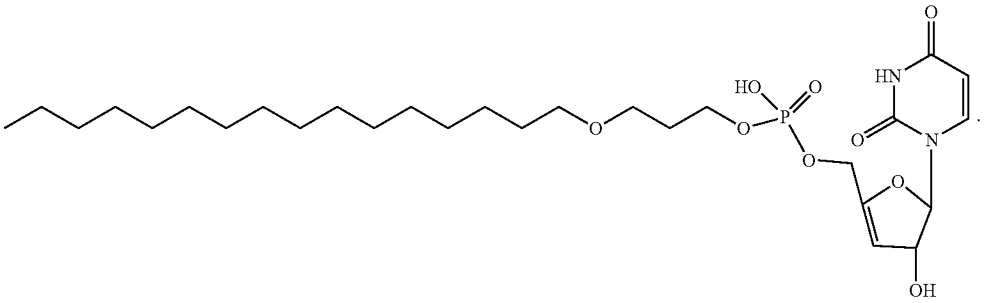

16. The method of claim 15, wherein said method terminates polynucleotide chain synthesis in a cell.

17. The method of claim 16, wherein said terminating polynucleotide chain synthesis increases termination of DNA chain synthesis, or increases termination of RNA chain synthesis, or a combination thereof.

18. A method of treating a disease caused by BK virus in a subject in need thereof, comprising administering to the subject a composition comprising Compound 103

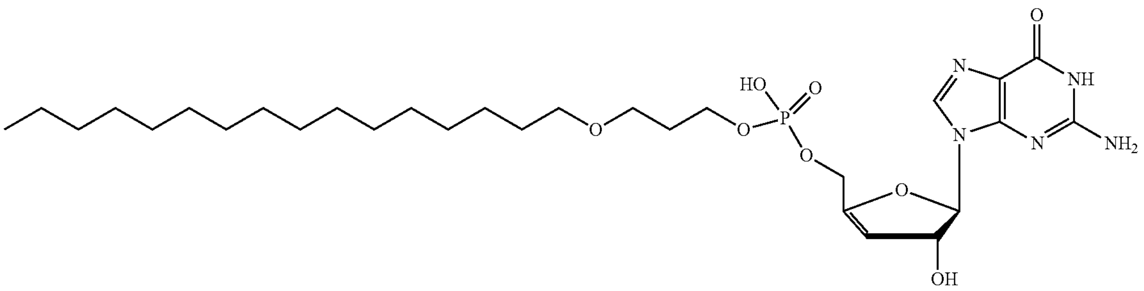

Compound 104

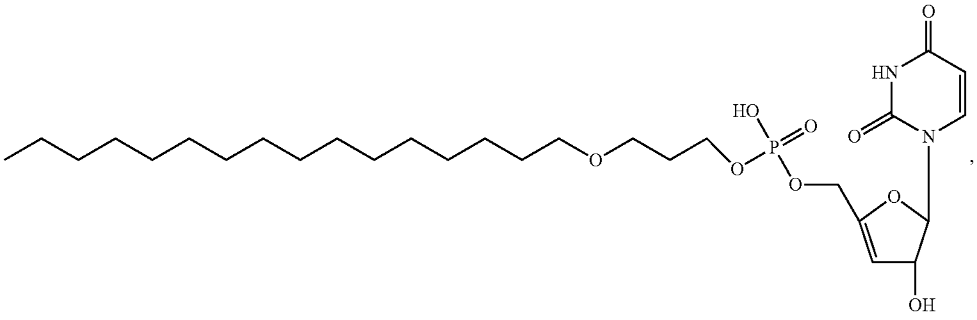

, or

-continued
Compound 26
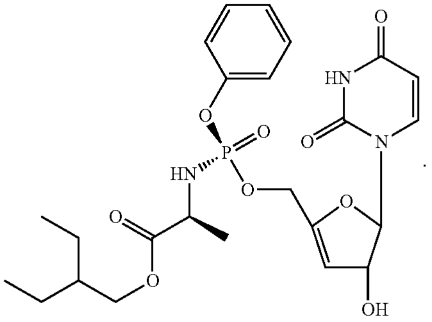
19. The method of claim 18, wherein said method terminates polynucleotide chain synthesis in a cell.
20. The method of claim 19, wherein said terminating polynucleotide chain synthesis increases termination of DNA chain synthesis, or increases termination of RNA chain synthesis, or a combination thereof.
* * * * *